United States Patent
Alonso-de Diego et al.

(10) Patent No.: US 10,106,542 B2
(45) Date of Patent: Oct. 23, 2018

(54) SUBSTITUTED 6,7-DIHYDROPYRAZOLO[1,5-A]PYRAZINES AS NEGATIVE ALLOSTERIC MODULATORS OF MGLUR2 RECEPTORS

(71) Applicant: Janssen Pharmaceutica NV, Beerse (BE)

(72) Inventors: Sergio-Alvar Alonso-de Diego, Toledo (ES); José Maria Cid-Núñez, Toledo (ES); Óscar Delgado-González, Santa Cruz de Tenerife (ES); Annelies Marie Antonius Decorte, Berchem (BE); Michiel Luc Maria Van Gool, Madrid (ES); Gregor James MacDonald, Zoersel (BE); Antonius Adrianus Hendrikus Petrus Megens, Beerse (BE); Andrés Avelino Trabanco-Suárez, Olias del Rey (Toledo) (ES); Aránzazu Garcia-Molina, Toledo (ES); José Ignacio Andrés-Gil, Madrid (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/896,230

(22) PCT Filed: Jun. 3, 2014

(86) PCT No.: PCT/EP2014/061478
§ 371 (c)(1),
(2) Date: Dec. 4, 2015

(87) PCT Pub. No.: WO2014/195311
PCT Pub. Date: Dec. 11, 2014

(65) Prior Publication Data
US 2016/0115169 A1    Apr. 28, 2016

(30) Foreign Application Priority Data

Jun. 4, 2013 (EP) ..................... 13170447
Jun. 27, 2013 (EP) ..................... 13173939
Apr. 29, 2014 (EP) ..................... 14166450

(51) Int. Cl.
*A61K 31/4985* (2006.01)
*C07D 487/04* (2006.01)

(52) U.S. Cl.
CPC ................. *C07D 487/04* (2013.01)

(58) Field of Classification Search
CPC ................. A61K 31/4985; C07D 487/04
USPC ................. 514/249; 544/350
See application file for complete search history.

(56) References Cited

U.S. PATENT DOCUMENTS

| | | |
|---|---|---|
| 2,976,146 A | 3/1961 | Salminen et al. |
| 4,051,244 A | 9/1977 | Matiioda et al. |
| 4,066,651 A | 1/1978 | Brittain et al. |
| 4,146,716 A | 3/1979 | Cox et al. |
| 4,196,207 A | 4/1980 | Webber et al. |
| 4,256,738 A | 3/1981 | Woitun et al. |
| 4,358,453 A | 11/1982 | Bristol et al. |
| 4,550,166 A | 10/1985 | Moran et al. |
| 4,866,074 A | 9/1989 | Spada et al. |
| 4,898,654 A | 2/1990 | Toda et al. |
| 4,978,663 A | 12/1990 | Effland et al. |
| 5,032,602 A | 7/1991 | Fey et al. |
| 5,130,442 A | 7/1992 | Meisel et al. |
| 5,175,157 A | 12/1992 | Psiorz et al. |
| 5,204,198 A | 4/1993 | Bugner et al. |
| 5,236,917 A | 8/1993 | Dunlap et al. |
| 5,254,543 A | 10/1993 | Hanko et al. |
| 5,260,293 A | 11/1993 | Baker et al. |

(Continued)

FOREIGN PATENT DOCUMENTS

| BE | 841390 | 11/1976 |
|---|---|---|
| CA | 1019323 | 10/1977 |

(Continued)

OTHER PUBLICATIONS

Jordan, V. C. Nature Reviews: Drug Discovery, 2, 2003, 205.*

(Continued)

*Primary Examiner* — Douglas M Willis

(57) ABSTRACT

The present invention relates to novel 6,7-dihydropyrazolo[1,5-a]pyrazin-4(5H)-one derivatives of formula (I)

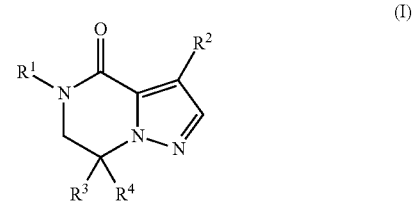

as negative allosteric modulators (NAMs) of the metabotropic glutamate receptor subtype 2 ("mGluR2") useful for the treatment of central nervous system disorders in which the mGluR2 subtype of metabotropic receptors is involved (e.g. mood disorder, schizophrenia, etc.). The invention is also directed to pharmaceutical compositions comprising such compounds, to processes for preparing such compounds and compositions, and to the use of such compounds and compositions for treatment of central nervous system disorders in which the mGluR2 subtype of metabotropic receptors is involved.

25 Claims, 7 Drawing Sheets

(56) References Cited

U.S. PATENT DOCUMENTS

| | | |
|---|---|---|
| 5,280,026 A | 1/1994 | Brown et al. |
| 5,332,750 A | 7/1994 | Mederski et al. |
| 5,356,911 A | 10/1994 | Muller-Gliemann et al. |
| 5,366,981 A | 11/1994 | Vecchietti et al. |
| 5,371,074 A | 12/1994 | Dunlap et al. |
| 5,374,513 A | 12/1994 | Ohzeki et al. |
| 5,378,720 A | 1/1995 | Hlasta et al. |
| 5,407,948 A | 4/1995 | Fey et al. |
| 5,418,243 A | 5/1995 | Angerbauer et al. |
| 5,424,435 A | 6/1995 | Hani et al. |
| 5,473,077 A | 12/1995 | Monn et al. |
| 5,498,774 A | 3/1996 | Mitsudera et al. |
| 5,500,420 A | 3/1996 | Maiese |
| 5,512,576 A | 4/1996 | Desai et al. |
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hoefgen et al. |
| 5,741,798 A | 4/1998 | Lazer et al. |
| 5,801,179 A | 9/1998 | Van Lommen et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van Lommen et al. |
| 6,103,475 A | 8/2000 | Burnett, Jr. et al. |
| 6,107,342 A | 8/2000 | Adam et al. |
| 6,110,920 A | 8/2000 | Rochus et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Tercero et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Bilodeau et al. |
| 6,472,392 B1 | 10/2002 | Starck et al. |
| 6,479,436 B1 | 11/2002 | Otten et al. |
| 6,498,180 B1 | 12/2002 | Collado Cano et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatierer et al. |
| 6,835,726 B2 | 12/2004 | Cushing et al. |
| 6,977,266 B2 | 12/2005 | Tada et al. |
| 7,393,549 B2 | 7/2008 | Ebinuma |
| 7,456,289 B2 | 11/2008 | Hsieh et al. |
| 7,572,807 B2 | 8/2009 | Li et al. |
| 7,579,360 B2 | 8/2009 | Li et al. |
| 7,700,593 B2 | 4/2010 | Chakrabarti et al. |
| 7,879,837 B2 | 2/2011 | Hayashi et al. |
| 7,960,563 B2 | 6/2011 | Johnson et al. |
| 7,977,325 B2 | 7/2011 | Schwede et al. |
| 8,252,937 B2 | 8/2012 | Cid-Nunez et al. |
| 8,299,101 B2 | 10/2012 | Cid-Nunez et al. |
| 8,399,493 B2 | 3/2013 | Bolea et al. |
| 8,937,060 B2 | 1/2015 | Cid-Nunez et al. |
| 9,012,448 B2 | 4/2015 | Cid-Nunez et al. |
| 2001/0011087 A1 | 8/2001 | Volkmar et al. |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | Defeo-Jones et al. |
| 2002/0137770 A1 | 9/2002 | Nara et al. |
| 2002/0147362 A1 | 10/2002 | Kozikowski et al. |
| 2002/0193367 A1 | 12/2002 | Adam et al. |
| 2002/0198197 A1 | 12/2002 | Adam et al. |
| 2003/0027807 A1 | 2/2003 | Volkmar et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazato et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado-Cano et al. |
| 2004/0106791 A1 | 6/2004 | Yoakim et al. |
| 2004/0116489 A1 | 6/2004 | Massey et al. |
| 2004/0127936 A1 | 7/2004 | Salahieh et al. |
| 2004/0132723 A1 | 7/2004 | Yoakim et al. |
| 2004/0138204 A1 | 7/2004 | Harrington, Jr. |
| 2004/0138238 A1 | 7/2004 | Dhanoa et al. |
| 2004/0167123 A1 | 8/2004 | Pratt et al. |
| 2004/0176385 A1 | 9/2004 | Nuss et al. |
| 2004/0204448 A1 | 10/2004 | Muller et al. |
| 2004/0220222 A1 | 11/2004 | Galley et al. |
| 2005/0004142 A1 | 1/2005 | Adams et al. |
| 2005/0026935 A1 | 2/2005 | Ford et al. |
| 2005/0054819 A1 | 3/2005 | Catalano et al. |
| 2005/0070538 A1 | 3/2005 | Cheng et al. |
| 2005/0107412 A1 | 5/2005 | Barber et al. |
| 2005/0113283 A1 | 5/2005 | Solow-Cordero et al. |
| 2005/0187227 A1 | 8/2005 | Himmelsbach et al. |
| 2005/0245530 A1 | 11/2005 | Borzilleri et al. |
| 2006/0083676 A1 | 4/2006 | Lesage et al. |
| 2006/0240501 A1 | 10/2006 | Ebinuma |
| 2007/0032469 A1 | 2/2007 | Isaac et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2008/0221179 A1 | 9/2008 | Gaul et al. |
| 2008/0286265 A1 | 11/2008 | Gaul et al. |
| 2008/0306077 A1 | 12/2008 | Clayton et al. |
| 2009/0031422 A1 | 1/2009 | Aaron et al. |
| 2009/0111855 A1 | 4/2009 | Gaul et al. |
| 2009/0124609 A1 | 5/2009 | Albrecht et al. |
| 2009/0124612 A1 | 5/2009 | Albrecht et al. |
| 2009/0203668 A1 | 8/2009 | Li et al. |
| 2009/0275751 A1 | 11/2009 | Nagato et al. |
| 2009/0318436 A1 | 12/2009 | Albrecht et al. |
| 2010/0063054 A1 | 3/2010 | Bressi et al. |
| 2010/0063092 A1 | 3/2010 | Cid-Nunez et al. |

(56) References Cited

U.S. PATENT DOCUMENTS

| | | |
|---|---|---|
| 2010/0087487 A1 | 4/2010 | Cid-Nunez et al. |
| 2010/0099715 A1 | 4/2010 | Cid-Nunez et al. |
| 2010/0166655 A1 | 7/2010 | Imogai et al. |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2010/0292241 A1 | 11/2010 | Brnardic et al. |
| 2011/0009441 A1 | 1/2011 | Trabanco-Suarez et al. |
| 2011/0245232 A1 | 10/2011 | Braje et al. |
| 2011/0245247 A1 | 10/2011 | Braje et al. |
| 2011/0275624 A1 | 11/2011 | Cid-Nunez et al. |
| 2011/0306642 A1 | 12/2011 | Cid-Nunez et al. |
| 2012/0035167 A1 | 2/2012 | Cid-Nunez et al. |
| 2012/0135977 A1 | 5/2012 | Beshore et al. |
| 2012/0184525 A1 | 7/2012 | Cid-Nunez et al. |
| 2012/0184527 A1 | 7/2012 | Cic-Nunez et al. |
| 2012/0184528 A1 | 7/2012 | Cic-Nunez et al. |
| 2012/0309793 A1 | 12/2012 | Duvey et al. |
| 2013/0109052 A1 | 5/2013 | Yan et al. |
| 2013/0150412 A1 | 6/2013 | Cid-Nunez et al. |
| 2013/0196992 A1 | 8/2013 | Cid-Nunez et al. |
| 2013/0197019 A1 | 8/2013 | Cid-Nunez et al. |
| 2013/0310555 A1 | 11/2013 | Chong |

FOREIGN PATENT DOCUMENTS

| | | |
|---|---|---|
| CA | 2035144 | 7/1991 |
| CA | 2390948 | 12/2000 |
| CN | 1842532 | 10/2006 |
| CN | 102002040 | 4/2011 |
| DE | 19507522 | 9/1996 |
| EP | 0082023 | 6/1983 |
| EP | 0154190 | 9/1985 |
| EP | 0292840 | 11/1988 |
| EP | 0308020 | 3/1989 |
| EP | 0365486 | 4/1990 |
| EP | 0373423 | 6/1990 |
| EP | 0379806 | 8/1990 |
| EP | 0430385 | 6/1991 |
| EP | 0441718 | 8/1991 |
| EP | 0447118 | 9/1991 |
| EP | 0447891 | 9/1991 |
| EP | 0478195 | 9/1991 |
| EP | 0452002 | 10/1991 |
| EP | 0482939 | 4/1992 |
| EP | 0530702 | 3/1993 |
| EP | 0542059 | 5/1993 |
| EP | 0547708 | 6/1993 |
| EP | 0548934 | 6/1993 |
| EP | 0557016 | 8/1993 |
| EP | 0612746 | 8/1994 |
| EP | 0626378 | 11/1994 |
| EP | 0728759 | 8/1996 |
| EP | 756200 | 1/1997 |
| EP | 0799826 | 10/1997 |
| EP | 0838458 | 4/1998 |
| EP | 0856255 | 8/1998 |
| EP | 0903343 | 3/1999 |
| EP | 0955301 | 11/1999 |
| EP | 1006112 | 6/2000 |
| EP | 1203766 | 5/2002 |
| EP | 1277726 | 1/2003 |
| EP | 1459765 | 9/2004 |
| EP | 1764099 | 3/2007 |
| EP | 1764367 | 3/2007 |
| EP | 2039687 | 3/2009 |
| EP | 2327704 | 6/2011 |
| EP | 2666775 | 11/2013 |
| GB | 1392849 | 4/1975 |
| GB | 1502312 | 3/1978 |
| JP | 50106981 | 8/1975 |
| JP | 53082783 | 7/1978 |
| JP | 57052334 | 11/1982 |
| JP | 6110557 | 1/1986 |
| JP | 02503317 | 10/1990 |
| JP | 2277044 | 11/1990 |
| JP | 5204071 | 8/1993 |
| JP | 2124871 | 5/1994 |
| JP | 6211797 | 8/1994 |
| JP | 6211798 | 8/1994 |
| JP | 7070018 | 3/1995 |
| JP | 7101861 | 4/1995 |
| JP | 10029979 | 2/1998 |
| JP | 10045750 | 2/1998 |
| JP | 2000/072731 | 3/2000 |
| JP | 2000/072751 | 3/2000 |
| JP | 2001/089367 | 4/2001 |
| JP | 2002/003401 | 1/2002 |
| JP | 2002/105085 | 4/2002 |
| JP | 2002/308882 | 10/2002 |
| JP | 2003/012653 | 1/2003 |
| JP | 2004/525192 | 8/2004 |
| JP | 2004/339080 | 12/2004 |
| JP | 2005/531501 | 10/2005 |
| JP | 2008/509714 | 4/2008 |
| JP | 2008/513414 | 5/2008 |
| RU | 1796625 | 2/1993 |
| RU | 2143433 | 12/1999 |
| SU | 509578 | 4/1976 |
| WO | WO 84/00544 | 2/1984 |
| WO | WO 84/00685 | 3/1984 |
| WO | WO 91/09848 | 7/1991 |
| WO | WO 92/18115 | 10/1992 |
| WO | WO 93/01195 | 1/1993 |
| WO | WO 93/15056 | 8/1993 |
| WO | WO 94/19315 | 9/1994 |
| WO | WO 95/04733 | 2/1995 |
| WO | WO 95/06032 | 3/1995 |
| WO | WO 95/11233 | 4/1995 |
| WO | WO 95/17397 | 6/1995 |
| WO | WO 95/24393 | 9/1995 |
| WO | WO 95/35293 | 12/1995 |
| WO | WO 96/05828 | 2/1996 |
| WO | WO 96/06167 | 2/1996 |
| WO | WO 96/15108 | 5/1996 |
| WO | WO 96/22021 | 7/1996 |
| WO | WO 96/33974 | 10/1996 |
| WO | WO 96/37481 | 11/1996 |
| WO | WO 96/41639 | 12/1996 |
| WO | WO 97/10229 | 3/1997 |
| WO | WO 97/10238 | 3/1997 |
| WO | WO 97/21701 | 6/1997 |
| WO | WO 97/46532 | 12/1997 |
| WO | WO 97/48724 | 12/1997 |
| WO | WO 98/06724 | 2/1998 |
| WO | WO 98/11075 | 3/1998 |
| WO | WO 98/17668 | 4/1998 |
| WO | WO 98/24780 | 6/1998 |
| WO | WO 98/32762 | 7/1998 |
| WO | WO 98/38168 | 9/1998 |
| WO | WO 98/50384 | 11/1998 |
| WO | WO 99/06041 | 2/1999 |
| WO | WO 99/11622 | 3/1999 |
| WO | WO 99/11628 | 3/1999 |
| WO | WO 99/11649 | 3/1999 |
| WO | WO 99/12532 | 3/1999 |
| WO | WO 99/16755 | 4/1999 |
| WO | WO 99/18096 | 4/1999 |
| WO | WO 99/21992 | 5/1999 |
| WO | WO 99/31062 | 6/1999 |
| WO | WO 99/31066 | 6/1999 |
| WO | WO 99/32448 | 7/1999 |
| WO | WO 99/33829 | 7/1999 |
| WO | WO 99/36072 | 7/1999 |
| WO | WO 99/52893 | 10/1999 |
| WO | WO 99/53956 | 10/1999 |
| WO | WO 99/62908 | 12/1999 |
| WO | WO 00/03990 | 1/2000 |
| WO | WO 00/12089 | 3/2000 |
| WO | WO 00/21934 | 4/2000 |
| WO | WO 00/34244 | 6/2000 |
| WO | WO 00/53605 | 9/2000 |
| WO | WO 00/61126 | 10/2000 |
| WO | WO 00/69816 | 11/2000 |

(56) References Cited

FOREIGN PATENT DOCUMENTS

| | | |
|---|---|---|
| WO | WO 00/73283 | 12/2000 |
| WO | WO 01/10846 | 2/2001 |
| WO | WO 01/29025 | 4/2001 |
| WO | WO 01/32632 | 5/2001 |
| WO | WO 01/32644 | 5/2001 |
| WO | WO 01/46190 | 6/2001 |
| WO | WO 01/53288 | 7/2001 |
| WO | WO 01/55132 | 8/2001 |
| WO | WO 01/56990 | 8/2001 |
| WO | WO 01/68097 | 9/2001 |
| WO | WO 01/70731 | 9/2001 |
| WO | WO 01/72712 | 10/2001 |
| WO | WO 01/83421 | 11/2001 |
| WO | WO 01/83431 | 11/2001 |
| WO | WO 01/83481 | 11/2001 |
| WO | WO 01/85716 | 11/2001 |
| WO | WO 01/96308 | 12/2001 |
| WO | WO 02/02568 | 1/2002 |
| WO | WO 02/10807 | 2/2002 |
| WO | WO 02/12236 | 2/2002 |
| WO | WO 02/14282 | 2/2002 |
| WO | WO 02/22598 | 3/2002 |
| WO | WO 02/28837 | 4/2002 |
| WO | WO 2002/096873 | 5/2002 |
| WO | WO 02/51849 | 7/2002 |
| WO | WO 02/074025 | 9/2002 |
| WO | WO 02/079498 | 10/2002 |
| WO | WO 02/090333 | 11/2002 |
| WO | WO 02/094264 | 11/2002 |
| WO | WO 02/096318 | 12/2002 |
| WO | WO 02/096363 | 12/2002 |
| WO | WO 02/098869 | 12/2002 |
| WO | WO 02/102807 | 12/2002 |
| WO | WO 03/011293 | 2/2003 |
| WO | WO 03/029209 | 4/2003 |
| WO | WO 03/035639 | 5/2003 |
| WO | WO 03/042989 | 5/2003 |
| WO | WO 03/044021 | 5/2003 |
| WO | WO 03/047577 | 6/2003 |
| WO | WO 03/051481 | 6/2003 |
| WO | WO 03/051842 | 6/2003 |
| WO | WO 03/055878 | 7/2003 |
| WO | WO 03/059871 | 7/2003 |
| WO | WO 03/059884 | 7/2003 |
| WO | WO 03/062392 | 7/2003 |
| WO | WO 03/064428 | 8/2003 |
| WO | WO 03/065994 | 8/2003 |
| WO | WO 03/068230 | 8/2003 |
| WO | WO 03/068750 | 8/2003 |
| WO | WO 03/070712 | 8/2003 |
| WO | WO 03/076405 | 9/2003 |
| WO | WO 03/082191 | 10/2003 |
| WO | WO 03/084610 | 10/2003 |
| WO | WO 03/092595 | 11/2003 |
| WO | WO 03/099808 | 12/2003 |
| WO | WO 03/104217 | 12/2003 |
| WO | WO 03/105846 | 12/2003 |
| WO | WO 04/000846 | 12/2003 |
| WO | WO 2004/004720 | 1/2004 |
| WO | WO 2004/011441 | 2/2004 |
| WO | WO 2004/014859 | 2/2004 |
| WO | WO 2004/014920 | 2/2004 |
| WO | WO 2004/017950 | 3/2004 |
| WO | WO 2004/018386 | 3/2004 |
| WO | WO 2004/019863 | 3/2004 |
| WO | WO 2004/021984 | 3/2004 |
| WO | WO 2004/024150 | 3/2004 |
| WO | WO 2004/029060 | 4/2004 |
| WO | WO 2004/031189 | 4/2004 |
| WO | WO 2004/041818 | 5/2004 |
| WO | WO 2004/043927 | 5/2004 |
| WO | WO 2004/054979 | 7/2004 |
| WO | WO 2004/065380 | 8/2004 |
| WO | WO 2004/067002 | 8/2004 |
| WO | WO 2004/072025 | 8/2004 |
| WO | WO 2004/076413 | 9/2004 |
| WO | WO 2004/078175 | 9/2004 |
| WO | WO 2004/078176 | 9/2004 |
| WO | WO 2004/080981 | 9/2004 |
| WO | WO 2004/024936 | 10/2004 |
| WO | WO 2004/092123 | 10/2004 |
| WO | WO 2004/092135 | 10/2004 |
| WO | WO 2005/002552 | 1/2005 |
| WO | WO 2005/002585 | 1/2005 |
| WO | WO 2005/007144 | 1/2005 |
| WO | WO 2005/021552 | 3/2005 |
| WO | WO 2005/028445 | 3/2005 |
| WO | WO 2005/040337 | 5/2005 |
| WO | WO 2005/061507 | 7/2005 |
| WO | WO 2005/080356 | 9/2005 |
| WO | WO 2005/097052 | 10/2005 |
| WO | WO 2005/100365 | 10/2005 |
| WO | WO 2005/123703 | 12/2005 |
| WO | WO 2006/012622 | 2/2006 |
| WO | WO 2006/014918 | 2/2006 |
| WO | WO 2006/015158 | 2/2006 |
| WO | WO 2006/015737 | 2/2006 |
| WO | WO 2006/018727 | 2/2006 |
| WO | WO 2006/020879 | 2/2006 |
| WO | WO 2006/029980 | 3/2006 |
| WO | WO 2006/030031 | 3/2006 |
| WO | WO 2006/030032 | 3/2006 |
| WO | WO 2006/030847 | 3/2006 |
| WO | WO 2006/047237 | 5/2006 |
| WO | WO 2006/050803 | 5/2006 |
| WO | WO 2006/057860 | 6/2006 |
| WO | WO 2006/057869 | 6/2006 |
| WO | WO 2006/071730 | 7/2006 |
| WO | WO 2006/074041 | 7/2006 |
| WO | WO 2006/091496 | 8/2006 |
| WO | WO 2006/099972 | 9/2006 |
| WO | WO 2006/109876 | 10/2006 |
| WO | WO 2006/137350 | 12/2006 |
| WO | WO 2007/021308 | 2/2007 |
| WO | WO 2007/021309 | 2/2007 |
| WO | WO 2007/027669 | 3/2007 |
| WO | WO 2007/031558 | 3/2007 |
| WO | WO 2007/039439 | 4/2007 |
| WO | WO 2007/059257 | 5/2007 |
| WO | WO 2007/078523 | 7/2007 |
| WO | WO 2007/084314 | 7/2007 |
| WO | WO 2007/095024 | 8/2007 |
| WO | WO 2007/103760 | 9/2007 |
| WO | WO 2007/104783 | 9/2007 |
| WO | WO 2007/113276 | 10/2007 |
| WO | WO 2007/122258 | 11/2007 |
| WO | WO 2007/135527 | 11/2007 |
| WO | WO 2007/135529 | 11/2007 |
| WO | WO 2008/001115 | 1/2008 |
| WO | WO 2008/006540 | 1/2008 |
| WO | WO 2008/008539 | 1/2008 |
| WO | WO 2008/012622 | 1/2008 |
| WO | WO 2008/012623 | 1/2008 |
| WO | WO 2008/032191 | 3/2008 |
| WO | WO 2008/045393 | 4/2008 |
| WO | WO 2008/051197 | 5/2008 |
| WO | WO 2008/057855 | 5/2008 |
| WO | WO 2008/076225 | 6/2008 |
| WO | WO 2008/078091 | 7/2008 |
| WO | WO 2008/078100 | 7/2008 |
| WO | WO 2008/100715 | 8/2008 |
| WO | WO 2008/107125 | 9/2008 |
| WO | WO 2008/107479 | 9/2008 |
| WO | WO 2008/107480 | 9/2008 |
| WO | WO 2008/107481 | 9/2008 |
| WO | WO 2008/112483 | 9/2008 |
| WO | WO 2008/124085 | 10/2008 |
| WO | WO 2008/130853 | 10/2008 |
| WO | WO 2008/141239 | 11/2008 |
| WO | WO 2008/145616 | 12/2008 |
| WO | WO 2008/150232 | 12/2008 |
| WO | WO 2008/150233 | 12/2008 |
| WO | WO 2009/004430 | 1/2009 |
| WO | WO 2009/033702 | 3/2009 |

(56) References Cited

FOREIGN PATENT DOCUMENTS

| | | |
|---|---|---|
| WO | WO 2009/033703 | 3/2009 |
| WO | WO 2009/033704 | 3/2009 |
| WO | WO 2009/041567 | 4/2009 |
| WO | WO 2009/045753 | 4/2009 |
| WO | WO 2009/062676 | 5/2009 |
| WO | WO 2009/091374 | 7/2009 |
| WO | WO 2009/094265 | 7/2009 |
| WO | WO 2009/095872 | 8/2009 |
| WO | WO 2009/110901 | 9/2009 |
| WO | 2009130232 A1 | 10/2009 |
| WO | WO 2009/118292 | 10/2009 |
| WO | WO 2009/124609 | 10/2009 |
| WO | WO 2009/140163 | 11/2009 |
| WO | WO 2009/140166 | 11/2009 |
| WO | WO 2009/148403 | 12/2009 |
| WO | WO 2010/009062 | 1/2010 |
| WO | WO 2010/022076 | 2/2010 |
| WO | WO 2010/022081 | 2/2010 |
| WO | WO 2010/025890 | 3/2010 |
| WO | WO 2010/043396 | 4/2010 |
| WO | WO 2010/060589 | 6/2010 |
| WO | WO 2010/063054 | 6/2010 |
| WO | WO 2010/089303 | 8/2010 |
| WO | WO 2010/114726 | 10/2010 |
| WO | WO 2010/117926 | 10/2010 |
| WO | WO 2010/130422 | 11/2010 |
| WO | WO 2010/130423 | 11/2010 |
| WO | WO 2010/130424 | 11/2010 |
| WO | WO 2010/141360 | 12/2010 |
| WO | WO 2011/022312 | 2/2011 |
| WO | WO 2011/034741 | 3/2011 |
| WO | WO 2011/034828 | 3/2011 |
| WO | WO 2011/034830 | 3/2011 |
| WO | WO 2011/034832 | 3/2011 |
| WO | WO 2011/051490 | 5/2011 |
| WO | WO 2011/109277 | 9/2011 |
| WO | WO 2011/116356 | 9/2011 |
| WO | WO 2011/136723 | 11/2011 |
| WO | WO 2011/137046 | 11/2011 |
| WO | WO 2011/156245 | 12/2011 |
| WO | WO 2012/021382 | 2/2012 |
| WO | WO 2012/035078 | 3/2012 |
| WO | WO 2012/062750 | 5/2012 |
| WO | WO 2012/062751 | 5/2012 |
| WO | WO 2012/062752 | 5/2012 |
| WO | WO 2012/062759 | 5/2012 |
| WO | WO 2012/083224 | 6/2012 |
| WO | WO 2012/143726 | 10/2012 |
| WO | WO 2012/151136 | 11/2012 |
| WO | WO 2012/151139 | 11/2012 |
| WO | WO 2012/151140 | 11/2012 |
| WO | WO 2013/012915 | 1/2013 |
| WO | WO 2013/012918 | 1/2013 |
| WO | WO 2013/066736 | 5/2013 |
| WO | WO 2013/154878 | 10/2013 |
| WO | WO 2013/156869 | 10/2013 |
| WO | WO 2013/174822 | 11/2013 |
| WO | WO 2013/192343 | 12/2013 |
| WO | WO 2013/192347 | 12/2013 |
| WO | WO 2013/192350 | 12/2013 |
| WO | WO 2014/064028 | 5/2014 |
| WO | WO 2014/195311 | 5/2014 |

OTHER PUBLICATIONS

Vippagunta, et al. Advanced Drug Delivery Reviews, 48, 2001, 18.*
Hackam, et al. JAMA, 296(14), 2006, 1731-1732.*
Alper, Richard H., Current Protocols in Pharmacology (1998) 2.6.1-2.6.10.
Bigotti et al., J. Fluorine Chem. 129, 2008, 767-774.
Cid et al. J. Med. Chem. 2012, 55, 8770-8789.
ClinicalTrials.gov Identifier NCT01457677, retrieved Feb. 19, 2014.
Dinklo et al., J. Pharmacol. Exp. Ther. 2011, 336(2), 560-574.
Embrechts et al. (2013) "Longitudinal characterization of the TauPS2APP mouse model of Alzheimer's disease in a two trial discrimination task of visuo-spatial recognition memory", 45$^{th}$ European Brain and Behaviour Society Meeting Sep. 6-9, 2013, Munich, Abstract p. 202.
Ferraguti & Shigemoto, Cell & Tissue Research, 326:483-504, 2006.
Gennaro et al. Remington's Pharmaceutical Sciences, 18$^{th}$ ed., Mack Publishing Company, 1990, Part 8: Pharmaceutical Preparations and Their Manufacture, pp. 1435-1712.
Gilfillan et al., Med Chem Commun, 2013, 4,1118-1123.
Goeldner et al, Neuropharmacology 64:337-346, 2013.
Higgins et al. Neuropharmacology, 2004, 46, 907-917.
Kelmendi et al, Primary Psychiatry 13:80-86, 2006.
Koike et al, Behavioural Brain Research 238:48-52, 2013.
Li et al., Org. Lett. 2014, 16, 5370-5373.
Niswender & Conn, Annual Review of Pharmacology & Toxicology 50:295-322, 2010.
Schaffhauser et al., Molecular Pharmacology, 2003, 4:798-810.
Shigemoto et al., The Journal of Neuroscience, Oct. 1, 1997, 17(19), 7503-7522.
International Search Report for PCT/EP2014/061478 dated May 8, 2014.
Kent et al. "Efficacy and Safety of a Novel mGlu2 Receptor Positive Allosteric Modulator as an Adjunctive Treatment to an SSRI/SNRI in the Treatment of Anxious Depression" Abstract to poster and oral presentation, American Society of Clinical Psychopharmacology (ASCP) 2014 Annual Meeting, Jun. 16-19, 2014 Westin Diplomat, Hollywood, Florida).
Salih et al. "Pharmacokinetic and pharmacodynamics characterization of JNJ-40411813, a positive allosteric modulator of mGluR2, in two randomized, double-blind phase-I studies" Journal of Psychopharmacology, 2015, vol. 29(4) 414-425.
Australian Patent Application No. 2005/284098: Office Action dated Oct. 11, 2010, 2 pages.
Australian Patent Application No. 2007/224431: Office Action dated Mar. 19, 2010, 6 pages.
Australian Patent Application No. 2008/223795: Office Action dated May 29, 2012, 2 pages.
Australian Patent Application No. 2008/223796: Examiner's Report dated Nov. 3, 2010, 2 pages.
Australian Patent Application No. 2008/297877: Examiner's Report dated Oct. 31, 2012, 3 pages.
Canadian Patent Application No. 2,581,144: Office Action dated Apr. 23, 2010, 2 pages.
Chilean Patent Application No. 2745-2008: Office Action dated Apr. 15, 2011, 2 pages.
Chilean Patent Application No. 671-2008: Office Action dated Oct. 29, 2010, 9 pages.
Chilean Patent Application No. 681-2007: Office Action dated Jan. 11, 2011, 6 pages.
Chinese Patent Application No. 200780009210.5: Office Action dated Jun. 19, 2012, 4 pages.
Chinese Patent Application No. 200880107135.0: Office Action dated Jul. 4, 2012, 4 pages.
Eurasian Patent Application No. 200801934/28: Office Action dated May 13, 2010, 4 pages.
Eurasian Patent Application No. 200901162/28: Office Action dated Apr. 18, 2011, 7 pages.
Eurasian Patent Organization : Euraisian Notification "On the Necessity to Present Additional Matters", dated Dec. 17, 2008, 3 pages.
European Patent Application No. EP 08166832: Search Report dated May 8, 2009, 5 pages.
Fell et al., "Activation of Metabotropic Glutamate (Mglu)2 Receptors Suppresses Histamine Release in Limbic Brain Regions Following Acute Ketamine Challenge", Neuropharmacology, 2010, 58, 632-639.
Israeli Patent Application No. 192868:, Office Action dated Dec. 21, 2011, 2 pages.
Itaya et al., "Purines. LXXV. Dimroth Rearrangement, Hydrolytic Deamination, and Pyrimidine-Ring Breakdown of 7-Alkylated

(56) References Cited

OTHER PUBLICATIONS

1-Alkoxyadenines: N(1)-C(2) Versus N(1)-C(6) Bond Fission", Chem. Pharm. Bull., 1997, 45 (5), 832-41.
Japanese Patent Application No. 2008-558820: Office Action dated Aug. 28, 2012, 14 pages.
Japanese Patent Application No. 2009-552215: Office Action dated Dec. 18, 2012, 3 pages.
Japanese Patent Application No. 2010-524405: Office Action dated Jun. 5, 2012, 4 pages.
Kenakin, "Collateral Efficacy in Drug Discovery: Taking Advantage of the Good (Allosteric) Nature of 7tm Receptors", Trends Pharmacol. Sci., 2007, 28(8), 407-415.
Lourenco et al., "Differential Distribution of Metabotropic Glutamate Receptor Subtype MRNAS in the Thalamus of the Rat", Brain Research, 2000, 854(1-2), 93-105.
Malatynska et al., "Submissive Behavior in Mice as a Test for Antidepressant Drug Activity", Pharmacol Biochem Behavior, 2005, 82, 306-313.
Marino et al., "Glutamate-Based Therapeutic Approaches: Allosteric Modulators of Metabotropic Glutamate Receptors", Current Opinion in Pharmacology, 2006, 6, 98-102.
McElroy, "A 52-Week, Open-Label Continuation Study of Lamotrigine in the Treatment of Bipolar Depression", J. Clin. Psychiatry, 2004, 204-210.
Mexican Patent Application No. MX/a/2009/009422: Office Action dated Jun. 28, 2011, 5 pages.
Redondo et al., "Selective Heteronuclear Noe Enhancements in Benzoheterocycles. Effect of Ring Size on Indirect Three-Spin Effects", Magnetic Resonance in Chemistry, 1988, 26, 511-517.
Ribeiro et al., "Metabotropic Glutamate Receptor-Mediated Cell Signaling Pathways are Altered in a Mouse Model of Huntington's Disease", Journal of Neuroscience, 2010, 30(1), 316-324.
Rickels et al., "Long-Term Diazepam Therapy and Clinical Outcome", Jama, 1983, 250, 767-771.
Ried et al., "Reactions with Cyclobutenediones, Ix. 3-Hydroxy-Pyridones-(2) From Phenylcyclobutenedione and Enamines", Liebigs Ann. Chem., 1969, 725, 230-233.
Riederer et al., "Pharmacotoxic Psychosis After Memantine in Parkinson's Disease", Lancet, 1991, 338, 1022-1023.
Roberts et al., "Pharmacological Tools for the Investigation of Metabotropic Glutamate Receptors (Mglurs): Phenylglycine Derivatives and Other Selective Antagonists—An Update", Neuropharmacology, 1995, 34(8), 813-819.
Rudd et al., "Positive Allosteric Modulators of the Metabotropic Glutamate Receptor Subtype 2 (Mglur2)", Current Topics in Medicinal Chemistry, 2005, 5, 869-884.
Rush et al., "The Inventory for Depressive Symptomatology (Ids): Preliminary Findings", Psychiatry Res, May 1986, 18(1), 65-87.
Rush et al., "The Inventory of Depressive Symptomatology (Ids)—Preliminary Findings", Psychopharmacology Bulletin, 1986, 22(3), 985-990.
Rush et al., "The Inventory of Depressive Symptomatology (Ids): Psychometric Properties", Psychol Med, May 1996, 26(3), 477-486.
Sahni et al., "Compound A, A Novel, Potent and Selective Metabotropic Glutamate Receptor 2 (Mglur2) Positive Allosteric Modulator: I. Pharmacological Characterization" Poster 767.6 Presented at the 40th Annual Meeting of Society for Neuroscience, Nov. 2010, 1 page.
Sakamoto et al., "Condensed Heteroaromatic Ring Systems. VIII. Synthesis 3-Substituted Isocournarins from O-Halobenzoic Acid Derivatives", Chem. Pharm. Bull., 1986, 34(7), 2754-2759.
Salinska et al., "Metabotropic Glutamate Receptors (Mglurs) are Involved in Early Phase of Memory Formation: Possible Role of Modulation of Glutamate Release", Neurochemistry Intl, 2003, 43, 469-474.
Santi et al., "Temporal and Depolarization-Induced Changes in the Absolute Amounts of Mrnas Encoding Metabotropic Glutamate Receptors in Cerebellar Granule Neurons in Vitro", Journal of Neurochemistry, 1994, 63(4), 1207-1217.

Sareen et al., "Anxiety Disorders and Risk for Suicidal Ideation and Suicide Attempts", Arch Gen Psychiatry, 2005, 62, 1249-1257.
Sarter et al., "Cortical Cholinergic Transmission and Cortical Information Processing in Schizophrenia", Schizophr. Bull, 2005, 31(1), 117-138.
Saugstad et al., "Cloning and Expression of a New Member of the L-2-Amino-4-Phosphonobutyric Acid-Sensitive Class of Metabotropic Glutamate Receptors", Mol Pharmacol, 1994, 45, 367-372.
Saugstad et al., "Metabotropic Glutamate Receptors Activate G-Protein-Coupled Inwardly Rectifying Potassium Channels in Xenopus Oocytes", J. Neurosci., 1996, 16(19), 5979-5985.
Schaffhauser et al., "Pharmacological Characterization of Metabotropic Glutamate Receptors Linked to the Inhibition of Adenylate Cyclase Activity in Rat Striatal Slices", Neuropharmacology, 1997, 36(7), 933-940.
Scheer et al., "Constitutively Active G Protein-Coupled Receptors: Potential Mechanisms of Receptor Activation", Journal of Receptor & Signal Transduction Research, 1997, 17(1-3), 57-73.
Schoepp et al., "Ly354740 is a Potent and Highly Selective Group II Metabotropic Glutamate Receptbr Agonist in Cells Expressing Human Glutamate Receptors", Neuropharmacology, 1997, 36, 1-11.
Seeman et al., "Dopamine Partial Agonist Actions of the Glutamate Receptor Agonists Ly354740 and Ly379268", Synapse, 2008, 62, 154-158.
Seeman, "Glutamate and Dopamine Components in Schizophrenia", J Psychiatry Neurosci., 2009, 34(2), 143-149.
Seneca, "Recent Advances in Positron Emission Tomography Imaging of Brain", Drugs of the Future, 2011, 36, 601-613.
Shear et al., "Multicenter Collaborative Panic Disorder Severity Scale", Am J Psychiatry, Nov. 1997, 154(11), 1571-1575.
Shekhar, "Gaba Receptors in the Region of the Dorsomedial Hypothalamus of Rats Regulate Anxiety in the Elevated Plus-Maze Test. I. Behavioral Measures", Brain Research, 1993, 627(1), 9-16.
Shih et al., "Protein Kinase C Deficiency Blocks Recovery From Agonist-Induced Desensitization", J. Biol. Chem., 1996, 271(35), 21478-21483.
Shipe et al., "Recent Advances in Positive Allosteric Modulators of Metabotropic Glutamate Receptors", Current Opiniori in Drug Discovery & Development, 2005, 8(4), 449-457.
SIPO Office Action dated Jun. 30, 2010, 12 pages.
Skerry et al., "Glutamate Signalling in Non-Neuronal Tissues", Trends Pharmacol. Sci., 2001, 22(4), 174-181.
Sodhi et al., "Role of Glutamate in Schizophrenia: Integrating Excitatory Avenues of Research", Expert Rev Neurother, 2008, 8(9), 1389-1406.
Sokoloff et al., "The [14c]Deoxyglucose Method for the Measurement of Local Cerebral Glucose Utilization: Theory, Procedure, and Normal Values in the Conscious and Anesthetized Albino Rat", J Neurochem, 1977, 28, 897-916.
Sortino et al., "Immortalized Hypothalamic Neurons Express Metabotropic Glutamate Receptors Positively Coupled to Cyclic Amp Formation", Eur. J Neurosci., 1996, 8(11), 2407-2415.
Souery et al., ."Group for the Study of Resistant Depression. Clinical Factors Associated with Treatment Resistance in Major Depressive Disorder: Results From a European Multicenter Study", J. Clin. Psychiatry, Jul. 2007, 68(7), 1062-1070.
South Korean Patent Application No. 2010-053694958: Office Action dated Nov. 25, 2010, 9 pages.
Star*D Research Methods Section (2001), Available from Http://Www.Edc.Gsph.Pitt.Edu/Stard/Public/Protocol/Star-D%20III%20research%20design%20methods.Pdf, 2001, 50 pages.
Steckler et al., "Chapter 7—Neuroimaging as a Translational Tool in Animal and Human Models of Schizophrenia", Translational Neuroimaging, 2013, 195-220.
Steru et al., "The Automated Tail Suspension Test: A Computerized Device Which Differentiates Psychotropic Drugs", Prog. Neuropsychopharmacol. Exp. Psychiatry, 1987, 11, 659-671.
Stone, "Imaging the Glutamate System in Humans: Relevance to Drug Discovery for Schizophrenia", Curr. Pharm. Des, 2009, 15(22), 2594-2602.
Stowell et al., "Axon/Dendrite Targeting of Metabotropic Glutamate Receptors by Their Cytoplasmic Carboxy-Terminal Domains", Neuron, 1999, 22(3), 525-536.

(56) References Cited

OTHER PUBLICATIONS

Structures, "Chemical Abstracts", May 2009. 23 pages.
Sun et al., "Mechanism of Glutamate Receptor Desensitization", Nature, 2002, 417, 245-253.
Suzuki et al., "Synthesis of the Selective 5-Hydroxytryptamine 4 (5-Ht4) Receptor Agonist (+)-(S)-2-Chloro-5-Methoxy-4-[5-(2-Piperidylmethyl)-1,2,4-Oxadiazol-3-Yl]Aniline", Chem. Pharm. Bull., 1999, 47(1), 120-122.
Svensson et al., "Ly2607540 (THLLC), A Novel Mglu2 Receptor Potentiator with Potential Anxiolytic/Antidepressant Properties: in Vivo Profiling Suggests a Link Between Behavioral and CNS Neurochemical Changes" Poster 642.4, 40$^{th}$ Annual Meeting of Society for Neuroscience, Nov. 2010, 1 page.
Swerdlow et al., "Assessing the Validity of an Animal Model of Deficient Sensorimotor Gating in Schizophrenic Patients", Arch. Gen. Psychiatry, 1994, 51, 139-154.
Taiwanese Patent Application No. 094132375: Office Action dated Aug. 25, 2011, 10 pages.
Taiwanese Patent Application No. 096108666: Office Action, dated 2007, 3 pages.
Testa et al., "Immunohistochemical Localization of Metabotropic Glutamate Receptors Mglur1a and Mglur2/3 in the Rat Basal Ganglia", Journal of Comparative Neurology, 1998, 390(1), 5-19.
Thase et al., "Remission Rates Following Antidepressant Therapy with Bupropion or Selective Serotonin Reuptake Inhibitors: A Meta-Analysis of Original Data From 7 Randomized Controlled Trials", J Clin Psychiatry, 2005, 66(8), 974-981.
Trabanco et al., "Discovery of 5- and 6-Substituted Isoquinolones: A New Class of Positive Allosteric Modulators of the Metabotropic Glutamate 2 Receptor", XXI'ST International Symposium on Medicinal Chemistry, Sep. 2010, 1 page.
Van Der Linden et al., "In Vitro Chracterization of the Binding of the Mglu2 Receptor Positive Allosteric Modulator [3h]Jnj-40068782 to Native and Recombinant Mglu2 Receptors", 7$^{th}$ Int. Meeting on Metabotropic Glutamate Receptors 2011', 1 page.
Vogel et al., "Evidence for REM Sleep Deprivation as the Mechanism of Action of Antidepressant Drugs", Prog Neuropsychopharmacol Biol Psychiatry, 1983, 7(2-3), 343-349.
West, "Solid State Chemistry and its Applications", Wiley, 1988, 2 pages.
Wittchen et al., "The Size and Burden of Mental Disorders and Other Disorders of the Brain in Europe 2010", European Neuropsychopharmacology, 2011, 21, 655-679.
Zarate, "A Randomized Trial of an N-Methyl-D-Aspartate Antagonist in Treatment-Resistant Major Depression," Arch. Gen. Psychiatry, Aug. 2006, 63(8), 856-864.
Abi-Saab et al., "The NMDA Antagonist Model for Schizophrenia: Promise and Pitfalls", Pharmacopschiatry, 31, 1998, 104-109.
Abshire et al., "Injection of L-Allylglycine Into the Posterior Hypothalamus in Rats Causes Decreases in Local GABA Which Correlate with Increases in Heart Rate", Neuropharmacology, 1988, 27(11), 1171-1177.
Adam, "Symptomatic Treatment of Huntington Disease", Neurotherapeutics: the Journal of the American Society for Experimental Neurotherapeutics, Apr. 2008, 5, 181-197.
Adams et al., "Effect of Clozapine, Haloperidol, or M100907 on Phencyclidine-Activated Glutamate Efflux in the Prefrontal Cortex", Biol. Psychiatry 2001, 50(10), 750-757.
Adams, "A Long-Term, Phase 2, Multicenter, Randomized, Open-Label, Comparative Safety Study of Pomaglumetad Methionil (LY2140023 Monohydrate) Versus Atypical Antipsychotic Standard of Care in Patients with Schizophrenia", BMC Psychiatry 2013, 13(143), 1-9.
Addex Partner Completes ADX71149 Phase I Program, Press release Aug. 25, 2010, http://www.addextherapeutics.com/investors/press-releases/news-details/?tx_ttnews%5Btt_news%5D%20=103&cHash=91fade38b1d3dc85979989357b1a9281, retrieved on Aug. 22, 2013.
Addex Partner Doses First Patient in Phase 2 Clinical Study of ADX71149 for the Treatment of Major Depressive Disorder Patients with Anxiety Symptoms, Press Release Sep. 17, 2012, http://www.addextherapeutics.com/investors/press-releases/news-details/?tx_ttnews%5Btt_news%5D%20=214&cHash=12a9cc5ffefdb63c27d5b87a673f74eb, retrieved on Aug. 22, 2013.
Addex Partner to Initiate Phase 2 Clinical Trial of ADX71149 for the Treatment of Major Depressive Disorder with Anxiety Symptoms, Press Release Jun. 5, 2012 http://www.addextherapeutics.com/investors/press-releases/news-details/?tx_ttnews%5Btt_news%5D%20=204&cHash=1865c3b31d0b9042f84c017bb2b5f32c, retrieved on Aug. 22, 2013.
Addex Reports Top-line Data from a Successful Phase 2a Clinical Study with ADX71149 in Schizophrenia Patients, Press Release Nov. 5, 2012, http://www.addextherapeutics.com/investors/press-releases/news-details/?tx_ttnews%5Btt_news%5D%20=225&cHash=9e5e13cb042971e6135f8ac786ce7453 retrieved on Aug. 22, 2013.
Addington et al., "A depression rating scale for schizophrenics", Schizophr Res. 1990, 3(4), 247-251.
Ader et al., "Effects of Chlorpromazine on the Acquisition and Extinction of an Avoidance Response in the Rat", J. Pharmacol. Exp. Ther., 1957, 131, 144-148.
Agami et al., "An Efficient Synthesis of Polysubstituted 3-Halo-2(1H)-Pyridinones." Synthesis, 2002, 79-82.
Agari et al., "Intrapallidal Metabotropic Glutamate Receptor Activation in a Rat Model of Parkinson's Disease: Behavioral and Histological Analyses", Brain Res., 2008, 1203, 189-196.
Aghajanian et al., "Serotonin model of schizophrenia: Emerging role of glutamate Mechanisms", Brain Research Reviews, 2000, 31, 302-312.
Aghajanian, "Modeling 'Psychosis' in Vitro by Inducing Disordered Neuronal Network Activity in Cortical Brain Slices", Psychopharmacology 2009, 206(4), 575-585.
Agid et al., "How Can Drug Discovery for Psychiatric Disorders Be Improved?" Nature Reviews Drug Discovery, 2007, 6, 189-201.
Ago et al., "Activation of Metabotropic Glutamate 2/3 Receptors Attenuates Methamphetamine-Induced Hyperlocomotion and Increase in Prefrontal Serotonergic Neurotransmission", Psychopharmacology, 2011, 217, 443-452.
Ahnaou et al., "Modulation of Group II Metabotropic Glutamate Receptor (Mglu2) Elicits Common Changes in Rat and Mice Sleep-Wake Architecture", European Journal of Pharmacology, 2009, 603, 62-72.
Ainslie et al., "Practical Drug Evaluation Method", Arch Gen Psychiat, 1965, 12, 368-373.
Alagarsamy et al., "Coordinate Regulation of Metabotropic Glutamate Receptors", Current Opinion in Neurobiology, 2001, 11(3), 357-362.
Albasanz et al., "Internalization of Metabotropic Glutamate Receptor in C6 Cells Through Clathrin-Coated Vesicles", Molecular Brain Research, 2002, 99, 54-66.
Alderson et al., "Purification and Characterization of a Soluble Cyclic Nucleotide-Independent Ca2+-Calmodulin-Sensitive Protein Kinase from Rat Brain", J. Neurochem., 1986, 46, 594-603.
Aleppo et al., "Metabotropic Glutamate Receptors and Neuronal Toxicity", Advances in Experimental Medicine & Biology, 1992, 318, 137-145.
Alexander et al., "Metabotropic Glutamate Receptors as a Strategic Target for the Treatment of Epilepsy", Epilepsy Res., 2006, 71(1), 1-22.
Allen et al., "Group II Metabotropic Glutamate Receptor Activation Attenuates Traumatic Neuronal Injury and Improves Neurological Recovery After Traumatic Brain Injury", J Pharmacol. Exp. Ther., 1999, 290(1), 112-120.
Alley et al., "Memantine Lowers Amyloid-Beta Peptide Levels in Neuronal Cultures and in APP/PS1 Transgenic Mice", J Neurosci Res, 2010, 88, 143-154.
Al-Omran et al., "Studies with Polyfunctionally Substituted Heteroaromatics: New Routes for the Synthesis of Polyfunctionally Substituted Pyridines and 1,2,4-Triazolo[1,5-a]pyridines", Heteratom. Chemistry, 1995, 6(6), 545-551.
Alper, "Agonist-Stimulated [35s]Gtpys Binding", Current Protocols in Pharmacology, 1998, 1-10.

(56) References Cited

OTHER PUBLICATIONS

Al-Shamma et al., "Nelotanserin, a Novel Selective Human 5-Hydroxytryptamine2a Inverse Agonist for the Treatment of Insomnia", J Pharmacol Exp Ther, 2010, 332, 281-290.

Altamura et al., "Designing Outcome Studies to Determine Efficacy and Safety of Antipsychotics for 'Real World' Treatment of Schizophrenia", Int J Neuropsychopharmacol, 2010;13(7):971-973.

Altamura et al., "Plasma and Platelet Exctitatory Amino Acids in Psychiatric Disorders", Am J Psychiatry, 1993, 150(11), 1731-1733.

Altamura et al., "Plasma Concentrations of Excitatory Amino Acids Serine, Glycine, Taurine and Histidine in Major Depression", Eur Neuropsychopharmacol, 1995; 5(Suppl), 71-75.

Amiri et al., "A Role for Leu118 of Loop E in Agonist Binding to the α7 Nicotinic Acetylcholine Receptor" Mol Pharmacol, 2008, 73, 1659-1667.

Amitai et al., "Effects of Metabotropic Glutamate Receptor 2/3 Agonism and Antagonism on Schizophrenia-Like Cognitive Deficits Induced by Phencyclidine in Rats", European Journal of Pharmacology, 2010, 639, 67-80.

Andreescu et al., "Comorbid Anxiety and Depression: Bête Noire or Quick Fix?", British Journal of Psychiatry 2012, 200:179-181.

Andreescu et al., "Effect of Comorbid Anxiety on Treatment Response and Relapse Risk in Late-Life Depression: Controlled Study", the British Journal of Psychiatry, 2007, 190, 344-349.

Andreescu et al., "The Default Mode Network in Late-Life Anxious Depression", Am J Geriatr Psychiatry, Nov. 2011, 19(11), 5 pages.

Andres et al., "2-(Dimethylaminomethyl)-Tetrahydroisoxazolopyridobenzazepine Derivatives. Synthesis of a New 5-HT2C Antagonist with Potential Anxiolytic Properties", Bioorganic & Medicinal Chemistry Letters, 2002, 12, 3573-3577.

Andres et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8699.

Angenstein et al., "Activation of Metabotropic Glutamate Receptors Increases Endogenous Protein Kinase C Substrate Phosphorylation in Adult Hippocampal Slices", Brain Research, 1997, 745(1-2), 46-54.

Angers et al., "Dimerization: An Emerging Concept for G Protein-Coupled Receptor Ontogeny and Function", Annu. Rev. Pharmacol. Toxicol., 2002, 42, 409-435.

Antuono, "Decreased Glutamate 1 Glutamine in Alzheimer's Disease Detected in Vivo with 1H-MRS at 0.5 T", Neurology, 2001, 56:737-742.

Anwyl "Metabotropic Glutamate Receptor-Dependent Long-Term Potentiation", Neuropharmacology, 2009, 56, 735-740.

Anwyl "Metabotropic Glutamate Receptors: Electrophysiological Properties and Role in Plasticity", Brain Res. Brain Res., 1999, 29, 83-120.

Aparicio-Legarza et al., "Deficits of [3h]D-Aspartate Binding to Glutamate Uptake Sites in Striatal and Accumbens Tissue in Patients with Schizophrenia", Neuroscience Letters, 1997, 232(1), 13-16.

Aparicio-Legarza et al., "Increased Density of Glutamate/N-Methyl-D-Aspartate Receptors in Putamen From Schizophrenic Patients", Neuroscience Letters, 1998, 241(2-3), 143-146.

Armstrong et al., "Characterization of Competitive Inhibitors for the Transferase Activity of Pseudomonas Aeruginosa Exotoxin A", Journal of Enzyme Inhibition and Medicinal Chemistry, 2002, 17(4), 235-246.

Arnt, "Differential Effects of Classical and Newer Antipsychotics on the Hypermotility Induced by Two Dose Levels of D-Amphetamine", European Journal of Pharmacology, 1995, 283, 55-62.

Arnt, "Pharmacological Specificity of Conditioned Avoidance Response Inhibition in Rats: Inhibition by Neuroleptics and Correlation to Dopamine Receptor Blockade", Acta Pharmacol. Toxicol., 1982, 51, 321-329.

Aronica et al., "Metabotropic Glutamate Receptors in Cultured Cerebellar Granule Cells: Developmental Profile", Journal of Neurochemistry, 1993, 60(2), 559-565.

Aronica et al., "Pharmacological Characterization of Metabotropic Glutamate Receptors in Cultured Cerebellar Granule Cells", Neurochemical Research, 1993, 18(5), 605-612.

Aronica et al., "Status Epilepticus-Induced Alterations in Metabotropic Glutamate Receptor Expression in Young and Adult Rats", J. Neurosci., 1997, 17(21), 8588-8595.

Aronson et al., "Triiodothyronine Augmentation in the Treatment of Refractory Depression. A Meta-Analysis", Arch Gen Psychiatry, 1996, 53, 842-848.

Arriza et al., "Functional Comparisons of Three Glutamate Transporter Subtypes Cloned From Human Motor Cortex", J. Neurosci., 1994, 14(9), 5559-5569.

Arundine, "Molecular Mechanisms of Glutamate-Dependent Neurodegeneration in Ischemia and Traumatic Brain Injury", Cellular and Molecular Life Sciences, 2004, 61, 657-668.

Atlante, "Glutamate Neurotoxicity, Oxidative Stress and Mitochondria", Febs Letters 497, 2001, 1-5.

Attwell et al., "Anticonvulsant and Glutamate Release-Inhibiting Properties of the Highly Potent Metabotropic Glutamate Receptor Agonist (2s,2'r, 3'r)-2-(2',3'-Dicarboxycyclopropyl)Glycine (Dcg-Iv)", Brain Res., 1998, 805(1-2), 138-143.

Auer et al., "Reduced Glutamate in the Anterior Cingulate Cortex in Depression: An in Vivo Proton Magnetic Resonance Spectroscopy Study", Biol Psychiatry, 2000, 47(4), 305-313.

Auerbach et al., "Mutations Causing Syndromic Autism Define an Axis of Synaptic Pathophysiology", Nature, 2011, 480, 63-68.

Aultman et al., "Distinct Contributions of Glutamate and Dopamine Receptors to Temporal Aspects of Rodent Working Memory Using a Clinically Relevant Task", Psychopharmacology (Berl), 2001, 153(3), 353-364.

Austin et al., "Symptomatic and Neuroprotective Effects Following Activation of Nigral Group III Metabotropic Glutamate Receptors in Rodent Models of Parkinson's Disease", British Journal of Pharmacology, 2010, 160, 1741-1753.

Awouters et al., "Astemizole: Effects on General Behavior and Interactions with the Central Nervous System", Jap. Pharmacol. & Therapeutics, 1991, 19, 73-89.

Ayalew et al., "Convergent Functional Genomics of Schizophrenia: From Comprehensive Understanding to Genetic Risk Prediction", Molecular Psychiatry 2012, 1-19.

Ayan-Oshodi et al., "Adverse Events in Healthy Subjects Exposed to Single and Multiple Doses of Ly2140023 Monohydrate", J Clin Psychopharmacol, 2012, 32, 408-411.

Azimov et al., "Chemical Abstracts", Abstract No. 78798, 1986, 105(10), 1 page.

Azuma et al., "Synthesis and Reactions of 4-Chloro-1, 2-Dihydro-6-Methyl-2-Oxo-3-Pyridinecarbonitrile", Heterocycles, 2003, 60(6), 1461-1468.

Backstrom, "Suppression of Alcohol Self-Administration and Cue-Induced Reinstatement of Alcohol Seeking by the Mglu2/3 Receptor Agonist Ly379268 and the Mglu8 Receptor Agonist (S)-3,4-Dcpg", Eur. J. Pharmacol., 2005, 528, 110-118.

Badawy et al., "Epilepsy: Ever-Changing States of Cortical Excitability" Neuroscience, 2012, 22, 89-99.

Baffa et al., "Norepinephrine and Serotonin Transporter Genes: Impact on Treatment Response in Depression", Neuropsychobiology, 2010, 62, 121-131.

Bagby et al., "Psychosocial and Clinical Predictors of Response to Pharmacotherapy for Depression" J Psychiatry Neurosci, 2002, 27(4), 250-7.

Bakker et al., "Activation of the Metabotropic Glutamate Receptor 2 (Mglu2) by Orthosteric and Allosteric Ligands", Poster 642.6/E30 Presented at the 40th Annual Meeting of Society for Neuroscience 2010, 1 page.

Bakker et al., "Reduction of Hippocampal Hyperactivity Improves Cognition in Amnestic Mild Cognitive Impairment", Neuron, 2012, 74(3), 467-474.

Balastrieri et al., "Assessing Mixed Anxiety-Depressive Disorder. A National Primary Care Survey", Psychiatry Research, 2010, 176, 197-201.

Balazs et al., "Metabotropic Glutamate Receptor Agonists Potentiate Cyclic Amp Formation Induced by Forskolin or Beta-

(56) References Cited

OTHER PUBLICATIONS

Adrenergic Receptor Activation in Cerebral Cortical Astrocytes in Culture", Journal of Neurochemistry, 1998, 70(6), 2446-2458.
Bandelow et al., "Adjunct Quetiapine XR in Patients with Major Depressive Disorder: A Pooled Analysis of Data From Patients with Anxious Depression", Abstracts of the 19th European Congress of Psychiatry, Mar. 2011, 1 page.
Barda et al., "Sar Study of a Subtype Selective Allosteric Potentiator of Metabotropic Glutamate 2 Receptor, N-(4-Phenoxyphenyl)-N-(3-Pyridinylmethyl)Ethanesulfonamide", Bioorganic & Medicinal Chemistry Letters, 2004, 14, 3099-3102.
Barker et al., "A Temporally Distinct Role for Group I and Group II Metabotropic Glutamate Receptors in Object Recognition Memory", Learn. Mem., 2006, 13(2), 178-186.
Barnes et al., "A Review of Central 5-Ht Receptors and their Function", Neuropharmacology, 1999, 38, 1083-1152.
Bar-Peled et al., "Distribution of Glutamate Transporter Subtypes During Human Brain Development", J Neurochem., 1997, 69(6), 2571-2580.
Barrett, "Mglur2-Positive Allosteric Modulators: Therapeutic Potential for Treating Cocaine Abuse?", Neuropsychopharmacology, 2010, 35, 2007-2008.
Bartha et al., "Measurement of Glutamate and Glutamine in the Medial Prefrontal Cortex of Never-Treated Schizophrenic Patients and Healthy Controls by Proton Magnetic Resonance Spectroscopy", Archives of General Psychiatry, 1997, 54(10), 959-965.
Barton et al., "Comparison of the Effect of Glutamate Receptor Modulators in the 6 Hz and Maximal Electroshock Seizure Models", Epilepsy Research, 2003, 56, 17-26.
Basan et al., "Valproate for Schizophrenia", Cochrane Collaboration, Cochrane Database Syst Rev., 2008, 2, 38 pages.
Batchelor et al., "Novel Synaptic Potentials in Cerebellar Purkinje Cells: Probable Mediation by Metabotropic Glutamate Receptors", Neuropharmacology, 1993, 32(1), 11-20.
Battaglia et al., "Selective Activation of Group-II Metabotropic Glutamate Receptors Is Protective Against Excitotoxic Neuronal Death," European Journal of Pharmacology, 1998, 356(2-3), 271-274.
Bauer et al., "Extended Release Quetiapine as Adjunct to an Antidepressant in Patients with Major Depressive Disorder: Results of a Randomized, Placebo-Controlled, Double-Blind Study", J Clin Psychiatry 2009, 70(4), 540-549.
Bauzo et al., "Interactions Between the Mglur2/3 Agonist, Ly379268, and Cocaine on in Vivo Neurochemistry and Behavior in Squirrel Monkeys", Pharmacol. Biochem. Behav., 2009, 94(1), 204-210.
Bech et al., "Quantitative Rating of Depressive States", Acta Psychiatr Scand, 1975, 51(3), 161-170.
Bech, "Dose-Response Relationship of Pregabalin in Patients with Generalized Anxiety Disorder. A Pooled Analysis of Four Placebo-Controlled Trials", Pharmacopsychiatry, 2007, 40, 163-168.
Bech, "The Bech-Rafaelsen Melancholia Scale (Mes) in of Therapies in Depressive Disorders: A 20-Year Review of Its Use as Outcome Measure", Acta Psychiatr Scand, 2002, 106(4), 252-264.
Beesdo, "Incidence and Risk Patterns of Anxiety and Depressive Disorders and Categorization of Generalized Anxiety Disorder", Arch Gen Psychiatry, 2010, 67(1), 47-57.
Behrens et al., "Ketamine-Induced Loss of Phenotype of Fast-Spiking Interneurons is Mediated by Nadph-Oxidase", Science, 2007, 318, 1645-1647.
Belenikin et al., "Comparative Analysis of the Ligand-Binding Sites of the Metabotropic Glutamate Receptors Mglur1-Mglur8", Doklady Biochemistry & Biophysics., 2002, 386, 251-256.
Bell et al., "Altered Synaptic Function in Alzheimer's Disease", European Journal of Pharmacology, 2006, 545(1), 11-21.
Bellani et al., "Brain Anatomy of Major Depression II. Focus on Amygdala", Epidemiology and Psychiatric, Sciences, 2011, 20(1), 33-36.
Bellesi et al., "The Mglur2/3 Agonist Ly379268 Blocks the Effects of Glt-I Upregulation on Prepulse Inhibition of the Startle Reflex in Adult Rats", Neuropsychopharmacology, 2010, 1-8.
Bellesi et al., "The Mglur2/3 Agonist Ly379268 Blocks the Effects of Glt-1 Upregulation on Prepulse Inhibition of the Startle Reflex in Adult Rats", Neuropsychopharmacology, 2010, 35(6), 1253-1260.
Belousov et al., "Non-Cholinergic Excitation in Neurons After a Chronic Glutamate Receptor Blockade", Neuroreport, 2004, 15(1), 113-117.
Benarroch, "Metabotropic Glutamate Receptors: Synaptic Modulators and Therapeutic Targets for Neurologic Disease", Neurology, 2008, 70(12), 964-968.
Benca et al., "Sleep and Psychiatric Disorders. A Meta-Analysis", Arch Gen Psychiatry, 1992, 49, 651-670.
Beneyto et al., "Abnormal Glutamate Receptor Expression in the Medial Temporal Lobe in Schizophrenia and Mood Disorders", Neuropsychopharmacology, 2007, 32(9), 1888-1902.
Benilova et al., "The Toxic Aβ Oligomer and Alzheimer's Disease: An Emperor in Need of Clothes", Nature Neuroscience, 2012, 15(3), 349-357.
Benneyworth et al., "A Selective Positive Allosteric Modulator of Metabotropic Glutamate Receptor Subtype 2 Blocks a Hallucinogenic Drug Model of Psychosis", Mol. Pharmacol., 2007, 72, 477-484.
Benneyworth et al., "Chronic Phenethylamine Hallucinogen Treatment Alters Behavioral Sensitivity to a Metabotropic Glutamate 2/3 Receptor Agonist", Neuropsychopharmacology, 2008, 33(9), 2206-2216.
Benquet et al., "Two Distinct Signaling Pathways Upregulate Nmda Receptor Responses via Two Distinct Metabotropic Glutamate Receptor Subtypes", Journal of Neuroscience, 2002, 22(22), 9679-9686.
Benson et al., "A Comparison of Observational Studies and Randomized, Controlled Studies", N Engl J Med., 2000, 342(25), 1878-1886.
Bergink et al., "Metabotropic Glutamate II Receptor Agonists in Panic Disorder: A Double Blind Clinical Trial with Ly354740", International Clinical Psychopharmacology, 2005, 20, 291-293.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, 68, 843-853.
Bermudo-Soriano, "New Perspectives in Glutamate and Anxiety", Pharmacol Biochem Behav, 2011, Epub, No Page Numbers, Doi:10.1016/J.Pbb.2011.04.010.
Berthele et al., "Distribution and Developmental Changes in Metabotropic Glutamate Receptor Messenger RNA Expression in the Rat Lumbar Spinal Cord", Developmental Brain Research, 1999, 112(1), 39-53.
Berthele et al., "Expression of Metabotropic Glutamate Receptor Subtype MRNA (Mglur1-8) in Human Cerebellum", Neuroreport, 1999, 10(18), 3861-3867.
Bertrand et al., "Common and Selective Molecular Determinants Involved in Metabotopic Glutamate Receptor Agonist Activity", J. Med. Chem., 2002, 45(15), 3171-3183.
Bespalov et al., "Behavioral Characterization of the Mglu Group II/III Receptor Antagonist, Ly-341495, in Animal Models of Anxiety and Depression", European Journal of Pharmacology 2008, 592, 96-102.
Bespalov et al., "Habituation Deficits Induced by Metabotropic Glutamate Receptors 2/3 Receptor Blockade in Mice: Reversal by Antipsychotic Drugs", Journal of Pharmacology & Experimental Therapeutics, 2007, 320(2), 944-950.
Bessho et al., "Glutamate and Quisqualate Regulate Expression of Metabotropic Glutamate Receptor MRNA in Cultured Cerebellar Granule Cells", Journal of Neurochemistry, 1993, 60(1), 253-259.
Bessis et al., "Metabotropic Glutamate Receptors: Exciting Possibilities in Excitatory Transmission", Celltransmissions, 2000, 17, 3-10.
Bick et al., "Photo-Oxidative Cleavage: An Alternative Method for Degrading Bisbenzylisoquinoline Alkaloids", Journal of Natural Products, 1986, 49(3), 373-385.
Bijl et al., "Current and Residual Functional Disability Associated with Psychopathology: Findings from the Netherlands Mental Health Survey and Incidence Study (Nemesis)", Psychological Medicine, May 2000, 657-668.

(56) References Cited

OTHER PUBLICATIONS

Bilkei-Gorzo et al., "MCPP-Induced Anxiety in the Light-Dark Box in Rats—A New Method for Screening Anxiolytic Activity", Psychopharmacology (Berl), 1998, 136(3), 291-298.
Binder et al., "Association of Polymorphisms in Genes Regulating the Corticotropin-Releasing Factor System with Antidepressant Treatment Response", Arc Gen Psychiatry, 2010, 67(4), 369-370.
Black et al., "Compound A, A Novel, Potent and Selective Mglur2 Positive Allosteric Modulator: II. Effects in Models Predictive of Therapeutic Activity Against Cognitive Impairment Associated with Schizophrenia", Poster 767.7 Presented at the 40$^{th}$ Annual Meeting of Society for Neuroscience, Nov. 2010, 1 page.
Blaha et al., "Stimulation of the Ventral Subiculum of the Hippocampus Evokes Glutamate Receptor-Mediated Changes in Dopamine Efflux in the Rat Nucleus Accumbens", European Journal of Neuroscience, 1997, 9(5), 902-911.
Blanco et al., "Changes in the Prevalence of Non-Medical Prescription Drug Use and Drug Use Disorders in the United States: 1991-1992 and 2001-2002", Drug and Alcohol Dependence, 2007, 90, 252-260.
Boatman et al., "Alkylations at the Methyl or Alpha-Methylene Group of 6- or 4-Alkyl-3-Cyano-2(1)-Pyridones Through Dianions", Journal of Organic Chemistry, 1965, 30(11), 3593-3597.
Bockaert et al., "Metabotropic Glutamate Receptors: An Original Family of G Protein-Coupled Receptors", Fundamental & Clinical Pharmacology, 1993, 7(9), 473-485.
Bockaert et al., "Molecular Tinkering of G Protein-Coupled Receptors: An Evolutionary Success", Embo Journal, 1999, 18(7), 1723-1729.
Bodick et al., "Protocols to Demonstrate Slowing of Alzheimer Disease Progression. Position Paper on the International Working Group on Harmonization of Dementia Drug Guidelines", Alzheimer Disease and Associated Disorders, 1997, 11(Suppl 3), 50-53.
Bohm et al., "Thieno Compounds Part 5: Basically Substituted Thieno[2,3-D]Pyrimidines", Pharmazie., 1986, 41, 23-25.
Bohme et al., "Darstellng Und Umsetzungen Von 3-Arylamino-2-Halogencrotononitilen", Chem. Ber., 1976, 109, 2908-2913.
Boldyrev et al., "Homocysteine and its Derivatives as Possible Modulators of Neuronal and Non-Neuronal Cell Glutamate Receptors in Alzheimer's Disease", J Alzheimers. Dis, 2007, 11(2), 219-228.
Bolton et al., "Exploring the Correlates of Suicide Attempts Among Individuals with Major Depressive Disorder: Findings from the National Epidemiologic Survey on Alcohol and Related Conditions", J Clin Psychiatry, 2008, 69, 1139-1149.
Bonanno et al., "Chronic Antidepressants Reduce Depolarization-Evoked Glutamate Release and Protein Interactions Favoring Formation of Snare Complex in Hippocampus", J Neurosci 2005, 25, 3270-3279.
Bond et al., "Neuroprotective Effects of Ly379268, A Selective Mglu2/3 Receptor Agonist: Investigations Into Possible Mechanism of Action in Vivo", J Pharmacol. Exp. Ther., 2000, 294(3), 800-809.
Bond et al., "Pharmacology of Metabotropic Glutamate Receptor-Mediated Enhancement of Responses to Excitatory and Inhibitory Amino Acids on Rat Spinal Neurones in Vivo", Neuropharmacology, 1995, 34(8), 1015-1023.
Bonnefous et al., "Biphenyl-Indanones: Allosteric Potentiators of Metabotropic Glutamate Subtype 2 Receptor", Bioorg Med Chem Lett, 2005, 15, 4354-4358.
Boris-Moller et al., "Changes in the Extracellular Levels of Glutamate and Aspartate During Ischemia and Hypoglycemia. Effects of Hypothermia", Experimental Brain Research, 1998, 121(3), 277-284.
Borowitz et al., "Organophosphorus Chemistry. III. The Reactions of Triphenylphosphine with Secondary A-Bromo Ketones and with 2-Bromodimedone", Journal of Organic Chemistry, Dec. 1966, 4031-4037.
Bortolotto et al., "Roles of Metabotropic Glutamate Receptors in LTP and LTD in the Hippocampus", Current Opinion in Neurobiology, 1999, 9(3), 299-304.
Boules et al., "Neurotensin Agonists: Potential in the Treatment of Schizophrenia", CNS Drugs, 2007, 21(1), 13-23.
Bouvrais-Veret et al., "Microtubule-Associated Stop Protein Deletion Triggers Restricted Changes in Dopaminergic Neurotransmission", J. Neurochem., 2008, 104, 745-756.
Boyette et al., "Factor Structure of the Yale-Brown Obsessive-Compulsive Scale (Y-Bocs) in a Large Sample of Patients with Schizophrenia or Related Disorders and Comorbid Obsessive-Compulsive Symptoms", Psychiatry Res., 2011, 409-413.
Brabet et al., "Comparative Effect of L-CCG-I, DCG-IV and Gamma-Carboxy-L-Glutamate on all Cloned Metabotropic Glutamate Receptor Subtypes", Neuropharmacology, 1998, 37, 1043-1051.
Bradley et al., "Activation of Group II Metabotropic Glutamate Receptors Inhibits Synaptic Excitation of the Subsantia Nigra Pars Reticulata", J. of Neuroscience, May 2000, 20(9), 3085-3094.
Braff et al., "Human Studies of Prepulse Inhibition of Startle: Normal Subjects, Patient Groups, and Pharmacological Studies", Psychopharmacology, 2001, 156, 234-258.
Braga et al., "Making Crystals from Crystals: A Green Route to Crystal Engineering and Polymorphism", Chem. Commun., 2005, 3635-3645.
Braish et al., "Construction of the (1x,5x,6x)-6-Amino-3-Azabicyclo[3.1.0]Hexane Ring System", Synlett, 1996, 1100-1102.
Brauner-Osborne et al., "A New Highly Selective Metabotropic Excitatory Amino Acid Agonist: 2-Amino-4-(3-Hydroxy-5-Methylisoxazol-4-Yl)Butyric Acid", Journal of Medicinal Chemistry, 1996, 39(16), 3188-3194.
Brauner-Osborne et al., "Interaction of CPCCOET with a Chimeric Mglu1b and Calcium Sensing Receptor", Neuroreport, 1999, 10(18), 3923-3925.
Brauner-Osborne et al., "Molecular Pharmacology of 4-Substituted Glutamic Acid Analogues at Ionotropic and Metabotropic Excitatory Amino Acid Receptors", European Journal of Pharmacology, 1997, 335(2-3), R1-R3.
Brauner-Osborne et al., "Pharmacology of (S)-Homoquisqualic Acid and (S)-2-Amino-5-Phosphonopentanoic Acid [(S)-Ap5] at Cloned Metabotropic Glutamate Receptors", British Journal of Pharmacology, 1998, 123(2), 260-274.
Brauner-Osborne, "Structure, Pharmacology and Therapeutic Prospects of Family C G-Protein Coupled Receptors", Current Drug Targets, 2007, 8, 169-184.
Breier et al., "Association of Ketamine-Induced Psychosis with Focal Activation of the Prefrontal Cortex in Healthy Volunteers", Am J Psychiatry, 1997, 154, 805-811.
Bremner et al., "Development and Preliminary Psychometric Properties of an Instrument for the Measurement of Childhood Trauma: The Early Trauma Inventory", Depress Anxiety, 2000, 12(1), 1-12.
Bremner et al., "Psychometric Properties of the Early Trauma Inventory—Self Report", J Nerv Ment Dis, 2007, 195(3), 211-218.
Brighty et al., "Synthesis of (1x,5x,6x)-6-Amino-3-Azabicyclo[3.1.0]Hexane: A Novel Achiral Diamine", Synlett, 1996, 1097-1099.
Brnardic et al., "3-Aryl-5-Phenoxymethyl-1,3-Oxazolidin-2-Ones as Positive Allosteric Modulators of Mglur2 for the Treatment of Schizophrenia: Hit-to-Lead Efforts", Bioorg Med Chem Lett, 2010, 20, 3129-3133.
Broekkamp et al., "Major Tranquillizers can be Distinguished From Minor Tranquillizers on the Basis of Effects on Marble Burying and Swim-Induced Grooming in Mice", Eur. J. Pharmacol., 1986, 126, 223-229.
Bruno et al., "Activation of Class II or III Metabotropic Glutamate Receptors Protects Cultured Cortical Neurons Against Excitotoxic Degeneration", European Journal of Neuroscience, 1995, 7(9), 1906-1913.
Bruno et al., "Activation of Metabotropic Glutamate Receptors Coupled to Inositol Phospholipid Hydrolysis Amplifies NMDA-Induced Neuronal Degeneration in Cultured Cortical Cells", Neuropharmacology, 1995, 34(8), 1089-1098.
Bruno et al., "Excitatory Amino Acids and Neurotoxicity", Functional Neurology 1993, 8(4), 279-292.
Bruno et al., "Metabotropic Glutamate Receptors and Neurodegeneration", Progress in Brain Research, 1998, 116, 209-221.

(56) References Cited

OTHER PUBLICATIONS

Bruno et al., "Metabotropic Glutamate Receptors and Neuronal Degeneration in Culture", Advances in Neurology, 1996, 71, 47-52.
Bruno et al., "Molecular Dynamics Simulation of the Heterodimeric Mglur2/5ht(2a) Complex. An Atomistic Resolution Study of a Potential New Target in Psychiatric Conditions", J. Chem. Inf. Model., 2009, 49(6), 1602-1616.
Bruno et al., "Neuroprotection by Glial Metabotropic Glutamate Receptors is Mediated by Transforming Growth Factor-Beta", J. Neurosci., 1998, 18(23), 9594-9600.
Bruno et al., "The Neuroprotective Activity of Group-II Metabotropic Glutamate Receptors Requires New Protein Synthesis and Involves a Glial-Neuronal Signaling", J. Neurosci., 1997, 17(6), 1891-1897.
Bruno, "Metabotropic Glutamate Receptor Subtypes as Targets for Neuroprotective Drugs", Journal of Cerebral Blood Flow and Metabolism, 2001, 21,1013-1033.
Buisson et al., "The Inhibitory Mglur Agonist, S-4-Carboxy-3-Hydroxy-Phenylglycine Selectively Attenuates NMDA Neurotoxicity and Oxygen-Glucose Deprivation-Induced Neuronal Death", Neuropharmacology, 1995, 34(8), 1081-1087.
Bunch et al., "Excitatory Amino Acid Transporters as Potential Drug Targets", Expert Opin Ther Targets, 2009, 13(60), 719-731.
Bunney et al., "Norepinephrine in Depression Reactions. A Review", Arch Gen Psychiatry, 1965, 13(6), 483-494.
Burford et al., "Strategies for the Identification of Allosteric Modulators of G-Protein-Coupled Receptors", Biochem Pharmacol, 2011, 1-12.
Bushell et al., "Pharmacological Antagonism of the Actions of Group II and III Mglur Agonists in the Lateral Perforant Path of Rat Hippocampal Slices", Br. J Pharmacol., 1996, 117(7), 1457-1462.
Bustillo et al., "1H-MRS at 4 Tesla in Minimally Treated Early Schizophrenia", Mol Psychiatry, 2010, 15(6), 629-636.
Butterfield et al., "The Glutamatergic System and Alzheimer's Disease: Therapeutic Implications" CNS Drugs, 2003, 17(9), 641-652.
Byrnes et al., "Metabotropic Glutamate Receptors as Targets for Multipotential Treatment of Neurological Disorders", Neurotherapeutics, 2009, 6(1), 94-107.
Cacabelos et al., "The Glutamatergic System and Neurodegeneration in Dementia: Preventive Strategies in Alzheimer's Disease", International Journal of Geriatric Psychiatry, 1999, 14(1), 3-47.
Cai et al., "Local Potentiation of Excitatory Synapses by Serotonin and its Alteration in Rodent Models of Depression", Nature Neuroscience, 2013, 16(4), 464-472.
Calabresi, "Antiepileptic Drugs in Migraine: From Clinical Aspects to Cellular Mechanisms", Trends in Pharmacological Sci., 2007, 28(4), 188-195.
Campbell et al., "An Update on Regional Brain Volume Differences Associated with Mood Disorders", Curr Opin Psychiatry, 2006, 19(1), 25-33.
Canadian Patent Application No. 2,581,144: Office Action dated Dec. 4, 2012, 5 pages.
Canadian Patent Application No. 2,581,144: Office Action dated May 13, 2009, 5 pages.
Caraci et al., "Metabotropic Glutamate Receptors in Neurodegeneration/Neuroprotection: Still a Hot Topic?", Neurochemistry Intl, 2012, 61(4), 559-565.
Caraci et al., "Targeting Group II Metabotropic Glutamate (MGLU) Receptors for the Treatment of Psychosis Associated with Alzheimer's Disease: Selective Activation of Mglu2 Receptors Amplifies B-Amyloid Toxicity in Cultured Neurons, Whereas Dual Activation of Mglu2 and Mglu3 Receptors is Neuroprotective", Mol Pharmacol, 2011, 79, 618-626.
Carlsson et al., "Neurotransmitter Aberrations in Schizophrenia: New Perspectives and Therapeutic Implications", Life Sciences, 1997, 61(2), 75-94.
Carlsson, "The Neurochemical Circuitry of Schizophrenia", Pharmacopsychiatry, 2006, 39, S10-S14.
Carter, "Schizophrenia Susceptibility Genes Converge on Interlinked Pathways Related to Glutamatergic Transmission and Long-Term Potentiation, Oxidative Stress and Oligodendrocyte Viability", Schizophr. Res., 2006, 86(1-3), 1-14.
Cartmell et al., "Acute Increases in Monoamine Release in the Rat Prefrontal Cortex by the Mglu2/3 Agonist Ly379268 are Similar in Profile to Risperidone, Not Locally Mediated, and Can Be Elicited in the Presence of Uptake Blockade", Neuropharmacology, 2001, 40(7), 847-855.
Cartmell et al., "Attenuation of Specific Pcp-Evoked Behaviors by the Potent Mglu2/3 Receptor Agonist, Ly379268 and Comparison with the Atypical Antipsychotic, Clozapine", Psychopharmacology, 2000, 148, 423-429.
Cartmell et al., "Characterization of [3h]-(2s,2'r,3'r0-2-(2'3'-Dicarboxycyclopropyl)Glycine ([3h]-Dcg Iv) Binding to Metabotropic Mglu2 Receptor-Transfected Cell Membranes", British Journal of Pharmacology, 1998, 123, 497-504.
Cartmell et al., "Dopamine and 5-Ht Turnover are Increased by the Mglu2/3 Receptor Agonist Ly379268 in Rat Medial Prefrontal Cortex, Nucleus Accumbens and Striatum", Brain Res., 2000, 887(2), 378-384.
Cartmell et al., "Effect of Metabotropic Glutamate Receptor Activation on Receptor-Mediated Cyclic Amp Responses in Primary Cultures of Rat Striatal Neurones", Brain Res., 1998, 791(1-2), 191-199.
Cartmell et al., "Regulation of Neurotransmitter Release by Metabotropic Glutamate Receptors", J. Neurochem., 2000, 75(3), 889-907.
Cartmell et al., "The Metabotropic Glutamate 2/3 Receptor Agonists Ly354740 and Ly379268 Selectively Attenuate Phencyclidine Versus D-Amphetamine Motor Behavior in Rats", J Pharmacol Exp Ther, 1999, 291, 161-170.
Cartmell et al., "The Mglu(2/3) Receptor Agonist Ly379268 Selectively Blocks Amphetamine Ambulations and Rearing", Eur. J Pharmacol., 2000, 400(2-3), 221-224.
Cartmell et al., "The Potent, Selective Mglu2/3 Receptor Agonist Ly379268 Increases Extracellular Levels of Dopamine, 3,4-Dihydroxyphenylacetic Acid, Homovanillic Acid, and 5-Hydroxyindole-3-Acetic Acid in the Medial Prefrontal Cortex of the Freely Moving Rat", J Neurochem., 2000, 75(3), 1147-1154.
Cartmell et al., "Tolerance to the Motor Impairment, But Not the Reversal of PCP-Induced Motor Activities by Oral Administration of the Mglu2/3 Receptor Agonist, Ly379268", Naunyn Schmiedebergs Arch Pharmacol, 2000, 361, 39-46.
Casado et al., "GPCR Homomers and Heteromers: A Better Choice as Targets for Drug Development Than GPCR Monomers?", Pharmacology & Therapeutics, 2009, 124, 248-257.
Castagne et al., "Preclinical Behavioral Models for Predicting Antipsychotic Activity", Adv. Pharmacol., 2009, 57, 381-418.
Catania et al., "Desensitization of Metabotropic Glutamate Receptors in Neuronal Cultures", Journal of Neurochemistry, 1991, 56(4), 1329-1335.
Catania et al., "Group I Metabotropic Glutamate Receptors: A Role in Neurodevelopmental Disorders?", Mol Neurobiol, 2007, 35, 298-307.
Catania et al., "Homologous Desensitization of Metabolotropic Glutamate Receptors in Neuronal Cultures", Pharmacological Research, 1990, 22(Suppl 1), 79-80.
Catania et al., "Metabotropic Glutamate Receptor Heterogeneity in Rat Brain", Molecular Pharmacology, 1994, 45(4), 626-636.
Catania et al., "Metabotropic Glutamate Receptors are Differentially Regulated During Development", Neuroscience, 1994, 61(3), 481-495.
Catterall, "Structure and Function of Neuronal Ca2+ Channels and Their Role in Neurotransmitter Release", Cell Calcium, 1998, 24(5-6), 307-323.
Cavalli et al., "Multi-Target-Directed Ligands to Combat Neurodegenerative Diseases", J. Med. Chem., 2007-2008, 26 pages.
Cavanni et al., "Pharmacological Analysis of Carboxyphenylglycines at Metabotropic Glutamate Receptors", European Journal of Pharmacology, 1994, 269(1), 9-15.
Celanire et al., "Recent Advances in the Drug Discovery of Metabotropic Glutamate Receptor 4 (mGluR4) Activators for the Treatment of CNS and Non-CNS Disorders", Expert Opin. Drug Discovery, 2012, 7(3), 261-280.

(56) References Cited

OTHER PUBLICATIONS

Chaki "Group II Metabotropic Glutamate Receptor Agonists as a Potential Drug for Schizophrenia", European Journal of Pharmacology, 2010, 639, 59-66.
Chaki et al, "Anxiolytic- and Antidepressant-Like Profile of a New Crf1 Receptor Antagonist, R278995/Cra0450", Eur J Pharmacol, 2004, 485, 145-158.
Chaki et al., "Mglu2/3 and Mglu5 Receptors: Potential Targets for Novel Antidepressants", Neuropharmacology, 2013, 66, 40-52.
Chaki et al., "Targeting of Metabotropic Glutamate Receptors for the Treatment of Schizophrenia", Current Pharmaceutical Design, 2011, 17, 94-102.
Chakos et al., "Baseline Use of Concomitant Psychotropic Medications to Treat Schizophrenia in the Catie Trial", Psychiatr Serv., 2006, 57(8), 1094-1101.
Chakrabarty et al., "Glutamatergic Dysfunction in OCD", Neuropsychopharmacology, 2005, 30(9), 1735-1740.
Chakrasali et al., "Reaction of Acylketene S,N-Acetals with Malonyl Chloride: Synthesis of Novel 1,5-Substituted 4-Hydroxy-6-Methylthio-2 (1h)-Pyridones and 6,8-Substituted 4-Hydroxy-7-Methylthio-2,5-Dioxo-5,6-Dihydro-2h-Pyrano [3,2-C] Pyridines", Synthesis, Jan. 1988, 87-89.
Charney et al., "Increased Anxiogenic Effects of Caffeine in Panic Disorders", Arch Gen Psychiatry, 1985, 42, 233-243.
Charney et al., "Life Stress, Genes, and Depression: Multiple Pathways Lead to Increased Risk and New Opportunities for Intervention", Science's Stke, 2004, (225), Re5, 12 pages.
Charney et al., "Noradrenergic Function in Panic Anxiety. Effects of Yohimbine in Healthy Subjects and Patients with Agoraphobia and Panic Disorder", Arch. Gen. Psychiatry, 1984, 41, 751-763.
Chaudhari et al., "A Metabotropic Glutamate Receptor Variant Functions as a Taste Receptor", Nature Neuroscience, 2000, 3, 113-119.
Chavez-Noriega et al., "Metabotropic Glutamate Receptors: Potential Drug Targets for the Treatment of Schizophrenia", Current Drug Targets—CNS & Neurological Disorders, 2002, 1(3), 261-281.
Chavis et al., "Facilitatory Coupling Between a Glutamate Metabotropic Receptor and Dihydropyridine-Sensitive Calcium Channels in Cultured Cerebellar Granule Cells", J. Neurosci., 1995, 15(1), 135-143.
Chavis et al., "Modulation of Calcium Channels by Metabotropic Glutamate Receptors in Cerebellar Granule Cells", Neuropharmacology, 1995, 34(8), 929-937.
Chen et al., "Second-Generation Antipsychotics in Major Depressive Disorder: Update and Clinical Perspective", Curr Opin Psychiatry, 2011, 24, 19-17.
Chen, "The Chemical Biology of Clinically Tolerated NMDA Receptor Antagonists", Journal of Neurochemistry, 2006, 97, 1611-1626.
Chiarugi et al., "Novel Isoquinolinone-Derived Inhibitors of Poly(Adp-Ribose) Polymerase-1: Pharmacological Characterization and Neuroprotective Effects in an in Vitro Model of Cerebral Ischemia", Journal of Pharmacology and Experimental Therapeutics, 2003, 305(3), 943-949.
Chiechio et al., "Epigenetic Modulation of Mglu2 Receptors by Histone Deacetylase Inhibitors in the Treatment of Inflammatory Pain", Mol. Pharmacol., 2009, 75(5), 1014-1020.
Chiechio et al., "Metabotropic Glutamate Receptors and the Control of Chronic Pain", Curr Opin Pharmacol, 2012, 12, 28-34.
Chiechio et al., "Transcriptional Regulation of Type-2 Metabotropic Glutamate Receptors: An Epigenetic Path to Novel Treatments for Chronic Pain", Trends in Pharmacological Sciences, 2010, 31(4), 153-160.
Chin et al., "Amyloid Beta Protein Modulates Glutamate-Mediated Neurotransmission in the Rat Basal Forebrain: Involvement of Presynaptic Neuronal Nicotinic Acetylcholine and Metabotropic Glutamate Receptors", J. Neurosci., 2007, 27(35), 9262-9269.
Chin et al., "Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals", Jpet, 2011, 336, 709-715.
Chin et al., "Awake Rat Pharmacological MRI as a Translational Pharmacodynamic Biomarker: Mglur2/3 Agonist Modulation of Ketamine-Induced Bold Signals", Jpet, 2010, 22 pages.
Choi, "Methods for Antagonizing Glutamate Neurotoxicity", Cerebrovascular & Brain Metabolism Reviews, 1990, 2(2), 105-147.
Chojnacka-Wojcik et al., "Glutamate Receptor Ligands as Anxiolytics", Current Opinion in Investigational Drugs, 2001, 2(8), 1112-1119.
Christopolous et al., "G Protein-Coupled Receptor Allosterism and Complexing", Pharmacol Rev, 2002, 54, 323-374.
Chrostopoulos., "Allosteric Binding Sites on Cell-Sturcture Receptors: Novel Targets for Drug Discovery", Nature Rev., Mar. 2002, 1, 198-210.
Cid et al., "Discovery of 1,4-Disubstituted 3-Cyano-2-Pyridones: A New Class of Positive Allosteric Modulators of the Metabotropic Glutamate 2 Receptor", J Med Chem, 2012, 55, 2388-2405.
Cid et al., "Discovery of 1,5-Disubstituted Pyridones: A New Class of Positive Allosteric Modulators of the Metabotropic Glutamate 2 Receptor", ACS Chem Neurosci, 2010, 1, 788-795.
Cid et al., "Discovery of 3Cyclopropylmethyl-7-(4-Phenylpiperidin-1-Yl)-8-Trifluoromethyl[1,2,4]Triazolo[4,3 A]Pyridine (Jnj-42153605): A Positive Allosteric Modulator of the Metabotropic Glutamate 2 Receptor", J Med Chem, 2012, 55, 8770-8789.
Cid, "Discovery of a Potent and Orally Bioavailable Positive Allosteric Modulator of Mglur2 for the Treatment of CNS Disorders", Presentation Slides, 16th SCI/RSC Medicinal Chemistry Symposium, Cambridge, Sep. 2011, 26 pages.
Cid, "JNJ-42153605: A Novel Positive Allosteric Modulator of Mglur2 for the Treatment of CNS Disorders" Presentation Slides, RICT 2012—48th International Conference on Medicinal Chemistry, Poitiers 2012, 28 pages.
Citrome, "Adjunctive Aripiprazole, Olanzapine, or Quetiapine for Major Depressive Disorder: An Analysis of Number Needed to Treat, Number Needed to Harm, and Likelihood to Be Helped or Harmed", Postgraduate Medicine, 2010, 122(4), 39-48.
Clark et al., "Effects of the Mglu2/3 Receptor Agonist Ly379268 on Motor Activity in Phencyclidine-Sensitized Rats", Pharmacol. Biochem. Behav., 2002, 73(2), 339-346.
Clark et al., "Synthesis of Thieno[2,3-Djpyrimidines from 4,6-Dichloropyrimidine-5-Carbaldehydes", Journal Heterocyclic Chem, 1993, 30, 1065-1072.
Clark, "Tripartite Model of Anxiety and Depression: Psychometric Evidence and Taxonomic Implications", J. Abnormal Psych., 1991, 100(3), 316-336.
Clayton et al., "Follow-Up and Family Study of Anxious Depression" Am J Psychiatry, 1991, 148, 1512-1517.
Cleary et al., "Factor Analysis of the Hamilton Depression Scale" Drugs Exptl Clin Res, 1977, 1(1-2), 115-120.
Clements et al., "The Time Course of Glutamate in the Synaptic Cleft", Science, 1992, 258(5087), 1498-1501.
Cleva et al., "Positive Allosteric Modulators of Type 5 Metabotropic Glutamate Receptors (mGluR5) and their Therapeutic Potential for the Treatment of CNS Disorders", Molecules, 2011, 16, 2097-2106.
Clinical Trials, "A Dose-Ranging Study of JNJ-40411813 in Healthy Male Volunteers", Available from http://clinicaltrials.gov/show/NCT01358006, retrieved on Aug. 1, 2013.
Clinical Trials, "A Study of [11C]JNJ-42491293, a Possible PET Ligand for the mGlu2 Receptor, in Healthy Adult Volunteers", Available from http://clinicaltrials.gov/show/NCT01359852, retrieved on Aug. 1, 2013.
Clinical Trials, "A Study of JNJ-40411813 as Supplementary Treatment to an Antidepressant in Adults with Depression and Anxiety Symptoms", Available from: http://clinicaltrials.gov/show/NCT01582815, retrieved on Aug. 1, 2013.
Clinical Trials, "AZD8529 Single Ascending Dose Study (Sad)", Clinicaltrials.Gov. No. NCT00755378, Available From: Http://Clinicaltrials.Gov/Show/Nct00755378, retrieved on Aug. 22, 2013.
Clinical Trials, "First-In-Patient Study to Assess the Safety and Tolerability and to Explore the Potential Therapeutic Efficacy of a Novel Glutamate Modulator as Monotherapy and as Add-On Therapy in Patients with Schizophrenia", Available From: Https://Www.Clinicaltrialsregister.Eu—Eudract No. 2010-023369-23, retrieved on Aug. 1, 2013.

(56) References Cited

OTHER PUBLICATIONS

Clinical Trials, "Investigation of the Safety, Tolerability and Potential Therapeutic Effects of JNJ-40411813 in Patients with Schizophrenia", Clinicaltrials Gov. No. NCT01323205, Available From: Http://Clinicaltrials.Gov/Show/NCT01323205, Retrieved Aug. 1, 2013.
Clinical Trials, "Ketamine Challenge Study with JNJ-40411813", Clinical Trials. Gov No. NCT01101659, Available From: Http://Clinicaltrials.Gov/Ct2/Show/Nct01101659, 2010, 3 pages.
Clinical Trials, "Study to Assess the Efficacy, Safety, and Tolerability of AZD8529 in Adult Schizophrenia Patients", Clinicaltrials. Gov. No. NCT00921804, Available From: Http://Clinicaltrials.Gov/Show/Nct00921804, retrieved on Aug. 23, 2013, 3 pages.
Clinical Trials, "The Effects Azd8529 on Cognition and Negative Symptoms in Schizophrenics", Clinicaltrials.Gov. No. NCT00986531, Available From: Http://Clinicaltrials.Gov/Show/Nct00986531, retrieved on Aug. 23, 2013, 2 pages.
Cloninger et al., "The Empirical Structure of Psychiatric Comorbidity and its Theoretical Significance", Comorbidity of Mood and Anxiety Disorders, 1990, 439-462.
Cohen et al., "A Global Measure of Perceived Stress", J Health Soc Behav, 1983 24(4), 385-396.
Colangelo et al., "Differential Effects of Acute Administration of Clozapine or Haloperidol on Local Cerebral Glucose Utilization in the Rat", Brain Research, 1997, 768, 273-278.
Collingridge et al., "Excitatory Amino Acid Receptors and Synaptic Plasticity", Trends in Pharmacological Sciences, 1990, 11(7), 290-296.
Collins et al., "Arachidonic Acid Metabolites and the Synaptic Potentiation Evoked by Activation of Metabotropic Glutamate Receptors", European Journal of Pharmacology, 1998, 342(2-3), 213-216.
Collins et al., "From Ligand Binding to Gene Expression: New Insights into the Regulation of G-Protein-Coupled Receptors", Trends in Biochemical Sciences, 1992, 17(1), 37-39.
Colpaert et al., "A Critical Study on Ro-4-1284 Antagonism in Mice", Arch. Int. Pharmacodyn., 1975, 215, 40-90.
Colzi et al., "Monoamine Oxidase-A Inhibitors and Dopamine Metabolism in Rat Caudatus: Evidence that an Increased Cytosolic Level of Dopamine Displaces Reversible Monoamine Oxidase-A Inhibitors in Vivo", J. Pharmacol. Exper. Therapeutics, 1993, 265, 103-111.
Comins et al., "N- Vs. O-Alkylation in the Mitsunobu Reaction of 2-Pyridone", Tetrahedron Letters, 1994, 35(18), 2819-2822.
Committee for Proprietary Medicinal Products (CPMP), European Agency for the Evaluation of Medicinal Products; Meeting Feb. 26, 1998, London (UK): Note for Guidance on the Clinical Investigation of Medicinal Products in the Treatment of Schizophrenia, 10.
Conigrave et al., "Allosteric Activation of Plasma Membrane Receptors—Physiological Implications and Structural Origins", Progress in Biophysics & Molecular Biology, 2003, 81(3), 219-40.
Conn et al., "Activation of Metabotropic Glutamate Receptors as a Novel Approach for the Treatment of Schizophrenia", Trends Pharmacol Sci, 2008, 30(1), 25-31.
Conn et al., "Allosteric Modulators of Gpcrs: A Novel Approach for the Treatment of CNS Disorders", Nature Reviews Drug Discovery, 2009, 8, 41-54.
Conn et al., "Metabotropic Glutamate Receptors in the Basal Ganglia Motor Circuit", Nature Reviews Neuroscience, 2005, 6, 787-798.
Conn et al., "Pharmacology and Functions of Metabotropic Glutamate Receptors", Annu Rev Pharmacol Toxicol, 1997, 37, 205-237.
Conn, "Physiological Roles and Therapeutic Potential of Metabotropic Glutamate Receptors", Annals of the New York Academy of Sciences, 2003, 1003, 12-21.
Connolly et al., "If at First You Don't Succeed: A Review of the Evidence for Antidepressant Augmentation, Combination and Switching Strategies", Drugs, 2011, 71(1), 43-64.
Cook et al., "Behavioral Effects of Some Psychopharmacological Agent", Ann. Ny Acad. Sci., 1957, 66, 740-752.
Cook et al., "Diethylaminoalkyl Ester Hydrochlorides of N-Alkyl-4-Carbostyrilcarboxylic Acids", J Am. Chem. Soc., 1952, 74, 543-554.
Cook et al., "Effects of Drugs on Avoidance and Escape Behavior", Fed. Proc. 23, 1964, 818-835.
Copani, "Activation of Metabotropic Glutamate Receptors Protects Cultured Neurons Against Apoptosis Induced By-Amyioid Peptide", Molecular Pharmacology, 1995, 47:890-897.
Copeland et al., "Positive Allosteric Modulation Reveals a Specific Role for Mglu2 Receptors in Sensory Processing in the Thalamus", J Physiol, 2012, 590.4, 937-951.
Corlett et al., "Glutamatergic Model Psychoses: Prediction Error, Learning, and Inference", Neuropsychopharmacology, 2011, 36(1), 294-315.
Corti, "The Use of Knock-Out Mice Unravels Distinct Roles for Mglu2 and Mglu3 Metabotropic Glutamate Receptors in Mechanisms of Neurodegeneration/Neuroprotection", J. Neurosci., 2007, 27(31), 8297-8308.
Coryell et al., "Effects of Anxiety on the Long-Term Course of Depressive Disorders", The British Journal of Psychiatry, 2012, 200, 210-215.
Costantino et al., "Modeling of Poly (Adp-Ribose) Polymerase (Parp) Inhibitors. Docking of Ligands and Quantitative Structure-Activity Relationship Analysis", Journal of Medicinal Chemistry, 2001, 440, 3786-3794.
Coyle, "The Gaba-Glutamate Connection in Schizophrenia: Which is the Proximate Cause?", Biochem. Pharmacol., 2004, 68(8), 1507-1514.
Cozzi et al., "Type 2 Metabotropic Glutamate (Mglu) Receptors Tonically Inhibit Transmitter Release in Rat Caudate Nucleus: in Vivo Studies with (2s,1's,2's,3'r)-2-(2'-Carboxy-3'-Phenylcyclopropyl)Glycine, A New Potent and Selective Antagonist", European Journal of Neuroscience, 1997, 9(7), 1350-1355.
Craddock et al., "The Genetics of Schizophrenia and Bipolar Disorder: Dissecting Psychosis", J Med Genet, 2005, 42, 193-204.
Cropley et al., "Molecular Imaging of the Dopaminergic System and its Association with Human Cognitive Function", Biol.Psychiatry, 2006, 59, 898-907.
Cube et al., "3-(2-Ethoxy-4-{4-[3-Hydroxy-2-Methyl-4-(3-Methylbutanoyl)-Phenoxy]Butoxy}Phenyl)Propanoic Acid: A Brain Penetrant Allosteric Potentiator at the Metabotropic Glutamate Receptor 2 (Mglur2)", Bioorganic & Medicinal Chemistry Letters, 2005, 15, 2389-2393.
Cummings, "Behavioral Effects of Memantine in Alzheimer Disease Patients Receiving Donepezil Treatment" Neurology 2006, 67, 57-63.
Cymbalta, "Highlights of Prescribing Information", 2004, 1 page.
Czapski et al., "Effect of Poly (Adp-Ribose) Polymerase Inhibitors on Oxidative Stress Evoked Hydroxyl Radical Level and Macromolecules Oxidation in Cell Free System of Rat Brain Cortex", Neuroscience Letters, 2004, 356, 45-48.
D'Alessandro et al., "The Identification of Structurally Novel, Selective, Orally Bioavailable Positive Allosteric Modulators of Mglur2", Bioorg Med Chem Lett, 2010, 20, 759-762.
D'Antoni et al., "Metabotropic Glutamate Receptors in Glial Cells", Neurochem. Res., 2008, 33(12), 2436-2443.
Dale et al., "Mechanisms of Metabotropic Glutamate Receptor Desensitization: Role in the Patterning of Effector Enzyme Activation", Neurochemistry Intl, 2002, 41, 319-326.
Dale et al., "Spatial-Temporal Patterning of Metabotropic Glutamate Receptor-Mediated Inositol 1,4,5-Triphosphate, Calcium, and Protein Kinase C Oscillations: Protein Kinase C-Dependent Receptor Phosphorylation Is Not Required", J. Biol. Chem., 2001, 276(38), 35900-35908.
Danner et al., "Integrating Patients' Views Into Health Technology Assessment: Analytic Hierarchy Process (AHP) as a Method to Elicit Patient Preferences", Intl Journal of Technology Assessment in Health Care, 2011, 27(4), 369-375.
D'Ascenzo et al., "Mglur5 Stimulates Gliotransmission in the Nucleus Accumbens", Proc. Natl. Acad. Sci., 2007, 104(6), 1995-2000.

(56) References Cited

OTHER PUBLICATIONS

Dash et al., "Long-Term Homeostasis of Extracellular Glutamate in the Rat Cerebral Cortex Across Sleep and Waking States", J Neurosci, 2009, 29, 620-629.
Datta et al., "Microinjection of Glutamate into the Pedunculopontine Tegmentum Induces Rem Sleep and Wakefulness in the Rat", Am J Physiol., Regul Integr Comp Physiol, 2001, 280, R752-R759.
Davidson et al., "Achieving Remission with Venlafaxine and Fluoxetine in Major Depression: Its Relationship to Anxiety Symptoms", Depression and Anxiety, 2002, 16, 4-13.
Davidson et al., "Differential Effects of Neuroleptic and Other Psychotropic Agents on Acquisition of Avoidance in Rats", Life Sci., 1976, 18, 1279-1284.
Davis et al., "2,1-Benzisothiazoles. Xii. [1]. The Use of N-Substituted-2,1-Benzisothiazolium Salts as Synthetic Equivalents of O-Aminobenz-Aldehydes. A Simple Synthesis of Some 2-Quinolones", Journal of Heterocyclic Chemistry, 1983, 20, 1707-1708.
Davis, "Diazepam and Flurazepam: Effects on Conditioned Fear as Measured with the Potentiated Startle Paradigm", Psychopharmacology, 1979, 62, 1-7.
Davis, "Pharmacological and Anatomical Analysis of Fear Conditioning Using the Fear-Potentiated Startle Paradigm", Behavioral Neuroscience, 1986, 100, 814-824.
Dawson et al., "Novel Analysis for Improved Validity in Semi-Quantitative 2-Deoxyglucose Autoradiographic Imaging", Journal of Neuroscience Methods, 2008, 175, 25-35.
De Blasi et al., "Molecular Determinants of Metabotropic Glutamate Receptor Signaling", Trends in Pharmacological Sciences, 2001, 22 (3), 114-120.
De Boer et al., "Characterization of the Clinical Effect of a Positive Allosteric Modulator of the Metabotropic Glutamate Receptor-2", Society of Biological Psychiatry 67$^{th}$ Annual Scientific Convention, May 2012, 2 pages.
De Montis et al., "Selective Adenylate Cyclase Increase in the Limbic Area of Long-Term Imipramine-Treated Rats", European Journal of Pharmacology, 1990, 180(1), 169-174.
De Novellis et al., "Type I and II Metabotropic Glutamate Receptors Modulate Periaqueductal Grey Glycine Release: Interaction Between Mglu2/3 and A1 Adenosine Receptors", Neuropharmacology, 2002, 43(7), 1061-1069.
Dean, "The Cortical Serotonin2a Receptor and the Pathology of Schizophrenia: A Likely Accomplice", J. Neurochem., 2003, 85, 1-13.
Dedeurwaerdere et al., "Memantine-Induced Brain Activation as a Model for the Rapid Screening of Potential Novel Antipsychotic Compounds: Exemplified by Activity of an Mglu2/3 Receptor Agonist", Psychopharmacology, 2011, 214, 505-514.
Del Rio et al., "Differential Coupling of G-Protein-Linked Receptors to Ca2+ Mobilization Through Inositol(1,4,5)Trisphosphate or Ryanodine Receptors in Cerebellar Granule Cells in Primary Culture", European Journal of Neuroscience, 1999, 11(9), 3015-3022.
Del'guidice et al., "Messing Up with Traffic: Different Effects of Antipsychotic Agents on Glutamate Receptor Complexes in Vivo", Mol. Pharmacol., 2008, 73(5), 1339-1342.
Delille et al., "Heterocomplex Formation of 5-HT2A-Mglu2 and its Relevance for Cellular Signaling Cascades", Neuropharmacology, 2012, 1-8.
Delille et al., "The Two Faces of the Pharmacological Interaction of Mglu2 and 5-Ht2a—Relevance of Receptor Heterocomplexes and Interaction Through Functional Brain Pathways", Neuropharmacology, 2013, 70, 296-305.
Derks et al., "Kreapelin Was Right: A Latent Class Analysis of Symptom Dimensions in Patients and Controls", Schizophrenia Bull., 2012, 38(3), 495-505.
Desseilles et al., "Assessing the Adequacy of Past Antidepressant Trials: A Clinician's Guide to the Antidepressant Treatment Response Questionnaire", J Clin Psychiatry, 2011, 72(8), 1152-1154.
Dhami et al., "G Protein-Coupled Receptor Kinase 2 Regulator of G Protein Signaling Homology Domain Binds to Both Metabotropic Glutamate Receptor 1a and Galphaq to Attenuate Signaling", Journal of Biological Chemistry, 2004, 279(16), 16614-16620.
Dhami et al., "Regulation of Metabotropic Glutamate Receptor Signaling, Desensitization and Endocytosis", Pharmacol. Ther., 2006, 111(1), 260-271.
Dhanya et al., "Design and Synthesis of an Orally Active Metabotropic Glutamate Receptor Subtype-2 (Mglur2) Positive Allosteric Modulator (Pam) That Decreases Cocaine Self-Administration in Rats", J Med Chem, 2011, 54, 342-353.
Dhonnchadha et al., "Anxiolytic-Like Effects of 5-Ht2 Ligands on Three Mouse Models of Anxiety", Behavioural Brain Research, 2003, 140, 203-214.
Di Liberto et al., "Group II Metabotropic Glutamate Receptor Activation by Agonist Ly379268 Treatment Increases the Expression of Brain Derived Neurotrophic Factor in the Mouse Brain", Neuroscience, 2010, 165, 863-873.
DiMichelle et al., "The Natural Course of Schizophrenia and Psychopathological Predictors of Outcome", 2004, 37(2), 98-104.
Dingledine et al., "Excitatory Amino Acid Receptors in Epilepsy", Trends in Pharmacological Sciences, 1990, 11(8), 334-338.
Dingledine et al., "Peripheral Glutamate Receptors: Molecular Biology and Role in Taste Sensation", J Nutr, 2000, 130(4s Suppl):1039s-1042s.
Doherty et al., "Functional Interactions Between Cannabinoid and Metabotropic Glutamate Receptors in the Central Nervous System", Current Opinion in Pharmacology, 2003, 3(1), 46-53.
Doherty et al., "Rapid Internalization and Surface Expression of a Functional, Fluorescently Tagged G-Protein-Coupled Glutamate Receptor", Biochemical Journal, 1999, 341(Pt 2), 415-422.
Domschke et al., "Anxious Versus Non-Anxious Depression: Difference in Treatment Outcome", J Psychopharmacol, 2010, 24, 621-622.
D'Onofrio et al., "Neuroprotection Mediated by Glial Group-II Metabotropic Glutamate Receptors Requires the Activation of the Map Kinase and the Phosphatidylinositol-3-Kinase Pathways", Journal of Neurochemistry, 2001, 78(3), 435-445.
D'Onofrio et al., "Advances in the identification of g-secretase inhibitors for the treatment of Alzheimer's disease", Expert Opinion on Investigational Drugs, 2012, 7, 20-37.
Doreulee et "The Role of the Mglur Allosteric Modulation in the Nmda-Hypofunction Model of Schizophrenia", Georgian Medical News, 2009, 177, 59-65.
Doumazene et al., "A New Approach to Analyze Cell Surface Protein Complexes Reveals Specific Heterodimeric Metabotropic Glutamate Receptors", Faseb, 2011, 25, 66-77.
Doumazene, "Illuminating the Activation Mechanisms and Allosteric Properties of Metabotropic Glutamate Receptors", PNAS, 2013, 1-10.
Downey et al., "Ecdysone-Based System for Controlled Inducible Expression of Metabotropic Glutamate Receptor Subtypes 2,5, and 8", Journal of Biomolecular Screening, 2005, 10(8), 841-848.
Doyle et al., "Quantifying the Attenuation of the Ketamine Phmri Response in Humans: a Validation Using Antipsychotic and Glutamatergic Agents", Jpet Fast Forward, Jan. 31, 2013, 42 pages.
Drevets et al., "Functional Anatomical Correlates of Antidepressant Drug Treatment Assessed Using Pet Measures of Regional Glucose Metabolism", European Neuropsychopharmacology, 2002, 12, 527-544.
Drew et al., "Multiple Metabotropic Glutamate Receptor Subtypes Modulate Gabaergic Neurotransmission in Rat Periaqueductal Grey Neurons in Vitro", Neuropharmacology, 2004, 46(7), 927-934.
Dunayevich, "Efficacy and Tolerability of an Mglu2/3 Agonist in the Treatment of Generalized Anxiety Disorder", Neuropsychopharmacol., 2008, 33, 1603-1610.
Duncan et al., "Comparison of the Effects of Clozapine, Risperidone, and Olanzapine on Ketamine-Induced Alterations in Regional Brain Metabolism", Jpet, 2000, 293, 8-14.
Duncan et al., "Differential Effects of Clozapine and Haloperidol on Ketamine-Induced Brain Metabolic Activation", Brain Res, 1998, 812, 65-75.
Duncan et al., "Metabolic Mapping of the Rat Brain After Subanesthetic Doses of Ketamine: Potential Relevance to Schizophrenia", Brain Research, 1998, 787, 181-190.

(56) References Cited

OTHER PUBLICATIONS

Duncan et al., "Topographic Patterns of Brain Activity in Response to Swim Stress: Assessment by 2-Deoxyglucose Uptake and Expression of Fos-Like Immunoreactivity", J Neurosci, 1993, 13, 3932-3943.
Dunlop, "Glutamate-Based Therapeutic Approaches: Targeting the Glutamate Transport System", Current Opinion in Pharmacology, 2006, 6 (1), 103-107.
Duong et al., "A Biogenetic Like Synthesis of Perloline, 6-(3,4-Dimethoxyphenyl)-5-Hydroxy-5,6-Dihydrobenzo[C][2,7]Naphthyridin-4(3h)-One", Aust. J. Chem., 1983, 36, 1431-1440.
Duplantier et al., "3-Benzyl-1,3-Oxazolidin-2-Ones as Mglur2 Positive Allosteric Modulators: Hit to Lead and Lead Optimization", Bioorg Med Chem Lett, 2009, 19, 2524-2529.
Durand et al., "Role of Metabotropic Glutamate Receptors in the Control of Neuroendocrine Function", Neuropharmacology, 2008, 55(4), 577-583.
During, "Extracellular Hippocampal Glutamate and Spontaneous Seizure in the Conscious Human Brain", Lancet, 1993, 341, 1607-1610.
Dutar et al., "Pharmacological Characterization of an Unusual Mglur-Evoked Neuronal Hyperpolarization Mediated by Activation of Girk Channels", Neuropharmacology, 1999, 38(4), 467-475.
Egan et al., "Neurobiology of Schizophrenia", Current Opinion in Neurobiology, 1997, 7(5), 701-707.
Egashira et al., "Impaired Social Interaction and Reduced Anxiety-Related Behavior in Vasopressin V1a Receptor Knockout Mice", Behav Brain Res, 2007, 5 pages.
Ehlert, "Analysis of Allosterism in Functional Assays", J Pharmacol. Exp. Ther., 2005, 315(2), 740-754.
Eintrei et al., "Effects of Diazepam and Ketamine Administered Individually or in Combination on Regional Rates of Glucose Utilization in Rat Brain", Br J Anaesth, 1999, 82, 596-602.
Eisa et al., "Synthesis of Some Novel Tetrazole Derivatives as Potential Antimicrobial Agents," Pakistan J. of Scientific and Industrial Res, 1990, 33, 417-420.
Elia et al., "Genome-Wide Copy Number Variation Study Associates Metabotropic Glutamate Receptor Gene Networks with Attention Deficit Hyperactivity Disorder", Nature Genetics, 2011, 9 pages.
Ellenbroek et al., "Animal Models with Construct Validity for Schizophrenia", Behavioural Pharmacolooy, 1990, 1, 469-490.
Emmitte,"Recent Advances in the Design and Development of Novel Negative Allosteric Modulators of Mglu5", Chem. Neurosci., 2011, 2, 411-432.
Engin et al., "The Effects of Intra-Cerebral Drug Infusions on Animals' Unconditioned Fear Reactions: A Systematic Review", Prog Neuropsychopharmacol Biol Psychiatry, 2008, 32, 1399-1419.
Enomoto et al., "Phencyclidine and Genetic Animal Models of Schizophrenia Developed in Relation to the Glutamate Hypothesis", Methods Find. Exp. Clin Pharmacol., 2007, 29(4), 291-301.
Erlenmeyer et al., "Uber Einige Derivate Des 2-Aminothiazols", Helvetica Chim Acta, 1949, 32, 35-38.
Ermolinsky et al., "Differential Changes in Mglu2 and Mglu3 Gene Expression Following Pilocarpine-Induced Status Epilepticus: A Comparative Real-Time PCR Analysis", Brain Research, 2008, 1226, 173-180.
Ershov et al., "Chemical Abstracts", 1985, 103, 1 page.
Esposito et al., "Patterns of Benzodiazepine Use in a Canadian Population Sample", Epidemiol Psichiatr Soc., 2009, 18(3), 248-254.
Etkin et al., "Common Abnormalities and Disorder-Specific Compensation During Implicit Regulation of Emotional Processing in Generalized Anxiety and Major Depressive Disorders", Am J Psychiatry, 2011, 168, 968-978.
Etkin, "Neurobiology of Anxiety: From Neural Circuits to Novel Solutions?", Depression and Anxiety, 2012, 29, 355-358.
European Patent Application No. 05787278.0: Office Action dated May 11, 2012, 4 pages.
European Patent Application No. 07726932.2: Office Action dated Sep. 8, 2009, 10 pages.
European Patent Application No. 08717514.7: Office Action dated Jun. 28, 2010, 6 pages.
European Patent Application No. 08717515.4: Official Communication dated May 3, 2010, 5 pages.
European Patent Application No. 11181481.1: Office Action dated Dec. 6, 2012, 6 pages.
Ezquerra et al., "Efficient Reagents for the Synthesis of 5-, 7-, and 5,7-Substituted Indoles Starting from Aromatic Amines: Scopes and Limitations", J Org Chem, 1996, 61, 5804-5812.
Fagni et al., "Identification and Functional Roles of Metabotropic Glutamate Receptor-Interacting Proteins", Seminars in Cell & Developmental Biology, 2004, 15(3), 289-298.
Farabaugh et al., "Anxious Depression and Early Changes in the Hamd-17 Anxietysomatization Factor Items and Antidepressant Treatment Outcome", Int Clin Psychopharmacol., Jul. 2010, 25(4), 214-217.
Faries et al., "The Double-Blind Variable Placebo Lead-in Period: Results from Two Antidepressant Clinical Trials", Journal of Clinical Psychopharmacology, 2001, 21, 561-568.
Fava et al., "Anxiety Disorders in Major Depression" Comprehensive Psychiatry 2000, 41(2), 97-102.
Fava et al., "Clinical Correlates and Symptom Patterns of Anxious Depression Among Patients with Major Depressive Disorder in Star*D", Psychological Medicine, 2004, 34, 1299-1308.
Fava et al., "Difference in Treatment Outcome in Outpatients with Anxious Versus Nonanxious Depression: A Star*D Report", Am J Psychiatry, 2008, 165, 342-351.
Fava et al., "Major Depressive Subtypes and Treatment Response", Biol. Psychiatry, 1997, 42, 568-576.
Fava et al., "Reliability and Validity of the Massachusetts General Hospital Cognitive and Physical Functioning Questionnaire", Psychother Psychosom, 2009, 78(2), 91-97.
Fava et al., "The Efficacy and Tolerability of Duloxetine in the Treatment of Anxious Versus Non-Anxious Depression: A Post-Hoc Analysis of an Open-Label Outpatient Study", Annals of Clinical Psychiatry, 2007, 19(3), 187-195.
Fava et al., "The Problem of the Placebo Response in Clinical Trials for Psychiatric Disorders: Culprits, Possible Remedies, and a Novel Study Design Approach", Psychother Psychosom, 2003, 72, 115-127.
Fava et al., "What Clinical and Symptom Features and Comorbid Disorders Characterize Outpatients with Anxious Major Depressive Disorder: A Replication and Extension", Can J Psychiatry, Nov. 2006, 51(13), 823-835.
Fawcett et al., "Anxiety Syndromes and Their Relationship to Depressive Illness", J Clin Psychiatry, Aug. 1983, 44(8 Pt 2), 8-11.
Fawcett et al., "The Detection and Consequences of Anxiety in Clinical Depression", J Clin Psychiatry, 1997, 58(Suppl 8), 35-40.
Fawcett, "Treating Impulsivity and Anxiety in the Suicidal Patient", Ann NY Acad Sci., Apr. 2001, 932, 94-102.
FDA Center for Drug Evaluation and Research, "Introduction and Drug History", Pharmacology Reviews, 2003, NDA 21-487.
Feeley et al., "Mglurs: A Target for Pharmacotherapy in Parkinson Disease", Experimental Neurology, 2003, 184(Suppl-6), S30-S36.
Feenstra et al., "Local Activation of Metabotropic Glutamate Receptors Inhibits the Handling-Induced Increased Release of Dopamine in the Nucleus Accumbens But Not That of Dopamine or Noradrenaline in the Prefrontal Cortex: Comparison with Inhibition of Ionotropic Receptors", Journal of Neurochemistry, 1998, 70(3), 1104-1113.
Feinberg et al., "The Metabotropic Glutamate (Mglu)2/3 Receptor Antagonist Ly341495 [2s-2-Amino-2-(1s,2s-2-Carboxycyclopropyl-1-Yl)-3-(Xanth-9-Yl)Propanoic Acid] Stimulates Waking and Fast Electroencephalogram Power and Blocks the Effects of the Mglu2/3 Receptor Agonist Ly379268 [(−)-2-Oxa-4-Aminobicyclo[3.1.0]Hexane-4,6-Dicarboxylate] in Rats", Jpet, 2005, 312, 826-833.
Feinberg et al., "The Selective Group Mglu2/3 Receptor Agonist Ly379268 Suppresses Rem Sleep and Fast Eeg in the Rat", Pharmacology, Biochemistry and Behavior, 2002, 73, 467-474.
Fell et al., "Evidence for the Role of Mglu2 Not Mglu3 Receptors in the Preclinical Antipsychotic Pharmacology of the Mglu2/3

(56) References Cited

OTHER PUBLICATIONS

Receptor Agonist Ly404039", Journal of Pharmacology & Experimental Therapeutics, 2008, 326, 209-217.
Fell et al., "Group II Metabotropic Glutamate Receptor Agonists and Positive Allosteric Modulators as Novel Treatments for Schizophrenia", Neuropharmacology 2012, 62, 1473-1483.
Fell et al., "In Vitro and in Vivo Evidence for a Lack of Interaction with Dopamine D2 Receptors by the Metabotropic Glutamate 2/3 Receptor Agonists 1s,2s,5r,6s-2-Aminobicyclo[3.1.0]Hexane-2,6-Bicaroxylate Monohydrate (Ly354740) and (−)-2-Oxa-4-Aminobicyclo[3.1.0] Hexane-4,6-Dicarboxylic Acid (Ly379268)", Jpet, 2009, 331, 1126-1136.
Fell et al., "N-(4-((2-(Trifluoromethyl)-3-Hydroxy-4-(Isobutyryl)Phenoxy)Methyl)Benzyl)-1-Methyl-1h-Imidazole-4-Carboxamide (Thiic), A Novel Metabotropic Glutamate 2 Potentiator with Potential Anxiolytic/Antidepressant Properties: in Vivo Profiling Suggests a Link Between Behavioral and Central Nervous System Neurochemical Changes", Jpet, 2011, 336, 165-177.
Fendt et al., "Metabotropic Glutamate Receptors are Involved in Amygdaloid Plasticity", European Journal of Neuroscience, 2002, 15(9), 1535-1541.
Fenton et al., "The Role of a Prescription in Anxiety Medication Use, Abuse, and Dependence", Am J Psychiatry, 2010, 167, 1247-1253.
Ferraguti et al., "Activation of the Extracellular Signal-Regulated Kinase 2 by Metabotropic Glutamate Receptors", European Journal of Neuroscience, 1999, 11(6), 2073-2082.
Ferraguti et al., "Metabotropic Glutamate 1 Receptor: Current Concepts and Perspectives", Pharmacol Rev, 2008, 60, 536-581.
Ferraguti et al., "Metabotropic Glutamate Receptors", Cell Tissue Res, 2006, 326, 483-504.
Ferris et al., "Interactions Between Ly354740, A Group II Metabotropic Agonist and the Gabaa-Benzodiazepine Receptor Complex in the Rat Elevated Plus-Maze", J Psychopharmacol, 2001, 15, 76-82.
Feyissa et al., "Elevated Level of Metabotropic Glutamate Receptor 2/3 in the Prefrontal Cortex in Major Depression", Prog. Neuropsychopharmacol. Biol. Psychiatry, 2010, 34(2), 279-283.
File, "The Use of Social Interaction as a Method for Detecting Anxiolytic Activity of Chlordiazepoxide-Like Drugs", Journal of Neuroscience Methods, 1980, 2(3), 219-38.
Filinger, "Effect of a Reserpine-Like Agent on the Release and Metabolism of [3h]Na in Cell Bodies and Terminals", Gen. Pharmac., 1994, 25, 1039-1043.
Fiorella et al., "The Role of the 5-Ht2a and 5-Ht2c Receptors in the Stimulus Effects of Hallucinogenic Drugs I: Antagonist Correlation Analysis", Psychopharmacology, 1995, 121, 347-356.
Fisher et al., "Antinociceptive Effects Following Intrathecal Pretreatment with Selective Metabotropic Glutamate Receptor Compounds in a Rat Model of Neuropathic Pain", Pharmacology, Biochemistry and Behavior, 2002, 73, 411-418.
Fisher et al., "Intrathecal Administration of the Mglur Compound, (S)-4cpg, Attenuates Hyperalgesia and Allodynia Associated with Sciatic Nerve Constriction Injury in Rats", Pain, 1998, 77(1), 59-66.
Fisher et al., "Non-Peptide Rgd Surrogates Which Mimic a Gly-Asp B-Turn: Potent Antagonists of Platelet Glycoprotein IIb-IIIa", J. Med. Chem., 1997, 40, 2085-2101.
Fisher et al., "The Contribution of Metabotropic Glutamate Receptors (Mglurs) to Formalin-Induced Nociception", Pain, 1996, 68(2-3), 255-263.
Flint et al., "Anxious Depression in Elderly Patients: Response to Antidepressant Treatment", Am J Geriatr Psychiatry, 1997, 5(2), 107-115.
Flohr et al., "Poly(Adp-Ribosyl)Ation Accelerates DNA Repair in a Pathway Dependent on Cockayne Syndrome B Protein", Nucleic Acids Research, 2003, 31(18), 5332-5337.
Flor et al., "Molecular Cloning, Functional Expression and Pharmacological Characterization of the Human Metabotropic Glutamate Receptor Type 2", Eur J Neurosci, 1995, 7, 622-629.
Fonnum et al., "Role of Glutamate and Glutamate Receptors in Memory Function and Alzheimer's Disease", Annals of the New York Academy of Sciences, 1995, 757, 475-486.
Forstl, "Clinical Features of Alzheimer's Disease", Eur Arch Psychiatry Clin Neurosci, 1999, 249, 288-290.
Fraley, "Positive Allosteric Modulators of the Metabotropic Glutamate Receptor 2 for the Treatment of Schizophrenia", Expert Opin. Ther. Patents, 2009, 19(9), 1259-1275.
Franco et al., "Novel Pharmacological Targets Based on Receptor Heteromers", Brain Research Reviews, 2008, 58, 475-482.
Franco et al., "The Two-State Dimer Receptor Model: A General Model for Receptor Dimers", Molecular Pharmacology, 2006, 69, 1906-1912.
Frank et al., "Depression and Health-Related Quality of Life for Low-Income African-American Women in the U.S.", Quality of Life Research, 2005, 14, 2293-2301.
Frauli et al., "Among the Twenty Classical L-Amino Acids, Only Glutamate Directly Activates Metabotropic Glutamate Receptors", Neuropharmacology, 2006, 50(2), 245-253.
Freedman et al., "Desensitization of G Protein-Coupled Receptors", Recent Progress in Hormone Research, 1996, 51, 319-351.
Freedman, "Schizophrenia", N. Engl. J. Med., 2003, 349, 1738-1749.
French et al., Subfield-Specific Immediate Early Gene Expression Associated with Hippocampal Long-Term Potentiation in Vivo. European Journal of Neuroscience 2001, 13(5), 968-976.
Fribourg et al., "Decoding the Signaling of a Gpcr Heteromeric Complex Reveals a Unifying Mechanism of Action of Antipsychotic Drugs", Cell, 2011, 147, 1011-1023.
Fricker et al., "Effects of N-Acetylaspartylglutamate (Naag) at Group II Mglurs and Nmdar", Neuropharmacology, 2009, 56(6-7), 1060-1067.
Fuentes et al., "Synthesis of Heterocyclic Compounds; XI. Regioselective. Synthesis of 4-Subtituted 2-Amino-5-Cyano-6-Methoxy-3-Benzenesulfonylpyridines", Synthesis, 1984, 768-770.
Fujii et al., "A Chemical LTP Induced by Co-Activation of Metabotropic and N-Methyl-D-Aspartate Glutamate Receptors in Hippocampal Ca1 Neurons", Brain Research, 2004, 999(1), 20-28.
Fujii et al., "Lactams. IX. Generation of Latam Carbonyl Function in 1,3-Disubstituted Piperidines by Mercuric Acetate-Edta Oxidation: Effects of Hydrocarbon Substituents at the 3-Postion", Chem. Pharm. Bull., 1977, 25(9), 2336-2342.
Fujimoto et al., "Motor and Cognitive Function Evaluation Following Experimental Traumatic Brain Injury", Neurosci. and Biobehav. Rev., 2004, 28, 365-378.
Fujita et al., "Studies on 1-Alkyl-2(1h)-Pyridone Derivatives XXXII. The Friedel-Crafts Reaction of 1-Alkyl-2(1h)-Pyridone Derivatives with Acid Anhydride", Journal of the Pharmaceutical Society of Japan, 1990, 110, 449-452.
Furukawa et al., "Antidepressants Plus Benzodiazepines for Major Depression", The Cochrane Collaboration, 2009, 31 pages.
Fuxe et al., "Integrated Signaling in Heterodimers and Receptor Mosaics of Different Types of GPCRS of the Forebrain: Relevance for Schizophrenia", J Neural Transm, 2009, 116(8), 923-939.
Galici et al., "A Selective Allosteric Potentiator of Metabotropic Glutamate (Mglu) 2 Receptors Has Effects Similar to an Orthosteric Mglu2/3 Receptor Agonist in Mouse Models Predictive of Antipsychotic Activity", J of Pharmacology and Experimental Therapeutics, 2005, 315(3), 1181-1187.
Galici et al., "Biphenyl-Indanone A, A Positive Allosteric Modulator of the Metabotropic Glutamate Receptor Subtype 2, Has Antipsychotic- and Anxiolytic-Like Effects in Mice", Journal of Phamacology and Experimental Therapeutics, 2006, 318(1),173-185.
Galimberti et al., "Long-Term Rearrangements of Hippocampal Mossy Fiber Terminal Connectivity in the Adult Regulated by Experience", Neuron 2006, 50, 749-763.
Gama et al., "Heterodimerization of Calcium Sensing Receptors with Metabotropic Glutamate Receptors in Neurons", J. Biol. Chem., 2001, 276(42), 39053-39059.
Garbaccio et al., "Discovery of Oxazolobenzimidazoles as Positive Allosteric Modulators for the Mglur2 Receptor", Acs Med Chem Lett, 2010, 1, 406-410.

(56) References Cited

OTHER PUBLICATIONS

Garrido-Sanabria et al., "Impaired Expression and Function of Group II Metabotropic Glutamate Receptors in Pilocarpine-Treated Chronically Epileptic Rats", Brain Res., 2008, 1240, 165-176.
Garriock et al., "Genetic Studies of Drug Response and Side Effects in the Star*D Study, Part 1", J Clin Psychiatry, 2009, 70(8), 1186-1187.
Gasparini et al., "Allosteric Modulators for Mglu Receptors", Curr Neuropharmacol, 2007, 5, 187-194.
Gavezzotti, "Are Crystal Structures Predictable?", Accounts of Chemical Research, 1994, 27, 309-314.
Gerber et al., "Metabotropic Glutamate Receptors: Intracellular Signaling Pathways", Current Opinion in Pharmacology, 2007, 7(1), 56-61.
Gerwitz et al., "Behavioral Evidence for Interactions Between a Hallucinogenic Drug and Group II Metabotropic Glutamate Receptors", Neuropsychopharmacology, 2000, 23, 569-576.
Gewald et al., "Heterocyclen Aus Ch-Aciden Nitrilen, VIII. 2-Amino-Thiophene Aus Methylenaktiven Nitrilen Carbonylverbindungen Und Schwefel", Chemische Berichte, 1966, 99, 94-100.
Gewald. "Heterocyclen Aus Ch-Aciden Nitrilen, VII. 2-Amino-Thiophene Aus A-Oxo-Mercaptanen Und Methylenaktiven Nitrilen", Chemische Berichte, 1965, 98, 3571-3577.
Geyer, "Are Cross-Species Measures of Sensorimotor Gating Useful for the Discovery of Procognitive Cotreatments for Schizophrenia?", Dialogues Clin Neurosci., 2006, 8(1), 9-16.
Ghammamy et al., "Cetyltrimethylammonium Bromochromate: A New and Efficient Oxidant for Organic Substrates", Synthetic Communications, 2007, 37, 599-605.
Ghose et al., "Differential Expression of Metabotropic Glutamate Receptors 2 and 3 in Schizophrenia: A Mechanism for Antipsychotic Drug Action?", Am J Psychiatry, 2009, 166, 812-820.
Gill et al., "Immunochemical Localization of the Metabotropic Glutamate Receptors in the Rat Heart", Brain Research Bulletin, 1999, 48(2), 143-146.
Gilling et al., "Potency, Voltage-Dependency, Agonist Concentration-Dependency, Blocking Kinetics and Partial Untrapping of the Uncompetitive N-Methyl-D-Aspartate (NMDA) Channel Blocker Memantine at Human Nmda (Glun1/Glun2a) Receptors", Neuropharmacology 2009, 56, 866-875.
Gilmour et al., "Diverse and Often Opposite Behavioural Effects of NMDA Receptor Antagonists in Rats: Implications for NMDA Antagonist Modelling of Schizophrenia", Psychopharmacology, 2009, 205, 203-216.
Giovannelli et al., "Comet Assay as a Novel Approach for Studying Dna Damage in Focal Cerebral Ischemia: Differential Effects of NMDA Receptor Antagonists and Poly(Adp-Ribose) Polymerase Inhibitors", Journal of Cerebral Blood Flow and Metabolism, 2002, 22, 697-704.
Girardi et al., "Differential Expression of Cerebellar Metabotropic Glutamate Receptors Mglur2/3 and Mglur4a After the Administration of a Convulsant Drug and the Adenosine Analogue Cyclopentyladenosine", Neurochem. Res., 2007, 32(7), 1120-1128.
Gjoni et al., "Receptor Activation Involving Positive Allosteric Modulation, Unlike Full Agonism, Does Not Result in Gabab Receptor Desensitization", Neuropharmacology, 2008, 55, 1293-1299.
Gleason et al., "Blockade of Phencyclidine-Induced Hyperlocomotion by Olanzapine, Clozapine, and Serotonin Receptor Subtype Selective Antagonists in Mice", Psychopharmacology, 1997, 129, 79-84.
Gleeson, "Generation of a Set of Simple, Interpretable Admet Rules of Thumb", J Med Chem, 2008, 51, 817-834.
Glick et al., "A Double-Blind Randomized Trial of Mood Stabilizer Augmentation Using Lamotrigine and Valproate for Patients with Schizophrenia Who Are Stabilized and Partially Responsive", J Clin Psychopharmacol, 2009, 29(3), 267-271.
Glick et al., "Concomitant Medications May Not Improve Outcome of Antipsychotic Monotherapy for Stabilized Patients with Non-Acute Schizophrenia", J Clin Psychiatry, 2006, 67(8), 1261-1265.
Glin et al., "The Intermediate Stage of Sleep in Mice", Physiology & Behavior, 1991, 50, 951-953.
Gnecco et al., "Oxidation of Chiral Non-Racemic Pyridinium Salts to Enantiopure 2-Pyridine and 3-Alkyl-2-Pyridones", Tetrahedron: Asymmetry, 1998, 9, 2027-2029.
Goff et al., "Lamotrigine as Add-On Therapy in Schizophrenia: Results of 2 Placebo-Controlled Trials", J Clin Psychopharmacol., 2007, 27(6), 582-589.
Goldberg et al., "Novel Non-Benzodiazepine Anxiolytics", Neuropharmacology, 1983, 22, 1499-1504.
Gonzalez-Maeso et al., "Identification of a Serotonin/Glutamate Receptor Complex Implicated in Psychosis", Nature, 2008, 452, 93-97.
Gonzalez-Maeso et al., "Psychedelics and Schizophrenia", Trends Neurosci., 2009, 32(4), 225-232.
Gonzalez-Maeso, "Hallucinogens Recruit Specific Cortical 5-Ht2a Receptor-Mediated Signaling Pathways to Affect Behavior", Neuron, 2007, 53, 439-452.
Gonzalez-Maeso, "Transcriptome Fingerprints Distinguish Hallucinogenic and Nonhallucinogenic 5-Hydroxytryptamine 2a Receptor Agonist Effects in Mouse Somatosensory Cortex", J. Neurosci., 2003, 23, 8836-8843.
Goodman et al., "The Pharmacological Basis of Therapeutics: Chapter 21—Pharmacotherapy of the Epilepsies", $12^{th}$ Edition, 2011, 27 pages.
Goodman et al., "The Yale-Brown Obsessive Compulsive Scale: I. Development, Use, and Reliability", Arch Gen Psychiatry, 1989, 46(11), 1006-1011.
Goodwin et al., "Advantages and Disadvantages of Combination Treatment with Antipsychotics", Nice. Eur Neuropsychoparmacol., 2009, 19(7), 520-532.
Gores et al., "Immunohistochemical Visualization of a Metabotropic Glutamate Receptor", Neuroreport, 1993, 4(3), 283-286.
Gorman et al., "A Hypothesized Role for Dendritic Remodeling in the Etiology of Mood and Anxiety Disorders", J Neuropsychiatry Clin Neurosci, 2010, 22(3), 256-264.
Gorman et al., "Anxiogenic Effects of Co2 and Hyperventilation in Patients with Panic Disorder", Am J Psychiatry, 1994, 151, 547-553.
Gorman, "Comorbid Depression and Anxiety Spectrum Disorders", Depression and Anxiety, 1996/1997, 4, 160-168.
Goudet et al., "Asymmetric Functioning of Dimeric Metabotropic Glutamate Receptors Disclosed by Positive Allosteric Modulators", J. Biol. Chem., 2005, 280(26), 24380-24385.
Goudet et al., "Metabotropic Receptors for Glutamate and Gaba in Pain", Brain Res. Rev., 2009, 60(1), 43-56.
Gouzoulis-Mayfrank, "Inhibition of Return in the Human 5ht2a Agonist and Nmda Antagonist Model of Psychosis", Neuropsychopharmacology, 2006, 31, 431-441.
Gouzoulis-Mayfrank, "Psychological Effects of (S)-Ketamine and N,N-Dimethyltryptamine (Dmt): A Double-Blind, Cross-Over Study in Healthy Volunteers", Pharmacopsychiatry, 2005, 38, 301-311.
Govek et al., "Benzazoles as Allosteric Potentiators of Metabotropic Glutamate Receptor 2 (Mglur2): Efficacy in an Animal Model for Schizophrenia", Bioorg. Med. Chem Lett., 2005, 15, 4068-4072.
Gozzi et al., "Differential Effects of Antipsychotic and Glutamatergic Agents on the Phmri Response to Phencyclidine", Neuropsychopharmacology, 2008, 33, 1690-1703.
Gray et al., "Functionalisation of 2-Methoxy-6-Methylpyridine", Synthetic Communications, 1994, 24(10), 1367-1379.
Gregory et al., "Allosteric Modulation of Metabotropic Glutamate Receptors: Structural Insights and Therapeutic Potential", Neuropharmacology, 2011, 60, 66-81.
Gregory et al., "Overview of Receptor Allosterism", Current Protocols in Pharmacology, 2010, 1.21.1-1.21.34.
Gregory et al., "Prefrontal Group II Metabotropic Glutamate Receptor Activation Decreases Performance on a Working Memory Task", Ann N Y. Acad. Sci., 2003, 1003, 405-409.
Grillon, et al., "Anxiolytic Effects of a Novel Group II Metabotropic Glutamate Receptor Agonist (Ly354740) in the Fear-Potentiated Startle Paradigm in Humans", Psychopharmacology, 2003, 168, 446-454.
Groebe, "Screening for Positive Allosteric Modulators of Biological Targets", Drug Discov. Today, 2006, 11(13-14), 632-639.

(56) References Cited

OTHER PUBLICATIONS

Grueter et al., "Group II and III Metabotropic Glutamate Receptors Suppress Excitatory Synaptic Transmission in the Dorsolateral Bed Nucleus of the Stria Terminalis", Neuropsychopharmacology, 2005, 30(7), 1302-1311.
Gu et al., "Distribution of Metabotropic Glutamate 2 and 3 Receptors in the Rat Forebrain: Implications in Emotional Responses and Central Disinhibition", Brain Res, 2008, 1197, 47-62.
Gu et al., "Expression of Functional Metabotropic Glutamate Receptors in Primary Cultured Rat Osteoblasts. Cross-Talk with N-Methyl-D-Aspartate Receptors", J. Biol. Chem., 2000, 275(44), 34252-34259.
Gueremy et al., "2-Amino-6-Chloro-4-(N-Methylpiperazino)Pyrimidines, Inhibitors of Spiroperidol Binding", Journal of Medicinal Chemistry, 1982, 25, 1459-1465.
Guerineau et al., "G-Protein-Mediated Desensitization of Metabotropic Glutamatergic and Muscarinic Responses in Ca3 Cells in Rat Hippocampus", Journal of Physiology, 1997, 500(Pt 2), 487-496.
Guerineau et al., "Activation of a Nonselective Cationic Conductance by Metabotropic Glutamatergic and Muscarinic Agonists in Ca3 Pyramidal Neurons of the Rat Hippocampus, J. Neurosci., 1995, 15(6), 4395-4407.
Guimaraes et al., "Ritanserin Facilitates Anxiety in a Simulated Public-Speaking Paradigm", Journal of Psychopharmacology, 1997, 11(3), 225-231.
Gunduz-Bruce, "The Acute Effects of Nmda Antagonism: from the Rodent to the Human Brain", Brain Res Rev, 2009, 60, 279-286.
Gupta et al., "Metabotropic Glutamate Receptor Protein Expression in the Prefrontal Cortex and Striatum in Schizophrenia", Synapse, 2005, 57(3), 123-131.
Gurevich et al., "Alterations in the Cortical Serotonergic System in Schizophrenia: A Postmortem Study", Biol. Psychiatry, 1997, 42, 529-545.
Haak et al., "Metabotropic Glutamate Receptor Activation Modulates Kainate and Serotonin Calcium Response in Astrocytes", J. Neurosci., 1997, 17(5), 1825-1837.
Hackler et al., "Selective Potentiation of the Metabotropic Glutamate Receptor Subtype 2 Blocks Phencyclidine-Induced Hyperlocomotion and Brain Activation", Neuroscience, 2010, 168(1), 209-218.
Hamaguchi et al., "Effects of Hetero Atom Substituents in the Decomposition of Pyrazolines: Abnormal Behavior of Methoxy Group Compared with Arylthio of Arylseleno Group.", Heterocycles, 1986, 24, 2111-2115.
Hamilton, "A Rating Scale for Depression", J Neurol Neurosurg Psychiatry, 1960, 23, 56-62.
Hamilton, "Diagnosis and Rating of Anxiety, in Studies of Anxiety", MM Lader, Ed., Meedley Bros., Kent, 1969, 76-79.
Hamilton, "Standardised Assessment and Recording of Depressive Symptoms", Psychiatr Neurol Neurochir, 1969, 72(2), 201-205.
Hamilton, "The Assessment of Anxiety States by Rating", Br J Med Psycho!, 1959, 32(1), 50-55.
Hampson et al., "Characterization of Two Alternatively Spliced Forms of a Metabotropic Glutamate Receptor in the Central Nervous System of the Rat", Neuroscience, 1994, 60(2), 325-336.
Handley et al., "Effects of Alpha-Adrenoceptor Agonists and Antagonists in a Maze-Exploration Model of Fear-Motivated Behavior", Naunyn-Schmied. Arch. Pharmacol., 327, 1-5, 1984.
Hanfeld et al., "Synthese Von 3-Cyan-6-Methyl-4-Pyridyl-Und 3-Cyan-4-Methyl-6-Pyridyl-Pyrid-2(1h)-Onen Und-Thionen", Pharmazie, 1988, 43, 762-764.
Hanna et al., "Differentiating the Roles of Mglu2 and Mglu3 Receptors Using Ly541850, an Mglu2 Agonist/Mglu3 Antagonist", Neuropharmacology, 2012, 1-8.
Hannah et al., "Heterocomplex Formation of 5-Ht2a-Mglu2 and Its Relevance for Cellular Signaling Cascades", Neuropharmacology, 2012, 62, 2184-2191.
Hansen et al., "Glutamate Joins the Ranks of Immunomodulators", Nature Medicine, 2010, 16(8), 856-858.

Happe et al., "Agonist-Stimulated [35s]Gtpgammas Autoradiograph: Optimization for High Sensitivity", Eur J Pharmacol, 2001, 422, 1-13.
Harald et al., "Meta-Review of Depressive Subtyping Models", Journal of Affective Disorders, 2012, 139, 126-140.
Harich, "Stimulation of the Metabotropic Glutamate 2/3 Receptor Attenuates Social Novelty Discrimination Deficits Induced by Neonatal Phencyclidine Treatment", Psychopharmacology, 2007, 192, 511-519.
Haro et al., "The Clinical Global Impression-Schizophrenia Scale: A Simple Instrument to Measure the Diversity of Symptoms Present in Schizophrenia", Acta Psychiatr Scand Suppl., 2003, 416, 16-23.
Harriman et al., "Synthesis of 4-Substituted 4-Arylpiperidines", Tetrahedron Letters, 2000, 41, 8853-8856.
Harrison et al., "The Group II Metabotropic Glutamate Receptor 3 (Mglur3, Mglu3, Grm3): Expression, Function and Involvement in Schizophrenia", J. Psychopharmacol., 2008, 22(3), 308-322.
Harrison, "Metabotropic Glutamate Receptor Agonists for Schizophrenia", The British Journal of Psychiatry, 2008, 192, 86-87.
Hartveit et al., "Expression of the Mrna of Seven Metabotropic Glutamate Receptors (Mglur1 to 7) in the Rat Retina. An in Situ Hybridization Study on Tissue Sections and Isolated Cells", Eur. J Neurosci., 1995, 7(7), 1472-1483.
Hascup et al., "An Allosteric Modulator of Metabotropic Glutamate Receptors (Mglur2), (+)-Tfmpip, Inhibits Retraint Stress-Induced Phasic Glutamate Release in Rat Prefrontal Cortex", Journal of Neurochemistry, 2012, 122, 619-627.
Hashimoto et al., "Increased Levels of Glutamate in Brains from Patients with Mood Disorders", Biol Psychiatry, 2007, 62(11), 1310-1316.
Hashimoto, "Emerging Role of Glutamate in the Pathophysiology of Major Depressive Disorder", Brain Research Reviews, 2009, 61, 105-123.
Hasin et al., "Epidemiology of Major Depressive Disorder. Results from the National Epidemiologic Survey on Alcoholism and Related Conditions", Arch Gen Psychiatry, 2005, 62, 1097-1106.
Hasler et al., "Reduced Prefrontal Glutamate/Glutamine and Gamma-Aminobutyric Acid Levels in Major Depression Determined Using Proton Magnetic Resonance Spectroscopy", Arch Gen Psychiatry, 2007, 64(2), 193-200.
Hawgood et al., "Anxiety Disorders and Suicidal Behavior: An Update", Current Opinion in Psychiatry, 2008, 21, 51-64.
He et al., "Conformational Color Polymorsphism and Control of Crystallization of 5-Methyl-2-[(4-Methyl-2-Mitrophenyl0amino}-3-Thiophenecarbonitrile", Journal of Pharmaceutical Sciences, 2001, 90(3), 371-388.
Helton et al., "Anxiolytic and Side-Effect Profile for Ly354740: A Potent, Highly Selective, Orally Active Agonist for Group II Metobotropic Glutamate Receptors", Journal of Phamacology and Experimental Therapeutics, 1998, 284(2), 651-660.
Helton et al., "Ly354740: A Metabotropic Glutamate Receptor Agonist Which Ameliorates Symptoms of Nicotine Withdrawal in Rats", Neuropharmacology, 1997, 36(11/12), 1511-1516.
Hemstapat et al., "A Novel Family of Potent Negative Allosteric Modulators of Group II Metabotropic Glutamate Receptors", Jpet, 2007, 322, 254-264.
Henley et al., "Characterization of the Allosteric Modulatory Protein Associated with Non-Nmda Receptors", Biochemical Society Transactions, 1993, 21(1), 89-93.
Henry et al., "The Mglur5 Antagonist Mpep, But Not the Mglur2/3 Agonist Ly314582, Augments Pcp Effects on Prepulse Inhibition and Locomotor Activity", Neuropharmacology, 2002, 43(8), 1199-209.
Herdeis et al., "[4+2] Cycloaducts of 5-Benzyloxy-2-Pyrindone with Electron Deficient Dienophiles. Regio- and Stereochemistry", Heterocycles, 1989, 29(2), 287-296.
Herdeis et al., "A Facile Entry to the 2-Azabicyclo[2.2.2]Octane-6-One Skeleton via [4+2]-Cycloaddition", Synthesis, Jan. 1988, 76-78.
Herdeis et al., "A Three-Step Synthesis of B-Aminolaevulinic Acid", Arch. Pharm., 1984, 317, 304-306.

(56) References Cited

OTHER PUBLICATIONS

Herdeis et al., "Stereochemistry and Reactivity of Phenylsulfonyl-Substituted 2-Azabicyclo[2.2.2]Octan-6-Ones", Arch. Pharm., 1990, 323, 937-942.
Heresco-Levy, "Glutamatergic Neurotransmission Modulators as Emerging New Drugs for Schizophrenia", Expert Opin Emerging Drugs, 2005, 10(4), 827-844.
Hermann et al., "Human Eeg Gamma Oscillations in Neuropsychiatric Disorders", Clinical Neurophysiology, 2005, 116, 2719-2733.
Hermans et al., "Structural, Signalling and Regulatory Properties of the Group I Metabotropic Glutamate Receptors: Prototypic Family C G-Protein-Coupled Receptors", Biochem. J., 2001, 359, 465-484.
Herminghaus, "Brain Metabolism in Alzheimer Disease and Vascular Dementia Assessed by In Vivo Proton Magnetic Resonance Spectroscopy", Psychiatry Research Neuroimaging, 2003, 123, 183-190.
Herrero et al., "Functional Switch from Facilitation to Inhibition in the Control of Glutamate Release by Metabotropic Glutamate Receptors", J. Biol. Chem., 1998, 273(4), 1951-1958.
Herrero et al., "Positive Feedback of Glutamate Exocytosis by Metabotropic Presynaptic Receptor Stimulation", Nature, 1992, 360(6400), 163-166.
Herrero et al., "Rapid Desensitization of the Metabotropic Glutamate Receptor that Facilitates Glutamate Release in Rat Cerebrocortical Nerve Terminals", European Journal of Neuroscience, 1994, 6(1), 115-120.
Hettema "The Nosologic Relationship Between Generalized Anxiety Disorder and Major Depression", Depression and Anxiety, 2008, 25, 300-316.
Hetzenauer et al., "Individual Contribution of Metabotropic Glutamate Receptor (Mglu) 2 and 3 to C Expression Pattern Evoked by Mglu2/3 Antagonism", Psychopharmacology, 2008, 201, 1 13.
Hickinbottom, "Reactions of Organic Compounds", Gonti: Moscow, 1939, 360-2 (Russian with English Translation).
Higashida et al., "Subtype-Specific Coupling with Adp-Ribosyl Cyclase of Metabotropic Glutamate Receptors in Retina, Cervical Superior Ganglion and Ng108-15 Cells", Journal of Neurochemistry, 2003, 85, 1148-1158.
Higgins, "Pharmacological Manipulation of Mglu2 Receptors Influences Cognitive Performance in the Rodent", Neuropharmacology, 2004, 46, 907-917.
Hijzen et al., "Predictive Validity of the Potentiated Startle Response as a Behavioral Model for Anxiolytic Drugs", Psychopharmacology, 1995, 118, 150-154.
Hirao et al., "Preparation of Optically Active 8,8'-Disubstituted 1,1'-Biisoquinoline", Heterocycles, 1996, 42(1), 415-422.
Hlavackova et al., "Evidence for a Single Heptahelical Domain Being Turned on Upon Activation of a Dimeric GPCR", Embo, 2005, 24, 499-509.
Hoang et al., "Expression of Metabotropic Glutamate Receptors in Nodose Ganglia and the Nucleus of the Solitary Tract", Am J Physiol Heart Circ Physiol, 2001, 281, 457-462.
Hoeben et al., "Prediction of Serotonin 2a Receptor (5-$Ht_{2a}$r) Occupancy in Man From Nonclinical Pharmacology Data. Exposure Vs. 5-$Ht_{2a}$r Occupancy Modeling Used to Help Design a Positron Emission Tomography (Pet) Study in Healthy Male Subjects", Abstract, 2013 Annual Meeting of the Population Approach Group in Europe, 2 pages.
Hoffman et al., "Human and Economic Burden of Generalized Anxiety Disorder", Depression and Anxiety, 2008, 25, 72-90.
Hofmeijer-Sevink et al., "Clinical Relevance of Comorbidity in Anxiety Disorders: A Report From the Netherlands Study of Depression and Anxiety (NESDA)", Journal of Affective Disorders, 2012, 137, 106-112.
Hohnadel et al., "Effect of Repeated Nicotine Exposure on High-Affinity Nicotinic Acetylcholine Receptor Density in Spontaneously Hypertensive Rats", Neuroscience Letters, 2005, 382, 158-163.
Holcomb et al., "Effects of Noncompetitive Nmda Receptor Blockade on Anterior Cingulate Cerebral Blood Flow in Volunteers with Schizophrenia", Neuropsychopharmacology, 2005, 30, 2275-2282.

Holden, "Excited by Glutamate", Science, Jun. 2003, 300, 1866-1868.
Holloway et al., "Prenatal Stress Induces Schizophrenia-Like Alterations of Serotonin 2a and Metabotropic Glutamate 2 Receptors in the Adult Offspring: Role of Maternal Immune System", J. Neurosci., 2013, 33(3), 1088-1098.
Holscher et al., "Metabotropic Glutamate Receptor Activation and Blockade: Their Role in Long-Term Potentiation, Learning and Neurotoxicity", Neuroscience & Biobehavioral Reviews, 1999, 23(3), 399-410.
Homayoun et al., "Activation of Metabotropic Glutamate 2/3 Receptors Reverses the Effects of Nmda Receptor Hypofunction on Prefrontal Cortex Unit Activity in Awake Rats", J. Neurophysiol., 2005, 93(4), 1989-2001.
Homayoun et al., "Group 5 Metabotropic Glutamate Receptors: Role in Modulating Cortical Activity and Relevance to Cognition", European Journal of Pharmacology, 2010, 639, 33-39.
Homayoun et al., "Orbitofrontal Cortex Neurons as a Common Target for Classic and Glutamatergic Antipsychotic Drugs", Proc. Natl. Acad. Sci. USA, 2008, 105(46), 18041-18046.
Honer et al., "Clozapine Alone Versus Clozapine and Risperidone with Refractory Schizophrenia", N Engl J Med., 2006, 354(5), 472-482.
Hook, "Neuroproteases in Peptide Neurotramission and Neurodegenerative Diseases Applications to Drug Discovery Research", Biodrugs, 2006, 20, 105-119.
Hopkins "Is There a Path Forward for Mglu2 Positive Allosteric Modulators for the Treatment of Schizophrenia?", ACS Chem. Neurosci., 2013, 4, 211-213.
Horiguchi et al., "Interaction of Mglu2/3 Agonism with Clozapine and Lurasidone to Restore Novel Object Recognition in Subchronic Phencyclidine-Treated Rats", Psychopharmacology, 2011, 217, 13-24.
Horiguchi et al., "Interactions Among the Atypical Antipsychotic Drug (APD), Lurasidone, 5-HT1A and Metabotropic Glutamate Receptor 2/3 (Mglur2/3) Agonism, and 5-HT2A Antagonism, to Attenuate Phencyclidine (PCP)-Induced Deficit in Rat Novel Object Recognition (NOR)" Poster 610.12 Presented at the 40th Annual Meeting of Society for Neuroscience, 2010, 1 page.
Hostetler, "PET Tracer Discovery for Subtype-Specific Mglur Allosteric Modulators: Challenges and Insights" Presentation Slides 7th International Meeting on Metabotropic Glutamate Receptors, Merck, Oct. 2011, 8 pages.
Houamed et al., "Cloning, Expression, and Gene Structure of a G Protein-Coupled Glutamate Receptor from Rat Brain", Science, 1991, 252(5010), 1318-1321.
Hovelso, "Therapeutic Potential of Metabotropic Glutamate Receptor Modulators", Current Neuropharmacology, 2012, 10, 12-48.
Hsia et al., "Evidence Against a Role for Metabotropic Glutamate Receptors in Mossy Fiber Ltp: the Use of Mutant Mice and Pharmacological Antagonists", Neuropharmacology, 1995, 34, 1567-1572.
Hu et al., "Altered Profile of Gene Expression in Rat Hearts Induced by Chronic Nicotine Consumption", Biochemical and Biophysical Research Communications, 2002, 297, 729-736.
Hu et al., "Emotion Enhances Learning via Norepinephrine Regulation of Ampa-Receptor Trafficking", Cells, 2007, 131, 160-173.
Hu et al., "Glutamate Receptors in Preclinical Research on Alzheimer's Disease: Update on Recent Advances", Pharmacology, Biochemistry and Behavior, 2012, 100, 855-862.
Hu et al., "Identification of Glutamate Receptors and Transporters in Mouse and Human Sperm", Journal of Andrology, 2004, 25(1), 140-6.
Hu et al., "Pyrimidine Methyl Anilines: Selective Potentiators for the Metabotropic Glutamate 2 Receptor", Bioorganic & Medicinal Chemistry Letters, 2004, 14, 5071-5074.
Hu et al., "The Regulation of Dopamine Transmission by Metabotropic Glutamate Receptors", J. Pharmacol. Exp. Ther., 1999, 289(1), 412-416.
Huang et al., "Alzheimer Mechanisms and Therapeutic Strategies", Cell, 2012, 148, 1204-1222.
Huang et al., "Inhibition of Microtubule Formation by Metabotropic Glutamate Receptors", Journal of Neurochemistry, 2000, 74(1), 104-113.

(56) References Cited

OTHER PUBLICATIONS

Huang et al., "Interdomain Movements in Metabotropic Glutamate Receptor Activation", Proc Natl Acad Sci USA, 2011, 108, 15480-15485.
Huang et al., "Potentiation of the Novel Atypical Antipsychotic Drug Lurasidone-Induced Dopamine Efflux in Rat Medial Prefrontal Cortex and Hippocampus by DA D1 and Mglur2/3 Agonism but not D3 Receptor Antagonism" Poster 610.13 Presented at the 40$^{th}$ Annual Meeting of Society for Neuroscience, Nov. 2010, 1 page.
Huang et al., "Prevalence, Correlates, and Comorbidity of Nonmedical Prescription Drug Use and Drug Use Disorders in the United States: Results of the National Epidemiologic Survey on Alcohol and Related Conditions", J Clin Psychiatry, 2006, 67, 1062-1073.
Hucho et al., "Epac Mediates a Camp-to-Pkc Signaling in Inflammatory Pain: An Isolectin B4(+) Neuron-Specific Mechanism", Journal of Neuroscience, 2005, 25(26), 6119-6126.
Hucho et al., "Estrogen Controls Pkce-Dependent Mechanical Hyperalgesia Through Direct Action on Nociceptive Neurons", European Journal of Neuroscience, 2006, 24, 527-534.
Huey et al., "Development of Subtle Psychotic Symptoms with Memantine: A Case Report", J Clin Psychiatry, 2005, 66, 658-659.
Hughes, "Progress in the Mitsunobu Reaction. A Review", Organic Preparations and Procedures International, 1996, 127-164.
Hughes, "The Mitsunobu Reaction", Organinc Reactions, 1992, 42, 335-656.
Huntington Study Group, "Dosage Effects of Riluzole in Huntington's Disease: A Multicenter Placebo-Controlled Study", Neurology, 2003, 61, 1551-1556.
Iacovelli et al., "Regulation of Group II Metabotropic Glutamate Receptors by G Protein-Coupled Receptor Kinases: Mglu2 Receptors are Resistant to Homologous Desensitization", Mol Pharmacol., 2009, 75(4), 991-1003.
Iglesias et al., "Metabotropic Glutamate Receptor/Phospholipase C System in Female Rat Heart", Brain Res., 2007, 1153, 1-11.
Imogai et al., "Cis-Disubstituted Cyclopropanes via Asymmetric Catalytic Cyclopropenation: Synthesis of Cyclopropyl-Dehydroamino Acids and of Dictyopterene C.", Helvetica Chimica Acta, 1998, 81, 1754-1764.
Imre et al., "Dose-Response Characteristics of Ketamine Effect on Locomotion, Cognitive Function and Central Neuronal Activity", Brain Res. Bull, 2006, 69(3), 338-345.
Imre et al., "Effects of the Mglur2/3 Agonist Ly379268 on Ketamine-Evoked Behaviours and Neurochemical Changes in the Dentate Gyrus of the Rat", Pharmacology, Biochemistry and Behavior, 2006, 84, 392-399.
Imre et al., "Subchronic Administration of Ly354740 Does Not Modify Ketamine-Evoked Behavior and Neuronal Activity in Rats", Eur. J Pharmacol., 2006, 544(1-3), 77-81.
Imre, "The Preclinical Properties of a Novel Group II Metabotropic Glutamate Receptor Agonist Ly379268", CNS Drug Reviews, 2007, 13(4), 444-464.
Insel, et al., "Research Domain Criteria (Rdoc): Toward a New Classification Framework for Research on Mental Disorders", Am. J. Psychiatry, Jul. 2010, 167(7), 748-751.
Inta et al., "Mice with Genetically Altered Glutamate Receptors as Models of Schizophrenia: A Comprehensive Review", Neuroscience & Biobehavioral Reviews, 2010, 34(3), 285-94.
International Patent Application No. PCT/EP2007/52442: International Search Report dated Sep. 7, 2007, 6 pages.
International Patent Application No. PCT/EP2008/52766: International Search Report dated Jun. 10, 2008, 3 pages.
International Patent Application No. PCT/EP2008/52767: International Search Report dated Jul. 2, 2008, 13 pages.
International Patent Application No. PCT/EP2008/52768: International Search Report dated Jun. 10, 2008, 3 pages.
International Patent Application No. PCT/EP2009/06326: International Search Report dated Oct. 26, 2009, 15 pages.
International Patent Application No. PCT/EP2011/69640: International Search Report dated Dec. 23, 2011, 3 pages.
International Patent Application No. PCT/EP2011/69641: International Search Report dated Dec. 23, 2011, 3 pages.
International Patent Application No. PCT/EP2011/69643: International Search Report dated Dec. 27, 2011, 4 pages.
International Patent Application No. PCT/EP2011/69654: International Search Report dated Dec. 23, 2011 3 pages.
Ionescu et al., "Defining Anxious Depression: A Review of the Literature", CNS Spectrums, 2013, 1-9.
Iovieno et al., "Does the Presence of an Open-Label Antidepressant Treatment Period Influence Study Outcome in Clinical Trials Examining Augmentation/Combination Strategies in Treatment Partial Responders/Nonresponders with Major Depressive Disorder?", J Clin Psychiatry, 2012, 8 pages.
Irifune et al., "Riluzole, a Glutamate Release Inhibitor, Induces Loss of Righting Reflex, Antinociception, and Immobility in Response to Noxious Stimulation in Mice", Anesthesia & Analgesia, 2007, 104(6), 1415-1421.
Jablensky et al., "Polymorphisms Associated with Normal Memory Variation Also Affect Memory Impairment in Schizophrenia", Genes, Brain and Behavior, 2011, 10, 410-417.
Jain, et al., "A One-Step Preparation of Functionalized 3-Cyano-2-Pyridones", Tetrahedron Letters, 1995, 36 (19), 3307-3310.
Jane et al., "Potent Antagonists at the L-AP4- and (1s,3s)-ACPD-Sensitive Presynaptic Metabotropic Glutamate Receptors in the Neonatal Rat Spinal Cord", Neuropharmacology, 1996, 35(8), 1029-1035.
Janssens et al., "Glutamate Receptor Subunit Expression in Primary Neuronal and Secondary Glial Cultures", J Neurochem, 2001, 77, 1457-1474.
Japanese Patent Application No. 2007-531759: Office Action dated Jun. 27, 2011, 12 pages.
Japanese Patent Application No. 2010-553485: Office Action dated Jul. 11, 2013, 3 pages.
Javitt, "Glutamatergic Theories of Schizophrenia", ISR J Psychiatry Relat Sci, 2010, 47(1), 4-16.
Javitt et al., "Recent Advances in the Phenylcyclidine Model of Schizophrenia", Am J Psychiatry, 1991, 148, 1301-1308.
Jenkins et al., "Disturbances in Social Interaction Occur Along with Pathophysiological Deficits Following Sub-Chronic Phencyclidine Administration in the Rat", Behavioural Brain Research, 2008, 194, 230-235.
Jensen et al., "Allosteric Modulation of the Calcium-Sensing Receptor", Current Neuropharmacology, 2007, 5, 180-186.
Jhee et al., "B-amyloid therapies in Alzheimer's disease", Expert Opinion on Investigational Drugs, 2001, 10, 593-605.
Jin et al., "The Mglur2 Positive Allosteric Modulator Bina Decreases Cocaine Self-Administration and Cue-Induced Cocaine-Seeking and Counteracts Cocaine-Induced Enhancement of Brain Reward Function in Rats", Neuropsych., 2010, 35(10), 2021-2036.
Jingami et al., "Structure of the Metabotropic Glutamate Receptor", Current Opinion in Neurobiology, 2003, 13(3), 271-278.
Joffe et al., "Anxious and Nonanxious Depression", Am J Psychiatry, 1993, 150, 1257-1258.
Joffe et al., "Lifetime History of Depression and Anxiety Disorders as a Predictor of Quality of Life in Midlife Women in the Absence of Current Illness Episodes", Arch Gen Psychiatry, 2012, 69(5), 484-492.
Johansen et al., "Excitatory Amino Acid Receptor Ligands: Resolution, Absolute Stereochemistry, and Enantiopharmacology of 2-Amino-3-(4-Butyl-3-Hydroxyisoxazol-5-Yl)Propionic Acid", J of Medicinal Chem, 1998, 41(6), 930-939.
John et al., "Rapid Changes in Glutamate Levels in the Posterior Hypothalamus Across Sleep-Wake States in Freely Behaving Rats", American Journal of Physiology—Regulatory Integrative & Comparative Physiology, 2008, 295(6), R2041-2049.
Johnson et al., "Activation of Group II Metabotropic Glutamate Receptors Induces Long-Term Depression of Excitatory Synaptic Transmission in the Substantia Nigra Pars Reticulata", Neuroscience Letters, 2011, 504, 102-106.
Johnson et al., "Allosteric Modulators of Metabotropic Glutamate Receptors: Lessons Learnt From Mglu1, Mglu2 and Mglu5 Potentiators and Antagonists", Biochemical Society Transactions, 2004, 32(5) 881-887.

(56) References Cited

OTHER PUBLICATIONS

Johnson et al., "Discovery of Allosteric Potentiators for the Metabotropic Glutamate 2 Receptor: Synthesis and Subtype Selectivity of N-(4-(2-Methoxyphenoxy)Phenyl)-N-(2,2,2-Trifluorethylsulfonyl)Pyrid-3-Ylmethyl-Amine", J. Med. Chem., 2003, 46, 3189-3192.

Johnson et al., "Disruption of Gabaergic Tone in the Dorsomedial Hypothalamus Attenuates Responses in a Subset of Serotonergic Neurons in the Dorsal Raphe Nucleus Following Lactate-Induced Panic", J Psychopharmacol, 2008, 22, 642-652.

Johnson et al., "Glutamate Receptors as Therapeutic Targets for Parkinson's Disease", CNS Neurol Disord Drug Targets, 2009, 8, 475-491.

Johnson et al., "Group II Metabotropic Glutamate Receptor Type 2 Allosteric Potentiators Prevent Sodium Lactate-Induced Panic Like Response in Panic-Vulnerable Rats", J Psychopharmacol, 2013, 27, 152-161.

Johnson et al., "Metabotropic Glutamate 2 Receptor Potentiators: Receptor Modulation, Frequency-Dependent Synaptic Activity, and Efficacy in Preclinical Anxiety and Psychosis Model(S)", Psychopharmacology, 2005, 179, 271-283.

Johnson et al., "Selective, Non-Amino Acid Allosteric Mglu2 Receptor Potentiators Inhibit Dural Plasma Protein Extravasation; A Potential Role in the Treatment of Migraine", Abstracts/Neuropharmacology, 2002, 43, 291.

Johnson et al., "Species Variations in Transmembrane Region V of the 5-Hydroxytryptamine Type 2a Receptor Alter the Structure-Activity Relationship of Certain Ergolines and Tryptamines", Molecular Pharmacology, 1994, 45, 277-286.

Jones et al., "A Rotarod Suitable for Quantitative Measurements of Motor Incoordination in Naïve Mice", Naunyn Schmiedebergs Arch. Exper. Pathol. Pharmacol., 1968, 259, 211.

Jones et al., "Analgesic Effects of the Selective Group II (Mglu2/3) Metabotropic Glutamate Receptor Agonists Ly379268 and Ly389795 in Persistent and Inflammatory Pain Models After Acute and Repeated Dosing", Neuropharmacology, 2005, 49, 206-218.

Jones et al., "Discovery, Synthesis, and Structure-Activity Relationship Development of a Series of N-4-(2,5-Dioxopyrrolidin-1-Yl)Phenylpicolinamides (Vu0400195, Ml182): Characterization of a Novel Positive Allosteric Modulator of the Metabotropic Glutamate Receptor 4 (Mglu4) with Oral Efficacy in an Antiparkinsonian Animal Model", J Med Chem, 2011, 54, 7639-7647.

Jones et al., "The Mglur2/3 Agonist Ly379268 Reverses Post-Weaning Social Isolation-Induced Recognition Memory Deficits in the Rat", Psychopharmacology, 2011, 214, 269-283.

Julio-Pieper et al., "Exciting Times Beyond the Brain: Metabotropic Glutamate Receptors in Peripheral and Non-Neural Tissues", Pharmacological Review, 2011, 63, 35-58.

Kagaya et al., "Heterologous Supersensitization Between Serotonin2 and Alpha 2-Adrenergic Receptor-Mediated Intracellular Calcium Mobilization in Human Platelets", Journal of Neural Transmission, 1992, 88(1), 25-36.

Kahn et al., "Group 2 Metabotropic Glutamate Receptors Induced Long Term Depression in Mouse Striatal Slices", Neurosci. Lett., 2001, 316(3), 178-182.

Kalivas et al., "Repeated Cocaine Administration Alters Extracellular Glutamate in the Ventral Tegmental Area", Journal of Neurochemistry, 1998, 70(4), 1497-1502.

Kambe et al., "A Convenient Method for the Preparation of 2-Pyridone Derivatives", Synthesis, 1977, 12, 841-842.

Kappe et al., "Aktive Malonester Als Synthons Fur Heterocyclen: Eine Methode Zur Herstellung Von 4-Hydroxy-2(1h)-Pyridonen", Journal of Heterocyclic Chemistry, 1988, 463-468.

Kapur et al., "From Dopamine to Salience to Psychosis—Linking Biology, Pharmacology and Phenomenology of Psychosis", Schizophr. Res., 2005, 79, 59-68.

Karlsson et al., "Loss of Glial Glutamate and Aspartate Transporter (Excitatory Amino Acid Transporter 1) Causes Locomotor Hyperactivity and Exaggerated Responses to Psychotomimetics: Rescue by Haloperidol and Metabotropic Glutamate 2/3 Agonist", Biol. Psychiatry, 2008, 64(9), 810-814.

Kato "Molecular Genetics of Bipolar Disorder and Depression" Psychiatry and Clinical Neurosciences 2007, 61, 3-19.

Katon et al., "Major Depression: The Importance of Clinical Characteristics and Treatment Response to Prognosis", Depression and Anxiety, 2010, 27, 19-26.

Kaupmann et al., "Expression Cloning of Gaba(B) Receptors Uncovers Similarity to Metabotropic Glutamate Receptors", Nature, 1997, 386(6622), 239-246.

Kawabata et al., "Diversity of Calcium Signaling by Metabotropic Glutamate Receptors", J. Biol. Chem., 1998, 273(28), 17381-17385.

Kearney et al., "Intrasubthalamic Nucleus Metabotropic Glutamate Receptor Activation: A Behavioral, FOS Immunohistochemical and [14c]2-Deoxyglucose Autoradiographic Study", Neuroscience, 2000, 95(2), 409-416.

Kearney et al., "Metabotropic Glutamate Agonist-Induced Rotation: A Pharmacological, FOS Immunohistochemical, and [14c]-2-Deoxyglucose Autoradiographic Study", J Neurosci., 1997, 17(11), 4415-4425.

Kehne et al., "Anxiolytic Effects of Buspirone and Gepirone in the Fear-Potentiated Startle Paradigm", Psychopharmacology, 1988, 94, 8-13.

Keller et al., "Anxiety Symptom Relief in Depression Treatment Outcomes", J Clin Psychiatry, 1995, 56(Suppl 6), 22-29.

Kellner et al., "Effects of Metabotropic Glutamate2/3 Receptor Agonist (Ly544344/Ly354740) on Panic Anxiety Induced by Cholecystokinin Tetrapeptide in Health Humans: Preliminary Results", Psychopharmacology, 2005, 179, 310-315.

Kenakin et al., "Seven Transmembrane Receptors as Shapeshifting Proteins: the Impact of Allosteric Modulation and Functional Selectivity on New Drug Discovery", Pharmacological Reviews, 2010, 62(2), 265-304.

Kenakin et al., "Signalling Bias in New Drug Discovery: Detection, Quantification and Therapeutic Impact", Nature Reviews Drug Discovery, 2013, 12, 205-216.

Kenakin, "A Holistic View of GPCR Signaling", Nature Biotechnology, 2010, 28, 928-929.

Kenakin, "Allosteric Agonist Modulators", Journal of Receptors and Signal Transduction, 2007, 27(4), 247-259.

Kenakin, "Allosteric Modulators: The New Generation of Receptor Antagonist", Molecular Interventions, Aug. 2004, 4(4), 222-229.

Kenakin, "Seven Transmembrane Receptors as Nature's Prototype Allosteric Protein: De-Emphasizing the Geography of Binding" Molecular Pharmacology 2008, 74, 541-543.

Kendler et al, "Major Depression and Generalized Anxiety Disorder: Same Genes, (Partly) Different Environments?", Arch Gen Psychiatry, 1992, 49, 716-722.

Kendler, "The Nosologic Validity of Paranoia (Simple Delusional Disorder)", Arch Gen Psychiatry, 1980, 37, 699-706.

Kennett et al., "Evidence That 5-Ht2c Receptor Antagonists are Anxiolytic in the Rat Geller-Seifter Model of Anxiety", Psychopharmacology, 1994, 114, 90-96.

Kenny et al., "Group II Metabotropic and Alpha-Amino-3-Hydroxy-5-Methyl-4-Isoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.

Kenny et al., "The Ups and Downs of Addiction: Role of Metabotropic Glutamate Receptors", Trends in Pharmacological Sciences, 2004, 25(5), 265-272.

Kent, "Safety, Tolerability and Potential Therapeutic Efficacy of a Novel Glutamate Modulator as Adjunctive Treatment in Patients with Schizophrenia", Abstract No. 3160, American Psychiatric Association Annual Meeting, 2013, 1 page.

Kessler et al., "Comorbid Major Depression and Generalized Anxiety Disorders in the National Comorbidity Survey Follow-Up", Psychol Med., Mar. 2008, 38(3), 365-374.

Kessler et al., "Epidemiology of Anxiety Disorders", Current Topics in Behavioral Neurosciences, 2010, 2, 21-35.

Kessler et al., "Impairment in Pure and Comorbid Generalized Anxiety Disorder and Major Depression at 12 Months in Two National Surveys", American Journal of Psychiatry, 1999, 156(12), 1915-1923.

(56) References Cited

OTHER PUBLICATIONS

Kessler et al., "Lifetime and 12-Month Prevalence of DSM-III-R Psychiatric Disorders in the United States: Results From the National Comorbidity Survey", Arch Gen Psych, 1994, 51, 8-19.
Kessler et al., "Rethinking the Duration Requirement for Generalized Anxiety Disorder: Evidence from the National Comorbidity Survey Replication", Psychological Medicine, 2005, 7, 1073-1082.
Kessler et al., "The Epidemiology of Co-Ocurring Addictive and Mental Disorders: Implications for Prevention and Service Utilization", American Journal of Orthopsychiatry, 1996, 66(1), 17-31.
Kessler et al., "The Epidemiology of Major Depressive Disorder: Results from the National Comorbidity Survey Replication (NCS-R)", JAMA, 2003, 289(23), 3095-3105.
Kew et al., "Activity-Dependent Presynaptic Autoinhibition by Group II Metabotropic Glutamate Receptors at the Perforant Path Inputs to the Dentate Gyrus and Ca1", Neuropharmacology, 2001, 40, 20-27.
Kew et al., "Differential Regulation of Synaptic Transmission by Mglu2 and Mglu3 at the Perforant Path Inputs to the Dentate Gyrus and Ca1 Revealed in Mglu2 −/− Mice", Neuropharmacology, 2002, 43, 215-221.
Kew et al., "Ionotropic and Metabotropic Glutamate Receptor Structure and Pharmacology", Psychopharmacology, 2005, 179, 4-29.
Kew, "Positive and Negative Allosteric Modulation of Metabotropic Glutamate Receptors: Emerging Therapeutic Potential", Pharmacology & Therapeutics, 2004, 104, 233-244.
Khimia Geterotsiklicheskikh Soedinenii, 1985, 5, 646-649.
Khimia Geterotsiklicheskikh Soedinenii, 1986, 8, 1118-1123.
Kilama et al., "A New Synthstic Approach to the C-D Ring Portion of Streptonigrin Analogues", Journal of Heterocyclic Chemistry, 1990, 27, 1437-1440.
Kilbride et al., "Presynaptic Group II Mglur Inhibition of Short-Term Depression in the Medial Perforant Path of the Dentate Gyrus in Vitro", Neurophysiol, 2001, 85, 2509-2515.
Kilbride et al., "Presynaptic Inhibitory Action of the Group II Metabotropic Glutamate Receptor Agonists, Ly354740 and DCG-IV", European Journal of Pharmacology, 1998, 356, 149-157.
Kim et al., "Activation of Metabotropic Glutamate Receptors in the Rat Nucleus Accumbens Increases Locomotor Activity in a Dopamine-Dependent Manner", Journal of Pharmacology & Experimental Therapeutics, 1997, 283(2), 962-968.
Kim et al., "Group II Metabotropic Glutamate Receptor Stimulation Triggers Production and Release of Alzheimer's Amyloid B42 From Isolated Intact Nerve Terminals", Journal of Neuroscience, 2010, 30(11), 3870-3875.
Kim et al., "Metabotropic Glutamate Receptors in the Rat Nucleus Accumbens Contribute to Amphetamine-Induced Locomotion", Journal of Pharmacology & Experimental Therapeutics, 1998, 284(1), 317-322.
Kim et al., "Metabotropic Glutamate Receptors, Phosphorylation and Receptor Signaling", Journal of Neuroscience Research, 2008, 86, 1-10.
Kim et al., "Neurofilament-M Interacts with the D1 Dopamine Receptor to Regulate Cell Surface Expression and Desensitization", Journal of Neuroscience, 2002, 22(14), 5920-5930.
Kim et al., "Predictors of 12-Week Remission in a Nationwide Cohort of People with Depressive Disorders: The Crescend Study", Hum. Psychopharmacol Clin Exp, 2011, 26, 41-50.
Kingston et al., "Ly341495 is a Nanomolar Potent and Selective Antagonist of Group II Metabotropic Glutamate Receptors", Neuropharmacology, 1998, 37, 1-12.
Kingston et al., "Neuroprotection by Metabotropic Glutamate Receptor Agonists: Ly354740, Ly379268 and Ly389795", European Journal of Pharmacology, 1999, 377, 155-165.
Kingston et al., "Neuroprotective Actions of Novel and Potent Ligands of Group I and Group II Metabotropic Glutamate Receptors", Annals New York Academy of Sciences, 1999, 890, 438-449.
Kinon, "A Multicenter, Inpatient, Phase 2, Double-Blind, Placebo-Controlled Dose-Ranging Study of Ly2140023 Monohydrate in Patients with DSM-IV Schizophrenia", J. Clin. Psychopharmacology, 2011, 31(3), 349-355.
Kiselyov et al., "A One Pot Synthesis of Polysubstituted Inidazo[1,2-A]Pyridines", Tetrahedron Letters, 2006, 47, 2941-2944.
Kitano et al., "Synthesis and Antifouling Activity of 3-Isocyanotheonellin and Its Analogues", Jour Chem Soc Perkin Trans, 2002, 2251-2255.
Kilts, "The Changing Roles and Targets for Animal Models of Schizophrenia", Biol. Psychiatr., 2001, 50, 845-855.
Klein "Mixed Anxiety Depression. For and Against", L'encéphale, 1993, 493-495.
Klein et al., "Glutamatergic Activation of Hippocampal Phospholipase D: Postnatal Fading and Receptor Desensitization", Journal of Neurochemistry, 1998, 70(4), 1679-1685.
Klemm et al., "Chemistry of Thienopyridines. VIII. Substitution Products Derived From Thieno[2,3-B] Pyridine 7-Oxide (1)", Journal of Heterocyclic Chemistry, 1970, 7(1), 81-89.
Klodzinska et al., "Group II Mglu Receptor Agonists Inhibit Behavioural and Electrophysiological Effects of Doi in Mice", Pharmacology, Biochemistry and Behavior, 2002, 73(2), 327-332.
Klodzinska et al., "Roles of Group II Metabotropic Glutamate Receptors in Modulation of Seizure Activity", Naunyn Schmiedebergs Arch Pharmacol, 2000, 361, 283-288.
Klodzinska et al., "Selective Group II Glutamate Metabotropic Receptor Agonist Ly354740 Attenuates Pentetrazole- and Picrotoxin-Induced Seizures", Pol J Pharmacol, 1999, 51, 543-545.
Knesevich, "Validity of Hamilton Rating-Scale for Depression", Br J Psychiatry, 1977, 131, 49-52.
Kniazeff et al., "Closed State of Both Binding Domains of Homodimeric Mglu Receptors is Required for Full Activity", Nat Struct Mol Biol, 2004, 11, 706-713.
Knight et al., "Pharmacological Characterization of the Agonist Radioligand Binding Site of 5-Ht2a, 5-Ht2b and 5-Ht2c Receptors", Naunyn-Schmiedeberg's Arch Pharmacol, 2004, 370, 114-123.
Knoflach et al., "R1315, A Potent Orally Active Non-Competitive Group II Metabotropic Glutamate Receptor Antagonist with Cognitive Enhancing Properties", 5th International Meeting on Metabotropic Glutamate Receptors, Taormina Sicily—Italy, Sep. 2005, 1 page.
Kodama et al., "Enhanced Glutamate Release During Rem Sleep in the Rostromedial Medulla as Measured by in Vivo Microdialysis", Brain Res, 1998, 780, 178-181.
Koh et al., "Deficits in Social Behavior and Sensorimotor Gating in Mice Lacking Phospholipase Cb1", Genes, Brain and Behavior, 2008, 7, 120-128.
Koh et al., "Non-NMDA Receptor-Mediated Neurotoxicity in Cortical Culture", J. Neurosci., 1990, 10(2), 693-705.
Koh et al., "Treatment Strategies Targeting Excess Hippocampal Activity Benefit Aged Rats with Cognitive Impairment", Neuropsychopharmacology, 2010, 35, 1016-1025.
Komossa et al., "Second-Generation Antipsychotics for Major Depressive Disorder and Dysthymia (Review)", The Cochrane Collaboration, 2012, 222 pages.
Konarski et al., "Volumetric Neuroimaging Investigations in Mood Disorders: Bipolar Disorder Versus Major Depressive Disorder", Bipolar Disord, 2008, 10(1), 1-37.
Konieczny et al., "Ly354740, A Group II Metabotropic Glutamate Receptor Agonist with Potential Antiparkinsonian Properties in Rats", Naunyn Schmiedebergs Arch. Pharmacol., 1998, 358(4), 500-502.
Konstantakopoulos et al., "Lamotrigine Associated Exacerbation of Positive Symptoms in Paranoid Schizophrenia", Schizophr Res., 2008, 98(1-3), 325-326.
Koolschijn et al., "Brain Volume Abnormalities in Major Depressive Disorder: A Meta-Analysis of Magenetic Resonance Imaging Studies", Hum Brain Mapp, 2009, 30(11), 3719-3735.
Koroshetz et al., "Emerging Treatments for Stroke in Humans", Trends in Pharmacological Sciences, 1996, 17(6), 227-233.
Kostrzewa et al., "Supersensitized D1 Receptors Mediate Enhanced Oral Activity After Neonatal 6-Ohda. Pharmacology", Biochemistry & Behavior, 1991, 39(3), 677-682.

(56) References Cited

OTHER PUBLICATIONS

Kotlinska et al., "The Role of Group I Mglu Receptors in the Expression of Ethanol-Induced Conditioned Place Preference and Ethanol Withdrawal Seizures in Rats", European Journal of Pharmacology, 2011, 670, 154-161.
Koulen et al., "Group II and Group III Metabotropic Glutamate Receptors in the Rat Retina: Distributions and Developmental Expression Patterns", European Journal of Neuroscience, 1996, 8(10), 2177-2187.
Kowal et al., "A [35s]Gtpgammas Binding Assessment of Metabotropic Glutamate Receptor Standards in Chinese Hamster Ovary Cell Lines Expressing the Human Metabotropic Receptor Subtypes 2 and 4", Neuropharmacology, 1998, 37(2), 179-187.
Kowal et al., "Functional Calcium Coupling with the Human Metabotropic Glutamate Receptor Subtypes 2 and 4 by Stable Co-Expression with a Calcium Pathway Facilitating G-Protein Chimera in Chinese Hamster Ovary Cells", Biochemical Pharmacology, 2003, 66(5), 785-790.
Krieger, "The Plasma Level of Cortisol as a Predictor of Suicide", Diseases of the Nervous System, 1974, 35(5), 237-240.
Krishnan et al., "The Molecular Neurobiology of Depression", Nature, 2008, 455, 894-902.
Krivoy et al., "The Possible Involvement of Metabotropic Glutamate Receptors in Schizophrenia", European Neuropsychopharmacology, 2008, 18, 395-405.
Krohnke et al., "Methylketon-Addukte Der Chinolinium-Und Isochinolinium-Reihe", Justus Liebigs Annalen Der Chemie, 1956, 211-228.
Krystal et al., "Comparative and Interactive Human Psychopharmacologic Effects of Ketamine and Amphetamine: Implications for Glutamatergic and Dopaminergic Model Psychoses and Cognitive Function", Archives of General Psychiatry, 2005, 62(9), 985-994.
Krystal et al., "Neuroplasticity as a Target for the Pharmacotherapy of Anxiety Disorders, Mood Disorders, and Schizophrenia", Drug Discov. Today, 2009, 14(13-14), 690-697.
Krystal et al., "NMDA Receptor Antagonist Effects, Cortical Glutamatergic Function, and Schizophrenia: Toward a Paradigm Shift in Medication Development", Psychopharmacology, 2003, 169(3-4), 215-33.
Krystal et al., "Potential Psychiatric Applications of Metabotropic Glutamate Receptor Agonists and Antagonists", CNS Drugs, 2010, 24(8), 669-693.
Krystal et al., "Preliminary Evidence of Attenuation of the Disruptive Effects of the Nmda Glutamate Receptor Antagonist, Ketamine, on Working Memory by Pretreatment with the Group II Metabotropic Glutamate Receptor Agonist, Ly354740, in Healthy Human Subjects", Psychopharmacology (Berl)., 2005, 179(1), 303-309.
Krystal et al., "Subanesthetic Effects of the Noncompetitive NMDA Antagonist, Ketamine, in Humans. Psychotomimetic, Perceptual, Cognitive, and Neuroendocrine Responses", Arch Gen Psychiatry, 1994, 51(3), 199-214.
Krystal, "N-Methyl-D-Aspartate Glutamate Receptors and Alcoholism: Reward, Dependence, Treatment, and Vulnerability", Pharmacol. & Therapeutics, 2003, 99, 79-94.
Kubo et al., "Structural Basis for a Ca2+-Sensing Function of the Metabotropic Glutamate Receptors", Science, 1998, 279(5357), 1722-1725.
Kubokawa et al., "Cloning and Characterization of a Bifunctional Metabotropic Receptor Activated by Both Extracellular Calcium and Glutamate", Febs Letters, 1996, 392(1), 71-76.
Kucukibrahimoglu et al., "The Change in Plasma Gaba, Glutamine and Glutamate Levels in Fluoxetine- or S-Citalopram-Treated Female Patients with Major Depression", Eur J Clin Pharmacol, 2009, 65(6), 571-577.
Kufahl et al., "Enhanced Sensitivity to Attenuation of Conditioned Reinstatement by the Mglur2/3 Agonist Ly379268 and Increased Functional Activity of Mglur2/3 in Rats with a History of Ethanol Dependence", Neuropsychopharmacology, 2011, 1-12.
Kugaya et al., "Beyond Monoamines: Glutamatergic Function in Mood Disorders", CNS Spectr, 2005, 10, 808-819.
Kullmann et al., "Extrasynaptic Glutamate Spillover in the Hippocampus: Evidence and Implications", Trends Neurosci., 1998, 21(1), 8-14.
Kunishima et al., "Structural Basis of Glutamate Recognition by a Dimeric Metabotropic Glutamate Receptor", Nature, 2000, 407, 971-977.
Kuo, "Allosteric Cofactor-Mediated Enzyme Cooperativity: A Theoretical Treatment", Proc. Natl. Acad. Sci. USA, Sep. 1983, 80, 5243-5247.
Kurita et al., "Hdac2 Regulates Atypical Antipsychotic Responses through the Modulation of Mglu2 Promoter Activity", Nature Neuroscience, 2012, 15(9), 1245-1254.
Kurumaji et al., "Effects of Mk-801 Upon Local Cerebral Glucose Utilization in Conscious Rats and in Rats Anaesthetized with Halothane",J Cereb Blood Flow Metab, 1989, 9, 786-794.
Lahti et al., "Ketamine Activates Psychosis and Alters Limbic Blood Flow in Schizophrenia", Neuroreport, 1995, 6(6), 869-872.
Lam et al., "Effects of the Selective Metabotropic Glutamate Agonist Ly354740 in a Rat Model of Permanent Ischaemia", Neuroscience Letters, 1998, 254(2), 121-123.
Lambeng et al., "Selective Mglur2 Negative Allosteric Modulators Reverse the Scopolamine-Induced Memory Deficit in the Novel Object Recognition Test", Society for Neuroscience 40th Annual Meeting, Nov. 2010, 1 page.
Lambert et al., "Current Issues in Schizophrenia: Overview of Patient Acceptability, Functioning Capacity and Quality of Life", CNS Drugs, 2004,18(Suppl 2), 5-17.
Lamers et al., "Comorbidity Patterns of Anxiety and Depressive Disorders in a Large Cohort Study: the Netherlands Study of Depression and Anxiety (Nesda)", J Clin Psychiatry, 2011, 72(3), 341-348.
Lamotrigine, "Highlights of Prescribing Information", 2012, 1-64.
Lan et al., "Activation of Metabotropic Glutamate Receptor-1 Accelerates NMDA Receptor Trafficking", Neuropharmacology, 2002, 43, 294.
Landen et al., "A Randomized, Double-Blind, Placebo-Controlled Trial of Buspirone in Combination with an Ssri in Patients with Treatment-Refractory Depression", J Clin Psychiatry, 1998, 59, 664-668.
Landin et al., "The Impact of Restrictive Entry Criterion During the Placebo Lead-in Period", Biometrics, 2000, 56, 271-278.
Landmark, "Antiepileptic Drugs in Non-Epilepsy Disorders", CNS Drugs, 2008, 22(1), 27-47.
Landwehrmeyer, "Riluzole in Huntington's Disease: A 3-Year, Randomized Controlled Study", Ann Neurol, 2007, 62, 262-272.
Lane et al., "Bridging the Gap: Bitopic Ligands of G-Protein-Coupled Receptors", Trends in Pharmacological Sciences, Jan. 2013, 34(1), 59-66.
Lang et al., "Molecular Mechanisms of Depression Perspective on New Treatment Strategies", Cell Physiol Biochem, 2013, 31, 761-777.
Lang et al., "Molecular Mechanisms of Schizophrenia", Cell Physiol Biochem., 2007, 20(6), 687-702.
Langmead, "Ligand Properties and Behaviours in an Allosteric Age", Trends Pharmacol Sci, 2012, 33, 621-622.
Langmead, "Screening for Positive Allosteric Modulators: Assessment of Modulator Concentration-Response Curves as a Screening Paradigm", Journal of Biomolecular Screening, 2007, 668-676.
Large, "Do NMDA Receptor Antagonist Models of Schizophrenia Predict the Clinical Efficacy of Antipsychotic Drugs?", J Psychopharmacol, 2007, 21, 283-301.
Large, "The Potential Role of Lamotrigine in Schizophrenia", Psychopharmacol., 2005, 181, 415-436.
Larock, "Comprehensive Organic Transformations", VCH Publishers, 1989, 595-596.
Larsson et al., "Neurochemical and Behavioral Studies on Ethanol and Nicotine Interactions", Neuroscience and Biobehavioral Reviews, 2004, 27, 713-720.
Laruelle et al., "Glutamate, Dopamine, and Schizophrenia: From Pathophysiology to Treatment", Ann Ny Acad Sci, 2003, 1003, 138-158.

(56) References Cited

OTHER PUBLICATIONS

Laruelle et al., "Relationships Between Radiotracer Properties and Image Quality in Molecular Imaging of the Brain with Positron Emission Tomography", Mol Imaging Biol, 2003, 5, 363-375.
Larzabal et al., "Distribution of the Grlup II Metabotropic Glutamate Receptors (Mglur2/3) in the Enteric Nervous System of the Rat", Neuroscience Letters, 1999, 276, 91-94.
Laughren et al., "Food and Drug Administration Perspective on Negative Symptoms in Schizophrenia as a Target for a Drug Treatment Claim", Schizophr Bull., 2006, 32(2), 220-222.
Laughren, "The Scientific and Ethical Basis for Placebo-Controlled Trials in Depression and Schizophrenia: An Fda Perspective", Eur Psychiatry, 2001, 16, 418-423.
Laurie et al., "Cloning, Distribution and Functional Expression of the Human Mglu6 Metabotropic Glutamate Receptor", Neuropharmacology, 1997, 36(2), 145-52.
Lavreysen et al., "[$^3$h]R214127: A Novel High-Affinity Radioligand for the Mglu1 Receptor Reveals a Common Binding Site Shared by Multiple Allosteric Antagonists", Mol Pharmacol, 2003, 63, 1082-1093.
Lavreysen et al., "A Study on the Molecular Interaction Between Mglu2 Receptor Agonists and Positive Allosteric Modulators", International Meeting on Metabotropic Glutamate Receptors, Poster, Sep. 2008, 1 page.
Lavreysen et al., "A Study on the Molecular Interaction Between Mglu2 Receptor Agonists and Positive Allosteric Modulators" Poster, Society for Neuroscience Annual Meeting, 2009, 1 page.
Lavreysen et al., "JNJ16259685, A Highly Potent, Selective and Systemically Active Mglu1 Receptor Antagonist" Neuropharmacology 2004, 47, 961-972.
Lavreysen et al., "JNJ-40068782: A Novel Potent, Selective and Systemically Active Positive Allosteric Modulator of the Mglu2 Receptor" Abstract, Society for Neuroscience Annual Meeting, 2010, 1 page.
Lavreysen et al., "Pharmacological Characterization of JNJ-40068782, A New Potent, Selective, and Systemically Active Positive Allosteric Modulator of the Mglu2 Receptor and Its Radioligand [3h]Jnj-40068782", J Pharmacol Exp Ther, Sep. 2013, 346, 514-527.
Lavreysen et al., "Therapeutic Potential of Group III Metabotropic Glutamate Receptors", Current Medicinal Chemistry, 2008, 15, 671-684.
Lavreysen, "The Development of Mglu2 Pams: Identification of JNJ-40068782 as a Novel Tool Compound", Allosteric Modulator Drug Discovery Congress, Nov. 2010, 34 pages.
Leach et al., "Allosteric Gpcr Modulators: Taking Advantage of Permissive Receptor Pharmacology", Trends in Pharmacological Sciences, 2007, 28(8), 382-389.
Leach et al., "Quantification of Allosteric Interactions Unit 1.22 at G Protein-Coupled Receptors Using Radioligand Binding Assays", Current Protocols in Pharmacology, Mar. 2011, 1.22.1-1.22.41.
Leber, "Observations and Suggestions on Antidementia Drug Development", Alzheimer . Disease and Associated Disorders, 1996, 10 (Suppl 1), 31-35.
Lebois, "Neither Typical nor Atypical: Ly404039 Provides Proof of Concept That Selective Targeting of Mglur2/3 Receptors is a Valid Mechanism for Obtaining Antipsychotic Efficacy", Curr. Top. Med. Chem., 2008, 8(16), 1480-1481.
Lecci et al., "Pharmacological Validation of a Novel Animal Model of Anticipatory Anxiety in Mice", Psychopharmacology, 1990, 101, 255-261.
Lee et al., "Amyloid Precursor Protein Processing is Stimulated by Metabotropic Glutamate Receptors", National Academy of Sciences USA, 1995, 92(17), 8083-8087.
Lee et al., "Benzylic Bromination of Alkylbenzenes with Sodium Bromate-Bromotrimethylsilane", Bull. Korean Chem. Soc, 1995, 16, 371-374.
Lee et al., "Characterization of the Inward Current Induced by Metabotropic Glutamate Receptor Stimulation in Rat Ventromedial Hypothalamic Neurones", Journal of Physiology, 1997, 504(Pt 3), 649-663.
Lee et al., "Glutamategic Afferent Projections to the Dorsal Raphe Nucleus of the Rat", Brain Res, 2003, 963, 57-71.
Lee et al., "Low Doses of Cannabinoids Enhance the Antinociceptive Effects of Intracisternally Administered Mglurs Groups II and III Agonists in Formalin-Induced Tmj Nociception in Rats", Pain, 2008, 139(2), 367-375.
Lee et al., "The Effect of Mglur2 Activation on Signal Transduction Pathways and Neuronal Cell Survival", Brain Res., 2009, 1249, 244-250.
Lee et al., "The Mglu2/3 Receptor Agonist Ly354740 Suppresses Immobilization Stress-Induced Increase in Rat Prefrontal Cortical Bdnf Mrna Expression", Neuroscience Letters, 2006, 398, 328-332.
Lee, "The Role of Metabotropic Glutamate Receptors in Alzheimer's Disease", Acta Neurobiol Exp, 2004, 64, 89-98.
Leeson et al., "The Influence of Drug-Like Concepts on Decision-Making in Medicinal Chemistry", Nat Rev Drug Discovery, 2007, 6, 881-890.
Leever et al., "Identification of a Site in Glur1 and Glur2 That is Important for Modulation of Deactivation and Desensitization", Mol Pharmacol, 2003, 64(1), 5.
Lennon et al., "Metabotropic Glutamate Receptor Mglu2 is Resistant to Homologous Agonist-Induced Desensitilization But Undergoes Protein Kinase C-Mediated Heterologous Desensitization", Eur J Phamacol, 2010, 649, 29-37.
Lenox et al., "Mechanism of Action of Antidepressants and Mood Stabilizers" Neuropsychopharmacology: Tthe Fifth Generation of Progress, American College of Neuropsychopharmacology, 2002, 1139-1163.
Leo et al., "The Application of Nuclear Magnetic Resonance-Based Metabonomics to the Dominant-Submissive Rat Behavioral Model", Analytical Biochemistry, 2005, 339, 174-178.
Lerner et al., "The Work Limitations Questionnaire", Med Care, 2001, 39(1), 72-85.
Leucht et al., "Second-Generation Versus First-Generation Antipsychotic Drugs for Schizophrenia: A Meta-Analysis", Lancet, 2009, 373(9657), 31-41.
Levine et al., "Abstracts/Neuropharmacology", 2002, 43, 294-295.
Levitz et al., "Optical Control of Metabotropic Glutamate Receptors", Nature Neuroscience, 2013, 16(4), 507-516.
Lewis et al., "Cognitive Dysfunction in Schizophrenia: Convergence of Gamma-Aminobutyric Acid and Glutamate Alterations", Arch. Neurol., 2006, 63(10), 1372-1376.
Lewis, "The Molecular Choreography of a Store-Operated Calcium Channel", Nature, 2007, 446, 284-287.
Leysen et al., "[3h]Ketanserin (R 41 468), A Selective 3h-Ligand for Serotonin2 Receptor Binding Sites. Binding Properties, Brain Distribution, and Functional Role", Molecular Pharmacology, 1982, 21(2), 301-314.
Leysen et al., "Receptor Interactions of New Antipsychotics: Relation to Pharmacodynamics and Clinical Effects", Intl Journal of Psychiatry in Clinical Practice, 1998, 2, S3-S17.
Li et al., "Design and Synthesis of 4-Arylpiperidinyl Amide and N-Arylpiperdin-3-Yl-Cyclopropane Carboxamide Derivatives as Novel Melatonin Receptor Ligands", Bioorganic & Medicinal Chemistry Letters, 2011, 21, 1236-1242.
Li et al., "Evaluation of the Motor Initiation Hypothesis of Apd-Induced Conditioned Avoidance Decreases", Pharmacol. Biochem. Behav., 2004, 78, 811-819.
Lieberman et al., "A Randomized, Placebo-Controlled Study of Memantine as Adjunctive Treatment in Patients with Schizophrenia", Neuropsychopharmacology, 2009, 34, 1322-1329.
Lieberman et al., "Antipsychotic Drugs: Comparison in Animal Models of Efficacy, Neurotransmitter Regulation, and Neuroprotection", Pharmacol. Rev, 2008, 60(3), 358-403.
Lieberman et al., "Effectiveness of Antipsychotic Drugs in Patients with Chronic Schizophrenia", N Engl J Med., 2005, 353(12), 1209-1223.
Lieberman, "Serotonergic Basis of Antipsychotic Drug Effects in Schizophrenia", Biol. Psychiatry, 1998, 44, 1099-1117.

(56) References Cited

OTHER PUBLICATIONS

Liebowitz et al., "Biological Accompaniments of Lactate-Induced Panic", Psychopharmacology Bulletin, 1984, 20(1), 43-44.
Liebowitz et al., "Lactate Provocation of Panic Attacks. I. Clinical and Behavioral Findings", Archives of General Psychiatry, 1984, 41(8), 764-70.
Liechti et al., "Interactive Effects of the Mglu5 Receptor Angatonist Mpep and the Mglu2/3 Receptor Antagonist Ly341495 on Nicotine Self-Administration and Reward Deficits Associated with Nicotine Withdrawal in Rats", European Journal of Pharmacology, 2007, 554, 164-174.
Liechti et al., "Metabotropic Glutamate 2/3 Receptor Activation Induced Reward Deficits But Did Not Aggravate Brain Reward Deficits Associated with Spontaneous Nicotine Withdrawal in Rats", Biochemical Pharmacology, 2007, 74, 1299-1307.
Liechti et al., "Metabotropic Glutamate 2/3 Receptors in the Ventral Tegmental Area and the Nucleus Accumbens Shell are Involved in Behaviors Relating to Nicotine Dependence", Journal of Neuroscience, 2007, 27(34), 9077-9085.
Liechti et al., "Role of the Glutamatergic System in Nicotine Dependence Implications for the Discovery and Development of New Pharmacological Smoking Cessation Therapies", CNS Drugs, 2008, 22(9), 705-724.
Lilly, "Stops Phase III Development of Pomaglumetad Methionil for the Treatment of Schizophrenia Based on Efficacy Results", Press Release, Aug. 29, 2012, 1 page.
Lin et al., "A Meta-Analytic Review of Double-Blind, Placebo-Controlled Trials of Antidepressant Efficacy of Omega-3 Fatty Acids", J Clin Psychiatry, 2007, 68(7), 1056-1061.
Lindemann et al., "Ctep: A Novel, Potent, Long-Acting, and Orally Bioavailable Metabotropic Glutamate Receptor 5 Inhibitor", Jpet, 2011, 339, 474-486.
Linden et al., "Anxiolytic Activity of the Mglu2/3 Receptor Agonist Ly354740 on the Elevated Plus Maze is Associated with the Suppression of Stress-Induced C-Fos in the Hippocampus and Increases in C-Fos Induction in Several Other Stress-Sensitive Brain Regions", Neuropsychopharmacology, 2004, 29, 502-513.
Linden et al., "Comparison of C-Fos Induction in the Brain by the Mglu2/3 Receptor Antagonist Ly341495 and Agonist Ly354740: Evidence for Widespread Endogenous Tone at Brain Mglu2/3 Receptors In Vivo", Neuropharmacology, 2005, 49(Suppl 1), 120-134.
Linden et al., "Effects of Mglu2 or Mglu3 Receptor Deletions on Mglu2/3 Receptor Agonist (Ly354740)-Induced Brain C-Fos Expression: Specific Roles for Mglu2 in the Amygdala and Subcortical Nuclei, and Mglu3 in the Hippocampus", Neuropharmacology, 2006, 51, 213-228.
Linden et al., "Use of Mglur2 and Mglur3 Knockout Mice to Explore In Vivo Receptor Specificity of the Mglur2/3 Selective Agonist Ly341495", Neuropharmacology, 2009, 57, 172-182.
Linden, "Anxiolytic-Like Activity of the Mglu2/3 Receptor Agonist Ly354740 in the Elevated Plus Maze Test is Disrupted in Metabotropic Glutamate Receptor 2 and 3 Knock-Out Mice", Psychopharmacol., 2005, 179, 284-291.
Lindsley et al., "Progress Towards Validating the NMDA Receptor Hypofunction Hypothesis of Schizophrenia", Current Topics in Medicinal Chemistry, 2006, 6, 771-785.
Linn et al., "Activation of Metabotropic Glutamate Receptors Modulates the Voltage-Gated Sustained Calcium Current in a Teleost Horizontal Cell", Journal of Neurophysiology, 1999, 81(2), 425-434.
Lipton, "Excitatory Amino Acids as a Final Common Pathway for Neurologic Disorders", Mechanisms of Disease, New England Journal of Medicine, 1994, 330(9), 613-622.
Lissin et al., "An Immunocytochemical Assay for Activity-Dependent Redistribution of Glutamate Receptors from the Postsynaptic Plasma Membrane", Annals of the New York Academy of Sciences, 1999, 868, 550-553.
Litman, "AZD8529, A Positive Allosteric Modulator at the Mglur2 Receptor, Does Not Improve Symptoms in Schizophrenia: A Proof of Principle Study", NCDEU: An Annual Meeting Sponsored by Am Soc. of Clin. Psychopharmacology, Poster and Abstract, 2013, 3 pages.
Liu et al., "A Unified Theory of Two-Stage Adaptive Designs", Theory and Methods, 2002, 97, 1034-1041.
Liu et al., "Doubly Randomized Delayed-Start Design for Enrichment Studies with Responders or Nonresponders", Journal of Biopharmaceutical Statistics, 2012, 22(4), 737-757.
Liu et al., "Ischemic Insults Direct Glutamate Receptor Subunit 2-Lacking AMPA Receptors to Synaptic Sites", Journal of Neuroscience, May 17, 2006, 26(20), 5309-5319.
Liu et al., "Pharmacogenetic Analysis of the Mglu2/3 Agonist Ly2140023 Monohydrate in the Treatment of Schizophrenia", Pharmacogenomics Journal, 2010, 1-9.
Lopez-Rodriguez et al., "Changes in Extracellular Glutamate Levels in Rat Orbitofrontal Cortext During Sleep and Wakefulness", Arch Med Res, 2007, 38, 52-55.
Lorenzetti et al., "Structural Brain Abnormalities in Major Depressive Disorder: A Selective Review of Recent MRI Studies", J Affect Disord, 2009, 117(1-2), 1-17.
Lorrain et al., "Group II Mglu Receptor Activation Suppresses Norepinephrine Release in the Ventral Hippocampus and Locomotor Responses to Acute Ketamine Challenge", Neuropsychopharmacology, 2003, 28, 1622-1632.
Lou et al., "Allosteric Modulation of the Presynaptic Ca2+ Sensor for Vesicle Fusion", Nature, 2005, 435, 497-501.
Lowe et al., "Effects of a Novel Mglu2/3 Receptor Agonist Prodrug, Ly2140023 Monohydrate, on Central Monoamine Turnover as Determined in Human and Rat Cerebrospinal Fluid", Psychopharmacology, 2011, 1-12.
Lowry et al., "Serotonergic Systems, Anxiety, and Affective Disorder: Focus on the Dorsomedial Part of the Dorsal Raphe Nucleus", Annals of the New York Academy of Sciences, 2008, 1148, 86-94.
Lujan et al., "Glutamate and Gaba Receptor Signalling in the Developing Brain", Neuroscience, 2005, 130, 567-580.
Luscher et al., "Group I Mglur-Dependent Synaptic Long-Term Depression: Mechanisms and Implications for Circuitry and Disease", Neuron, 2010, 65, 445-459.
Lyon et al., "Altered Hippocampal Expression of Glutamate Receptors and Transporters in Grm2 and Grm3 Knockout Mice", Synapse, 2008, 62, 842-850.
Lyon et al., "Fractionation of Spatial Memory in Grm2/3 (Mglu2/Mglu3) Double Knockout Mice Reveals a Role for Group II Metabotropic Glutamate Receptors at the Interface Between Arousal and Cognition", Neuropsychopharmacology, 2011, 1-13.
Macchiarulo et al., "The Role of Electrostatic Interaction in the Molecular Recognition of Selective Agonists to Metabotropic Glutamate Receptors", Proteins, 2003, 50(4), 609-619.
Macdonald "The Design of Allosteric Modulators for the Treatment of CNS Disorders", 11th Advances and Progress in Drug Design, Feb. 2012, 36 pages.
Macdonald, "The Design of Mglur Modulators for the Treatment of CNS Disorders" Presentation Slides, 6th Anglo-Swedish Medicinal Chemistry Symposium, Stockholm, Jun. 19, 2013, 1 page.
Macdonald, "Positive Allosteric Modulation of Mglur2 Receptors in the Treatment of CNS Disorders", 3rd Symposium on GPCRS in Medicinal Chemistry, Oss, Sep. 2010, 29 pages.
Macek et al., "Differential Involvement of Group II and Group III Mglurs as Autoreceptors at Lateral and Medial Perforant Path Synapses", J Neurophysiol, 1996, 76(6), 3798-3806.
Macek et al., "Protein Kinase C and A3 Adenosine Receptor Activation Inhibit Presynaptic Metabotropic Glutamate Receptor (Mglur) Function and Uncouple Mglurs from Gtp-Binding Proteins", J. Neurosci., 1998, 18(16), 6138-6146.
Mackrill, "Protein-Protein Interactions in Intracellular Ca2+-Release Channel Function", Biochemical Journal, 1999, 337(Pt 3), 345-361.
Maeda et al., "Different Roles of Group I and Group II Metabotropic Glutamate Receptors on Phencyclidine-Induced Dopamine Release in the Rat Prefrontal Cortex", Neuroscience Letters, 2003, 336 (3), 171-174.

(56) References Cited

OTHER PUBLICATIONS

Maeng, "Cellular Mechanisms Underlying the Antidepressant Effects of Ketamine: Role of Alpha-Amino-3-Hydroxy-5-Methylisoxazole-4-Propionic Acid Receptors," Biol. Psychiatry, 2008, 63, 349-352.
Maione et al., "Characterisation of Mglurs Which Modulate Nociception in the Pag of the Mouse", Neuropharmacology,1998, 37(12), 1475-1483.
Makoff et al., "Molecular Characterization and Localization of Human Metabotropic Glutamate Receptor Type 3", Molecular Brain Research, 1996, 40(1), 55-63.
Malames et al., "N-Substituted Spirosuccinimide, Spiropyridazine, Spiroazetidine, and Acetic Acid Aidose Reductase Inhibitiors Derived From Isoquinoline-1,3-Dinoes. 2", J Med Chem., 1994, 37(13), 2059-2070.
Malatynska et al., "Assessing Activity Onset Time and Efficacy for Clinically Effective Antidepressant and Antimanic Drugs in Animal Models Based on Dominant-Submissive Relationships", Neuroscience and Biobehavioral Reviews, 2007, 31, 904-919.
Malatynska et al., "Dominant-Submissive Behavior as Models of Mania and Depression", Neuroscience and Biobehavioral Reviews, 2005, 29(4-5), 715-37.
Malatynska et al., "Levels of Mrna for A-, B-, and ⌈-Synuclein in the Brains of Newborn, Juvenile, and Adult Rats", J Mol Neurosci., 2006, 29(3), 269-77.
Malatynska et al., "Reduction of Dominant or Submissive Behaviors as Models for Antimanic or Antidepressant Drug Testing: Technical Considerations", J Neurosci Methods, 2007, 165(2), 175-182.
Malenka et al., "Ltp and Ltd: An Embarrassment of Riches", Neuron, 2004, 44, 5-21.
Malherbe et al., "Identification of Essential Residues Involved in the Glutamate Binding Pocket of the Group II Metabotropic Glutamate Receptor", Molecular Pharmacology., 2001, 60 (5), 944-954.
Malherbe et al., "Opposite Effects of Zn on the In Vitro Binding of [3h]Ly354740 to Recombinant and Native Metabotropic Glutamate 2 and 3 Receptors", J Neurochem., 2005, 94(1), 150-160.
Malhi et al., "Recognizing the Anxious Face of Depression", Journal of Nervous and Mental Disease, 2002, 190(6), 366-73.
Malhotra et al., "NMDA Receptor Function and Human Cognition: The Effects of Ketamine in Healthy Volunteers", Neuropsychopharmacology, May 1996, 14(5), 301-307.
Mansbach et al., "Blockade of Potentiated Startle Responding in Rats by 5-Hydroxytryptamine1a Receptor Ligands", Eur. J. Pharmacology, 1988, 156, 375-383.
Marcotte, "Animal Models of Schizophrenia: A Critical Review", Psychiatry Neurosci., 2001, 26(5), 395-410.
Marcus et al., "The Efficacy and Safety of Aripiprazole as Adjunctive Therapy in Major Depressive Disorder: A Second Multicenter, Randomized, Double-Blind, Placebo-Controlled Study", Journal of Clinical Psychopharmacology, 2008, 28(2), 156-165.
Marek, "Metabotropic Glutamate2/3 (Mglu2/3) Receptors, Schizophrenia and Cognition", European Journal of Pharmacology, 2010, 639, 81-90.
Marek et al., "5-Hydroxytryptamine2a (5-Ht2a) Receptor Regulation in Rat Prefrontal Cortex: Interaction of a Phenethylamine Hallucinogen and the Metabotropic Glutamate2/3 Receptor Agonist Ly354740", Neuroscience Letters, 2006, 403(3), 256-260.
Marek et al., "Glutamatergic (N-Methyl-D-Aspartate Receptor) Hypofrontality in Schizophrenia: Too Little Juice or a Miswired Brain?", Molecular Pharmacology, 2010, 77(3), 317-326.
Marek et al., "Physiological Antagonism Between 5-Hydroxytryptamine2a and Group II Metabotropic Glutamate Receptors in Prefrontal Cortex", J. Pharm. Exper. Therapeut., 2000, 292, 76-87.
Marek et al., "The Electrophysiology of Prefrontal Serotonin Systems: Therapeutic Implications for Mood and Psychosis", Biol Psychiatry, 1998, 44, 1118-1127.
Marek, "Metabotropic Glutamate 2/3 Receptors as Drug Targets", Curr. Opin. Pharmacol., 2004, 4, 18-22.
Markou, "The Role of Metabotropic Glutamate Receptors in Drug Reward, Motivation and Dependence", Drug News Perspect, 2007, 20(2), 103-108.
Marquet et al., "VIII. Nouvelle Methode De Synthese Des Furo[2,3-D]Pyrimidines Sustituees En Position 4 Et De Certains Thieno[2,3-D]Pyrimidines", Bulletin De La Societe Chimique De France, 1969, 12, 4344-4348.
Martella et al., "Enhanced Sensitivity to Group II Mglu Receptor Activation at Corticostriatal Synapses in Mice Lacking the Familial Parkinsonism-Linked Genes Pink1 or Parkin.", Exp. Neurol., 2009, 215(2), 388-396.
Martin et al., "Cellular Localization of a Metabotropic Glutamate Receptor in Rat Brain", Neuron, 1992, 9(2), 259-270.
Martin et al., "Cross-Talk Between Beta-Adrenergic and Metabotropic Glutamate Receptors in Rat C6 Glioma Cells", Biochimica Et Biophysica Acta, 1998, 1393(1), 186-192.
Mason, "Acamprosate in the Treatment of Alcohol Dependence", Expert Opin. Pharmacother., 2005, 6(12), 2103-2115.
Masu et al., "Sequence and Expression of a Metabotropic Glutamate Receptor", Nature, 1991, 349(6312), 760-765.
Matrisciano et al., "Activation of Group-II Metabotropic Glutamate Receptors Promotes DNA Demethylation in the Mouse Brain", Molecular Pharmacology, Apr. 2011, 52 pages.
Matrisciano et al., "Defective Group-II Metaboropic Glutamate Receptors in the Hippocampus of Spontaneously Depressed Rats", Neuropharmacology, 2008, 55(4), 525-531.
Matrisciano et al., "Group-II Metabotropic Glutamate Receptor Ligands as Adjunctive Drugs in the Treatment of Depression: A New Strategy to Shorten the Latency of Antidepressant Medication?", Molecular Psychiatry, 2007, 12, 704-706.
Matrisciano et al., "Imipramine Treatment Up-Regulates the Expression and Function of Mglu2/3 Metabotropic Glutamate Receptors in the Rat Hippocampus", Neuropharmacology, 2002, 42(8), 1008-1015.
Matrisciano, "Metabotropic Glutamate Receptors and Neuroadaptation to Antidepressants: Imipramine-Induced Down-Regulation of B-Adrenergic Receptors in Mice Treated with Metabotropic Glutamate 2/3 Receptor Ligands", Journal of Neurochemistry, 2005, 93, 1345-1352.
Matrisciano, "Synergism Between Fluoxetine and the Mglu2/3 Receptor Agonist, Ly379268, in an In Vitro Model for Antidepressant Drug-Induced Neurogenesis", Neuropharmacology, 2008, 54, 428-437.
Maurel et al., "Cell-Surface Protein-Protein Interaction Analysis with Time-Resolved Fret and Snap-Tag Technologies: Application to Gpcr Oligomerization", Nat Methods, 2008, 5(6), 561-567.
Maxwell et al., "Ketamine Produces Lasting Disruptions in Encoding of Sensory Stimuli", J Pharmacol Exp Ther, 2006, 316, 315-324.
May et al., "Allosteric Modulation of G Protein-Coupled Receptors", Annu Rev Pharmacol Toxicol, 2007, 47, 14.1-14.51.
May et al., "Regional Serotonin Receptor Studies: Chronic Methysergide Treatment Induces a Selective and Dose-Dependent Decrease in Serotonin-2 Receptors in Mouse Cerebral Cortex", Life Sciences, 1986, 38(19), 1741-1747.
Mayers et al., "Antidepressants and Their Effect on Sleep", Hum Psychopharmacol., 2005, 20, 5333-559.
Mayo Clinic, "Mental Illness", 2012, 1-13.
McClintock et al., "Assessing Anxious Features in Depressed Outpatients" Int. J. Methods Psychiatr. Res., 2011, 20(4), E69-E82.
McDermott et al., "Design and Analysis of Two-Period Studies of Potentially Disease-Modifying Treatments", Controlled Clinical Trials, 2002, 23, 635-649.
McElvain et al., "Piperidine Derivatives. XXX. 1,4-Dialky1-4-Arylpiperidines", J. Am. Chem. Soc, 1958, 80, 3915-3923.
McEvoy et al., "Effectiveness of Clozapine Versus Olanzapine, Quetiapine, and Risperidone in Patients with Chronic Schizophrenia Who Did Not Respond to Prior Atypical Antipsychotic Treatment", Am J Psychiatry, 2006, 163(4), 600-610.
McIntyre et al., "Quetiapine Adjunct to Selective Serotonin Reuptake Inhibitors or Venlafaxine in Patients with Major Depression, Comorbid Anxiety, and Residual Depressive Symptoms: A Randomized, Placebo-Controlled Pilot Study", Depression and Anxiety, 2007, 24, 487-494.

(56) References Cited

OTHER PUBLICATIONS

Meador-Woodruff et al., "Glutamate Receptor Expression in Schizophrenic Brain", Brain Res., 2000, 31(2-3), 288-294.
Melancon et al., "Allosteric Modulation of 7 Transmembrane Spanning Receptors: Theory, Practice and Opportunities for CNS Drug Discovery", J Med Chem, 2012, 55(4), 1445-1464.
Melartin et al., "Current Comorbidity of Psychiatric Disorders Among DSM-IV Major Depressive Disorder Patients in Psychiatric Care in the Vantaa Depression Study", J Clin Psychiatry, 2002, 63, 126-134.
Meldrum et al., "Excitatory Amino Acid Neurotoxicity and Neurodegenerative Disease", Trends in Pharmacological Sciences, 1990, 11(9), 379-387.
Meldrum et al.,"Glutamate Receptors and Trasnporters in Genetic and Acquired Models of Epilepsy", Epilepsy Res, 1999, 36, 189-204.
Meltzer et al., "Serotonin Receptors: Their Key Role in Drugs to Treat Schizophrenia", Prog. Neuropsychopharmacol. Biol. Psychiatry, 2003, 27(7), 1159-1172.
Meltzer, "Illuminating the Molecular Basis for Some Antipsychotic Drug-Induced Metabolic Burden", Proc. Natl. Acad. Sci. USA, 2007, 104(9), 3019-3020.
Merikangas et al., "Longitudinal Trajectories of Depression and Anxiety in a Prospective Community Study", Arch Gen Psychiatry, 2003, 60, 993-1000.
Metman, "Huntington's Disease a Randomized, Controlled Trial Using the NMDA-Antagonist Amantadine", Neurology, 2002, 59, 694-699.
Mezler et al., "Ly2140023, a Prodrug of the Group II Metabotropic Glutamate Receptor Agonist Ly-404039 for the Potential Treatment of Schizophrenia", Current Opinion in Investigational Drugs, 2010, 11(7), 833-845.
Michael et al., "Metabolic Changes Within the Left Dorsolateral Prefrontal Cortex Occurring with Electroconvulsive Therapy in Patients with Treatment Resistant Unipolar Depression", Psychol Med, 2003, 33(7), 1277-1284.
Michael et al., "Neurotrophic Effects of Eletroconvulsive Therapy: A Proton Magnetic Resonance Study of the Left Amygdalar Region in Patients with Treatment-Resistant Depression", Neuropsychopharmacology, 2003, 28(4), 720-725.
Michelson, "Clinical Studies with Mglur2/3 Agonists: Ly354740 Compared with Placebo in Patients with Generalized Anxiety Disorder", Neuropharmacol., 2005, 49, 257.
Miller, "Mechanisms of Action of Antipsychotic Drugs of Different Classes, Refractoriness to Therapeutic Effects of Classical Neuroleptics, and Individual Variation in Sensitivity to Their Actions: Part I", Current Neuropharmacology, 2009, 7, 302-314.
Miller et al., "Roles of Metabotropic Glutamate Receptors in Brain Plasticity and Pathology", Annals of the New York Academy of Sciences, 1995, 757, 460-474.
Mills et al., "Epidemiology and Reporting of Randomized Trials Employing Re-Randomization of Patient Groups: A Systematic Survey", Contemporary Clinical Trials, 2007, 28, 268-275.
Mitchell et al., "An Update on the Role of Glutamate in the Pathophysiology of Depression", Acta Psychiatrica Scandinavica, 2010, 122(3), 192-210.
Mitri et al., "Divergent Evolution in Metabotropic Glutamate Receptors. A New Receptor Activated by an Endogenous Ligand Different from Glutamate in Insects", Journal of Biological Chemistry, 2004, 279(10), 9313-9320.
Mittal et al., "Impact of Comorbid Anxiety Disorders on Health-Related Quality of Live Among Patients with Major Depressive Disorder", Psychiatric Services, 2006, 57(12), 1731-1737.
Miuller et al., "The Immunological Basis of Glutamatergic Disturbance in Schizophrenia: Towards an Integrated View", J Neural Transm, 2007, 72, 269-280.
Miyamoto et al., "Effects of Ketamine, Mk-801, and Amphetamine on Regional Brain 2-Deoxyglucose Uptake in Freely Moving Mice", Neuropsychopharmacology, 2000, 22, 400-412.

Miyamoto et al., "Treatments for Schizophrenia: A Critical Review of Pharmacology and Mechanisms of Action of Antipsychotic Drugs", Mol. Psychiatry, 2005, 10, 79-104.
Modafferi "Morphine Withdrawal Increases Metabotropic Glutamate 2/3 Receptors Expression in Nucleus Accumbens", Neurochemistry, 2008, 19(9), 911-914.
Moffitt et al., "Depression and Generalized Anxiety Disorder", Arch. Gen. Psychiatry, 2007, 64, 651-660.
Moghaddam et al., "Activation of Glutamatergic Neurotransmission by Ketamine: A Novel Step in the Pathway from NMDA Receptor Blockade to Dopaminergic and Cognitive Disruptions Associated with the Prefrontal Cortex", J Neurosci. 1997, 17(8), 2921-2927.
Moghaddam et al., "From Revolution to Evolution: the Glutamate Hypothesis of Schizophrenia and Its Implication for Treatment", Neuropsychopharmacology, 2012, 37, 4-15.
Moghaddam el al., "Reversal of Phencyclidine Effects by a Group II Metabotropic Glutamate Receptor Agonist in Rats", Science, 1998, 281, 1349-1352.
Moghaddam, "Targeting Metabotropic Glutamate Receptors for Treatment of the Cognitive Symptoms of Schizophrenia", Psychopharmacology, 2004, 174(1), 39-44.
Moldrich et al., "Anti-Epileptic Activity of Group II Metabotropic Glutamate Receptor Agonists (--)-2-Oxa-4-Aminobicyclo[3.1.0]Hexane-4,6-Dicarboxylate (Ly379268) and (--)-2-Thia-4-Aminobicyclo[3.1.0]Hexane-4,6-Dicarboxylate (Ly389795)", Neuropharmacology, 2001, 41, 8-18.
Moldrich et al., "Astrocyte Mglu(2/3)-Mediated Camp Potentiation is Calcium Sensitive: Studies in Murine Neuronal and Astrocyte Cultures", Neuropharmacology, 2002, 43(2), 189-203.
Moldrich et al., "Emerging Signalling and Protein Interactions Mediated via Metabotropic Glutamate Receptors", Curr. Drug Targets. CNS Neurol. Disord., 2003, 2(2), 109-122.
Moldrich et al., "Glutamate Metabotropic Receptors as Targets for Drug Therapy in Epilepsy", European Journal of Pharmacology, 2003, 476, 3-16.
Molina et al., "Polymorphic Variation at the Serotonin 1-A Receptor Gene is Associated with Comorbid Depression and Generalized Anxiety", Psychiatry Genetics, 2011, 21, 195-201.
Molinaro et al., "Activation of Mglu2/3 Metabotropic Glutamate Receptors Negatively Regulates the Stimulation of Inositol Phospholipid Hydrolysis Mediated by 5-Hydroxytryptamine2a Serotonin Receptors in the Frontal Cortex of Living Mice", Mol. Pharmacol., 2009, 76(2), 379-387.
Mondon et al., "Synthesis of Narciprimine and Related Compounds", Chem. Ber., 1972, 105, 3726-3747.
Mongin et al., "Advances in the Directed Metallation of Azines and Diazines (Pyridines, Pyrimidines, Pyrazines, Pyridazines, Quinolines, Benzodiazines and Carbolines). Part 1: Metallation of Pyridines, Quinolines and Carbolines", Tetrahedron, 2001, 57(19), 4059-4090.
Monn et al., "Design, Synthesis, and Pharmacological Characterization of (+)-2-Aminobicyclo[3.1.0]Hexane-2,6-Dicarboxylic Acid (Ly354740): A Potent, Selective, and Orally Active Group 2 Metabotropic Glutamate Receptor Agonist Possessing Anticonvulsant and Anxiolytic Properties", J Med Chem, 1997, 40, 528-537.
Monn et al., "Synthesis and Metabotropic Glutamate Receptor Activity of S-Oxidized Variants of (-)-4-Amino-2-Thiabicyclo-[3.1.0]Hexane-4,6-Dicarboxylate: Identification of Potent, Selective, and Orally Bioavailable Agonists for Mglu2/3 Receptors", J. Med. Chem., 2007, 50, 233-240.
Monn et al., "Synthesis, Pharmacological Characterization, and Molecular Modeling of Heterobicyclic Amino Acids Related to (+)-2-Aminobicyclo[3.1.0] Hexane-2,6-Dicarboxylic Acid (Ly354740): Identification of Two New Potent, Selective, and Systemically Active Agonists for Group II Metabotropic Glutamate Receptors", Journal of Medicinal Chemistry, 1999, 42(6), 1027-1040.
Monti et al., "Conventional and Power Spectrum Analysis of the Effects of Zolpidem on Sleep Eeg in Patients with Chronic Primary Insomnia", Sleep, 2000, 23, 1075-1084.
Moore et al., "Cycloadditions of Cyanoketenes to Cinnamylideneamines and Benzylideneamines. Synthetic Scope, Stereochemistry, and Mechanism", Journal Org. Chem., 1985, 50, 4231-4238.

(56) References Cited

OTHER PUBLICATIONS

Mora et al., "Role of 5-Ht2a and 5-Ht2c Receptor Subtypes in the Two Types of Fear Generated by the Elevated T-Maze", Pharmacology Biochemistry and Behavior, 1997, 58, 1051-1057.
Moreno et al. "Group II Metabotropic Glutamate Receptors and Schizophrenia", Cell Mol. Life Sci., 2009, 66(23), 3777-3785.
Moreno et al., "Maternal Influenza Viral Infection Causes Schizophrenia-Like Alterations of 5-Ht2a and Mglu2 Receptors in the Adult Offspring", Journal of Neuroscience, 2011, 31(5), 1863-1872.
Moreno et al., "Metabotropic Glutamate Mglu2 Receptor is Necessary for the Pharmacological and Behavioral Effects Induced by Hallucinogenic 5-Ht2a Receptor Agonists", Neurosci. Lett., 2011, 493, 76-79.
Moreno et al., "Pindolol Augmentation of Treatment-Resistant Depressed Patients" J Clin Psychiatry 1997, 58, 437-439.
Morgan et al., "Is Persistent Ketamine Use a Valid Model of the Cognitive and Oculomotor Deficits in Schizophrenia?", Biol. Psychiatry, 2009, 65(12), 1099-1102.
Morikawa et al., "Two Intracellular Pathways Mediate Metabotropic Glutamate Receptor-Induced Ca2+ Mobilization in Dopamine Neurons", Journal of Neuroscience, 2003, 23(1), 149-157.
Morishima et al., "Enhanced Cocaine Responsiveness and Impaired Motor Coordination in Metabotropic Glutamate Receptor Subtype 2 Knockout Mice", Proc. Natl. Acad. Sci., 2005, 102(11), 4170-4175.
Morishita, "Clonazepam as a Therapeutic Adjunct to Improve the Management of Depression: A Brief Review", Hum Psychopharmacol Clin Exp, 2009, 24, 191-198.
Moroni et al., "Poly(Adp-Ribose) Polymerase Inhibitors Attenuate Necrotic But Not Apoptotic Neuronal Death in Experimental Models of Cerebral Ischemia", Cell Death and Differentiation, 2001, 8, 921-932.
Morpurgo et al., "Drug-Induced Modifications of Discriminated Avoidance Behavior in Rats", Psychopharmacol., 1965, 8, 91-99.
Morrill et al., "Synthesis of 4-Arylpiperidines from 1-Benzyl-4piperidone: Application of the Sharpiro Reaction and Alkenylsilane Cross-Coupling", Organic Letters, 2007, 9, 1505-1508.
Morrison et al., "Schizophrenia: More Evidence for Less Glutamate", Expert Rev Neurother., 2007, 7 (1), 29-31.
Moussawi et al., "Group II Metabotropic Glutamate Receptors (Mglu2/3) in Drug Addiction", European Journal of Pharmacology, 2010, 639, 115-122.
Mudge et al., "Genomic Convergence Analysis of Schizophrenia: Mrna Sequencing Reveals Altered Synaptic Vesicular Transport in Post-Mortem Cerebellum", Plos One, 2008, 3(11) 1-24.
Mukhin et al., "Mglur Modulation of Post-Traumatic Neuronal Death: Role of NMDA Receptors", Neuroreport, 1997, 8(11), 2561-2566.
Muller, "Inflammation and the Glutamate System in Schizophrenia: Implications for Therapeutic Targets and Drug Development", Expert Opin. Ther. Targets, 2008, 12(12), 1497-1507.
Muly et al., "Group II Metabotropic Glutamate Receptors in Anxiety Circuitry: Correspondence of Physiological Response and Subcellular Distribution", J Comp Neurol., 2007, 505(6), 682-700.
Muntasir et al., "Inverse Agonist Activity of Sarpogrelate, a Selective 5-Ht2a-Receptor Antagonist, at the Constitutively Active Human 5-Ht2a Receptor", Journal of Pharmacological Sciences, 2006, 102(2), 189-195.
Murck et al., "State Markers of Depression in Sleep Eeg: Dependency on Drug and Gender in Patients Treated with Tianepine or Paroxetine", Neuropsychopharmacol. 2003, 28, 348-358.
Mutel et al., "Characterization of (2s,2'r,3'r)-2-(2',3'-[3h]-Dicarboxycyclopropyl)Glycine Binding in Rat Brain", J Neurochemistry, 71(6), 1998, 2558-2564.
Mutel, "Therapeutic Potential of Non-Competitive, Subtype-Selective Metabotropic Glutamate Receptor Ligands", Expert Opin. Ther. Patents, 2002, 12(12), 1845-1852.
Muto et al., "Structures of the Extracellular Regions of the Group II/III Metabotropic Glutamate Receptors", Proc. Natl. Acad. Sci. USA, 2007, 104(10), 3759-3764.

Nabeshima et al., "Animal Model of Schizophrenia. Dysfunction of Nmda Receptor-Signaling in Mice Following Withdrawal from Repeated Administration of Phencyclidine", Ann. N.Y. Acad. Sci., 2006, 1086, 160-168.
Nadin et al., "Synthesis of Tricyclic Pyridones by Radical Cyclization", Tetrahedron Letters, 1999, 40, 4073-4076.
Naimoli et al., "Compound A, A Novel Potent and Selective Mglur2 Positive Allosteric Modulator: III. Effects in Clinically Relevant Translational Cognition Models That Could be Used as Biomarkers" Poster 767.1 Presented at the 40th Annual Meeting of Society for Neuroscience, Nov. 2010, 1 page.
Nakamura et al., "An Efficient Synthesis of Platelet-Activating Factor (Paf) J'ij L-Qalkyl-2-~-(3-Isoxazolyl)-Sn_Glycero-3-Phosphocholine, A New Paf Agonist. Utilization of the 3-Isoxazolyloxy Group as a Protected Hydroxyl", Tetrahedron Letters, 1990, 31, 699-702.
Nakanishi, et al., "Glutamate Receptors: Brain Function and Signal Transduction", Brain Research Reviews, 1998, 26, 230-235.
Nakano et al., "1-Alkyl-3-Phenylpyridinium 1-Alkyl-2(1h)-Pyridone 3-Phenyl 5-Phenyl", Annual Report of Tohoku College of Pharmacy, 1998, 45, 145-148.
Nasca et al., "L-Acetylcarnitine Causes Rapid Antidepressant Effects Through the Epigenetic Induction of Mglu2 Receptors", Proceedings of the Nat. Acad. of Sci. of US, 2013, 110(12), 4804-4809.
Neale, "The Neurotransmitter N-Acetylaspartylglutamate in Models of Pain, Als, Diabetic Neuropathy CNS Injury and Schizophrenia", Trends in Pharmacological Sciences 2005, 26(9), 477-484.
Neki et al., "Metabotropic Glutamate Receptors Mglur2 and Mglur5 are Expressed in Two Non-Overlapping Populations of Golgi Cells in the Rat Cerebellum", Neuroscience, 1996, 75(3), 815-826.
Neki et al., "Pre- and Postsynaptic Localization of a Metabotropic Glutamate Receptor, Mglur2, in the Rat Brain: An Immunohistochemical Study with a Monoclonal Antibody", Neurosci. Lett., 1996, 202(3), 197-200.
Nell et al., "Preparation of 4-Amino-3,5-Dicyano-2-Thiopyridines as Cardiovascular Agents", Caplus, 2008, 1 page.
Nelson, "Anxiety Does Not Predict Response to Duloxetine in Major Depression: Results of a Pooled Analysis of Individual Patient Data From 11 Placebo-Controlled Trials", Depression and Anxiety, 2010, 27, 12-18.
Nelson et al., "Anxiety Does Not Predict Response to Antidepressant Treatment in Late Life Depression: Results of a Meta-Analysis", Int J Geriatr Psychiatry, 2009, 24, 539-544.
Nelson et al., "Species Differences in the Pharmacology of the 5-Hydroxytrayptamine2 Receptor: Structurally Specific Differentiation by Ergolines and Tryptamines", Jpet, 1993, 265, 1272-1279.
Nelson, "Anxious Depression and Response to Treatment", Am J Psychiatry, 2008, 165(3), 297-299.
Nestler, "Common Molecular and Cellular Substrates of Addiction and Memory", Neurobiol. of Learning and Memory, 2002, 78, 637-647.
Neubig et al., "Specificity of Receptor-G Protein Coupling: Protein Structure and Cellular Determinants", Seminars in Neuroscience, 1998, 9, 189-197.
Neugebauer et al., "Groups II and III Metabotropic Glutamate Receptors Differentially Modulate Brief and Prolonged Nociception in Primate Stt Cells", J Neurophysiol, 2000, 84, 2998-3009.
Neugebauer et al., "Peripheral Metabotropic Glutamate Receptors as Drug Targets for Pain Relief", Expert Opinion on Therapeutic Targets, 2002, 6(3), 349-361.
Neugebauer et al., "Requirement of Metabotropic Glutamate Receptors for the Generation of Inflammation-Evoked Hyperexcitability in Rat Spinal Cord Neurons", European Journal of Neuroscience, 1994, 6(7), 1179-1186.
Neugebauer, "Metabotropic Glutamate Receptors—Important Modulators of Nociception and Pain Behavior", Pain, 2002, 98, 1-8.
"Neuroprotection As Initial Therapy in Acute Stroke", Third Report of an Ad Hoc Consensus Group Meeting, European Ad Hoc Consensus Group, Cerebrovascular Diseases 1998, 8(1), 59-72.
Ngomba et al., "Metabotropic Glutamate Receptors in the Thalamocortical Network: Strategic Targets for the Treatment of Absence Epilepsy", Epilepsia, 2011, 52(7), 1211-1222.

(56) References Cited

OTHER PUBLICATIONS

Ngomba et al., "The Preferential Mglu2/3 Receptor Antagonist, Ly341495, Reduces the Frequency of Spike-Wave Discharges in the Wag/Rij Rat Model of Absence Epilepsy", Neuropharmacology, 2005, 49, 89-103.

Nguyen et al., "An in Vivo Biosensor for Neurotransmitter Release and In Situ Receptor Activity", Nature Neuroscience, 2010, 13(1), 127-32.

Nicholls et al., "Mglur2 Acts Through Inhibitory G? Subunits to Regulate Transmission and Long-Term Plasticity at Hippocampal Mossy Fiber-Ca3 Synapses", Proc. Natl. Acad. Sci. USA, 2006, 103(16), 6380-6385.

Nicholls et al., "The Release and Uptake of Excitatory Amino Acids", Trends in Pharmacological Sciences, 1990, 11(11), 462-468.

Nicolas et al., "A Combined Marble Buyring-Locomotor Activity Test in Mice: A Practical Screening Test with Sensitivity to Different Classes of Anxiolytics and Antidepressants", Eur J Pharmacol., 2006, 547(1-3), 106-115.

Nicoletti et al., "Lesions of Putative Glutamatergic Pathways Potentiate the Increase of Inositol Phospholipid Hydrolysis Elicited by Excitatory Amino Acids", Brain Research, 1987, 436(1), 103-112.

Nicoletti et al., "Metabotropic Glutamate Receptors: Beyond the Regulation of Synaptic Transmission", Psychoneuroendocrinology, 2007, 32(Suppl 1), S40-S45.

Nicoletti et al., "Metabotropic Glutamate Receptors: from the Workbench to the Bedside", Neuropharmacology, 2011, 60, 1017-1041.

Nicoletti et al., "Metabotropic Glutamate Receptors: New Targets for the Control of Tumor Growth", Trends in Pharmacological Sciences, 2007, 206-213.

Nicoletti et al., "Pertussis Toxin Inhibits Signal Transduction at a Specific Metabolotropic Glutamate Receptor in Primary Cultures of Cerebellar Granule Cells", Neuropharmacology, 1988, 27(6), 551-556.

Nielson et al., "Phosphoramides XIV. Phosphorus Pentozide and Amine Hydrochlorides as Reagents in the Synthesis of Thieno{2,3-D]Pyrimidin-4(3h)-Ones", Chemica Scripta, 1981, 18, 135-138.

Niemegeers et al., "Direct Measurement of the Ph in the Stomach of the Conscious Rat, Using a Special Electrode", Experentia, 1979, 35, 1538-1539.

Niemegeers et al., "Interaction of Drugs with Apomorphine, Tryptamine, and Norepinephrine. A New 'in Vivo' Approach: the Atn-Test in Rats", Arch. Int. Pharmacodyn., 1977, 227, 238-253.

Niemegeers et al., "Protection of Rats from Compound 48/80-Induced Lethality. A Simple Test for Inhibitors of Mast Cell-Mediated Shock", Arch. Int. Pharmacodyn., 1978, 234, 164-176.

Nierenberg et al., "Lithium Augmentation of Nortriptyline for Subject Resistant to Multiple Antidepressants", J Clin Psychopharmacol, 2003, 23, 92-95.

Nijholt et al., "Neuronal Akap150 Coordinates Pka and Epac-Mediated Pkb/Akt Phosphorylation", Cellular Signaling, 2008, 20, 1715-1724.

Nikiforuk et al., "Effects of a Positive Allosteric Modulator of Group II Metabotropic Glutamate Receptors, Ly487379, On Cognitive Flexibility and Impulsive-Like Responding in Rats", Jpet, 2010, 335, 665-673.

Ninomiya et al., "Photocyclisation of Enamides. Part 14. Substituent Effects in the Photocyclisation of N-A,B-Unsaturated Acylanilides", J. Chem. Soc. Perkin Transactions, 1980, 1, 197-202.

Nishi et al., "Pharmacological Characterization of Metabotropic Glutamate Receptor-Mediated High-Affinity Gtpase Activity in Rat Cerebral Cortical Membranes", British Journal of Pharmacology, 2000, 130, 1664-1670.

Niswender et al., "Metabotropic Glutamate Receptors: Physiology, Pharmacology, and Disease", Annu Rev Pharmacol Toxicol, 2010, 50, 295-322.

Nofzinger et al., "Changes in Forebrain Function from Waking to Rem Sleep in Depression: Preliminary Analyses of [18f]Fdg Pet Studies", Psychiatry Res, 1999, 91, 59-78.

Noguchi et al., "Quantum Chemical Study on Conformational Properties of Bipyridine Cardiotonics", Chem. Pharm. Bull., 1993, 41(8), 1331-1336.

Nordquist, "Metabotropic Glutamate Receptor Modulation, Translational Methods, and Biomarkers: Relationships with Anxiety", Psychopharmacology, 2008, 199, 389-402.

Norman et al., "Structure-Activity Relationships of a Series of Pyrrolo[3,2-D]Pyrimidine Derivatives and Related Compounds as Neuropeptide Y5 Receptor Antagonists", J. Med. Chem., 2000, 43, 4288-4312.

O'Brien et al., "Molecular Mechanisms of Glutamate Receptor Clustering at Excitatory Synapses", Current Opinion in Neurobiology, 1998, 8(3), 364-369.

O'Connor et al., "Metabotropic Glutamate Receptor 7: At the Interface of Cognition and Emotion", European Journal of Pharmacology, 2010, 639, 123-131.

O'Neill et al., "Effects of Ischaemic Conditions on Uptake of Glutamate, Aspartate, and Noradrenaline by Cell Lines Derived from the Human Nervous System", Journal of Neurochemistry, 1994, 63(2), 603-611.

O'Neill et al., "Recent Developments in Metabotropic Glutamate Receptors as Novel Drug Targets", Drugs of the Future, 2010, 35, 307-324.

Odagaki et al., "Functional Coupling Between Metabotropic Glutamate Receptors and G-Proteins in Rat Cerebral Cortex Assessed by Guanosine-5'-O-(3-[35s]Thio)Triphosphate ([35s]Gtpys) Binding Assay", Basic & Clinical Pharmacology & Toxicology, 2011, 44 pages.

Odagaki et al., "Group II Metabotropic Glutamate Receptor-Mediated Activation of G-Proteins in Rat Hippocampal and Striatal Membranes", Neuroscience Letters, 2013, 24 pages.

Oehlrich, "Positive Allosteric Modulation of Mglur2 Receptors in the Treatment of CNS Disorders", Neuroscience Med Chem, 2012, 31 pages.

Ohishi et al., "Distribution of a Metabotropic Glutamate Receptor, Mglur2, in the Central Nervous System of the Rat and Mouse: An Immunohistochemical Study with a Monoclonal Antibody", Neuroscience Research, 1998, 30, 65-82.

Ohishi et al., "Distribution of the Messenger Rna for Metabotropic Glutamate Receptor, Mglu2, in the Central Nervous System of the Rat", Neuroscience, 1993, 53, 1009-1018.

Ojima et al., "Hydroformation of Fluoro Olefins, Rfch=Ch2, Catalyzed by Group VIII Transition-Metal Catalysts. Crucial Factors for Extremly High Regioselectivity", Journal of American Chemical Society, 1987, 109, 7714-7720.

Olbrich et al., "Frontolimbic Glutamate Alterations in First Episode Schizophrenia: Evidence From a Magnetic Resonance Spectroscopy Study", World J Biol Psychiatry, 2008, 9(1), 59-63.

Oldenziel et al., "In Vivo Monitoring of Extracellular Glutamate in the Brain with a Microsensor", Brain Res., 2006, 1118(1), 34-42.

Olive, "Cognitive Effects of Group I Metabotropic Glutamate Receptor Ligands in the Context of Drug Addiction", European Journal of Pharmacology, 2010, 639, 47-58.

Olive, Metabotropic Glutamate Receptor Ligands as Potential Therapeutics for Addiction. Curr. Drug Abuse Rev 2009, 2 (1), 83-98.

Olivier et al., "Stress-Induced Hyperthermia and Anxiety: Pharmacological Validation", Eur J Pharmacol, 2003, 463, 117-132.

Olney et al., "NMDA Receptor Hypofunction Model of Schizophrenia", Journal of Psychiatric Research, 1999, 33, 523-533.

Olszewski et al., "Naag Peptidase Inhibition Reduces Locomotor Activity and Some Stereotypes in the Pcp Model of Schizophrenia via Group II Mglur", J. Neurochem., 2004, 89(4), 876-885.

Olszewski et al., "Phencyclidine and Dizocilpine Induced Behaviors Reduced by N-Acetylaspartylglutamate Peptidase Inhibition via Metabotropic Glutamate Receptors", Biol. Psychiatry, 2008, 63(1), 86-91.

Ong et al., "Localisation of Glutamate Receptors in the Substantia Nigra Pars Compacta of the Monkey", Journal Fur Hirnforschung, 1997, 38(3), 291-298.

Oquendo et al., "A Computer Algorithm for Calculating the Adequacy of Antidepressant Treatment in Unipolar and Bipolar Depression", J Clin Psychiatry, 2003, 64(7), 825-833.

(56) References Cited

OTHER PUBLICATIONS

Orlando, "The Role of Group I and Group II Metabotropic Glutamate Receptors in Modulation of Striatal Nmda and Quinolinic Acid Toxicity", Experimental Neurology, 2001, 167, 196-204.
Orlowski et al., "D-and L-Stereoisomers of Allylglycine: Convulsive Action and Inhibition of Brain L-Glutamate Decarboxylase", J Neurochem, 1977, 28, 349-353.
Orrenius et al., "Calcium Ions and Oxidative Cell Injury", Annals of Neurology, 1992, 32(Suppl-42), S33-S42.
Osikowicz et al., "Glutamate Receptor Ligands Attenuate Allodynia and Hyperalgesia and Potentiate Morphine Effects in a Mouse Model of Neuropathic Pain", Pain, 2008, 139, 117-126.
Ossowska et al., "The Role of Glutamate Receptors in Antipsychotic Drug Action", Amino. Acids, 2000, 19(1), 87-94.
Ossowska et al., "The Striatum as a Target for Anti-Rigor Effects of an Antagonist of Mglur1, But Not an Agonist of Group II Metabotropic Glutamate Receptors", Brain Research, 2002, 950, 88-94.
O'suilleabhain, "A Randomized Trial of Amantadine in Huntington Disease", Arch Neurol, 2003, 60, 996-998.
Othmer et al., "Brain Functions and Psychiatric Disorders: A Clinical View", Diagnostic Dilemmas, Part I, the Psychiatryc Clinics of N.A., Sep. 1998, 21(3), 517-566.
Ottersen et al., "Organization of Glutamate Receptors at the Synapse", European Journal of Neuroscience, 1997, 9(11), 2219-2224.
Overstreet et al., "A 5-Ht1a Agonist and a 5-Ht2c Antagonist Reduce Social Interaction Deficit Induced by Multiple Ethanol Withdrawals in Rats", Psychopharmacology, 2003, 167, 344-352.
Ozawa et al., "Glutamate Receptors in the Mammalian Central Nervous System", Progress in Neurobiology, 1998, 54(5), 581-618.
Page et al., "Metabotropic Glutamate Receptors Inhibit Mechanosensitivity in Vagal Sensory Neurons", Gastroenterology, 2005, 128(2), 402-410.
Pajer et al., "Discovery of Blood Transcriptomic Markers for Depression in Animal Models and Pilot Validation in Subjects with Early-Onset Major Depression", Transl Psychiatry, 2012, 2(E101), 10 pages.
Pajonk et al., "Comparing the Efficacy of Atypical Antipsychotics in Open Uncontrolled Versus Double-Blind Controlled Trials in Schizophrenia", Psychopharmacology (Berl.), 2002, 162(1), 29-36.
Palazzo et al., "Metabotropic and Nmda Glutamate Receptors Participate in the Cannabinoid-Induced Antinociception", Neuropharmacology, 2001, 40(3), 319-326.
Palop et al., "Amyloid-B-Induced Neuronal Dysfunction in Alzheimer's Disease: From Synapses Toward Neural Networks", Nature Neuroscience, 2010, 13(7), 812-818.
Palucha et al., "Chronic Imipramine Treatment Reduces Inhibitory Properties of Group II Mglu Receptors Without Affecting Their Density or Affinity", Pharmacol. Rep., 2007, 59(5), 525-530.
Palucha et al., "Metabotropic Glutamate Receptor Ligands as Possible Anxiolytic and Antidepressant Drugs", Pharmacology & Therapeutics, 2007, 115, 116-147.
Palucha et al., "The Involvement of Glutamate in the Pathophysiology of Depression", Drug News Perspect, 2005, 18(4), 262-268.
Palucha, "Are Compounds Acting at Metabotropic Glutamate Receptors the Answer to Treating Depression?", Expert Opin. Investig. Drugs, 2006, 15(12), 1545-1553.
Palucha-Poniewiera et al., "On the Mechanism of the Antidepressant-Like Action of Group II Mglu Receptor Antagonist, Mgs0039", Psychopharmacology, 2010, 212, 523-535.
Panzer, "Are SSRIs Really More Effective for Anxious Depression?", Annals of Clinical Psychiatry, 2005, 17(1), 23-29.
Papakostas et al., "Augmentation of Antidepressants with Atypical Antipsychotic Medications for Treatment-Resistant Major Depressive Disorder: A Meta-Analysis", J Clin Psychiatry 2007, 68(6), 826-831.
Papakostas et al., "Efficacy of Bupropion and the Selective Serotonin Reuptake Inhibitors in the Treatment of Major Depressive Disorder with High Levels of Anxiety (Anxious Depression): A Pooled Analysis of 10 Studies", J Clin Psychiatry, 2008, 69(8), 1287-1292.
Papakostas et al., "Fluxetine-Clonazepam Cotherapy for Anxious Depression: An Exploratory, Post-Hoc Analysis of a Randomized, Double Blind Study", International Clinical Psychopharmacology, 2010, 25, 17-21.
Papakostas et al., "Predictors, Moderators, and Mediators (Correlates) of Treatment Outcome in Major Depressive Disorder", Dialogues Clin Neurosci., 2008, 10, 439-451.
Papakostas et al., "Severe and Anxious Depression: Combining Definitions of Clinical Sub-Types to Identify Patients Differentially Responsive to Selective Serotonin Reuptake Inhibitors", European Neuropsychopharmacology, 2012, 22, 347-355.
Papakostas et al., "Testing Anxious Depression as a Predictor and Moderator of Symptom Improvement in Major Depressive Disorder During Treatment with Escitalopram", Eur Arch Psychiatry Clin Neurosci, 2011, 261, 147-156.
Parmentier et al., "A Model for the Functioning of Family 3 Gpcrs", Trends in Pharmacological Sciences, 2002, 23(6), 268-274.
Parnot et al., "Toward Understanding Gpcr Dimers", Nature Structural & Molecular Biology, 2004, 11(8), 691-692.
Parry et al., "Functionalized Pyridylboronic Acids and Their Suzuki Cross-Coupling Reactions to Yield Novel Heteroarylpyridines", J. Org. Chem., 2002, 67, 7541-7543.
Parsons et al., "Memantine: A NMDA Receptor Antagonist That Improves Memory by Restoration of Homeostasis in the Glutamatergic System—Too Little Activation Is Bad, Too Much Is Even Worse", Neuropharmacology, 2007, 53, 699-723.
Passchier et al., "Measuring Drug-Related Receptor Occupancy with Positron Emission Tomography", Methods, 2002, 27, 278-286.
Pastorino et al., "Pin1 Protects Against Alzheimer's Disease: One Goal, Multiple Mechanisms", Intech, 2013, 36 pages.
Patani et. al. "Bioisosterism: A Rational Approach in Drug Design" Chemical Reviews 1996, 96, 314 7-3176.
Patil, "Activation of Mglu2/3 Receptors as a New Approach to Treat Schizophrenia: A Randomized Phase 2 Clinical Trial", Nature Medicine, 2007, 13(9), 1102-1107.
Patkar et al., "A Randomized, Double-Blind, Placebo-Controlled Trial of Augmentation with an Extended Release Formulation of Methylphenidate in Outpatients with Treatment-Resistant Depression", J Clin Psychopharmacol, 2006, 26, 653-656.
Paykel et al., "Response to Phenelzine and Amitriptyline in Subtypes of Outpatient Depression", Arch Gen Psychiatry, 1982, 39, 1041-1049.
Pehrson et al., "Impact of Metabotropic Glutamate 2/3 Receptor Stimulation on Activated Dopamine Release and Locomotion", Psychopharmacology, 2010, 211, 443-455.
Pellicciari et al., "Metabotropic Glutamate Receptors: Structure and New Subtype-Selective Ligands", Il Farmaco, 2001, 56(1-2), 91-94.
Pellicciari et al., "Metabotropic G-Protein-Coupled Glutamate Receptors as Therapeutic Targets", Current Opinion in Chemical Biology, 1999, 3(4), 433-440.
Pellicciari et al., "Modulation of Glutamate Receptor Pathways in the Search for New Neuroprotective Agents", Farmaco, 1998, 53(4), 255-261.
Penninx et al., "Two-Year Course of Depressive and Anxiety Disorders: Results from the Netherlands Study of Depression and Anxiety (Nesda)", Journal of Affective Disorders, 2011, 133, 76-85.
Pereira et al., "Study Pharmacologic of the Gabaergic and Glutamatergic Drugs on Seizures and Status Epilepticus Induced by Pilocarpine in Adult Wistar Rats", Neuroscience Letters, 2007, 419, 253-257.
Perkins et al., "Pharmacokinetics, Metabolism, and Excretion of the Intestinal Peptide Transporter 1 (Slc15a1)-Targeted Prodrug (1s,2s,5r,6s)-2-[(2's)-(2-Amino)Propionyl]Aminobicyclo[3.1.0]Hexen-2,6-Dicarboxylic Acid (Ly544344) in Rats and Dogs: Assessment of First-Pass Bioactivation and Dose Linearity", Drug Metabolism and Disposition, 2007, 35, 1903-1909.
Perroy et al., "The C Terminus of the Metabotropic Glutamate Receptor Subtypes 2 and 7 Specifies the Receptor Signaling Pathways", Journal of Biological Chemistry, 2001, 276(49), 45800-45805.
Petroff, "Glutamate-Glutamine Cycling in the Epileptic Human Hippocampus", Epilepsia, 2002, 43(7) 703-710.
Pettmann et al., "Neuronal Cell Death", Neuron, 1998, 20(4), 633-647.

(56) References Cited

OTHER PUBLICATIONS

Pfeiffer et al., "Benzodiazepines and Adequacy of Initial Antidepressant Treatment for Depression", J Clin Psychopharmacol, 2011, 31, 360-364.
Piccinin et al., "Interaction Between Ephrins and Mglu5 Metabotropic Glutamate Receptors in the Induction of Long-Term Synaptic Depression in the Hippocampus", Journal of Neuroscience, 2010, 30(8), 2835-2843.
Pietraszek et al., "The Role of Group I Metabotropic Glutamate Receptors in Schizophrenia", Amino Acids, 2006, 7 pages.
Pike, "Pet Radiotracers: Crossing the Blood-Brain Barrier and Surviving Metabolism", Trends Pharmacol Sci, 2009, 30, 431-440.
Pilc et al., "Mood Disorders: Regulation by Metabotropic Glutamate Receptors", Biochemical Pharmacology, 2008, 75, 997-1006.
Pin et al., "Evolution, Structure, and Activation Mechanism of Family 3/C G-Protein-Coupled Receptors", Pharmacology & Therapeutics, 2003, 98, 325-354.
Pin et al., "Get Receptive to Metabotropic Glutamate Receptors", Current Opinion in Neurobiology, 1995, 5(3), 342-349.
Pin et al., "New Perspectives for the Development of Selective Metabotropic Glutamate Receptor Ligands", European J of Pharmacology, 1999, 375, 277-294.
Pin et al., "Positive Allosteric Modulators for—Aminobutyric Acidb Receptors Open New Routes for the Development of Drugs Targeting Family 3 G-Protein-Coupled Receptors" Mol Pharmacol 2001, 60, 881-884.
Pin et al., "Release of Endogenous Amino Acids From Striatal Neurons in Primary Culture", Journal of Neurochemistry, 1986, 47(2), 594-603.
Pin et al., "The Metabotropic Glutamate Receptors: Structure and Functions", Neuropharmacology, 1995, 34(1), 1-26.
Pin et al., "Alternative Splicing Generates Metabotropic Glutamate Receptors Inducing Different Patterns of Calcium Release in Xenopus Oocytes", Proceedings of the National Academy of Sciences of the USA, 1992, 89(21), 10331-10335.
Pinhasov et al., "Reduction of Submissive Behavior Model for Antidepressant Drug Activity Testing: Study Using a Video-Tracking System", Behav Pharmacol, 2005, 16, 657-664.
Pinheiro et al., "Presynaptic Glutamate Receptors: Physiological Functions and Mechanisms of Action", Nat. Rev Neurosci., 2008, 9(6), 423-436.
Pinkerton et al., "Allosteric Potentiators of the Metabotropic Glutamate Receptor 2 (Mglu2). Part 1: Identification and Synthesis of Phenyl-Tetrazolyl Acetophenones", Bioorganic & Medicinal Chemistry Letters, 2004, 14, 5329-5332.
Pinkerton et al., "Allosteric Potentiators of the Metabotropic Glutamate Receptor 2 (Mglu2). Part 2: 4-Thiopyridyl Acetophenones as Non-Tetrazole Containing Mglu2 Receptor Potentiators", Bioorganic & Medicinal Chemistry Letters, 2004, 14, 5867-5872.
Pinkerton et al., "Substituted Acetophenones as Selective and Potent Allosteric Potentiators of the Metabotropic Glutamate Receptor 2 (Mglur2)", 229th ACS National Meeting, Mar. 2005, 1 page.
Pinkerton, "Allosteric Potentiators of the Metabotropic Glutamate Receptor 2 (Mglu2). Part 3: Identification and Biological Activity of Indanone Containing Mglu2 Receptor Potentiators", Bioorganic & Medicinal Chemistry Letters, 2005, 15, 1565-1571.
Pinkerton et al., "Phenyl-Tetrazolyl Acetophenones: Discovery of Positive Allosteric Potentiators for the Metabotropic Glutamate 2 Receptor", J. Med. Chem, 2004, 47, 4595-4599.
Pittenger et al., "Stress, Depression, and Neuroplasticity: A Convergence of Mechanisms", Neuropsychopharmacology, 2008, 33(1), 88-109.
Pitts et al., "Lactate Metabolism in Anxiety Neurosis", New England Journal of Medicine, 1967, 277, 1329-1336.
Pizzi et al., "Activation of Multiple Metabotropic Glutamate Receptor Subtypes Prevents NMDA-Induced Excitotoxicity in Rat Hippocampal Slices", European Journal of Neuroscience, 1996, 8(7), 1516-1521.
Poisik, et al., "Metabotropic Glutamate Receptor 2 Modulates Excitatory Synaptic Transmission in the Rat Globus Pallidus", Neuropharmacology, 2005, 49, 57-69.
Popik et al., "Selective Agonist of Group II Glutamate Metabotropic Receptors, Ly354740, Inhibits Tolerance to Analgesic Effects of Morphine in Mice", British Journal of Pharmacology, 2000, 130, 1425-1431.
Porsolt et al., "Behavioural Despair in Mice: A Primary Screening Test for Antidepressants", Arch. Int. Pharmacodyn., 1977, 229, 327-336.
Porsolt et al., "Behavioural Despair in Rats: A New Model Sensitive to Antidepressant Treatments", Eur. J. Pharmacol., 1978, 47(4), 379-391.
Porter et al., "(S)-Homoquisqualate: A Potent Agonist at the Glutamate Metabotropic Receptor", British Journal of Pharmacology, 1992, 106(3), 509-510.
Posluns, "An Analysis of Chlorpromazine-Induced Suppression of the Avoidance Response.", Psychopharmacol. 3: 361-373 (1962).
Posner et al., "Columbia Classification Algorithm of Suicide Assessment (C-Casa): Classification of Suicidal Events in the FDA's Pediatric Suicidal Risk Analysis of Antidepressants", American Journal of Psychiatry, 2007, 164, 1035-1043.
Potts et al., "1,2,4-Triazoles. Xii. Derivatives of the S-Triazolo[4,3-A]Pyridine Ring System", Journal of Organic Chemistry, 1966, 251-260.
Potts et al., "1,2,4-Trizoles. Xxv. The Effect of Pyridine Substitution on the Isomerization of S-Triazolo [4,3-A] Pyridines Into S-Triazolo [1,5-A] Pyridines (1)", J. Heterocycl. Chem., 1970, 7, 1019-1027.
Poyurovsky et al., "Lamotrigine Augmentation in Schizophrenia and Schizoaffective Patients with Obsessive-Compulsive Symptoms", J Psychopharmacol., 2010, 24(6), 861-866.
Prabakaran et al., "2-D Dige Analysis of Liver and Red Blood Cells Provides Further Evidence for Oxidative Stress in Schizophrenia", Journal of Proteome Research, 2007, 6, 141-149.
Prager et al., "The Synthesis of Peroline, 6-(3,4-Dimethoxyphenyl)-5-Hydroxy-5,6-Dihydrobenzo[C][2,7]Naphthyridin-4(3h)-One", Aust. J. Chem., 1983, 36, 1441-1453.
Pralong et al., "Cellular Perspectives on the Glutamate-Monoamine Interactions in Limbic Lobe Structures and Their Relevance for Some Psychiatric Disorders", Progress in Neurobiology, 2002, 67, 173-202.
Prezeau et al., "Functional Crosstalk Between Gpcrs: With or Without Oligomerization", Current Opinion in Pharmacology, 2010, 10, 6-13.
Prezeau et al., "Pharmacological Characterization of Metabotropic Glutamate Receptors in Several Types of Brain Cells in Primary Cultures", Mol Pharmacol, 1993, 45(4), 570-577.
Prina et al., "Co-occurrence of Anxiety and Depression Amongst Older Adults in Low and Middle Income Countries: Findings From the 10/66 Study", Psychological Medicine, Oct. 2011, 41(10), 2047-2056.
Priolo et al., "Panic-Like Attack Induced by Microinfusion Into the Locus Coeruleus of Antagonists and Inverse Agonists at Gabaa-Receptors in Rodents", Funct Neurol, 1991, 6, 393-403.
Profaci et al., "Group II Mglur Agonist Ly354740 and Naag Peptidase Inhibitor Effects on Prepulse Inhibition in Pcp and D-Amphetamine Models of Schizophrenia", Psychopharmacology, 2011, 216, 235-243.
Prous Science Integrity 2007—Chemical Structure Ly-404039.
Prous Science Integrity 2007—Chemical Synthesis Ly-2140023.
Pszczolkowski et al., "Effect of Metabotropic Glutamate Receptor Agonists and Signal Transduction Modulators on Feeding by a Caterpillar", Pharmacology, Biochemistry and Behavior, 2005, 82, 678-685.
Putt et al., "An Enzymatic Assay for Poly(Adp-Ribose) Polymerase-1 (Parp-1) via the Chemical Quantitation of Nad+: Application to the High-Throughput Screening of Small Molecules as Potential Inhibitors", Analytical Biochemistry, 2004, 326, 78-86.
Quitkin et al., "Placebo Run-in Period in Studies of Depressive Disorders: Clinical, Heuristic and Research Implications", British Journal of Psychiatry, 1998, 173, 242-248.

(56) References Cited

OTHER PUBLICATIONS

Raffray et al., "Apoptosis and Necrosis in Toxicology: A Continuum or Distinct Modes of Cell Death?", Pharmacology & Therapeutics, 1997, 75(3), 153-177.
Rani et al., "Thiazoline Analogues of Epiderstatin, New Inhibitiors of Cell Cycle of Tsft-210 Cells", Journal of Antibiotics, 1995, 48(10), 1179-1181.
Rao et al., "Anxious Depression: Clinical Features and Treatment", Current Psychiatry Reports, 2009, 11, 429-436.
Raskin et al., "Differential Response to Chlorpromazine, Imipramine, and Placebo. A Study of Subgroups of Hospitalized Depressed Patients", Arch Gen Psychiat, 1970, 23, 164-173.
Ravaris et al., "Phenelzine and Amitriptyline in the Treatment of Depression: A Comparison of Present and Past Studies", Arch Gen Psychiatry, 1980, 37, 1075-1080.
Recasens et al., "Metabotropic Glutamate Receptors as Drug Targets", Current Drug Targets, 2007, 8(5), 651-681.
Regier et al., "Comorbidity of Mental Disorders with Alcohol and Other Drug Abuse. Results From the Epidemiologic Catchment Area (Eca) Study", Jama, 1990, 264, 2511-2518.
Rehwald et al., "3-Amino-2(1h)-Quinolones by Cyclization of N-Acylated Anthranilic Acid Derivatives", Heterocycles, 1997, 45(3), 483-492.
Reiner et al., "Bdnf May Play a Differential Role in the Protective Effect of the Mglur2/3 Agonist Ly379258 on Striatal Projection Neurons in R6/2 Huntington's Disease Mice", Brain Research, 2012, 1473, 161-172.
Reis et al., "Reactions of Tricarbonyl(Vinylketene)Iron(0) Complexes with Imines", Organometallics, 1995, 14, 1586-1591.
Renslo et al., "Synthesis of Aza-, Oxa-, and Thiabicyclo[3.1.0]Hexane Heterocycles From a Common Synthetic Intermediate", Organic Letters, 2005, 7(13), 2627-2630.
Reynolds et al., "New Approaches to the Drug Treatment of Schizophrenia", Adv. Pharmacol., 1995, 32, 461-503.
Reynolds et al., "Sleep Research in Affective Illness: State of the Art Circa", Sleep, 1987, 10, 199-215.
Rhebergen et al., "The 7-Year Course of Depression and Anxiety in the General Population", Acta Psychiatr Scand, 2011, 123, 297-306.
Ribeiro et al., "Group I Metabotropic Glutamate Receptor Signaling and Its Implication in Neurological Disease", CNS & Neurological Disorders—Drug Targets, 2010, 9, 574-595.
Richards et al., "Distribution and Abundance of Metabotropic Glutamate Receptor Subtype 2 in Rat Brain Revealed by [3h]Ly354740 Binding in Vitro and Quantitative Radioautography: Correlation with the Sites of Synthesis, Expression, and Agonist Stimulation of [35s]Gtps Binding", J Comp Neurology, 2005, 487, 15-27.
Richardson-Burns et al., Metabotropic Glutamate Receptor Mrna Expression in the Schizophrenic Thalamus, Biol. Psychiatry, 2000, 47(1), 22-28.
Rickels et al., "Efficacy of Extended-Release Venlafaxine in Nondepressed Outpatients with Generalized Anxiety Disorder", Am J Psychiatry, 2000, 157, 968-974.
Riedel et al., "Glutamate Receptor Function in Learning and Memory", Behavioural Brain Research, 2003, 140(1-2), 1-47.
Ritzen et al., "Molecular Pharmacology and Therapeutic Prospects of Metabotropic Glutamate Receptor Allosteric Modulators", Basic Clin Pharmacol Toxicol, 2005, 97, 202-213.
Robbe et al., "Role of P/Q-Ca2+ Channels in Metabotropic Glutamate Receptor 2/3-Dependent Presynaptic Long-Term Depression at Nucleus Accumbens Synapses", J Neurosci., 2002, 22(11), 4346-4356.
Robbe et al., "Metabotropic Glutamate Receptor 2 3-Dependent Long-Term Depression in the Nucleus Accumbens is Blocked in Morphine Withdrawn Mice", Eur. J Neurosci., 2002, 16(11), 2231-2235.
Robbins et al., "The Neuropsychopharmacology of Fronto-Executive Function: Monoaminergic Modulation", Annu Rev Neurosci, 2009, 32, 267-287.
Robins et al., "Establishment of Diagnostic Validity in Psychiatric Illness: Its Application to Schizophrenia", Amer J Psychiat, 1970, 126(7), 107-111.
Robison et al., "The Rearrangement of Isoquinoline-N-Oxides", J Org Chem, 1957, 21, 1337-1341.
Rodd et al., "The Metabotropic Glutamate 2/3 Receptor Agonist Ly404039 Reduces Alcohol-Seeking But Not Alcohol Self-Administration in Alcohol-Preferring (P) Rats", Behavioural Brain Research, 2006, 171, 207-215.
Rodriguez et al., "Attenuation of Ketamine-Induced Hyperactivity Responses in Rats Following Administration of a Novel Metabotropic Glutamate Receptor 2 Selective Positive Modulator",Annual Meeting of the Society for Neuroscience, Oct. 2004, Abstract No. 798.8, 2 pages.
Rodriguez et al., "Relationships Among Psychosocial Functioning, Diagnostic Comorbidity, and the Recurrence of Generalized Anxiety Disorder, Panic Disorder, and Major Depression", Anxiety Disorders, 2005, 19, 752-766.
Rodriguez-Moreno et al., "Kainate Receptors with a Metabotropic Modus Operandi", Trends Neurosci., 2007, 30(12), 630-637.
Roma et al., "1,8-Naphthyridines Vii. New Substituted 5-Amino[L,2,4]Triazolo[4,3-A] [1 , 8]Naphthyridine-6-Carboxamides and Their Isosteric Analogues, Exhibiting Notable Anti-Inflammatory and/or Analgesic Activities, But No Acute Gastrolesivity", European Journal of Medical Chemistry, 2008, 43, 1665-1680.
Rondard et al., "Coupling of Agonist Binding to Effector Domain Activation in Metabotropic Glutamate-Like Receptors", J Biol. Chem., 2006, 281(34), 24653-24661.
Rorick-Kehn et al., "Improved Bioavailability of the Mglu2/3 Receptor Agonist Ly354740 Using a Prodrug Strategy: In Vivo Pharmacology of Ly544344", J. Pharmacol. Exper. Therapeut., 2006, 316, 905-913.
Rorick-Kehn et al., "In Vivo Pharmacological Characterization of the Structurally Novel, Potent, Selective Mglu2/3 Receptor Agonist Ly404039 in Animal Models of Psychiatric Disorders", Psychopharmacology, 2007, 193, 121-136.
Rorick-Kehn et al., "Pharmacological and Pharmacokinetic Properties of a Structurally Novel, Potent, and Selective Metabotropic Glutamate 2/3 Receptor Agonist: in Vitro Characterization of Agonist (−)-(1r,4s,5s,6s)-4-Amino-2-Sulfonylbicyclo[3.1.0]-Hexane-4,6-Dicarboxylic Acid (Ly404039)" J. Pharmacol. Exper. Therapeut., 2007, 321, 308-317.
Rorick-Kehn et al., "Pharmacological Characterization of Stress-Induced Hyperthermia in Dba/2 Mice Using Metabotropic and Ionotropic Glutamate Receptor Ligands", Psychopharmacology (Berl)., 2005, 183(2), 226-40.
Rosowsky et al., "2,4-Diaminothieno[2,3-D]Pyrimidines as Antifolates and Antimalarials. 3. Synthesis of 5,6-Disubstituted Derivatives and Related Tetracyclic Analogs", Journal of Medicinal Chemistry, 1973, 16(3),191-194.
Ross et al., "Expression of Functional Metabotropic and Ionotropic Glutamate Receptors in Baculovirus-Infected Insect Cells", Neuroscience Letters, 1994, 173(1-2), 139-142.
Roth et al., "G Protein-Coupled Receptor (Gpcr) Trafficking in the Central Nervous System: Relevance for Drugs of Abuse", Drug & Alcohol Dependence, 1998, 51(1-2), 73-85.
Roth et al., "Synthesis of Small Molecule Inhibitors of the Orphan Nuclear Receptor Steroidogenic Factor-1 (Nr5a1) Based on Isoquinolinone Scaffolds", Bioorg Med Chem Lett, 2008, 18, 2628-2632.
Rothman et al., "Excitatory and the NMDA Receptor", Trends in Neurosciences, 1987, 10(7), 299-302.
Rovira et al., "Modeling the Binding and Function of Metabotropic Glutamate Receptors", Jpet, 2008, 325, 443-456.
Rowe et al., "Transposition of Three Amino Acids Transforms the Human Metabotropic Glutamate Receptor (Mglur)-3 Positive Allosteric Modulation Site to Mglur2, and Additional Characterization of the Mglur2 Positive Allosteric Modulation Site", J. Pharmacol. Exper. Therapeut., 2008, 326, 240-251.
Roy et al., "A Twin Study of Generalized Anxiety Disorder and Major Depression" Psychological Medicine, 1995, 5, 1037-1049.

(56) References Cited

OTHER PUBLICATIONS

Roychowdhury et al., "G Protein Alpha Subunits Activate Tubulin Gtpase and Modulate Microtubule Polymerization Dynamics", J. Biol. Chem., 1999, 274(19), 13485-13490.
Roychowdhury et al., "G Protein Beta1gamma2 Subunits Promote Microtubule Assembly", J. Biol. Chem., 1997, 272(50), 31576-31581.
Rozenfeld et al., "Receptor Heteromerization and Drug Discovery", Trends in Pharmacological Sciences, 2010, 31(3), 124-130.
Rush et al., "Comorbid Psychiatric Disorders in Depressed Outpatients: Demographic and Clinical Features", Journal of Affective Disorders, 2005, 87, 43-55.
Rush et al., "Response in Relation to Baseline Anxiety Levels in Major Depressive Disorder Treated with Bupropion Sustained Release or Sertraline", Neuropsychopharmacology, 2001, 25(1), 131-138.
Rush et al., "Sequenced Treatment Alternatives to Relieve Depression (Star*D): Rationale and Design", Controlled Clinical Trials, 2004, 25, 119-142.
Russell et al., "Amyloid-B Acts as a Regulator of Neurotransmitter Release Disrupting the Interaction Between Synaptophysin and Vamp2", Plos One, 2012, 7(8), E43201, 1-14.
Ryndina, et al., "Torp-Ziegler Cyclization in the Synthesis of 3-Amino-4-Cyanopyrrole Derivatives", Chemistry of Heterocyclic Compounds, 2000, 36(12), 1409-1420.
Sackheim et al., "The Impact of Medication Resistance and Continuation Pharmacotherapy on Relapse Following Response to Electroconvulsive Therapy in Major Depression", J Clin Psychpharmacol, Apr. 1990, 10(2), 96-104.
Sagara et al., "The Activation of Metabotropic Glutamate Receptors Protects Nerve Cells from Oxidative Stress", J. Neurosci., 1998, 18(17), 6662-6671.
Sahara et al., "Cellular Localization of Metabotropic Glutamate Receptors Mglur1, 2/3, 5 and 7 in the Main and Accessory Olfactory Bulb of the Rat", Neuroscience Letters, 2001, 312(2), 59-62.
Sajdyk et al., "Measurement of Panic-Like Responses Unit 9.17 Following Intravenous Infusion of Sodium Lactate in Panic-Prone Rats", Current Protocols in Neuroscience, 2003, 9.17.1-9.17.19.
Sakamoto et al., "Condensed Heteroaromatic Ring Systems. VIII. Synthesis 3-Substituted Isocoumarins from O-Halobenzoic Acid Derivatives", Chem. Pharm. Bull., 1986, 34(7), 2754-2759.
Sakharkar et al., "Druggability of Human Disease Genes", Int J Biochem. Cell Biol., 2007, 39(6), 1156-1164.
Samadi et al., "Basal Ganglia Group II Metabotropic Glutamate Receptors Specific Binding in Non-Human Primate Model of L-Dopa-Induced Dyskinesias", Neuropharmacology, 2008, 54(2), 258-268.
Samadi et al., "Metabotropic Glutamate Receptor II in the Brains of Parkinsonian Patients", J. Neuropathol. Exp. Neurol., 2009, 68(4), 374-382.
Sanacora et al., "Subtype-Specific Alterations of Gamma-Aminobutyric Acid and Glutamate in Patients with Major Depression", Arch Gen Psychiatry, 2004, 61, 705-713.
Sanacora et al., "Targeting the Glutamatergic System to Develop Novel, Improved Therapeutics for Mood Disorders", Nat Rev Drug Discov, May 2008, 7(5), 426-437.
Sanacora et al., "Towards a Glutamate Hypothesis of Depression: An Emerging Frontier of Neuropsychopharmacology for Mood Disorders", Neuropharmacology, 2012, 62, 63-77.
Sanders et al., "Regulation of Anxiety by Gabaa Receptors in the Rat Amygdala", Pharmacology, Biochemistry and Behavior, 1995, 52(4), 701-706.
Sanderson et al., "Syndrome Comorbidity in Patients with Major Depression or Dysthymia: Prevalence and Temporal Relationships", Am J Psychiatry, Aug. 1990, 147(8), 1025-1028.
Sanger et al., "Pharmacological Profiling of Native Group II Metabotropic Glutamate Receptors in Primary Cortical Neuronal Cultures Using a Flipr", Neuropharmacology 2012, 1-10.
Sarichelou et al., "Metabotropic Glutamate Receptors Regulate Differentiation of Embryonic Stem Cells Into Gabaergic Neurons", Cell Death. Differ., 2008, 15(4), 700-707.

Satow et al., "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Detailed Investigations with a Selective Allosteric Metabotropic Glutamate Receptor 1 Antagonist, Ftidc [4-[1-(2-Fluoropyridine-3-Yl)-5-Methyl-1h-1,2,3-Triazol-4-Yl]-Nisopropyl-N-Methyl-3,6-Dihydropyridine-1(2h)-Carboxamide]", J. Pharmacol. Exper. Therapeut., 2008, 326, 577-586.
Sawamoto et al., "Cognitive Slowing in Parkinson Disease is Accompanied by Hypofunctioning of the Striatum", Neurology, 2007, 68, 1062-1068.
Sawamoto et al., "Cognitive Slowing in Parkinson's Disease: A Behavioral Evaluation Independent of Motor Slowing", J.Neurosci., 2002, 22, 5198-5203.
Scaccianoce et al., "Endogenous Activation of Group-II Metabotropic Glutamate Receptors Inhibits the Hypothalamic-Pituitary-Adrenocortical Axis", Neuropharmacology, 2003, 44, 555-561.
Scanziani et al., "Use-Dependent Increases in Glutamate Concentration Active Presynaptic Metabotropic Glutamate Receptors", Nature, 1997, 385, 630-634.
Schaffhauser et al., "Camp-Dependent Protein Kinase Inhibits Mglur2 Coupling to G-Proteins by Direct Receptor Phosphorylation", J Neurosci., 2000, 20(15), 5663-5670.
Schaffhauser et al., "In Vitro Binding Characteristics of a New Selective Group II Metabotropic Glutamate Receptor Radioligand, [3h]Ly354740, in Rat Brain", Mol Pharmacology, 1998, 53, 228-233.
Schaffhauser et al., "In Vitro Characterization of N-(4'-(2-Methoxyphenoxy)Phenyl-N-(2,2,2-Trifluoroethylsulfonyl)Pyrid-3-Ylmethylamine (Ly487379) a Selective Mglu2 Receptor Positive Modulator", Neuropharmacology, 2002, 43, 307.
Schaffhauser et al., "Multiple Pathways for Regulation of the Kcl-Induced [3h]-Gaba Release by Metabotropic Glutamate Receptors, in Primary Rat Cortical Cultures", Brain Res., 1998, 782(1-2), 91-104.
Schaffhauser et al., "Pharmacological Characterization and Identification of Amino Acids Involved in the Positive Modulation of Metabotropic Glutamate Receptor Subtype 2", Mol Pharmacol, 2003, 64, 798-810.
Schapira, "Science, Medicine, and the Future: Parkinson's Disease", Brit.Med.J., 1999, 318, 311-314.
Schiefer et al., "The Metabotropic Glutamate Receptor 5 Antagonist Mpep and the Mglur2 Agonist Ly379268 Modify Disease Progression in a Transgenic Mouse Model of Huntington's Disease", Brain Research, 2004, 1019, 246-254.
Schiffer et al., "Optimizing Experimental Protocols for Quantitative Behavioral Imaging with 18f-Fdg in Rodents", J Nucl Med, 2007, 48, 277-287.
Schlumberger et al., "Comparison of the Mglu5 Receptor Positive Allosteric Modulator Adx47273 and the Mglu2/3 Receptor Agonist Ly354740 in Tests for Antipsychotic-Like Activity", European Journal of Pharmacology, 2009, 623, 73-83.
Schlumberger et al., "Effects of a Metabotropic Glutamate Receptor Group II Agonist Ly354740 in Animal Models of Positive Schizophrenia Symptoms and Cognition", Behav Pharmacol., 2009, 20, 56-66.
Schoepp et al., "Ly354740, an Mglu2/3 Receptor Agonist as a Novel Approach to Treat Anxiety/Stress", Stress, 2003, 6(3), 189-197.
Schoepp et al., "Metabotropic Glutamate Receptors" Pharmacol Biochem Behav, 2002, 74, 255-256.
Schoepp et al., "Pharmacological Agents Acting at Subtypes of Metabotropic Glutamate Receptors", Neuropharmacology, 1999, 38, 1431-1476.
Schoepp et al., "Potent, Stereoselective, and Brain Region Selective Modulation of Second Messengers in the Rat Brain by (+)Ly354740, A Novel Group II Metabotropic Glutamate Receptor Agonist", Naunyn-Schmiedebergs Archives of Pharmacology, 1998, 358(2), 175-180.
Schoepp et al., "Preclinical Pharmacology of Mglu2/3 Receptor Agonists: Novel Agents for Schizophrenia?", CNS & Neurological Disorders, 2002, 1, 215-225.

(56) References Cited

OTHER PUBLICATIONS

Schoepp, "Unveiling the Functions of Presynaptic Metabotropic Glutamate Receptors in the Central Nervous System", J Pharmacol Exp Ther, 2001, 299, 12-20.
Schoppa et al., "Modulation of Mepscs in Olfactory Bulb Mitral Cells by Metabotropic Glutamate Receptors", J Neurophysiol., 1997, 78(3), 1468-1475.
Schreiber et al., "Ly354740 Affects Startle Responding But Not Sensorimotor Gating or Discriminative Effects of Phencyclidine", Eur. J Pharmacol., 2000, 388(2), R3-R4.
Schulze-Osthoff et al., "Apoptosis Signaling by Death Receptors", European Journal of Biochemistry, 1998, 254(3), 439-459.
Schwartz et al., "Ago-Allosteric Modulation and Other Types of Allostery in Dimeric 7tm Receptors", J Recept. Signal. Transduct. Res., 2006, 26(1-2), 107-128.
Schwartz et al., "Allosteric Enhancers, Allosteric Agonists and Ago-Allosteric Modulators: Where Do They Bind and How Do They Act?", Trends Pharmacol. Sci., 2007, 28(8), 366-373.
Schweitzer et al., "Characterization of [(3)H]-Ly354740 Binding to Rat Mglu2 and Mglu3 Receptors Expressed in Cho Cells Using Semliki Forest Virus Vectors", Neuropharmacology, 2000, 39(10), 1700-1706.
Seddon, "Pseudopolymorph: A Polemic", Crystal Growth & Design, 2004, 4(6), 1087.
Seebahn et al., "Ranbpm is Expressed in Synaptic Layers of the Mammalian Retina and Binds to Metabotropic Glutamate Receptors",. Febs Lett., 2008, 582(16), 2453-2457.
Seedat et al., "Measuring Anxiety in Patients with Schizophrenia", J Nerv Ment Dis. Apr. 2007, 195(4), 320-324.
Seeman et al., "Glutamate Receptor Mglu2 and Mglu3 Knockout Striata are Dopamine Supersensitive, with Elevated D2(High) Receptors and Marked Supersensitivity to the Dopamine Aqonist (+)Phno", Synapse, 2009, 63(3), 247-251.
Seeman, "An Agonist at Glutamate and Dopamine D2 Receptors, Ly404039" Neuropharmacology, 2012, 7 pages.
Seeman, "Glutamate Agonists for Schizophrenia Stimulate D2high Receptors", Schizophrenia Research, 2008, 99, 373-374.
Semba et al., "Regional Differences in the Effects of Glutamate Uptake Inhibitor L-Trans-Pyrrolidine-2,4-Dicarboxylic Acid on Extracellular Amino Acids and Dopamine in Rat Brain: An in Vivo Microdialysis Study", General Pharmacology, 1998, 31(3), 399-404.
Semple et al., "3-Aryl Pyridone Derivatives. Potent and Selective Kappa Opioid Receptor Agonists", Bioorganic and Medicinal Chemistry Lett, 2002, 12, 197-200.
Senda et al., "Ring Transformation of Uracils to 2-Pyridones. Hydrolysis of 6-(Dimethylaminovinyl) Uracils", Heterocycles, 1978, 9(6), 1-6.
Seo et al., "Distinctive Clinical Characteristics and Suicidal Tendencies of Patients with Anxious Depression", J Nerv Ment Dis, 2011, 199, 42-48.
Seroquel XR® Highlights of Prescribing Information 2013.
Shalev, "Neurobiology of Relapse to Heroin and Cocaine Seeking: A Review", Pharmacol. Rev., 2002, 54(1), 1-42.
Sharpe et al., "Systemic Pre-Treatment with a Group II Mglu Agonist, Ly379268, Reduces Hyperalgesia in Vivo", British Journal of Pharmacology, 2002, 135, 1255-1262.
Shear et al., "Reliability and Validity of a Structured Interview Guide for the Hamilton Axiety Rating Scale (Sigh-A)", Depress Anxiety, 2001, 13(4), 166-178.
Sheffler et al., "Recent Progress in the Synthesis and Characterization of Group II Metabotropic Glutamate Receptor Allosteric Modulators", Acs Chem Neurosci, 2011, 2, 382-393.
Shekhar et al., "Ly354740, a Potent Group II Metabotropic Glutamate Receptor Agonist Prevents Lactate-Induced Panic-Like Response in Panic-Prone Rats", Neuropharmacology, 2000, 39, 1139-1146.
Shekhar et al., "Dorsomedial Hypothalamic Gaba Dysfunction Produces Physiological Arousal Following Sodium Lactate Infusions", Pharmacol Biochem Behav., Oct. 1996, 55(2), 249-256.
Shekhar et al., "Dorsomedial Hypothalamic Gaba Regulates Anxiety in the Social Interaction Test", Pharmacology, Biochemistry and Behavior, 1995, 50(2), 253-258.
Shekhar et al., "The Circumventricular Organs Form a Potential Neural Pathway for Lactate Sensitivity: Implications for Panic Disorder", Journal of Neuroscience, 1997, 17(24), 9726-9735.
Shepherd et al., "Behavioural and Pharmacological Characterisation of the Elevated 'Zero-Maze' as an Animal Model of Anxiety", Psychopharmacology, 1994, 116, 56-64.
Sherbourne et al., "Course of Depression in Patients with Comorbid Anxiety Disorders" Journal of Affective Disorders 1997, 43, 245-250.
Shi et al., "L-Homocysteine Sulfinic Acid and Other Acidic Homocysteine Derivatives are Potent and Selective Metabotropic Glutamate Receptor Agonists", J Pharmacol Exp Ther, 2003, 305(1), 131-142.
Shiba et al., "Synthesis and Binding Affinities of Methylvesamicol Analogs for the Acetylcholine Transporter and Sigma Receptor", Bioorganic and Medicinal Chemistry, 2006, 14, 2620-2626.
Shigemoto et al., "Differential Presynaptic Localization of Metabotropic Glutamate Receptor Subtypes in the Rat Hippocampus", Journal of Neuroscience, 1997, 17(19), 7503-7522.
Shigemoto et al., "Metabotropic Glutamate Receptors—Immunocytochemical and in Situ Hybridization Analysis", Ottersen Op, Storm-Mathisen J (Eds) Handbook of Chemical Neuroanatomy, Elxevier Science, 2000, 63-98.
Shigemoto et al., "Target-Cell-Specific Concentration of a Metabotropic Glutamate Receptor in the Presynaptic Active Zone", Nature, 1996, 381(6582), 523-525.
Shimazaki et al., "Blockade of the Metabotropic Glutamate 2/3 Receptors Enhances Social Memory via the Ampa Receptor in Rats", Eur.J.Pharmacol., 2007, 575, 94-97.
Shin et al., "Metabotropic Glutamate Receptors (Mglus) and Cellular Transformation", Neuropharmacology, 2008, 55(4), 396-402.
Shin et al., "The Neurocircuitry of Fear, Stress, and Anxiety Disorders", Neuropsychopharmacology, 2010, 35(1), 169-191.
Sidique et al., "Orally Active Metabotropic Glutamate Subtype 2 Receptor Positive Allosteric Modulators: Structure-Activity Relationships and Assessment in a Rat Model of Nicotine Dependence", J Med Chem, 2012, 55, 9434-9445.
Silver et al., "Multifunctional Pharmacotherapy: What Can We Learn From Study of Selective Serotonin Reuptake Inhibitor Augmentation of Antipsychotics in Negative-Symptom Schizophrenia?", Neurotherapeutics, 2009, 6, 86-93.
Silverstone et al., "Defining Anxious Depression: Going Beyond Comorbidity", Can J Psychiatry, 2003, 48, 675-680.
Simmons et al., "Group II Mglur Receptor Agonists are Effective in Persistent and Neuropathic Pain Models in Rats", Pharmacology, Biochemistry and Behavior, 2002, 73, 419-427.
Simon et al., "Advances in the Treatment of Anxiety: Targeting Glutamate", Journal of the American Society for Exp Neur, Jan. 2006, 3, 57-68.
Simon et al., "Comparing Anxiety Disorders and Anxiety-Related Traits in Bipolar Disorder and Unipolar Depression", Journal of Psychiatric Research, 2003, 37, 187-192.
Simonyi et al., "Chronic Ethanol-Induced Subtype- and Subregion-Specific Decrease in the Mrna Expression of Metabotropic Glutamate Receptors in Rat Hippocampus", Alcoholism: Clinical & Experimental Research, 2004, 28(9), 1419-1423.
Simonyi et al., "Expression of Groups I and II Metabotropic Glutamate Receptors in the Rat Brain During Aging", Brain Res, 2005, 1043, 95-106.
Simonyi et al., "Metabotropic Glutamate Receptor Subtype 5 Antagonism in Learning and Memory", European Journal of Pharmacology, 2010, 639, 17-25.
Simpson et al., "A Possible Role for the Striatum in the Pathogenesis of the Cognitive Symptoms of Schizophrenia", Neuron., 2010, 65(5), 585-596.
Siok et al., "Comparative Analysis of the Neurophysiological Profile of Group I Metabotropic Glutamate Receptor Activators and Diazepam: Effects on Hippocampal and Cortical Eeg Patterns in Rats", Neuropharmacology, 2012, 62, 226-236.

(56) References Cited

OTHER PUBLICATIONS

Skofic et al., "Syntheses of 4-{2-naphthyl)pyridine derivatives from DDNP", Slovenian Chemical Society (Acta Chimica Slovencia), 2005, 52(4), 391-397.
Sladeczek et al., "The Metabotropic Glutamate Receptor (Mgr): Pharmacology and Subcellular Location", Journal of Physiology, 1992, 86(1-3), 47-55.
Slattery et al., "Potentiation of Mouse Vagal Afferent Mechanosensitivity by Ionotropic and Metabotropic Glutamate Receptors", J Physiol, 2006, 577(Pt 1), 295-306.
Sleight et al., "Radiolabelling of the Human 5-Ht2a Receptor with an Agonist, a Partial Agonist and an Antagonist: Effects on Apparent Agonist Affinities", Biochemical Pharmacology, 1996, 51, 71-76.
Smalley et al., "Pyrolysis of Aryle Azides in Acetic Anhydride", J. Chem. Soc., 1963, 5571-5572.
Smialowska et al., "The Effect of Intrahippocampal Injection of Group II and III Metobotropic Glutamate Receptor Agonists on Anxiety; the Role of Neuropeptide Y", Neuropsychopharmacology, 2007, 32(6), 1242-1250.
Smith et al., "Ionotropic and Metabotropic Gaba and Glutamate Receptors in Primate Basal Ganglia", Journal of Chemical Neuroanatomy, 2001, 22(1-2), 13-42.
Smith et al., "Is Extended Clonazepam Cotherapy of Fluoxetine Effective for Outpatients with Major Depression?", Journal of Affective Disorders, 2002, 70, 251-259.
Smith et al., "Schizophrenia (Maintenance Treatment)", Clin Evid (Online), 2009, 1007.
Smith et al., "Short-Term Augmentation of Fluoxetine Clonazepam in the Treatment of Depression: A Double-Blind Study", Am J Psychiatry, 1998, 155, 1339-1345.
Smith, "Regulation of Glutamate Uptake in Astrocytes Continuously Exposed to Ethanol", Life Sciences, 1997, 61(25), 2499-2505.
Smits et al., "Outcomes of Acute Phase Cognitive Therapy in Outpatients with Anxious Versus Nonaxious Depression", Psychother Psychosom, 2012, 81, 153-160.
Smolders et al., "In Vivo Modulation of Extracellular Hippocampal Glutamate and Gaba Levels and Limbic Seizures by Group I and Ii Metabotropic Glutamate Receptor Ligands", Journal of Neurochemistry, 2004, 88(5), 1068-1077.
Sokolowski et al., "The Behavioral Effects of Sertraline, Fluoxetine, and Paroxetine Differ on the Differential-Reinforcement-of-Low-Rate 72-Second Operant Schedule in the Rat", Psychopharmacology, 1999, 147, 153-161.
Spencer et al., "Novel Strategies for Alzheimer's Disease Treatment", Expert Opin. Biol. Ther., 2007, 7(12), 1853-1867.
Spiegel et al., "Defects in G Protein-Coupled Signal Transduction in Human Disease", Annual Review of Physiology, 1996, 58, 143-170.
Spiegel et al., "Psychosis Induced by the Interaction of Memantine and Amantadine: Lending Evidence to the Glutamatergic Theory of Schizophrenia", Clinical Schizophrenia & Related Psychoses, 2007, 1(3), 273-276.
Spijker, "The Course of Anxiety and Depression in Nemesis and Nesda", Abstract AS36-04 of the 20th European Congress of Psychiatry, Mar. 2012, 1 page.
Spooren et al., "Anxiolytic-Like Effects of the Prototypical Metabotropic Glutamate Receptor 5 Antagonist 2-Methyl-6-(Phenylethynyl)Pyridine in Rodents", Journal of Pharmacology & Experimental Therapeutics, 2000, 295(3), 1267-1275.
Spooren et al., "Insight Into the Function of Group I and Group II Metabotropic Glutamate (Mglu) Receptors: Behavioural Characterization and Implications for the Treatment of CNS Disorders", Behavioural Pharmacology, 2003, 14(4), 257-277.
Spooren et al., "Lack of Effect of Ly314582 (A Group 2 Metabotropic Glutamate Receptor Agonist) on Phencyclidine-Induced Locomotor Activity in Metabotropic Glutamate Receptor 2 Knockout Mice", Eur J Pharmacol., 2000, 397, R1-R2.
Spooren et al., "Metabotropic Glutamate Receptors: Their Therapeutic Potential in Anxiety", Current Topics in Behavioral Neurosciences, 2010, 2, 391-413.
Spooren et al., "Pharmacological and Endocrinological Characterization of Stress-Induced Hyperthermia in Singly Housed Mice Using Classical and Candidate Anxiolytics (Ly314582, Mpep and Nkp608)", Eur J Pharmacol, 2002, 435, 161-170.
Srivastava et al., "Novel Anchorage of Glur2/3 to the Postsynaptic Density by the Ampa Receptor-Binding Protein Abp", Neuron, 1998, 21(3), 581-591.
Stachowicz et al., "Anxiolytic-Like Activity of Mgs0039, A Selective Group II Mglu Receptor Antagonist, Is Serotonin- and Gaba-Dependent", Pharmacological Reports, 2011, 63, 880-887.
Stahl et al., "Negative Symptoms of Schizophrenia: A Problem That Will Not Go Away", Acta Psychiatr. Scand., 2007, 115(1), 4-11.
Steckler, "Glutamatergic Anxiolytics Are They Any Better?", (Presentation Slides), European College of Neuropsychopharmacology, 2009, 18 pages.
Steckler et al., "Effects of Mglu1 Receptor Blockade on Anxiety-Related Behavior in the Rat Lick Suppression Test", Psychopharmacology, 2005, 179, 198-206.
Steckler et al., "Pharmacological Treatment of PTSD—Established and New Approaches", Neuropharmacology, 2012, 62, 617-627.
Stefani et al., "Activation of Type 5 Metabotropic Glutamate Receptors Attenuates Deficits in Cognitive Flexibility Induced by NMDA Receptor Blockade", European Journal of Pharmacology, 2010, 639, 26-32.
Stefani et al., "The Modulation of Calcium Currents by the Activation of Mglurs. Functional Implications", Molecular Neurobiology, 1996, 13(1), 81-95.
Steinpreis, "The Behavioral and Neurochemical Effects of Phencyclidine in Humans and Animals: Some Implications for Modeling Psychosis", Behavioral Brain Research, 1996, 74, 45-55.
Stella et al., "4. Prodrugs: the Contrul of Drug Delivery via Bioreversible Chemical Modification", Drug Delivery Systems: Characteristics and Biomedical Applications. New York: Oxford University Press, 1980, 67 pages.
Stella et al., "Prodrugs: Do They Have Advantages in Clinical Practice?", Drugs, 1985, 29, 455-473.
Stepulak et al., "Expression of Glutamate Receptor Subunits in Human Cancers", Histochem. Cell Biol., 2009, 12 pages.
Steru et al., "The Tail Suspension Test: A New Method for Screening Antidepressants in Mice", Psychopharmacology, 1985, 85, 367-370.
Stewart et al., "Discovery of Inhibitors of Cell Adhesion Molecule Expression in Human Endothelial Cell. 1. Selective Inhibition of Icam-1 and E-Selectin Expression", J Med Chem, 2001, 44, 998-1002.
Stogryn et al., "5-Hetarylmethylene-2,4-Diaminopyrimidines (1)", J. Heterocyclic Chem., Apr. 1974. 11, 251-253.
Stone et al., "Glutamate and Dopamine Dysregulation in Schizophrenia—A Synthesis and Selective Review", J Psychopharmacol., 2007, 21(4), 440-452.
Stout et al., "High-Affinity Calcium Indicators Underestimate Increases in Intracellular Calcium Concentrations Associated with Excitotoxic Glutamate Stimulations", Neuroscience, 1999, 89(1), 91-100.
Straiker et al., "Metabotropic Suppression of Excitation in Murine Autaptic Hippocampal Neurons", J Physiol, 2007, 578(Pt 3), 773-785.
Strange, "Use of the Gtpgs ([35s]Gtpgs and Eu-Gtpgs) Binding Assay for Analysis of Ligand Potency and Efficacy at G Protein-Coupled Receptors", British Journal of Pharmacology, 2010, 161, 1238-1249.
Stroup et al., "Results of Phase 3 of the Catie Schizophrenia Trial", Schizophr Res., 2009, 107(1),1-12.
Stulz et al., "Distinguishing Anxiety and Depression in Self-Report: Purification of the Beck Anxiety Inventory and Beck Depression Inventory—II", J Clin Psychol, 2010, 66, 927-940.
Suh et al., "Hypoglycemic Neuronal Death and Cognitive Impairment are Prevented by Poly(Adp-Ribose) Polymerase Inhibitors Administered After Hypoglycemia", Journal of Neuroscience, 2003, 23(33), 10681-10690.
Sutton et al., "Regulation of Akt and Wnt Signaling by the Group II Metabotropic Glutamate Receptor Antagonist Ly341495 and Agonist Ly379268", Journal of Neurochemistry, 2011, 117, 973-983.

(56) References Cited

OTHER PUBLICATIONS

Swanson et al., "A Role for Noradrenergic Transmission in the Actions of Phencyclidine and the Antipsychotic and Antistress Effects of Mglu2/3 Receptor Agonists", Annals of the New York Academy of Sciences, 2003, 1003, 309-17.
Swanson et al., "Metabotropic Glutamate Receptors as Novel Targets for Anxiety and Stress Disorders", Nature Reviews Drug Discovery, 2005, 4, 131-144.
Swanson et al., "The Group II Metabotropic Glutamate Receptor Agonist (−)-2-Oxa-4-Aminobicyclo[3.1.0.]Hexane-4,6-Dicarboxylate (Ly379268) and Clozapine Reverse Phencyclidine-Induced Behaviors in Monoamine-Depleted Rats", Journal of Pharmacology & Experimental Therapeutics, 2002, 303(3), 919-927.
Swerdlow et al., "Strain Differences in the Disruption of Prepulse Inhibition of Startle After Systemic and Intra-Accumbens Amphetamine Administration",. Pharmacol. Biochem. Behav., 2007, 87 (1), 1-10.
Szapiro et al., "Facilitation and Inhibition of Retrieval in Two Aversive Tasks in Rats by Intrahippocampal Infusion of Agonists of Specific Glutamate Metabotropic Receptor Subtypes", Psychopharmacology, 2001, 156(4), 397-401.
Takahashi et al., "In Vitro Systems for the Study of Apoptosis", Advances in Pharmacology, 1997, 41, 89-106.
Takahashi et al., "Post-Treatment with an Inhibitor of Poly(Adp-Ribose) Polymerase Attenuates Cerebral Damage in Focal Ischemia", Brain Research, 1999, 829, 46-54.
Takahashi et al., "Role of the Large Extracellular Domain of Metabotropic Glutamate Receptors in Agonist Selectivity Determination", J. Biol. Chem., 1993, 268(26), 19341-19345.
Takamori et al., "Antipsychotic Action of Selective Group II Metabotropic Glutamate Receptor Agonist Mgs0008 and Mgs0028 on Conditioned Avoidance Responses in the Rat", Life Sci., 2003, 73, 1721-1728.
Takamori, "Vgluts: 'Exciting' Times for Glutamatergic Research?", Neuroscience Research, 2006, 55(4), 343-351.
Takumi et al., "The Arrangement of Glutamate Receptors in Excitatory Synapses", Annals of the New York Academy of Sciences, 1999, 868, 474-482.
Tamminga et al., "Glutamate Pharmacology and the Treatment of Schizophrenia: Current Status and Future Directions", Intl Clinical Psychopharmacology, 1995, 10(Suppl-37), 29-37.
Tamminga, "Schizophrenia and Glutamatergic Transmission", Critical Reviews in Neurobiology, 1998, 12(1-2), 21-36.
Tanabe et al, "A Family of Metabotropic Glutamate Receptors", Neuron, 1992, 8(1), 169-179.
Tandon et al., "Schizophrenia, Just the Facts, 5.Treatment and Prevention Past, Present, and Future", Schizophr Res., Jul. 2010, 122, 1-23.
Tang et al., "Metabotropic Glutamate Receptors in the Control of Neuronal Activity and as Targets for Development of Anti-Epileptogenic Drugs", Curr. Med. Chem, 2009, 16(17), 2189-2204.
Tang et al., "Prolonged Anticonvulsant Action of Glutamate Metabotropic Receptor Agonists in Inferior Colliculus of Genetically Epilepsy-Prone Rats", European Journal of Pharmacology, 1997, 327(2-3), 109-115.
Targum et al., "Redefining Affective Disorders: Relevance for Drug Development", CNS Neuroscience and Therapeutics, 2008, 14, 2-9.
Targum et al., "The Relevance of Anxious Depression as a Distinct Entity for Psychopharmacology and Drug Development", US Psychiatry, 2009, 2(1), 29-31.
Tarrier et al., "A Trial of Two Cognitive Behavioural Methods of Treating Drug-Resistant Residual Psychotic Symptoms in Schizophrenic Patients: I. Outcome", Br J Psychiatry, 1993, 162, 524-532.
Tatarczyska et al., "The Antianxiety-Like Effects of Antagonists of Group I and Agonists of Group II and III Metabotropic Glutamate Receptors After Intrahippocampal Administration", Psychopharmacology, 2001, 158, 94-99.
Taylor et al., "Stimulation of Microglial Metabotropic Glutamate Receptor Mglu2 Triggers Tumor Necrosis Factor?-Induced Neurotoxicity in Concert with Microglial-Derived Fas Ligand", Journal of Neuroscience, 2005, 25(11), 2952-2964.
Taylor et al., "The Efficacy of Nefazodone Augmentation for Treatment-Resistant Depression with Anxiety Symptoms or Anxiety Disorder", Depression and Anxiety, 2003, 18, 83-88.
Teitler et al., "4-[125i]Iodo-(2,5-Dimethoxy)Phenylisopropylamine and [3h]Ketanserin Labeling of 5-Hydroxytryptamine2 (5ht2) Receptors in Mammalian Cells Transfected with a Rat 5ht2 Cdna: Evidence for Multiple States and Not Multiple 5ht2 Receptor Subtypes", Molecular Pharmacology, 1990, 38, 594-598.
Teran et al., "Regioselective Oxidation of 3-Substituted Pyridinium Salts", Molecules, 2000, 5, 1175-1181.
Testa et al., "Metabotropic Glutamate Receptor Mrna Expression in the Basal Ganglia of the Rat", Journal of Neuroscience, 1994, 14(5), 3005-3018.
Thase et al., "Extended Release Quetiapine Fumarate in Major Depressive Disorder: Analysis in Patients with Anxious Depression", Depression and Anxiety, 2012, 29, 574-586.
Thase, "Augmentation Strategies for Depression: History and Concepts", CNS Spectr, 2007, 12(12), (Suppl 22), 3-5.
Thase, "Depression and Sleep: Pathophysiology and Treatment", Dialogues Clin Neurosci, 2006, 8, 217-226.
Thathiah et al., "The Role of G Protein-Coupled Receptors in the Pathology of Alzheimer's Disease", Nature Reviews Neuroscience, 2011, 12, 73-87.
Theberge, "Glutamate and Glutamine in the Anterior Cingulate and Thalamus of Medicated Patients with Chronic Schizophrenia and Healthy Comparison Subjects Measured with 4.0-T Proton MRS", Am. J. Psychiatry, 2003, 160, 2231-2233.
Theberge, "Glutamate and Glutamine Measured with 4.0t Proton Mrs in Never-Treated Patients with Schizophrenia and Healthy Volunteers", Am. J. Psychiatry, 2002, 159, 1944-1946.
Thompson et al., "Activation of Group II and Group III Metabotropic Glutamate Receptors by Endogenous Ligand(S) and the Modulation of Synaptic Transmission in the Superficial Superior Colliculus", Neuropharmacology, 2004, 47(6), 822-832.
Thomsen et al., "Actions of Phenylglycine Analogs at Subtypes of the Metabotropic Glutamate Receptor Family", European Journal of Pharmacology, 1994, 267(1), 77-84.
Thomsen et al., "Roles of Metabotropic Glutamate Receptor Subtypes in Modulation of Pentylenetetrazole-Induced Seizure Activity in Mice", Neuropharmacology, 1998, 37(12), 1465-1473.
Tiihonen et al., "The Efficacy of Lamotrigine in Clozapine-Resistant Schizophrenia: A Systematic Review and Meta-Analysis", Schizophr Res. 2009, 109(1-3), 10-14.
Tilakaratne et al., "Chronic Fluoxetine or Desmethylimipramine Treatment Alters 5-Ht2 Receptor Mediated C-Fos Gene Expression", European Journal of Pharmacology, 1995, 290(3), 263-266.
Tizzano et al., "Induction or Protection of Limbic Seizures in Mice by Mglur Subtype Selective Agonists", Neuropharmacology, 1995, 34(8), 1063-1067.
Tizzano et al., "The Anxiolytic Action of Mglu2/3 Receptor Agonist, Ly354740, in the Fear-Potentiated Startle Model in Rats is Mechanistically Distinct From Diazepam", Pharmacology, Biochemistry and Behavior, 2002, 73, 367-374.
Tokita et al., "Roles of Glutamate Signaling in Preclinical and/or Mechanistic Models of Depression", Pharmacology, Biochemistry and Behavior, 2012, 100, 688-704.
Tokunaga et al., "Neuroimaging and Physiological Evidence for Involvement of Glutamatergic Transmission in Regulation of the Striatal Dopaminergic System", Journal of Neuroscience, 2009, 29(6), 1887-1896.
Tolchard et al., "Modulation of Synaptic Transmission in the Rat Ventral Septal Area by the Pharmacological Activation of Metabotropic Glutamate Receptors", European Journal of Neuroscience, 2000, 12(5), 1843-1847.
Tollefson et al., "Fluoxetine, Placebo, and Tricyclic Antidepressants in Major Depression with and without Anxious Features", J Clin Psychiatry, 1994, 55(2), 50-59.
Toms et al., "Latest Eruptions in Metabotropic Glutamate Receptors", Trends in Pharmacological Sciences, 1996, 17(12), 429-435.
Tong et al., "Signal Transduction in Neuronal Death", Journal of Neurochemistry, 1998, 71(2), 447-459.

(56) References Cited

OTHER PUBLICATIONS

Trabanco et al., "Imidazo[1,2-A]pyridines: Orally Active Positive Allosteric Modulators of the Metabotropic Glutamate 2 Receptor", J Med Chem, 2012, 55, 2688-2701.
Trabanco et al., "Mglur2 Positive Allosteric Modulators (Pams): A Patent Review (2009-Present)", Expert Opin, 2013, 19 pages.
Trabanco et al., "New Positive Allosteric Modulators of the Metabotropic Glutamate Receptor 2 (Mglur2). Identification and Synthesis of N-Propyl-5-Substituted Isoquinolones", Med Chem Commun, 2011, 2, 132-139.
Trabanco et al., "New Positive Allosteric Modulators of the Metabotropic Glutamate Receptor 2 (Mglur2): Identification and Synthesis of N-Propyl-8-Chloro-6-Substituted Isoquinolones", Bioorganic & Medicinal Chemistry Letters, 2011, 21, 971-976.
Trabanco et al., "Progress in the Developement of Positive Allosteric Modulators of the Metabotropic Glutamate Receptor 2", Current Medicinal Chemistry, 2011, 18, 47-68.
Trabanco et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8689.
Tresadern et al., "Scaffold Hopping From Pyridones to Imidazo[1,2-A]Pyridines. New Positive Allosteric Modulators of Metabotropic Glutamate 2 Receptor", Bioorganic & Medicinal Chemistry Letters, 2010, 20, 175-179.
Trettel et al., "Endocannabinoid Signalling Selectively Targets Perisomatic Inhibitory Inputs to Pyramidal Neurones in Juvenile Mouse Neocortex", Journal of Physiology, 2004, 556(Pt 1), 95-107.
Treutlein et al., "Dissection of Phenotype Reveals Possible Association Between Schizophrenia and Glutamate Receptor Delta 1 (Grid1) Gene Promoter", Schizophr. Res., 2009, 111(1-3), 123-130.
Trivedi et al., "Adjunctive Aripiprazole in Major Depressive Disorder: Analysis of Efficacy and Safety in Patients with Anxious and Atypical Features", J Clin Psychiatry, 2008, 69, 1928-1936.
Trivedi et al., "Evaluation of Outcomes with Citalopram for Depression Using Measurement-Based Care in Star*D: Implications for Clinical Practice", Am J Psychiatry, 2006; 163, 28-40.
Trofimova et al., "The Lability of Behavior as a Marker of Comorbid Depression and Anxiety", Advances in Bioscience and Biotechnology, 2010, 1, 190-199.
Trullas et al., "Functional Antagonists at the NMDA Receptor Complex Exhibit Antidepressant Actions", Eur J Pharmacol, Aug. 1990, 185(1), 1-10.
Tsai et al., "Immunocytochemical Distribution of N-Acetylaspartylglutamate in the Rat Forebrain and Glutamatergic Pathways", Journal of Chemical Neuroanatomy, 1993, 6(5), 277-292.
Tsai, "Central N-Acetyl Aspartylglutamate Deficit: A Possible Pathogenesis of Schizophrenia", Med Sci. Monit., 2005, 11(9), Hy39-Hy45.
Tsai, "Glutamatergic Mechanisms in Schizophrenia", Ann. Rev. Pharmacol. Toxicol., 2002, 42, 165-179.
Tsiveriotis et al., "Nickel(II) and Cobalt(II) Complexes of 2,4-Diaminothieno[2,3-D]-Pyrimidines", Transition Metal Chemistry, 1994, 19, 335-339.
Tsunoka et al., "Association Analysis of Grm2 and Htr2a with Methamphetamine-Induced Psychosis and Schizophrenia in the Japanese Population", Progress in Neuro-Psychopharmacology & Biological Psychiatry, 2010, 34(4), 639-644.
Tsunoka et al., "Association Analysis of Group II Metabotropic Glutamate Receptor Genes (Grm2 and Grm3) with Mood Disorders and Fluvoxamine Response in a Japanese Population", Progress in Neuro-Psychopharmacology & Biological Psychiatry, 2009, 33(5), 875-879.
Tuominen et al., "Glutamatergic Drugs for Schizophrenia", The Cochrane Collaboration, Cochrane Database Syst Rev., Apr. 2006, 1, 8 pages.
Tuominen, "Glutamatergic Drugs for Schizophrenia: A Systematic Review and Meta-Analysis", Schiz. Res., 2005, 72, 225-234.
Turck et al., "Advances in the Directed Metallation of Azines and Diazines (Pyridines, Pyrimidines, Pyrazines, Pyridazines, Quinolines, Benzodiazines and Carbolines). Part 2: Metallation of Pyrimidines, Pyrazines, Pyridazines and Benzodiazines", Tetrahedron, 2001, 57(21), 4489-4505.
Tutonda et al., "Diels-Alder Reactions of the Heterodiene System in 2(1h)-Pyrazinones", Tetrahedron Letters, 1986, 27, 22, 2509-2512.
Tyrer, "The Case for Cothymia: Mixed Anxiety and Depression as a Single Diagnosis", British Journal of Psychiatry, 2001, 179, 191-193.
Uher et al., "Differential Efficacy of Escitalopram and Nortriptyline on Dimensional Measures of Depression", British Journal of Psychiatry, 2009, 194, 252-259.
Uher et al., "Melancholic, Atypical and Anxious Depression Subtypes and Outcome of Treatment with Escitalopram and Nortriptyline", Journal of Affective Disorders, 2011, 132, 112-120.
Urn et al., "Alzheimer Amyloid-B Oligomer Bound to Postsynaptic Prion Protein Activates Fyn to Impair Neurons", Nature Neuroscience, 2012, 15(9), 1227-1235.
Undine et al., "Molecular Mechanisms of Schizophrenia", Cell Physiol Biochem, 2007, 20, 687-702.
Ung et al., "Synthesis and Biological Activities of Conformationally Restricted Cyclopentenyl-Glutamate Analogues", Journal of Organic Chemistry, 2002, 67(1), 227-233.
Urwyler, "Allosteric Modulation of Family C G-Protein-Coupled Receptors From Molecular Insights to Therapeutic Perspectives", Pharmacol Rev, 2011, 63, 59-126.
Uslaner et al., "Combined Administration of an Mglu2/3 Receptor Agonist and a 5-Ht 2a Receptor Antagonist Markedly Attenuate the Psychomotor-Activating and Neurochemical Effects of Psychostimulants", Psychopharmacology (Berl), 2009, 206(4), 641-651.
Uys et al., "Glutamate: the New Frontier in Pharmacotherapy for Cocaine Addiction", CNS & Neurological Disorders—Drug Targets, 2008, 7, 482-491.
Vaccarino et al., "Symptoms of Anxiety in Depression: Assessment of Item Performance of the Hamilton Anxiety Rating Scale in Patients with Depression", Depression and Anxiety, 2008, 25, 1006-1013.
Valentine et al., "Targeting Glial Physiology and Glutamate Cycling in the Treatment of Depression", Biochem. Pharmacol., 2009, 78(5), 431-439.
Vales et al., "The Difference in Effect of Mglu2/3 and Mglu5 Receptor Agonists on Cognitive Impairment Induced by Mk-801", European Journal of Pharmacology, 2010, 639, 91-98.
Valproate Information Available from Http://Www.Fda.Gov/Drugs/Drugsafety/Postmarketdrugsafetyinformationforpatientsandproviders/Ucm192645.Htm, 2011, 2 pages.
Van Beljouw et al., "The Course of Untreated Anxiety and Depression, and Determinants of Poor On-Year Outcome: A One-Year Cohort Study", BMC Psychiatry, 2010, 10, 86.
Van Berckel et al., "Modulation of Amphetamine-Induced Dopamine Release by Group Ii Metabotropic Glutamate Receptor Agonist Ly354740 in Non-Human Primates Studied with Positron Emission Tomography", Neuropsychopharmacology, 2006, 31, 967-977.
Van Den Pol, "Presynaptic Metabotropic Glutamate Receptors in Adult and Developing Neurons: Autoexcitation in the Olfactory Bulb", Journal of Comparative Neurology, 1995, 359(2), 253-271.
Van Tol et al., "Regional Brain Volume in Depression and Anxiety Disorders", Arch Gen Psychiatry, 2010, 67(10), 1002-1011.
Van Valkenberg et al., "Anxious Depressions. Clinical, Family History, and Naturalistic Outcome—Comparisons with Panic and Major Depressive Disorders", Journal of Affective Disorders, 1984, 6(1), 67-82.
Van Vliet et al., "Adaptive Changes in the Number of Gs- and Gi-Proteins Underlie Adenylyl Cyclase Sensitization in Morphine-Treated Rat Striatal Neurons", European Journal of Pharmacology, 1993, 245(1), 23-29.
Vanallan et al., "Reactions of Some 4-Methylene-4h-Pyran Derivatives with Primary and Secondary Amines", Journal of Heterocyclic Chemistry, 1970, 7, 495-507.
Vandergriff et al., "The Selective Mglu2/3 Receptor Agonist Ly354740 Attenuates Morphine-Withdrawal-Induced Activation of Locus

(56) References Cited

OTHER PUBLICATIONS

Coeruleus Neurons and Behavioral Signs of Morphine Withdrawal", Neuropharmacology, 1999, 38, 217-222.
Vandesompele et al., "Accurate Normalization of Real-Time Quantitative Rt-Pcr Data by Geometric Averaging of Multiple Internal Control Genes", Genome Biology, 2002, 3(7), 1-12.
Varney et al., "Metabotropic Glutamate Receptor Involvement in Models of Acute and Persistent Pain: Prospects for the Development of Novel Analgesics", Current Drug Targets—CNS & Neurological Disorders, 2002, 1, 283-296.
Vasilieva, "Clinical-Dynamic Characteristics of Depressive Disorders Comorbid with Anxiety Disorders", Abstract P01-109 of 18th European Congress of Psychiatry, 2010, 1 page.
Vaughan et al., "Reactivity of 3-Alkyl-4-Arylazomethylene-3,4-Dihydro-1,2,3-Benzotriazines in Protic Solvents: 1,4-Addition Reactions and Dimroth Rearrangement", Journal of Heterocyclic Chemistry, Nov. 1991, 1709-1713.
Ver Donck et al., "Low Dose Subchronic Phencyclidine (PCP) Pretreatment Potentiates Acute PCP-Induced Hyperlocomotion in Adult Rats: A Model of Schizophrenia?", Presentation Abstract, Society for Neuroscience, 2011, 2 pages.
Verhagen et al., "Effect of the 5-Httlpr Polymorphism in the Serotonin Transporter Gene on Major Depressive Disorder and Related Comorbid Disorders", Psychiatric Genetics, 2009, 19, 39-44.
Verma et al., "Regulation of Striatal Dopamine Release by Metabotropic Glutamate Receptors", Synapse 1998, 28(3), 220-226.
Vernon et al., "Additive Neuroprotection by Metabotropic Glutamate Receptor Subtype-Selective Ligands in aRat Parkinson's Model", Neuroreport, 2008, 19(4), 475-478.
Versiani et al., "Fluoxetine Versus Amitriptyline in the Treatment of Major Depression with Associated Anxiety (Anxious Depression): A Double-Blind Comparison", International Clinical Psychopharmacology, 1999, 14, 321-327.
Vezina et al., "Metabotropic Glutamate Receptors and the Generation of Locomotor Activity: Interactions with Midbrain Dopamine", Neuroscience & Biobehavioral Reviews, 1999, 23(4), 577-589.
Vilsmaier et al., "Diastereoselective Syntheses of N-Protected Derivatives of La,5a,6fi-6-Amino-3-Azabicyclo [3.101]Hexane: A Route to Trovafloxacin 6fl-Diastereomer", Synthesis, 1998, 739-744.
Vinson et al., "Metabotropic Glutamate Receptors as Therapeutic Targets for Schizophrenia", Neuropharmacology, 2012, 62, 1461-1472.
Vippagunta et al., "Crystalline Solids", Adv. Drug Deliv. Rev., 2001, 48, 3-26.
Vogel et al., "A Simple and Reliable Conflict Procedure for Testing Anti-Anxiety Agents", Psychopharmacologia, 1971, 21, 1-7.
Vogel et al., "Drug Effects on Rem Sleep and on Endogenous Depression", Neuroscience & Biobehavioral Reviews, 1990, 14, 49-63.
Vollenweider et al., "A Systems Model of Altered Consciousness: Integrating Natural and Drug-Induced Psychoses", Brain Res. Bull., 2001, 56, 495-507.
Vollenweider et al., "Differential Psychopathology and Patterns of Cerebral Glucose Utilization Produced by (S)- and (R)-Ketamine in Healthy Volunteers Using Positron Emission Tomography (Pet)", Eur Neuropsychopharmacol, 1997, 7, 25-38.
Vollenweider et al., "Effect of Clozapine and Ketanserin on S-Ketamine-Induced Brain Activation and Psychotic Symptoms in Healthy Humans", Abstract, Symposia, 28th Cinp World Congress of Neuropsychopharmacology, 2012, 2 pages.
Vollenweider et al., "Metabolic Hyperfrontality and Psychopathology in the Ketamine Model of Psychosis Using Positron Emission Tomography (Pet) and [18f]fluorodeoxyglucose (Fdg)", Eur Neuropsychopharmacol, 1997, 7, 9-24.
Vollenweider et al., "Psilocybin Induces Schizophrenia-Like Psychosis in Humans via a Serotonin-2 Aqonist Action", Neuroreport, 1998, 9, 3897-3902.
Vollenweider, "Positron Emission Tomography and Fluorodeoxyglucose Studies of Metabolic Hyperfrontality and Psychopathology in the Psilocybin Model of Psychosis", Neuropsychopharmacology, 1997, 16, 357-373.
Wachtel et al., "Glutamate: A New Target in Schizophrenia?", Trends in Pharmacological Sciences, 1990, 11(6), 219-220.
Wadenberg, "Conditioned Avoidance Response in the Development of New Antipsychotics", Curr Pharm Des, 2010, 16, 358-370.
Wadenberg et al., "The Conditioned Avoidance Response Test Re-Evaluated: Is it a Sensitive Test for the Detection of Potentially Atypical Antipsychotics?", Neurosci. Biobehav. Rev., 1999, 23, 851-862.
Wainer, "Finding Time for Allosteric Interactions", Nature Biotechnology, 2004, 22(11), 1376-1377.
Wakefield, "Fluorinated Pharmaceuticals: Fluorinated Compounds are of Increasing Interest as Pharmaceuticals, and an Extensive Range of Techniques for Making Them is Now Available", Innovations in Pharmaceutical Technology, 2003, 74-78.
Walker et al., "Group II Metabotropic Glutamate Receptors Within the Amygadale Regulate Fear as Assessed with Potentiated Startle in Rats", Behav Neurosci, 2002, 116, 1075-1083.
Walker et al., "The Role of Amygdala Glutamate Receptors in Fear Learning, Fear-Potentiated Startle, and Extinction", Pharmacol. Biochem. Behav., 2002, 71(3), 379-392.
Wang et al., "A Simple and Effcient Automatable One Step Synthesis of Triazolopyridines Form Carboxylic Acids", Tetrahedron Letters, 2007, 48, 2237-2240.
Wang et al., "Allosteric Modulators of G Protein-Coupled Receptors: Future Therapeutics for Complex Physiological Disorders", J Pharmacol. Exp. Ther., 2009, 331(2), 340-348.
Wang et al., "Development of Metabotropic Glutamate Receptor Ligands for Neuroimaging", Curr Med Imaging Rev, 2007, 3, 186-205.
Wang et al., "Radiosynthesis of Pet Radiotracer as a Prodrug for Imaging Group II Metabotropic Glutamate Receptors in Vivo", Bioorganic & Medicinal Chemistry Letters, 2012, 22, 1958-1962.
Warden et al., "The Star*D Project Results: A Comprehensive Review of Findings", Current Psychiatry Reports, 2007, 9, 449-459.
Warnock et al., "In Vivo Evidence for Ligand-Specific Receptor Activation in the Central CRF System, as Measured by Local Cerebral Glucose Utilization", Peptides, 2009, 30, 947-954.
Watanabe et al., "Mglur2 Postsynaptically Senses Granule Cell Inputs at Golgi Cell Synapses" Neuron, 2003, 39, 821-829.
Watanabe et al., "Pd/P(T-Bu)3-Catalyzed Synthesis of Aromatic Amines", Journal of Tosoh Research, 1999, 43, 38-50.
Watkins, "L-Glutamate as a Central Neurotransmitter: Looking Back", Biochem Soc Trans, 2000, 28, 297-310.
Watkins et al., "Structure-Activity Relationships in the Development of Excitatory Amino Acid Receptor Agonists and Competitive Antagonists", Trends in Pharmacological Sciences, 1990, 11(1), 25-33.
Webb et al., "Apoptosis: An Overview of the Process and its Relevance in Disease", Advances in Pharmacology, 1997, 41, 1-34.
Weinberger et al., "Schizophrenia Drug Says Goodbye to Dopamine", Nature Medicine, 2007, 13, 1018-1019.
Weinberger, "The Biological Basis of Schizophrenia: New Directions", Journal of Clinical Psychiatry, 1997, 58(Suppl 10), 22-27.
Weiner et al., "5-Hydroxytryptamine2a Receptor Inverse Agonists as Antipsychotics", Journal of Pharmacology & Experimental Therapeutics, 2001, 299(1), 268-276.
Weisstaub, "Cortical 5-Ht2a Receptor Signaling Modulates Anxiety-Like Behaviors in Mice", Science, 2006, 313, 536-540.
Wenner et al., "Derivatives of 2-Pyridone", Journal of Organic Chemistry, 1946, 11, 751-759.
Wheeler et al., "(2s,1's,2'r,3'r)-2(2'-Carboxy-3'-Hydroxymethyl-Cyclopropyl)Glycine-[3h], a Potent and Selective Radioligand for Labeling Group 2 and 3 Metabotropic Glutamate Receptors", Bioorganic & Medicinal Chemistry Letters, 2005, 15, 349-351.
Whitehouse et al., "Clinical Trial Designs for Demonstrating Disease-Course-Altering Effects in Dementia", Alzheimer Disease and Associated Disorders, 1998, 12, 281-294.

(56) References Cited

OTHER PUBLICATIONS

Wicke et al., "Effects of Metabotropic Glutamate Receptor (Mglur) 2/3 Agonists and Antagonist on Rat Sleep Eeg", Program No. 839.2/M9, Neuroscience Meeting Planner, Society for Neuroscience, 2009, 2 pages.
Wieronska et al., "Anxiolytic Action of Group II and III Metabotropic Glutamate Receptors Agonists Involves Neuropeptide Y in the Amygdala", Pharmacol. Rep., 2005, 57(6), 734-743.
Wieronska et al., "Glutamate-Based Anxiolytic Ligands in Clinical Trials", Expert Opin Investig Drugs, 2013, 22(8), 1007-1022.
Wieronska et al., "Metabotropic Glutamate Receptor 4 Novel Agonist Lsp1-2111 with Anxiolytic, but not Antidepressant-Like Activity, Mediated by Serotonergic and Gabaergic Systems", Neuropharmacology, 2010, 59, 627-634.
Wieronska et al., "Metabotropic Glutamate Receptors in the Tripartite Synapse as a Target for New Psychotropic Drugs", Neurochem. Int, 2009, 55(1-3), 85-97.
Wieronska et al., "On the Mechanism of Anti-Hyperthermic Effects of Ly379268 and Ly487379, Group II Mglu Receptors Activators, in the Stress-Induced Hyperthermia in Singly Housed Mice", Neuropharmacology, 2012, 62, 322-331.
Wieronska et al., "Opposing Efficacy of Group III Mglu Receptor Activators, Lsp1-2111 and Amn082, in Animal Models of Positive Symptoms of Schizophrenia", Psychopharmacology, Sep. 2011, 14 pages.
Wiethoff et al., "Prevalence and Treatment Outcome in Anxious Versus Nonanxious Depression: Results From the German Algorithm Project", J Clin Psychiatry, 2010, 71(8), 1047-1054.
Wikipedia, "Allosteric Regulation", 2010, 1-4.
Wiley et al., "2-Pyrones. XVIII. 5-Aroyl-2-Pyridones", J. Am. Chem. Soc., Jun. 1956, 78, 2393-2398.
Williams et al., "Characterization of Polyamines Having Agonist, Antagonist, and Inverse Agonist Effects at the Polyamine Recognition Site of the NMDA Receptor", Neuron, 1990, 5(2), 199-208.
Williams et al., "International Study to Predict Optimized Treatment for Depression (Ispot-D), A Randomized Clinical Trial: Rationale and Protocol", Trials, 2011, 12(4), 17 pages.
Wilsch et al., "Metabotropic Glutamate Receptor Agonist DCG-IV as NMDA Receptor Agonist in Immature Rat Hippocampal Neurons", European Journal of Pharmacology, 1994, 262(3), 287-291.
Wilson et al., "Antidepressants and Sleep: A Qualitative Review of the Literature", Drugs, 2005, 65, 927-947.
Winter et al., "Serotonergic/Glutamatergic Interactions: The Effects of Mglur2/3 Receptor Ligands in Rats Trained with LSD and PCP as Discriminative Stimuli.", Psychopharmacol. (Berl), 2004, 172, 233-240.
Wischhof et al., "Pre-Treatment with the Mglu2/3 Receptor Agonist Ly379268 Attenuates DOI-Induced Impulsive Responding and Regional C-Fos Protein Expression", Psychopharmacology, Aug. 2011, 14 pages.
Witkin et al., "Metabotropic Glutamate Receptors in the Control of Mood Disorders", CNS & Neurological Disorders—Drug Targets, 2007, 6, 87-100.
Wittchen et al., "Disabilities and Quality of Live in Pure and Comorbid Generalized Anxiety Disorder and Major Depression in a National Survey", Intl Clinical Psychopharmacology, 2000, 15, 319-328.
Wittchen et al., "DSM-III-R Generalized Anxiety Disorder in the National Comorbidity Survey", Arch Gen Psychiatry, 1994, 51, 355-364.
Wittmann et al., "Dopamine Modulates the Function of Group II and Group III Metabotropic Glutamate Receptors in the Substantia Nigra Pars Reticulata", J Pharmacol. Exp. Ther., 2002, 302(2), 433-441.
Wong et al., "The Role of Imaging in Proof of Concept for CNS Drug Discovery and Development", Neuropsychopharmacology, 2009, 34, 187-203.
Woolley et al., "The Mglu2 but not the Mglu3 Receptor Mediates the Actions of the Mglur2/3 Agonist, Ly379268, in Mouse Models Predictive of Antipsychotic Activity", Psychopharmacology, 2008, 196, 431-440.
World Health Organization, "Mental Health: New Understanding, New Hope", 2001, 169 pages.
Wright e al., "[3h]Ly341495 Binding to Group II Metabotropic Glutamate Receptors in Rat Brain", Journal of Pharmacology & Experimental Therapeutics, 2001, 298(2), 453-460.
Wroblewska et al., "N-Acetylaspartylglutamate Activates Cyclic Amp-Coupled Metabotropic Glutamate Receptors in Cerebellar Astrocytes", Glia, 1998, 24(2), 172-179.
Xi et al., "Group II Metabotropic Glutamate Receptors Modulate Extracellular Glutamate in the Nucleus Accumbens", Journal of Pharmacology & Experimental Therapeutics, 2002, 300(1), 162-171.
Xiao et al., "Desensitization of G-Protein-Coupled Receptors. Agonist-Induced Phosphorylation of the Chemoattractant Receptor Car1 Lowers its Intrinsic Affinity for Camp", J. Biol. Chem., 1999, 274(3), 1440-1448.
Xiao et al., "Metabotropic Glutamate Receptor Activation Causes a Rapid Redistribution of Ampa Receptors", Neuropharmacology, 2001, 41(6), 664-671.
Xu et al., "Neurotransmitter Receptors and Cognitive Dysfunction in Alzheimer's Disease and Parkinson's Disease", Progress in Neurobiology, 2012, 97, 1-13.
Yakovidis et al., "Copper(II) Complexes of Thieno[2,3-D] Pyrimidine Derivatives", Inorganica Chimica Acta, 1988, 151, 165-167.
Yalyaheva et al.,"Chemical Abstract", Heterocycles, 1987, 2 pages.
Yanamala et al., "Preferential Binding of Allosteric Modulators to Active and Inactive Conformational States of Metabotropic Glutamate Receptors", BMC Bioinformatics, 2008, 9(Suppl 1), S16.
Yao et al., "Enhancement of Glutamate Uptake Mediates the Neuroprotection Exerted by Activating Group II or III Metabotropic Glutamate Receptors on Astrocytes", Journal of Neurochemistry, 2005, 92(4), 948-961.
Yasuhara et al., "Metabotropic Glutamate Receptors: Potential Drug Targets for Psychiatric Disorders",Open Medicinal Chemistry Journal, 2010, 4, 20-36.
Ye et al, "Metabotropic Glutamate Receptor Agonists Reduce Glutamate Release From Cultured Astrocytes", Glia, 1999, 25(3), 270-281.
Yokoi et al., "Impairment of Hippocampal Mossy Fiber Ltd in Mice Lacking Mgiur2", Science, 1996, 273, 645-647.
Young et al., "Biomarkers of Oxidative Stress in Schizophrenic and Control Subjects", Prostaglandins Leukot. Essent. Fatty Acids, 2007, 76(2), 73-85.
Young et al., "Evidence for a Role of Metabotropic Glutamate Receptors in Sustained Nociceptive Inputs to Rat Dorsal Horn Neurons," Neuropharmacology, 1994, 33(1), 141-144.
Young et al., "The Involvement of Metabotropic Glutamate Receptors and Their Intracellular Signalling Pathways in Sustained Nociceptive Transmission in Rat Dorsal Horn Neurons", Neuropharmacology, 1995, 34(8), 1033-1041.
Yousif et al., "Studies on Tertiary Amine Oxides. LXXV. Reactions of Aromatic N-Oxides with Meldrum's Acid in the Presence of Acetic Anhydride", Chem. Pharm. Bull., 1982, 30(5), 1680-1691.
Yuan et al., "Glutamate-Induced Swelling of Cultured Astrocytes is Mediated by Metabotropic Glutamate Receptor", Science in China, Series C, Life Sciences, 1996, 39(5), 517-522.
Yucel et al., "Anterior Cingulate Volumes in Never-Treated Patients with Major Depressive Disorder", Neuropsychopharmanology, 2008, 33, 3157-3163.
Yui et al., "Studies of Amphetamine or Methamphetamine Psychosis in Japan: Relation of Methamphetamine Psychosis to Schizophrenia", Annals New York Academy of Sciences, 2000, 914, 1-12.
Yuzwa et al., "O-GlcNAc and neurodegeneration: biochemical mechanisms and potential roles in Alzheimer's disease and beyond", Chem. Soc. Rev., 2014, 43, 6839-6858.
Yuzaki et al., "Pharmacological and Immunocytochemical Characterization of Metabotropic Glutamate Receptors in Cultured Purkinje Cells", J. Neurosci., 1992, 12(11), 4253-4263.

(56) References Cited

OTHER PUBLICATIONS

Zarate et al., "An Open-Label Trial of Riluzole in Patients with Treatment-Resistant Major Depression", Am J Psychiatry, 2004, 161, 171-174.
Zeilhofer et al., "Differential Effects of Ketamine Enantiomers on NMDA Receptor Currents in Cultured Neurons", Eur J Pharmacol, 1992, 213, 155-158.
Zhang et al., "1-[(1-Methyl-1h-Imidazol-2-Yl)Methyl]-4-Phenylpiperidines as Mglur2 Positive Allosteric Modulators for the Treatment of Psychosis", J Med Chem, 2011, 54, 1724-1739.
Zhang et al., "3-(ImidazolylMethyl)-3-Aza-Bicyclo[3.1.0]Hexan-6-Yl)Methyl Ethers: a Novel Series of Mglur2 Positive Allosteric Modulators", Bioorg Med Chem Lett, 2008, 18, 5493-5496.
Zhang et al., "Neuroprotective Effects of Poly(Adp-Ribose) Polymerase Inhibition on Focal Cerebral Ischemia", Biology of Nitric Oxide, Portland Press Proceedings, 1998, 15, 125.
Zhao et al., "Activation of Group II Metabotropic Glutamate Receptors Attenuates Both Stress and Cue-Induced Ethanol-Seeking and Modulates C-Fos Expression in the Hippocampus and Amygdala", Journal of Neuroscience, 2006, 26(39), 9967-9974.
Zhu et al., "Rapid Enhancement of High Affinity Glutamate Uptake by Glucocorticoids in Rat Cerebral Cortex Synaptosomes and Human Neuroblastoma Clone Sk-N-Sh: Possible Involvement of G-Protein", Biochemical & Biophysical Research Communications, 1998, 247(2), 261-265.
Zhu, "The Competitive and Noncompetitive Antagonism of Receptor-Mediated Drug Actions in the Presence of Spare Receptors", Journal of Pharmacological & Toxicological Methods, 1993, 29(2), 85-91.
Zimmerman et al., "Frequency of Anxiety Disorders in Psychiatric Outpatients with Major Depressive Disorder", Am J Psychiatry, 2000, 157, 1337-1340.
Zuena et al., "Prenatal Restraint Stress Generates Two Distinct Behavioral and Neurochemical Profiles in Male and Female Rats", Plos. One, 2008, 3(5), E2170.
Zusso et al., "Cerebellar Granular Cell Cultures as an In Vitro Model for Antidepressant Drug-Induced Meurogenesis", Critical Reviews in Neurobiology, 2004, 16(1&2), 59-65.
Zwart et al., "Sazetidine-A is a Potent and Selective Agonist at Native and Recombinant A4β2 Nicotinic Acetylcholine Receptors", Mol Pharmacol, 2008, 73, 1838-1843.
Hickinbottom, English translation of the relevent from reaction of organic complonents, Reactions of organic compounds, 1939, pp. 360-362, Page Number.
Moscow., Chemical Encyclopedia, Soviet encyclopedia, 1988, pp. 242-243, vol. 1.

* cited by examiner

Stimulation electrode

SUBSTITUTED 6,7-DIHYDROPYRAZOLO[1,5-A]PYRAZINES AS NEGATIVE ALLOSTERIC MODULATORS OF MGLUR2 RECEPTORS

CROSS REFERENCE TO RELATED APPLICATIONS

This application is the national stage of PCT Application No. PCT/EP2014/061478 filed Jun. 3, 2014, which claims priority from European Patent Application No. 13170447.0, filed Jun. 4, 2013, European Patent Application No. 13173939.3, filed Jun. 27, 2013 and European Patent Application No. 14166450.8 filed Apr. 29, 2014, the entire disclosures of which are hereby incorporated in their entirety.

FIELD OF THE INVENTION

The present invention relates to novel 6,7-dihydropyrazolo[1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013).

Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain therapeutics) describes 4H-pyrazolo[1,5-a]quinazolin-5-ones and 4H-pyrrolo[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

DESCRIPTION OF THE INVENTION

The present invention is directed to 6,7-dihydropyrazolo[1,5-a]pyrazin-4(5H)-one derivatives of Formula (I)

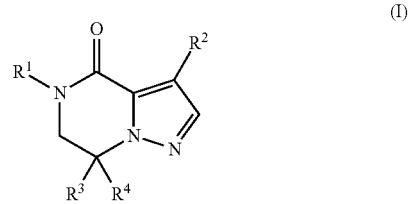

and stereoisomeric forms thereof,
wherein
$R^1$ is phenyl or 2-pyridinyl, each optionally substituted with one or more substituents each independently selected from the group of halo, $C_{1-4}$alkyl, mono- or poly-halo$C_{1-4}$alkyl, —O—$C_{1-4}$alkyl, —$C_{1-4}$alkyl-O—$C_{1-4}$alkyl, mono- or poly-halo$C_{1-4}$alkyloxy, —$C_{1-4}$alkyl-OH, $C_{1-4}$alkylthio, mono- or poly-halo$C_{1-4}$alkylthio, cyano, $C_{3-7}$cycloalkyl optionally substituted with trifluoromethyl, and —$SF_5$; or is

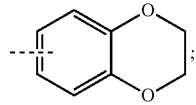

$R^2$ is selected from

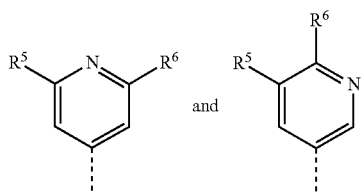

wherein $R^5$ and $R^6$ are each independently selected from the group of hydrogen, halo, cyano, $C_{1-4}$alkyl, —$C_{1-4}$alkyl-OH, $C_{3-7}$cycloalkyl, mono- or poly-halo$C_{1-4}$alkyl, —$C_{1-4}$alkyl-O—$C_{1-4}$alkyl, —O—$C_{1-4}$alkyl, mono- or poly-halo$C_{1-4}$alkyloxy, 1-acetylazetidin-3-yl, and NR'R";
wherein R' is selected from hydrogen and $C_{1-4}$alkyl;
R" is selected from hydrogen and $C_{1-4}$alkyl; or
R' and R" together with the Nitrogen atom to which they are attached form a heterocyclic group selected from the group of 1-azetidinyl, 1-pyrrolidinyl, 1-piperidinyl, 1-piperazinyl, and 4-morpholinyl; wherein each of the heterocyclic groups may be optionally substituted with a substituent selected from halo, hydroxyl, $C_{1-4}$alkyl, mono- or poly-halo$C_{1-4}$alkyl, and —(CO)$C_{1-4}$alkyl;
$R^3$ is selected from hydrogen and $C_{1-4}$alkyl;
$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;
and the N-oxides, and the pharmaceutically acceptable salts and the solvates thereof The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of a compound of Formula (I) in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder comprising administering to a subject in need thereof, a therapeutically effective amount of a compound of Formula (I) or a therapeutically effective amount of a pharmaceutical composition according to the invention.

The invention also relates to a product comprising a compound of Formula (I) and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

DESCRIPTION OF THE FIGURES

In FIG. 1, ▬ corresponds to scopolamine+JNJ 42153605; - - - corresponds to scopolamine alone; and ― ― ― corresponds to no challenge.

Figure 3A:
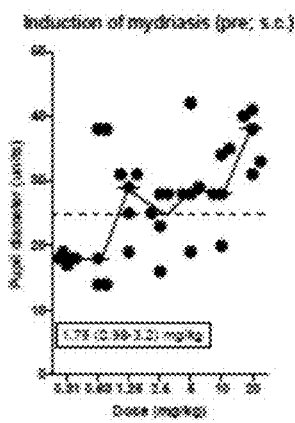
FIG. 3 shows the interaction of Co. No. 1 with reserpine in rats.
Figure 3A:
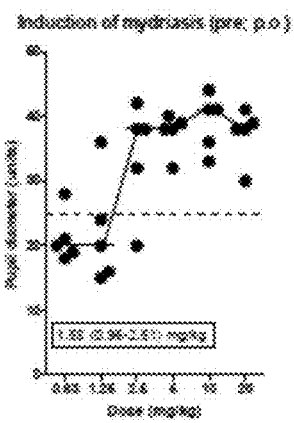
Figure 3A:
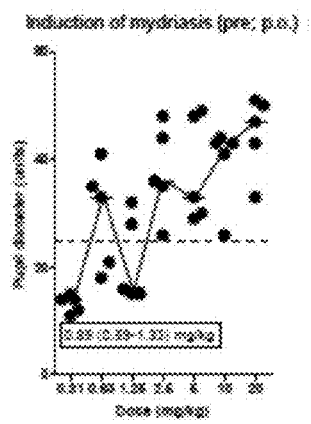
Figure 3B:
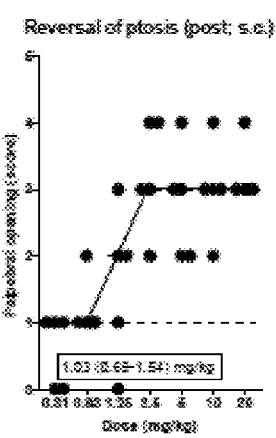
Figure 3B:
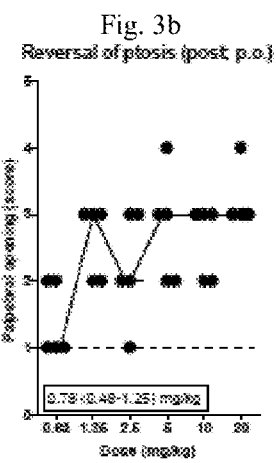
Figure 3B:
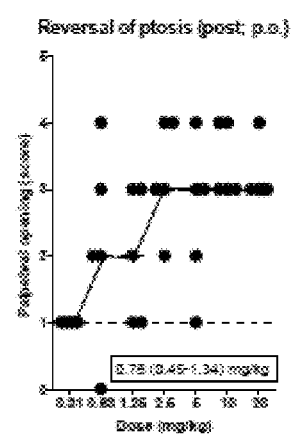
Figure 3C:
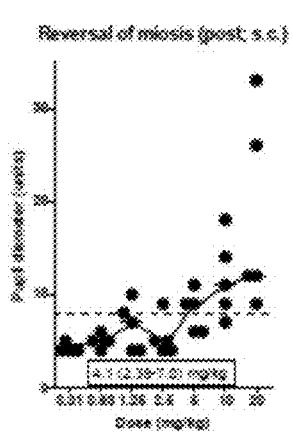
Figure 3C:
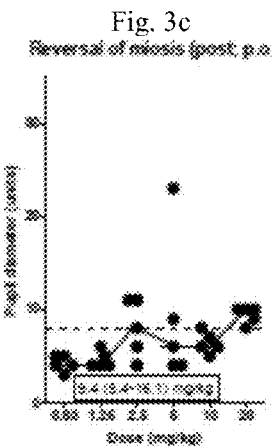
Figure 3C:
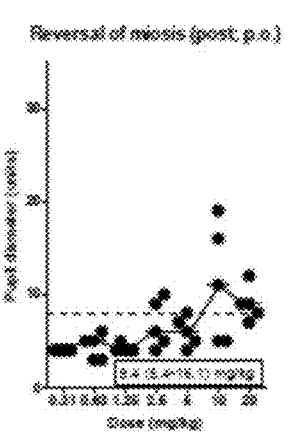
Figure 3D:
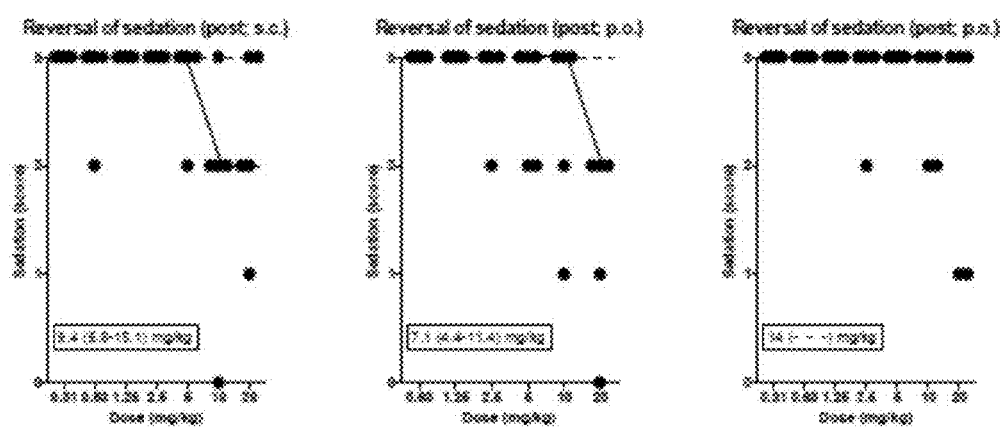

Shown are the effects on pupil diameter before reserpine challenge (FIG. 3a) and the reversal of the reserpine-induced ptosis (FIG. 3b), miosis (FIG. 3c) and sedation (FIG. 3d) measured 1 h after s.c. (left panel), 1 h after p.o. (middle panel) and 4 h after p.o. (right panel) administration of Co. No. 1.

Figure 4A:
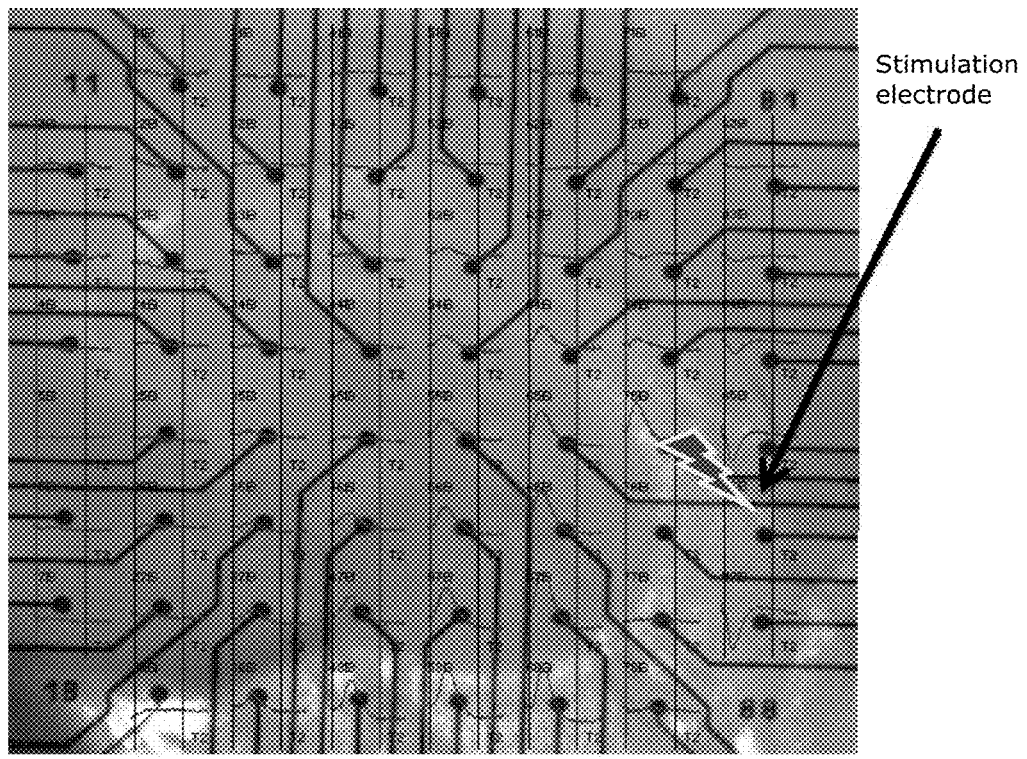
Figure 4B:
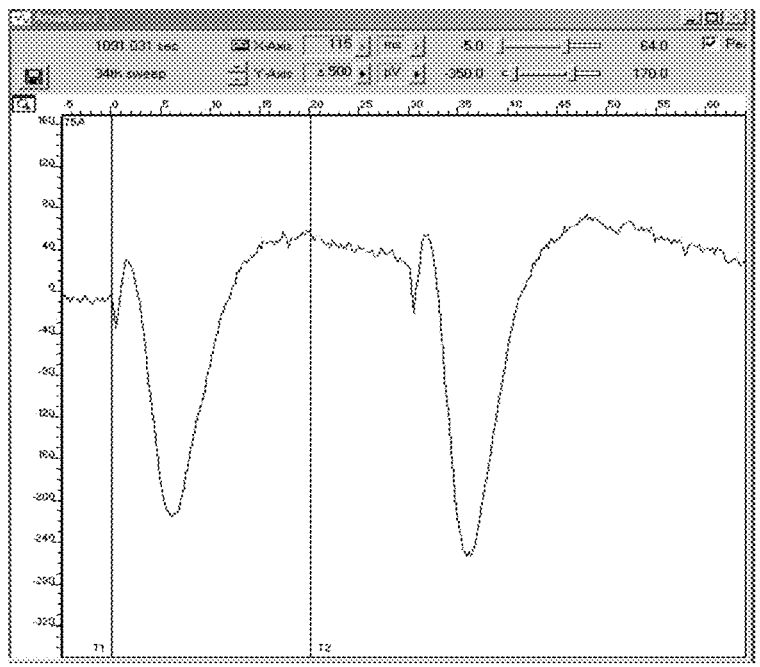

FIG. 4 illustrates the placement of the hippocampus brain slice in a well of a MEA biochip, with 60×3D-tip electrodes (black dots). Traces show the recorded potential at each electrode (FIG. 4a), and the captured fEPSP traces of paired pulses separated by 30 ms (FIG. 4b). The preparation was perfused with artificial cerebrospinal fluid (ACSF). (3D=three-dimensional; fEPSP=field excitatory postsynaptic potentials; MEA=micro-electrode array; ms=milliseconds).

FIG. 5 shows how Co. No. 1 restores fEPSP depressed by 1 μM LY-354740 in the dentate gyrus of rat hippocampal brain slices.

Figure 5A:
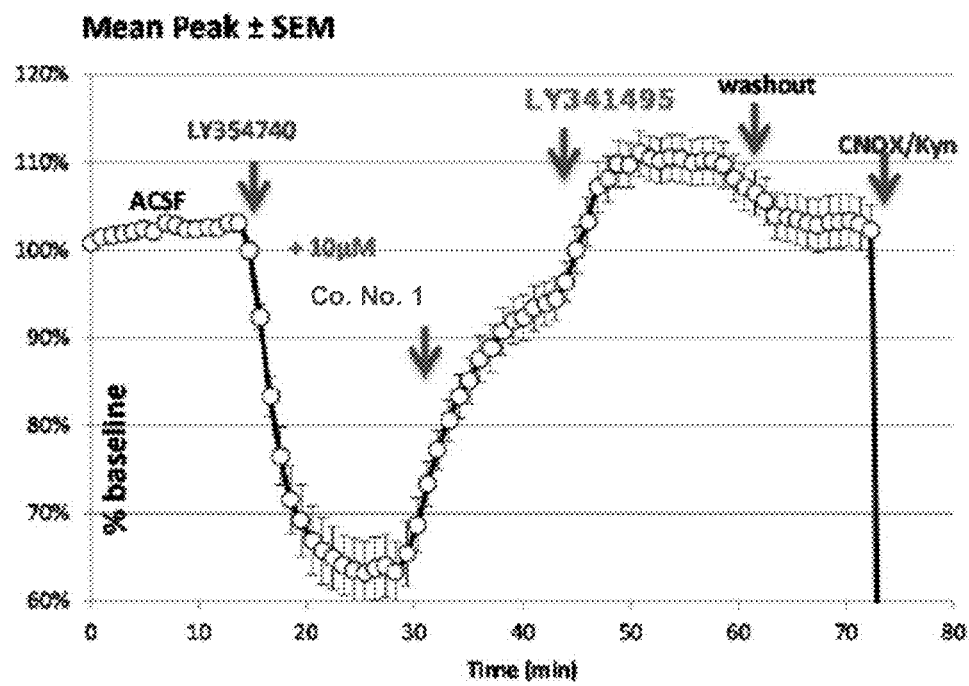

FIG. 5a: fEPSP amplitude (% of baseline) is shown after the application of LY-354740 (1 μM), followed by the application of Co. No. 1 (10 μM), and then by the application of the mGlu2 antagonist LY-341495, and finally by a washout. At the end of experiments, the AMPA antagonist CNQX (6-cyano-7-nitroquinoxaline-2,3-dione, 50 μM) and kynurenic acid (1 mM) were added as controls to block glutamate-mediated fEPSP.

Figure 5B:
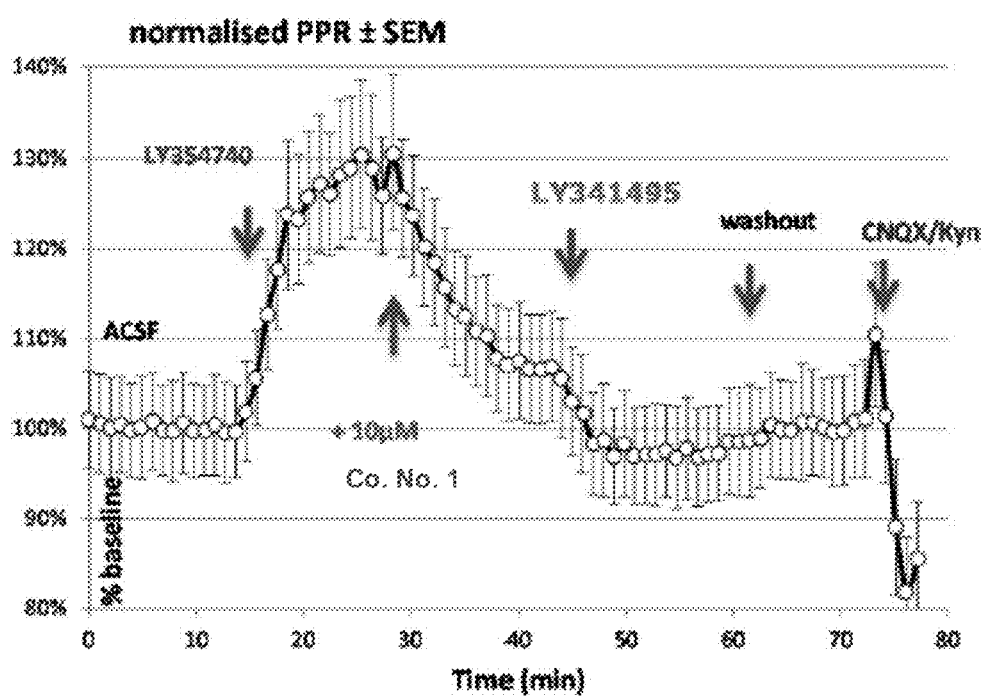

FIG. 5b: The same experiments as shown in FIG. 5a, but presenting the PPR results. The error bars represent the SEM of 17 independent slices from 4 SD rats. (ACSF=artificial cerebrospinal fluid; fEPSP=field excitatory postsynaptic potential; PPR=paired-pulse ratio; SEM=standard error of the mean).

FIG. 6 shows how Co. No. 1 facilitates long-term potentiation in the dentate gyrus of rat hippocampal brain slices.

Monitoring of the post-synaptic response for 80 min shows induction of LTP after weak theta stimulation (at 30 min).

Figure 6A:
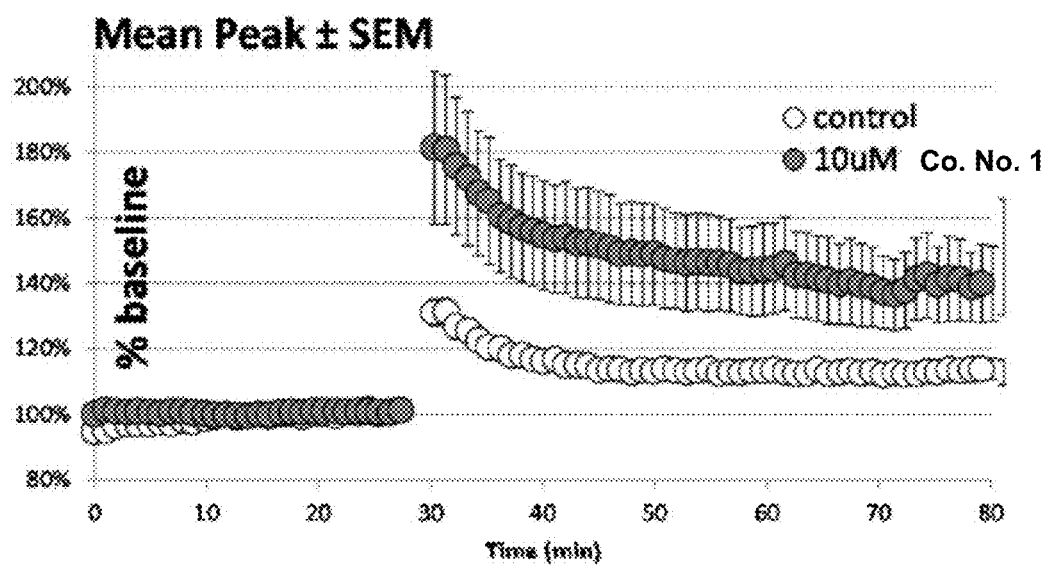

FIG. 6a: fEPSP in response to the weak theta stimulus under control conditions (vehicle: open circles) and following the application of 10 µM Co. No. 1 (solid circles).

Figure 6B:
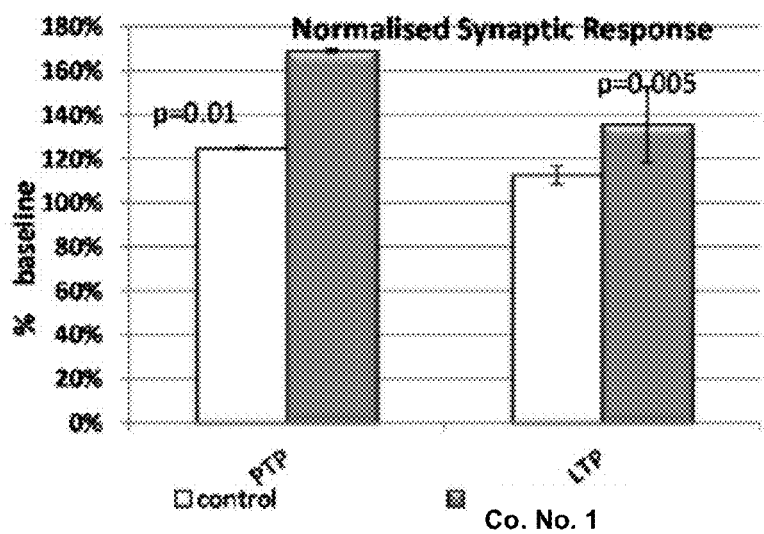

FIG. 6b: PTP and LTP under control conditions and after application of 10 µM Co. No. 1. The error bars represent the SEM of 22 independent slices from 4 SD rats. LTP=long-term potentiation; NAM=negative allosteric modulator; PTP=post-theta potentiation; SEM=standard error of the mean.

DETAILED DESCRIPTION OF THE INVENTION

The present invention relates in particular to compounds of Formula (I) as defined hereinabove, and stereoisomeric forms thereof, wherein
$R^1$ is phenyl or 2-pyridinyl, each optionally substituted with one or more substituents each independently selected from the group of halo, $C_{1-4}$alkyl, mono- or poly-halo$C_{1-4}$alkyl, —O—$C_{1-4}$alkyl, —$C_{1-4}$alkyl-O—$C_{1-4}$alkyl, mono- or poly-halo$C_{1-4}$alkyloxy, —$C_{1-4}$alkyl-OH, mono- or poly-halo$C_{1-4}$alkylthio, cyano, and —SF$_5$; or is

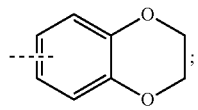

$R^2$ is selected from

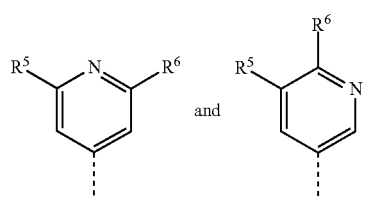

wherein $R^5$ and $R^6$ are each independently selected from the group of hydrogen, halo, cyano, $C_{1-4}$alkyl, —$C_{1-4}$alkyl-OH, $C_{3-7}$cycloalkyl, mono- or poly-halo$C_{1-4}$alkyl, —$C_{1-4}$alkyl-O—$C_{1-4}$alkyl, —O—$C_{1-4}$alkyl, mono- or poly-halo$C_{1-4}$alkyloxy, and NR'R"; wherein R' is selected from hydrogen and $C_{1-4}$alkyl;
R" is selected from hydrogen and $C_{1-4}$alkyl; or
R' and R" together with the Nitrogen atom to which they are attached form a heterocyclic group selected from the group of 1-azetidinyl, 1-pyrrolidinyl, and 1-piperidinyl; wherein each of the heterocyclic groups may be optionally substituted with a halo substituent;
$R^3$ is selected from hydrogen and $C_{1-4}$alkyl;
$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;
and the N-oxides, and the pharmaceutically acceptable salts and the solvates thereof.

In an additional embodiment, the present invention relates to compounds of Formula (I) as defined hereinabove, and stereoisomeric forms thereof, wherein
$R^1$ is phenyl optionally substituted with one, two or three substituents each independently selected from the group of halo, $C_{1-4}$alkyl, mono- or poly-halo$C_{1-4}$alkyl, —O—$C_{1-4}$alkyl, —$C_{1-4}$alkyl-O—$C_{1-4}$alkyl, mono- or poly-halo$C_{1-4}$alkyloxy, mono- or poly-halo$C_{1-4}$alkylthio, cyano, and —SF$_5$;
or 2-pyridinyl optionally substituted with one or two substituents each independently selected from the group of halo, $C_{1-4}$alkyl, mono- or poly-halo$C_{1-4}$alkyl, and —O—$C_{1-4}$alkyl;
$R^2$ is

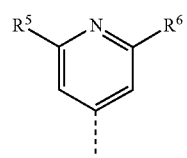

wherein $R^5$ and $R^6$ are each independently selected from the group of hydrogen, halo, cyano, $C_{1-4}$alkyl, $C_{3-7}$cycloalkyl, mono- or poly-halo$C_{1-4}$alkyl, —O—$C_{1-4}$alkyl, mono- or poly-halo$C_{1-4}$alkyloxy, and NR'R";
wherein R' is selected from hydrogen and $C_{1-4}$alkyl;
R" is selected from hydrogen and $C_{1-4}$alkyl; or R' and R" together with the Nitrogen atom to which they are attached form a heterocyclic group selected from the group of 1-azetidinyl, 1-pyrrolidinyl, and 1-piperidinyl; wherein each of the heterocyclic groups may be optionally substituted with a halo substituent;
$R^3$ is selected from hydrogen and $C_{1-4}$alkyl;
$R^4$ is selected from the group of $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >CH(CH$_3$), >CH(CH$_2$CH$_3$), >CH(CH$_2$F), and >CH(CH$_2$OCH$_3$);
and the N-oxides, and the pharmaceutically acceptable salts and the solvates thereof.

In an additional embodiment, the present invention relates to compounds of Formula (I) as defined hereinabove, and stereoisomeric forms thereof, wherein
$R^1$ is phenyl optionally substituted with one, two or three substituents each independently selected from the group of halo, $C_{1-4}$alkyl, poly-halo$C_{1-4}$alkyl, —O—$C_{1-4}$alkyl, —$C_{1-4}$alkyl-O—$C_{1-4}$alkyl, poly-halo$C_{1-4}$alkyloxy, poly-halo$C_{1-4}$alkylthio, cyano, and —SF$_5$;
or 2-pyridinyl optionally substituted with one or two substituents each independently selected from the group of halo, $C_{1-4}$alkyl, mono- or poly-halo$C_{1-4}$alkyl, and —O—$C_{1-4}$alkyl;
$R^2$ is

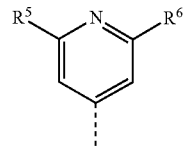

wherein $R^5$ and $R^6$ are each independently selected from the group of hydrogen, cyano, $C_{1-4}$alkyl, poly-halo$C_{1-4}$alkyl, —O—$C_{1-4}$alkyl, and NR'R";
wherein R' is selected from hydrogen and $C_{1-4}$alkyl;
R" is $C_{1-4}$alkyl; or
R' and R" together with the Nitrogen atom to which they are attached form a 1-azetidinyl;
$R^3$ is selected from hydrogen and $C_{1-4}$alkyl;

$R^4$ is selected from the group of $C_{1-4}$alkyl, mono- or polyhalo$C_{1-4}$alkyl, and —$C_{1-4}$alkyl-O—$C_{1-4}$alkyl; in particular >$CR^3R^4$ is selected from the group of >CH(CH$_3$), >CH(CH$_2$CH$_3$), >CH(CH$_2$F), and >CH(CH$_2$OCH$_3$);

and the N-oxides, and the pharmaceutically acceptable salts and the solvates thereof.

In an additional embodiment, the present invention relates to compounds of Formula (I) as defined hereinabove, and stereoisomeric forms thereof, wherein $R^1$ is selected from (a) a substituted phenyl selected from the group of

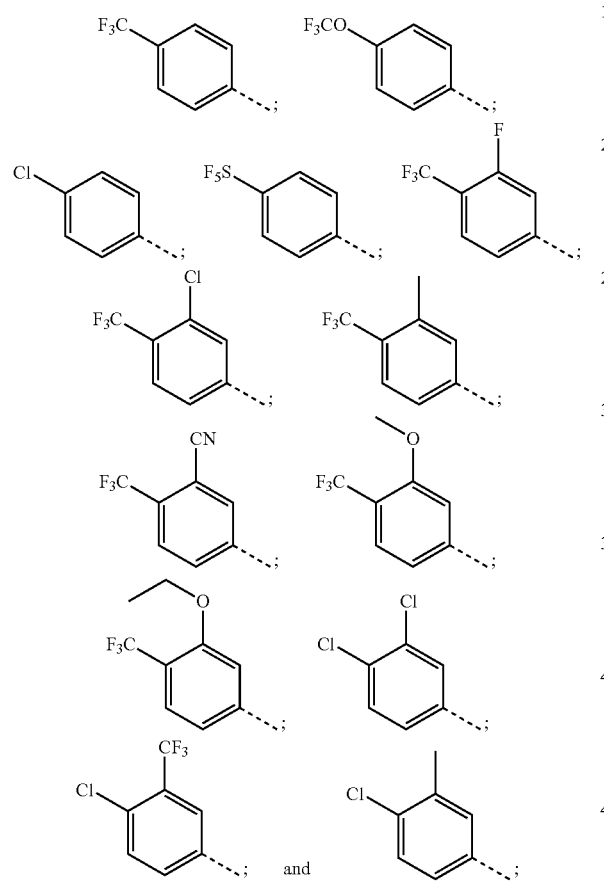

or (b) a substituted 2-pyridinyl selected from the group of

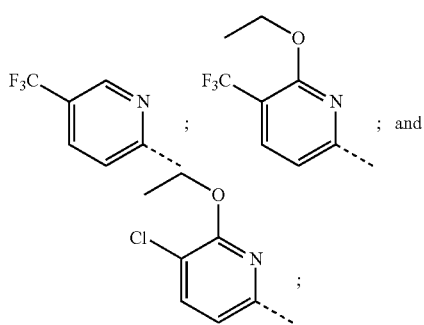

$R^2$ is selected from the group of

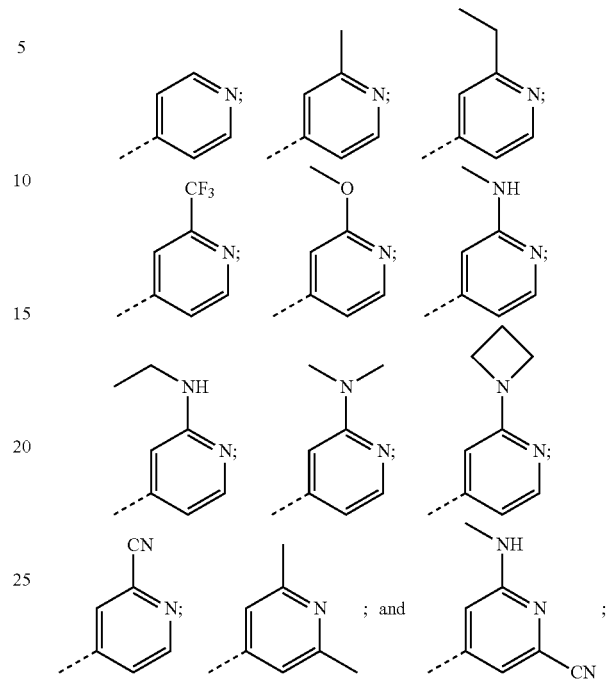

$R^3$ is selected from hydrogen and $C_{1-4}$alkyl;
$R^4$ is selected from the group of $C_{1-4}$alkyl, mono- or polyhalo$C_{1-4}$alkyl, and —$C_{1-4}$alkyl-O—$C_{1-4}$alkyl; in particular >$CR^3R^4$ is selected from the group of >CH(CH$_3$), >CH(CH$_2$CH$_3$), >CH(CH$_2$F), and >CH(CH$_2$OCH$_3$);

and the N-oxides, and the pharmaceutically acceptable salts and the solvates thereof In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one;

(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-5-(4-Chlorophenyl)-7-methyl-3-(2-methylpyridin-4-yl)-6,7-dihydropyrazolo[1,5-a]pyrazin-4(5H)-one;

(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-3-pyridin-4-yl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(3,4-Dichlorophenyl)-7-methyl-3-(2-methylpyridin-4-yl)-6,7-dihydropyrazolo[1,5-a]pyrazin-4(5H)-one;

(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(pentafluoro-$\lambda^6$-sulfanyl)phenyl]-6,7-dihydropyrazolo[1,5-a]pyrazin-4(5H)-one;

(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one;

(7S)-3-(2,6-Dimethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;

(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;

5-[(7S)-7-Methyl-3-(2-methylpyridin-4-yl)-4-oxo-6,7-dihydropyrazolo[1,5-a]pyrazin-5(4H)-yl]-2-(trifluoromethyl)benzonitrile;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-3-(2-Ethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-(2,6-dimethylpyridin-4-yl)-7-methyl-6,7-dihydropyrazolo[1,5-a]pyrazin-4(5H)-one;

(7S)-5-(3,4-Dichlorophenyl)-3-(2,6-dimethylpyridin-4-yl)-7-methyl-6,7-dihydropyrazolo[1,5-a]pyrazin-4(5H)-one;

(7S)-3-[2-(Ethylamino)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one; and (7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

and the N-oxides, and the pharmaceutically acceptable salts and the solvates thereof.

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;

(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-5-(4-Chlorophenyl)-7-methyl-3-(2-methylpyridin-4-yl)-6,7-dihydropyrazolo[1,5-a]pyrazin-4(5H)-one or a hydrochloride salt thereof;

(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one or a hydrochloride salt thereof;

(7S)-7-Methyl-3-pyridin-4-yl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(3,4-Dichlorophenyl)-7-methyl-3-(2-methylpyridin-4-yl)-6,7-dihydropyrazolo[1,5-a]pyrazin-4(5H)-one or a hydrochloride salt thereof;

(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(pentafluoro-$\lambda^6$-sulfanyl)phenyl]-6,7-dihydropyrazolo[1,5-a]pyrazin-4(5H)-one;

(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one or a hydrochloride salt thereof;

(7S)-3-(2,6-Dimethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;

(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;

5-[(7S)-7-Methyl-3-(2-methylpyridin-4-yl)-4-oxo-6,7-dihydropyrazolo[1,5-a]pyrazin-5(4H)-yl]-2-(trifluoromethyl)benzonitrile;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-3-(2-Ethylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-(2,6-dimethylpyridin-4-yl)-7-methyl-6,7-dihydropyrazolo[1,5-a]pyrazin-4(5H)-one;

(7S)-5-(3,4-Dichlorophenyl)-3-(2,6-dimethylpyridin-4-yl)-7-methyl-6,7-dihydropyrazolo[1,5-a]pyrazin-4(5H)-one;

(7S)-3-[2-(Ethylamino)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one or a hydrochloride salt thereof;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one; and (7S)-7-Methyl-3-(2-methylpyridin-4-yl)-5-[5-(trifluoromethyl)pyridin-2-yl]-6,7-dihydropyrazolo[1,5-a]pyrazin-4(5H)-one.

In an additional embodiment, the present invention relates to compounds of Formula (I) as defined hereinabove, and stereoisomeric forms thereof, wherein $R^1$ is phenyl, optionally substituted with one, two or three substituents each independently selected from the group of halo, $C_{1-4}$alkyl, poly-halo$C_{1-4}$alkyl, —O—$C_{1-4}$alkyl, —$C_{1-4}$alkyl-OH and cyano; or 2-pyridinyl, substituted with one or two substituents each independently selected from the group of halo, poly-halo-$C_{1-4}$alkyl, and —O—$C_{1-4}$alkyl;

$R^2$ is

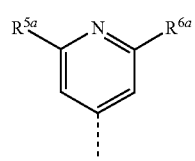

wherein $R^{5a}$ is selected from hydrogen and $C_{1-4}$alkyl, and $R^{6a}$ is selected from the group of hydrogen, $C_{1-4}$alkyl, —$C_{1-4}$alkyl-O—$C_{1-4}$alkyl, —O$C_{1-4}$alkyl, and —$C_{1-4}$alkyl-OH; or

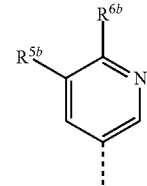

wherein one of $R^{5b}$ and $R^{6b}$ is hydrogen, and the other $R^{5b}$ or $R^{6b}$ is $C_{1-4}$alkyl; $R^3$ is selected from hydrogen and $C_{1-4}$alkyl;

$R^4$ is selected from the group of hydrogen, $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >$CH_2$, >$CH(CH_3)$, >$CH(CH_2CH_3)$, >$CH(CH_2F)$, >$CH(CH_2OCH_3)$ and >$C(CH_3)_2$;

and the N-oxides, and the pharmaceutically acceptable salts and the solvates thereof In an additional embodiment, the present invention relates to compounds of Formula (I) as defined hereinabove, and stereoisomeric forms thereof, wherein $R^1$ is phenyl, optionally substituted with one, two or three substituents each independently selected from the group of fluoro, chloro, methyl, $CF_3$, —O—$CH_3$, —O—$CH_2CH_3$, cyano, —$CH(CH_3)(OH)$; or 2-pyridinyl, substituted with one or two substituents each independently selected from the group of fluoro, chloro, $CF_3$, and —O—$CH_2CH_3$;

$R^2$ is

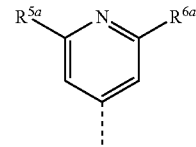

wherein $R^{5a}$ is selected from hydrogen and methyl, and $R^{6a}$ is selected from the group of hydrogen, methyl, —$CH_2$—O—$CH_3$, —O—$CH_3$, and —$CH_2$—OH; or

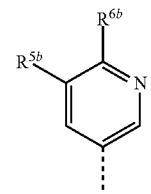

wherein one of $R^{5b}$ and $R^{6b}$ is hydrogen, and the other $R^{5b}$ or $R^{6b}$ is methyl;

$R^3$ is selected from hydrogen and $C_{1-4}$alkyl;

$R^4$ is selected from the group of hydrogen, $C_{1-4}$alkyl, mono- or poly-halo$C_{1-4}$alkyl, and —$C_{1-4}$alkyl-O—$C_{1-4}$alkyl; in particular >$CR^3R^4$ is selected from the group of >$CH_2$, >$CH(CH_3)$, >$CH(CH_2CH_3)$, >$CH(CH_2F)$, >$CH(CH_2OCH_3)$ and >$C(CH_3)_2$;

and the N-oxides, and the pharmaceutically acceptable salts and the solvates thereof.

In an additional embodiment, the present invention relates to compounds of Formula (I) as defined hereinabove, and stereoisomeric forms thereof, wherein R¹ is (a) a phenyl substituent selected from the group of

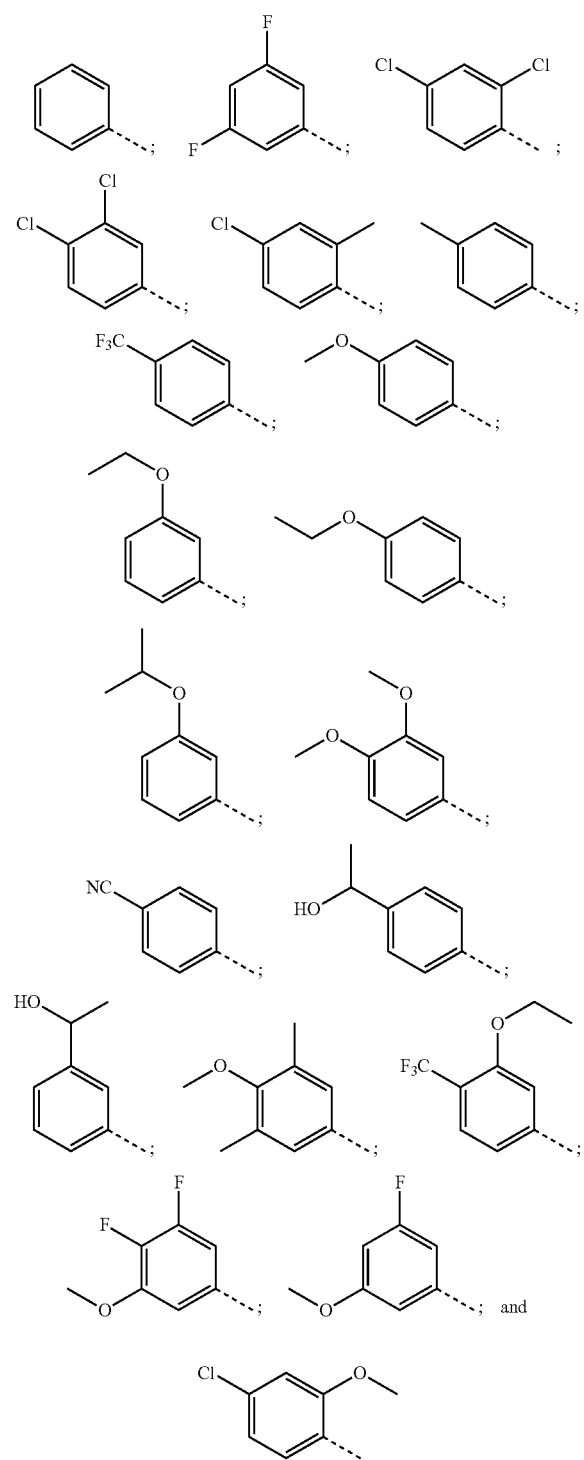

or (b) a 2-pyridinyl substituent selected from the group of

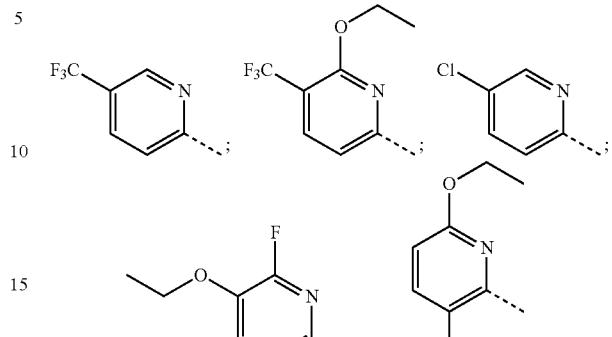

R² is

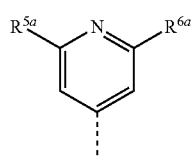

wherein $R^{5a}$ is selected from hydrogen and methyl, and $R^{6a}$ is selected from the group of hydrogen, methyl, —CH₂—O—CH₃, —O—CH₃, and —CH₂—OH; or

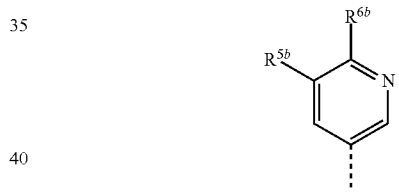

wherein one of $R^{5b}$ and $R^{6b}$ is hydrogen, and the other $R^{5b}$ or $R^{6b}$ is methyl;

$R^3$ is selected from hydrogen and $C_{1-4}$alkyl;

$R^4$ is selected from the group of hydrogen, $C_{1-4}$alkyl, mono- or poly-halo$C_{1-4}$alkyl, and —$C_{1-4}$ alkyl-O—$C_{1-4}$alkyl; in particular >$CR^3R^4$ is selected from the group of >CH₂, >CH(CH₃), >CH(CH₂CH₃), >CH(CH₂F), >CH(CH₂OCH₃) and >C(CH₃)₂;

and the N-oxides, and the pharmaceutically acceptable salts and the solvates thereof In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one;

(7S)-7-Methyl-3-pyridin-4-yl-5-[4-(trifluoromethyl)phenyl]-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(5-methylpyridin-3-yl)-5-[4-(trifluoromethyl)phenyl]-6,7-dihydropyrazolo[1,5-a]pyrazin-4(5H)-one;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;
5-[3-Ethoxy-4-(trifluoromethyl)phenyl]-3-(2-methylpyridin-4-yl)-6,7-dihydropyrazolo[1,5-a]pyrazin-4(5H)-one;
(7S)-5-(4-Methoxy-3,5-dimethylphenyl)-7-methyl-3-(2-methylpyridin-4-yl)-6,7-dihydropyrazolo[1,5-a]pyrazin-4(5H)-one;
(7S)-7-Methyl-3-(6-methylpyridin-3-yl)-5-[4-(trifluoromethyl)phenyl]-6,7-dihydropyrazolo[1,5-a]pyrazin-4(5H)-one;
(7S)-5-(4-Methoxyphenyl)-7-methyl-3-(2-methylpyridin-4-yl)-6,7-dihydropyrazolo[1,5-a]pyrazin-4(5H)-one;
3-(2-Methylpyridin-4-yl)-5-[4-(trifluoromethyl)phenyl]-6,7-dihydropyrazolo[1,5-a]pyrazin-4(5H)-one;
(7S)-5-(3,4-Dimethoxyphenyl)-7-methyl-3-(2-methylpyridin-4-yl)-6,7-dihydropyrazolo[1,5-a]pyrazin-4(5H)-one;
(7S)-3-(2-Methoxypyridin-4-yl)-7-methyl-5-[4-(trifluoromethyl)phenyl]-6,7-dihydropyrazolo[1,5-a]pyrazin-4(5H)-one;
(7S)-7-Methyl-5-(4-methylphenyl)-3-(2-methylpyridin-4-yl)-6,7-dihydropyrazolo[1,5-a]pyrazin-4(5H)-one;
(7S)-7-Methyl-5-[3-(1-methylethoxy)phenyl]-3-(2-methylpyridin-4-yl)-6,7-dihydropyrazolo[1,5-a]pyrazin-4(5H)-one;
4-[(7S)-7-Methyl-3-(2-methylpyridin-4-yl)-4-oxo-6,7-dihydropyrazolo[1,5-a]pyrazin-5(4H)-yl]benzonitrile;
(7S)-5-(4-Ethoxyphenyl)-7-methyl-3-(2-methylpyridin-4-yl)-6,7-dihydropyrazolo[1,5-a]pyrazin-4(5H)-one;
(7S)-5-(3,5-Difluorophenyl)-7-methyl-3-(2-methylpyridin-4-yl)-6,7-dihydropyrazolo[1,5-a]pyrazin-4(5H)-one;
(7S)-5-(3-Ethoxyphenyl)-7-methyl-3-(2-methylpyridin-4-yl)-6,7-dihydropyrazolo[1,5-a]pyrazin-4(5H)-one;
(7S)-5-(3,4-Difluoro-5-methoxyphenyl)-7-methyl-3-(2-methylpyridin-4-yl)-6,7-dihydropyrazolo[1,5-a]pyrazin-4(5H)-one;
(7S)-5-(3-Fluoro-5-methoxyphenyl)-7-methyl-3-(2-methylpyridin-4-yl)-6,7-dihydropyrazolo[1,5-a]pyrazin-4(5H)-one;
(7S)-7-Methyl-3-(2-methylpyridin-4-yl)-5-phenyl-6,7-dihydropyrazolo[1,5-a]pyrazin-4(5H)-one;
(7S)-5-[4-(1-Hydroxyethyl)phenyl]-7-methyl-3-(2-methylpyridin-4-yl)-6,7-dihydropyrazolo[1,5-a]pyrazin-4(5H)-one;
(7R)-5-(3,4-Dichlorophenyl)-7-(fluoromethyl)-3-(2-methylpyridin-4-yl)-6,7-dihydropyrazolo[1,5-a]pyrazin-4(5H)-one;
(7R)-5-(3,4-Dichlorophenyl)-7-(methoxymethyl)-3-(2-methylpyridin-4-yl)-6,7-dihydropyrazolo[1,5-a]pyrazin-4(5H)-one; and
(7S)-5-(3,4-Dichlorophenyl)-3-[2-(hydroxymethyl)pyridin-4-yl]-7-methyl-6,7-dihydropyrazolo[1,5-a]pyrazin-4(5H)-one;
(7R)-7-Ethyl-3-(2-methylpyridin-4-yl)-5-[4-(trifluoromethyl)phenyl]-6,7-dihydropyrazolo[1,5-a]pyrazin-4(5H)-one;
(7S)-7-Methyl-3-[2-(methylamino)pyridin-4-yl]-5-[4-(trifluoromethyl)phenyl]-6,7-dihydropyrazolo[1,5-a]pyrazin-4(5H)-one;
(7S)-5-[3-(1-Hydroxyethyl)phenyl]-7-methyl-3-(2-methylpyridin-4-yl)-6,7-dihydropyrazolo[1,5-a]pyrazin-4(5H)-one;
(7S)-5-(4-Chloro-2-methoxyphenyl)-7-methyl-3-(2-methylpyridin-4-yl)-6,7-dihydropyrazolo[1,5-a]pyrazin-4(5H)-one;
(7S)-5-(2,4-Dichlorophenyl)-7-methyl-3-(2-methylpyridin-4-yl)-6,7-dihydropyrazolo[1,5-a]pyrazin-4(5H)-one;
7,7-Dimethyl-3-(2-methylpyridin-4-yl)-5-[4-(trifluoromethyl)phenyl]-6,7-dihydropyrazolo[1,5-a]pyrazin-4(5H)-one;
(7S)-5-(4-Chloro-2-methylphenyl)-7-methyl-3-(2-methylpyridin-4-yl)-6,7-dihydropyrazolo[1,5-a]pyrazin-4(5H)-one;
(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;
(7S)-5-(5-Chloropyridin-2-yl)-7-methyl-3-(2-methylpyridin-4-yl)-6,7-dihydropyrazolo[1,5-a]pyrazin-4(5H)-one;
(7S)-7-Methyl-3-pyridin-4-yl-5-[5-(trifluoromethyl)pyridin-2-yl]-6,7-dihydropyrazolo[1,5-a]pyrazin-4(5H)-one;
(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;
(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;
(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and
(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;
and the N-oxides, and the pharmaceutically acceptable salts and the solvates thereof In an additional embodiment, the present invention relates to compounds selected from the group of
(7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;
(7S)-7-Methyl-3-pyridin-4-yl-5-[4-(trifluoromethyl)phenyl]-6,7-dihydropyrazolo[1,5-a]pyrazin-4(5H)-one;
(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one or a hydrochloride salt thereof;
(7S)-7-Methyl-3-(5-methylpyridin-3-yl)-5-[4-(trifluoromethyl)phenyl]-6,7-dihydropyrazolo[1,5-a]pyrazin-4(5H)-one;
(7R)-7-Methyl-3-(2-methylpyridin-4-yl)-5-[4-(trifluoromethyl)phenyl]-6,7-dihydropyrazolo[1,5-a]pyrazin-4(5H)-one;
(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;
5-[3-Ethoxy-4-(trifluoromethyl)phenyl]-3-(2-methylpyridin-4-yl)-6,7-dihydropyrazolo[1,5-a]pyrazin-4(5H)-one;
(7S)-5-(4-Methoxy-3,5-dimethylphenyl)-7-methyl-3-(2-methylpyridin-4-yl)-6,7-dihydropyrazolo[1,5-a]pyrazin-4(5H)-one;
(7S)-7-Methyl-3-(6-methylpyridin-3-yl)-5-[4-(trifluoromethyl)phenyl]-6,7-dihydropyrazolo[1,5-a]pyrazin-4(5H)-one;
(7S)-5-(4-Methoxyphenyl)-7-methyl-3-(2-methylpyridin-4-yl)-6,7-dihydropyrazolo[1,5-a]pyrazin-4(5H)-one;
3-(2-Methylpyridin-4-yl)-5-[4-(trifluoromethyl)phenyl]-6,7-dihydropyrazolo[1,5-a]pyrazin-4(5H)-one;
(7S)-5-(3,4-Dimethoxyphenyl)-7-methyl-3-(2-methylpyridin-4-yl)-6,7-dihydropyrazolo[1,5-a]pyrazin-4(5H)-one;
(7S)-3-(2-Methoxypyridin-4-yl)-7-methyl-5-[4-(trifluoromethyl)phenyl]-6,7-dihydropyrazolo[1,5-a]pyrazin-4(5H)-one;
(7S)-7-Methyl-5-(4-methylphenyl)-3-(2-methylpyridin-4-yl)-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one or a hydrochloride salt thereof;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one or a hydrochloride salt thereof;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-Difluoro-5-methoxyphenyl)-7-methyl-3-(2-methylpyridin-4-yl)-6,7-dihydropyrazolo[1,5-a]pyrazin-4(5H)-one;

(7S)-5-(3-Fluoro-5-methoxyphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-phenyl-6,7-dihydropyrazolo[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7R)-5-(3,4-Dichlorophenyl)-7-(fluoromethyl)-3-(2-methylpyridin-4-yl)-6,7-dihydropyrazolo[1,5-a]pyrazin-4(5H)-one;

(7R)-5-(3,4-Dichlorophenyl)-7-(methoxymethyl)-3-(2-methylpyridin-4-yl)-6,7-dihydropyrazolo[1,5-a]pyrazin-4(5H)-one; and (7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7R)-7-Ethyl-3-(2-methylpyridin-4-yl)-5-[4-(trifluoromethyl)phenyl]-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and (7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

and the pharmaceutically acceptable salts and the solvates thereof

In an additional embodiment, the present invention relates to compounds selected from the group of (7S)-7-Methyl-3-(2-methylpyridin-4-yl)-5-[4-(trifluoromethyl)phenyl]-6,7-dihydropyrazolo[1,5-a]pyrazin-4(5H)-one, or a hydrochloride salt, or a sulfate salt, or a methanesulfonate salt, or a maleate salt thereof;

(7S)-7-Methyl-3-pyridin-4-yl-5-[4-(trifluoromethyl)phenyl]-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one or a hydrochloride salt thereof;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-3-(2-Methoxypyridin-4-yl)-7-methyl-5-[4-(trifluoromethyl)phenyl]-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one or a hydrochloride salt thereof;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one or a hydrochloride salt thereof;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-Difluoro-5-methoxyphenyl)-7-methyl-3-(2-methylpyridin-4-yl)-6,7-dihydropyrazolo[1,5-a]pyrazin-4(5H)-one;

(7S)-5-(3-Fluoro-5-methoxyphenyl)-7-methyl-3-(2-methylpyridin-4-yl)-6,7-dihydropyrazolo[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7R)-5-(3,4-Dichlorophenyl)-7-(methoxymethyl)-3-(2-methylpyridin-4-yl)-6,7-dihydropyrazolo[1,5-a]pyrazin-4(5H)-one; and (7S)-5-(3,4-Dichlorophenyl)-3-[2-(hydroxymethyl)pyridin-4-yl]-7-methyl-6,7-dihydropyrazolo[1,5-a]pyrazin-4(5H)-one;
(7S)-7-Methyl-3-[2-(methylamino)pyridin-4-yl]-5-[4-(trifluoromethyl)phenyl]-6,7-dihydropyrazolo[1,5-a]pyrazin-4(5H)-one;
(7S)-5-[3-(1-Hydroxyethyl)phenyl]-7-methyl-3-(2-methylpyridin-4-yl)-6,7-dihydropyrazolo[1,5-a]pyrazin-4(5H)-one;
(7S)-5-(4-Chloro-2-methoxyphenyl)-7-methyl-3-(2-methylpyridin-4-yl)-6,7-dihydropyrazolo[1,5-a]pyrazin-4(5H)-one;
(7S)-5-(2,4-Dichlorophenyl)-7-methyl-3-(2-methylpyridin-4-yl)-6,7-dihydropyrazolo[1,5-a]pyrazin-4(5H)-one;
7,7-Dimethyl-3-(2-methylpyridin-4-yl)-5-[4-(trifluoromethyl)phenyl]-6,7-dihydropyrazolo[1,5-a]pyrazin-4(5H)-one;
(7S)-5-(4-Chloro-2-methylphenyl)-7-methyl-3-(2-methylpyridin-4-yl)-6,7-dihydropyrazolo[1,5-a]pyrazin-4(5H)-one;
(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;
(7S)-5-(5-Chloropyridin-2-yl)-7-methyl-3-(2-methylpyridin-4-yl)-6,7-dihydropyrazolo[1,5-a]pyrazin-4(5H)-one;
(7S)-7-Methyl-3-pyridin-4-yl-5-[5-(trifluoromethyl)pyridin-2-yl]-6,7-dihydropyrazolo[1,5-a]pyrazin-4(5H)-one;
(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;
(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;
(7S)-5-(3-Chloro-6-ethoxypyridin-2-yl)-7-methyl-3-(2-methylpyridin-4-yl)-6,7-dihydropyrazolo[1,5-a]pyrazin-4(5H)-one; and
(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one.

In an additional embodiment, the present invention relates to compounds of Formula (I) as defined hereinabove, and stereoisomeric forms thereof, wherein
$R^1$ is phenyl, optionally substituted with one or more substituents each independently selected from the group of halo, $C_{1-4}$alkyl, mono- or poly-halo$C_{1-4}$alkyl, —O—$C_{1-4}$alkyl, mono- or poly-halo$C_{1-4}$alkyloxy, cyano and —$SF_5$; or is

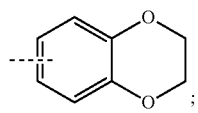

$R^2$ is selected from

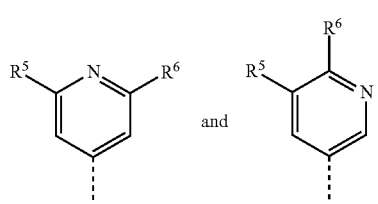

wherein $R^5$ and $R^6$ are each independently selected from the group of hydrogen, $C_{1-4}$alkyl, mono- or poly-halo$C_{1-4}$alkyl, —$C_{1-4}$alkyl-O—$C_{1-4}$alkyl, —O—$C_{1-4}$alkyl, and NR'R";
wherein R' is selected from hydrogen and $C_{1-4}$alkyl;
R" is selected from hydrogen and $C_{1-4}$alkyl;
$R^3$ is selected from hydrogen and $C_{1-4}$alkyl;
$R^4$ is selected from the group of hydrogen, $C_{1-4}$alkyl, mono- or poly-halo$C_{1-4}$alkyl, —$C_{1-4}$alkyl-O—$C_{1-4}$alkyl, and —$C_{1-4}$alkyl-OH;
and the pharmaceutically acceptable salts and the solvates thereof.

In an additional embodiment, the present invention relates to compounds of Formula (I) as defined hereinabove, and stereoisomeric forms thereof, wherein
$R^1$ is phenyl, optionally substituted with one or more substituents each independently selected from the group of halo, $C_{1-4}$alkyl, mono- or poly-halo$C_{1-4}$alkyl, —O—$C_{1-4}$alkyl, mono- or poly-halo$C_{1-4}$alkyloxy, cyano and —$SF_5$; or is

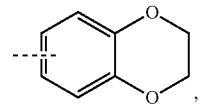

in particular

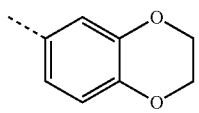

$R^2$ is selected from

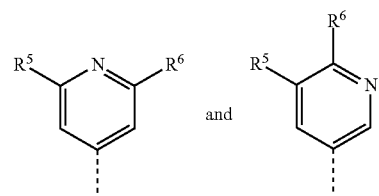

wherein $R^5$ and $R^6$ are each independently selected from the group of hydrogen, $C_{1-4}$alkyl, —$C_{1-4}$alkyl-O—$C_{1-4}$alkyl, —O—$C_{1-4}$alkyl, and NR'R";
wherein R' is hydrogen;
R" is hydrogen;
$R^3$ is selected from hydrogen and $C_{1-4}$alkyl;
$R^4$ is selected from the group of hydrogen and $C_{1-4}$alkyl;
and the pharmaceutically acceptable salts and the solvates thereof In an additional embodiment, the present invention relates to compounds of Formula (I) as defined hereinabove, and stereoisomeric forms thereof, wherein
$R^1$ is phenyl, optionally substituted with one or more substituents each independently selected from the group of halo, $C_{1-4}$alkyl, poly-halo$C_{1-4}$alkyl and —$SF_5$;

$R^2$ is selected from

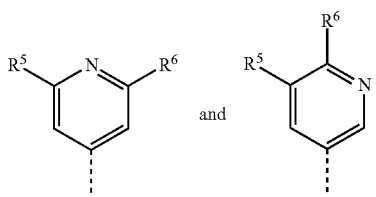

wherein $R^5$ and $R^6$ are each independently selected from the group of hydrogen, $C_{1-4}$alkyl and —O—$C_{1-4}$alkyl;
$R^3$ is selected from hydrogen and $C_{1-4}$alkyl;
$R^4$ is hydrogen;
and the pharmaceutically acceptable salts and the solvates thereof In an additional embodiment, the present invention relates to compounds of Formula (I) as defined hereinabove, and stereoisomeric forms thereof, wherein
$R^1$ is phenyl, optionally substituted with one or more substituents each independently selected from the group of halo, $C_{1-4}$alkyl, poly-halo$C_{1-4}$alkyl and —$SF_5$;
$R^2$ is selected from

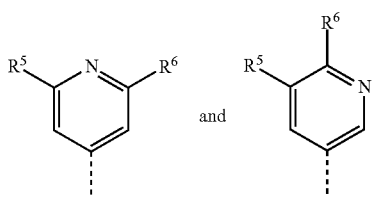

wherein $R^5$ and $R^6$ are each independently selected from the group of hydrogen, $C_{1-4}$alkyl and —O—$C_{1-4}$alkyl;
$R^3$ is hydrogen;
$R^4$ is selected from hydrogen and $C_{1-4}$alkyl;
and the pharmaceutically acceptable salts and the solvates thereof In an additional embodiment, the present invention relates to compounds of Formula (I) as defined hereinabove, and stereoisomeric forms thereof, wherein
$R^1$ is phenyl, substituted with one, two or three substituents each independently selected from the group of halo, and poly-halo$C_{1-4}$alkyl;
$R^2$ is

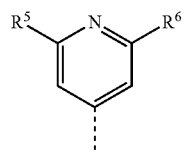

wherein $R^5$ and $R^6$ are each independently selected from the group of hydrogen,
$C_{1-4}$alkyl, —O—$C_{1-4}$alkyl, and NR'R";
wherein R' is hydrogen;
R" is $C_{1-4}$alkyl;
$R^3$ is hydrogen;
$R^4$ is hydrogen or $C_{1-4}$alkyl; in particular $R^4$ is $C_{1-4}$alkyl;
and the pharmaceutically acceptable salts and the solvates thereof In an additional embodiment, $R^1$ is selected from the group of

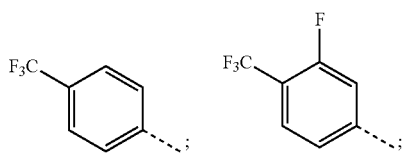

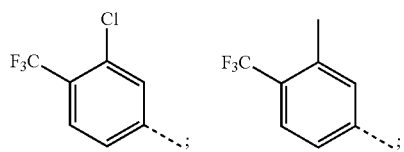

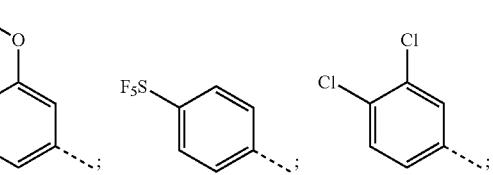

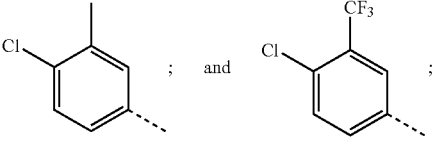

and the rest of variables are as defined in Formula (I) herein.

In an additional embodiment, $R^1$ is selected from the group of

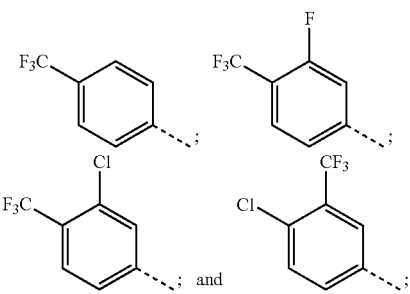

and the rest of variables are as defined in Formula (I) herein;
and the pharmaceutically acceptable salts and the solvates thereof In a further embodiment, the present invention relates to compounds of Formula (I) as defined herein wherein $R^3$ is hydrogen and $R^4$ is a substituent different from hydrogen having a configuration as depicted in the Formula (I') below, wherein the 6,7-dihydropyrazolo[1,5-a]pyrazin-4(5H)-one core, $R^1$ and $R^2$ are in the plane of the drawing and $R^4$ is projected above the plane of the drawing (bond shown with a bold wedge), and the rest of variables are as defined in Formula (I) herein

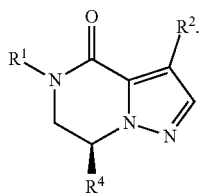

(I')

In a yet further embodiment, the present invention relates to compounds of Formula (I) as defined herein wherein $R^4$ is hydrogen and $R^3$ is a substituent different from hydrogen, for example a $C_{1-4}$alkyl substituent having a configuration as depicted in the Formula (I") below, wherein the 6,7-dihydropyrazolo[1,5-a]pyrazin-4(5H)-one core, $R^1$ and $R^2$ are in the plane of the drawing and $R^3$ is projected above the plane of the drawing (bond shown with a bold wedge), and the rest of variables are as defined in Formula (I) herein

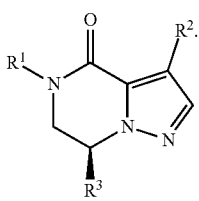

(I")

In an additional embodiment, the present invention relates to compounds of Formula (I') as defined hereinabove, and stereoisomeric forms thereof, wherein $R^1$ is phenyl, substituted with one or two substituents each independently selected from the group of halo, and poly-halo$C_{1-4}$alkyl; $R^2$ is

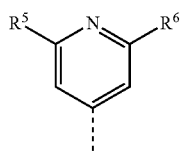

wherein $R^5$ and $R^6$ are each independently selected from the group of hydrogen, $C_{1-4}$alkyl, —O—$C_{1-4}$alkyl, and NR'R";
wherein R' is hydrogen;
R" is $C_{1-4}$alkyl;
$R^4$ is hydrogen or $C_{1-4}$alkyl; in particular $R^4$ is $C_{1-4}$alkyl, more in particular methyl;
and the pharmaceutically acceptable salts and the solvates thereof In an additional embodiment, the present invention relates to compounds of Formula (I') as defined hereinabove, and stereoisomeric forms thereof, wherein
$R^1$ is phenyl, substituted with one or two substituents each independently selected from the group of halo, and poly-halo$C_{1-4}$alkyl;
$R^2$ is

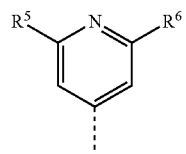

wherein one of $R^5$ and $R^6$ is hydrogen or methyl, in particular hydrogen; and
the other one of $R^5$ or $R^6$ is selected from the group of $C_{1-4}$alkyl, —O—$C_{1-4}$alkyl, and NR'R";
wherein R' is hydrogen;
R" is $C_{1-4}$alkyl;
$R^4$ is hydrogen or $C_{1-4}$alkyl; in particular $R^4$ is $C_{1-4}$alkyl, more in particular methyl;
and the pharmaceutically acceptable salts and the solvates thereof Specific compounds according to the invention include:
(7S)-7-Methyl-3-(2-methylpyridin-4-yl)-5-[4-(trifluoromethyl)phenyl]-6,7-dihydropyrazolo[1,5-a]pyrazin-4(5H)-one;
(7S)-7-Methyl-3-pyridin-4-yl-5-[4-(trifluoromethyl)phenyl]-6,7-dihydropyrazolo[1,5-a]pyrazin-4(5H)-one;
(7S)-5-[3-Chloro-4-(trifluoromethyl)phenyl]-7-methyl-3-(2-methylpyridin-4-yl)-6,7-dihydropyrazolo[1,5-a]pyrazin-4(5H)-one;
(7S)-7-Methyl-3-(2-methylpyridin-4-yl)-5-[4-(pentafluoro-$\lambda^6$-sulfanyl)phenyl]-6,7-dihydropyrazolo[1,5-a]pyrazin-4(5H)-one;
(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one;
(7S)-5-(3,4-Dichlorophenyl)-7-methyl-3-(2-methylpyridin-4-yl)-6,7-dihydropyrazolo[1,5-a]pyrazin-4(5H)-one;
(7S)-5-(4-Chloro-3-methylphenyl)-7-methyl-3-(2-methylpyridin-4-yl)-6,7-dihydropyrazolo[1,5-a]pyrazin-4(5H)-one;
(7S)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;
(7S)-5-[4-Chloro-3-(trifluoromethyl)phenyl]-7-methyl-3-(2-methylpyridin-4-yl)-6,7-dihydropyrazolo[1,5-a]pyrazin-4(5H)-one;
(7S)-5-[3-Fluoro-4-(trifluoromethyl)phenyl]-7-methyl-3-(2-methylpyridin-4-yl)-6,7-dihydropyrazolo[1,5-a]pyrazin-4(5H)-one;
7-Methyl-3-(2-methylpyridin-4-yl)-5-[4-(trifluoromethyl)phenyl]-6,7-dihydropyrazolo[1,5-a]pyrazin-4(5H)-one;
(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one;
5-[(7S)-7-Methyl-3-(2-methylpyridin-4-yl)-4-oxo-6,7-dihydropyrazolo[1,5-a]pyrazin-5(4H)-yl]-2-(trifluoromethyl)benzonitrile;
(7S)-3-(2,6-Dimethylpyridin-4-yl)-7-methyl-5-[4-(trifluoromethyl)phenyl]-6,7-dihydropyrazolo[1,5-a]pyrazin-4(5H)-one;
(7S)-5-(4-Chlorophenyl)-7-methyl-3-(2-methylpyridin-4-yl)-6,7-dihydropyrazolo[1,5-a]pyrazin-4(5H)-one;
(7S)-5-(3-Chlorophenyl)-7-methyl-3-(2-methylpyridin-4-yl)-6,7-dihydropyrazolo[1,5-a]pyrazin-4(5H)-one;
(7S)-5-(3-Chloro-4-ethoxyphenyl)-7-methyl-3-(2-methylpyridin-4-yl)-6,7-dihydropyrazolo[1,5-a]pyrazin-4(5H)-one;

(7S)-5-(4-Chloro-3-ethoxyphenyl)-7-methyl-3-(2-methyl-pyridin-4-yl)-6,7-dihydropyrazolo[1,5-a]pyrazin-4(5H)-one;

(7S)-5-(4-Chloro-3-methoxyphenyl)-7-methyl-3-(2-methyl-pyridin-4-yl)-6,7-dihydropyrazolo[1,5-a]pyrazin-4(5H)-one;

(7S)-5-(3-Chloro-4-methoxyphenyl)-7-methyl-3-(2-methyl-pyridin-4-yl)-6,7-dihydropyrazolo[1,5-a]pyrazin-4(5H)-one;

(7S)-5-(4-Fluoro-3-methylphenyl)-7-methyl-3-(2-methyl-pyridin-4-yl)-6,7-dihydropyrazolo[1,5-a]pyrazin-4(5H)-one;

(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[3-(trifluoromethyl)phenyl]-6,7-dihydropyrazolo[1,5-a]pyrazin-4(5H)-one;

(7S)-7-Methyl-3-(5-methylpyridin-3-yl)-5-[4-(trifluoromethyl)phenyl]-6,7-dihydropyrazolo[1,5-a]pyrazin-4(5H)-one;

(7S)-5-(3,4-Difluorophenyl)-7-methyl-3-(2-methylpyridin-4-yl)-6,7-dihydropyrazolo[1,5-a]pyrazin-4(5H)-one;

(7R)-7-Methyl-3-(2-methylpyridin-4-yl)-5-[4-(trifluoromethyl)phenyl]-6,7-dihydropyrazolo[1,5-a]pyrazin-4(5H)-one;

(7S)-5-[4-(Difluoromethoxy)phenyl]-7-methyl-3-(2-methylpyridin-4-yl)-6,7-dihydropyrazolo[1,5-a]pyrazin-4(5H)-one;

(7S)-5-(4-Fluorophenyl)-7-methyl-3-(2-methylpyridin-4-yl)-6,7-dihydropyrazolo[1,5-a]pyrazin-4(5H)-one;

(7S)-3-(5,6-Dimethylpyridin-3-yl)-7-methyl-5-[4-(trifluoromethyl)phenyl]-6,7-dihydropyrazolo[1,5-a]pyrazin-4(5H)-one;

(7S)-5-(4-Chloro-2-fluorophenyl)-7-methyl-3-(2-methyl-pyridin-4-yl)-6,7-dihydropyrazolo[1,5-a]pyrazin-4(5H)-one;

(7R)-5-[3-Ethoxy-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-3-pyridin-3-yl-5-[4-(trifluoromethyl)phenyl]-6,7-dihydropyrazolo[1,5-a]pyrazin-4(5H)-one;

5-[3-Ethoxy-4-(trifluoromethyl)phenyl]-3-(2-methylpyridin-4-yl)-6,7-dihydropyrazolo[1,5-a]pyrazin-4(5H)-one;

(7S)-5-(4-Methoxy-3,5-dimethylphenyl)-7-methyl-3-(2-methylpyridin-4-yl)-6,7-dihydropyrazolo[1,5-a]pyrazin-4(5H)-one;

(7S)-5-(3-Fluoro-4-methoxyphenyl)-7-methyl-3-(2-methyl-pyridin-4-yl)-6,7-dihydropyrazolo[1,5-a]pyrazin-4(5H)-one;

(7S)-7-Methyl-3-(6-methylpyridin-3-yl)-5-[4-(trifluoromethyl)phenyl]-6,7-dihydropyrazolo[1,5-a]pyrazin-4(5H)-one;

(7S)-3-(6-Aminopyridin-3-yl)-7-methyl-5-[4-(trifluoromethyl)phenyl]-6,7-dihydropyrazolo[1,5-a]pyrazin-4(5H)-one;

(7S)-5-(4-Methoxyphenyl)-7-methyl-3-(2-methylpyridin-4-yl)-6,7-dihydropyrazolo[1,5-a]pyrazin-4(5H)-one;

5-[3-Fluoro-4-(trifluoromethyl)phenyl]-3-(2-methylpyridin-4-yl)-6,7-dihydropyrazolo[1,5-a]pyrazin-4(5H)-one;

3-(2-Methylpyridin-4-yl)-5-[4-(trifluoromethyl)phenyl]-6,7-dihydropyrazolo[1,5-a]pyrazin-4(5H)-one;

(7S)-5-(3,4-Dimethoxyphenyl)-7-methyl-3-(2-methylpyridin-4-yl)-6,7-dihydropyrazolo[1,5-a]pyrazin-4(5H)-one;

(7S)-5-(2,3-Dihydro-1,4-benzodioxin-6-yl)-7-methyl-3-(2-methylpyridin-4-yl)-6,7-dihydropyrazolo[1,5-a]pyrazin-4(5H)-one;

(7S)-5-[3-chloro-4-(trifluoromethyl)phenyl]-3-(2,6-dimethyl-4-pyridyl)-7-methyl-6,7-dihydropyrazolo[1,5-a]pyrazin-4-one;

(7S)-3-[2-(ethylamino)-4-pyridyl]-7-methyl-5-[4-(trifluoromethyl)phenyl]-6,7-dihydropyrazolo[1,5-a]pyrazin-4-one;

(7S)-3-(2-methoxy-4-pyridyl)-7-methyl-5-[4-(trifluoromethyl)phenyl]-6,7-dihydropyrazolo[1,5-a]pyrazin-4-one;

(7S)-3-(2-ethyl-4-pyridyl)-7-methyl-5-[4-(trifluoromethyl)phenyl]-6,7-dihydropyrazolo[1,5-a]pyrazin-4-one;

(7S)-5-(3,4-dichlorophenyl)-3-(2,6-dimethyl-4-pyridyl)-7-methyl-6,7-dihydropyrazolo[1,5-a]pyrazin-4-one;

(7S)-5-[3-(2-Fluoroethoxy)-4-(trifluoromethyl)phenyl]-7-methyl-3-(2-methylpyridin-4-yl)-6,7-dihydropyrazolo[1,5-a]pyrazin-4(5H)-one;

(7S)-3-(2,6-dimethyl-4-pyridyl)-5-[3-ethoxy-4-(trifluoromethyl)phenyl]-7-methyl-6,7-dihydropyrazolo[1,5-a]pyrazin-4-one;

(7S)-5-[3-chloro-4-(trifluoromethyl)phenyl]-7-methyl-3-(4-pyridyl)-6,7-dihydropyrazolo[1,5-a]pyrazin-4-one;

(7S)-3-(2,6-dimethyl-4-pyridyl)-5-[3-methoxy-4-(trifluoromethyl)phenyl]-7-methyl-6,7-dihydropyrazolo[1,5-a]pyrazin-4-one;

7-(fluoromethyl)-3-(2-methyl-4-pyridyl)-5-[4-(trifluoromethyl)phenyl]-6,7-dihydropyrazolo[1,5-a]pyrazin-4-one;

(7S)-3-(2,6-dimethyl-4-pyridyl)-7-methyl-5-[4-(pentafluoro-$\lambda^6$-sulfanyl)phenyl]-6,7-dihydropyrazolo[1,5-a]pyrazin-4-one;

(7S)-5-[4-chloro-3-(trifluoromethyl)phenyl]-3-(2,6-dimethyl-4-pyridyl)-7-methyl-6,7-dihydropyrazolo[1,5-a]pyrazin-4-one;

(7S)-5-[3-ethoxy-4-(trifluoromethyl)phenyl]-7-methyl-3-(4-pyridyl)-6,7-dihydropyrazolo[1,5-a]pyrazin-4-one;

(7S)-7-methyl-5-[4-(pentafluoro-$\lambda^6$-sulfanyl)phenyl]-3-(4-pyridyl)-6,7-dihydropyrazolo[1,5-a]pyrazin-4-one;

(7S)-5-(3,4-dichlorophenyl)-7-methyl-3-(4-pyridyl)-6,7-dihydropyrazolo[1,5-a]pyrazin-4-one;

(7S)-7-methyl-3-(2-methyl-4-pyridyl)-5-[3-(trifluoromethoxy)phenyl]-6,7-dihydropyrazolo[1,5-a]pyrazin-4-one;

5-[(7S)-3-(2,6-dimethyl-4-pyridyl)-7-methyl-4-oxo-6,7-dihydropyrazolo[1,5-a]pyrazin-5-yl]-2-(trifluoromethyl)benzonitrile;

(7S)-5-[3-fluoro-4-(trifluoromethyl)phenyl]-7-methyl-3-(4-pyridyl)-6,7-dihydropyrazolo[1,5-a]pyrazin-4-one;

(7S)-3-(2,6-dimethyl-4-pyridyl)-5-[3-fluoro-4-(trifluoromethyl)phenyl]-7-methyl-6,7-dihydropyrazolo[1,5-a]pyrazin-4-one;

(7S)-5-(4-Chloro-3-fluorophenyl)-7-methyl-3-(2-methyl-pyridin-4-yl)-6,7-dihydropyrazolo[1,5-a]pyrazin-4(5H)-one;

(7S)-5-(3-chloro-5-fluoro-phenyl)-7-methyl-3-(2-methyl-4-pyridyl)-6,7-dihydropyrazolo[1,5-a]pyrazin-4-one;

(7S)-5-[3-methoxy-4-(trifluoromethyl)phenyl]-7-methyl-3-(4-pyridyl)-6,7-dihydropyrazolo[1,5-a]pyrazin-4-one;

(7S)-5-(4-isopropylphenyl)-7-methyl-3-(2-methyl-4-pyridyl)-6,7-dihydropyrazolo[1,5-a]pyrazin-4-one;

(7S)-7-methyl-3-(2-methyl-4-pyridyl)-5-(4-propylphenyl)-6,7-dihydropyrazolo[1,5-a]pyrazin-4-one;

(7S)-5-[4-Fluoro-3-(trifluoromethyl)phenyl]-7-methyl-3-(2-methylpyridin-4-yl)-6,7-dihydropyrazolo[1,5-a]pyrazin-4(5H)-one;

(7S)-5-[4-chloro-3-(trifluoromethyl)phenyl]-7-methyl-3-(4-pyridyl)-6,7-dihydropyrazolo[1,5-a]pyrazin-4-one;

(7S)-5-[3-(difluoromethoxy)-5-fluoro-phenyl]-7-methyl-3-(2-methyl-4-pyridyl)-6,7-dihydropyrazolo[1,5-a]pyrazin-4-one;

7-ethyl-3-(2-methyl-4-pyridyl)-5-[4-(trifluoromethyl)phenyl]-6,7-dihydropyrazolo[1,5-a]pyrazin-4-one;

(7S)-3-(2-Aminopyridin-4-yl)-7-methyl-5-[4-(trifluoromethyl)phenyl]-6,7-dihydropyrazolo[1,5-a]pyrazin-4(5H)-one;

(7S)-5-(4-chlorophenyl)-3-(2,6-dimethyl-4-pyridyl)-7-methyl-6,7-dihydropyrazolo[1,5-a]pyrazin-4-one;

(7S)-5-(4-chlorophenyl)-7-methyl-3-(4-pyridyl)-6,7-dihydropyrazolo[1,5-a]pyrazin-4-one;

5-[3-Ethoxy-4-(trifluoromethyl)phenyl]-7-(hydroxymethyl)-3-(2-methylpyridin-4-yl)-6,7-dihydropyrazolo[1,5-a]pyrazin-4(5H)-one;

2-Fluoro-4-[(7S)-7-methyl-3-(2-methylpyridin-4-yl)-4-oxo-6,7-dihydropyrazolo[1,5-a]pyrazin-5(4H)-yl]benzonitrile;

(7S)-5-(3-Fluoro-4-methylphenyl)-7-methyl-3-(2-methylpyridin-4-yl)-6,7-dihydropyrazolo[1,5-a]pyrazin-4(5H)-one;

(7S)-5-[4-(2-fluoroethoxy)-3-(trifluoromethyl)phenyl]-7-methyl-3-(2-methyl-4-pyridyl)-6,7-dihydropyrazolo[1,5-a]pyrazin-4-one;

(7S)-7-Methyl-5-(4-methylphenyl)-3-(2-methylpyridin-4-yl)-6,7-dihydropyrazolo[1,5-a]pyrazin-4(5H)-one;

(7S)-7-Methyl-5-[3-(1-methylethoxy)phenyl]-3-(2-methylpyridin-4-yl)-6,7-dihydropyrazolo[1,5-a]pyrazin-4(5H)-one;

4-[(7S)-7-Methyl-3-(2-methylpyridin-4-yl)-4-oxo-6,7-dihydropyrazolo[1,5-a]pyrazin-5(4H)-yl]benzonitrile;

(7S)-5-(4-Ethoxyphenyl)-7-methyl-3-(2-methylpyridin-4-yl)-6,7-dihydropyrazolo[1,5-a]pyrazin-4(5H)-one;

(7S)-5-(3,5-Difluorophenyl)-7-methyl-3-(2-methylpyridin-4-yl)-6,7-dihydropyrazolo[1,5-a]pyrazin-4(5H)-one;

(7S)-5-(3-Ethoxyphenyl)-7-methyl-3-(2-methylpyridin-4-yl)-6,7-dihydropyrazolo[1,5-a]pyrazin-4(5H)-one;

(7S)-5-(3,4-difluoro-5-methoxy-phenyl)-7-methyl-3-(2-methyl-4-pyridyl)-6,7-dihydropyrazolo[1,5-a]pyrazin-4-one;

(7S)-5-(3-fluoro-5-methoxy-phenyl)-7-methyl-3-(2-methyl-4-pyridyl)-6,7-dihydropyrazolo[1,5-a]pyrazin-4-one;

(7S)-7-Methyl-3-(2-methylpyridin-4-yl)-5-phenyl-6,7-dihydropyrazolo[1,5-a]pyrazin-4(5H)-one;

7-(Hydroxymethyl)-3-(2-methyl-4-pyridyl)-5-[4-(trifluoromethyl)phenyl]-6,7-dihydropyrazolo[1,5-a]pyrazin-4-one;

5-[(7S)-3-(2-Methoxypyridin-4-yl)-7-methyl-4-oxo-6,7-dihydropyrazolo[1,5-a]pyrazin-5(4H)-yl]-2-(trifluoromethyl)benzonitrile;

(7S)-5-(4-Chlorophenyl)-3-(2-methoxypyridin-4-yl)-7-methyl-6,7-dihydropyrazolo[1,5-a]pyrazin-4(5H)-one;

5-(3,4-Dichlorophenyl)-3-[2-(dimethylamino)pyridin-4-yl]-7-(fluoromethyl)-6,7-dihydropyrazolo[1,5-a]pyrazin-4(5H)-one (7R or 7S);

5-(3,4-Dichlorophenyl)-3-[2-(dimethylamino)pyridin-4-yl]-7-(fluoromethyl)-6,7-dihydropyrazolo[1,5-a]pyrazin-4(5H)-one (7S or 7R);

(7S)-5-[3-Chloro-4-(trifluoromethyl)phenyl]-3-[2-(3-fluoroazetidin-1-yl)pyridin-4-yl]-7-methyl-6,7-dihydropyrazolo[1,5-a]pyrazin-4(5H)-one;

5-(3,4-Dichlorophenyl)-7-(fluoromethyl)-3-[2-(methylamino)pyridin-4-yl]-6,7-dihydropyrazolo[1,5-a]pyrazin-4(5H)-one;

(7S)-3-[2-(3-Fluoroazetidin-1-yl)pyridin-4-yl]-7-methyl-5-[4-(trifluoromethyl)phenyl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}-6-(methylamino)pyridine-2-carbonitrile;

(7S)-3-(2-Azetidin-1-ylpyridin-4-yl)-5-[3-chloro-4-(trifluoromethyl)phenyl]-7-methyl-6,7-dihydropyrazolo[1,5-a]pyrazin-4(5H)-one;

(7S)-3-(2-Azetidin-1-ylpyridin-4-yl)-5-(3,4-dichlorophenyl)-7-methyl-6,7-dihydropyrazolo[1,5-a]pyrazin-4(5H)-one;

(7S)-5-[3-(Fluoromethyl)-4-(trifluoromethyl)phenyl]-7-methyl-3-(2-methylpyridin-4-yl)-6,7-dihydropyrazolo[1,5-a]pyrazin-4(5H)-one;

(7S)-7-Methyl-5-[4-(trifluoromethyl)phenyl]-3-[2-(trifluoromethyl)pyridin-4-yl]-6,7-dihydropyrazolo[1,5-a]pyrazin-4(5H)-one;

4-{(7S)-5-[3-Chloro-4-(trifluoromethyl)phenyl]-7-methyl-4-oxo-4,5,6,7-tetrahydropyrazolo[1,5-a]pyrazin-3-yl}pyridine-2-carbonitrile;

(7S)-3-[2-(3-Hydroxyazetidin-1-yl)pyridin-4-yl]-7-methyl-5-[4-(trifluoromethyl)phenyl]-6,7-dihydropyrazolo[1,5-a]pyrazin-4(5H)-one;

(7S)-3-(2-Azetidin-1-ylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-7-methyl-3-[2-(methylamino)pyridin-4-yl]-6,7-dihydropyrazolo[1,5-a]pyrazin-4(5H)-one;

(7S)-5-[3-Chloro-4-(trifluoromethyl)phenyl]-3-(2-methoxypyridin-4-yl)-7-methyl-6,7-dihydropyrazolo[1,5-a]pyrazin-4(5H)-one;

(7S)-7-Methyl-3-(2-pyrrolidin-1-ylpyridin-4-yl)-5-[4-(trifluoromethyl)phenyl]-6,7-dihydropyrazolo[1,5-a]pyrazin-4(5H)-one;

(7S)-3-[2-(4-Acetylpiperazin-1-yl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-piperidin-1-ylpyridin-4-yl)-5-[4-(trifluoromethyl)phenyl]-6,7-dihydropyrazolo[1,5-a]pyrazin-4(5H)-one;

(7S)-7-Methyl-3-(2-morpholin-4-ylpyridin-4-yl)-5-[4-(trifluoromethyl)phenyl]-6,7-dihydropyrazolo[1,5-a]pyrazin-4(5H)-one;

4-[(7S)-5-(3,4-Dichlorophenyl)-7-methyl-4-oxo-4,5,6,7-tetrahydropyrazolo[1,5-a]pyrazin-3-yl]pyridine-2-carbonitrile;

(7S)-5-(3,4-Dichlorophenyl)-7-methyl-3-[2-(methylamino)pyridin-4-yl]-6,7-dihydropyrazolo[1,5-a]pyrazin-4(5H)-one;

(7S)-5-(3,4-Dichlorophenyl)-3-[2-(1-hydroxyethyl)pyridin-4-yl]-7-methyl-6,7-dihydropyrazolo[1,5-a]pyrazin-4(5H)-one;

(7S)-3-[2-(Fluoromethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-[4-(2,2,2-trifluoro-1-methylethyl)phenyl]-6,7-dihydropyrazolo[1,5-a]pyrazin-4(5H)-one;

(7S)-5-(3,4-Dichlorophenyl)-3-[2-(difluoromethyl)pyridin-4-yl]-7-methyl-6,7-dihydropyrazolo[1,5-a]pyrazin-4(5H)-one;

5-(3,4-Dichlorophenyl)-7-(fluoromethyl)-3-(2-methylpyridin-4-yl)-6,7-dihydropyrazolo[1,5-a]pyrazin-4(5H)-one (7S or 7R);

5-(3,4-Dichlorophenyl)-7-(fluoromethyl)-3-(2-methylpyridin-4-yl)-6,7-dihydropyrazolo[1,5-a]pyrazin-4(5H)-one (7R or 7S);

(7S)-5-(3,4-Dichlorophenyl)-3-[2-(fluoromethyl)pyridin-4-yl]-7-methyl-6,7-dihydropyrazolo[1,5-a]pyrazin-4(5H)-one;

5-(3,4-Dichlorophenyl)-7-(methoxymethyl)-3-(2-methylpyridin-4-yl)-6,7-dihydropyrazolo[1,5-a]pyrazin-4(5H)-one (7S or 7R);

5-(3,4-Dichlorophenyl)-7-(methoxymethyl)-3-(2-methylpyridin-4-yl)-6,7-dihydropyrazolo[1,5-a]pyrazin-4(5H)-one (7R or 7S);

7-(Methoxymethyl)-3-(2-methylpyridin-4-yl)-5-[4-(trifluoromethyl)phenyl]-6,7-dihydropyrazolo[1,5-a]pyrazin-4(5H)-one (7R or 7S);

7-(Methoxymethyl)-3-(2-methylpyridin-4-yl)-5-[4-(trifluoromethyl)phenyl]-6,7-dihydropyrazolo[1,5-a]pyrazin-4(5H)-one (7S or 7R);

(7S)-3-(2-Cyclopropylpyridin-4-yl)-5-(3,4-dichlorophenyl)-7-methyl-6,7-dihydropyrazolo[1,5-a]pyrazin-4(5H)-one;

(7S)-3-(2-Ethoxypyridin-4-yl)-7-methyl-5-[4-(trifluoromethyl)phenyl]-6,7-dihydropyrazolo[1,5-a]pyrazin-4(5H)-one;

(7S)-5-(3,4-Dichlorophenyl)-7-methyl-3-[2-(1-methylethyl)pyridin-4-yl]-6,7-dihydropyrazolo[1,5-a]pyrazin-4(5H)-one;

(7S)-5-(3,4-Dichlorophenyl)-3-[2-(hydroxymethyl)pyridin-4-yl]-7-methyl-6,7-dihydropyrazolo[1,5-a]pyrazin-4(5H)-one;

(7S)-7-Methyl-3-[2-(1-methylethyl)pyridin-4-yl]-5-[4-(trifluoromethyl)phenyl]-6,7-dihydropyrazolo[1,5-a]pyrazin-4(5H)-one;

4-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-3-[2-(1-Hydroxyethyl)pyridin-4-yl]-7-methyl-5-[4-(trifluoromethyl)phenyl]-6,7-dihydropyrazolo[1,5-a]pyrazin-4(5H)-one;

(7R)-7-Ethyl-3-(2-methylpyridin-4-yl)-5-[4-(trifluoromethyl)phenyl]-6,7-dihydropyrazolo[1,5-a]pyrazin-4(5H)-one;

(7S)-7-Ethyl-3-(2-methylpyridin-4-yl)-5-[4-(trifluoromethyl)phenyl]-6,7-dihydropyrazolo[1,5-a]pyrazin-4(5H)-one;

(7S)-3-[2-(Difluoromethyl)pyridin-4-yl]-7-methyl-5-[4-(trifluoromethyl)phenyl]-6,7-dihydropyrazolo[1,5-a]pyrazin-4(5H)-one;

(7S)-5-[3,5-Difluoro-4-(trifluoromethyl)phenyl]-7-methyl-3-(2-methylpyridin-4-yl)-6,7-dihydropyrazolo[1,5-a]pyrazin-4(5H)-one;

(7S)-5-(3,4-Dichlorophenyl)-3-(2-ethoxypyridin-4-yl)-7-methyl-6,7-dihydropyrazolo[1,5-a]pyrazin-4(5H)-one;

(7S)-5-(3,4-Dichlorophenyl)-3-(2-ethylpyridin-4-yl)-7-methyl-6,7-dihydropyrazolo[1,5-a]pyrazin-4(5H)-one;

(7S)-3-[2-(Hydroxymethyl)pyridin-4-yl]-7-methyl-5-[4-(trifluoromethyl)phenyl]-6,7-dihydropyrazolo[1,5-a]pyrazin-4(5H)-one;

(7S)-7-Methyl-3-(2-methylpyridin-4-yl)-5-{4-[1-(trifluoromethyl)cyclopropyl]phenyl}-6,7-dihydropyrazolo[1,5-a]pyrazin-4(5H)-one;

(7S)-5-(3,4-Dichlorophenyl)-7-methyl-3-[2-(1-methylethoxy)pyridin-4-yl]-6,7-dihydropyrazolo[1,5-a]pyrazin-4(5H)-one;

(7S)-7-Methyl-3-[2-(1-methylethoxy)pyridin-4-yl]-5-[4-(trifluoromethyl)phenyl]-6,7-dihydropyrazolo[1,5-a]pyrazin-4(5H)-one;

(7S)-5-(4-Bromophenyl)-7-methyl-3-(2-methylpyridin-4-yl)-6,7-dihydropyrazolo[1,5-a]pyrazin-4(5H)-one;

(7S)-7-Methyl-3-(2-methyl-1-oxidopyridin-4-yl)-5-[4-(trifluoromethyl)phenyl]-6,7-dihydropyrazolo[1,5-a]pyrazin-4(5H)-one;

(7S)-5-(4-tert-Butylphenyl)-7-methyl-3-(2-methylpyridin-4-yl)-6,7-dihydropyrazolo[1,5-a]pyrazin-4(5H)-one;

(7S)-5-(3,4-Dichlorophenyl)-3-(2-methoxypyridin-4-yl)-7-methyl-6,7-dihydropyrazolo[1,5-a]pyrazin-4(5H)-one;

5-(3,4-Dichlorophenyl)-7-(methoxymethyl)-3-(2-methylpyridin-4-yl)-6,7-dihydropyrazolo[1,5-a]pyrazin-4(5H)-one;

7-(Methoxymethyl)-3-(2-methylpyridin-4-yl)-5-[4-(trifluoromethyl)phenyl]-6,7-dihydropyrazolo[1,5-a]pyrazin-4(5H)-one;

(7S)-3-(2-Methoxy-6-methylpyridin-4-yl)-7-methyl-5-[4-(trifluoromethyl)phenyl]-6,7-dihydropyrazolo[1,5-a]pyrazin-4(5H)-one;

(7S)-5-(3,4-Dichlorophenyl)-3-(2-methoxy-6-methylpyridin-4-yl)-7-methyl-6,7-dihydropyrazolo[1,5-a]pyrazin-4(5H)-one;

(7S)-7-Methyl-3-[2-(methylamino)pyridin-4-yl]-5-[4-(trifluoromethyl)phenyl]-6,7-dihydropyrazolo[1,5-a]pyrazin-4(5H)-one;

(7S)-5-[3-(1-Hydroxyethyl)phenyl]-7-methyl-3-(2-methylpyridin-4-yl)-6,7-dihydropyrazolo[1,5-a]pyrazin-4(5H)-one;

(7S)-5-[4-(1-Hydroxyethyl)phenyl]-7-methyl-3-(2-methylpyridin-4-yl)-6,7-dihydropyrazolo[1,5-a]pyrazin-4(5H)-one;

(7S)-3-(6-Methoxypyridin-3-yl)-7-methyl-5-[4-(trifluoromethyl)phenyl]-6,7-dihydropyrazolo[1,5-a]pyrazin-4(5H)-one;

5-{(7S)-7-Methyl-4-oxo-5-[4-(trifluoromethyl)phenyl]-4,5,6,7-tetrahydropyrazolo[1,5-a]pyrazin-3-yl}pyridine-2-carbonitrile;

(7S)-7-Methyl-3-(2-methylpyridin-4-yl)-5-[4-(trifluoromethoxy)phenyl]-6,7-dihydropyrazolo[1,5-a]pyrazin-4(5H)-one;

(7S)-7-Methyl-5-[3-methyl-4-(trifluoromethyl)phenyl]-3-pyridin-4-yl-6,7-dihydropyrazolo[1,5-a]pyrazin-4(5H)-one;

(7S)-7-Methyl-5-[3-(1-methylethoxy)-4-(trifluoromethyl)phenyl]-3-(2-methylpyridin-4-yl)-6,7-dihydropyrazolo[1,5-a]pyrazin-4(5H)-one;

5-[(7S)-7-Methyl-4-oxo-3-pyridin-4-yl-6,7-dihydropyrazolo[1,5-a]pyrazin-5(4H)-yl]-2-(trifluoromethyl)benzonitrile;

(7S)-5-(4-Cyclopropylphenyl)-7-methyl-3-(2-methylpyridin-4-yl)-6,7-dihydropyrazolo[1,5-a]pyrazin-4(5H)-one;

(7S)-3-(2,6-Dimethylpyridin-4-yl)-7-methyl-5-[3-methyl-4-(trifluoromethyl)phenyl]-6,7-dihydropyrazolo[1,5-a]pyrazin-4(5H)-one;

(7S)-5-[3-(Methoxymethyl)-4-(trifluoromethyl)phenyl]-7-methyl-3-(2-methylpyridin-4-yl)-6,7-dihydropyrazolo[1,5-a]pyrazin-4(5H)-one;

(7S)-5-(3,5-Dichlorophenyl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[4-(2,2,2-trifluoroethoxy)phenyl]-6,7-dihydropyrazolo[1,5-a]pyrazin-4(5H)-one;

(7S)-5-(4-Chloro-2-methoxyphenyl)-7-methyl-3-(2-methylpyridin-4-yl)-6,7-dihydropyrazolo[1,5-a]pyrazin-4(5H)-one;

(7S)-5-[4-(Difluoromethyl)phenyl]-7-methyl-3-(2-methylpyridin-4-yl)-6,7-dihydropyrazolo[1,5-a]pyrazin-4(5H)-one;

(7S)-5-[4-Chloro-3-(difluoromethoxy)phenyl]-7-methyl-3-(2-methylpyridin-4-yl)-6,7-dihydropyrazolo[1,5-a]pyrazin-4(5H)-one;

(7S)-5-(3,4-Dichlorophenyl)-3-(2-fluoropyridin-4-yl)-7-methyl-6,7-dihydropyrazolo[1,5-a]pyrazin-4(5H)-one;

(7S)-7-Methyl-3-(2-methylpyridin-4-yl)-5-[4-(2,2,2-trifluoro-1-methylethoxy)phenyl]-6,7-dihydropyrazolo[1,5-a]pyrazin-4(5H)-one;

(7S)-3-[2-(Dimethylamino)pyridin-4-yl]-7-methyl-5-[4-(trifluoromethyl)phenyl]-6,7-dihydropyrazolo[1,5-a]pyrazin-4(5H)-one;

(7S)-5-(2,4-Dichlorophenyl)-7-methyl-3-(2-methylpyridin-4-yl)-6,7-dihydropyrazolo[1,5-a]pyrazin-4(5H)-one;

(7S)-5-[3-Chloro-4-(difluoromethoxy)phenyl]-7-methyl-3-(2-methylpyridin-4-yl)-6,7-dihydropyrazolo[1,5-a]pyrazin-4(5H)-one;

(7S)-5-[4-Chloro-3-(trifluoromethoxy)phenyl]-7-methyl-3-(2-methylpyridin-4-yl)-6,7-dihydropyrazolo[1,5-a]pyrazin-4(5H)-one;

(7S)-5-(3,4-Dichlorophenyl)-7-methyl-3-(2-methyl-1-oxidopyridin-4-yl)-6,7-dihydropyrazolo[1,5-a]pyrazin-4(5H)-one;

7,7-Dimethyl-3-(2-methylpyridin-4-yl)-5-[4-(trifluoromethyl)phenyl]-6,7-dihydropyrazolo[1,5-a]pyrazin-4(5H)-one;

(7S)-5-(4-Chloro-2-methylphenyl)-7-methyl-3-(2-methylpyridin-4-yl)-6,7-dihydropyrazolo[1,5-a]pyrazin-4(5H)-one;

(7S)-3-(2-Cyclopropylpyridin-4-yl)-7-methyl-5-[4-(trifluoromethyl)phenyl]-6,7-dihydropyrazolo[1,5-a]pyrazin-4(5H)-one;

(7S)-5-[3-Chloro-4-(difluoromethyl)phenyl]-7-methyl-3-(2-methylpyridin-4-yl)-6,7-dihydropyrazolo[1,5-a]pyrazin-4(5H)-one;

(7S)-7-Methyl-3-(2-piperazin-1-ylpyridin-4-yl)-5-[4-(trifluoromethyl)phenyl]-6,7-dihydropyrazolo[1,5-a]pyrazin-4(5H)-one;

(7S)-7-Methyl-3-(6-piperazin-1-ylpyridin-3-yl)-5-[4-(trifluoromethyl)phenyl]-6,7-dihydropyrazolo[1,5-a]pyrazin-4(5H)-one;

(7S)-5-[3-Chloro-4-(trifluoromethyl)phenyl]-3-[2-(2-fluoroethoxy)pyridin-4-yl]-7-methyl-6,7-dihydropyrazolo[1,5-a]pyrazin-4(5H)-one;

(7S)-5-(4-Chlorophenyl)-7-methyl-3-[2-(methylamino)pyridin-4-yl]-6,7-dihydropyrazolo[1,5-a]pyrazin-4(5H)-one;

5-[(7S)-7-Methyl-3-[2-(methylamino)pyridin-4-yl]-4-oxo-6,7-dihydropyrazolo[1,5-a]pyrazin-5 (4H)-yl]-2-(trifluoromethyl)benzonitrile;

(7S)-3-(2-Methoxypyridin-4-yl)-5-[3-methoxy-4-(trifluoromethyl)phenyl]-7-methyl-6,7-dihydropyrazolo[1,5-a]pyrazin-4(5H)-one;

7-(Difluoromethyl)-3-(2-methylpyridin-4-yl)-5-[4-(trifluoromethyl)phenyl]-6,7-dihydropyrazolo[1,5-a]pyrazin-4(5H)-one;

(7S)-5-[3-Fluoro-4-(trifluoromethyl)phenyl]-7-methyl-3-[2-(methylamino)pyridin-4-yl]-6,7-dihydropyrazolo[1,5-a]pyrazin-4(5H)-one;

(7S)-5-[3-Methoxy-4-(trifluoromethyl)phenyl]-7-methyl-3-[2-(methylamino)pyridin-4-yl]-6,7-dihydropyrazolo[1,5-a]pyrazin-4(5H)-one;

5-(3,4-Dichlorophenyl)-7-(fluoromethyl)-3-[2-(methylamino)pyridin-4-yl]-6,7-dihydropyrazolo[1,5-a]pyrazin-4(5H)-one (7R or 7S);

5-(3,4-Dichlorophenyl)-7-(fluoromethyl)-3-[2-(methylamino)pyridin-4-yl]-6,7-dihydropyrazolo[1,5-a]pyrazin-4(5H)-one (7S or 7R);

(7S)-7-Methyl-3-(2-methylpyridin-4-yl)-5-[5-(trifluoromethyl)pyridin-2-yl]-6,7-dihydropyrazolo[1,5-a]pyrazin-4(5H)-one;

(7S)-5-(5-Chloropyridin-2-yl)-7-methyl-3-(2-methylpyridin-4-yl)-6,7-dihydropyrazolo[1,5-a]pyrazin-4(5H)-one;

(7S)-5-[6-Chloro-5-(trifluoromethyl)pyridin-2-yl]-7-methyl-3-(2-methylpyridin-4-yl)-6,7-dihydropyrazolo[1,5-a]pyrazin-4(5H)-one;

(7S)-5-[4-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-7-Methyl-3-pyridin-4-yl-5-[5-(trifluoromethyl)pyridin-2-yl]-6,7-dihydropyrazolo[1,5-a]pyrazin-4(5H)-one;

(7S)-5-(5-Ethoxy-6-fluoropyridin-2-yl)-7-methyl-3-(2-methylpyridin-4-yl)-6,7-dihydropyrazolo[1,5-a]pyrazin-4(5H)-one;

(7S)-7-Methyl-3-(2-methylpyridin-4-yl)-5-[6-methyl-5-(trifluoromethyl)pyridin-2-yl]-6,7-dihydropyrazolo[1,5-a]pyrazin-4(5H)-one;

(7S)-7-Methyl-3-(2-methylpyridin-4-yl)-5-[4-methyl-5-(trifluoromethyl)pyridin-2-yl]-6,7-dihydropyrazolo[1,5-a]pyrazin-4(5H)-one;

(7S)-3-(2,6-Dimethylpyridin-4-yl)-7-methyl-5-[5-(trifluoromethyl)pyridin-2-yl]-6,7-dihydropyrazolo[1,5-a]pyrazin-4(5H)-one;

(7S)-5-(3-Chloro-6-ethoxypyridin-2-yl)-7-methyl-3-(2-methylpyridin-4-yl)-6,7-dihydropyrazolo[1,5-a]pyrazin-4(5H)-one;

(7S)-5-(5-Chloro-6-methylpyridin-2-yl)-7-methyl-3-(2-methylpyridin-4-yl)-6,7-dihydropyrazolo[1,5-a]pyrazin-4(5H)-one;

(7S)-3-(2-Fluoropyridin-4-yl)-7-methyl-5-[5-(trifluoromethyl)pyridin-2-yl]-6,7-dihydropyrazolo[1,5-a]pyrazin-4(5H)-one;

(7S)-5-(4-Chloro-5-methylpyridin-2-yl)-7-methyl-3-(2-methylpyridin-4-yl)-6,7-dihydropyrazolo[1,5-a]pyrazin-4(5H)-one;

(7S)-5-[6-Ethoxy-3-(trifluoromethyl)pyridin-2-yl]-7-methyl-3-(2-methylpyridin-4-yl)-6,7-dihydropyrazolo[1,5-a]pyrazin-4(5H)-one;

(7S)-5-[6-Ethoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-5-(5-Chloro-6-ethoxypyridin-2-yl)-7-methyl-3-(2-methylpyridin-4-yl)-6,7-dihydropyrazolo[1,5-a]pyrazin-4(5H)-one;

(7S)-5-(5,6-Dichloropyridin-2-yl)-7-methyl-3-(2-methylpyridin-4-yl)-6,7-dihydropyrazolo[1,5-a]pyrazin-4(5H)-one;

(7S)-5-(4,5-Dichloropyridin-2-yl)-7-methyl-3-(2-methylpyridin-4-yl)-6,7-dihydropyrazolo[1,5-a]pyrazin-4(5H)-one;

(7S)-5-[4-Chloro-5-(trifluoromethyl)pyridin-2-yl]-7-methyl-3-(2-methylpyridin-4-yl)-6,7-dihydropyrazolo[1,5-a]pyrazin-4(5H)-one;

(7S)-3-(2,6-Dimethylpyridin-4-yl)-5-[6-ethoxy-5-(trifluoromethyl)pyridin-2-yl]-7-methyl-6,7-dihydropyrazolo[1,5-a]pyrazin-4(5H)-one;

(7S)-5-(5-Chloro-6-methoxypyridin-2-yl)-7-methyl-3-(2-methylpyridin-4-yl)-6,7-dihydropyrazolo[1,5-a]pyrazin-4(5H)-one;

(7S)-5-[6-Methoxy-5-(trifluoromethyl)pyridin-2-yl]-7-methyl-3-(2-methylpyridin-4-yl)-6,7-dihydropyrazolo[1,5-a]pyrazin-4(5H)-one;

(7S)-5-[6-Ethoxy-5-(trifluoromethyl)pyridin-2-yl]-7-methyl-3-pyridin-4-yl-6,7-dihydropyrazolo[1,5-a]pyrazin-4(5H)-one;

(7S)-3-(2-Azetidin-1-ylpyridin-4-yl)-5-[6-methoxy-5-(trifluoromethyl)pyridin-2-yl]-7-methyl-6,7-dihydropyrazolo[1,5-a]pyrazin-4(5H)-one;

(7S)-7-Methyl-3-[2-(methylamino)pyridin-4-yl]-5-[5-(trifluoromethyl)pyridin-2-yl]-6,7-dihydropyrazolo[1,5-a]pyrazin-4(5H)-one;

3-(2-Methylpyridin-4-yl)-5-[5-(trifluoromethyl)pyridin-2-yl]-6,7-dihydropyrazolo[1,5-a]pyrazin-4(5H)-one;

(7S)-5-[4-Iodo-5-(trifluoromethyl)pyridin-2-yl]-7-methyl-3-(2-methylpyridin-4-yl)-6,7-dihydropyrazolo[1,5-a]pyrazin-4(5H)-one;

(7S)-5-(4-Chloro-5-iodopyridin-2-yl)-7-methyl-3-(2-methylpyridin-4-yl)-6,7-dihydropyrazolo[1,5-a]pyrazin-4(5H)-one;

(7S)-7-Methyl-3-[2-(methylamino)-1-oxidopyridin-4-yl]-5-[4-(trifluoromethyl)phenyl]-6,7-dihydropyrazolo[1,5-a]pyrazin-4(5H)-one;

(7S)-3-(2-Chloropyridin-4-yl)-7-methyl-5-[4-(trifluoromethyl)phenyl]-6,7-dihydropyrazolo[1,5-a]pyrazin-4(5H)-one;

7-(1-Hydroxyethyl)-3-(2-methylpyridin-4-yl)-5-[4-(trifluoromethyl)phenyl]-6,7-dihydropyrazolo[1,5-a]pyrazin-4(5H)-one (1R or 1S);

7-(1-Hydroxyethyl)-3-(2-methylpyridin-4-yl)-5-[4-(trifluoromethyl)phenyl]-6,7-dihydropyrazolo[1,5-a]pyrazin-4(5H)-one (1S or 1R);

(7S)-3-(2-Chloropyridin-4-yl)-5-(3,4-dichlorophenyl)-7-methyl-6,7-dihydropyrazolo[1,5-a]pyrazin-4(5H)-one;

5-(3,4-Dichlorophenyl)-7-(hydroxymethyl)-3-(2-methylpyridin-4-yl)-6,7-dihydropyrazolo[1,5-a]pyrazin-4(5H)-one;

(7S)-5-(4,5-Dichloro-2-iodophenyl)-7-methyl-3-(2-methylpyridin-4-yl)-6,7-dihydropyrazolo[1,5-a]pyrazin-4(5H)-one;

(7S)-5-(3,4-Dichloro-2-iodophenyl)-7-methyl-3-(2-methylpyridin-4-yl)-6,7-dihydropyrazolo[1,5-a]pyrazin-4(5H)-one;

5-(3,4-Dichlorophenyl)-7-(fluoromethyl)-3-(2-methylpyridin-4-yl)-6,7-dihydropyrazolo[1,5-a]pyrazin-4(5H)-one;

(7S)-3-(2-Bromopyridin-4-yl)-7-methyl-5-[4-(trifluoromethyl)phenyl]-6,7-dihydropyrazolo[1,5-a]pyrazin-4(5H)-one;

5-(3,4-Dichlorophenyl)-3-(2-fluoropyridin-4-yl)-7-(hydroxymethyl)-6,7-dihydropyrazolo[1,5-a]pyrazin-4(5H)-one;

(7S)-3-(2-Iodopyridin-4-yl)-7-methyl-5-[4-(trifluoromethyl)phenyl]-6,7-dihydropyrazolo[1,5-a]pyrazin-4(5H)-one;

5-(3,4-Dichlorophenyl)-3-(2-fluoropyridin-4-yl)-7-(hydroxymethyl)-6,7-dihydropyrazolo[1,5-a]pyrazin-4(5H)-one (7S or 7R);

5-(3,4-Dichlorophenyl)-3-(2-fluoropyridin-4-yl)-7-(hydroxymethyl)-6,7-dihydropyrazolo[1,5-a]pyrazin-4(5H)-one (7R or 7S);

(7S)-5-[3-Chloro-4-(trifluoromethyl)phenyl]-3-(2-fluoropyridin-4-yl)-7-methyl-6,7-dihydropyrazolo[1,5-a]pyrazin-4(5H)-one;

(7S)-5-[3-Bromo-4-(trifluoromethyl)phenyl]-7-methyl-3-(2-methylpyridin-4-yl)-6,7-dihydropyrazolo[1,5-a]pyrazin-4(5H)-one;

(7S)-5-(4-Iodophenyl)-7-methyl-3-(2-methylpyridin-4-yl)-6,7-dihydropyrazolo[1,5-a]pyrazin-4(5H)-one;

5-(3,4-Dichlorophenyl)-3-[2-(dimethylamino)pyridin-4-yl]-7-(hydroxymethyl)-6,7-dihydropyrazolo[1,5-a]pyrazin-4(5H)-one (7S or 7R);

5-(3,4-Dichlorophenyl)-3-[2-(dimethylamino)pyridin-4-yl]-7-(hydroxymethyl)-6,7-dihydropyrazolo[1,5-a]pyrazin-4(5H)-one (7R or 7S);

5-(3,4-Dichlorophenyl)-7-(hydroxymethyl)-3-[2-(methylamino)pyridin-4-yl]-6,7-dihydropyrazolo[1,5-a]pyrazin-4(5H)-one;

(7S)-3-(2-Chloro-6-methoxypyridin-4-yl)-7-methyl-5-[4-(trifluoromethyl)phenyl]-6,7-dihydropyrazolo[1,5-a]pyrazin-4(5H)-one;

(7S)-3-[6-(1-Acetylazetidin-3-yl)pyridin-3-yl]-7-methyl-5-[4-(trifluoromethyl)phenyl]-6,7-dihydropyrazolo[1,5-a]pyrazin-4(5H)-one (7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one;

(7S)-5-[6-Methoxy-5-(trifluoromethyl)pyridin-2-yl]-7-methyl-3-[2-(methylamino)pyridin-4-yl]-6,7-dihydropyrazolo[1,5-a]pyrazin-4(5H)-one;

3-(2-Methylpyridin-4-yl)-7-(trifluoromethyl)-5-[4-(trifluoromethyl)phenyl]-6,7-dihydropyrazolo[1,5-a]pyrazin-4(5H)-one;

(7S)-5-[3-(hydroxymethyl)-4-(trifluoromethyl)phenyl]-7-methyl-3-(2-methyl-4-pyridyl)-6,7-dihydropyrazolo[1,5-a]pyrazin-4-one;

(7S)-3-(2-methoxy-4-pyridyl)-5-[6-methoxy-5-(trifluoromethyl)-2-pyridyl]-7-methyl-6,7-dihydropyrazolo[1,5-a]pyrazin-4-one;

(7S)-7-methyl-3-[2-methyl-6-(methylamino)-4-pyridyl]-5-[4-(trifluoromethyl)phenyl]-6,7-dihydropyrazolo[1,5-a]pyrazin-4-one;

(7S)-3-[2-methoxy-6-(methylamino)-4-pyridyl]-7-methyl-5-[4-(trifluoromethyl)phenyl]-6,7-dihydropyrazolo[1,5-a]pyrazin-4-one;

(7S)-3-[2-fluoro-6-(methylamino)-4-pyridyl]-7-methyl-5-[4-(trifluoromethyl)phenyl]-6,7-dihydropyrazolo[1,5-a]pyrazin-4-one;

5-(2,4-dichlorophenyl)-3-(2-methyl-4-pyridyl)-6,7-dihydropyrazolo[1,5-a]pyrazin-4-one;

(7S)-3-[2-(dimethylamino)-4-pyridyl]-5-[3-(hydroxymethyl)-4-(trifluoromethyl)phenyl]-7-methyl-6,7-dihydropyrazolo[1,5-a]pyrazin-4-one;

(7S)-3-[2-(dimethylamino)-4-pyridyl]-5-[3-(fluoromethyl)-4-(trifluoromethyl)phenyl]-7-methyl-6,7-dihydropyrazolo[1,5-a]pyrazin-4-one;

(7S)-3-(2-fluoro-4-pyridyl)-7-methyl-5-[4-(trifluoromethyl)phenyl]-6,7-dihydropyrazolo[1,5-a]pyrazin-4-one;

(7S)-5-(3,4-dichlorophenyl)-3-[2-(dimethylamino)-4-pyridyl]-7-methyl-6,7-dihydropyrazolo[1,5-a]pyrazin-4-one;

(7S)-3-[2-(dimethylamino)-4-pyridyl]-5-[3-(2-fluoroethoxy)-4-(trifluoromethyl)phenyl]-7-methyl-6,7-dihydropyrazolo[1,5-a]pyrazin-4-one;

(7S)-3-[2-(dimethylamino)-4-pyridyl]-5-[6-methoxy-5-(trifluoromethyl)-2-pyridyl]-7-methyl-6,7-dihydropyrazolo[1,5-a]pyrazin-4-one;

(7S)-7-methyl-3-[2-(methylamino)-4-pyridyl]-5-[3-methyl-4-(trifluoromethyl)phenyl]-6,7-dihydropyrazolo[1,5-a]pyrazin-4-one;

(7S)-5-[3-chloro-4-(trifluoromethyl)phenyl]-7-methyl-3-(2-methyl-1-oxido-pyridin-1-ium-4-yl)-6,7-dihydropyrazolo[1,5-a]pyrazin-4-one;

(7S)-3-[2-[ethyl(methyl)amino]-4-pyridyl]-7-methyl-5-[4-(trifluoromethyl)phenyl]-6,7-dihydropyrazolo[1,5-a]pyrazin-4-one;

(7S)-5-[3-chloro-4-(trifluoromethyl)phenyl]-3-[2-[ethyl(methyl)amino]-4-pyridyl]-7-methyl-6,7-dihydropyrazolo[1,5-a]pyrazin-4-one;

(7S)-5-[3-chloro-4-(trifluoromethyl)phenyl]-3-[2-(ethylamino)-4-pyridyl]-7-methyl-6,7-dihydropyrazolo[1,5-a]pyrazin-4-one;

(7S)-3-[2-(ethylamino)-4-pyridyl]-7-methyl-5-[3-methyl-4-(trifluoromethyl)phenyl]-6,7-dihydropyrazolo[1,5-a]pyrazin-4-one;
(7S)-5-(3,4-dichlorophenyl)-3-[2-(ethylamino)-4-pyridyl]-7-methyl-6,7-dihydropyrazolo[1,5-a]pyrazin-4-one;
(7S)-7-methyl-5-[3-methyl-4-(trifluoromethyl)phenyl]-3-[2-(propylamino)-4-pyridyl]-6,7-dihydropyrazolo[1,5-a]pyrazin-4-one;
(7S)-7-methyl-3-[2-(propylamino)-4-pyridyl]-5-[4-(trifluoromethyl)phenyl]-6,7-dihydropyrazolo[1,5-a]pyrazin-4-one;
(7S)-3-[2-(azetidin-1-yl)-4-pyridyl]-7-methyl-5-[3-methyl-4-(trifluoromethyl)phenyl]-6,7-dihydropyrazolo[1,5-a]pyrazin-4-one;
(7S)-3-[2-(isopropylamino)-4-pyridyl]-7-methyl-5-[3-methyl-4-(trifluoromethyl)phenyl]-6,7-dihydropyrazolo[1,5-a]pyrazin-4-one;
(7S)-3-[2-(isopropylamino)-4-pyridyl]-7-methyl-5-[4-(trifluoromethyl)phenyl]-6,7-dihydropyrazolo[1,5-a]pyrazin-4-one;
(7S)-5-[3-chloro-4-(trifluoromethyl)phenyl]-3-[2-(fluoromethyl)-4-pyridyl]-7-methyl-6,7-dihydropyrazolo[1,5-a]pyrazin-4-one;
(7S)-5-[3-chloro-4-(trifluoromethyl)phenyl]-7-methyl-3-[2-(propylamino)-4-pyridyl]-6,7-dihydropyrazolo[1,5-a]pyrazin-4-one;
(7S)-5-(3,4-dichlorophenyl)-7-methyl-3-[2-(propylamino)-4-pyridyl]-6,7-dihydropyrazolo[1,5-a]pyrazin-4-one;
(7S)-5-[3-chloro-4-(trifluoromethyl)phenyl]-3-[2-(isopropylamino)-4-pyridyl]-7-methyl-6,7-dihydropyrazolo[1,5-a]pyrazin-4-one;
(7S)-5-(3,4-dichlorophenyl)-3-[2-(isopropylamino)-4-pyridyl]-7-methyl-6,7-dihydropyrazolo[1,5-a]pyrazin-4-one;
and the pharmaceutically acceptable salts and solvates of such compounds.

In another embodiment, specific compounds according to the invention include:
(7S)-7-Methyl-3-(2-methylpyridin-4-yl)-5-[4-(trifluoromethyl)phenyl]-6,7-dihydropyrazolo[1,5-a]pyrazin-4(5H)-one hydrochloride salt;
(7S)-7-Methyl-3-(2-methylpyridin-4-yl)-5-[4-(trifluoromethyl)phenyl]-6,7-dihydropyrazolo[1,5-a]pyrazin-4(5H)-one sulfate salt;
(7S)-7-Methyl-3-(2-methylpyridin-4-yl)-5-[4-(trifluoromethyl)phenyl]-6,7-dihydropyrazolo[1,5-a]pyrazin-4(5H)-one methane sulfonate salt;
(7S)-7-Methyl-3-(2-methylpyridin-4-yl)-5-[4-(trifluoromethyl)phenyl]-6,7-dihydropyrazolo[1,5-a]pyrazin-4(5H)-one maleate salt;
(7S)-7-Methyl-3-(2-methylpyridin-4-yl)-5-[3-methyl-4-(trifluoromethyl)phenyl]-6,7-dihydropyrazolo[1,5-a]pyrazin-4(5H)-one hydrochloride salt;
(7S)-5-(3,4-Dichlorophenyl)-7-methyl-3-(2-methylpyridin-4-yl)-6,7-dihydropyrazolo[1,5-a]pyrazin-4(5H)-one hydrochloride salt;
(7S)-5-[3-Methoxy-4-(trifluoromethyl)phenyl]-7-methyl-3-(2-methylpyridin-4-yl)-6,7-dihydropyrazolo[1,5-a]pyrazin-4(5H)-one hydrochloride salt;
(7S)-5-(4-Chlorophenyl)-7-methyl-3-(2-methylpyridin-4-yl)-6,7-dihydropyrazolo[1,5-a]pyrazin-4(5H)-one hydrochloride salt;
(7S)-5-(3-Chloro-4-ethoxyphenyl)-7-methyl-3-(2-methylpyridin-4-yl)-6,7-dihydropyrazolo[1,5-a]pyrazin-4(5H)-one hydrochloride salt;
(7S)-5-(3-Chloro-4-methoxyphenyl)-7-methyl-3-(2-methylpyridin-4-yl)-6,7-dihydropyrazolo[1,5-a]pyrazin-4(5H)-one hydrochloride salt;
(7S)-3-[2-(Methoxymethyl)pyridin-4-yl]-7-methyl-5-[4-(trifluoromethyl)phenyl]-6,7-dihydropyrazolo[1,5-a]pyrazin-4(5H)-one hydrochloride salt;
(7S)-5-(3,4-Difluorophenyl)-7-methyl-3-(2-methylpyridin-4-yl)-6,7-dihydropyrazolo[1,5-a]pyrazin-4(5H)-one hydrochloride salt;
(7S)-5-(4-Fluorophenyl)-7-methyl-3-(2-methylpyridin-4-yl)-6,7-dihydropyrazolo[1,5-a]pyrazin-4(5H)-one hydrochloride salt;
(7S)-5-(3-Fluoro-4-methoxyphenyl)-7-methyl-3-(2-methylpyridin-4-yl)-6,7-dihydropyrazolo[1,5-a]pyrazin-4(5H)-one hydrochloride salt;
(7S)-5-(4-Methoxyphenyl)-7-methyl-3-(2-methylpyridin-4-yl)-6,7-dihydropyrazolo[1,5-a]pyrazin-4(5H)-one hydrochloride salt;
(7S)-7-methyl-3-(2-methyl-4-pyridyl)-5-[3-(trifluoromethoxy)phenyl]-6,7-dihydropyrazolo[1,5-a]pyrazin-4-one hydrochloride salt;
(7S)-5-(3-chloro-5-fluoro-phenyl)-7-methyl-3-(2-methyl-4-pyridyl)-6,7-dihydropyrazolo[1,5-a]pyrazin-4-one hydrochloride salt;
(7S)-5-(4-isopropylphenyl)-7-methyl-3-(2-methyl-4-pyridyl)-6,7-dihydropyrazolo[1,5-a]pyrazin-4-one hydrochloride salt;
(7S)-7-methyl-3-(2-methyl-4-pyridyl)-5-(4-propylphenyl)-6,7-dihydropyrazolo[1,5-a]pyrazin-4-one hydrochloride salt;
(7S)-5-[3-(difluoromethoxy)-5-fluoro-phenyl]-7-methyl-3-(2-methyl-4-pyridyl)-6,7-dihydropyrazolo[1,5-a]pyrazin-4-one hydrochloride salt;
(7S)-7-Methyl-5-[3-(1-methylethoxy)phenyl]-3-(2-methyl-pyridin-4-yl)-6,7-dihydropyrazolo[1,5-a]pyrazin-4(5H)-one hydrochloride salt;
(7S)-5-(4-Ethoxyphenyl)-7-methyl-3-(2-methylpyridin-4-yl)-6,7-dihydropyrazolo[1,5-a]pyrazin-4(5H)-one hydrochloride salt;
(7S)-7-Methyl-3-(2-piperidin-1-ylpyridin-4-yl)-5-[4-(trifluoromethyl)phenyl]-6,7-dihydropyrazolo[1,5-a]pyrazin-4(5H)-one hydrochloride salt;
(7S)-3-(2-Cyclopropylpyridin-4-yl)-5-(3,4-dichlorophenyl)-7-methyl-6,7-dihydropyrazolo[1,5-a]pyrazin-4(5H)-one hydrochloride salt;
(7S)-5-(3,4-Dichlorophenyl)-3-(2-ethoxypyridin-4-yl)-7-methyl-6,7-dihydropyrazolo[1,5-a]pyrazin-4(5H)-one hydrochloride salt;
(7S)-5-(3,4-Dichlorophenyl)-7-methyl-3-[2-(1-methylethoxy)pyridin-4-yl]-6,7-dihydropyrazolo[1,5-a]pyrazin-4(5H)-one hydrochloride salt;
(7S)-7-Methyl-3-[2-(1-methylethoxy)pyridin-4-yl]-5-[4-(trifluoromethyl)phenyl]-6,7-dihydropyrazolo[1,5-a]pyrazin-4(5H)-one hydrochloride salt;
(7S)-3-(2-Cyclopropylpyridin-4-yl)-7-methyl-5-[4-(trifluoromethyl)phenyl]-6,7-dihydropyrazolo[1,5-a]pyrazin-4(5H)-one hydrochloride salt;
(7S)-7-Methyl-3-(2-piperazin-1-ylpyridin-4-yl)-5-[4-(trifluoromethyl)phenyl]-6,7-dihydropyrazolo[1,5-a]pyrazin-4(5H)-one hydrochloride salt, and
(7S)-7-Methyl-3-(2-methylpyridin-4-yl)-5-{4-[(trifluoromethyl)sulfanyl]phenyl}-6,7-dihydropyrazolo[1,5-a]pyrazin-4(5H)-one hydrochloride salt.

The names of the compounds of the present invention were generated according to the nomenclature rules agreed upon by the Chemical Abstracts Service (C.A.S.) using Advanced Chemical Development, Inc., software (ACD/

Name product version 10.01.0.14105, October 2006). In case of tautomeric forms, the name of the depicted tautomeric form of the structure was generated. However it should be clear that the other non-depicted tautomeric form is also included within the scope of the present invention.

Definitions

The notation "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl, 1,1-dimethylethyl and the like. The notation "—$C_{1-4}$alkyl-OH" as used herein alone or as part of another group, refers to $C_{1-4}$alkyl as defined before, substituted with one OH group at any available carbon atom.

The notation "halogen" or "halo" as used herein alone or as part of another group, refers to fluoro, chloro, bromo or iodo, with fluoro or chloro being preferred.

The notation "mono- and polyhalo$C_{1-4}$alkyl" as used herein alone or as part of another group, refers to $C_{1-4}$alkyl as defined before, substituted with 1, 2, 3 or where possible with more halo atoms as defined before.

The notation "$C_{3-7}$cycloalkyl" as used herein refers to a saturated, cyclic hydrocarbon radical having from 3 to 7 carbon atoms, such as cyclopropyl, cyclobutyl, cyclopentyl, cyclohexyl and cycloheptyl. A particular $C_{3-7}$cycloalkyl group is cyclopropyl.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide/appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, e.g are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

In a particular embodiment, the invention relates to a compound of Formula (I) wherein $R^2$ is

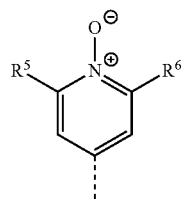

and the rest of variables are as defined herein.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above formula are intended to be included within the scope of the present invention.

It follows that a single compound may exist in both stereisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form, for example $^2H$. Radiolabelled compounds of Formula (I) may comprise a radioactive isotope selected from the group of $^3H$, $^{11}C$, $^{14}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Preparation

The compounds according to the invention can generally be prepared by a succession of steps, each of which is known to the skilled person. In particular, the compounds can be prepared according to the following synthesis methods.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase or chiral supercritical fluid chromatography (SFC). Said pure stereochemically isomeric forms may also be derived from the corresponding pure stereochemically isomeric forms of the appropriate starting materials, provided that the reaction occurs stereospecifically. The absolute configuration of compounds of the invention reported herein was determined by analysis of the racemic mixture by supercritical fluid chromatography (SFC) followed by SFC comparison of the separate enantiomer(s) which were obtained by asymmetric synthesis or by chiral separation of mixtures, followed by vibrational circular dichroism (VCD) analysis of the particular enantiomer(s).

A. Preparation of the Final Compounds

Experimental Procedure 1

Final compounds according to Formula (I) can be prepared by a Goldberg coupling reaction of a compound of Formula (II) with an appropriate aryl halide of Formula (III)

where X is halo, in particular bromo or iodo, according to conditions known to the skilled person. Such conditions include for example using a suitable copper(I) catalyst such as copper(I) iodide, in the presence of a ligand, such as N,N'-dimethylethylenediamine, in the presence of a base, such as inorganic carbonates, for example sodium carbonate (Na$_2$CO$_3$) or potassium carbonate (K$_2$CO$_3$), in a suitable solvent, such as toluene or a mixture of toluene and N,N-dimethylformamide (DMF), under suitable reaction conditions, such as at a convenient temperature, typically ranging between 100° C. and 140° C., in particular 110° C., for a period of time to ensure the completion of the reaction. A compound of Formula (III) can be obtained commercially or made according to procedures known in the art. In Reaction Scheme 1, all variables are defined as in Formula (I).

Reaction Scheme 1

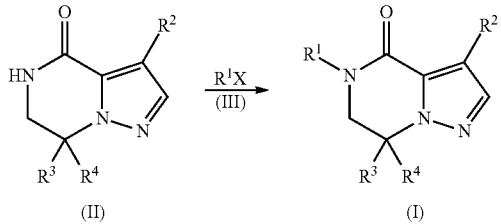

Experimental Procedure 2

Alternatively, final compounds according to Formula (I) can be prepared by a Suzuki type coupling reaction of a compound of Formula (IVa) with a suitable boron species or a compound of Formula (IVb), wherein R$^{7a}$ and R$^{8a}$ may be each independently selected from H, C$_{1-4}$alkyl or R$^{7a}$ and R$^{8a}$ are taken together to form for example a bivalent radical of formula —CH$_2$CH$_2$—, —CH$_2$CH$_2$CH$_2$— or —C(CH$_3$)$_2$C(CH$_3$)$_2$—, with a suitable heteroaryl halide or aryl halide derivative in the presence of a palladium catalyst, according to reaction conditions known to the skilled person. Such reaction conditions include the use of a palladium catalyst, such as tetrakis(triphenylphosphine)palladium(0) or an alternative catalyst system prepared in situ from Pd(OAc)$_2$ and PPh$_3$, a suitable base, such as Na$_2$CO$_3$, K$_2$CO$_3$, NaOAc, NaHCO$_3$ or K$_3$PO$_4$, and in a suitable solvent, such as 1,4-dioxane, or a mixture of dimethoxyethane (DME) and water. Degassing the reaction mixture with an inert gas, such as N$_2$ or argon, and heating the reaction mixture to high temperatures, such as reflux temperature under classical heating or microwave irradiation, in particular 80° C., may enhance the reaction outcome. In Reaction Schemes 2a and 2b, all variables are defined as in Formula (I).

Reaction Scheme 2a

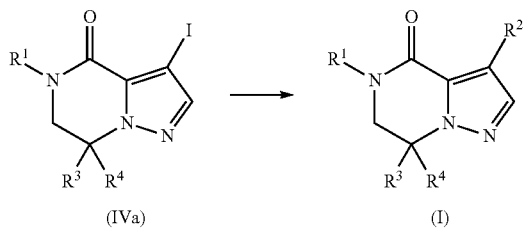

Reaction Scheme 2b

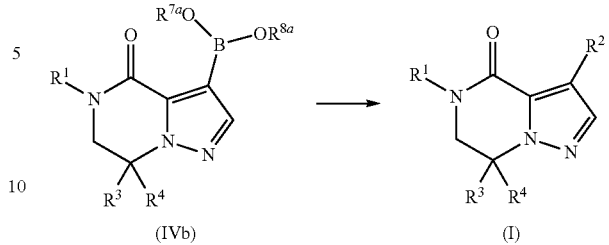

The suitable boron species may be selected for example from a boronic acid or a boronate ester, which may be conveniently represented as a compound of Formula (IIIa)

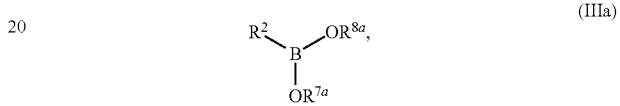

wherein R$^2$ is as defined in Formula (I) herein and R$^{7a}$ and R$^{8a}$ may be each independently selected from H, C$_{1-4}$alkyl or R$^{7a}$ and R$^{8a}$ are taken together to form for example a bivalent radical of formula —CH$_2$CH$_2$—, —CH$_2$CH$_2$CH$_2$— or —C(CH$_3$)$_2$C(CH$_3$)$_2$—. A skilled person can envisage that the reaction under Reaction Scheme 2a can also be performed under similar conditions, when the compound of Formula (IVa) bears a bromo group in place of an iodo group. Such a reaction can be represented as in Reaction Scheme 2c, wherein the compound of Formula (IV), wherein R$^a$ is halo, in particular bromo or iodo and all other variables are as defined in Formula (I), undergoes a Suzuki type coupling as described hereinbefore.

Reaction Scheme 2c

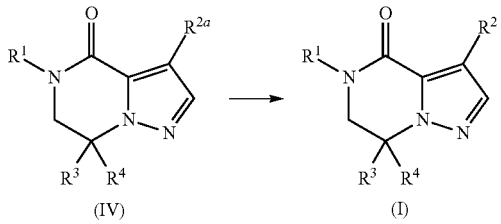

Experimental Procedure 3

Alternatively, final compounds according to Formula (I), wherein R$^2$ is an optionally substituted 4-pyridinyl or 3-pyridinyl, hereby referred to as compounds of Formula (Ia) or Formula (Ib), respectively, can be prepared by a reaction of deprotection of a compound of Formula (Ia-1) or a compound of Formula (Ia-2) following art known procedures. A compound of Formula (Ia) or a compound Formula (Ib) can be obtained by removal of the protecting group such as for example a Boc protecting group in the compound of Formula (Ia-1) or compound of Formula (Ia-2), in the presence of acidic media, such as trifluoroacetic acid, in an inert solvent such as dichloromethane (DCM), under suitable reaction conditions, such as at a convenient temperature, typically rt, for a period of time to ensure the completion of the reaction. In Reaction Schemes 3a and 3b, all variables are defined as in Formula (I) and $R^{5a'}$ and $R^{6a'}$ include the residues indicated in the scope as $R^5$ and $R^6$ as well as their protected forms.

Reaction Scheme 3a

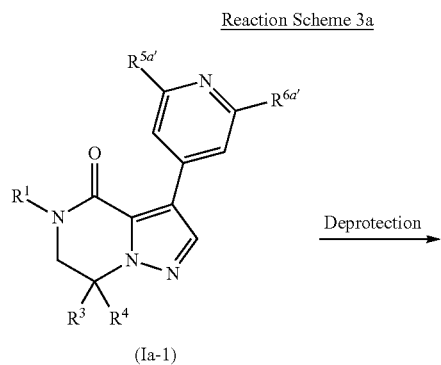

(Ia-1)

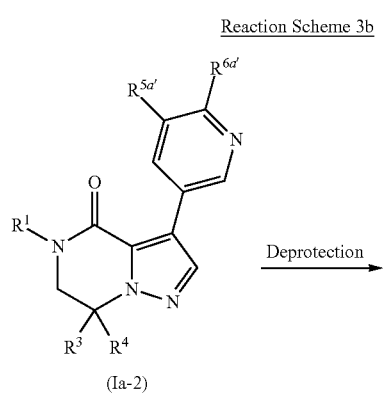

(Ia-2)

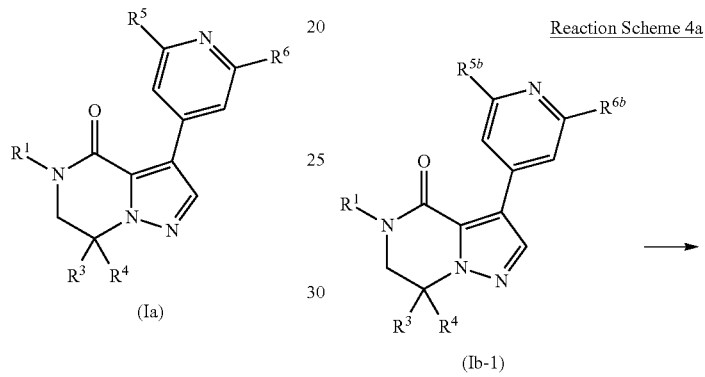

respectively, bearing one or more functional groups which can be converted to the residues $R^5$ and $R^6$ by means of simple reactions known to the person skilled in the art, such as for example introduction of an alcohol or an amine in presence of a base and a suitable solvent or acylation with an acyl chloride in the presence of a base and a suitable solvent or reduction for example by using a suitable reducing agent such as sodium borohydride, in a suitable solvent or by means of cross coupling reactions known to the person skilled in the art, such as for example the Suzuki reaction with a suitable boron species or the Stille reaction with a suitable tin species. In Reaction Schemes 4a and 4b, all variables are defined as in Formula (I) and $R^{5b}$ and $R^{6b}$ include the residues indicated in the scope as $R^5$ and $R^6$ as well as their possible precursors. The person skilled in the art will recognize that suitable reaction conditions should be chosen for different $R^{5b}$ and $R^{6b}$ combinations, to avoid undesired side reactions.

Reaction Scheme 4a

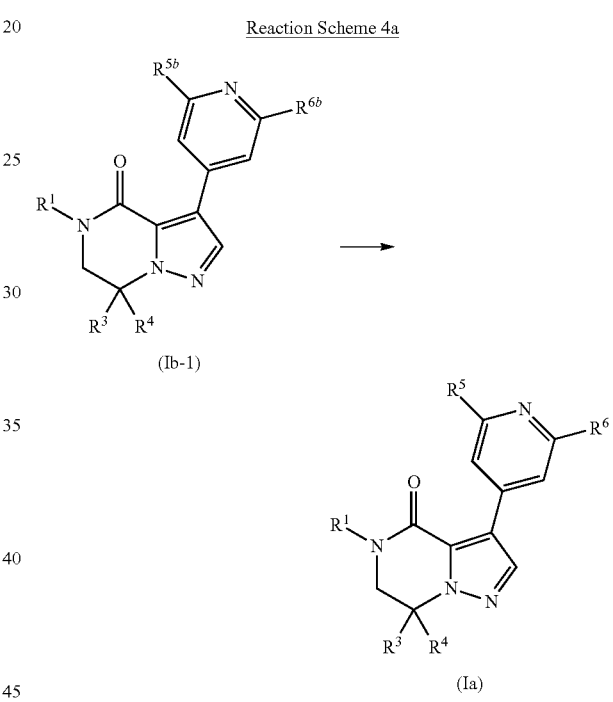

Reaction Scheme 4b

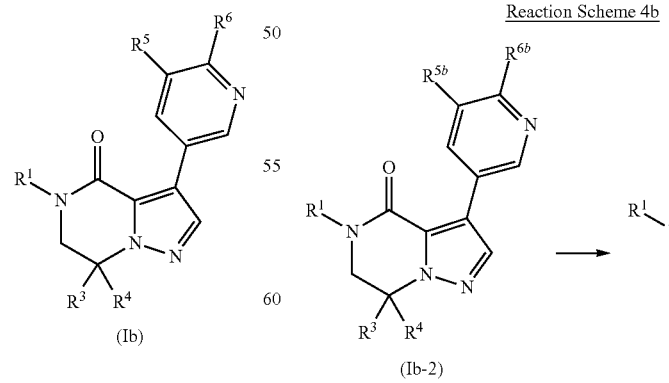

Experimental Procedure 4

Alternatively, final compounds according to Formula (Ia) and Formula (Ib) can be prepared by manipulation of a suitable precursor of Formula (Ib-1) and of Formula (Ib-2)

Experimental Procedure 5

Alternatively, final compounds according to Formula (Ia) and Formula (Ib) can be prepared respectively by a reaction of fluorination of a compound of Formula (Ic-1) and of Formula (Ic-2) wherein Y is N, CH or $CR^{9c}$ and one of $R^{5c}$, $R^{6c}$, $R^{3c}$, $R^{4c}$, $R^{9c}$ and $R^{10c}$ may be each independently selected from $C_{1-4}$alkyl-OH or $C_{1-3}$alkyl-CHO and herein referred to as a compound of Formula (Ic-1) and compound of Formula (Ic-2) respectively. A compound of Formula (Ic-1) or compound of Formula (Ic-2) can be treated in the presence of a fluorinating agent such as for example ®Deoxofluor ([Bis(2-methoxyethyl)amino]sulfur trifluoride) or (diethylamino)sulfur trifluoride in a suitable solvent such as, for example DCM, and stirring the reaction mixture at rt. In Reaction Schemes 5a and 5b, all variables are defined as in Formula (I) and $R^{5c}$, $R^{6c}$, $R^{3c}$, and $R^{4c}$ include the residues indicated in the scope of Formula (I) as $R^5$, $R^6$, $R^3$, $R^4$ as well as their possible precursors, and $R^{9c}$ and $R^{10e}$, when present, include the residues indicated in the scope of Formula (I) as substituents in $R^1$ as well as their possible precursors, wherein one of $R^{5c}$, $R^{6c}$, $R^{3c}$, $R^{4c}$, and $R^{9c}$ and $R^{10c}$ when present, is $C_{1-4}$ alkyl-OH or $C_{1-3}$alkyl-CHO and in $(R^{10d})_n$, n=0-4.

Reaction Scheme 5a

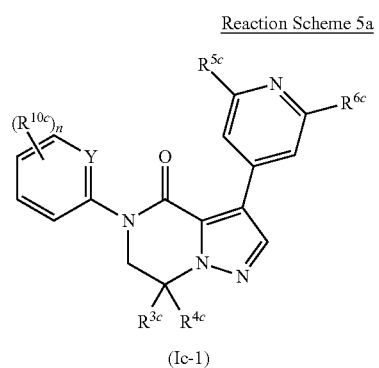

(Ic-1)

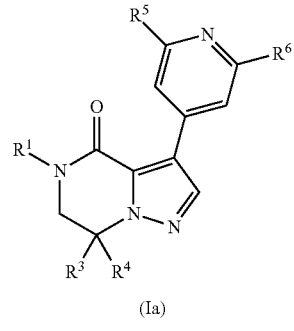

(Ia)

Reaction Scheme 5b

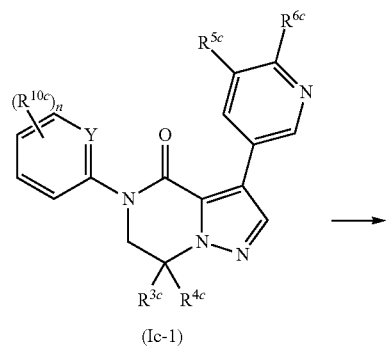

(Ic-1)

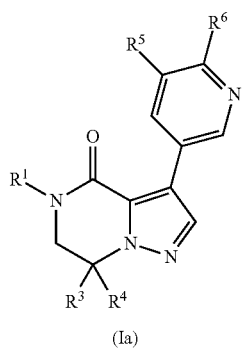

(Ia)

Experimental Procedure 6

Alternatively, final compounds according to Formula (Ia) and Formula (Ib) can be prepared by manipulation of a suitable precursor of Formula (Id-1) or of Formula (Id-2) respectively, wherein Y is N, CH or $CR^{9d}$, bearing one or more functional groups, $R^{5d}$, $R^{6d}$, $R^{9d}$ and $R^{10d}$, which can be converted to the residues $R^5$, $R^6$ and the substituents of $R^1$ as defined in Formula (I) by means of simple reactions known to the person skilled in the art, such as for example by reduction of a double bond to the corresponding saturated form, for example by means of catalytic hydrogenation. In Reaction Schemes 6a and 6b, all variables are defined as in Formula (I) and $R^{5d}$ and $R^{6d}$, include the residues indicated in the scope as $R^5$, $R^6$ as well as their possible precursors, and $R^{9d}$ and $R^{10d}$ when present include the substituents of $R^1$ as well as their possible precursors. The person skilled in the art will recognize that suitable reaction conditions should be chosen for different $R^{5d}$, $R^{6d}$, $R^{9d}$ and $R^{10d}$ combinations to avoid undesired side reactions and in $(R^{10d})_n$, n=0-4.

Reaction Scheme 6a

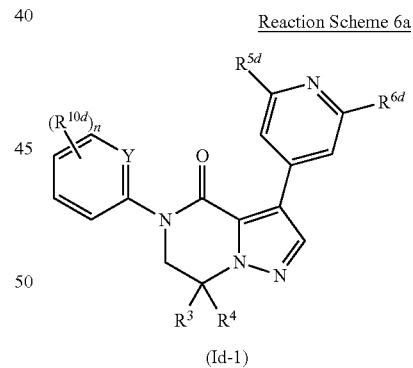

(Id-1)

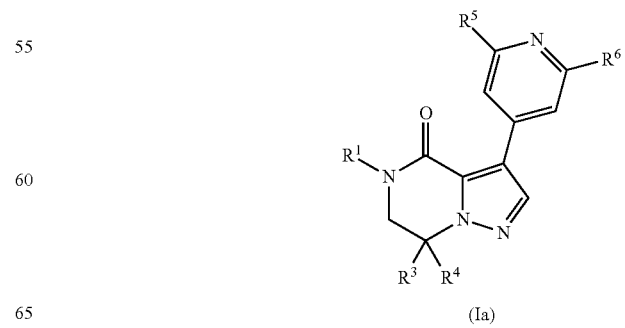

(Ia)

Reaction Scheme 6b

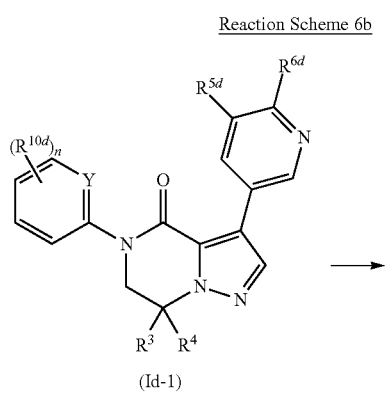

Experimental Procedure 7

Alternatively, final compounds according to Formula (Id) can be prepared by means of an oxidation reaction of a compound of Formula (I) in the presence of an oxidant, such as for example 3-chloroperoxybenzoic acid and in a suitable solvent. In Reaction Scheme 7, all variables are defined as in Formula (I).

Reaction Scheme 7

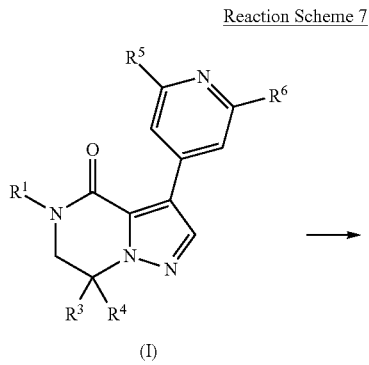

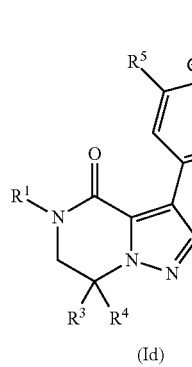

Experimental Procedure 8

Alternatively, final compounds according to Formula (I) can be prepared by intramolecular amidation starting from a compound of Formula (VI). Typically, amidation conditions can be applied, such as stirring the starting materials, dissolved in a suitable solvent, such as DMF, in the presence of a coupling agent, such as HATU (2-(7-aza-1H-benzotriazole-1-yl)-1,1,3,3-tetramethyluronium hexafluorophosphate) and in the presence of a base, such as TEA (triethylamine) In Reaction Scheme 8, all variables are defined as in Formula (I).

Reaction Scheme 8

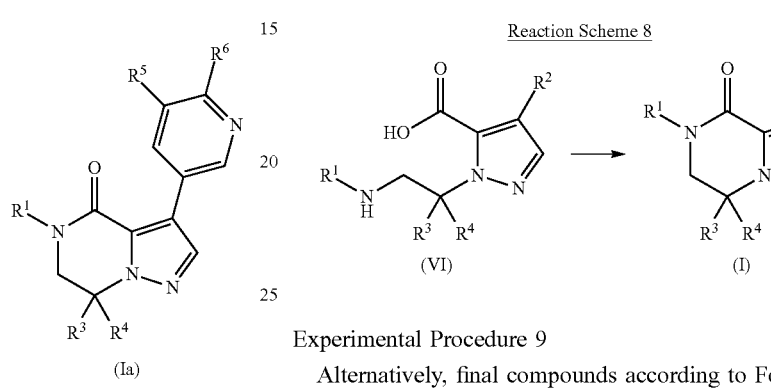

Experimental Procedure 9

Alternatively, final compounds according to Formula (I) can be prepared in one pot starting from a compound of Formula (II). First, a reaction of nucleophilic substitution of a compound of Formula (II) with an appropriate (hetero)aryl halide of Formula (III) where X is halo in the presence of a base such as for example sodium hydride in a suitable solvent such as for example DMF, followed by an intramolecular peptide type coupling of compound of Formula (VI) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 9, all variables are defined as in Formula (I).

Reaction Scheme 9

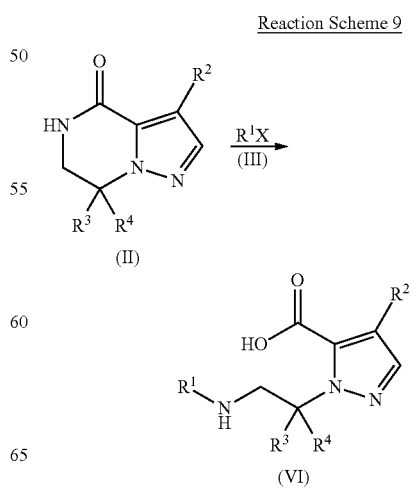

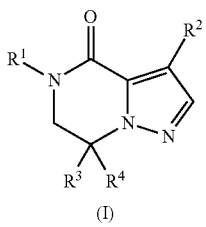

(I)

Alternatively, final compounds according to Formula (I) can be prepared in one pot starting from a compound of Formula (II). First by a coupling reaction of a compound of Formula (II) with an appropriate heteroaryl halide of Formula (III) where X is halo in the presence of a palladium catalyst, such as tetrakis(triphenylphosphine)palladium(0), in the presence of a ligand, such as 4,5-bis(diphenylphosphino)-9,9-dimethylxanthene, in the presence of a base, such as $Cs_2CO_3$ and in a suitable solvent, such as 1,4-dioxane, under suitable reaction conditions, such as at a convenient temperature, typically ranging between 100° C. and 140° C., for a period of time to ensure the completion of the reaction, followed by an intramolecular peptide type coupling of compound of Formula (VI) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 9, all variables are defined as in Formula (I).

B. Preparation of the Intermediate Compounds

Experimental Procedure 10

Intermediate compound according to Formula (II) (Reaction Scheme 10a) can be prepared following art known procedures, such as by subjecting an intermediate compound of Formula (Va) to a Suzuki type coupling reaction under conditions known to a skilled person. Such conditions include for example, reacting the intermediate compound of Formula (Va) with a suitable boron species, such as for example a boronic acid or a boronate ester, for example as described in Experimental procedure 2 hereinbefore, in the presence of a palladium catalyst, such as tetrakis(triphenylphosphine)palladium(0) or an alternative catalyst system prepared in situ from $Pd(OAc)_2$ and $PPh_3$, a suitable base, such as $Na_2CO_3$, $K_2CO_3$, $NaHCO_3$ and $K_3PO_4$, and in a suitable solvent, such as 1,4-dioxane, or a mixture of DME and water. Degassing the reaction mixture with an inert gas, such as $N_2$ or argon, and heating the reaction mixture to high temperatures, such as reflux temperature, in particular 80° C., may enhance the reaction outcome. In Reaction Scheme 10a, all variables are defined as in Formula (I).

Reaction Scheme 10a

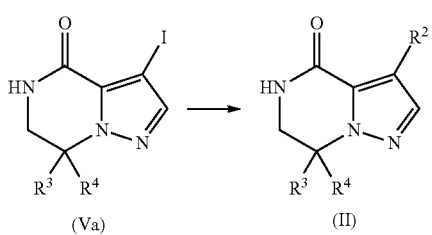

A skilled person can envisage that the reaction under Reaction Scheme 10a can also be performed under similar conditions, when the compound of Formula (Va) bears a bromo group in place of a iodo group. Such a reaction can be represented as in Reaction Scheme 10b, wherein the compound of Formula (V), wherein $R^{2a}$ is halo, in particular bromo or iodo and all other variables are as defined in Formula (I), undergoes a Suzuki type coupling as described hereinbefore.

Reaction Scheme 10b

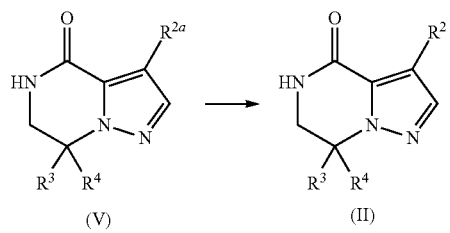

In particular aspect, the invention therefore relates to an intermediate compound of Formula (V), wherein $R^{2a}$ is halo, in particular Br or I

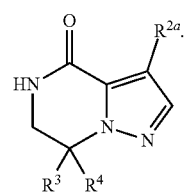

(V)

In a particular embodiment, the invention relates to an intermediate compound of Formula (V'), wherein $R^{2a}$ is halo, in particular, Br (referred to herein as compound (I-13a) or I (referred to herein as compound (I-13))

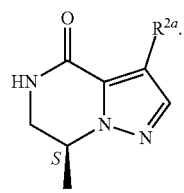

(V')

Experimental Procedure 11

Intermediate compound of Formula (Va) or of Formula (V) can be prepared by removal of the protecting group, for example a Boc group, in an intermediate of Formula (VIa) or of Formula (VIb), respectively, for example in the presence of acidic media, such as hydrochloric acid, in an inert solvent such as 1,4-dioxane or acetonitrile or ethyl acetate (EtOAc), under suitable reaction conditions, such as at a convenient temperature, such as from 15 to 80° C., typically 80° C. or from 15-30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., for a period of time to ensure the completion of the reaction. In Reaction Schemes 11a and 11b, $R^{2a}$ is halo, in particular bromo or iodo, $R^7$ is $C_{1-4}$alkyl, PG is a protecting group, for example Boc, and all other variables are defined as in Formula (I).

Reaction Scheme 11a

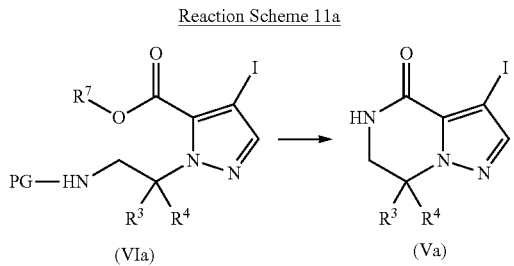

(VIa) → (Va)

Reaction Scheme 11b

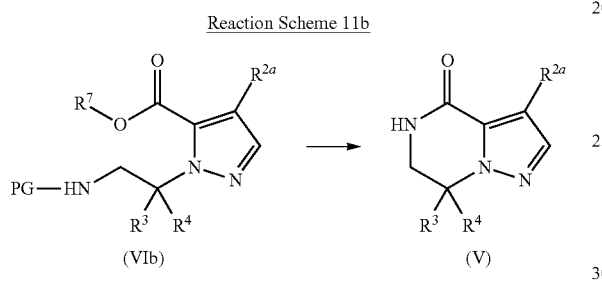

(VIb) → (V)

Experimental Procedure 12

Intermediate compound of Formula (VIa) or (VIb) wherein $R^7$ is $C_{1-4}$alkyl and PG is a protecting group, for example Boc, can be prepared by a Mitsunobu type reaction between an intermediate compound of Formula (VIIa) or (VII) respectively, and an appropriate alcohol of Formula (VIII), in the presence of a suitable triarylphosphine, such as triphenylphosphine typically 1.5 equivalents, or a suitable trialkylphosphine, and a suitable dialkyl azodicarboxylate reagent, such as di-tert-butyl azodicarboxylate or diethyl azodicarboxylate typically 1.5 equivalents, in a suitable inert solvent, such as tetrahydrofuran (THF), under suitable reaction conditions, such as at a convenient temperature, typically ranging 0° C. and rt, e.g. 20° C., for a period of time to ensure the completion of the reaction. An intermediate compound of Formula (VIII) can be obtained commercially or synthesized according to literature procedures.

Intermediate compound of Formula (VIIa) wherein $R^7$ is $C_{1-4}$alkyl, can be prepared via a reaction of halogenation of intermediate of Formula (IX) with a halogenating reagent such as N-iodosuccinimide, in an inert solvent such as dichloromethane, under suitable reaction conditions, such as at a convenient temperature, typically rt, for a period of time to ensure the completion of the reaction. Intermediate compound of Formula (VII), wherein $R^7$ is methyl and $R^{2a}$ is bromo, can be obtained commercially and is a particularly preferred material for use in the synthesis, including large scale, of a variety of final compounds of Formula (I) according to the general procedures described herein. An intermediate compound of Formula (IX) can be obtained commercially or synthesized according to literature procedures.

In Reaction Scheme 12a and 12b, $R^{2a}$ is halo, in particular bromo or iodo, $R^7$ is $C_{1-4}$alkyl, PG is a protecting group, such as for example Boc, and all other variables are defined as in Formula (I).

Reaction Scheme 12a

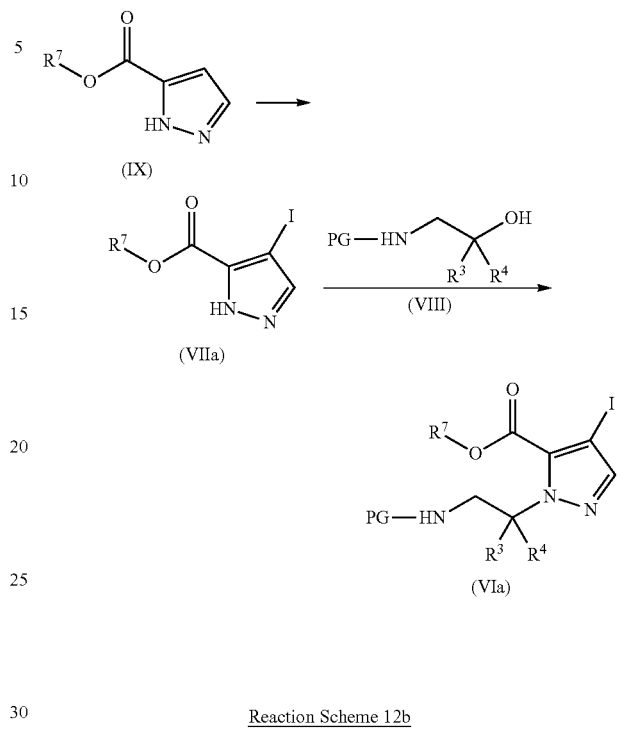

Reaction Scheme 12b

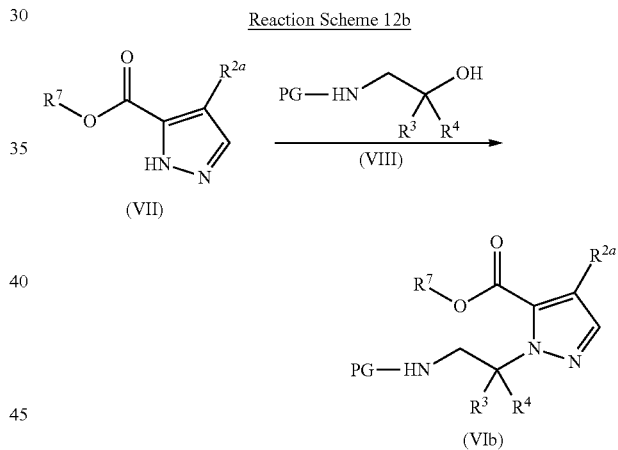

Experimental Procedure 13

Intermediate compound of Formula (IVb) can be prepared via a reaction of boronic ester or boronic acid formation starting from an intermediate of Formula (IVa) with a trans metallating agent such as for example BuLi or a Grignard reagent, a particular example of reagents includes isopropylmagnesium chloride lithium chloride complex solution and a boron species such as 2-isopropoxy-4,4,5,5-tetramethyl-1,3,2-dioxaborolane, in an inert solvent such as anhydrous THF, under suitable reaction conditions, such as at a convenient temperature, typically −25° C., for a period of time to ensure the completion of the reaction. Depending on reaction conditions, boronic ester or boronic acid are obtained. In Reaction Scheme 13, $R^{7a}$ and $R^{8a}$ are H or $C_{1-4}$ alkyl or $R^{7a}$ and $R^{8a}$ are taken together to form for example a bivalent radical of formula —$CH_2CH_2$—, —$CH_2CH_2CH_2$— or —$C(CH_3)_2C(CH_3)_2$—, and all other variables are defined as in Formula (I).

Reaction Scheme 13

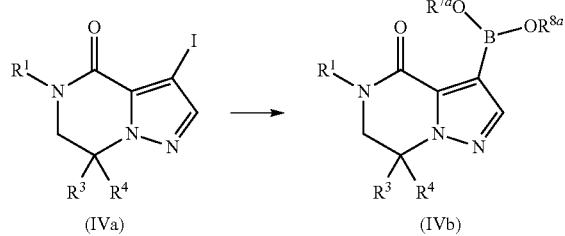

(IVa) → (IVb)

Experimental Procedure 14

Intermediate compound of Formula (IVa) can be prepared via a reaction of halogenation of an intermediate of Formula (X) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction. In an analogous manner, intermediate compound of Formula (Va) can be prepared from intermediate of Formula (XI). In Reaction Schemes 14a and 14b, all variables are defined as in Formula (I).

Reaction Scheme 14a

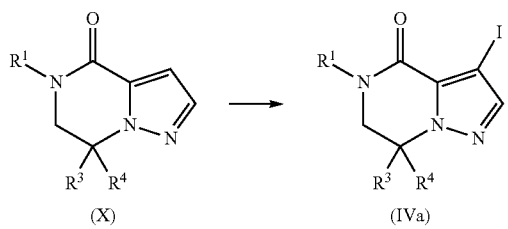

(X) → (IVa)

Reaction Scheme 14b

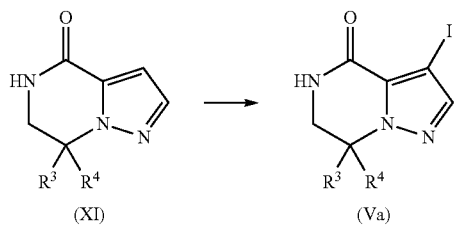

(XI) → (Va)

Experimental Procedure 15

Intermediate compound of Formula (X) can be prepared by a coupling reaction of an intermediate compound of Formula (XI) with an appropriate aryl/heteroaryl halide of Formula (III) where X is halo with a suitable copper(I) catalyst such as copper(I) iodide, in the presence of a ligand, such as N,N'-dimethylethylenediamine, in the presence of a base, such as $Na_2CO_3$, in a suitable solvent, such as toluene, under suitable reaction conditions, such as at a convenient temperature, typically ranging between 100° C. and 140° C., for a period of time to ensure the completion of the reaction. In an analogous manner, intermediate compound of Formula (IV) can be prepared from intermediate of Formula (V). An intermediate compound of Formula (III) can be obtained commercially. In Reaction Schemes 15a and 15b, all variables are defined as in Formula (I) and $R^{2a}$ is halo, in particular bromo or iodo.

Reaction Scheme 15a

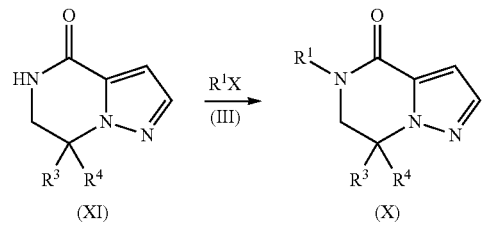

(XI) → (X)

Reactopn Scheme 15b

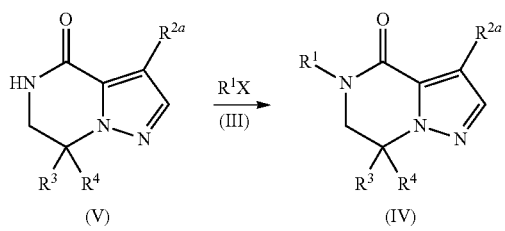

(V) → (IV)

Experimental Procedure 16

Intermediate compound of Formula (XI) can be prepared by removal of the protecting group in an intermediate of Formula (XII), for example in the presence of acidic media, such as hydrochloric acid, in an inert solvent such as 1,4-dioxane, under suitable reaction conditions, such as at a convenient temperature, typically 80° C., for a period of time to ensure the completion of the reaction followed by treatment with a base, such as $Na_2CO_3$ or $NaHCO_3$, under suitable reaction conditions, such as at a convenient temperature, typically ranging between 0° C. and 40° C., for a period of time to ensure the completion of the reaction. In an analogous manner, intermediate compound of Formula (V) can be prepared from intermediate of Formula (VIb). In Reaction Schemes 16a and 16b, $R^{2a}$ is halo, in particular bromo or iodo, $R^7$ is $C_{1-4}$alkyl, PG is a protecting group and all other variables are defined as in Formula (I).

Reaction Scheme 16a

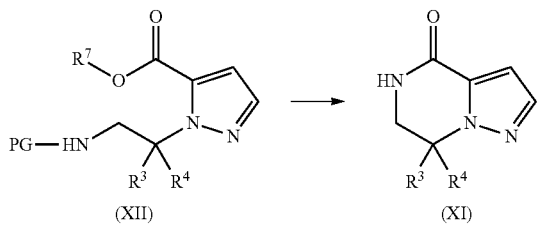

(XII) → (XI)

Reaction Scheme 16b

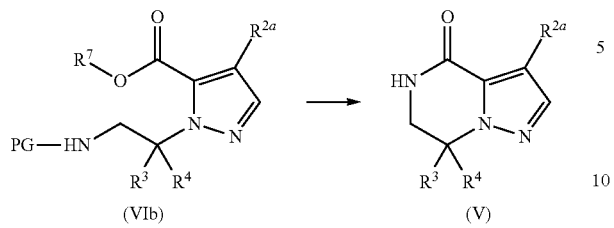

(VIb) → (V)

Experimental Procedure 17

Intermediate compound of Formula (XII) wherein $R^7$ is $C_{1-4}$alkyl and PG is a protecting group, can be prepared by a Mitsunobu type reaction between a compound of Formula (IX) and an appropriate alcohol of Formula (VIII), in the presence of a suitable triarylphosphine, such as triphenylphosphine, or a suitable trialkylphosphine, and a suitable dialkyl azodicarboxylate reagent, such as di-tert-butyl azodicarboxylate, in a suitable inert solvent, such as THF, under suitable reaction conditions, such as at a convenient temperature, typically rt, for a period of time to ensure the completion of the reaction. Intermediate compounds of Formula (IX) and of Formula (VIII) can be obtained commercially or synthesized according to literature procedures. In Reaction Scheme 17, $R^7$ is $C_{1-4}$alkyl, PG is a protecting group and all other variables are defined as in Formula (I).

Reaction Scheme 17

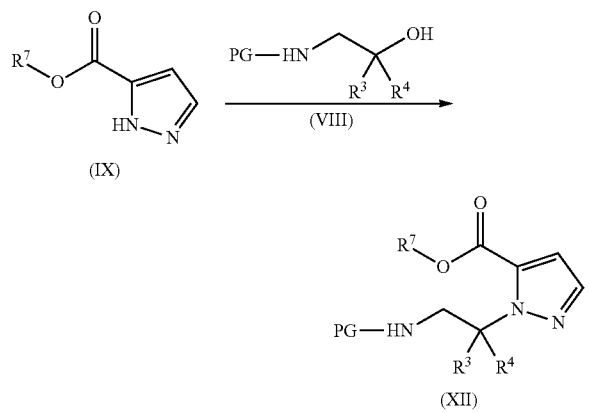

Experimental Procedure 18

Intermediate compound of Formula (IX) wherein $R^7$ is $C_{1-4}$alkyl can be obtained by esterification of the commercially available intermediate compound of Formula (XIII), by methods known to the person skilled in the art, or may be commercially available. The reaction can be performed for example in the presence of an acidic agent, such as sulfuric acid, and an alcohol, such as EtOH, in a suitable solvent, such as EtOH, under suitable reaction conditions, such as at a convenient temperature, typically between 80° C. and 100° C., for a period of time to ensure the completion of the reaction. In Reaction Scheme 18, $R^7$ is $C_{1-4}$alkyl.

Reaction Scheme 18

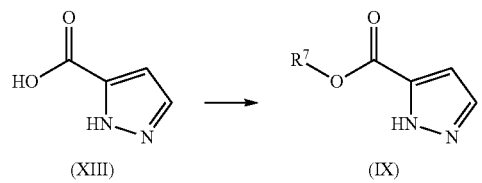

(XIII) → (IX)

Experimental Procedure 19

Intermediate compound of Formula (XI) wherein $R^3$ is H and $R^4$ is $CF_3$ herein referred to as compounds of Formula (XIa) can be prepared by hydrogenation of an intermediate of Formula (XIV) followed by one pot intramolecular cyclization, in the presence of a hydrogenation catalyst, such as Pd/C (palladium on carbon), under hydrogen atmosphere generated by using ammonium formate, in an inert solvent such as MeOH, under suitable reaction conditions, such as at a convenient temperature, typically 70° C., for a period of time to ensure the completion of the reaction. In Reaction Scheme 19, $R^7$ is $C_{1-4}$alkyl.

Reaction Scheme 19

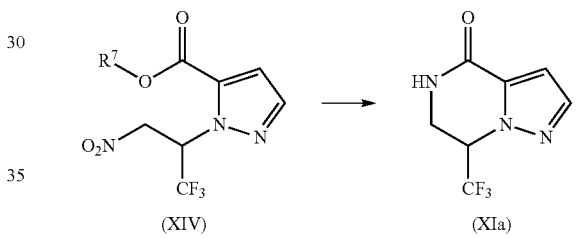

(XIV) → (XIa)

Experimental Procedure 20

Intermediate compound of Formula (XIV) wherein $R^7$ is $C_{1-4}$alkyl, can be prepared by an intermolecular reaction between an appropriate hydrazine of Formula (XV), in the presence of a suitable ketoester of Formula (XVI), such as ethyl pyruvate, in a suitable inert solvent, such as EtOH, under suitable reaction conditions, such as at a convenient temperature, typically rt, for a period of time to ensure the completion of the reaction. Intermediate compound of Formula (XVI) can be obtained commercially or synthesized according to literature procedures. In Reaction Scheme 20, $R^7$ is $C_{1-4}$alkyl.

Reaction Scheme 20

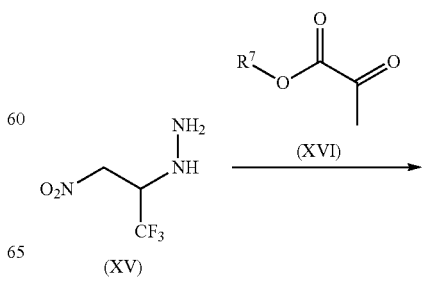

(XV)  (XVI)

-continued

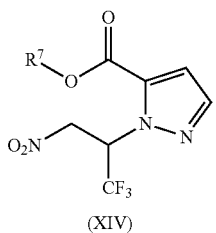

(XIV)

Experimental Procedure 21

Intermediate compound of Formula (XV) can be prepared by a reaction of deprotection of a compound of Formula (XVI) following art known procedures. A compound of Formula (XV) can be obtained by removal of the protecting group such as for example a Boc protecting group in the compound of Formula (XVI), in the presence of acidic media, such as hydrochloric acid, in an inert solvent such as MeOH, under suitable reaction conditions, such as at a convenient temperature, typically rt, for a period of time to ensure the completion of the reaction.

Intermediate compound of Formula (XVI) can be obtained by addition of a protected hydrazine of Formula (XVIII) to 3,3,3-trifluoro-1-nitro-prop-1-ene (XVII) (prepared as described in *J. Fluorine Chem.* 2008, 767-774). In Reaction Scheme 21, PG is a protecting group, for example BOC.

Reaction Scheme 21

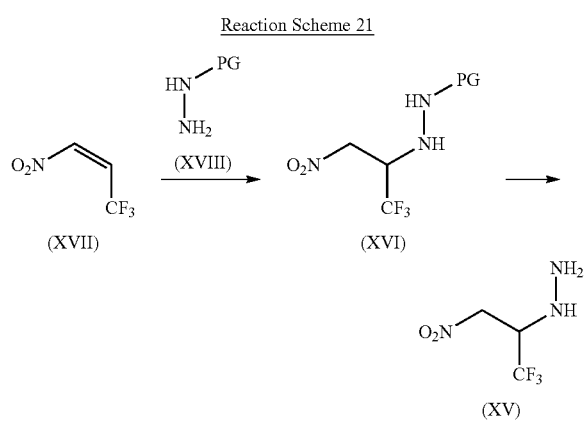

In order to obtain the HCl salt forms of the compounds, several procedures known to those skilled in the art can be used. In a typical procedure, for example, the free base can be dissolved in DIPE or Et$_2$O and subsequently, a 6N HCl solution in 2-propanol, 4N HCl solution in dioxane, or a 1N HCl solution in Et$_2$O can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds provided in this invention are negative allosteric modulators (NAMs) of metabotropic glutamate receptors, in particular they are negative allosteric modulators of mGluR2. The compounds of the present invention do not appear to bind to the glutamate recognition site, the orthosteric ligand site, but instead to an allosteric site within the seven transmembrane region of the receptor. In the presence of glutamate, the compounds of this invention decrease the mGluR2 response. The compounds provided in this invention are expected to have their effect at mGluR2 by virtue of their ability to decrease the response of such receptors to glutamate, attenuating the response of the receptor.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof for use as a medicament.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of negative allosteric modulators of mGluR2.

Also, the present invention relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of negative allosteric modulators of mGluR2.

In particular, the neurological and psychiatric disorders associated with glutamate dysfunction, include one or more of the following central nervous system conditions or diseases: mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

In particular, the central nervous system disorder is a psychotic disorder selected from the group of schizophrenia (in particular in antipsychotic-stabilized patients), schizophreniform disorder, schizoaffective disorder, delusional disorder, brief psychotic disorder, and substance-induced psychotic disorder.

In particular, the central nervous system disorder is a substance-related disorder selected from the group of alcohol dependence, alcohol abuse, amphetamine dependence, amphetamine abuse, caffeine dependence, caffeine abuse, cannabis dependence, cannabis abuse, cocaine dependence, cocaine abuse, hallucinogen dependence, hallucinogen abuse, nicotine dependence, nicotine abuse, opioid dependence, opioid abuse, phencyclidine dependence, and phencyclidine abuse.

In particular, the central nervous system disorder is a mood disorder selected from the group of major depressive disorder, depression, treatment resistant depression, dysthymic disorder, cyclothymic disorder, and substance-induced mood disorder.

In particular, the central nervous system disorder is a disorder usually first diagnosed in infancy, childhood, or adolescence selected from mental retardation, learning disorder, motor skills disorder, communication disorder, attention-deficit and disruptive behaviour disorders (such as Attention-Deficit/Hyperactivity Disorder (ADHD)). An additional disorder usually first diagnosed in infancy, childhood, or adolescence is autistic disorder.

In particular, the central nervous system disorder is a cognitive disorder selected from the group of dementia, in particular, dementia of the Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and substance-induced persisting dementia.

In particular, the central nervous system disorder is an amnestic disorder, such as substance-induced persisting amnestic disorder.

As already mentioned hereinabove, the term "treatment" does not necessarily indicate a total elimination of all symptoms, but may also refer to symptomatic treatment in any of the disorders mentioned above. In particular, symptoms that may be treated include but are not limited to, memory impairment in particular in dementia or in major depressive disorder, age-related cognitive decline, mild cognitive impairment, and depressive symptoms.

Of the disorders mentioned above, the treatment of dementia, major depressive disorder, depression, treatment resistant depression, attention-deficit/hyperactivity disorder and schizophrenia, in particular in antipsychotic-stabilized patients, are of particular importance.

The fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opiod use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; somatic symptom disorders; hypersomnolence disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder. In particular, the disorder is autism. Specifiers associated with ASD include those where the individual has a genetic disorder, such as in Rett syndrome or Fragile X syndrome.

Therefore, the invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in the treatment of any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in treating any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the treatment or prevention, in particular treatment, of any one of the diseases mentioned hereinbefore.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof, or an N-oxide thereof, or a pharmaceutically acceptable salt or solvate thereof, in particular a compound of Formula (I) or a stereoisomeric form thereof, or a pharmaceutically acceptable salt or a solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a subject in need thereof.

One skilled in the art will recognize that a therapeutically effective amount of the NAMs of the present invention is the amount sufficient to modulate the activity of the mGluR2 and that this amount varies inter alia, depending on the type of disease, the concentration of the compound in the therapeutic formulation, and the condition of the patient. Generally, an amount of NAM to be administered as a therapeutic agent for treating diseases in which modulation of the mGluR2 is beneficial, such as the disorders described herein, will be determined on a case by case by an attending physician.

Generally, a suitable dose is one that results in a concentration of the NAM at the treatment site in the range of 0.5 nM to 200 μM, and more usually 5 nM to 50 μM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone. Examples of such combinations include the compounds of the invention in combination with antipsychotic(s), NMDA receptor antagonists (e.g. memantine), NR2B antagonists, acetylcholinesterase inhibitors (e.g. donepezil, galantamine, physostigmine and rivastigmine) and/or antidepressant neurotransmitter reuptake inhibitors. Particular combinations include the compounds of the invention in combination with antipsychotics, or the compounds of the invention in combination with memantine and/or NR2B antagonists.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), an N-oxide, a pharmaceutically acceptable salt thereof, a solvate thereof or a stereochemically isomeric form thereof, more in particular, a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the N-oxides thereof, the pharmaceutically acceptable salts thereof, the solvates and the stereochemically isomeric forms thereof, more in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-3-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional drug selected from the group of antipsychotics; NMDA receptor antagonists (e.g. memantine); NR2B antagonists; acetylcholinesterase inhibitors (e.g. donepezil, galantamine, physostigmine and rivastigmine) and/or antidepressant neurotransmitter reuptake inhibitors. In particular, the present invention also relates to a combination of a compound according to the present invention and antipsychotic(s), or to a combination of a compound according to the present invention and memantine and/or an NR2B antagonist. The present invention also relates to such a combination for use as a medicine. The present invention also relates to a product comprising (a) a compound according to the present invention, an N-oxide thereof, a pharmaceutically acceptable salt thereof or a solvate thereof, in particular, a pharmaceutically acceptable salt thereof or a solvate thereof, and (b) an additional component selected from antipsychotics, NMDA receptor antagonists (e.g. memantine), NR2B antagonists, acetylcholinesterase inhibitors and/or antidepressant neurotransmitter reuptake inhibitor(s), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular negative mGluR2 allosteric modulators. More in particular the additional component (b) is selected from antipsychotic(s) or memantine and/or an NR2B antagonist. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "Boc" or "BOC" means tert-Butyloxycarbonyl; "CI" means chemical ionisation; "DAD" means diode-array detector; "THF" means tetrahydrofuran; "TEA" means triethylamine; "DIPE" means diisopropylether; "DMF" means N,N-dimethylformamide; "Et$_2$O" means diethylether; "EtOAc" means ethyl acetate; "DCM" means dichloromethane; "DMSO" means dimethylsulfoxide; "L" means liter; "LRMS" means low-resolution mass spectrometry/spectra; "HATU" means 2-(7-aza-1H-benzotriazole-1-yl)-1,1,3,3-tetramethyluronium hexafluorophosphate; "HPLC" means high performance liquid chromatography; "HRMS" means high-resolution mass spectrometry/spectra; "mL" or "ml" means milliliter; "NH$_4$Ac" means ammonium acetate; "EtOH" means ethanol; "ES" means electrospray; "iPrOH" means isopropanol; "iPrNH$_2$" means isopropylamine; "MeOH" means methanol; "eq" means equivalent(s); "RP" means Reverse Phase; "rt" means room temperature; "M.p." means melting point; "min" means minutes; "h" means hour(s); "s" means second(s); "TOF" means time of flight; "QTOF" means Quadrupole-Time of Flight; "sat." means saturated; "SFC" means supercritical fluid chromatography; "sol." means solution.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques.

Automated flash column chromatography was performed using ready-to-connect cartridges, on irregular silica gel, particle size 15-40 μm (normal phase disposable flash columns) on different flash systems: either a SPOT or LAFLASH systems from Armen Instrument, or PuriFlash® 430evo systems from Interchim, or 971-FP systems from Agilent, or Isolera 1SV systems from Biotage.

Nuclear Magnetic Resonance (NMR): For a number of compounds, $^1$H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

Synthesis of Intermediate Compounds

Intermediate 1 (I-1)

2H-Pyrazole-3-carboxylic acid ethyl ester (I-1)

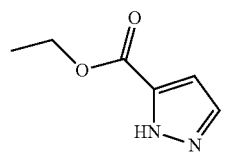

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K$_2$CO$_3$ and extracted with EtOAc. The organic layer was separated, dried (MgSO$_4$), filtered and the solvent evaporated in vacuo to yield intermediate compound I-1 as a white solid (2.28 g, 93% purity, 94%) which was used in the following step without further purification.

Intermediate 2 (I-2)

4-Iodo-2H-pyrazole-3-carboxylic acid ethyl ester (I-2)

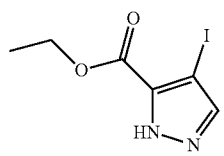

Intermediate I-1 (100 g, 0.68 mol), N-iodosuccinimide (213.5 g, 0.95 mol) were dissolved in DCM (2 L). The mixture was stirred at rt for 24 h. The mixture was treated with a sat. sol. of $Na_2S_2O_3$ and a sat. sol. of $Na_2CO_3$ and extracted with DCM. The organic layer was separated, dried ($MgSO_4$), filtered and the solvent evaporated in vacuo to yield intermediate compound I-2 as a white solid (160 g, 85%).

Intermediate 3 (I-3)

(2R-Hydroxy-propyl)-carbamic acid tert-butyl ester (I-3)

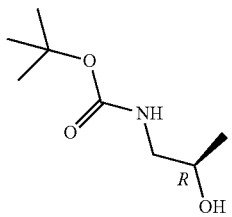

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried ($Na_2SO_4$), filtered and the solvents evaporated in vacuo to yield intermediate I-3 as a colorless oil (47 g, quant.). The product was used in the next step without further purification.

Intermediate 4 (I-4)

(2S-Hydroxy-propyl)-carbamic acid tert-butyl ester (I-4)

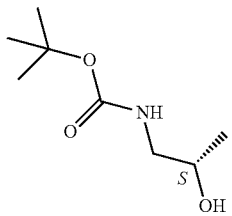

Intermediate compound I-4 was synthesized following a similar approach described for intermediate I-3. Starting from (S)-(−)-1-amino-2-propanol (3 mL, 38.1 mmol), intermediate compound I-4 was obtained as a colorless oil (6.13 g, 89% purity, 82%), that solidified upon standing at rt.

Intermediate 5 (I-5)

(2-Hydroxy-propyl)-carbamic acid tert-butyl ester (I-5)

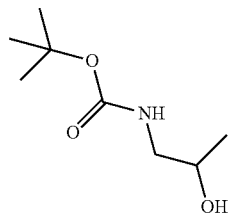

Intermediate compound I-5 was synthesized following a similar approach described for intermediate I-3. Starting from 1-amino-2-propanol (3 mL, 38.1 mmol), intermediate compound I-5 was obtained as a colorless oil (6.69 g, 98%).

Intermediate 6 (I-6)

2-(2-tert-Butoxycarbonylamino-1S-methyl-ethyl)-4-iodo-2H-pyrazole-3-carboxylic acid ethyl ester (I-6)

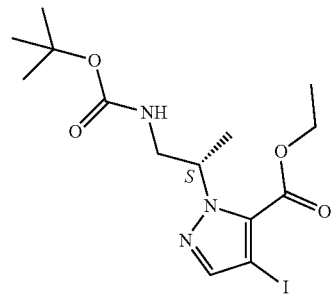

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in Heptane 0/100 to 30/70). The desired fractions were collected and the solvents evaporated in vacuo to give intermediate compound I-6 as a colorless oil (4.9 g, 91% purity, 93%).

Intermediate 7 (I-7)

2-(2-tert-Butoxycarbonylamino-1R-methyl-ethyl)-4-iodo-2H-pyrazole-3-carboxylic acid ethyl ester (I-7)

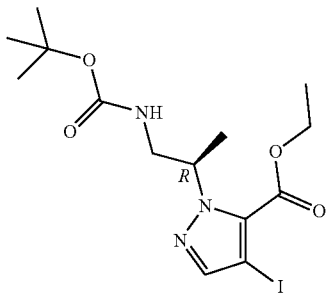

Intermediate compound I-7 was synthesized following a similar approach described for intermediate I-6. Starting from intermediate I-2 (1.18 g, 4.44 mmol) and intermediate I-4 (1.75 g, 8.87 mmol), intermediate compound I-7 was obtained as a white solid as two fractions (790 mg, 41%) and (900 mg, 86% purity, 41%).

Intermediate 8 (I-8)

2-(2-tert-Butoxycarbonylamino-1-methyl-ethyl)-4-iodo-2H-pyrazole-3-carboxylic acid ethyl ester (I-8)

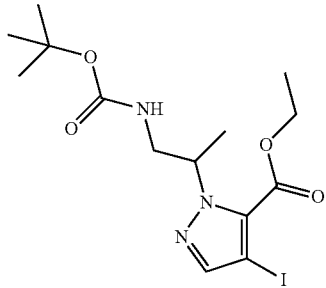 [SMILES: CCOC(=O)c1c(I)cnn1C(C)CNC(=O)OC(C)(C)C]

Intermediate compound I-8 was synthesized following a similar approach described for intermediate I-6. Starting from intermediate I-2 (2.87 g, 10.79 mmol) and intermediate I-5 (3.78 g, 21.6 mmol), intermediate compound I-8 was obtained as a colorless oil (3.46 g, 75%).

Intermediate 9 (I-9)

2-(2-tert-Butoxycarbonylamino-ethyl)-4-iodo-2H-pyrazole-3-carboxylic acid ethyl ester (I-9)

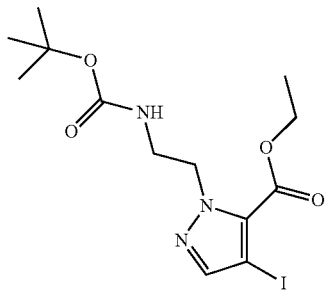 [SMILES: CCOC(=O)c1c(I)cnn1CCNC(=O)OC(C)(C)C]

Intermediate compound I-9 was synthesized following a similar approach described for intermediate I-6. Starting from intermediate I-2 (3.18 g, 11.95 mmol) and N-(tert-butoxycarbonyl)ethanolamine (3.78 g, 23.9 mmol), intermediate compound I-9 was obtained as a colorless oil (3.46 g, 75%).

Intermediate 10 (I-10)

2-(2-tert-Butoxycarbonylamino-1S-methyl-ethyl)-2H-pyrazole-3-carboxylic acid ethyl ester (I-10)

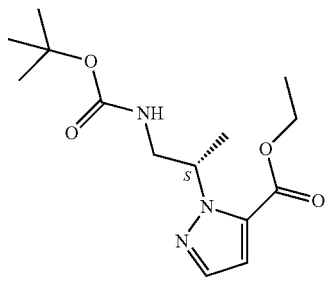

Intermediate compound I-10 was synthesized following a similar approach described for intermediate I-6. Starting from intermediate I-1 (25.82 g, 184.25 mmol) and intermediate I-3 (47.16 g, 239.5 mmol), intermediate compound I-10 was obtained as a yellow oil (123 g, quant) which was used in the following step without further purification.

Intermediate 11 (I-11)

2-(2-Amino-1S-methyl-ethyl)-4-iodo-2H-pyrazole-3-carboxylic acid ethyl ester hydrochloride salt (I-11)

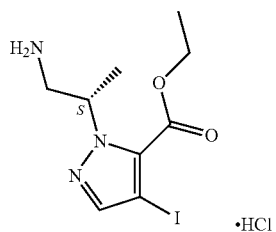

A 4M solution of HCl in 1,4-dioxane (10 mL, 40 mmol) was added to a solution of intermediate I-6 (4.2 g, 9.63 mmol) in acetonitrile (20 mL). The mixture was stirred at 80° C. for 2 h. The solvent was evaporated in vacuo to yield intermediate compound I-11 (3.5 g, 97%).

71

Intermediate 12 (I-12)

2-(2-Amino-1S-methyl-ethyl)-2H-pyrazole-3-carboxylic acid ethyl ester hydrochloride salt (I-12)

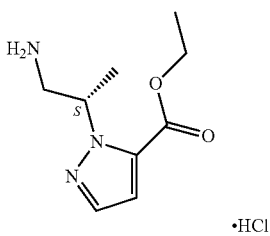

Intermediate compound I-12 was synthesized following a similar approach described for intermediate I-11. Starting from intermediate I-10 (54.79 g, 184.25 mmol) and a 4M solution of HCl in 1,4-dioxane (415 mL, 1.66 mol), intermediate compound I-12 was obtained as a white solid (32.5 g, 82% purity, 75%) which was used in the following step without further purification.

Intermediate 13 (I-13)

3-Iodo-7S-methyl-6,7-dihydro-5H-pyrazolo[1,5-a]pyrazin-4-one (I-13)

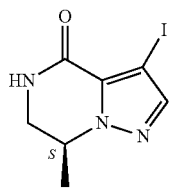

Intermediate I-11 as HCl salt (180 g, 350.4 mmol) was dissolved in a sat. sol. of NaHCO$_3$ (2 L). The mixture was stirred at rt for 12 h. The mixture was diluted with water and extracted with DCM. The organic layers were separated, dried (Na$_2$SO$_4$), filtered and the solvents evaporated in vacuo. Then the residue was washed with ten-butyl methyl ether to yield intermediate compound I-13 (92 g, 90%), mp 182.6-186.1° C. $^1$H NMR (500 MHz, DMSO-d$_6$) δ ppm 1.42 (d, J=6.65 Hz, 3H) 3.26-3.35 (m, 1H) 3.57-3.71 (m, 1H) 4.44-4.60 (m, 1H) 7.68 (s, 1H) 8.26 (br. s., 1H). LC-HRMS (ESI+) Calculated for C$_7$H$_8$IN$_3$O (M+H)$^+$: 277.9790. Found: m/z 277.9796 (+0.6 mDa), Rt=0.76 min (Method 13, see table 2). [α]=+11.7° (589 nm, c 1.00 w/v %, CH$_3$OH, 25° C.).

72

Intermediate 13a (I-13a)

(7S)-3-Bromo-7-methyl-6,7-dihydro-5H-pyrazolo[1,5-a]pyrazin-4-one (I-13a)

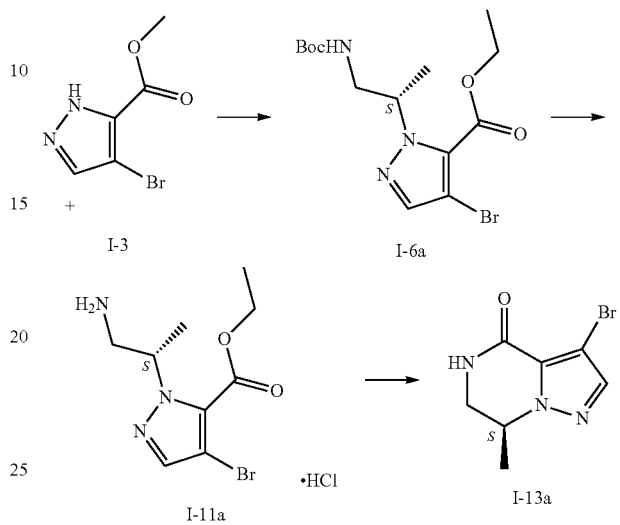

Intermediate 13a was prepared in 71% yield according to the following general description of a synthesis performed at a large scale:

A mixture of methyl 4-bromo-1H-pyrazole-5-carboxylate (referred to as "pyrazole SM" herein) (1 eq.), triphenyl phosphine (1.2 eq.), I-3 (1.2 eq.) and anhydrous THF (15 mL/g pyrazole SM) under nitrogen was cooled to 5-10° C. Di-tert-butyl azodicarboxylate (1.2 eq.) was added in portions at 5-15° C. under nitrogen. The solution was heated to 20-30° C. and stirred at 20-30° C. for 2-3 h. The obtained solution was concentrated and co-evaporated with isopropyl acetate to remove THF to afford a solution of crude 4-bromo-1-[(1S)-1-[[(1,1-dimethylethoxy)carbonyl]amino]ethyl]-1H-pyrazole-5-carboxylic acid methyl ester I-6a in isopropyl acetate (20 mL/g pyrazole SM). To the solution of I-6a was bubbled HCl gas at 15-30° C. until cleavage of the Boc protecting group was completed. The suspension was bubbled with nitrogen gas to remove most of the HCl gas. The suspension was concentrated to a volume of about 5 mL/g pyrazole SM below 50° C., and then isopropyl acetate (15 mL/g pyrazole SM) was added to the residue. Water (10 mL/g pyrazole SM) was added at 10-20° C. The mixture was stirred at 10-20° C. for 20-30 min. The mixture was filtered and the aqueous layer was separated. The organic layer was extracted with water (2 mL/g pyrazole SM). The combined aqueous layers were washed with isopropyl acetate (2×10 mL/g pyrazole SM) to remove residual triphenylphosphine oxide. I-11a was obtained as an aqueous solution (6.25 mL/g pyrazole SM). To the aqueous solution of I-11a was added potassium carbonate (~1 g/g pyrazole SM) to adjust to pH=8-9 at 10-25° C. The mixture was stirred at 10-25° C. for 5-6 h and solid I-13a precipitated. The suspension was cooled to 5-10° C. and stirred at 5-10° C. for 2-3 h, it was then filtered and washed with water (1 mL/g pyrazole SM) and heptanes (1 mL/g pyrazole SM), then dried in vacuo at 40-45° C. to afford I-13a as a white solid, mp. 196.12° C. $^1$H NMR (500 MHz, CDCl$_3$) δ ppm 1.61 (d, J=6.36 Hz, 3H) 3.48 (ddd, J=12.72, 7.22, 2.60 Hz, 1H) 3.75-3.84 (m, 1H)

4.49-4.59 (m, 1H) 6.54 (br. s., 1H) 7.56 (s, 1H). LC-HRMS (ESI+) Calculated for $C_7H_8BrN_3O$ (M+H)$^+$: 229.9929. Found: m/z 229.9931 (+0.2 mDa), Rt=0.62 min (Method 13, see table 2). [α]=+25.2° (589 nm, c 0.53 w/v %, DMF, 20° C.).

Intermediate 14 (I-14)

7S-Methyl-6,7-dihydro-5H-pyrazolo[1,5-a]pyrazin-4-one (I-14)

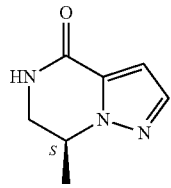

Intermediate compound I-14 was synthesized following a similar approach described for intermediate I-13. Starting from intermediate I-12 (32.5 g, 139.1 mmol), intermediate compound I-14 was obtained as a solid (14.8 g, 70%).

Intermediate 15 (I-15)

3-Iodo-7R-methyl-6,7-dihydro-5H-pyrazolo[1,5-a]pyrazin-4-one (I-15)

A 4M solution of HCl in 1,4-dioxane (2.3 mL, 9.2 mmol) was added to a solution of intermediate I-7 (0.78 g, 1.84 mmol) in $CH_3CN$ (8.3 mL). The mixture was stirred at 80° C. for 7 h. After Boc deprotection was complete, part of the solvent was evaporated in vacuo and the solution was basified with a sat. sol. of $NaHCO_3$. The mixture was stirred for 16 h at rt. Then the mixture was diluted with water and extracted with DCM. The organic layers were separated, dried ($MgSO_4$), filtered and the solvents evaporated in vacuo. The solid was triturated with DIPE to yield intermediate compound I-15 as a white solid (0.42 g, 82%).

Intermediate 16 (I-16)

3-Iodo-7-methyl-6,7-dihydro-5H-pyrazolo[1,5-a]pyrazin-4-one (I-16)

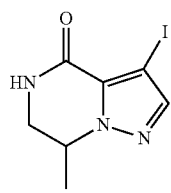

Intermediate compound I-16 was synthesized following a similar approach described for intermediate I-15. Starting from intermediate I-8 (3.46 g, 8.17 mmol), intermediate compound I-16 was obtained as a white solid (1.87 g, 82%).

Intermediate 17 (I-17)

3-Iodo-6,7-dihydro-5H-pyrazolo[1,5-a]pyrazin-4-one (I-17)

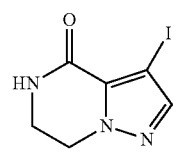 [SMILES: O=C1NCCn2ncc(I)c21]

Intermediate compound I-17 was synthesized following a similar approach described for intermediate I-15. Starting from intermediate I-9 (4.89 g, 11.95 mmol), intermediate compound I-17 was obtained as a white solid (1.87 g, 59%).

Intermediate 18 (I-18)

7S-Methyl-3-(2-methyl-pyridin-4-yl)-6,7-dihydro-5H-pyrazolo[1,5-a]pyrazin-4-one (I-18)

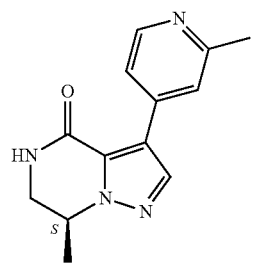

Pd(PPh$_3$)$_4$ (0.33 g, 0.29 mmol) was added to a stirred suspension of intermediate I-13 (1.6 g, 5.77 mmol) and 2-picoline-4-boronic acid (0.95 g, 6.93 mmol) in 1,4-dioxane (8 mL) and a sat. sol. of $NaHCO_3$ (4 mL) in a sealed tube under nitrogen. The mixture was stirred at 100° C. for 16 h. Then the mixture was diluted with $H_2O$ and extracted with DCM. The organic layer was separated, dried ($Na_2SO_4$), filtered and the solvent evaporated in vacuo. The crude product was purified by flash column chromatography (silica; MeOH in DCM 0/100 to 6/94). The desired fractions were collected and the solvents evaporated in vacuo to yield intermediate compound I-18 as a white solid (1 g, 71%), mp 173.20° C. $^1$H NMR (500 MHz, CDCl$_3$) δ ppm 1.67 (d, J=6.65 Hz, 3H) 2.60 (s, 3H) 3.52 (ddd, J=12.79, 7.15, 2.89 Hz, 1H) 3.84 (dt, J=12.72, 4.00 Hz, 1H) 4.57-4.66 (m, 1H) 6.10 (br. s., 1H) 7.51 (dd, J=5.20, 1.44 Hz, 1H) 7.55 (s, 1H) 7.78 (s, 1H) 8.50 (d, J=5.20 Hz, 1H). LC-HRMS (ESI+) Calculated for $C_{13}H_{14}IN_4O$ (M+H)$^+$: 243.1246. Found: m/z 243.1250 (+0.4 mDa), Rt=0.82 min (Method 13, see table 2). [α]=+32.8° (589 nm, c 0.52 w/v %, DMF, 20° C.).

Intermediate I-18 was alternatively prepared in 70% yield according to the following general description of a synthesis performed at a large scale:

A mixture of I-13a (1 eq.), 2-methyl-4-(4,4,5,5-tetramethyl-1,3,2-dioxaborolan-2-yl)-pyridine (1.1 eq.), anhydrous potassium phosphate (2 eq.), DME (7.5 mL/g I-13a) and purified water (2.5 mL/g I-13a) was evacuated and backfilled with nitrogen 3 times. Triphenyl phosphine (0.261 eq.) and palladium (II) acetate (0.131 eq.) were added in one portion under nitrogen. The mixture was evacuated and backfilled with nitrogen 3 times again, it was heated to 75-80° C. and stirred at 75-80° C. for 12-15 h under nitrogen. The aqueous layer was separated at 60-70° C. and discarded, and then water (8 mL/g I-13a) was added to the organic layer. DME was removed by concentration below 40° C. Isopropyl acetate (15 mL/g I-13a) was added, the pH of the mixture was adjusted to I-2 with conc. HCl. The mixture was filtered and the filter cake was washed with water (1 mL/g I-13a), the aqueous layer was separated and the organic layer was extracted with water (2 mL/g I-13a). The combined aqueous layers were washed with Isopropyl acetate (2×15 mL/g I-13a). The aqueous layer was concentrated to remove residual DME and isopropyl acetate. MTBE (2 mL/g I-13a) was added and the mixture was cooled to 0-5° C., stirred at 0-5° C. for 2-3 h. I-18 was filtered, washed with cooled water (1 mL/g I-13a), and dried in vacuum at 45-50° C. to afford I-18 as an off-white solid.

Intermediate 19 (I-19)

7R-Methyl-3-(2-methyl-pyridin-4-yl)-6,7-dihydro-5H-pyrazolo[1,5-a]pyrazin-4-one (I-19)

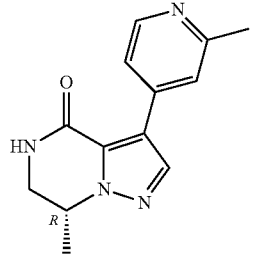

Intermediate compound I-19 was synthesized following a similar approach described for intermediate I-18. Starting from intermediate I-15 (0.62 g, 2.24 mmol), intermediate compound I-19 was obtained as a white solid (0.38 g, 70%).

Intermediate 20 (I-20)

7-Methyl-3-(2-methyl-pyridin-4-yl)-6,7-dihydro-5H-pyrazolo[1,5-a]pyrazin-4-one (I-20)

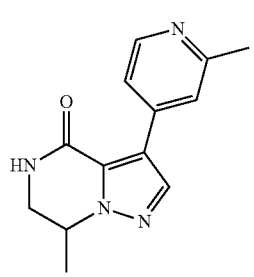

Intermediate compound I-20 was synthesized following a similar approach described for intermediate I-18. Starting from intermediate I-16 (846 mg, 3.05 mmol), intermediate compound I-20 was obtained as a yellowish solid (585 mg, 79%).

Intermediate 18 (I-18) and Intermediate 19 (I-19)

7S-Methyl-3-(2-methyl-pyridin-4-yl)-6,7-dihydro-5H-pyrazolo[1,5-a]pyrazin-4-one (I-18) and
7R-Methyl-3-(2-methyl-pyridin-4-yl)-6,7-dihydro-5H-pyrazolo[1,5-a]pyrazin-4-one (I-19)

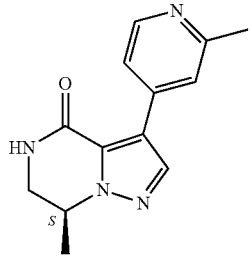

(I-18)

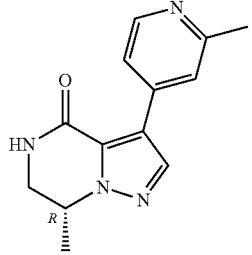 [SMILES: Cc1cc(-c2cnn3c2C(=O)NCC3C)ccn1]

(I-19)

Intermediate I-20 (975 mg, 4.02 mmol) was purified by RP HPLC (Stationary phase: irregular bare silica 40 g), Mobile phase: 0.5% NH₄OH, 95% DCM, 5% MeOH) then by chiral SFC ((Stationary phase: CHIRALCEL® OD-H 5 µm 250×20 mm), (Mobile phase: 75% CO$_2$, 25% iPrOH (0.3% iPrNH$_2$)) to yield intermediate compound I-18 (390 mg) and intermediate compound I-19 (395 mg).

Intermediate 21 (I-21)

3-(2-Methyl-pyridin-4-yl)-6,7-dihydro-5H-pyrazolo[1,5-a]pyrazin-4-one (I-21)

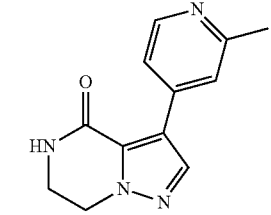 [SMILES: Cc1cc(-c2cnn3c2C(=O)NCC3)ccn1]

Intermediate compound I-21 was synthesized following a similar approach described for intermediate I-18. Starting from intermediate I-17 (908 mg, 3.45 mmol), intermediate compound I-21 was obtained as a white solid (0.5 g, 63%).

Intermediate 22 (I-22)

7S-Methyl-5-(4-trifluoromethyl-phenyl)-6,7-dihydro-5H-pyrazolo[1,5-a]pyrazin-4-one (I-22)

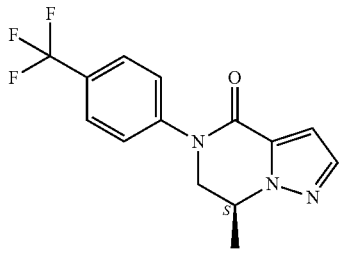

A mixture of intermediate I-14 (5 g, 33.01 mmol), copper (I) iodide (3.78 g, 19.85 mmol) and $K_2CO_3$ (9.14 g, 66.15 mmol) in toluene (150 mL) was nitrogen flushed for a few min. Then 4-bromobenzotrifluoride (9.3 mL, 66.1 mmol) and N,N'-dimethylethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried ($Na_2SO_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-22 as a pale yellow oil (9.6 g, 98%).

Intermediate 23 (I-23)

3-Iodo-7S-methyl-5-(4-trifluoromethyl-phenyl)-6,7-dihydro-5H-pyrazolo[1,5-a]pyrazin-4-one (I-23)

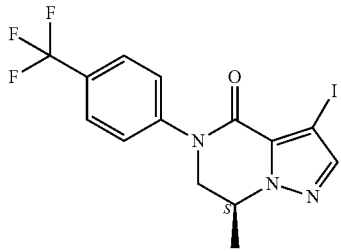

Iodine (11.55 g, 45.5 mmol) was added to a solution of intermediate I-22 (19.2 g, 65.0 mmol) and ammonium cerium(IV) nitrate (24.95 g, 45.5 mmol) in acetonitrile (350 mL). The mixture was stirred at 70° C. for 1 h. Then the mixture was diluted with EtOAc and washed with a sat. sol. of $Na_2S_2O_3$ and brine. The organic layer was separated, dried ($Na_2SO_4$), filtered and the solvents evaporated in vacuo. The residue was precipitated with DIPE and then was purified by short column chromatography (silica; DCM) then by flash column chromatography (silica; DCM in heptane 50/50 to 100/0). The desired fractions were collected and the solvents evaporated in vacuo to yield intermediate compound I-23 as a solid (24.8 g, 90%).

Intermediate 24 (I-24)

2-Amino-pyridine-4-boronic acid (I-24)

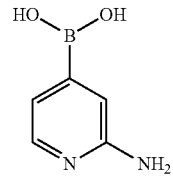

2-Amino-4-chloropyridine (3 g, 23.34 mmol) was added to a mixture of bis(pinacolato)diboron (17.78 g, 70.01 mmol), 2-dicyclohexylphosphino-2',6'-dimethoxybiphenyl (0.38 g, 0.93 mmol), tris(dibenzylideneacetone)dipalladium (0) (0.21 g, 0.23 mmol) and potassium acetate (3.89 g, 39.67 mmol) in 1,4-dioxane (78 mL) under nitrogen atmosphere. The resulting mixture was stirred at 100° C. for 3 h. The hot reaction mixture was filtered through diatomaceous earth and washed with EtOAc. The organic layer was evaporated in vacuo. The residue was precipitated with DIPE to yield intermediate compound I-24 as a white solid (5.84 g, quant.) that was used in the next reaction step without further purification.

Intermediate 25 (I-25)

3-(2-Methoxy-pyridin-4-yl)-7S-methyl-6,7-dihydro-5H-pyrazolo[1,5-a]pyrazin-4-one (I-25)

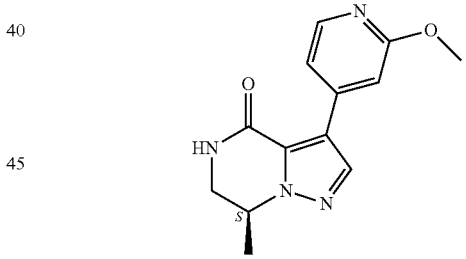

Pd(PPh$_3$)$_4$ (0.42 g, 0.36 mmol) was added to a stirred suspension of intermediate I-13 (2 g, 7.22 mmol) and 2-methoxypyridine-4-boronic acid (1.77 g, 11.55 mmol) in 1,4-dioxane (16 mL) and a sat. sol. of $NaHCO_3$ (8 mL) in a sealed tube under nitrogen atmosphere. The mixture was stirred at 100° C. for 3 days. Then the mixture was diluted with $H_2O$ and extracted with DCM. The organic layer was separated, dried ($Na_2SO_4$), filtered and the solvent evaporated in vacuo. The crude product was purified by flash column chromatography (silica; MeOH in DCM 0/100 to 6/94). The desired fractions were collected and the solvents evaporated in vacuo to yield intermediate compound I-25 as a pale brown solid (1.6 g, 86%).

Intermediate 26 and Final Compound 215 (I-26 and Co. No. 215)

3-(2-Chloro-pyridin-4-yl)-7S-methyl-5-(4-trifluoromethyl-phenyl)-6,7-dihydro-5H-pyrazolo[1,5-a]pyrazin-4-one (I-26 and Co. No. 215)

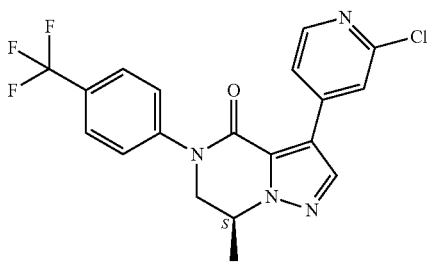

This reaction was divided in four batches to a combined total amount indicated herein and combined for workup and purification. Pd(PPh$_3$)$_4$ (401 mg, 0.35 mmol) was added to a stirred suspension of intermediate I-23 (2.92 g, 6.94 mmol) and 2-chloropyridine-4-boronic acid (1.42 g, 9.02 mmol) in 1,4-dioxane (39 mL) and a sat. sol. of NaHCO$_3$ (19.5 mL). The mixture was stirred at 150° C. for 10 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; EtOAc in DCM 0/100 to 20/80). The desired fractions were collected and the solvents evaporated in vacuo to yield intermediate compound I-26 as a yellow solid (1.84 g, 65%).

Intermediate 27 (I-27)

7S-Methyl-5-(4-trifluoromethyl-phenyl)-3-(2-vinyl-pyridin-4-yl)-6,7-dihydro-5H-pyrazolo[1,5-a]pyrazin-4-one (I-27)

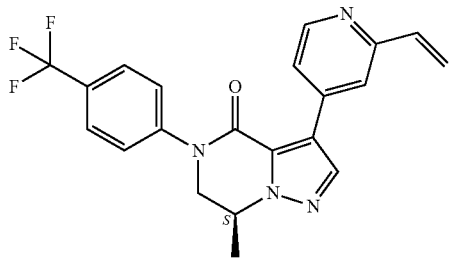

Pd(PPh$_3$)$_4$ (51 mg, 0.044 mmol) was added to a stirred suspension of intermediate I-26 (600 mg, 1.48 mmol) and vinylboronic acid pinacolester (0.325 mL, 1.92 mmol) in 1,4-dioxane (10 mL) and a sat. sol. of NaHCO$_3$ (5 mL). The mixture was stirred at 150° C. for 15 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; EtOAc in DCM 0/100 to 30/70). The desired fractions were collected and the solvents evaporated in vacuo to yield intermediate compound I-27 as a yellow oil (0.53 g, 90%).

Intermediate 28 (I-28)

Ethyl 2-[1-[(tert-butoxycarbonylamino)methyl]-2-[tert-butyl)dimethyl)silyl]oxy-ethyl]-4-iodo-pyrazole-3-carboxylate (I-28)

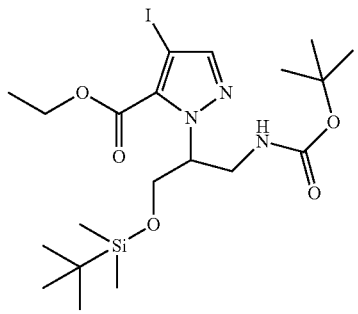 [SMILES: CCOC(=O)c1c(I)cnn1C(CNC(=O)OC(C)(C)C)CO[Si](C)(C)C(C)(C)C]

Di-tert-butyl azodicarboxylate (1.97 g, 8.53 mmol) was added to a stirred solution of 4-iodo-1H-pyrazole-3-carboxylic acid ethyl ester (1.26 g, 4.74 mmol), [3-(tert-butyldimethylsilanyloxy)-2-hydroxypropyl]carbamic acid tert-butyl ester (2.90 g, 9.48 mmol) and triphenylphosphine (2.24 g, 8.53 mmol) in THF (23.6 mL) under nitrogen atmosphere. The mixture was stirred at rt for 2.5 h. The solvent was evaporated and the residue was treated with DIPE. The solid (Ph$_3$PO) was filtered off and the filtrate was evaporated in vacuo. The crude product was purified by flash column chromatography (silica; DCM in Heptane 50/50 to 100/0 then EtOAc in DCM 0/100 to 3/97). The desired fractions were collected and concentrated in vacuo to yield intermediate compound I-28 (2.57 g, 98%) as a colorless oil.

Intermediate 29 (I-29)

Ethyl 2-[1-(aminomethyl)-2-hydroxy-ethyl]-4-iodo-pyrazole-3-carboxylate hydrochloride salt (I-29)

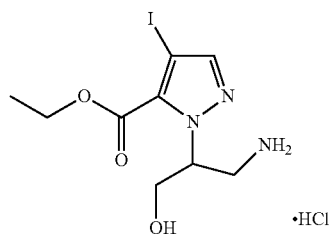 [SMILES: CCOC(=O)c1c(I)cnn1C(CN)CO ; Cl]

Hydrochloric acid (4 M in 1,4-dioxane, 5.80 mL, 23.21 mmol) was added to a stirred solution of intermediate I-28 (2.57 g, 4.64 mmol) in CH$_3$CN (21 mL). The mixture was stirred at rt for 1 h. The mixture was concentrated in vacuo to yield intermediate compound I-29 (1.69 g) as a beige solid which was used in the next step without any further purification.

Intermediate 30 (I-30)

7-(Hydroxymethyl)-3-iodo-6,7-dihydro-5H-pyrazolo pyrazin-4-one (I-30)

TEA (1.38 mL, 9.93 mmol) was added to a stirred solution of intermediate I-29 (1.68 g, 4.48 mmol) in DMF (16.8 mL). The mixture was stirred at rt for 3 h. The mixture was treated with a sat. sol. of $NaHCO_3$ and EtOAc and filtered. The filtrate was partitioned between water and EtOAc and extracted with EtOAc and EtOAc/THF. The organic layer was separated, dried ($Na_2SO_4$), filtered and concentrated in vacuo. The crude product was purified by flash column chromatography (silica; MeOH in DCM 0/100 to 20/80). The desired fractions were collected and concentrated in vacuo to yield intermediate compound I-30 (0.88 g, 67%) as a white solid.

Intermediate 31 (I-31)

7-(Hydroxymethyl)-3-(2-methyl-4-pyridyl)-6,7-dihydro-5H-pyrazolo[1,5-a]pyrazin-4-one (I-31)

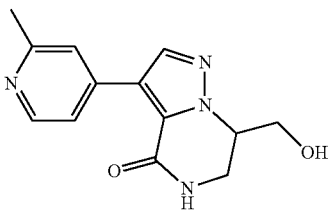 [SMILES: Cc1cc(-c2cnn3c2C(=O)NCC3CO)ccn1]

Pd(PPh$_3$)$_4$ (134 mg, 0.12 mmol) was added to a stirred suspension of intermediate I-30 (0.88 g, 3.00 mmol) and 2-picoline-4-boronic acid (658 mg, 3.00 mmol) in 1,4-dioxane (15.4 mL) and a sat. aq. $NaHCO_3$ (10 mL) under nitrogen atmosphere. The mixture was stirred at 90° C. for 16 h. Then additional 2-picoline-4-boronic acid (263 mg, 1.20 mmol) and Pd(PPh$_3$)$_4$ (35 mg, 0.03 mmol) were added at rt and under nitrogen. The mixture was stirred at 100° C. for 7 h. Then the mixture was diluted with water and extracted with EtOAc. The organic layer was separated, dried ($Na_2SO_4$), filtered and the solvents evaporated in vacuo. The crude product was purified by flash column chromatography (silica; MeOH in DCM 0/100 to 10/90). The desired fractions were collected and concentrated in vacuo to yield intermediate compound I-31 (347 mg, 45%) as pale orange solid.

Intermediate 32 (I-32)

7-(Hydroxymethyl)-6,7-dihydro-5H-pyrazolo[1,5-a] pyrazin-4-one (I-32)

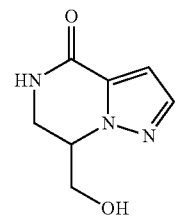 [SMILES: O=C1NCC(CO)n2nccc21]

Palladium 10% on charcoal (907 mg, 0.0.853 mmol) was added to a solution of intermediate I-30 (2.5 g, 8.53 mmol) and TEA (4.74 mL, 34.12 mmol) in DMF (125 mL) under nitrogen atmosphere. The mixture was hydrogenated (at atmospheric pressure) at rt for 16 h. The mixture was filtered through a pad of diatomaceous earth and the residue was washed with MeOH and 7M solution of ammonia in MeOH. The filtrate was concentrated in vacuo and the residue was treated with a small amount of water and extracted with EtOAc/THF. The organic layer was separated, dried ($Na_2SO_4$), filtered and concentrated in vacuo to yield intermediate compound I-32 (1.4 g, quant.) as a brown oil.

Intermediate 33a (I-33a) and intermediate 33b (I-33b)

(7S)-7-methyl-3-(4,4,5,5-tetramethyl-1,3,2-dioxaborolan-2-yl)-5-[4-(trifluoromethyl)phenyl]-6,7-dihydropyrazolo[1,5-a]pyrazin-4-one (I-33a) and [(7S)-7-methyl-4-oxo-5-[4-(trifluoromethyl)phenyl]-6,7-dihydropyrazolo-[1,5-a]pyrazin-3-yl]boronic acid (I-33b)

(I-33a)
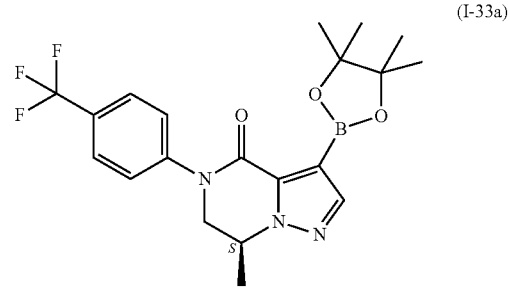

(I-33b)
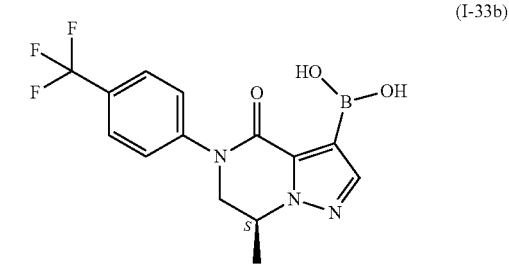

Isopropylmagnesium chloride lithium chloride complex (1.3M solution, 32.9 mL, 42.7 mmol) was added dropwise to a stirred solution of intermediate I-23 (10 g, 23.7 mmol)

and 2-isopropoxy-4,4,5,5-tetramethyl-1,3,2-dioxaborolane (9.7 mL, 47.5 mmol) in anhydrous THF (100 mL) at −25° C. under nitrogen atmosphere. The mixture was stirred for 30 min at −25° C. Then the reaction was quenched with a 10% NH₄Cl aq sol. and extracted with EtOAc. The organic layer was separated, dried (Na₂SO₄), filtered and the solvents evaporated in vacuo. The crude product was purified by flash column chromatography (silica; MeOH in DCM 0/100 to 3/97). The desired fractions were collected and the solvents evaporated in vacuo. The crude product was triturated with DIPE, filtered and dried to yield intermediate compound I-33a (6.4 g, 64%) as a white solid. The solution and impure fractions from the column purification were combined and repurified by flash column chromatography (silica, EtOAc in Heptane 30/70 to 70/30). The desired fractions were collected and the solvents evaporated in vacuo. The product was triturated in DIPE/Heptane, filtered and dried to yield intermediate compound I-33b (1 g, 10%) as a white solid.

Intermediates I-34 to I-37

The following intermediates were synthesized by following an analogous synthetic procedure as reported for intermediate 22.

| Structure | Intermediate number | Starting materials |
|---|---|---|
| (3,4-dichlorophenyl-N, 3-(2-methylpyridin-4-yl)-pyrazolo-pyrazinone with S-methyl) | I-34 | I-18; 1,2-dichloro-4-bromobenzene |
| (4-acetylphenyl-N, 3-(2-methylpyridin-4-yl)-pyrazolo-pyrazinone with S-methyl) | I-35 | I-18; 4-bromoacetophenone |
| (4-bromophenyl-N, 3-(2-methylpyridin-4-yl)-pyrazolo-pyrazinone with S-methyl) | I-36 | I-18; 1-iodo-4-bromobenzene |
| (4-trifluoromethylphenyl-N, pyrazolo-pyrazinone with CH₂OH) | I-37 | I-32; 1-chloro-4-trifluoromethylbenzene |

85

Intermediate 38 and Final Compound 170

(7S)-5-(3,4-dichlorophenyl)-7-methyl-3-(2-methyl-1-oxido-pyridin-1-ium-4-yl)-6,7-dihydropyrazolo[1,5-a]pyrazin-4-one (I-38 and Co. No. 170)

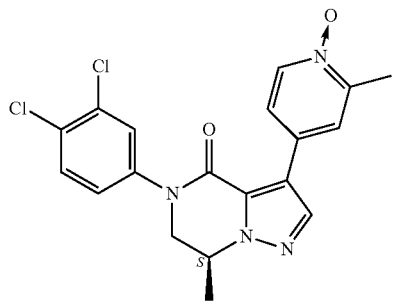

3-Chloroperoxybenzoic acid (2.03 g, 11.77 mmol) was added to a stirred solution of intermediate I-34 (2.28 g, 5.88 mmol) in DCM (37 mL) at 0° C. The mixture was allowed to reach rt and stirred at rt for 2 h. The mixture was treated with a sat sol. of Na₂CO₃ and diluted with DCM. The organic layer was separated, dried (Na₂SO₄), filtered and the solvents evaporated in vacuo to yield intermediate compound I-38 (1.84 g, 77%) that was used in the next step without any further purification.

Intermediate 39 (I-39)

4-[(7S)-5-(3,4-dichlorophenyl)-7-methyl-4-oxo-6,7-dihydropyrazolo[1,5-a]pyrazin-3-yl]pyridine-2-carbaldehyde (I-39)

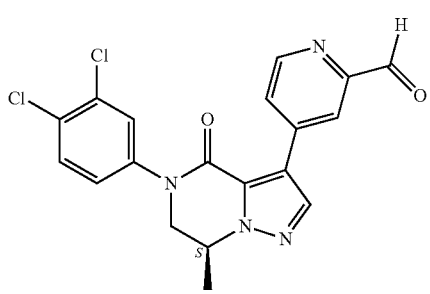

Manganese dioxide (2.39 g, 27.57 mmol) was added to a solution of final compound 125 (E-14) (1.11 g, 2.75 mmol) in chloroform (11.7 mL). The mixture was stirred at rt for 16 h, at 60° C. for 5 h and then at rt for 16 h. Then, the mixture was filtered through a pad of diatomaceous earth and washed with DCM. The solvent was evaporated in vacuo. The crude product was purified by flash column chromatography (silica; EtOAc in DCM 0/100 to 50/50). The desired fractions were collected and evaporated in vacuo to yield intermediate compound I-39 (537 mg, 48%) as a pale yellow solid.

Intermediate 40 (I-40)

The following intermediate was synthesized by following an analogous synthetic procedure as reported for intermediate 39.

| Structure | Intermediate number | Starting material |
|---|---|---|
| 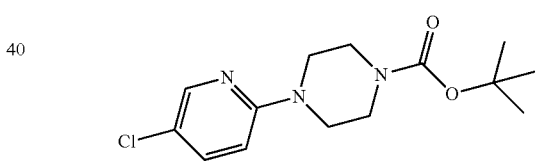 | I-40 | I-37 |

Intermediate 41 (I-41)

tert-Butyl 4-(5-chloro-2-pyridyl)piperazine-1-carboxylate (I-41)

A mixture of 2-bromo-5-chloropyridine (1.5 g, 7.79 mmol), 1-BOC-piperazine (2.18 g, 11.69 mmol), sodium tert-butoxide (1.49 g, 15.59 mmol), 9,9-dimethyl-4,5-bis(diphenylphosphino)xanthene (0.451 g, 0.78 mmol) and tris(dibenzylideneacetone)dipalladium(0) (0.357 g, 0.390 mmol) in toluene (25 mL) was stirred at 120° C. for 16 h. The mixture was poured into water, and extracted with EtOAc. The mixture was filtered through a short pad of diatomaceous earth. The organic layer was separated, washed with water and brine, dried (MgSO₄) and evaporated in vacuo. The crude product was purified by flash column chromatography (silica, EtOAc in DCM 0/100 to 20/80). The desired fractions were collected and evaporated in vacuo to yield intermediate compound I-41 (0.888 g, 38%) as an orange solid.

Intermediate 42 (I-42)

tert-Butyl 4-[5-[(7S)-7-methyl-4-oxo-5-[4-(trifluoromethyl)phenyl]-6,7-dihydropyrazolo[1,5-a]pyrazin-3-yl]-2-pyridyl]piperazine-1-carboxylate (I-42)

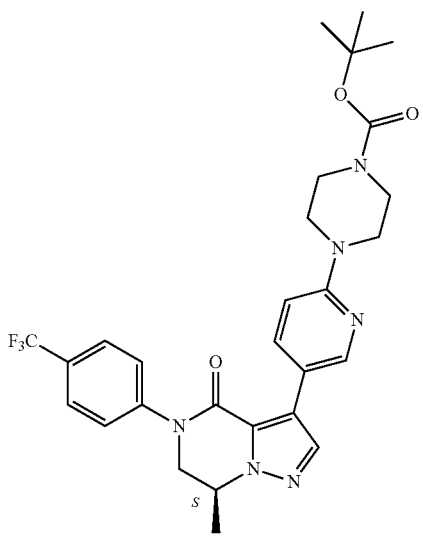

A suspension of intermediate I-41 (478 mg, 1.60 mmol), intermediate I-33a (653 mg, 1.55 mmol), palladium(II) acetate (7 mg, 0.032 mmol), 2-dicyclohexylphosphino-2',6'-dimethoxybiphenyl (26 mg, 0.064 mmol) and $K_2CO_3$ (554 mg, 4.013 mmol) in $CH_3CN$ (1.6 mL) and $H_2O$ (2.5 mL) was flushed with nitrogen for a few minutes and the mixture was stirred at 80° C. for 24 h. Then the mixture was diluted with $H_2O$ and extracted with EtOAc. The organic layer was separated, dried ($Na_2SO_4$), filtered and the solvent evaporated in vacuo. The crude product was purified by flash column chromatography (silica; EtOAc in DCM 0/100 to 50/50). The desired fractions were collected and evaporated in vacuo to yield intermediate compound I-42 (663 mg, 74%) as a yellow oil.

Intermediate 43 and Final Compound 188

(7S)-5-[6-chloro-5-(trifluoromethyl)-2-pyridyl]-7-methyl-3-(2-methyl-4-pyridyl)-6,7-dihydropyrazolo[1,5-a]pyrazin-4-one (I-43 and Co. No. 188)

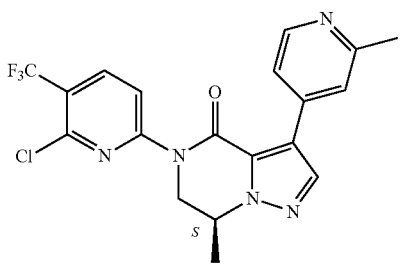

Pd(PPh$_3$)$_4$ (47 mg, 0.041 mmol) was added to a stirred suspension of intermediate I-18 (100 mg, 0.413 mmol), 2,6-dichloro-3-(trifluoromethyl)pyridine (86 μL, 0.620 mmol), 4,5-bis(diphenylphosphino)-9,9-dimethylxanthene (47 mg, 0.082 mmol), $Cs_2CO_3$ (269 mg, 0.825 mmol) in 1,4-dioxane (3 mL) in a sealed tube and under nitrogen. The mixture was stirred at 120° C. for 4 h. The mixture was filtered through a pad of diatomaceous earth and washed with DCM. The filtrate was evaporated in vacuo. The crude product was purified by flash column chromatography (silica, EtOAc in DCM 0/100 to 30/70). The desired fractions were collected and concentrated in vacuo. Then the product was triturated with Et$_2$O and filtered to yield intermediate compound I-43 (71 mg, 40%) as a white solid.

Intermediate 44 (I-44)

7-(Difluoromethyl)-5-[4-(trifluoromethyl)phenyl]pyrazolo[1,5-a]pyrazin-4-one (I-44)

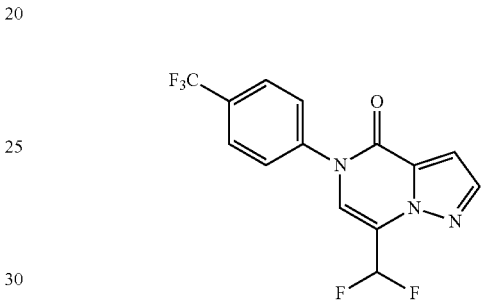

Diethylaminosulfur trifluoride (0.373 mL, 3.866 mmol) was added to a stirred solution of intermediate I-40 (297 mg, 0.966 mmol) in DCM (33 mL) at 0° C. The mixture was allowed to warm to rt and stirred for 5 h. Then additional diethylaminosulfur trifluoride (0.355 mL, 2.9 mmol) was added at 0° C. and the mixture was stirred at rt for 20 h. The mixture was treated with water and extracted with DCM. The organic layer was separated, dried ($Na_2SO_4$), filtered and concentrated in vacuo. The crude product was purified by flash column chromatography (silica; DCM). The desired fractions were collected and concentrated in vacuo to yield intermediate compound I-44 (258 mg, 81%) as a colorless oil.

Intermediate 45 (I-45)

The following intermediate was synthesized by following an analogous synthetic procedure as reported for intermediate 23.

| Structure | Intermediate number | Starting materials |
|---|---|---|
| 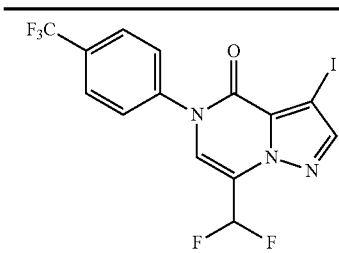 | I-45 | I-44 |

Intermediate 46 (I-46)

The following intermediate was synthesized by following an analogous synthetic procedure as reported for intermediate 18.

| Structure | Intermediate number | Starting materials |
|---|---|---|
| 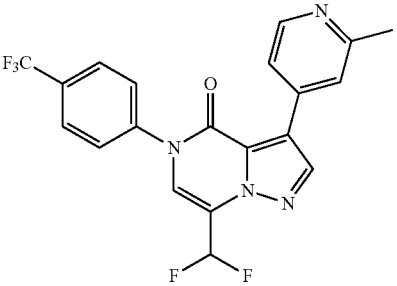 [SMILES: Cc1cc(-c2cnn3c(C(F)F)cn(-c4ccc(C(F)(F)F)cc4)c(=O)c23)ccn1] | I-46 | I-45 |

Intermediates 47 and 48 (I-47 and I-48)

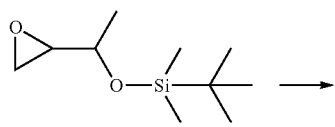

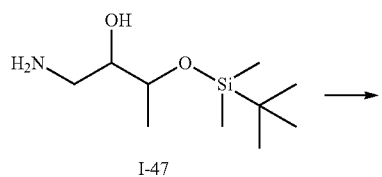
I-47

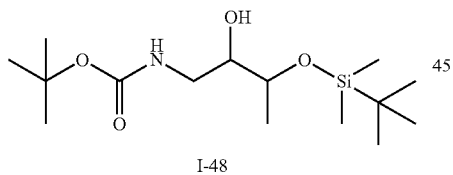
I-48 i) NH$_3$ (28% in water, 54 mL) was added over 2-[1-[[(1,1-dimethylethyl)dimethylsilyl]oxy]ethyl]-oxirane (4.73 g, 23.373 mmol) and the mixture was stirred at 120° C. for 40 min under microwave irradiation. The solvent was then concentrated in vacuo to yield intermediate compound I-47 as an orange oil (3.298 g, 64%).

ii) Intermediate I-48 was synthesized following an analogous synthetic procedure as reported for intermediate I-3. Starting from intermediate I-47 (3.269 g, 14.9 mmol), intermediate compound I-48 was obtained as a colorless oil (4.642 g, 97.5%).

Intermediates 49-52 (I-49 to I-52)

The following intermediates were synthesized by following an analogous synthetic procedure as reported for intermediate 6.

| Structure | Intermediate number | Starting materials |
|---|---|---|
| 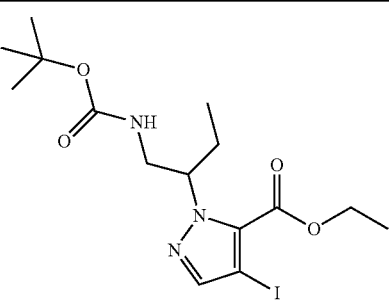 | I-49 | I-2<br>N-(2-hydroxybutyl)-carbamic acid 1,1-dimethylethyl ester |

-continued

| Structure | Intermediate number | Starting materials |
|---|---|---|
| 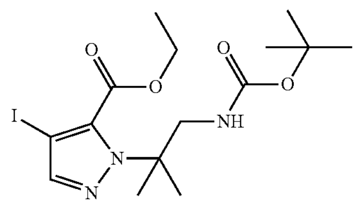 [SMILES: CCOC(=O)c1c(I)cnn1C(C)(C)CNC(=O)OC(C)(C)C] | I-50 | I-2<br>N-(2-hydroxy-2-methylpropyl)-carbamic acid 1,1-dimethylethyl ester |
| 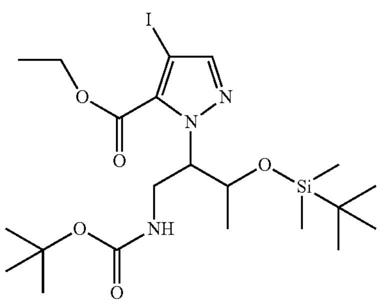 [SMILES: CCOC(=O)c1c(I)cnn1C(CNC(=O)OC(C)(C)C)C(C)O[Si](C)(C)C(C)(C)C] | I-51 | I-2<br>I-48 |
| 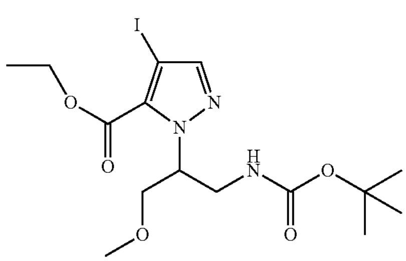 [SMILES: CCOC(=O)c1c(I)cnn1C(CNC(=O)OC(C)(C)C)COC] | I-52 | I-2<br>tert-butyl N-(2-hydroxy-3-methoxypropyl)carbamate |

Intermediate 53 (I-53)

The following intermediate was synthesized following the procedure for the synthesis of intermediate I-29, followed by the procedure for the synthesis of intermediate I-30.

| Structure | Intermediate number | Starting materials |
|---|---|---|
| 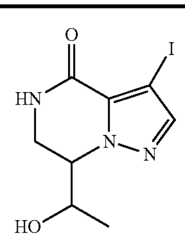 | I-53 | I-51 |

Intermediate 54 (I-54)

Ethyl 2-[1-(aminomethyl)-2-methoxy-ethyl]-4-iodo-pyrazole-3-carboxylate (I-54)

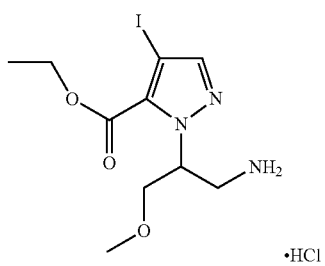 [SMILES: CCOC(=O)c1c(I)cnn1C(CN)COC ; Cl]

HCl (4 M in dioxane, 2.2 mL, 8.82 mmol) was added to a solution of intermediate I-52 (0.8 g, 1.765 mmol) in $CH_3CN$ (8 mL). The mixture was stirred at rt for 1 h and then the solvent was concentrated in vacuo to give intermediate compound I-54 (700 mg, 87%) as a cream solid.

Intermediate 55 (I-55)

3-Iodo-7-(methoxymethyl)-6,7-dihydro-5H-pyrazolo[1,5-a]pyrazin-4-one (I-55)

Et₃N (0.55 mL, 3.98 mmol) was added to a solution of intermediate I-54 (0.7 g, 1.80 mmol) in DMF (6.7 mL). The mixture was stirred at rt for 3 h then neutralized with a sat. sol. of NaHCO₃ and extracted with DCM. The organic layer was separated, dried (Na₂SO₄), filtered and the solvents evaporated in vacuo to give intermediate compound I-55 (440 mg, 80%) as a white solid.

Intermediates 56 and 57 (I-56 and I-57)

The following intermediates were synthesized by following an analogous synthetic procedure as that reported for intermediate 15.

| Structure | Intermediate number | Starting material |
|---|---|---|
| 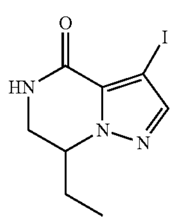 | I-56 | I-49 |
| 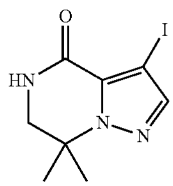 | I-57 | I-50 |

Intermediates 58-61 (I-58 to I-61)

The following intermediates were synthesized by following an analogous synthetic procedure as reported for intermediate 25.

| Structure | Intermediate number | Starting materials |
|---|---|---|
| 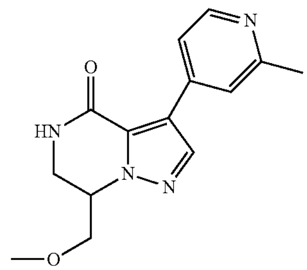 | I-58 | I-55<br>2-picoline-4-boronic acid |
| 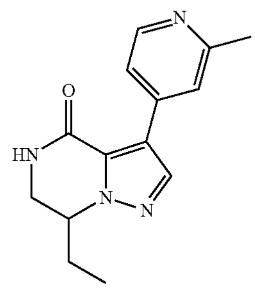 [SMILES: CCC1CNC(=O)c2c(-c3ccnc(C)c3)cnn21] | I-59 | I-56<br>2-picoline-4-boronic acid |
| 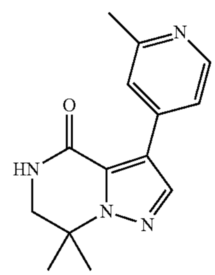 [SMILES: Cc1cc(-c2cnn3c2C(=O)NCC3(C)C)ccn1] | I-60 | I-57<br>2-picoline-4-boronic acid |
| 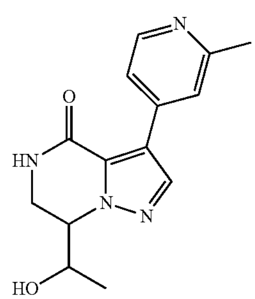 [SMILES: Cc1cc(-c2cnn3c2C(=O)NCC3C(C)O)ccn1] | I-61 | I-53<br>2-picoline-4-boronic acid |

Intermediate 62 (I-62)

2-[(1S)-2-(3,4-dichloroanilino)-1-methyl-ethyl]-4-(2-methyl-4-pyridyl)pyrazole-3-carboxylic acid (I-62)

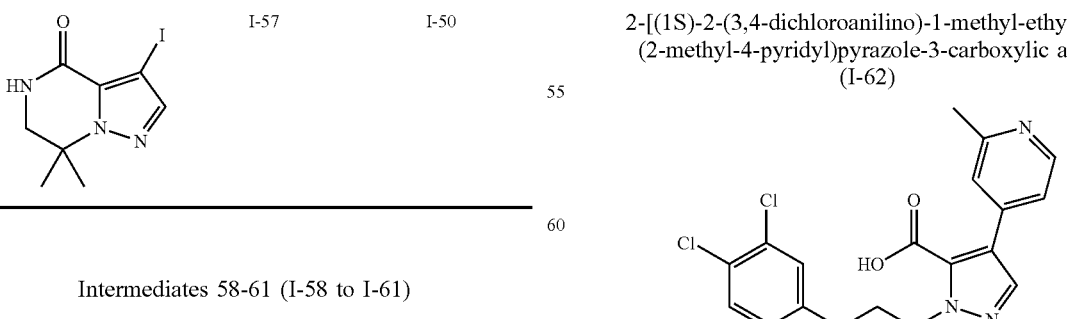

Sodium hydride (60% dispersion in mineral oil, 20 mg, 0.344 mmol) was added to a solution of compound Co. No. 6a (200 mg, 0.516 mmol) in DMF (4 mL) and the mixture was stirred at 60° C. for 24 h. Then more sodium hydride (60% dispersion in mineral oil, 11 mg, 0.172 mmol) was added and the mixture was stirred at 60° C. for 3 h. Then, the mixture was quenched with a NH$_4$Cl sat. sol. and extracted with EtOAc. The organic layer was separated, dried (MgSO$_4$), filtered and the solvents evaporated in vacuo to give intermediate compound I-62 (230 mg, quantitative) as a solid which was used in the next step without further purification.

Intermediate 63 (I-63)

2-[(1S)-2-(4,5-dichloro-2-iodo-anilino)-1-methyl-ethyl]-4-(2-methyl-4-pyridyl)pyrazole-3-carboxylic acid (I-63a) and 2-[(1S)-2-(3,4-dichloro-2-iodo-anilino)-1-methyl-ethyl]-4-(2-methyl-4-pyridyl)pyrazole-3-carboxylic acid (I-63b)

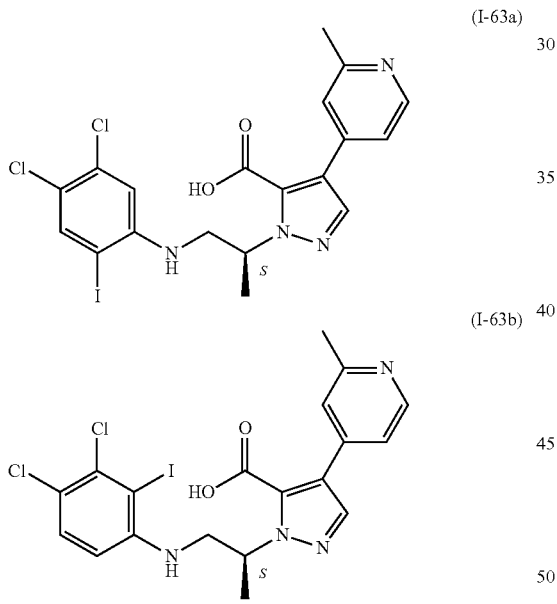

N-iodosuccimide (124 mg, 0.552 mmol) was added to a solution of intermediate compound I-62 (224 mg, 0.5523 mmol) in chloroform (5 mL) and the mixture was stirred at rt for 3 h. Then more N-iodosuccimide (62 mg, 0.277 mmol) was added and the mixture was stirred at rt for 18 h. Then the reaction was quenched with a sat. sol. of Na$_2$SO$_3$ and extracted with DCM. The organic layer was separated, dried (MgSO$_4$), filtered and the solvent evaporated in vacuo to give a mixture of intermediates compounds I-63a and I-63b (240 mg, 41%) which was used in next step without further purification.

Intermediate 64 (I-64)

tert-Butyl N-[[2,2,2-trifluoro-1-(nitromethyl)ethyl]amino]carbamate (I-64)

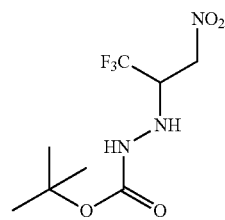 [SMILES: CC(C)(C)OC(=O)NNC(C[N+](=O)[O-])C(F)(F)F]

tert-Butyl carbazate (281 mg, 2.13 mmol) was added to a stirred solution of 3,3,3-trifluoro-1-nitro-prop-1-ene (prepared as described in *J. Fluorine Chem.* 2008, 767-774) (73 µL, 0.709 mmol) in MeOH (3.1 mL) at rt. The mixture was stirred for 1 h and the solvents evaporated in vacuo. The crude product was purified by flash column chromatography (silica, EtOAc in Heptane 40/60 to 60/40) to yield intermediate compound I-64 (200 mg, quant.)

Intermediate 65 (I-65)

[2,2,2-Trifluoro-1-(nitromethyl)ethyl]hydrazine hydrochloride salt (I-65)

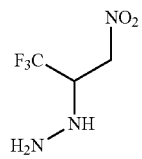

HCl (6M in 1,4-dioxane, 10.5 mL, 42 mmol) was added to a solution of intermediate I-64 (1.15 g, 4.2 mmol) in MeOH (10 mL) at rt. The mixture was stirred for 2 h and the solvents were evaporated in vacuo to yield intermediate compound I-65 (880 mg, quant.) that was used in the next step without further purification.

Intermediate 66 (I-66)

Ethyl 2-[2,2,2-trifluoro-1-(nitromethyl)ethyl]pyrazole-3-carboxylate (I-66a) and ethyl 1-[2,2,2-trifluoro-1-(nitromethyl)ethyl]pyrazole-3-carboxylate (I-66b)

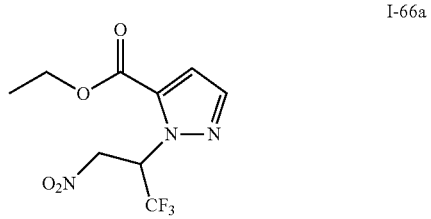

97
-continued

I-66b

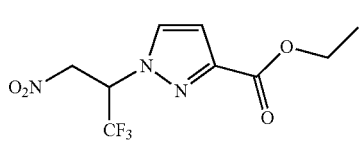

Ethyl pyruvate (77 μL, 0.692 mmol) and N,N-dimethylformamide dimethyl acetal (92 μL, 0.692 mmol) were stirred at rt for 16 h. The dark red/brown solution was added to a solution of intermediate I-65 (145 mg, 0.692 mmol) in EtOH (2 mL). The mixture was stirred at 85° C. for 3 h. The solvent was concentrated in vacuo. The crude product was purified by flash column chromatography (silica; EtOAc in Heptane 30/70 to 60/40) to yield intermediate compounds I-66a (78 mg, 40%) and I-66b (54 mg, 28%).

Intermediate 67 (I-67)

7-Methyl-6,7-dihydro-5H-pyrazolo[1,5-a]pyrazin-4-one (I-67)

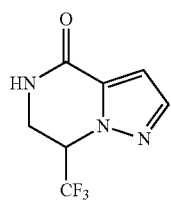

Pd (10% on charcoal, 100 mg, 0.094 mmol) and ammonium formate (112 mg, 1.78 mmol) were added to a stirred solution of intermediate I-66 (100 mg, 0.355 mmol) in MeOH (3.3 mL). The mixture was stirred in a sealed tube at 70° C. for 2 h. The solvent was concentrated in vacuo to yield intermediate compound I-67 (70 mg, 96%) that was used in the following step without further purification.

Intermediate 68 (I-68)

3-Iodo-7-(trifluoromethyl)-5-[4-(trifluoromethyl)phenyl]-6,7-dihydropyrazolo[1,5-a]pyrazin-4-one (I-68)

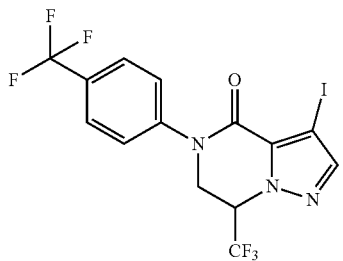 [SMILES: O=C1c2c(I)cnn2C(C(F)(F)F)CN1c1ccc(C(F)(F)F)cc1]

Intermediate compound I-68 was synthesized by following the sequence of an analogous synthetic procedure as reported for intermediate I-22 starting from intermediate I-67 and 4-bromobenzotrifluoride, followed by the procedure for intermediate I-23.

98
Final Compounds

Example 1

(7S)-7-Methyl-3-(2-methylpyridin-4-yl)-5-[4-(trifluoromethyl)phenyl]-6,7-dihydropyrazolo[1,5-a]pyrazin-4(5H)-one (E-1, Co. No. 1)

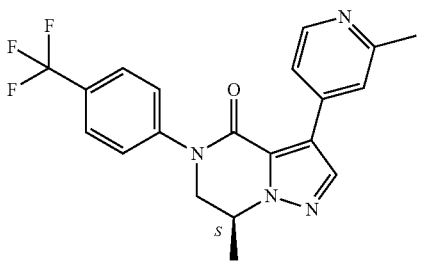

Procedure A: Copper(I) iodide (872 mg, 4.58 mmol) was added to a stirred suspension of intermediate I-18 (1.85 g, 7.64 mmol), 4-bromobenzotrifluoride (2.14 mL, 15.27 mmol), $K_2CO_3$ (2.11 g, 15.27 mmol) and N,N'-dimethylethylenediamine (0.492 mL, 4.58 mmol) in toluene (70 mL) in a sealed tube and under nitrogen. The mixture was stirred at 100° C. for 16 h. Then DMF (10 mL) was added and the mixture was stirred at 100° C. for additional 8 h. The mixture was filtered through diatomaceous earth and washed with EtOAc. The organic layer was washed with diluted $NH_4OH$ sol, dried ($Na_2SO_4$), filtered and the solvents evaporated in vacuo. The crude product was purified by flash column chromatography (silica; EtOAc in Heptane 20/80 to 50/50). The desired fractions were collected and the solvents evaporated in vacuo. The product was precipitated with heptane, filtered and dried in vacuo to yield final product compound 1 as a white solid (2.32 g, 78%). $^1$H NMR (500 MHz, $CDCl_3$) δ ppm 1.75 (d, J=6.4 Hz, 3H), 2.57 (s, 3H), 4.02 (dd, J=12.7, 7.2 Hz, 1H), 4.30 (dd, J=12.6, 4.2 Hz, 1H), 4.75-4.84 (m, 1H), 7.44 (d, J=5.2 Hz, 1H), 7.49 (d, J=3.8 Hz, 2H), 7.51 (s, 1H), 7.71 (d, J=8.4 Hz, 2H), 7.80 (s, 1H), 8.48 (d, J=5.2 Hz, 1H).

Procedure B: Copper(I) iodide (94 mg, 0.495 mmol) was added to a stirred suspension of intermediate I-18 (200 mg, 0.825 mmol), 4-bromobenzotrifluoride (0.231 mL, 1.651 mmol), $K_2CO_3$ (228 mg, 1.65 mmol) and N,N'-dimethylethylenediamine (53 μL) in toluene (7.5 mL) in a sealed tube and under nitrogen. The mixture was stirred at 100° C. overnight. The mixture was filtered through a pad of diatomaceous earth and washed with DCM. The organic layer was separated, dried ($MgSO_4$), filtered and the solvents evaporated in vacuo. The crude product was purified by flash column chromatography (silica, EtOAc in Heptane 0/100 to 70/30). The desired fractions were collected and concentrated in vacuo to yield compound 1 (283 mg, 89%) as a pinkish solid.

Procedure C: $Pd(PPh_3)_4$ (384 mg, 0.332 mmol) was added to a stirred suspension of intermediate I-23 (2 g, 4.74 mmol) and 2-methylpyridine-4-boronic acid pinacol ester (1.66 g, 7.60 mmol) in 1,4-dioxane (10 mL) and a sat. sol. of $Na_2CO_3$ (5 mL) in a sealed tube under nitrogen. The mixture was stirred at 100° C. for 16 h. Then the mixture was diluted with $H_2O$ and extracted with DCM and DCM with a small amount of EtOH. The organic layer was dried ($Na_2SO_4$), filtered and the solvent evaporated in vacuo. The crude product was purified by flash column chromatography (silica; 7M solution of ammonia in MeOH in DCM 0/100 to 3/97 then EtOAc in Heptane 0/100 to 100/0). The desired fractions were collected and evaporated in vacuo to yield compound 1 as a white solid (480 mg, 26%). (1.31 g of starting material was recovered).

Procedure D; general description of a synthesis performed at a large scale by which Co. No. 1 was isolated in 90% yield before purification:

A mixture of I-18 (1 eq.), potassium carbonate (2 eq.), copper(I) iodide (0.3 eq.), 4-bromobenzotrifluoride (1.3 eq.), N,N'-Dimethyl ethylenediamine (0.35 eq.), DMF (5 mL/g I-18) and toluene (8 mL/g I-18) was evacuated and back-filled with nitrogen 3 times. It was heated to 100-110° C. and stirred at 100-110° C. for 7-8 h under nitrogen. The reaction solution was concentrated to remove toluene below 50° C. Isopropyl acetate (15 mL/g I-18) was added. The mixture was washed with 5% NH$_4$OH aqueous solution (3×7 mL/g I-18), and then 5% N-acetyl-L-cysteine and 5% K$_2$CO$_3$ aqueous solution (2×7 mL/g I-18) at 10-25° C. Finally, it was washed with 5% NaCl aqueous solution (5 mL/g I-18). The obtained solution was concentrated and co-evaporated with MTBE to remove isopropyl acetate. The resulting solid was filtered and dried in vacuo at 45-50° C. Co. No. 1 was obtained as an off-white solid which was further purified as follows:

Co. No. 1 was dissolved in a solvent mixture of IPA (4 mL/g Co. No. 1) and water (1 mL/g Co. No. 1) at 48-55° C. The solution was filtered and cooled to 0-5° C. An IPA/water mixture (0.5 mL/g Co. No. 1, 4/1 v/v) was used to rinse. Water (650 μL/g Co. No. 1) was added drop-wise and seeding with Co. No. 1 was performed. The mixture was stirred at 0-5° C. for 3-4 h. Water (14 mL/g Co. No. 1) was added drop-wise at 0-5° C. for 3-4 h, and then the suspension was stirred at 0-5° C. for 5-6 h. The wet product was filtered and rinsed with water (2 mL/g Co. No. 1), then dried in vacuo at 45-50° C. for 16 h to afford Co. No. 1 as a white solid.

For compound 1 (DSC mp=155.35° C.), the hydrochloride salt (.HCl) (DSC mp=decomposes above 200° C.); the sulfate salt (.H$_2$SO$_4$) (DSC mp=decomposes above 200° C.); the methane sulfonate salt (.CH$_3$SO$_3$H) (DSC mp=252° C.); and the maleate salt (.HO$_2$CCH=CHCO$_2$H-cis) (DSC mp=163° C.); wherein the mp were determined by DSC (Mettler Toledo Q2000 MDSC, heating from 25 to 350° C. at 10° C./min) were obtained following the procedure described below:

Compound 1 (1.5 g) in 9 mL of IPA or acetone (hydrochloride and sulfate salts were generated in acetone; methanesulfonate and maleate salts were generated in IPA) were stirred at 50° C. until all the solid was dissolved. The acid (1.1 mol equivalents) was added to the solution and the reaction mixture was further stirred for 2 h at 50° C., then cooled to 20° C. in 1 h and further stirred for 30 h at 20° C. The suspension was filtered and the solids were dried at 50° C. in a vacuum oven overnight.

Example 2

(7S)-7-Methyl-3-pyridin-4-yl-5-[4-(trifluoromethyl)phenyl]-6,7-dihydropyrazolo[1,5-a]pyrazin-4(5H)-one (E-2, Co. No. 2)

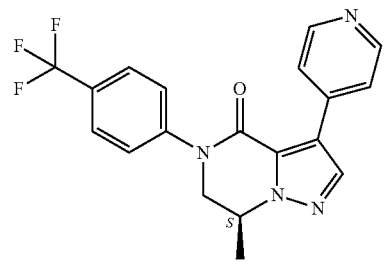

Pd(PPh$_3$)$_4$ (41 mg, 0.036 mmol) was added to a stirred suspension of intermediate I-23 (300 mg, 0.71 mmol) and pyridine-4-boronic acid (114 mg, 0.93 mmol) in 1,4-dioxane (3.3 mL) and a sat. sol. of NaHCO$_3$ (1.5 mL). The mixture was stirred at 150° C. for 10 min under microwave irradiation. Then the mixture was diluted with H$_2$O and extracted with DCM. The organic layer was separated, dried (Na$_2$SO$_4$), filtered and the solvent evaporated in vacuo. The crude product was purified by flash column chromatography (silica; MeOH in DCM 0/100 to 6/94). The desired fractions were collected and the solvents evaporated in vacuo. The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo. The residue was precipitated with DIPE to yield compound 2 as a white solid (215 mg, 81%). $^1$H NMR (400 MHz, CDCl$_3$) δ ppm 1.76 (d, J=6.5 Hz, 3H), 4.03 (dd, J=12.7, 7.2 Hz, 1H), 4.31 (dd, J=12.7, 4.2 Hz, 1H), 4.81 (qdd, J=6.7, 6.7, 6.7, 6.5, 4.3 Hz, 1H), 7.51 (d, J=8.1 Hz, 2H), 7.65 (dd, J=4.4, 1.6 Hz, 2H), 7.71 (d, J=8.3 Hz, 2H), 7.83 (s, 1H), 8.60 (dd, J=4.6, 1.8 Hz, 2H).

Example 3

(7S)-3-(2-Aminopyridin-4-yl)-7-methyl-5-[4-(trifluoromethyl)phenyl]-6,7-dihydropyrazolo[1,5-a]pyrazin-4(5H)-one (E-3, Co. No. 71)

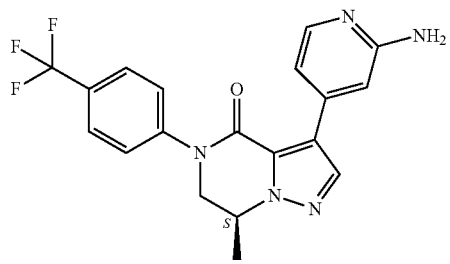

Pd(PPh$_3$)$_4$ (96 mg, 0.083 mmol) was added to a stirred suspension of intermediate I-23 (700 mg, 1.66 mmol) and intermediate I-24 (458 mg, 3.32 mmol) in 1,4-dioxane (10 mL) and a sat. sol. of NaHCO$_3$ (5 mL). The mixture was stirred at 150° C. for 10 min under microwave irradiation. Then the mixture was diluted with H₂O and extracted with DCM. The organic layer was separated, dried (Na₂SO₄), filtered and the solvent evaporated in vacuo. The crude product was purified by flash column chromatography (silica; MeOH in DCM 0/100 to 10/90). The desired fractions were collected and the solvents evaporated in vacuo and the residue was purified by RP HPLC (RP C18 XBridge™ 30×100 mm 5 um), mobile phase (gradient from 67% 0.1% NH₄CO₃H/NH₄OH pH 9 solution in Water, 33% CH₃CN to 50% 0.1% NH₄CO₃H/NH₄OH pH 9 solution in Water, 50% CH₃CN). The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo to yield final product compound 71 as a white solid (163 mg, 25%). ¹H NMR (500 MHz, CDCl₃) δ ppm 1.74 (d, J=6.4 Hz, 3H) 4.01 (dd, J=12.6, 7.1 Hz, 1H) 4.29 (dd, J=12.6, 4.2 Hz, 1H) 4.43 (br. s., 2H) 4.78 (quind, J=6.6, 4.3 Hz, 1H) 6.94 (dd, J=5.5, 1.4 Hz, 1H) 6.98 (s, 1H) 7.51 (br. d, J=8.4 Hz, 2H) 7.71 (br. d, J=8.4 Hz, 2H) 7.79 (s, 1H) 8.06 (d, J=4.9 Hz, 1H).

Example 4

(7S)-3-[2-(Ethylamino)-4-pyridyl]-7-methyl-5-[4-(trifluoromethyl)phenyl]-6,7-dihydropyrazolo[1,5-a]pyrazin-4-one (E-4, Co. No. 44)

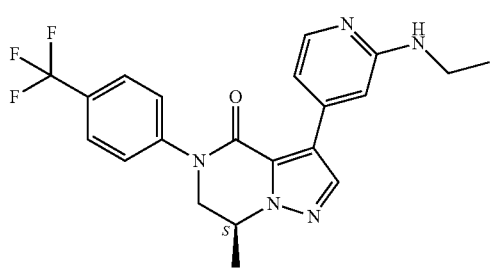

Sodium triacetoxyborohydride (246 mg, 1.16 mmol) was added to a stirred solution of compound 71 (300 mg, 0.77 mmol) and acetaldehyde (0.048 mL, 0.85 mmol) in 1,2-dichloroethane (3 mL). The mixture was stirred at rt for 16 h. Then the mixture was diluted with a sat. sol. of NaHCO₃ and extracted with DCM. The organic layer was separated, dried (Na₂SO₄), filtered and the solvent evaporated in vacuo. The crude product was purified by flash column chromatography (silica; EtOAc in heptane 0/100 to 40/60). The desired fractions were collected and the solvents evaporated in vacuo. The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo and the residue was purified by RP HPLC (RP C18 XBridge™ 30×100 mm 5 um), mobile phase (gradient from 60% 0.1% NH₄CO₃H/NH₄OH pH 9 solution in Water, 40% CH₃CN to 43% 0.1% NH₄CO₃H/NH₄OH pH 9 solution in Water, 57% CH₃CN). The residue was precipitated with DIPE to yield compound 44 as a white solid (28 mg, 9%). ¹H NMR (500 MHz, CDCl₃) δ ppm 1.24 (t, J=7.2 Hz, 3H) 1.74 (d, J=6.4 Hz, 3H) 3.29-3.37 (m, 2H) 4.00 (dd, J=12.6, 7.1 Hz, 1H) 4.29 (dd, J=12.6, 4.2 Hz, 1H) 4.42 (br. t, J=4.6 Hz, 1H) 4.74-4.82 (m, 1H) 6.83 (s, 1H) 6.84 (dd, J=5.3, 1.3 Hz, 1H) 7.51 (br. d, J=8.7 Hz, 2H) 7.70 (br. d, J=8.7 Hz, 2H) 7.79 (s, 1H) 8.07 (d, J=5.5 Hz, 1H).

Example 5

(7S)-3-(2-Methoxy-4-pyridyl)-7-methyl-5-[4-(trifluoromethyl)phenyl]-6,7-dihydropyrazolo[1,5-a]pyrazin-4-one (E-5, Co. No. 45)

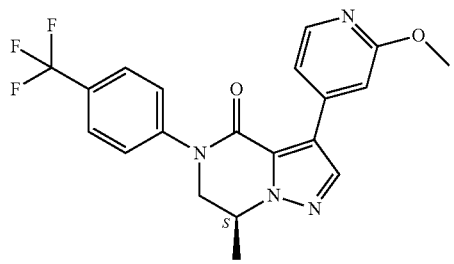

Copper(I) iodide (66 mg, 0.348 mmol) was added to a stirred suspension of intermediate I-25 (150 mg, 0.58 mmol), 4-bromobenzotrifluoride (209 mg, 0.93 mmol), K₂CO₃ (161 mg, 1.16 mmol) and N,N-dimethylethylenediamine (0.037 mL, 0.348 mmol) in toluene (3.75 mL) in a sealed tube and under nitrogen. The mixture was stirred at 100° C. for 24 h. Then, more 4-bromobenzotrifluoride (131 mg, 0.58 mmol) was added and the mixture was stirred at 100° C. for additional 16 h. The mixture was filtered through diatomaceous earth and washed with DCM. The organic layer was evaporated in vacuo. The crude product was purified by flash column chromatography (silica; EtOAc in Heptane 0/100 to 20/80). The desired fractions were collected and the solvents evaporated in vacuo. The product was precipitated with Et₂O. The solid was purified by RP HPLC (RP C18 XBridge™ 30×100 mm 5 um), mobile phase (gradient from 60% 0.1% NH₄CO₃H/NH₄OH pH 9 solution in Water, 40% CH₃CN to 43% 0.1% NH₄CO₃H/NH₄OH pH 9 solution in Water, 57% CH₃CN) to yield compound 45 as a white solid (130 mg, 56%). %). ¹H NMR (500 MHz, CDCl₃) δ ppm 1.75 (d, J=6.6 Hz, 3H) 3.94 (s, 3H) 4.02 (dd, J=12.7, 7.2 Hz, 1H) 4.30 (dd, J=12.6, 4.2 Hz, 1H) 4.75-4.83 (m, 1H) 7.09 (s, 1H) 7.23 (dd, J=5.5, 1.2 Hz, 1H) 7.50 (br. d, J=8.7 Hz, 2H) 7.70 (br. d, J=8.7 Hz, 2H) 7.79 (s, 1H) 8.14 (d, J=5.5 Hz, 1H).

Example 6

(7S)-3-(2-Ethyl-4-pyridyl)-7-methyl-5-[4-(trifluoromethyl)phenyl]-6,7-dihydropyrazolo[1,5-a]pyrazin-4-one (E-6, Co. No. 46)

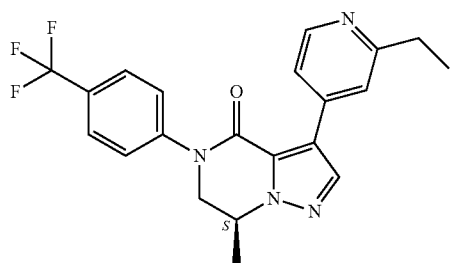

A solution of intermediate I-27 (114 mg, 0.29 mmol) in EtOH (5.7 mL) was hydrogenated in a H-Cube® reactor (1 mL/min, 30 mm Pd(OH)₂/C 20% cartridge, full H₂ mode, rt, 1 cycle). Then, the solvent was evaporated in vacuo. The crude product was purified by RP HPLC (RP C18 XBridge™ 30×100 mm 5 um), mobile phase (gradient from 60% 0.1% NH₄CO₃H/NH₄OH pH 9 solution in Water, 40% CH₃CN to 43% 0.1% NH₄CO₃H/NH₄OH pH 9 solution in Water, 57% CH₃CN) to yield compound 46 as a white solid (84 mg, 73%). ¹H NMR (400 MHz, CDCl₃) δ ppm 1.32 (t, J=7.6 Hz, 3H) 1.75 (d, J=6.7 Hz, 3H) 2.85 (q, J=7.6 Hz, 2H) 4.02 (dd, J=12.7, 7.2 Hz, 1H) 4.31 (dd, J=12.7, 4.2 Hz, 1H) 4.80 (quind, J=6.7, 4.2 Hz, 1H) 7.46 (dd, J=5.1, 1.6 Hz, 1H) 7.48 (br. s, 1H) 7.51 (br. d, J=8.3 Hz, 2H) 7.71 (br. d, J=8.3 Hz, 2H) 7.81 (s, 1H) 8.51 (dd, J=5.3, 0.7 Hz, 1H).

Example 7

7-(Hydroxymethyl)-3-(2-methyl-4-pyridyl)-5-[4-(trifluoromethyl)phenyl]-6,7-dihydropyrazolo[1,5-a]pyrazin-4-one (E-7, Co. No. 87)

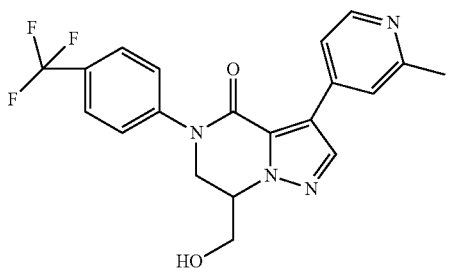 [SMILES: Cc1cc(-c2cnn3c2C(=O)N(c2ccc(C(F)(F)F)cc2)CC3CO)ccn1]

Copper(I) iodide (0.135 g, 0.709 mmol) was added to a stirred suspension of intermediate I-31 (305 mg, 1.18 mmol), 4-bromobenzotrifluoride (298 μL, 2.12 mmol), K₂CO₃ (330 mg, 2.36 mmol) and N,N'-dimethylethylenediamine (76 μL, 0.71 mmol) in toluene (7.63 mL) in a sealed tube and under nitrogen. The mixture was stirred at 100° C. for 18 h. Then additional K₂CO₃ (160 mg, 1.18 mmol), copper(I) iodide (0.067 g, 0.354 mmol), N,N'-dimethylethylenediamine (38 μL, 0.35 mmol) and 4-bromobenzotrifluoride (132 μL, 0.95 mmol) were added under nitrogen and the mixture was stirred at 100° C. for 5 h. The mixture was filtered through a pad of diatomaceous earth and washed with DCM. The organic layer was separated, dried (Na₂SO₄), filtered and concentrated in vacuo. The crude product was purified by flash column chromatography (silica; methanol in DCM 0/100 to 7/93). The desired fractions were collected and concentrated in vacuo to yield compound 87 (321 mg, 68%) as yellow oil that precipitated upon standing at rt.

Example 8

7-(Fluoromethyl)-3-(2-methyl-4-pyridyl)-5-[4-(trifluoromethyl)phenyl]-6,7-dihydropyrazolo[1,5-a]pyrazin-4-one (E-8, Co. No. 52)

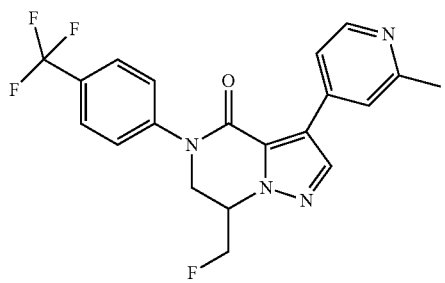 [SMILES: Cc1cc(-c2cnn3c2C(=O)N(c2ccc(C(F)(F)F)cc2)CC3CF)ccn1]

(Diethylamino)sulfur trifluoride (23 μL, 0.185 mmol) was added to a stirred solution of compound 87 (50 mg, 0.124 mmol) in DCM (2.4 mL) at −10° C. The mixture was allowed to warm to rt and stirred for 18 h. The mixture was treated with water and extracted with DCM. The organic layer was separated, dried (Na₂SO₄), filtered and concentrated in vacuo. The crude product was purified by flash column chromatography (silica; EtOAc in DCM 0/100 to 100/0 and MeOH in EtOAc 0/100 to 1/99). The desired fractions were collected and concentrated in vacuo. Then the compound was triturated with DIPE to yield compound 52 (14.5 mg, 29%) as a white solid. ¹H NMR (500 MHz, CDCl₃) δ ppm 2.58 (s, 3H) 4.31 (dd, J=13.1, 4.8 Hz, 1H) 4.47-4.53 (m, 1H) 4.86-5.07 (m, 3H) 7.45 (br. d, J=4.6 Hz, 1H) 7.51 (br. d, J=8.7 Hz, 2H) 7.50 (s, 1H) 7.72 (br. d, J=8.7 Hz, 2H) 7.85 (s, 1H) 8.49 (d, J=5.2 Hz, 1H).

Example 9

(7S)-5-[4-Fluoro-3-(trifluoromethyl)phenyl]-7-methyl-3-(2-methyl-4-pyridyl)-6,7-dihydropyrazolo[1,5-a]pyrazin-4-one (E-9, Co. No. 67)

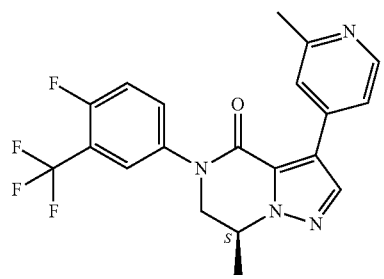

Compound 67 was obtained starting from intermediate I-18 (160 mg, 0.66 mmol), 5-bromo-2-fluorobenzotrifluoride (149 μL, 1.06 mmol), N,N'-dimethylethylenediamine (42 μL, 0.396 mmol), copper(I) iodide (75 mg, 0.396 mmol), K₂CO₃ (182 mg, 1.32 mmol) in toluene (4.27 mL), following a procedure similar to that described in E-1, yielding compound 67 (224 mg, 84%) as a pale yellow solid. ¹H NMR (500 MHz, CDCl₃) δ ppm 1.76 (d, J=6.4 Hz, 3H) 2.58 (s, 3H) 3.98 (dd, J=12.7, 7.2 Hz, 1H) 4.25 (dd, J=12.6, 4.2 Hz, 1H) 4.80 (quind, J=6.6, 4.3 Hz, 1H) 7.29 (d, J=9.5 Hz, 1H) 7.43 (dd, J=5.2, 1.2 Hz, 1H) 7.48 (s, 1H) 7.54-7.61 (m, 2H) 7.80 (s, 1H) 8.49 (d, J=5.2 Hz, 1H).

Example 10

(7S)-5-[4-(2-Fluoroethoxy)-3-(trifluoromethyl)phenyl]-7-methyl-3-(2-methyl-4-pyridyl)-6,7-dihydropyrazolo[1,5-a]pyrazin-4-one (E-10, Co. No. 77)

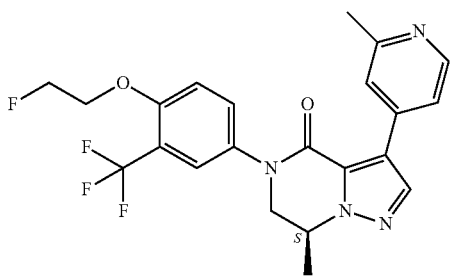

Sodium hydride (60% dispersion in mineral oil, 22 mg, 0.544 mmol) was added to a solution of 2-fluoroethanol (453 μL, 0.495 mmol) in DMF (4.5 mL) at 0° C. and the mixture was stirred at rt for 10 minutes. Then compound 67 (200 mg, 0.495 mmol) was added. The mixture was stirred at 110° C. for 23 h. The reaction mixture was cooled to rt and a solution of 2-fluoroethanol (227 μL, 0.247 mmol) and Sodium hydride (60% dispersion in mineral oil, 12 mg, 0.297 mmol) in DMF (0.5 ml) was added. The resulting mixture was stirred at 110° C. for 16 h. The mixture was quenched with water and extracted with EtOAc. The organic layer was separated, dried (Na$_2$SO$_4$) and the solvents were evaporated in vacuo. The crude product was purified by flash column chromatography (silica; 7M solution of ammonia in MeOH in DCM/DCM 0/100 to 2/98). The desired fractions were collected and the solvents evaporated in vacuo to afford 164 mg of compound 77, which was further purified by RP HPLC (Stationary phase: C18 XBridge™ 30×100 mm 5 um), mobile phase: Gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN), yielding 125 mg of compound 77, which was further purified by RP HPLC (Stationary phase: C18 XBridge™ 30×100 mm 5 um), mobile phase: Gradient from 67% 0.1% NH$_4$CO$_3$H/NH$_4$OH pH 9 solution in Water, 33% CH$_3$CN to 50% 0.1% NH$_4$CO$_3$H/NH$_4$OH pH 9 solution in Water, 50% CH$_3$CN), yielding 117 mg of compound 77 which was further purified by RP HPLC (Stationary phase: C18 XBridge™ 30×100 mm 5 μm), mobile phase: Gradient from 47% 0.1% NH$_4$CO$_3$H/NH$_4$OH pH 9 solution in Water, 53% MeOH to 30% 0.1% NH$_4$CO$_3$H/NH$_4$OH pH 9 solution in Water, 70% MeOH), yielding compound 77 (39 mg, 18%), also recovering 38 mg of starting material, compound 67. For compound 77: $^1$H NMR (400 MHz, CDCl$_3$) δ ppm 1.75 (d, J=6.5 Hz, 3H) 2.57 (s, 3H) 3.96 (dd, J=12.8, 7.3 Hz, 1H) 4.24 (dd, J=12.7, 4.4 Hz, 1H) 4.28-4.38 (m, 2H) 4.70-4.87 (m, 2H) 4.75-4.83 (m, 1H) 7.08 (d, J=8.6 Hz, 1H) 7.44 (dd, J=5.2, 1.3 Hz, 1H) 7.48-7.57 (m, 3H) 7.79 (s, 1H) 8.47 (dd, J=5.3, 0.5 Hz, 1H).

Example 11

(7S)-5-(4-Ethoxyphenyl)-7-methyl-3-(2-methyl-4-pyridyl)-6,7-dihydropyrazolo[1,5-a]pyrazin-4-one hydrochloride salt (E-11, Co. No. 81)

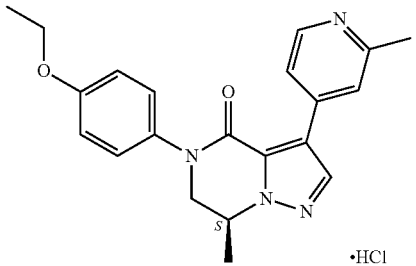

Copper(I) iodide (47 mg, 0.247 mmol) was added to a stirred suspension of intermediate I-18 (0.1 g, 0.413 mmol), 4-iodophenetole (0.164 g, 0.661 mmol), K$_2$CO$_3$ (114 mg, 0.825 mmol) and N,N'-dimethylethylenediamine (26 μL, 0.211 mmol) in toluene (6 mL) in a sealed tube and under nitrogen. The mixture was stirred at 100° C. for 24 h. The mixture was filtered through a pad of diatomaceous earth and washed with DCM. The organic layer was evaporated in vacuo. The crude product was purified by flash column chromatography (silica; EtOAc in DCM 0/100 to 40/60). The desired fractions were collected and concentrated in vacuo to yield compound 81 as an oil. The residue was dissolved in EtOAc and HCl (4N) (103 μL, 0.413 mmol) was added. The residue was triturated from DIPE, filtered and dried in vacuo to yield compound 81 (163 mg, 99%) as a white solid. Free base: $^1$H NMR (300 MHz, CDCl$_3$) δ ppm 1.35 (t, J=6.9 Hz, 3H) 1.65 (d, J=6.5 Hz, 3H) 2.50 (s, 3H) 3.84 (dd, J=12.9, 7.0 Hz, 1H) 3.97 (q, J=7.0 Hz, 2H) 4.16 (dd, J=12.9, 4.3 Hz, 1H) 4.60-4.76 (m, 1H) 6.87 (br. d, J=8.8 Hz, 2H) 7.18 (br. d, J=8.7 Hz, 2H) 7.43 (br. d, J=4.8 Hz, 1H) 7.48 (br. s, 1H) 7.72 (s, 1H) 8.39 (br. d, J=4.3 Hz, 1H); HCl salt: $^1$H NMR (300 MHz, DMSO-d$_6$) δ ppm 1.34 (t, J=6.9 Hz, 3H) 1.60 (d, J=6.3 Hz, 3H) 2.68 (s, 3H) 3.38 (br. s., 1H) 3.90-4.14 (m, 3H) 4.28 (dd, J=13.0, 4.1 Hz, 1H) 4.78-4.94 (m, 1H) 7.00 (br. d, J=8.9 Hz, 2H) 7.35 (br. d, J=8.8 Hz, 2H) 8.23-8.42 (m, 3H) 8.69 (d, J=6.3 Hz, 1H).

Example 12

4-[(7S)-7-Methyl-4-oxo-5-[4-(trifluoromethyl)phenyl]-6,7-dihydropyrazolo[1,5-a]pyrazin-3-yl]pyridine-2-carbonitrile (E-12, Co. No. 127)

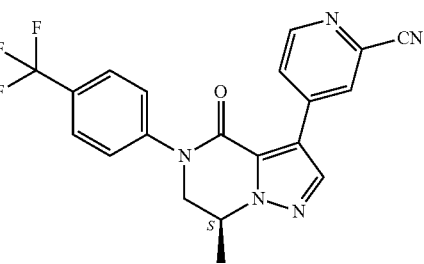

Pd(PPh$_3$)$_4$ (42 mg, 0.036 mmol) was added to a stirred suspension of intermediate I-33a (250 mg, 0.593 mmol) and 4-bromopyridine-2-carbonitrile (162 mg, 0.884 mmol) in 1,4-dioxane (4 mL) and a sat. sol. of Na$_2$CO$_3$ (2 mL). The mixture was stirred at 150° C. for 10 min under microwave irradiation. Then the mixture was diluted with H$_2$O and extracted with DCM. The organic layer was dried (Na$_2$SO$_4$), filtered and the solvent evaporated in vacuo. The crude product was purified by flash column chromatography (silica; EtOAc in DCM 0/100 to 50/50). The desired fractions were collected and evaporated in vacuo. The residue was precipitated with DIPE. The solid was filtered to yield compound 127 as a white solid. $^1$H NMR (500 MHz, CDCl$_3$) δ ppm 1.77 (d, J=6.4 Hz, 3H) 4.05 (dd, J=12.9, 7.4 Hz, 1H) 4.32 (dd, J=12.7, 4.0 Hz, 1H) 4.79-4.88 (m, 1H) 7.51 (br. d, J=8.4 Hz, 2H) 7.74 (br. d, J=8.4 Hz, 2H) 7.86 (s, 1H) 7.92 (dd, J=5.2, 1.7 Hz, 1H) 8.04-8.14 (m, 1H) 8.67 (d, J=5.2 Hz, 1H).

Example 13

(7S)-3-(2-Isopropyl-4-pyridyl)-7-methyl-5-[4-(trifluoromethyl)phenyl]-6,7-dihydropyrazolo[1,5-a]pyrazin-4-one (E-13, Co. No. 126)

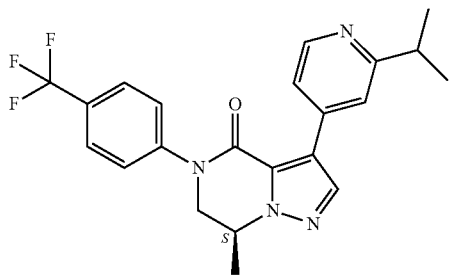

Pd(PPh$_3$)$_4$ (26 mg, 0.022 mmol) was added to a stirred suspension of intermediate I-33b (150 mg, 0.442 mmol) and 4-bromo-2-isopropyl-pyridine (prepared as described in WO2009/118292) (97 mg, 0.486 mmol) in a sat. aq. sol. NaHCO$_3$ (1 mL) and 1,4-dioxane (1 mL). The mixture was stirred at 120° C. for 10 min under microwave irradiation. The mixture was filtered through diatomaceous earth and washed with DCM. The organic layer was washed with water, separated, dried (Na$_2$SO$_4$), filtered and concentrated in vacuo. The crude product was purified by flash column chromatography ((silica; 7N solution of ammonia in MeOH in DCM 0/100 to 10/90) then (silica, EtOAc in DCM 0/100 to 30/70)) then by RP HPLC (Stationary phase: C18 XSelect™ 19×100 mm 5 μm, Mobile phase: Gradient from 80% 0.1% NH$_4$CO$_3$H/NH$_4$OH pH 9 solution in Water, 20% CH$_3$CN to 0% 0.1% NH$_4$CO$_3$H/NH$_4$OH pH 9 solution in Water, 100% CH$_3$CN)). The desired fractions were collected and evaporated in vacuo to yield compound 126 as a white solid. $^1$H NMR (400 MHz, CDCl$_3$) δ ppm 1.32 (d, J=6.9 Hz, 6H) 1.75 (d, J=6.7 Hz, 3H) 3.08 (spt, J=6.9 Hz, 1H) 4.02 (dd, J=12.7, 7.2 Hz, 1H) 4.31 (dd, J=12.6, 4.0 Hz, 1H) 4.80 (quind, J=6.7, 4.3 Hz, 1H) 7.45-7.48 (m, 2H) 7.51 (br. d, J=8.3 Hz, 2H) 7.71 (br. d, J=8.6 Hz, 2H) 7.81 (s, 1H) 8.50-8.55 (m, 1H)

Example 14

(7S)-5-(3,4-Dichlorophenyl)-3-[2-(hydroxymethyl)-4-pyridyl]-7-methyl-6,7-dihydropyrazolo[1,5-a]pyrazin-4-one (E-14, Co. No. 125)

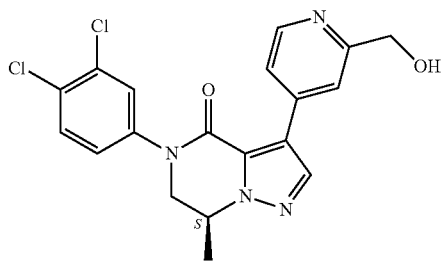

A suspension of intermediate I-34 (1.09 g, 4.56 mmol) in acetic anhydride (8 mL) was stirred at 100° C. for 2 h. The mixture was cooled to rt, and poured into water (15 mL) and EtOAc (30 mL). The organic layer was separated, washed with a sat. NaHCO$_3$ sol., dried (Na$_2$SO$_4$), filtered and concentrated in vacuo. The resultant oil was stirred with lithium hydroxide (259 mg, 10.81 mmol) in MeOH (5.45 mL) and H$_2$O (2.72 mL) at rt for 30 min. Then, EtOAc was added and the organic layer was washed with water, brine, dried (Na$_2$SO$_4$), filtered and concentrated in vacuo. The crude product was purified by flash column chromatography (silica; 7M solution of ammonia in MeOH in DCM 0/100 to 3/97). The desired fractions were collected and evaporated in vacuo to yield compound 125 (670 mg, 61%).

Crude compound 125 (100 mg) was purified by RP HPLC (Stationary phase: C18 XBridge 30×100 mm 5 um), Mobile phase: Gradient from 54% 0.1% NH$_4$CO$_3$H/NH$_4$OH pH 9 solution in Water, 46% CH$_3$CN to 64% 0.1% NH$_4$CO$_3$H/NH$_4$OH pH 9 solution in Water, 36% CH$_3$CN), yielding 72 mg compound 125. $^1$H NMR (500 MHz, CDCl$_3$) δ ppm 1.74 (d, J=6.4 Hz, 3H) 3.73 (br. s., 1H) 3.96 (dd, J=12.7, 7.2 Hz, 1H) 4.24 (dd, J=12.7, 4.3 Hz, 1H) 4.72-4.83 (m, 3H) 7.23 (dd, J=8.7, 2.3 Hz, 1H) 7.49 (d, J=2.3 Hz, 1H) 7.51 (d, J=8.7 Hz, 1H) 7.55 (d, J=4.9 Hz, 1H) 7.59 (s, 1H) 7.82 (s, 1H) 8.54 (d, J=4.9 Hz, 1H).

Example 15

(7S)-5-(3,4-Dichlorophenyl)-3-[2-(1-hydroxyethyl)-4-pyridyl]-7-methyl-6,7-dihydropyrazolo[1,5-a]pyrazin-4-one (E-15, Co. No. 111)

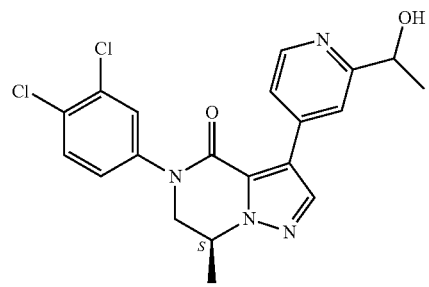

Methylmagnesium chloride 3M in THF (249 μL, 0.747 mmol) was added dropwise to a solution of intermediate I-39 (150 mg, 0.374 mmol) in THF (1.24 mL) at −78° C. and under nitrogen. The mixture was stirred at −78° C. for 2 h. Then, more methylmagnesium chloride 3M in THF (125 μL, 0.374 mmol) was added and the mixture was stirred at −78° C. for 1 h. Then, it was quenched at −78° C. with a sat. NH₄Cl sol. and allowed to reach rt. The mixture was extracted with EtOAc. The organic layer was separated, dried (MgSO₄), filtered and the solvents evaporated in vacuo. The crude product was purified by flash column chromatography (silica; MeOH in DCM 0/100 to 5/95). The desired fractions were collected and evaporated in vacuo. The residue was precipitated with Ether/Heptane to yield compound 111 as a pale yellow solid. ¹H NMR (400 MHz, CDCl₃) δ ppm 1.52 (dd, J=6.6, 0.8 Hz, 3H) 1.74 (dd, J=6.5, 2.3 Hz, 3H) 3.91-4.02 (m, 1H) 4.13-4.31 (m, 2H) 4.72-4.84 (m, 1H) 4.92 (q, J=6.5 Hz, 1H) 7.23 (dd, J=8.6, 2.5 Hz, 1H) 7.49 (d, J=2.3 Hz, 1H) 7.51 (d, J=8.6 Hz, 1H) 7.56 (br. d, J=5.3 Hz, 1H) 7.59-7.63 (m, 1H) 7.82 (s, 1H) 8.52 (dd, J=5.1, 0.7 Hz, 1H)

Example 16

(7S)-7-Methyl-3-(2-methyl-1-oxido-pyridin-1-ium-4-yl)-5-[4-(trifluoromethyl)phenyl]-6,7-dihydropyrazolo[1,5-a]pyrazin-4-one (E-16, Co. No. 140)

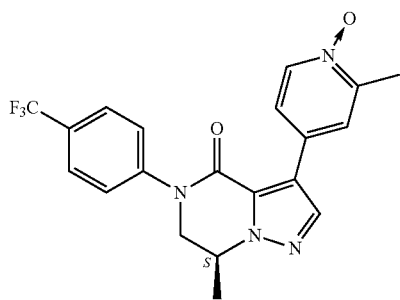

3-Chloroperoxybenzoic acid (2.96 g, 17.18 mmol) was added to a stirred solution of final compound E-1 (3.32 g, 8.59 mmol) in DCM (133 mL) at 0° C. The mixture was allowed to reach rt and stirred at rt for 3 h. The mixture was treated with Na₂CO₃ sat sol. and diluted with DCM. The organic layer was separated, dried (Na₂SO₄), filtered and the solvents evaporated in vacuo to yield compound 140 (3.4 g, 98%) as a pale yellow solid.

A small fraction (350 mg) was purified by flash column chromatography (silica; MeOH in DCM 0/100 to 5/95). The desired fractions were collected and evaporated in vacuo. The residue was precipitated with Et₂O and filtered to yield pure compound 140 (290 mg, 8%). ¹H NMR (500 MHz, CDCl₃) δ ppm 1.75 (d, J=6.4 Hz, 3H) 2.53 (s, 3H) 4.02 (dd, J=12.7, 7.2 Hz, 1H) 4.30 (dd, J=12.7, 4.0 Hz, 1H) 4.75-4.85 (m, 1H) 7.50 (d, J=8.4 Hz, 2H) 7.63 (dd, J=6.8, 2.5 Hz, 1H) 7.67-7.77 (m, 3H) 7.81 (s, 1H) 8.21 (d, J=6.6 Hz, 1H).

Example 17

(7S)-5-[4-(1-Hydroxyethyl)phenyl]-7-methyl-3-(2-methyl-4-pyridyl)-6,7-dihydropyrazolo[1,5-a]pyrazin-4-one (E-17, Co. No. 149)

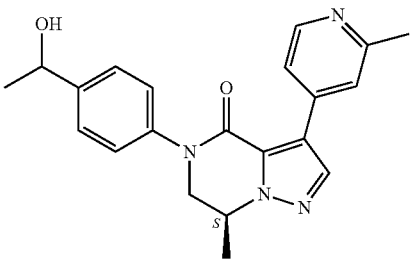

Sodium borohydride (6 mg, 0.166 mmol) was added to a stirred solution of intermediate I-35 (60 mg, 0.166 mmol) in MeOH (5 mL) at 0° C. The mixture was stirred at rt for 16 h. The solvent was concentrated in vacuo. The residue was dissolved with DCM and washed with a sat. Na₂CO₃ sol. The organic layer was separated, dried (MgSO₄), filtered and the solvents evaporated in vacuo. The crude product was purified by flash column chromatography (silica; MeOH in DCM 0/100 to 100/0). The desired fractions were collected and concentrated in vacuo to yield compound 149 (40 mg, 66%). ¹H NMR (300 MHz, CDCl₃) δ ppm 1.52 (d, J=6.5 Hz, 3H) 1.73 (d, J=6.5 Hz, 3H) 2.31 (br. s., 1H) 2.57 (s, 3H) 3.97 (dd, J=12.8, 6.9 Hz, 1H) 4.16-4.39 (m, 1H) 4.60-4.86 (m, 1H) 4.95 (q, J=6.4 Hz, 1H) 7.35 (br. d, J=8.2 Hz, 2H) 7.42-7.59 (m, 4H) 7.81 (s, 1H) 8.37-8.49 (m, 1H).

Example 18

(7S)-5-(4-Cyclopropylphenyl)-7-methyl-3-(2-methyl-4-pyridyl)-6,7-dihydropyrazolo[1,5-a]pyrazin-4-one (E-18, Co. No. 156)

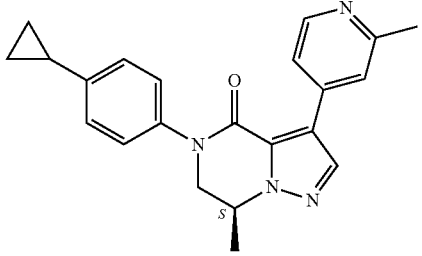

Pd(PPh₃)₄ (37 mg, 0.032 mmol) was added to a stirred suspension of intermediate I-36 (255 mg, 0.642 mmol), cyclopropylboronic acid (165 mg, 1.92 mmol) and K₂CO₃ (177 mg, 1.28 mmol) in CH₃CN (5 mL) and H₂O (2 mL). The mixture was stirred at 150° C. for 10 min under microwave irradiation. Then more cyclopropylboronic acid (165 mg, 1.92 mmol) and Pd(PPh₃)₄ (37 mg, 0.032 mmol) were added. The mixture was stirred at 150° C. for another 10 min under microwave irradiation. Then the mixture was diluted with H₂O and extracted with DCM. The organic layer was dried (MgSO₄), filtered and the solvent evaporated in vacuo. The crude product was purified by flash column chromatography (silica; EtOAc in Heptane 0/100 to 75/25)

and by RP HPLC (Stationary phase: C18 XBridge™ 30×100 mm 5 um, Mobile phase: Gradient from 67% 0.1% NH₄CO₃H/NH₄OH pH 9 solution in Water, 33% CH₃CN to 50% 0.1% NH₄CO₃H/NH₄OH pH 9 solution in Water, 50% CH₃CN). The desired fractions were collected and concentrated in vacuo to yield compound 156 (80 mg, 24%) as a solid. ¹H NMR (400 MHz, CDCl₃) δ ppm 0.62-0.77 (m, 2H) 0.91-1.06 (m, 2H) 1.72 (d, J=6.7 Hz, 3H) 1.91 (tt, J=8.5, 5.1 Hz, 1H) 2.56 (s, 3H) 3.93 (dd, J=12.9, 6.9 Hz, 1H) 4.25 (dd, J=12.9, 4.2 Hz, 1H) 4.75 (quind, J=6.6, 4.4 Hz, 1H) 7.09-7.18 (m, 2H) 7.18-7.25 (m, 2H) 7.48 (dd, J=5.1, 1.2 Hz, 1H) 7.53 (s, 1H) 7.79 (s, 1H) 8.45 (d, J=5.1 Hz, 1H)

Example 19

(7S)-7-Methyl-3-(6-piperazin-1-yl-3-pyridyl)-5-[4-(trifluoromethyl)phenyl]-6,7-dihydropyrazolo[1,5-a]pyrazin-4-one (E-19, Co. No. 176)

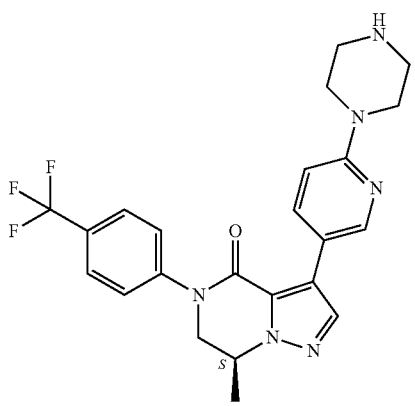

Trifluoroacetic acid (0.911 mL, 11.91 mmol) was added to a stirred solution of intermediate I-42 (663 mg, 1.19 mmol) in DCM (1.9 mL). The mixture was stirred at rt for 1 h. The solvent was concentrated in vacuo. The crude product was purified by flash column chromatography (silica; MeOH in DCM 0/100 to 20/80). The desired fractions were collected and evaporated in vacuo. The residue was precipitated with Et₂O and filtrated a solid that was purified by RP HPLC (Stationary phase: C18 XBridge™ 50×100 5 μm, Mobile phase: Gradient from 53% 0.1% NH₄CO₃H/NH₄OH pH 9 solution in Water, 43% CH₃CN to 40% 0.1% NH₄CO₃H/NH₄OH pH 9 solution in Water, 60% CH₃CN), to yield compound 176 (151 mg, 28%) as a solid. ¹H NMR (500 MHz, CDCl₃) δ ppm 1.73 (d, J=6.6 Hz, 3H) 1.76 (br. s., 1H) 2.92-3.02 (m, 4H) 3.50-3.57 (m, 4H) 4.00 (dd, J=12.4, 7.2 Hz, 1H) 4.27 (dd, J=12.4, 4.0 Hz, 1H) 4.70-4.82 (m, 1H) 6.63 (d, J=8.7 Hz, 1H) 7.50 (br. d, J=8.7 Hz, 2H) 7.68 (br. d, J=8.7 Hz, 2H) 7.71 (s, 1H) 7.96 (dd, J=9.0, 2.3 Hz, 1H) 8.42 (d, J=2.3 Hz, 1H)

Example 20

(7S)-7-Methyl-3-(2-methyl-4-pyridyl)-5-[6-(trifluoromethyl)-3-pyridyl]-6,7-dihydropyrazolo[1,5-a]pyrazin-4-one (E-20, Co. No. 186)

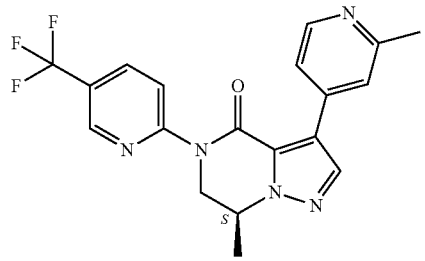

Pd(PPh₃)₄ (155 mg, 0.134 mmol) was added to a stirred suspension of intermediate I-18 (325 mg, 1.341 mmol), 2-chloro-5-(trifluoromethyl)pyridine (365 mg, 2.012 mmol), 4,5-bis(diphenylphosphino)-9,9-dimethylxanthene (155 mg, 0.268 mmol), Cs₂CO₃ (874 mg, 2.683 mmol) in 1,4-dioxane (10 mL) in a sealed tube and under nitrogen. The mixture was stirred at 120° C. for 7 h. The mixture was filtered through a pad of diatomaceous earth and washed with DCM. The filtrate was evaporated in vacuo and the crude product was purified by flash column chromatography (silica, EtOAc in DCM 0/100 to 30/70). The desired fractions were collected and concentrated in vacuo. The residue was purified by ion exchange chromatography using an (ISOLUTE® SCX2 cartridge) eluting first with MeOH then with 7M solution of ammonia in MeOH. The desired fractions contained in the 7M solution of ammonia in MeOH were collected and the solvents evaporated in vacuo. The residue was triturated with Et₂O to yield compound 186 (415 mg, 80%) as a white solid. ¹H NMR (500 MHz, CDCl₃) δ ppm 1.73 (d, J=6.4 Hz, 3H) 2.60 (s, 3H) 4.35-4.44 (m, 1H) 4.68-4.80 (m, 2H) 7.41 (dd, J=5.2, 1.2 Hz, 1H) 7.45 (s, 1H) 7.78 (s, 1H) 7.94 (dd, J=8.8, 2.2 Hz, 1H) 8.24 (d, J=9.0 Hz, 1H) 8.52 (d, J=5.2 Hz, 1H) 8.69-8.73 (m, 1H).

Example 21

(7S)-7-Methyl-3-(2-methyl-4-pyridyl)-5-[6-methyl-5-(trifluoromethyl)-2-pyridyl]-6,7-dihydropyrazolo[1,5-a]pyrazin-4-one (E-21, Co. No. 192)

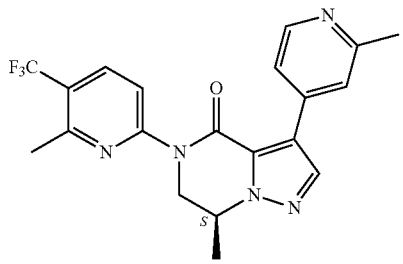

Tetramethyltin (32 μL, 0.231 mmol) was added to a mixture of intermediate I-43 (65 mg, 0.154 mmol), lithium chloride (13 mg, 0.308 mmol) and bis(triphenylphosphine) palladium(II) dichloride (6 mg, 0.007 mmol) in degassed DMF (2.4 mL), in a sealed tube under nitrogen. The mixture was stirred at 110° C. for 5 h. The mixture was diluted with a sat. sol. of NaHCO₃ and extracted with EtOAc. The organic layer was separated, dried (Na₂SO₄), filtered and the solvents evaporated in vacuo. The crude product was purified by flash column chromatography (silica; EtOAc in DCM 0/100 to 30/70). The desired fractions were collected and concentrated in vacuo. Then the product was triturated with Et₂O to yield compound 192 (26 mg, 42%) as a white solid. ¹H NMR (400 MHz, CDCl₃) δ ppm 1.73 (d, J=6.5 Hz, 3H) 2.60 (s, 3H) 2.69 (br. d, J=1.6 Hz, 3H) 4.34-4.46 (m, 1H) 4.66-4.80 (m, 2H) 7.41 (dd, J=5.1, 1.2 Hz, 1H) 7.44 (s, 1H) 7.78 (s, 1H) 7.90 (d, J=8.8 Hz, 1H) 8.02 (d, J=8.6 Hz, 1H) 8.52 (d, J=4.9 Hz, 1H).

Example 22a (7S)-5-[6-Ethoxy-5-(trifluoromethyl)-2-pyridyl]-7-methyl-3-(2-methyl-4-pyridyl)-6,7-dihydropyrazolo[1,5-a]pyrazin-4-one (E-22a, Co. No. 189)

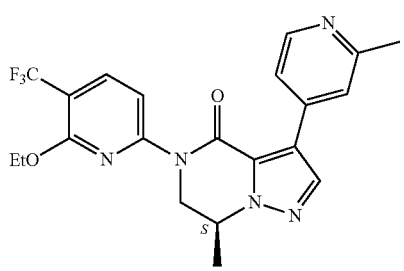

EtOH (114 μL, 1.95 mmol) was added to a stirred suspension of sodium hydride (60% dispersion in mineral oil) (78 mg, 1.95 mmol) in DMF (5 mL) at 0° C. The mixture was stirred at rt for 10 min. Then, a solution of 2-chloro-4-iodo-5-(trifluoromethyl)pyridine (0.5 g, 1.62 mmol) in DMF (5 mL) was added at 0° C. and the mixture was stirred at rt for 18 h. Then, more sodium hydride (60% dispersion in mineral oil) (26 mg, 0.65 mmol) and EtOH (38 μL, 0.65 mmol) were added at 0° C. and the mixture was stirred at rt for 2 h. Intermediate I-18 (157 mg, 0.65 mmol) was then added and the mixture was cooled to 0° C. More sodium hydride (60% dispersion in mineral oil) (52 mg, 1.301 mmol) was added and the mixture was stirred at rt for 1 h and at 80° C. for 16 h. Then more sodium hydride (60% dispersion in mineral oil) (13 mg, 0.325 mmol) was added at rt and the mixture was stirred at 80° C. for 2 h more. The mixture was treated with a 10% NH₄Cl sol. and extracted with EtOAc/THF. The organic layer was separated, dried (Na₂SO₄), filtered and the solvents evaporated in vacuo. The residue was dissolved in DMF (10 mL). TEA (0.226 mL, 1.626 mmol) and HATU (0.247 g, 0.605 mmol) were added. The mixture was stirred at rt for 1 h. The mixture was treated with a sat. NaHCO₃ sol./brine at 0° C. and extracted with EtOAc. The organic layer was separated, dried (Na₂SO₄), filtered and the solvents evaporated in vacuo. The crude product was purified by flash column chromatography (silica; EtOAc in DCM 0/100 to 100/0). The desired fractions were collected and concentrated in vacuo. Then the residue was repurified by RP HPLC (Stationary phase: C18 XBridge™ 30×100 mm 5 um, Mobile phase: Gradient from 54% 0.1% NH₄CO₃H/NH₄OH pH 9 solution in Water, 46% CH₃CN to 64% 0.1% NH₄CO₃H/NH₄OH pH 9 solution in Water, 36% CH₃CN) to yield compound 189 (27 mg, 4%) as a beige solid. ¹H NMR (500 MHz, CDCl₃) δ ppm 1.46 (t, J=6.9 Hz, 3H) 1.71 (d, J=6.6 Hz, 3H) 2.60 (s, 3H) 4.15-4.27 (m, 2H) 4.39 (dd, J=13.3, 7.2 Hz, 1H) 4.65-4.80 (m, 2H) 7.40 (dd, J=5.2, 1.2 Hz, 1H) 7.43 (s, 1H) 7.77 (s, 1H) 7.82 (s, 1H) 8.47 (s, 1H) 8.52 (d, J=5.2 Hz, 1H).

Example 22b (7S)-5-[4-Chloro-5-(trifluoromethyl)-2-pyridyl]-7-methyl-3-(2-methyl-4-pyridyl)-6,7-dihydropyrazolo[1,5-a]pyrazin-4-one (E-22b, Co. No. 204)

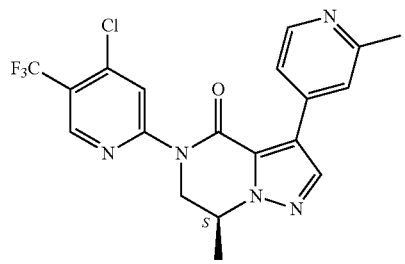

Pd(PPh₃)₄ (47 mg, 0.041 mmol) and 2,4-dichloro-5-(trifluoromethyl)pyridine (134 mg, 0.619 mmol) were added to a stirred suspension of intermediate I-18 (100 mg, 0.413 mmol), 4,5-bis(diphenylphosphino)-9,9-dimethylxanthene (48 mg, 0.082 mmol) and Cs₂CO₃ (269 mg, 0.082 mmol) in 1,4-dioxane (2.5 mL) in a sealed tube and under nitrogen. The mixture was stirred at 110° C. for 4 h and at 100° C. for 2 days. The mixture was filtered through a pad of diatomaceous earth and washed with DCM. The filtrate was evaporated in vacuo. The residue was dissolved in DMF (7 mL) and TEA (57 μL, 0.413 mmol) then HATU (157 mg, 0.413 mmol) were added. The mixture was stirred at rt for 2 h. The mixture was treated at 0° C. with a sat. sol. NaHCO₃/brine then EtOAc was added. The mixture was filtered through a pad of diatomaceous earth. The organic layer was separated, dried (Na₂SO₄), filtered and the solvents evaporated in vacuo. The crude product was purified by flash column chromatography (silica; EtOAc in DCM 0/100 to 100/0). The desired fractions were collected and concentrated in vacuo. The residue was repurified by RP HPLC (Stationary phase: C18 XBridge™ 30×100 mm 5 um, Mobile phase: Gradient from 54% 0.1% NH₄CO₃H/NH₄OH pH 9 solution in Water, 46% CH₃CN to 64% 0.1% NH₄CO₃H/NH₄OH pH 9 solution in Water, 36% CH₃CN) to yield compound 204 (27 mg, 15%) as a white solid. ¹H NMR (500 MHz, CDCl₃) δ ppm 1.72 (d, J=6.4 Hz, 3H) 2.61 (s, 3H) 4.36-4.45 (m, 1H) 4.68-4.79 (m, 2H) 7.39 (dd, J=5.2, 1.7 Hz, 1H) 7.43 (s, 1H) 7.78 (s, 1H) 8.42 (s, 1H) 8.54 (d, J=5.2 Hz, 1H) 8.68 (s, 1H).

Example 23

(7S)-3-(2-Iodo-4-pyridyl)-7-methyl-5-[4-(trifluoromethyl)phenyl]-6,7-dihydropyrazolo[1,5-a]pyrazin-4-one (E-23, Co. No. 225)

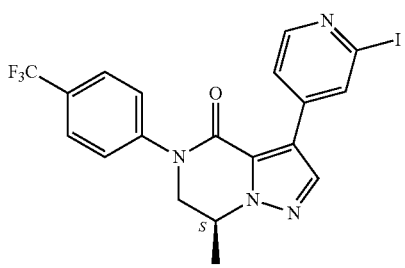

Acetyl chloride (84 μL, 1.18 mmol) was added to a stirred suspension of intermediate I-26 (320 mg, 0.786 mmol) and NaI (1.18 g, 7.866 mmol) in CH$_3$CN (12.8 mL) at rt. The mixture was stirred at 120° C. for 30 min under MW irradiation. Then the mixture was diluted with EtOAc and washed with a sat. sol. of Na$_2$S$_2$O$_3$ and brine. The organic layer was separated, dried (Na$_2$SO$_4$), filtered and the solvents evaporated in vacuo. The crude product was purified by flash column chromatography (silica; EtOAc in Heptane 0/100 to 60/40). The desired fractions were collected and evaporated in vacuo to yield compound 225 (289 mg, 74%). $^1$H NMR (400 MHz, CDCl$_3$) δ ppm 1.75 (d, J=6.5 Hz, 3H) 4.02 (dd, J=12.8, 7.3 Hz, 1H) 4.30 (dd, J=12.7, 4.2 Hz, 1H) 4.80 (quind, J=6.7, 4.2 Hz, 1H) 7.50 (br. d, J=8.3 Hz, 2H) 7.67 (dd, J=5.1, 1.6 Hz, 1H) 7.72 (br. d, J=8.3 Hz, 2H) 7.80 (s, 1H) 8.03-8.05 (m, 1H) 8.32 (dd, J=5.2, 0.6 Hz, 1H)

Example 24

(7S)-7-Methyl-3-(2-piperazin-1-yl-4-pyridyl)-5-[4-(trifluoromethyl)phenyl]-6,7-dihydropyrazolo[1,5-a]pyrazin-4-one hydrochloride salt (E-24, Co. No. 175)

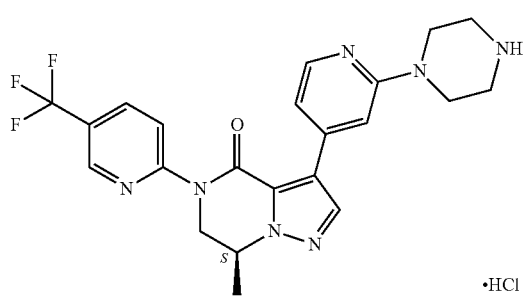

Compound 175 was obtained starting from intermediate I-33a (200 mg, 0.474 mmol), 1-(4-bromo-2-pyridyl)piperazine (CAS: 1201643-59-5, 157 mg, 0.649 mmol, 1.06 mmol), Pd(PPh$_3$)$_4$ (34 mg, 0.029 mmol) in 1,4-dioxane (4 mL) and a sat. sol. of Na$_2$CO$_3$ (2 mL), following a procedure similar to that described in E-12, then treatment with a solution of HCl 5N in iPrOH, yielded compound 175 (224 mg, 84%) as a pale yellow solid. $^1$H NMR (400 MHz, DMSO-d$_6$) δ ppm 1.59 (d, J=6.5 Hz, 3H) 3.22 (br. s., 4H) 3.83 (br. s., 4H) 4.10 (dd, J=12.9, 7.4 Hz, 1H) 4.39 (dd, J=12.9, 4.2 Hz, 1H) 4.81-4.92 (m, 1H) 7.29 (br. d, J=4.4 Hz, 1H) 7.56 (br. s., 1H) 7.69 (br. d, J=8.6 Hz, 2H) 7.84 (br. d, J=8.6 Hz, 2H) 8.11 (d, J=5.8 Hz, 1H) 8.19 (br. s, 1H) 9.20 (br. s., 2H).

Example 25

(7S)-3-[2-(4-Acetylpiperazin-1-yl)-4-pyridyl]-7-methyl-5-[4-(trifluoromethyl)phenyl]-6,7-dihydropyrazolo[1,5-a]pyrazin-4-one (E-25, Co. No. 106)

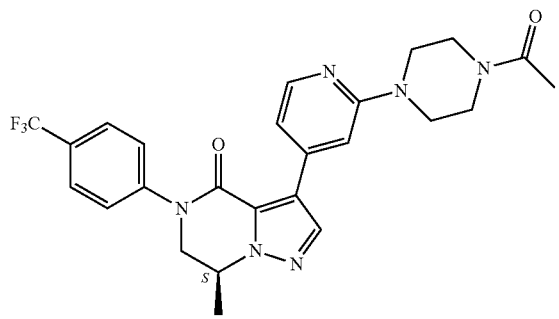

Acetyl chloride (4 μL, 0.060 mmol) was added to a solution of compound 175 (25 mg, 0.054 mmol) and TEA (16 μL, 0.115 mmol) in DCM (1 mL) under nitrogen. The mixture was stirred at rt for 5 h. Then the mixture was diluted with HCl 0.1N and extracted with DCM. The organic layer was separated, dried (MgSO$_4$), filtered and the solvent evaporated in vacuo. The crude product was purified by flash column chromatography (silica; MeOH in DCM 0/100 to 05/95). The desired fractions were collected and concentrated in vacuo to yield compound 106 (17 mg, 62%) as a solid. $^1$H NMR (400 MHz, CDCl$_3$) δ ppm 1.75 (d, J=6.5 Hz, 3H) 2.13 (s, 3H) 3.49-3.55 (m, 2H) 3.55-3.61 (m, 2H) 3.61-3.67 (m, 2H) 3.70-3.77 (m, 2H) 4.01 (dd, J=12.7, 6.9 Hz, 1H) 4.30 (dd, J=12.7, 4.2 Hz, 1H) 4.79 (quind, J=6.6, 4.4 Hz, 1H) 6.94 (dd, J=5.2, 1.3 Hz, 1H) 7.17 (br. s, 1H) 7.46-7.55 (m, 2H) 7.66-7.76 (m, 2H) 7.80 (s, 1H) 8.19 (dd, J=5.2, 0.6 Hz, 1H).

Example 26

7-(Difluoromethyl)-3-(2-methyl-4-pyridyl)-5-[4-(trifluoromethyl)phenyl]-6,7-dihydropyrazolo[1,5-a]pyrazin-4-one (E-26, Co. No. 181)

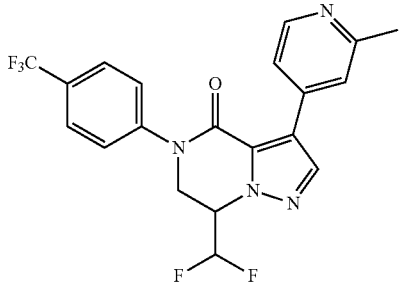 [SMILES: Cc1cc(-c2cnn3c2C(=O)N(c2ccc(C(F)(F)F)cc2)CC3C(F)F)ccn1]

Compound 181 was obtained starting from intermediate I-46 (71 mg, 0.169 mmol) using Pd/C 10% (36 mg, 0.033 mmol) in EtOH (3 mL) under H₂ atmospheric pressure, following a procedure similar to that described in E-6, yielding compound 181 (13 mg, 19%) as a white solid. ¹H NMR (400 MHz, CDCl₃) δ ppm 2.58 (s, 3H) 4.36 (dd, J=13.6, 3.2 Hz, 1H) 4.61 (ddd, J=13.6, 5.0, 1.3 Hz, 1H) 4.88-4.99 (m, 1H) 6.21-6.55 (m, 1H) 7.45 (dd, J=5.2, 1.3 Hz, 1H) 7.47-7.54 (m, 3H) 7.73 (br. d, J=8.3 Hz, 2H) 7.89 (s, 1H) 8.50 (d, J=5.1 Hz, 1H).

Example 27

(7S)-7-Methyl-3-[2-(methylamino)-4-pyridyl]-5-[4-(trifluoromethyl)phenyl]-6,7-dihydropyrazolo[1,5-a]pyrazin-4-one (E-27, Co. No. 147)

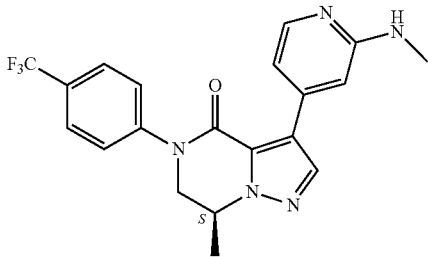

Compound 147 was obtained starting from intermediate I-33a (1.5 g, 3.561 mmol), 4-bromo-N-methyl-pyridin-2-amine (799 mg, 4.273 mmol, 1.06 mmol), Pd(PPh₃)₄ (206 mg, 0.178 mmol) in 1,4-dioxane (8.1 mL) and a sat. sol. of Na₂CO₃ (8.2 mL), following a procedure similar to that described in E-12, yielding compound 147 (1.14 g, 80%) as a white solid. ¹H NMR (500 MHz, CDCl₃) δ ppm 1.74 (d, J=6.4 Hz, 3H) 2.93 (d, J=5.2 Hz, 3H) 4.00 (dd, J=12.6, 7.1 Hz, 1H) 4.29 (dd, J=12.7, 4.0 Hz, 1H) 4.54 (br. d, J=3.2 Hz, 1H) 4.73-4.82 (m, 1H) 6.84 (s, 1H) 6.86 (d, J=5.2 Hz, 1H) 7.50 (br. d, J=8.4 Hz, 2H) 7.70 (br. d, J=8.4 Hz, 2H) 7.79 (s, 1H) 8.09 (d, J=5.2 Hz, 1H).

Example 28

(7S)-5-[4-Iodo-5-(trifluoromethyl)-2-pyridyl]-7-methyl-3-(2-methyl-4-pyridyl)-6,7-dihydropyrazolo[1,5-a]pyrazin-4-one (E-28, Co. No. 212)

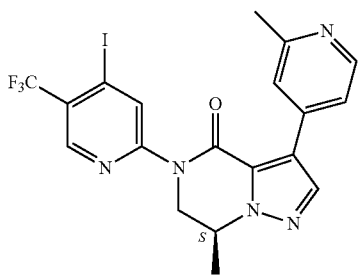

Intermediate I-18 (320 mg, 1.32 mmol) was added portionwise to a stirred suspension of sodium hydride (60% dispersion in mineral oil, 78 mg, 1.98 mmol) in DMF (5 mL) at rt. The mixture was stirred at rt for 15 min and a solution of 2-chloro-4-iodo-5-(trifluoromethyl)pyridine (446 mg, 1.453 mmol) in DMF (5 mL) was added at rt. The mixture was stirred at 80° C. for 16 h. Then more sodium hydride (60% dispersion in mineral oil, 27 mg, 0.66 mmol) was added at rt and the mixture was stirred at 80° C. for 1 h. The mixture was treated with 10% NH₄Cl sol./brine and extracted with EtOAc. The organic layer was separated, washed with brine, dried (Na₂SO₄), filtered and the solvents evaporated in vacuo. The crude product was purified by flash column chromatography (silica; EtOAc in DCM 0/100 to 100/0). The desired fractions were collected and the solvents concentrated in vacuo to yield compound 212 (220 mg, 32%) as a white foam.

Example 29

(7S)-5-(3,4-Dichloro-2-iodo-phenyl)-7-methyl-3-(2-methyl-4-pyridyl)-6,7-dihydropyrazolo[1,5-a]pyrazin-4-one (Co. No. 220) and (7S)-5-(3,4-dichloro-6-iodo-1-methyl-cyclohexa-1,3,5-trien-1-yl)-7-methyl-3-(2-methyl-4-pyridyl)-6,7-dihydropyrazolo[1,5-a]pyrazin-4-one (Co. No. 221) (E-29, Co. No. 220 and Co. No. 221)

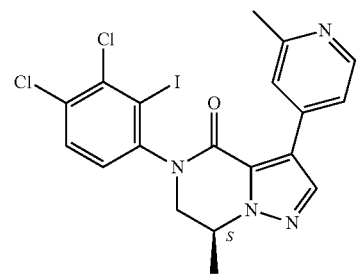

220

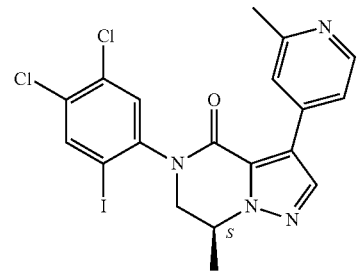

221

HATU (89 mg, 0.235 mmol) was added to a stirred solution of mixture intermediate compounds I-63a and I-63b (250 mg, 0.235 mmol) and TEA (65 μL, 0.471 mmol) in DMF (3 mL). The mixture was stirred at rt for 2 h. The mixture was treated with a sat. sol. of NH₄Cl and a sat. sol. of NaHCO₃ and extracted with EtOAc. The organic layer was separated, dried (MgSO₄), filtered and the solvents evaporated in vacuo. The crude product was purified by flash column chromatography (silica; EtOAc in Heptane 0/100 to 90/10). The desired fractions were collected and the solvents concentrated in vacuo to give two fractions that were triturated with DCM/Heptane to yield compound 220 (55 mg, 45%) and compound 221 (20 mg, 16%) as solids. Compound 220: ¹H NMR (500 MHz, CDCl₃) δ ppm 1.78 (d, J=6.4 Hz, 2H) 1.85 (d, J=6.6 Hz, 1H) 2.58 (s, 3H) 3.82 (dd, J=12.7, 9.2 Hz, 0.65H) 3.97 (dd, J=12.7, 7.2 Hz, 0.35H) 4.00-4.07 (m, 1H) 4.76-4.84 (m, 0.35H) 4.92-5.00 (m, 0.65H) 7.39 (s, 0.35H) 7.40 (s, 0.65H) 7.48 (br. d, J=5.2 Hz, 1H) 7.52-7.56 (m, 1H) 7.82 (s, 1H) 8.03 (s, 0.35H) 8.03 (s, 0.65H) 8.48 (d, J=5.2 Hz, 1H); compound 221: ¹H NMR (500 MHz, CDCl₃) δ ppm 1.78 (d, J=6.6 Hz, 2H) 1.85 (d, J=6.6 Hz, 1H) 2.57 (s, 3H) 3.81 (dd, J=12.7, 9.0 Hz, 0.65H) 3.98 (dd, J=12.7, 4.6 Hz, 0.35H) 4.02-4.11 (m, 1H) 4.76-4.84 (m, 0.35H) 4.95-5.04 (m, 0.65H) 7.16 (d, J=8.7 Hz, 0.35H) 7.17 (d, J=8.7 Hz, 0.65H) 7.49 (br. d, J=5.2 Hz, 1H) 7.52-7.61 (m, 2H) 7.83 (s, 0.65H) 7.83 (s, 0.35H) 8.47 (d, J=5.2 Hz, 1H).

The following final compounds were synthesized by following an analogous synthetic procedure as reported for compound 1 (E-1) followed by the procedure for intermediates I-18 and I-19 when needed.

| Structure | Compound number | Starting material |
|---|---|---|
| 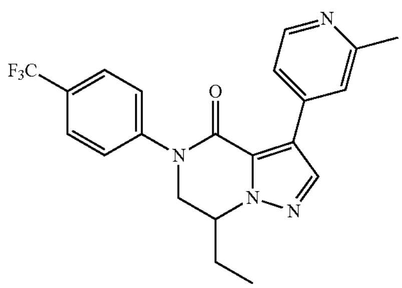 [SMILES: CCC1CN(c2ccc(C(F)(F)F)cc2)C(=O)c2c(-c3ccnc(C)c3)cnn21] | Co. No. 70 | I-59 |
| 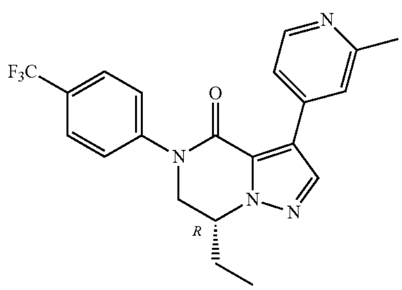 | Co. No. 129 | Co. No. 70 |
| 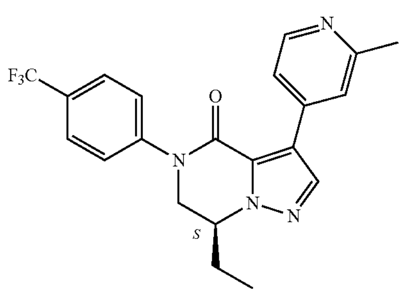 | Co. No. 130 | |
| 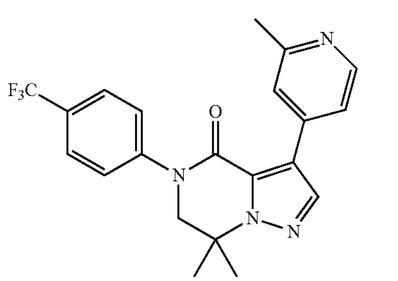 [SMILES: Cc1cc(-c2cnn3c2C(=O)N(c2ccc(C(F)(F)F)cc2)CC3(C)C)ccn1] | Co. No. 171 | I-60 |
| | Co. No. 216 | I-61 |
| | Co. No. 217 | |
| | Co. No. 120 | I-58 |
| | Co. No. 121 | |

The following compound was synthesized by following the sequence of an analogous synthetic procedure as reported for intermediate I-22 starting from intermediate I-14 and 1-bromo-3,4-dichlorobenzene, followed by the procedure for intermediates I-23 then following an analogous synthetic procedure as reported for compound 2 (E-2) using 2-methyl-4-(4,4,5,5-tetramethyl-1,3,2-dioxaborolan-2-yl)pyridine.

| Structure | Intermediate number | Starting material |
|---|---|---|
| 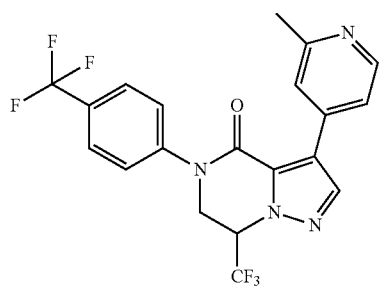 [SMILES: Cc1cc(-c2cnn3c2C(=O)N(c2ccc(C(F)(F)F)cc2)CC3C(F)(F)F)ccn1] | Co. No. 6a | I-14 |

Example 30

3-(2-Methyl-4-pyridyl)-7-(trifluoromethyl)-5-[4-(trifluoromethyl)phenyl]-6,7-dihydropyrazolo[1,5-a]pyrazin-4-one (Co. No. 238)

Compound 238 (E-30) was obtained starting from intermediate I-68 (20 mg, 0.042 mmol), 2-picoline-4-boronic acid (8 mg, 0.059 mmol), Pd(PPh$_3$)$_4$ (2 mg, 0.002 mmol) in 1,4-dioxane (0.4 mL) and a sat. sol. of NaHCO$_3$ (0.4 mL) following a procedure similar to that described in E-12 and purified by RP HPLC ((Stationary phase: C18 XBridge 30×100 5 um), (Mobile phase: Gradient from 60% 0.1% NH$_4$CO$_3$H/NH$_4$OH pH 9 solution in Water, 40% CH$_3$CN to 43% 0.1% NH$_4$CO$_3$H/NH$_4$OH pH 9 solution in Water, 57% CH$_3$CN)), yielding compound 238 (14 mg, 75%). $^1$H NMR (500 MHz, CDCl$_3$) δ ppm 2.53 (s, 3H) 4.23 (dd, J=14.0, 1.3 Hz, 1H) 4.67-4.74 (m, 1H) 5.07-5.14 (m, 1H) 7.38-7.43 (m, 3H) 7.47 (s, 1H) 7.67 (br. d, J=8.4 Hz, 2H) 7.87 (s, 1H) 8.44 (d, J=5.2 Hz, 1H).

Tables 1a (compounds I-87) and 1b (with an alternative representation for compounds I-87) below list additional compounds of Formula (I).

Tables 1a and 1b.

The following compounds were prepared following the methods exemplified in the Experimental Part (Ex. No.). Compounds exemplified and described in the experimental part are marked with an asterisk *. The work-up for compounds synthesized by an analogous procedure to E1 can be performed either by filtration through a pad of diatomaceous earth or by extraction with an organic solvent, washing with aqueous ammonia. The coupling agent used in the synthesis of compounds synthesized by an analogous procedure to E2 was either a boronic acid or a boronic ester. For some compounds the stereochemical configuration has been designated as *R or *S when the absolute stereochemistry is undetermined although the compound itself has been isolated as a single stereoisomer and is enantiomerically pure.

TABLE 1a

| Co. No. | Ex. No. | R$^1$ | R$^2$ | R$^4$ | R$^3$ | Salt form |
|---|---|---|---|---|---|---|
| 1 | E1* | 4-CF$_3$-phenyl | 2-methyl-4-pyridyl | —Me (S) | —H | |
| 1a | | | | | | •HCl |
| 1b | | | | | | •H$_2$SO$_4$ |
| 1c | | | | | | •CH$_3$SO$_3$H |
| 1d | | | | | | •HO$_2$CCH=CHCO$_2$H-cis |
| 2 | E2* | 4-CF$_3$-phenyl | 4-pyridyl | —Me (S) | —H | |
| 3 | E1 | 2-Cl-4-CF$_3$-phenyl | 2-methyl-4-pyridyl | —Me (S) | —H | |
| 4 | E1 | 4-SF$_5$-phenyl | 2-methyl-4-pyridyl | —Me (S) | —H | |
| 5 | E1 | 2-methyl-4-CF$_3$-phenyl | 2-methyl-4-pyridyl | —Me (S) | —H | •HCl |

TABLE 1a-continued

| Co. No. | Ex. No. | R¹ | R² | R⁴ | R³ | Salt form |
|---|---|---|---|---|---|---|
| 6 | E1 | 3,4-dichlorophenyl | 4-pyridyl (2-position bond) | —Me (S) | —H | •HCl |
| 6a | E1 | 3,4-dichlorophenyl | 4-pyridyl (2-position bond) | —Me (S) | —H | |
| 7 | E1 | 3-methyl-4-chlorophenyl | 4-pyridyl | —Me (S) | —H | |
| 8 | E1 | 3-OEt-4-CF₃-phenyl | 4-pyridyl | —Me (S) | —H | |
| 9 | E1 | 3-CF₃-4-Cl-phenyl | 4-pyridyl | —Me (S) | —H | |
| 10 | E1 | 3-F-4-CF₃-phenyl | 4-pyridyl | —Me (S) | —H | |
| 11 | E1 | 4-CF₃-phenyl | 4-pyridyl | —Me (S) | —H | |
| 12 | E1 | 3-OMe-4-CF₃-phenyl | 4-pyridyl | —Me (S) | —H | •HCl |
| 13 | E1 | 3-CN-4-CF₃-phenyl | 4-pyridyl | —Me (S) | —H | |
| 14 | E2 | 4-CF₃-phenyl | 2,6-dimethyl-4-pyridyl | —Me (S) | —H | |
| 15 | E1 | 4-Cl-phenyl | 4-pyridyl | —Me (S) | —H | •HCl |

TABLE 1a-continued

| Co. No. | Ex. No. | R¹ | R² | R⁴ | R³ | Salt form |
|---|---|---|---|---|---|---|
| 16 | E1 | 3-Cl-phenyl | 2-methylpyridin-4-yl | —Me (S) | —H | |
| 17 | E1 | 3-Cl-4-OEt-phenyl | 2-methylpyridin-4-yl | —Me (S) | —H | •HCl |
| 18 | E1 | 3-OEt-4-Cl-phenyl | 2-methylpyridin-4-yl | —Me (S) | —H | |
| 19 | E1 | 3-OMe-4-Cl-phenyl | 2-methylpyridin-4-yl | —Me (S) | —H | |
| 20 | E1 | 3-Cl-4-OMe-phenyl | 2-methylpyridin-4-yl | —Me (S) | —H | •HCl |
| 21 | E1 | 3-Me-4-F-phenyl | 2-methylpyridin-4-yl | —Me (S) | —H | |
| 22 | E2 | 4-CF₃-phenyl | 2-(methoxymethyl)pyridin-4-yl | —Me (S) | —H | •HCl |
| 23 | E1 | 3-CF₃-phenyl | 2-methylpyridin-4-yl | —Me (S) | —H | |
| 24 | E2 | 4-CF₃-phenyl | 5-methylpyridin-3-yl | —Me (S) | —H | |
| 25 | E1 | 3,4-diF-phenyl | 2-methylpyridin-4-yl | —Me (S) | —H | •HCl |
| 26 | E1 | 4-CF₃-phenyl | 2-methylpyridin-4-yl | —Me (R) | —H | |

TABLE 1a-continued

| Co. No. | Ex. No. | R¹ | R² | R⁴ | R³ | Salt form |
|---|---|---|---|---|---|---|
| 27 | E1 | 4-(OCHF₂)-phenyl | pyridin-4-yl (2-Me) | —Me (S) | —H | |
| 28 | E1 | 4-F-phenyl | pyridin-4-yl (2-Me) | —Me (S) | —H | •HCl |
| 29 | E2 | 4-CF₃-phenyl | pyridin-5-yl (2,3-diMe) | —Me (S) | —H | |
| 30 | E1 | 3-F-4-Cl-phenyl | pyridin-4-yl (2-Me) | —Me (S) | —H | |
| 31 | E1 | 3-OEt-4-CF₃-phenyl | pyridin-4-yl (2-Me) | —Me (R) | —H | |
| 32 | E2 | 4-CF₃-phenyl | pyridin-3-yl | —Me (S) | —H | |
| 33 | E1 | 3-OEt-4-CF₃-phenyl | pyridin-4-yl (2-Me) | —H | —H | |
| 34 | E1 | 3,5-diMe-4-OMe-phenyl | pyridin-4-yl (2-Me) | —Me (S) | —H | |
| 35 | E1 | 4-OMe-3-F-phenyl | pyridin-4-yl (2-Me) | —Me (S) | —H | •HCl |
| 36 | E2 | 4-CF₃-phenyl | pyridin-5-yl (2-Me) | —Me (S) | —H | |
| 37 | E2 | 4-CF₃-phenyl | pyridin-5-yl (2-NH₂) | —Me (S) | —H | |

TABLE 1a-continued
| Co. No. | Ex. No. | R¹ | R² | R⁴ | R³ | Salt form |
|---|---|---|---|---|---|---|
| 38 | E1 | 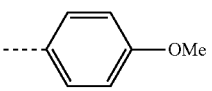 | 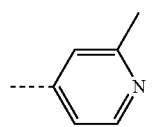 | —Me (S) | —H | •HCl |
| 39 | E1 | 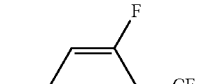 | 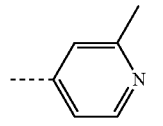 | —H | —H | |
| 40 | E1 | 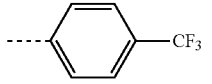 | 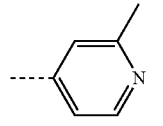 | —H | —H | |
| 41 | E1 | 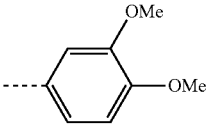 | 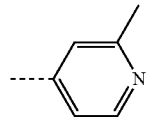 | —Me (S) | —H | |
| 42 | E1 | 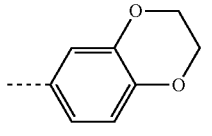 | 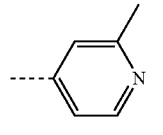 | —Me (S) | —H | |
| 43 | E1 | 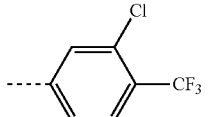 | 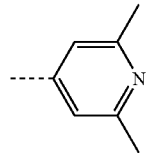 | —Me (S) | —H | |
| 44 | E4* | 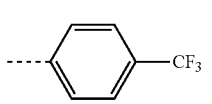 | 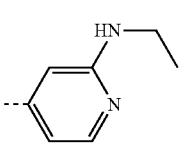 | —Me (S) | —H | |
| 45 | E5* | 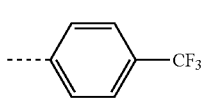 | 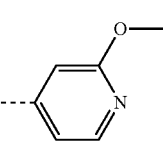 | —Me (S) | —H | |
| 46 | E6* | 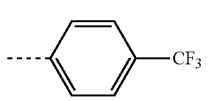 | 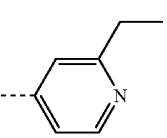 | —Me (S) | —H | |
| 47 | E1 | 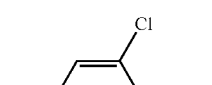 | 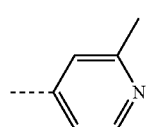 | —Me (S) | —H | |
| 48 | E1 | 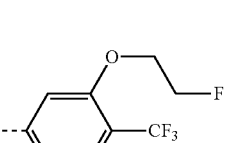 | 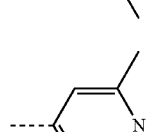 | —Me (S) | —H | |

TABLE 1a-continued

| Co. No. | Ex. No. | R¹ | R² | R⁴ | R³ | Salt form |
|---|---|---|---|---|---|---|
| 49 | E1 | 3-ethoxy-4-(trifluoromethyl)phenyl | 2,6-dimethylpyridin-4-yl | —Me (S) | —H | |
| 50 | E1 | 3-chloro-4-(trifluoromethyl)phenyl | pyridin-4-yl | —Me (S) | —H | |
| 51 | E1 | 3-methoxy-4-(trifluoromethyl)phenyl | 2,6-dimethylpyridin-4-yl | —Me (S) | —H | |
| 52 | E8* | 4-(trifluoromethyl)phenyl | 2-methylpyridin-4-yl | —CH₂F | —H | |
| 53 | E1 | 4-(pentafluorosulfanyl)phenyl | 2,6-dimethylpyridin-4-yl | —Me (S) | —H | |
| 54 | E1 | 3-(trifluoromethyl)-4-chlorophenyl | 2,6-dimethylpyridin-4-yl | —Me (S) | —H | |
| 55 | E1 | 3-ethoxy-4-(trifluoromethyl)phenyl | pyridin-4-yl | —Me (S) | —H | |
| 56 | E1 | 4-(pentafluorosulfanyl)phenyl | pyridin-4-yl | —Me (S) | —H | |
| 57 | E1 | 3,4-dichlorophenyl | pyridin-4-yl | —Me (S) | —H | |
| 58 | E1 | 3-(trifluoromethoxy)phenyl | 2-methylpyridin-4-yl | —Me (S) | —H | •HCl |

TABLE 1a-continued
| Co. No. | Ex. No. | R¹ | R² | R⁴ | R³ | Salt form |
|---|---|---|---|---|---|---|
| 59 | E1 | 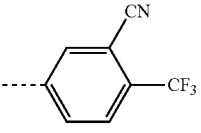 | 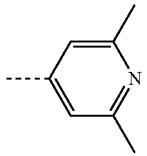 | —Me (S) | —H | |
| 60 | E1 | 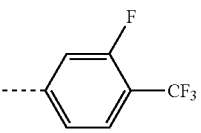 | 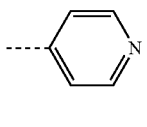 | —Me (S) | —H | |
| 61 | E1 | 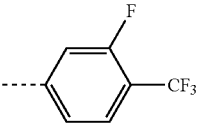 | 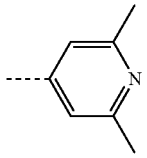 | —Me (S) | —H | |
| 62 | E1 | 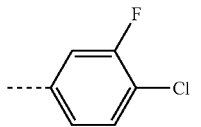 | 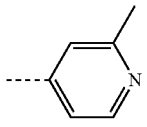 | —Me (S) | —H | |
| 63 | E1 | 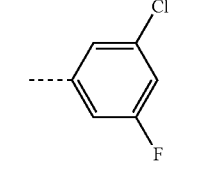 | 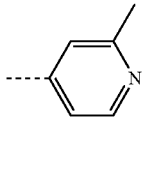 | —Me (S) | —H | •HCl |
| 64 | E1 | 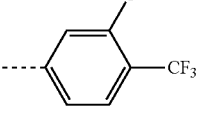 | 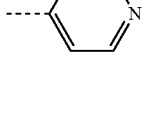 | —Me (S) | —H | |
| 65 | E1 | 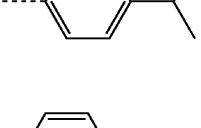 | 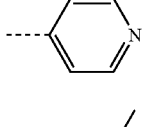 | —Me (S) | —H | •HCl |
| 66 | E1 | 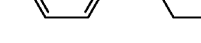 |  | —Me (S) | —H | •HCl |
| 67 | E9* | 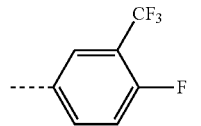 | 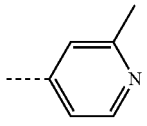 | —Me (S) | —H | |
| 68 | E1 | 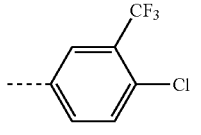 | 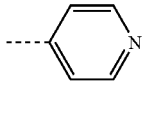 | —Me (S) | —H | |

TABLE 1a-continued
| Co. No. | Ex. No. | R¹ | R² | R⁴ | R³ | Salt form |
|---|---|---|---|---|---|---|
| 69 | E1 | 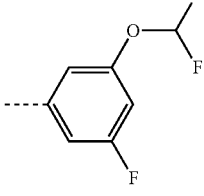 | 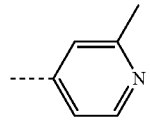 | —Me (S) | —H | •HCl |
| 70 | E1 | 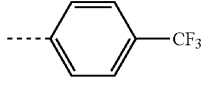 | 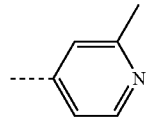 | —CH₂CH₃ | —H | |
| 71 | E3* | 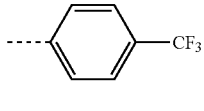 | 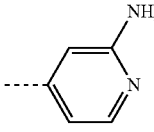 | —Me (S) | —H | |
| 72 | E1 | 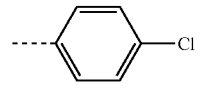 | 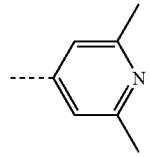 | —Me (S) | —H | |
| 73 | E1 | 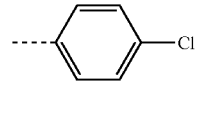 | 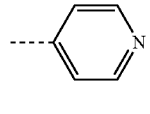 | —Me (S) | —H | |
| 74 | E1 | 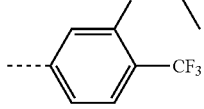 | 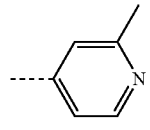 | —CH₂OH | —H | |
| 75 | E1 | 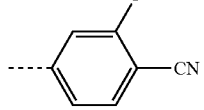 | 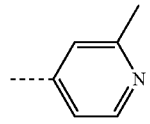 | —Me (S) | —H | |
| 76 | E1 | 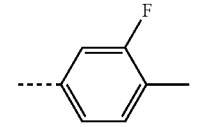 | 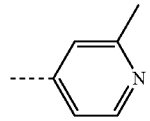 | —Me (S) | —H | |
| 77 | E10* | 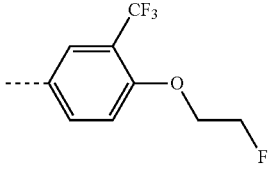 | 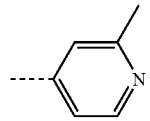 | —Me (S) | —H | |
| 78 | E1 | 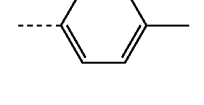 | 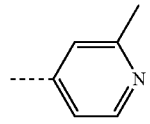 | —Me (S) | —H | |

TABLE 1a-continued

| Co. No. | Ex. No. | R¹ | R² | R⁴ | R³ | Salt form |
|---|---|---|---|---|---|---|
| 79 | E1 | 3-isopropoxyphenyl | 4-pyridyl | —Me (S) | —H | ·HCl |
| 80 | E1 | 4-cyanophenyl | 4-pyridyl | —Me (S) | —H | |
| 81 | E11* | 4-ethoxyphenyl | 4-pyridyl | —Me (S) | —H | ·HCl |
| 82 | E1 | 3,5-difluorophenyl | 4-pyridyl | —Me (S) | —H | |
| 83 | E1 | 3-ethoxyphenyl | 4-pyridyl | —Me (S) | —H | |
| 84 | E1 | 3,4-difluoro-5-methoxyphenyl | 4-pyridyl | —Me (S) | —H | |
| 85 | E1 | 3-fluoro-5-methoxyphenyl | 4-pyridyl | —Me (S) | —H | |
| 86 | E1 | phenyl | 4-pyridyl | —Me (S) | —H | |
| 87 | E7* | 4-(trifluoromethyl)phenyl | 4-pyridyl | —CH₂OH | —H | |

TABLE 1b
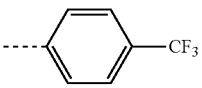
| Co. No. | Ex. No. | R¹ | R² | CR³R⁴ | Salt form |
|---|---|---|---|---|---|
| 1<br>1a<br>1b<br>1c<br>1d | E1* | 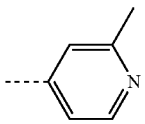 | 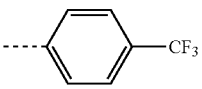 | CH(CH₃)<br>(S) | <br>•HCl<br>•H₂SO₄<br>•CH₃SO₃H<br>•HO₂CCH=CHCO₂H-cis |
| 2 | E2* | 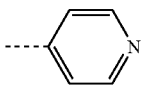 | 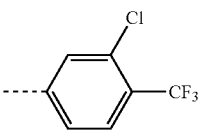 | CH(CH₃)<br>(S) | |
| 3 | E1 | 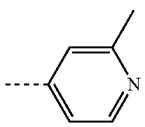 | 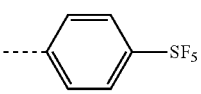 | CH(CH₃)<br>(S) | |
| 4 | E1 | 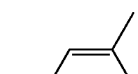 | 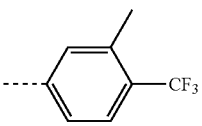 | CH(CH₃)<br>(S) | |
| 5 | E1 | 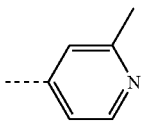 | 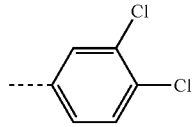 | CH(CH₃)<br>(S) | •HCl |
| 6 | E1 | 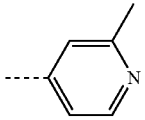 | 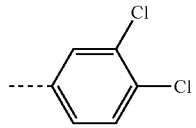 | CH(CH₃)<br>(S) | •HCl |
| 6a | E1 | 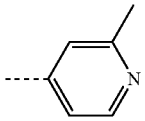 | 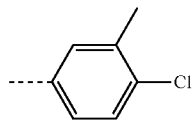 | CH(CH₃)<br>(S) | |
| 7 | E1 | 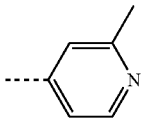 | 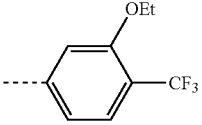 | CH(CH₃)<br>(S) | |
| 8 | E1 | 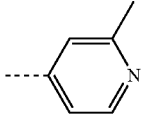 | 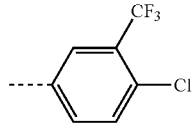 | CH(CH₃)<br>(S) | |
| 9 | E1 | 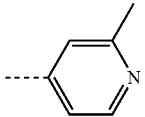 | | CH(CH₃)<br>(S) | |

TABLE 1b-continued

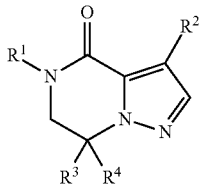

| Co. No. | Ex. No. | R¹ | R² | CR³R⁴ | Salt form |
|---|---|---|---|---|---|
| 10 | E1 | 3-F, 4-CF₃-phenyl | 2-methylpyridin-4-yl | CH(CH₃) (S) | |
| 11 | E1 | 4-CF₃-phenyl | 2-methylpyridin-4-yl | CH(CH₃) | |
| 12 | E1 | 3-OMe, 4-CF₃-phenyl | 2-methylpyridin-4-yl | CH(CH₃) (S) | •HCl |
| 13 | E1 | 3-CN, 4-CF₃-phenyl | 2-methylpyridin-4-yl | CH(CH₃) (S) | |
| 14 | E2 | 4-CF₃-phenyl | 2,6-dimethylpyridin-4-yl | CH(CH₃) (S) | |
| 15 | E1 | 4-Cl-phenyl | 2-methylpyridin-4-yl | CH(CH₃) (S) | •HCl |
| 16 | E1 | 3-Cl-phenyl | 2-methylpyridin-4-yl | CH(CH₃) (S) | |
| 17 | E1 | 3-Cl, 4-OEt-phenyl | 2-methylpyridin-4-yl | CH(CH₃) (S) | •HCl |
| 18 | E1 | 3-OEt, 4-Cl-phenyl | 2-methylpyridin-4-yl | CH(CH₃) (S) | |

TABLE 1b-continued

| Co. No. | Ex. No. | R¹ | R² | CR³R⁴ | Salt form |
|---|---|---|---|---|---|
| 19 | E1 | 3-OMe, 4-Cl phenyl | pyridin-4-yl | CH(CH₃) (S) | |
| 20 | E1 | 3-Cl, 4-OMe phenyl | pyridin-4-yl | CH(CH₃) (S) | •HCl |
| 21 | E1 | 3-methyl, 4-F phenyl | pyridin-4-yl | CH(CH₃) (S) | |
| 22 | E2 | 4-CF₃ phenyl | 2-(methoxymethyl)pyridin-4-yl | CH(CH₃) (S) | •HCl |
| 23 | E1 | 3-CF₃ phenyl | pyridin-4-yl | CH(CH₃) (S) | |
| 24 | E2 | 4-CF₃ phenyl | pyridin-3-yl | CH(CH₃) (S) | |
| 25 | E1 | 3,4-diF phenyl | pyridazin-4-yl | CH(CH₃) (S) | •HCl |
| 26 | E1 | 4-CF₃ phenyl | pyridin-4-yl | CH(CH₃) (R) | |
| 27 | E1 | 4-OCHF₂ phenyl | pyridin-4-yl | CH(CH₃) (S) | |
| 28 | E1 | 4-F phenyl | pyridin-4-yl | CH(CH₃) (S) | •HCl |

TABLE 1b-continued

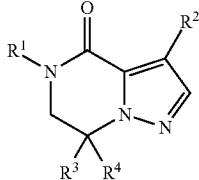

| Co. No. | Ex. No. | R¹ | R² | CR³R⁴ | Salt form |
|---|---|---|---|---|---|
| 29 | E2 | 4-CF₃-phenyl | 2,3-dimethylpyridin-5-yl | CH(CH₃) (S) | |
| 30 | E1 | 3-F,4-Cl-phenyl | 2-methylpyridin-4-yl | CH(CH₃) (S) | |
| 31 | E1 | 3-OEt,4-CF₃-phenyl | 2-methylpyridin-4-yl | CH(CH₃) (R) | |
| 32 | E2 | 4-CF₃-phenyl | pyridin-3-yl | CH(CH₃) (S) | |
| 33 | E1 | 3-OEt,4-CF₃-phenyl | 2-methylpyridin-4-yl | CH₂ | |
| 34 | E1 | 3,5-dimethyl-4-OMe-phenyl | 2-methylpyridin-4-yl | CH(CH₃) (S) | |
| 35 | E1 | 4-OMe,3-F-phenyl | 2-methylpyridin-4-yl | CH(CH₃) (S) | ·HCl |
| 36 | E2 | 4-CF₃-phenyl | 6-methylpyridin-3-yl | CH(CH₃) (S) | |
| 37 | E2 | 4-CF₃-phenyl | 6-aminopyridin-3-yl | CH(CH₃) (S) | |
| 38 | E1 | 4-OMe-phenyl | 2-methylpyridin-4-yl | CH(CH₃) (S) | ·HCl |

TABLE 1b-continued

| Co. No. | Ex. No. | R¹ | R² | CR³R⁴ | Salt form |
|---|---|---|---|---|---|
| 39 | E1 | 3-fluoro-4-(trifluoromethyl)phenyl | pyridin-4-yl | CH₂ | |
| 40 | E1 | 4-(trifluoromethyl)phenyl | pyridin-4-yl | CH₂ | |
| 41 | E1 | 3,4-dimethoxyphenyl | pyridin-4-yl | CH(CH₃) (S) | |
| 42 | E1 | 2,3-dihydro-1,4-benzodioxin-6-yl | pyridin-4-yl | CH(CH₃) (S) | |
| 43 | E1 | 3-chloro-4-(trifluoromethyl)phenyl | 2,6-dimethylpyridin-4-yl | CH(CH₃) (S) | |
| 44 | E4* | 4-(trifluoromethyl)phenyl | 2-(ethylamino)pyridin-4-yl | CH(CH₃) (S) | |
| 45 | E5* | 4-(trifluoromethyl)phenyl | 2-methoxypyridin-4-yl | CH(CH₃) (S) | |
| 46 | E6* | 4-(trifluoromethyl)phenyl | 2-ethylpyridin-4-yl | CH(CH₃) (S) | |
| 47 | E1 | 3,4-dichlorophenyl | 2,6-dimethylpyridin-4-yl | CH(CH₃) (S) | |

TABLE 1b-continued
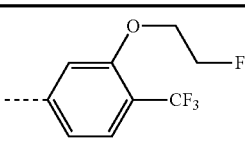
| Co. No. | Ex. No. | R¹ | R² | CR³R⁴ | Salt form |
|---|---|---|---|---|---|
| 48 | E1 | 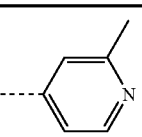 | 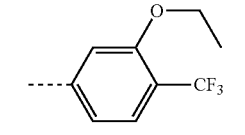 | CH(CH₃) (S) | |
| 49 | E1 | 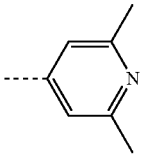 | 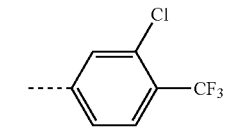 | CH(CH₃) (S) | |
| 50 | E1 | 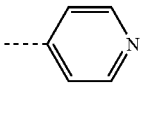 | 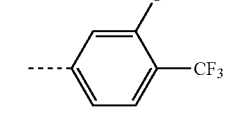 | CH(CH₃) (S) | |
| 51 | E1 | 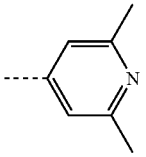 | 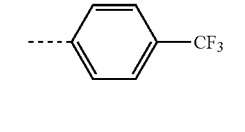 | CH(CH₃) (S) | |
| 52 | E8* | 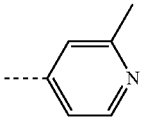 | 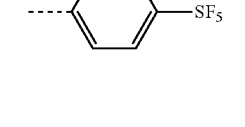 | CH(CH₂F) | |
| 53 | E1 | 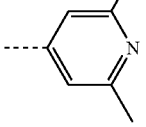 | 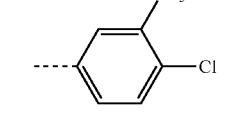 | CH(CH₃) (S) | |
| 54 | E1 | 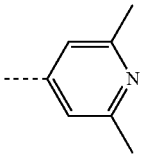 | 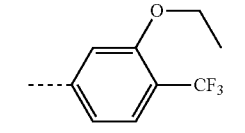 | CH(CH₃) (S) | |
| 55 | E1 | 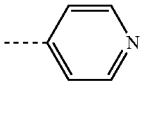 | 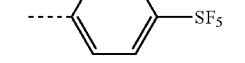 | CH(CH₃) (S) | |
| 56 | E1 | 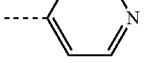 |  | CH(CH₃) (S) | |

TABLE 1b-continued

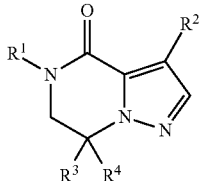

| Co. No. | Ex. No. | R¹ | R² | CR³R⁴ | Salt form |
|---|---|---|---|---|---|
| 57 | E1 | 3,4-dichlorophenyl | pyridin-4-yl | CH(CH₃) (S) | |
| 58 | E1 | 3-(trifluoromethoxy)phenyl | 2-methylpyridin-4-yl | CH(CH₃) (S) | •HCl |
| 59 | E1 | 3-cyano-4-(trifluoromethyl)phenyl | 2,6-dimethylpyridin-4-yl | CH(CH₃) (S) | |
| 60 | E1 | 3-fluoro-4-(trifluoromethyl)phenyl | pyridin-4-yl | CH(CH₃) (S) | |
| 61 | E1 | 3-fluoro-4-(trifluoromethyl)phenyl | 2,6-dimethylpyridin-4-yl | CH(CH₃) (S) | |
| 62 | E1 | 3-fluoro-4-chlorophenyl | 2-methylpyridin-4-yl | CH(CH₃) (S) | |
| 63 | E1 | 3-chloro-5-fluorophenyl | 2-methylpyridin-4-yl | CH(CH₃) (S) | •HCl |
| 64 | E1 | 3-methoxy-4-(trifluoromethyl)phenyl | pyridin-4-yl | CH(CH₃) (S) | |
| 65 | E1 | 4-isopropylphenyl | 2-methylpyridin-4-yl | CH(CH₃) (S) | •HCl |

TABLE 1b-continued
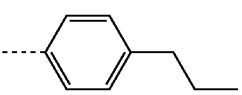
| Co. No. | Ex. No. | R¹ | R² | CR³R⁴ | Salt form |
|---|---|---|---|---|---|
| 66 | E1 | 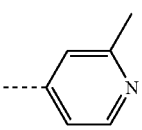 | 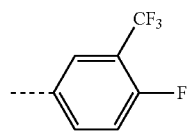 | CH(CH₃) (S) | •HCl |
| 67 | E9* | 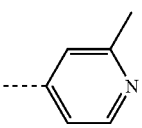 | 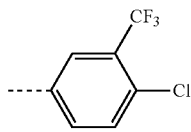 | CH(CH₃) (S) | |
| 68 | E1 | 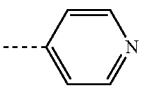 | 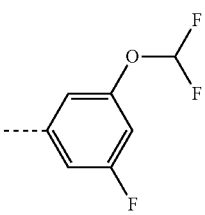 | CH(CH₃) (S) | |
| 69 | E1 | 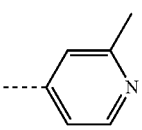 | 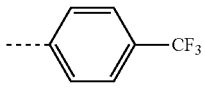 | CH(CH₃) (S) | •HCl |
| 70 | E1 | 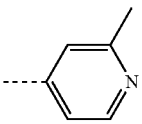 | 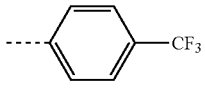 | CH(CH₂CH₃) | |
| 71 | E3* | 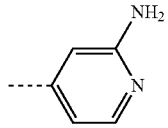 | 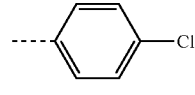 | CH(CH₃) (S) | |
| 72 | E1 | 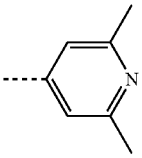 | 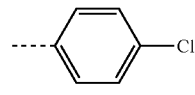 | CH(CH₃) (S) | |
| 73 | E1 | 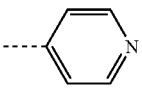 | 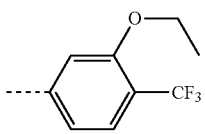 | CH(CH₃) (S) | |
| 74 | E1 | 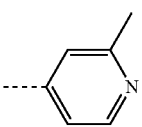 | | CH(CH₂OH) | |

TABLE 1b-continued

| Co. No. | Ex. No. | R¹ | R² | CR³R⁴ | Salt form |
|---|---|---|---|---|---|
| 75 | E1 | 2-F, 4-(...)-benzonitrile | 2-methylpyridin-4-yl | CH(CH₃) (S) | |
| 76 | E1 | 3-fluoro-4-methylphenyl | 2-methylpyridin-4-yl | CH(CH₃) (S) | |
| 77 | E10* | 2-CF₃, 4-(2-fluoroethoxy)phenyl | 2-methylpyridin-4-yl | CH(CH₃) (S) | |
| 78 | E1 | 4-methylphenyl | 2-methylpyridin-4-yl | CH(CH₃) (S) | |
| 79 | E1 | 3-isopropoxyphenyl | 2-methylpyridin-4-yl | CH(CH₃) (S) | •HCl |
| 80 | E1 | 4-cyanophenyl | 2-methylpyridin-4-yl | CH(CH₃) (S) | |
| 81 | E11* | 4-ethoxyphenyl | 2-methylpyridin-4-yl | CH(CH₃) (S) | •HCl |
| 82 | E1 | 3,5-difluorophenyl | 2-methylpyridin-4-yl | CH(CH₃) (S) | |
| 83 | E1 | 3-ethoxyphenyl | 2-methylpyridin-4-yl | CH(CH₃) (S) | |

TABLE 1b-continued

| Co. No. | Ex. No. | R¹ | R² | CR³R⁴ | Salt form |
|---|---|---|---|---|---|
| 84 | E1 | 3,4-difluoro-5-methoxyphenyl | 2-methylpyridin-4-yl | CH(CH₃) (S) | |
| 85 | E1 | 3-fluoro-5-methoxyphenyl | 2-methylpyridin-4-yl | CH(CH₃) (S) | |
| 86 | E1 | phenyl | 2-methylpyridin-4-yl | CH(CH₃) (S) | |
| 87 | E7* | 4-(trifluoromethyl)phenyl | 2-methylpyridin-4-yl | CH(CH₂OH) | |
| 88 | E3 | 3-cyano-4-(trifluoromethyl)phenyl | 2-methoxypyridin-4-yl | CH(CH₃) (S) | |
| 89 | E3 | 4-chlorophenyl | 3-methoxypyridazin-6-yl | CH(CH₃) (S) | |
| 90 | E8 | 3,4-dichlorophenyl | 2-(dimethylamino)pyridin-4-yl | CH(CH₂F) (*R) | |
| 91 | E8 | 3,4-dichlorophenyl | 2-(dimethylamino)pyridin-4-yl | CH(CH₂F) (*S) | |

TABLE 1b-continued
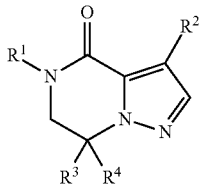
| Co. No. | Ex. No. | R¹ | R² | CR³R⁴ | Salt form |
|---|---|---|---|---|---|
| 92 | E13 | 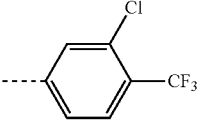 | 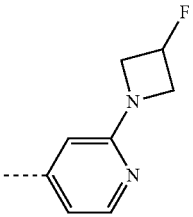 | CH(CH₃) (S) | |
| 93 | E8 | 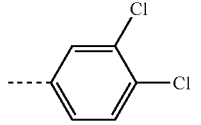 | 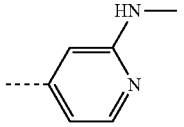 | CH(CH₂F) | |
| 94 | E13 |  | 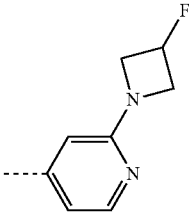 | CH(CH₃) (S) | |
| 95 | E13 | 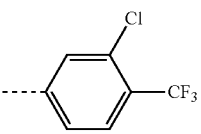 | 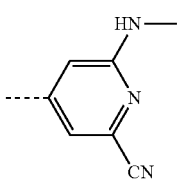 | CH(CH₃) (S) | |
| 96 | E1 | 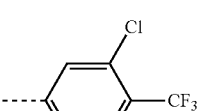 | 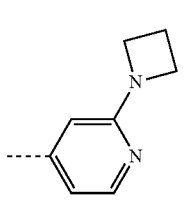 | CH(CH₃) (S) | |
| 97 | E13 | 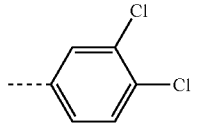 | 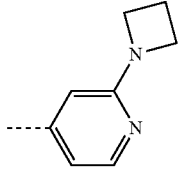 | CH(CH₃) (S) | |
| 98 | E8 | 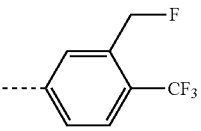 | 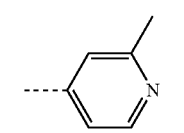 | CH(CH₃) (S) | |

TABLE 1b-continued
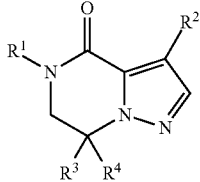
| Co. No. | Ex. No. | R¹ | R² | CR³R⁴ | Salt form |
|---|---|---|---|---|---|
| 99 | E13 | 4-CF₃-phenyl | 2-CF₃-pyridin-4-yl | CH(CH₃) (S) | |
| 100 | E13 | 3-Cl-4-CF₃-phenyl | 2-CN-pyridin-4-yl | CH(CH₃) (S) | |
| 101 | E12 | 4-CF₃-phenyl | 2-(3-hydroxyazetidin-1-yl)pyridin-4-yl | CH(CH₃) (S) | |
| 102 | E12 | 4-CF₃-phenyl | 2-(azetidin-1-yl)pyridin-4-yl | CH(CH₃) (S) | |
| 103 | E3 | 3-Cl-4-CF₃-phenyl | 3-(methylamino)pyridazin-5-yl | CH(CH₃) (S) | |
| 104 | E3 | 3-Cl-4-CF₃-phenyl | 2-methoxypyridin-4-yl | CH(CH₃) (S) | |
| 105 | E12 | 4-CF₃-phenyl | 2-(pyrrolidin-1-yl)pyridin-4-yl | CH(CH₃) (S) | |

TABLE 1b-continued
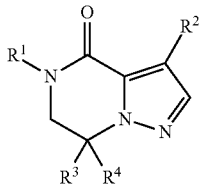
| Co. No. | Ex. No. | R¹ | R² | CR³R⁴ | Salt form |
|---|---|---|---|---|---|
| 106 | E25* | 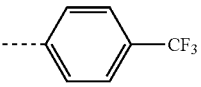 | 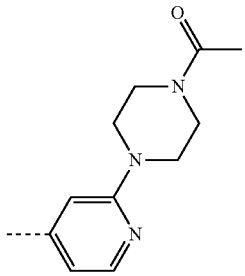 | CH(CH₃) (S) | |
| 107 | E12 | 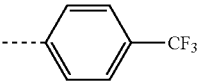 | 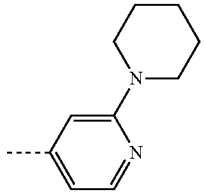 | CH(CH₃) (S) | •HCl |
| 108 | E12 | 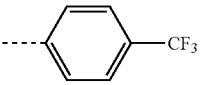 | 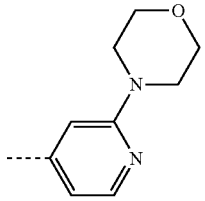 | CH(CH₃) (S) | |
| 109 | E12 | 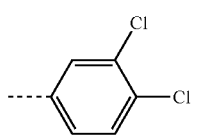 | 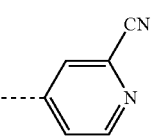 | CH(CH₃) (S) | |
| 110 | E13 | 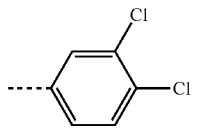 | 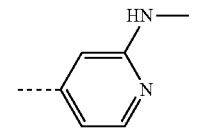 | CH(CH₃) (S) | |
| 111 | E15* | 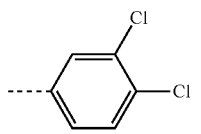 | 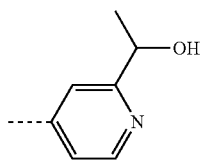 | CH(CH₃) (S) | |
| 112 | E8 | 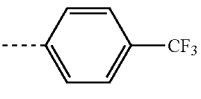 | 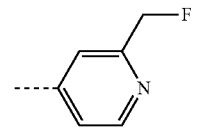 | CH(CH₃) (S) | |

TABLE 1b-continued
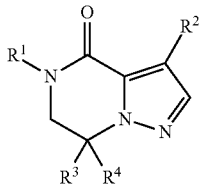
| Co. No. | Ex. No. | R¹ | R² | CR³R⁴ | Salt form |
|---|---|---|---|---|---|
| 113 | E6 | 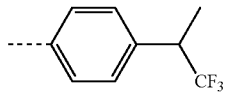 | 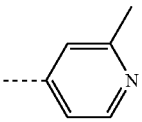 | CH(CH₃) (S) | |
| 114 | E8 | 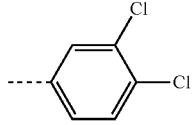 | 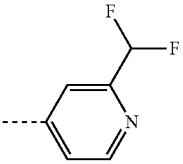 | CH(CH₃) (S) | |
| 115 | E8 | 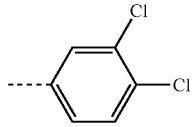 | 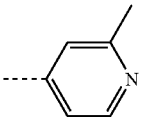 | CH(CH₂F) (*S) | |
| 116 | E8 | 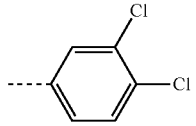 | 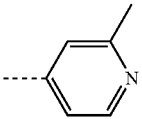 | CH(CH₂F) (*R) | |
| 117 | E8 | 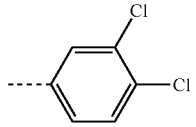 | 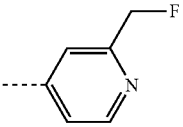 | CH(CH₃) (S) | |
| 118 | E1 | 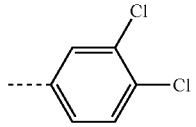 | 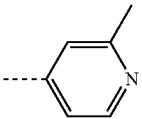 | CH(CH₂OMe) (*S) | |
| 119 | E1 | 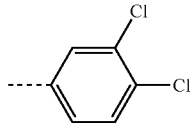 | 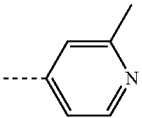 | CH(CH₂OMe) (*R) | |
| 120 | E1 | 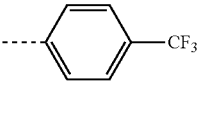 | 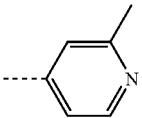 | CH(CH₂OMe) (*R) | |
| 121 | E1 | 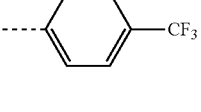 | 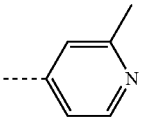 | CH(CH₂OMe) (*S) | |

TABLE 1b-continued

| Co. No. | Ex. No. | R¹ | R² | CR³R⁴ | Salt form |
|---|---|---|---|---|---|
| 122 | E13 | 3,4-dichlorophenyl | 2-cyclopropylpyridin-4-yl | CH(CH₃) (S) | ·2HCl |
| 123 | E2 | 4-(trifluoromethyl)phenyl | 2-ethoxypyridin-4-yl | CH(CH₃) (S) | |
| 124 | E13 | 3,4-dichlorophenyl | 2-isopropylpyridin-4-yl | CH(CH₃) (S) | |
| 125 | E14* | 3,4-dichlorophenyl | 2-(hydroxymethyl)pyridin-4-yl | CH(CH₃) (S) | |
| 126 | E13 | 4-(trifluoromethyl)phenyl | 2-isopropylpyridin-4-yl | CH(CH₃) (S) | |
| 127 | E12* | 4-(trifluoromethyl)phenyl | 2-cyanopyridin-4-yl | CH(CH₃) (S) | |
| 128 | E14 | 4-(trifluoromethyl)phenyl | 2-(1-hydroxyethyl)pyridin-4-yl | CH(CH₃) (S) | |
| 129 | E1 | 4-(trifluoromethyl)phenyl | 2-methylpyridin-4-yl | CH(CH₂CH₃) (R) | |
| 130 | E1 | 4-(trifluoromethyl)phenyl | 2-methylpyridin-4-yl | CH(CH₂CH₃) (S) | |

TABLE 1b-continued

| Co. No. | Ex. No. | R¹ | R² | CR³R⁴ | Salt form |
|---|---|---|---|---|---|
| 131 | E8 | 4-CF₃-phenyl | 2-(difluoromethyl)pyridin-4-yl | CH(CH₃) (S) | |
| 132 | E1 | 3,5-difluoro-4-CF₃-phenyl | 2-methylpyridin-4-yl | CH(CH₃) (S) | |
| 133 | E2 | 3,4-dichlorophenyl | 2-ethoxypyridin-4-yl | CH(CH₃) (S) | •HCl |
| 134 | E6 | 3,4-dichlorophenyl | 2-ethylpyridin-4-yl | CH(CH₃) (S) | |
| 135 | E17 | 4-CF₃-phenyl | 2-(hydroxymethyl)pyridin-4-yl | CH(CH₃) (S) | |
| 136 | E1 | 4-(1-CF₃-cyclopropyl)phenyl | 3-methylpyridazin-5-yl | CH(CH₃) (S) | |
| 137 | E2 | 3,4-dichlorophenyl | 2-isopropoxypyridin-4-yl | CH(CH₃) (S) | •HCl |
| 138 | E2 | 4-CF₃-phenyl | 2-isopropoxypyridin-4-yl | CH(CH₃) (S) | •HCl |

TABLE 1b-continued

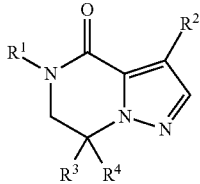

| Co. No. | Ex. No. | R¹ | R² | CR³R⁴ | Salt form |
|---|---|---|---|---|---|
| 139 | E1 | 4-Br-phenyl | 2-methylpyridin-4-yl | CH(CH₃) (S) | |
| 140 | E16* | 4-CF₃-phenyl | 2-methylpyridin-4-yl N-oxide | CH(CH₃) (S) | |
| 141 | E1 | 4-tBu-phenyl | 2-methylpyridin-4-yl | CH(CH₃) (S) | |
| 142 | E3 | 3,4-diCl-phenyl | 2-methoxypyridin-4-yl | CH(CH₃) (S) | |
| 143 | E1 | 3,4-diCl-phenyl | 2-methylpyridin-4-yl | CH(CH₂OMe) | |
| 144 | E1 | 4-CF₃-phenyl | 2-methylpyridin-4-yl | CH(CH₂OMe) | |
| 145 | E2 | 4-CF₃-phenyl | 3-methoxy-6-methylpyridazin-4-yl | CH(CH₃) (S) | |
| 146 | E2 | 3,4-diCl-phenyl | 2-methoxy-6-methylpyridin-4-yl | CH(CH₃) (S) | |
| 147 | E27* | 4-CF₃-phenyl | 2-(methylamino)pyridin-4-yl | CH(CH₃) (S) | |

TABLE 1b-continued
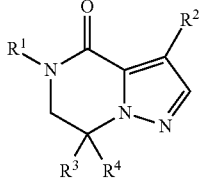
| Co. No. | Ex. No. | R¹ | R² | CR³R⁴ | Salt form |
|---|---|---|---|---|---|
| 148 | E1 | 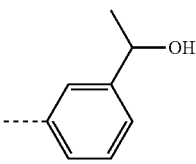 | 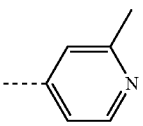 | CH(CH₃) (S) | |
| 149 | E17* | 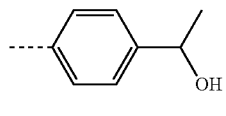 | 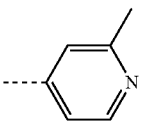 | CH(CH₃) (S) | |
| 150 | E3 | 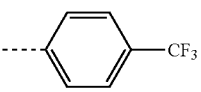 | 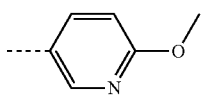 | CH(CH₃) (S) | |
| 151 | E2 | 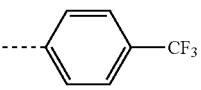 | 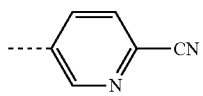 | CH(CH₃) (S) | |
| 152 | E1 | 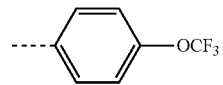 | 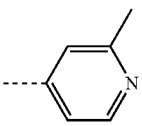 | CH(CH₃) (S) | |
| 153 | E1 | 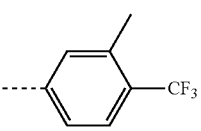 | 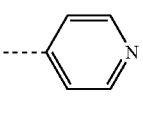 | CH(CH₃) (S) | |
| 154 | E1 | 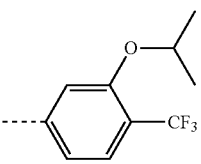 | 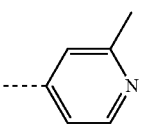 | CH(CH₃) (S) | |
| 155 | E1 | 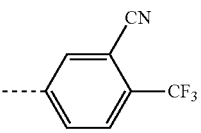 | 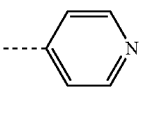 | CH(CH₃) (S) | |
| 156 | E18* | 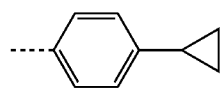 | 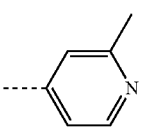 | CH(CH₃) (S) | |

TABLE 1b-continued
| Co. No. | Ex. No. | R¹ | R² | CR³R⁴ | Salt form |
|---|---|---|---|---|---|
| 157 | E1 | 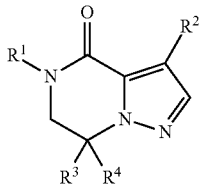 | 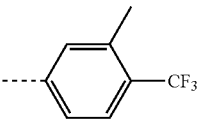 | CH(CH₃) (S) | |
| 158 | E1 | 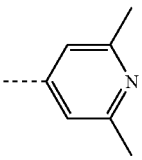 | 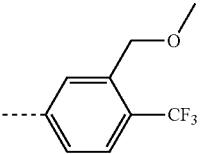 | CH(CH₃) (S) | |
| 159 | E1 | 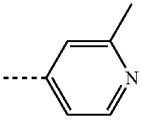 | 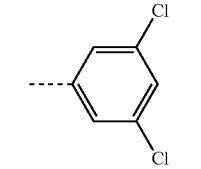 | CH(CH₃) (S) | |
| 160 | E1 | 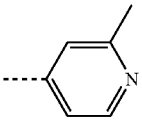 | 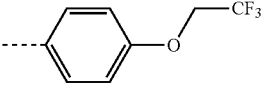 | CH(CH₃) (S) | |
| 161 | E1 | 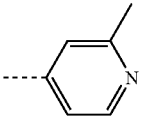 | 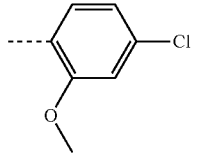 | CH(CH₃) (S) | |
| 162 | E1 | 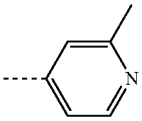 | 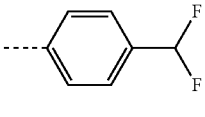 | CH(CH₃) (S) | |
| 163 | E1 | 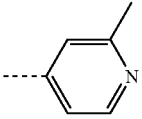 | 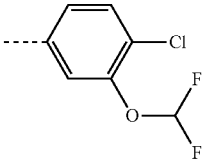 | CH(CH₃) (S) | |
| 164 | E3 | 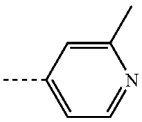 | 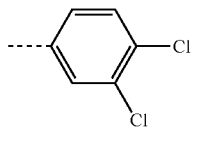 | CH(CH₃) (S) | |

TABLE 1b-continued

| Co. No. | Ex. No. | R¹ | R² | CR³R⁴ | Salt form |
|---|---|---|---|---|---|
| 165 | E1 | 4-(1,1,1-trifluoropropan-2-yloxy)phenyl | 2-methylpyridin-4-yl | CH(CH₃) (S) | |
| 166 | E13 | 4-(trifluoromethyl)phenyl | 2-(dimethylamino)pyridin-4-yl | CH(CH₃) (S) | |
| 167 | E1 | 2,4-dichlorophenyl | 2-methylpyridin-4-yl | CH(CH₃) (S) | |
| 168 | E1 | 3-chloro-4-(difluoromethoxy)phenyl | 2-methylpyridin-4-yl | CH(CH₃) (S) | |
| 169 | E1 | 4-chloro-3-(trifluoromethoxy)phenyl | 2-methylpyridin-4-yl | CH(CH₃) (S) | |
| 170 | I-38* E16 | 3,4-dichlorophenyl | 2-methylpyridin-4-yl N-oxide | CH(CH₃) (S) | |
| 171 | E1 | 4-(trifluoromethyl)phenyl | 2-methylpyridin-4-yl | CH(CH₃)₂ | |
| 172 | E1 | 4-chloro-2-methylphenyl | 2-methylpyridin-4-yl | CH(CH₃) (S) | |
| 173 | E13 | 4-(trifluoromethyl)phenyl | 2-cyclopropylpyridin-4-yl | CH(CH₃) (S) | •HCl |

TABLE 1b-continued

[Structure: pyrazolo-pyrazinone core with R¹ on N, R² on pyrazole, R³R⁴ on CR position]

| Co. No. | Ex. No. | R¹ | R² | CR³R⁴ | Salt form |
|---|---|---|---|---|---|
| 174 | E1 | 3-chloro-4-(difluoromethyl)phenyl | 2-methylpyridin-4-yl | CH(CH₃) (S) | |
| 175 | E24* | 4-(trifluoromethyl)phenyl | 2-(piperazin-1-yl)pyridin-4-yl | CH(CH₃) (S) | •HCl |
| 176 | E19* | 4-(trifluoromethyl)phenyl | 6-(piperazin-1-yl)pyridin-3-yl | CH(CH₃) (S) | |
| 177 | E10 | 3-chloro-4-(trifluoromethyl)phenyl | 2-(2-fluoroethoxy)pyridin-4-yl | CH(CH₃) (S) | |
| 178 | E3 | 4-chlorophenyl | 2-(methylamino)pyridin-4-yl | CH(CH₃) (S) | |
| 179 | E3 | 3-cyano-4-(trifluoromethyl)phenyl | 2-(methylamino)pyridin-4-yl | CH(CH₃) (S) | |
| 180 | E3 | 3-methoxy-4-(trifluoromethyl)phenyl | 2-methoxypyridin-4-yl | CH(CH₃) (S) | |
| 181 | E26* | 4-(trifluoromethyl)phenyl | 2-methylpyridin-4-yl | CH(CHF₂) | |
| 182 | E3 | 3-fluoro-4-(trifluoromethyl)phenyl | 2-(methylamino)pyridin-4-yl | CH(CH₃) (S) | |

TABLE 1b-continued

| Co. No. | Ex. No. | R¹ | R² | CR³R⁴ | Salt form |
|---|---|---|---|---|---|
| 183 | E3 | 3-OMe, 4-CF₃-phenyl | 2-(NH)-pyridin-4-yl | CH(CH₃) (S) | |
| 184 | E8 | 3,4-dichlorophenyl | 2-(NH)-pyridin-4-yl | CH(CH₂F) (*R) | |
| 185 | E8 | 3,4-dichlorophenyl | 2-(NH)-pyridin-4-yl | CH(CH₂F) (*S) | |
| 186 | E20* | 5-CF₃-pyridin-2-yl | 2-methylpyridin-4-yl | CH(CH₃) (S) | |
| 187 | E1 | 5-Cl-pyridin-2-yl | 2-methylpyridin-4-yl | CH(CH₃) (S) | |
| 188 | I-43* E20 | 2-Cl-3-CF₃-pyridin-6-yl | 2-methylpyridin-4-yl | CH(CH₃) (S) | |
| 189 | E22a* | 5-CF₃-4-ethoxy-pyridin-2-yl | 2-methylpyridin-4-yl | CH(CH₃) (S) | |
| 190 | E20 | 5-CF₃-pyridin-2-yl | pyridin-4-yl | CH(CH₃) (S) | |
| 191 | E1 | 2-F-3-ethoxy-pyridin-6-yl | 2-methylpyridin-4-yl | CH(CH₃) (S) | |
| 192 | E21* | 2-methyl-3-CF₃-pyridin-6-yl | 2-methylpyridin-4-yl | CH(CH₃) (S) | |

TABLE 1b-continued
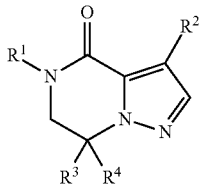
| Co. No. | Ex. No. | R¹ | R² | CR³R⁴ | Salt form |
|---|---|---|---|---|---|
| 193 | E21 | 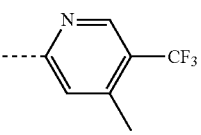 | 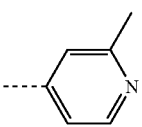 | CH(CH$_3$) (S) | |
| 194 | E20 | 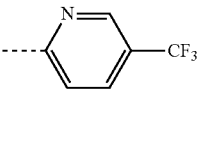 | 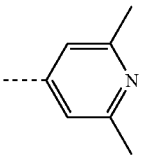 | CH(CH$_3$) (S) | |
| 195 | E20 | 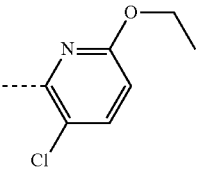 | 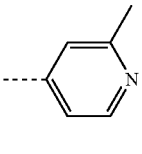 | CH(CH$_3$) (S) | |
| 196 | E20 | 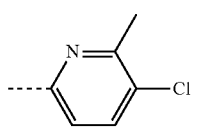 | 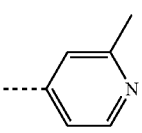 | CH(CH$_3$) (S) | |
| 197 | E3 | 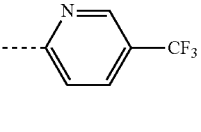 | 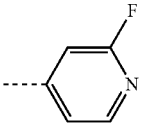 | CH(CH$_3$) (S) | |
| 198 | E18 | 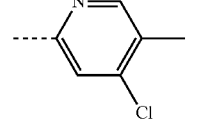 | 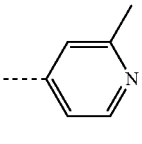 | CH(CH$_3$) (S) | |
| 199 | E20 | 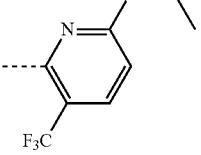 | 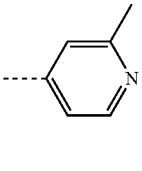 | CH(CH$_3$) (S) | |
| 200 | E20 | 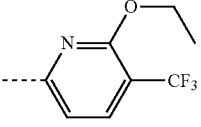 | 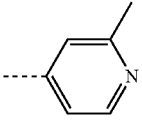 | CH(CH$_3$) (S) | |

TABLE 1b-continued
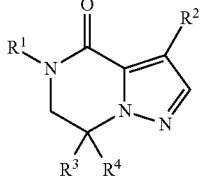
| Co. No. | Ex. No. | R¹ | R² | CR³R⁴ | Salt form |
|---|---|---|---|---|---|
| 201 | E20 | 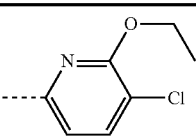 | 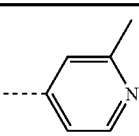 | CH(CH₃) (S) | |
| 202 | E20 | 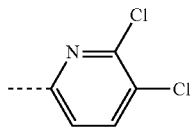 | 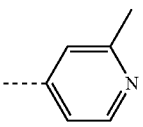 | CH(CH₃) (S) | |
| 203 | E20 | 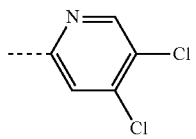 | 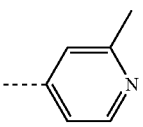 | CH(CH₃) (S) | |
| 204 | E22b* | 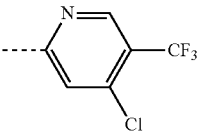 | 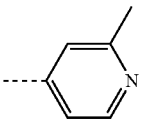 | CH(CH₃) (S) | |
| 205 | E20 | 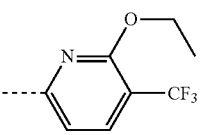 | 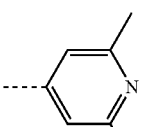 | CH(CH₃) (S) | |
| 206 | E20 | 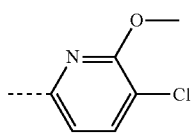 | 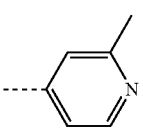 | CH(CH₃) (S) | |
| 207 | E20 | 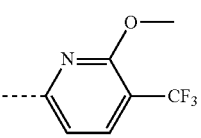 | 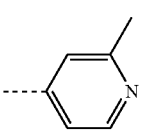 | CH(CH₃) (S) | |
| 208 | E20 | 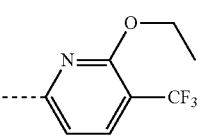 | 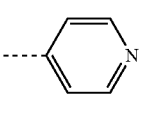 | CH(CH₃) (S) | |
| 209 | E1 | 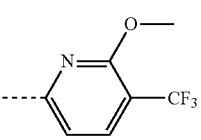 | 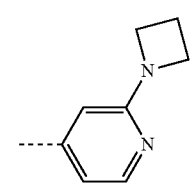 | CH(CH₃) (S) | |

TABLE 1b-continued

| Co. No. | Ex. No. | R¹ | R² | CR³R⁴ | Salt form |
|---|---|---|---|---|---|
| 210 | E3 | 5-CF₃-pyridin-2-yl | 2-(NHCH₃)-pyridin-4-yl | CH(CH₃) (S) | |
| 211 | E1 | 5-CF₃-pyridin-2-yl | 2-methyl-pyridin-4-yl | CH₂ | |
| 212 | E28* | 5-CF₃-4-I-pyridin-2-yl | 2-methyl-pyridin-4-yl | CH(CH₃) (S) | |
| 213 | E28 | 5-I-4-Cl-pyridin-2-yl | 2-methyl-pyridin-4-yl | CH(CH₃) (S) | |
| 214 | E13 | 4-CF₃-phenyl | 2-(NHCH₃)-pyridin-4-yl N-oxide | CH(CH₃) (S) | |
| 215 | I-26* E3 | 4-CF₃-phenyl | 2-Cl-pyridin-4-yl | CH(CH₃) (S) | |
| 216 | E1 | 4-CF₃-phenyl | 2-methyl-pyridin-4-yl | CH(OH)CH₃ *R | |
| 217 | E1 | 4-CF₃-phenyl | 2-methyl-pyridin-4-yl | CH(OH)CH₃ *S | |
| 218 | E3 | 3,4-diCl-phenyl | 2-Cl-pyridin-4-yl | CH(CH₃) (S) | |

TABLE 1b-continued
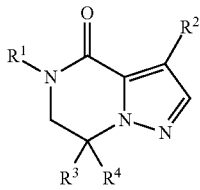
| Co. No. | Ex. No. | R¹ | R² | CR³R⁴ | Salt form |
|---|---|---|---|---|---|
| 219 | E2 | 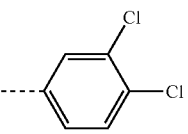 | 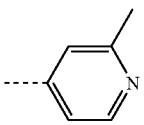 | CH(CH₂OH) | |
| 220 | E29* | 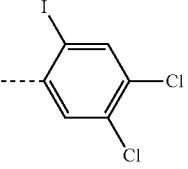 | 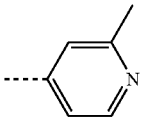 | CH(CH₃) (S) | |
| 221 | E29* | 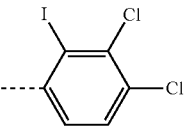 | 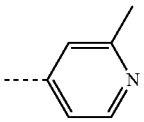 | CH(CH₃) (S) | |
| 222 | E8 | 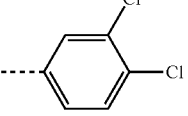 | 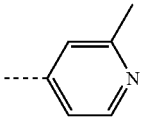 | CH(CH₂F) | |
| 223 | E2 | 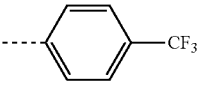 | 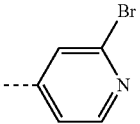 | CH(CH₃) (S) | |
| 224 | E3 | 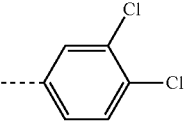 | 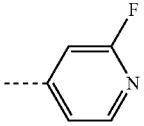 | CH(CH₂OH) | |
| 225 | E23* | 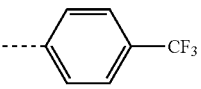 | 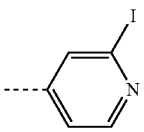 | CH(CH₃) (S) | |
| 226 | E3 | 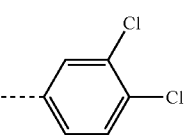 | 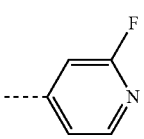 | CH(CH₂OH) (*S) | |
| 227 | E3 | 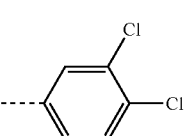 | 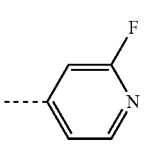 | CH(CH₂OH) (*R) | |

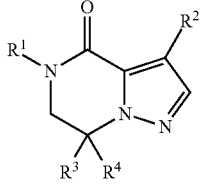

TABLE 1b-continued
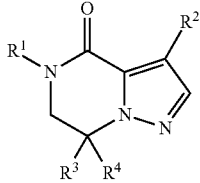
| Co. No. | Ex. No. | R¹ | R² | CR³R⁴ | Salt form |
|---|---|---|---|---|---|
| 237 | E3 | 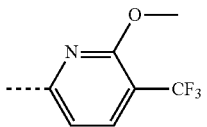 | 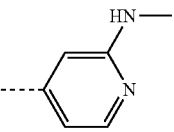 | CH(CH₃) (S) | |
| 238 | E30* | 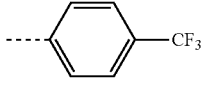 | 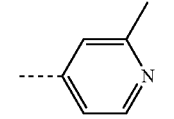 | CH(CF₃) | |
| 239 | E1 | 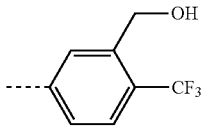 | 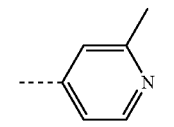 | CH(CH₃) (S) | |
| 240 | E3 | 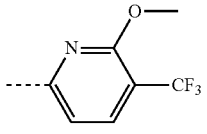 | 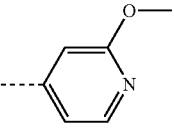 | CH(CH₃) (S) | |
| 241 | E3 | 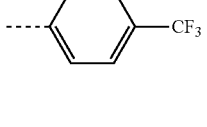 | 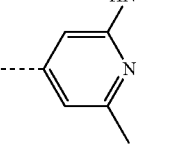 | CH(CH₃) (S) | |
| 242 | E2 | 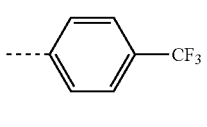 | 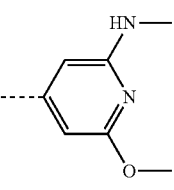 | CH(CH₃) (S) | |
| 243 | E2 | 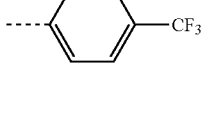 | 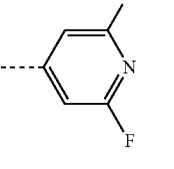 | CH(CH₃) (S) | |
| 244 | E1 | 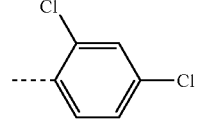 | 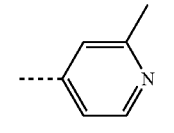 | CH₂ | |

TABLE 1b-continued
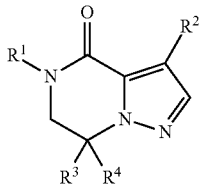
| Co. No. | Ex. No. | R¹ | R² | CR³R⁴ | Salt form |
|---|---|---|---|---|---|
| 245 | E1 | 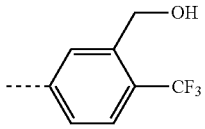 | 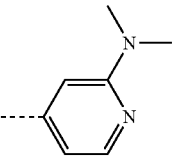 | CH(CH₃) (S) | |
| 246 | E8 | 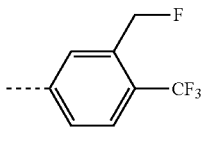 | 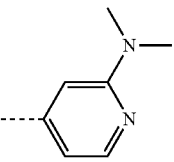 | CH(CH₃) (S) | |
| 247 | E13 | 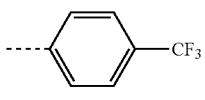 | 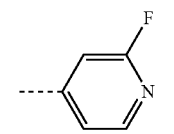 | CH(CH₃) (S) | |
| 248 | E12 | 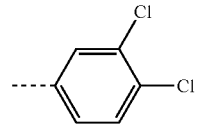 | 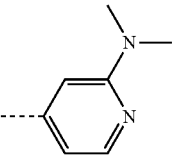 | CH(CH₃) (S) | |
| 249 | E1 | 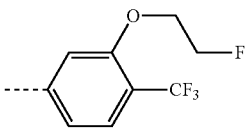 | 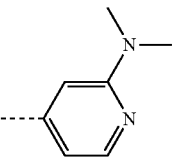 | CH(CH₃) (S) | |
| 250 | E20 | 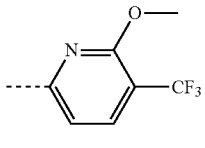 | 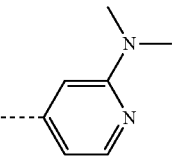 | CH(CH₃) (S) | |
| 251 | E12 | 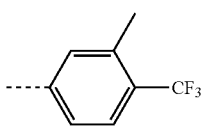 | 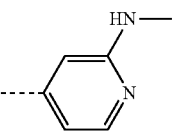 | CH(CH₃) (S) | |
| 252 | E16 | 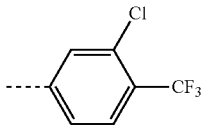 | 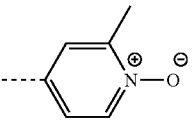 | CH(CH₃) (S) | |

TABLE 1b-continued
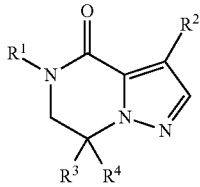
| Co. No. | Ex. No. | R¹ | R² | CR³R⁴ | Salt form |
|---|---|---|---|---|---|
| 253 | E13 | 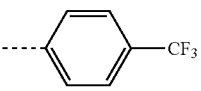 | 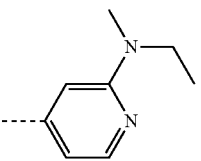 | CH(CH₃) (S) | |
| 254 | E4 | 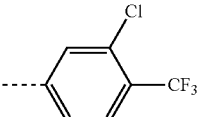 | 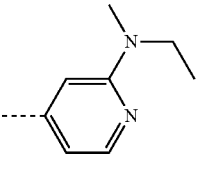 | CH(CH₃) (S) | |
| 255 | E13 | 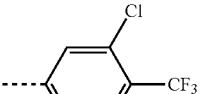 | 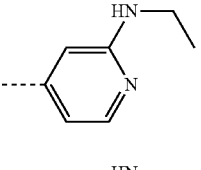 | CH(CH₃) (S) | |
| 256 | E12 | 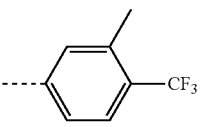 | 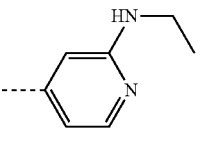 | CH(CH₃) (S) | |
| 257 | E13 | 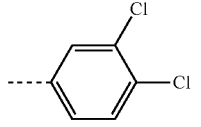 | 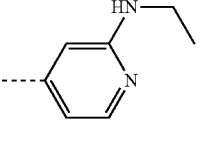 | CH(CH₃) (S) | |
| 258 | E12 | 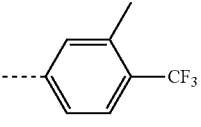 | 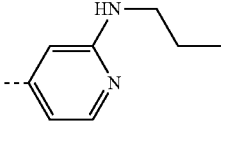 | CH(CH₃) (S) | |
| 259 | E13 | 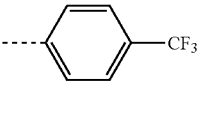 | 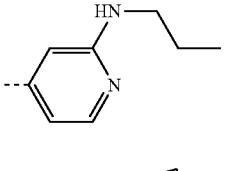 | CH(CH₃) (S) | |
| 260 | E12 | 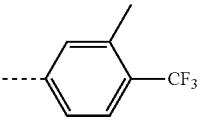 | 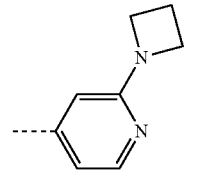 | CH(CH₃) (S) | |

TABLE 1b-continued
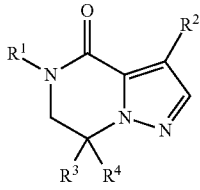
| Co. No. | Ex. No. | R¹ | R² | CR³R⁴ | Salt form |
|---|---|---|---|---|---|
| 261 | E12 | 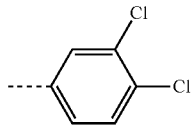 | 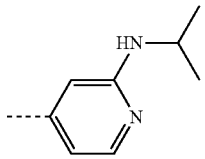 | CH(CH₃) (S) | |
| 262 | E12 | 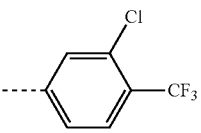 | 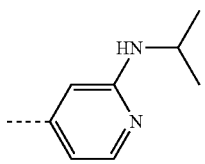 | CH(CH₃) (S) | |
| 263 | E12 | 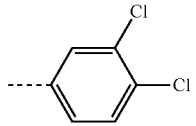 | 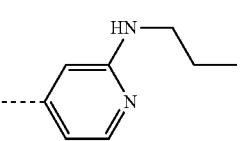 | CH(CH₃) (S) | |
| 264 | E12 | 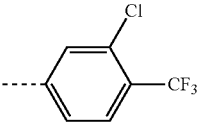 | 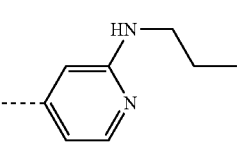 | CH(CH₃) (S) | |
| 265 | E8 | 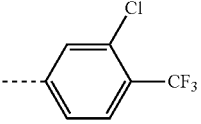 | 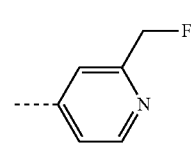 | CH(CH₃) (S) | |
| 266 | E13 | 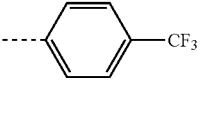 | 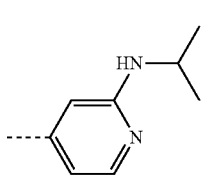 | CH(CH₃) (S) | |
| 267 | E12 | 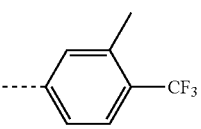 | 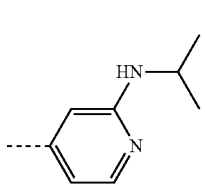 | CH(CH₃) (S) | |

The values of salt stoichiometry or acid content in the compounds as provided herein, are those obtained experimentally and may vary when using different analytical methods. The content of hydrochloric acid reported herein was determined by $^1$H NMR integration and/or elemental analysis. For compound 1 the salt stoichiometry was determined by ion chromatography (hydrochloride and sulfate salts) and by NMR (methanesulfonate and maleate salts).

Analytical Part

Melting Points

Values are peak values, and are obtained with experimental uncertainties that are commonly associated with this analytical method.

Mettler FP 62 (A):

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display.

Mettler FP 62 (A1):

Melting points (m.p.) were determined in open capillary tubes on a Mettler FP62 apparatus. Melting points were measured with a temperature ranging from 50° C. to 300° C., using a gradient of 10° C./minute. The melting point value was read from a digital display.

Mettler FP 81HT/FP90 (B):

For a number of compounds, melting points were determined in open capillary tubes on a FP 81HT/FP90 apparatus (Mettler-Toledo). Melting points were measured with a temperature gradient of 1, 3, 5 or 10° C./minute. Maximum temperature was 300° C. The melting point was read from a digital display.

Mettler Toledo MP50 (C):

For a number of compounds, melting points were determined in open capillary tubes on a Mettler Toledo MP50. Melting points were measured with a temperature gradient of 10° C./minute. Maximum temperature was 300° C. The melting point data was read from a digital display and checked from a video recording system.

DSC823e (D):

For a number of compounds, melting points (m.p.) were determined with a DSC823e (Mettler-Toledo). Melting points were measured with a temperature gradient of 30° C./minute. Maximum temperature was 400° C. Peak values were recorded.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, [M+CH$_3$COO]$^-$ etc. . . . ). For molecules with multiple isotopic patterns (Br, Cl.), the reported value is the one obtained for the lowest isotope mass. All results were obtained with experimental uncertainties that are commonly associated with the method used.

Hereinafter, "LCT" means LC-Time of Flight, "SQD" Single Quadrupole Detector, "MSD" Mass Selective Detector, "QTOF" Quadrupole-Time of Flight, "RT" room temperature, "BEH" bridged ethylsiloxane/silica hybrid, "DAD" Diode Array Detector.

TABLE 2

LC-MS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| 1 | Waters: Acquity ® UPLC ®-DAD and SQD | Agilent: Eclipse Plus C18 RRHD (1.8 μm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1<br>50 | 5 |
| 2 | Agilent: HP1100-DAD Waters: SQD | Agilent: Eclipse Plus C18 (3.5 μm, 2.1 × 30 mm) | A: 95% CH$_3$COONH$_4$ 6.5 mM + 5% CH$_3$CN, B: 1/1 CH$_3$CN/ CH$_3$OH | 95% A kept for 0.2 min, to 0% A in 2.8 min, held for 0.15 min, back to 95% A in 0.15 min, held for 1.7 min | 1<br>60 | 5 |
| 3 | Agilent 1100-DAD-MSD G1956A | YMC-pack ODS-AQ C18 (50 × 4.6 mm, 3 μm) | A: 0.1% HCOOH in H$_2$O B: CH$_3$CN | From 95% A to 5% A in 4.8 min, held for 1.0 min, to 95% A in 0.2 min. | 2.6<br>35 | 6.0 |
| 4 | Waters: Acquity ® UPLC ®-DAD/SQD | Agilent: Eclipse Plus C18 RRHD (1.8 μm, 2.1 × 50 mm) | A: 95% CH$_3$COONH$_4$ 6.5 mM + 5% CH$_3$CN, B: CH$_3$CN | From 95% A to 5% A in 1.8 min, held for 0.2 min | 1<br>50 | 2 |

TABLE 2-continued

LC-MS Methods (Flow expressed in mL/min; column temperature (T) in ° C.; Run time in minutes).

| Method | Instrument | Column | Mobile phase | Gradient | Flow | Col T | Run time |
|---|---|---|---|---|---|---|---|
| 5 | Waters: Acquity ® UPLC ®-DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0 4 min | 1 | 50 | 5 |
| 6 | Agilent: HP1100-DAD, MSD G1956B | Agilent: Eclipse Plus C18 (3.5 μm, 2.1 × 30 mm) | A: 95% $CH_3COONH_4$ 6.5 mM + 5% $CH_3CN$, B: $CH_3CN$ | 95% A for 0.2 min, to 0% A in 2.8 min, held for 0.15 min, back to 95% A in 0.15 min, held for 1.7 min | 1 | −60 | 5 |
| 7 | Waters: Acquity ® UPLC ®-DAD/SQD | Waters: CSH ™ C18 (1.7 μm, 2.1 × 50 mm) | A: 95% $CH_3COONH_4$ 6.5 mM + 5% $CH_3CN$, B: $CH_3CN$ | From 95% A to 40% A in 1.2 min, to 5% A in 0.6 min, held for 0.2 min | 1 | −50 | 2 |
| 8 | Waters: Acquity UPLC ®-DAD/ Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 | −40 | 6.2 |
| 9 | Agilent: HP1100-DAD, Waters: LCT | Agilent: Eclipse Plus C18 (3.5 μm, 2.1 × 30 mm) | A: 95% $CH_3COONH_4$ 6.5 mM + 5% $CH_3CN$, B: $CH_3CN/CH_3OH$, 1/1 | From 95% A to 0% A in 5.0 min, for 0.15 min, back to 95% A in 0.15 min, held for 1.7 min | 1 | −60 | 7 |
| 10 | Agilent: HP1100-DAD, Waters: SQD | Agilent: Eclipse Plus C18 (3.5 μm, 2.1 × 30 mm) | A: 95% $CH_3COONH_4$ 6.5 mM + 5% $CH_3CN$, B: $CH_3CN/CH_3OH$, 1/1 | From 95% A to 0% A in 5.0 min, held for 0.15 min, back to 95% A in 0.15 min, held for 1.7 min | 1 | −60 | 7 |
| 11 | Waters: Acquity ® UPLC ®-DAD/SQD | Agilent: Eclipse Plus C18 RRHD (1.8 μm, 2.1 × 50 mm) | A:95% $CH_3COONH_4$ 6.5 mM + 5% $CH_3CN$, B: $CH_3CN$ | From 95% A to 40% A in 1.2 min, to 5% A in 0.6 min, held for 0.2 min | 1 | 50 | 2 |
| 12 | Waters: Acquity ® UPLC ®-DAD/ QTOF G2-S | Waters: CSH ™ C18 (1.7 μm, 2.1 × 50 mm) | A: 95% CH3COONH4 6.5 mM + 5% CH3CN, B: CH3CN | From 95% A to 40% A in 1.2 min, to 5% A in 0.6 min, held for 0.2 min | 1 | −50 | 2 |
| 13 | Waters: Acquity ® UPLC ®-DAD/ QTOF G2-S | Waters: CSH ™ C18 (1.7 μm, 2.1 × 50 mm) | A: 95% CH3COONH4 6.5 mM + 5% CH3CN, B: CH3CN | From 95% A to 5% A in 4.6 min, held for 0.4 min | 1 | −50 | 5 |

TABLE 3a

Analytical data - melting point (M.p.) and LCMS: [M + H]⁺ means the protonated mass of the free base of the compound, [M − H]⁻ means the deprotonated mass of the free base of the compound or the type of adduct specified [M + CH₃COO]⁻). $R_t$ means retention time (in min). For some compounds, exact mass was determined.

| Co. No. | M.p. (° C.) | [M + H]⁺ | [M − H]⁻ or adduct | $R_t$ | LCMS Method |
|---|---|---|---|---|---|
| 1 | 152.6 (B) | 387 | 445 (M + CH₃COO)⁻ | 2.73 | 2 |
| 2 | 181.9 (A) | 373 | 431 (M + CH₃COO)⁻ | 2.07 | 1 |
| 3 | 103.3 (B) | 421 | 479 (M + CH₃COO)⁻ | 2.48 | 1 |
| 4 | 247.0 (A) | 445 | 503 (M + CH₃COO)⁻ | 2.4 | 1 |
| 5 | >300 (A) | 401 | 459 (M + CH₃COO)⁻ | 2.42 | 1 |
| 6 | >300 (A) | 387 | 445 (M + CH₃COO)⁻ | 2.29 | 1 |
| 7 | 126.7 (B) | 367 | 425 (M + CH₃COO)⁻ | 2.25 | 1 |
| 8 | 126.1 (B) | 431 | 489 (M + CH₃COO)⁻ | 2.5 | 1 |
| 9 | 143.6 (B) | 421 | 479 (M + CH₃COO)⁻ | 2.44 | 1 |
| 10 | 85.1 (B) | 405 | 463 (M + CH₃COO)⁻ | 2.32 | 1 |
| 11 | 159.3 (B) | 387 | 445 (M + CH₃COO)⁻ | 2.19 | 1 |
| 12 | 269.9 (A) | 417 | 475 (M + CH₃COO)⁻ | 2.22 | 1 |
| 13 | 128.9 (B) | 412 | 470 (M + CH₃COO)⁻ | 2.12 | 1 |
| 14 | 201.1 (B) | 401 | 459 (M + CH₃COO)⁻ | 2.33 | 1 |
| 15 | >300 (A) | 353 | 411 (M + CH₃COO)⁻ | 1.96 | 1 |
| 17 | >300 (B) | 397 | 455 (M + CH₃COO)⁻ | 2.25 | 1 |
| 18 | 98.5 (B) | 397 | 455 (M + CH₃COO)⁻ | 2.28 | 1 |
| 19 | 137 (B) | 383 | 441 (M + CH₃COO)⁻ | 2.01 | 1 |
| 20 | 293.6 (B) | 383 | 441 (M + CH₃COO)⁻ | 1.98 | 1 |
| 21 | 219.2 (A) | 351 | 409 (M + CH₃COO)⁻ | 1.99 | 1 |
| 22 | 282.3 (B) | 417 | 475 (M + CH₃COO)⁻ | 2.19 | 1 |
| 23 | 139.2 (A) | 387 | 445 (M + CH₃COO)⁻ | 2.18 | 1 |
| 24 | 119.6 (B) | 387 | 445 (M + CH₃COO)⁻ | 2.29 | 1 |
| 26 | 153.6 (B) | 387 | 445 (M + CH₃COO)⁻ | 2.73 | 2 |
| 27 | 137.1 (A) | 385 | 443 (M + CH₃COO)⁻ | 1.96 | 1 |
| 29 | 140.8 (B) | 401 | 459 (M + CH₃COO)⁻ | 2.41 | 1 |
| 30 | 78.6 (B) | 371 | 429 (M + CH₃COO)⁻ | 2.07 | 1 |
| 31 | 112.8 (B) | 431 | 489 (M + CH₃COO)⁻ | 2.49 | 1 |
| 32 | n.d. | 373 | 431 (M + CH₃COO)⁻ | 2.05 | 1 |
| 33 | 162.8 (B) | 417 | 475 (M + CH₃COO)⁻ | 2.26 | 1 |
| 34 | >300 (B) | 377 | 435 (M + CH₃COO)⁻ | 2.1 | 1 |
| 36 | 128.2 (B) | 387 | 445 (M + CH₃COO)⁻ | 2.25 | 1 |
| 37 | 254.0 (B) | 388 | 446 (M + CH₃COO)⁻ | 1.89 | 1 |
| 38 | 294.0 (B) | 349 | 407 (M + CH₃COO)⁻ | 1.71 | 1 |
| 39 | 185.2 (B) | 391 | 449 (M + CH₃COO)⁻ | 2.08 | 1 |
| 40 | 137.0 (B) | 373 | 431 (M + CH₃COO)⁻ | 1.97 | 1 |
| 41 | 166.9 (B) | 379 | 437 (M + CH₃COO)⁻ | 1.56 | 1 |
| 43 | 203.9 (B) | 435 | 493 (M + CH₃COO)⁻ | 2.59 | 1 |
| 44 | >300 (B) | 416 | 474 (M + CH₃COO)⁻ | 2.21 | 5 |
| 45 | 143.9 (A1) | 403 | 461 (M + CH₃COO)⁻ | 2.51 | 1 |
| 46 | 124.6 (B) | 401 | 459 (M + CH₃COO)⁻ | 2.46 | 1 |
| 47 | 185.6 (B) | 401 | 459 (M + CH₃COO)⁻ | 2.3 | 5 |
| 49 | 183.9 (B) | 445 | 503 (M + CH₃COO)⁻ | 2.61 | 1 |
| 50 | 146.8 (B) | 407 | 465 (M + CH₃COO)⁻ | 2.23 | 1 |
| 51 | 93 (B) | 431 | 489 (M + CH₃COO)⁻ | 2.4 | 1 |
| 52 | >300 (B) | 405 | 463 (M + CH₃COO)⁻ | 1.99 | 5 |
| 53 | 233.1 (B) | 459 | 517 (M + CH₃COO)⁻ | 2.37 | 5 |
| 54 | 205.1 (B) | 435 | 493 (M + CH₃COO)⁻ | 2.39 | 5 |
| 55 | 104.2 (B) | 417 | 475 (M + CH₃COO)⁻ | 2.29 | 5 |
| 56 | 199 (B) | 431 | 489 (M + CH₃COO)⁻ | 2.17 | 5 |
| 57 | 153.2 (B) | 373 | 431 (M + CH₃COO)⁻ | 2.04 | 5 |
| 59 | 214.1 (B) | 426 | 484 (M + CH₃COO)⁻ | 2.1 | 5 |
| 60 | 163.8 (B) | 391 | 449 (M + CH₃COO)⁻ | 2.07 | 5 |
| 61 | 73.3 (B) | 419 | 477 (M + CH₃COO)⁻ | 2.29 | 5 |
| 62 | 141.7 (B) | 371 | 429 (M + CH₃COO)⁻ | 2.09 | 1 |
| 64 | 273.9 (B) | 403 | 461 (M + CH₃COO)⁻ | 2.03 | 5 |
| 68 | >300 (B) | 407 | 465 (M + CH₃COO)⁻ | 2.19 | 5 |
| 70 | n.d. | 401 | 459 (M + CH₃COO)⁻ | 2.29 | 5 |
| 71 | 218.9 (B) | 388 | 446 (M + CH₃COO)⁻ | 1.88 | 1 |
| 72 | 88 (B) | 367 | 425 (M + CH₃COO)⁻ | 2.15 | 1 |
| 73 | 144.3 (B) | 339 | 397 (M + CH₃COO)⁻ | 1.77 | 1 |
| 74 | 99.1 (B) | 447 | 505 (M + CH₃COO)⁻ | 2.03 | 1 |
| 77 | 60.8 (A, Temp. grad.: 3° C./min) | 449 | 507 (M + CH₃COO)⁻ | 2.19 | 1 |
| 88 | 157.75° C. (D) | 428 | 486 (M + CH₃COO)⁻ | 2.29 | 5 |
| 92 | n.d. | 480 | 538 (M + CH₃COO)⁻ | 2.48 | 5 |
| 93 | n.d. | 420 | 478 (M + CH₃COO)⁻ | 2.00 | 5 |
| 94 | n.d. | 446 | 504 (M + CH₃COO)⁻ | 2.28 | 5 |
| 95 | 210.61° C. (D) | 461 | 519 (M + CH₃COO)⁻ | 2.62 | 5 |
| 97 | n.d. | 428 | 486 (M + CH₃COO)⁻ | 2.39 | 5 |
| 99 | 126.4° C. (B) | 441 | 499 (M + CH₃COO)⁻ | 2.63 | 5 |
| 100 | 144.9° C. (B) | 432 | 490 (M + CH₃COO)⁻ | 2.56 | 5 |
| 101 | >300° C. (B) | 444 | 502 (M + CH₃COO)⁻ | 1.91 | 5 |
| 102 | 129.8° C. (B) | 428 | 486 (M + CH₃COO)⁻ | 2.33 | 5 |
| 103 | 164.7° C. (B) | 436 | 494 (M + CH₃COO)⁻ | 2.25 | 5 |
| 104 | 183° C. (B) | 437 | 495 (M + CH₃COO)⁻ | 2.66 | 5 |
| 105 | 124° C. (B) | 442 | 500 (M + CH₃COO)⁻ | 2.61 | 5 |
| 106 | n.d. | 441 | 499 (M + CH₃COO)⁻ | 2.04 | 5 |
| 107 | 294° C. (B) | 456 | 514 (M + CH₃COO)⁻ | 2.92 | 5 |
| 108 | 128.1° C. (B) | 458 | 516 (M + CH₃COO)⁻ | 2.27 | 5 |
| 109 | 149.8° C. (B) | 398 | 456 (M + CH₃COO)⁻ | 2.38 | 5 |
| 110 | 257.9° C. (B) | 402 | 460 (M + CH₃COO)⁻ | 2.09 | 5 |
| 111 | >300° C. (B) | 417 | 475 (M + CH₃COO)⁻ | 1.96 | 5 |
| 113 | n.d. | 415 | 473 (M + CH₃COO)⁻ | 2.29 | 11 |
| 114 | 177.6° C. (B) | 423 | 481 (M + CH₃COO)⁻ | 2.94 | 2 |
| 115 | n.d. | 405 | 463 (M + CH₃COO)⁻ | 2.79 | 8 |
| 116 | n.d. | 405 | 463 (M + CH₃COO)⁻ | 2.79 | 8 |
| 118 | n.d. | 417 | 475 (M + CH₃COO)⁻ | 2.87 | 8 |
| 119 | n.d. | 417 | 475 (M + CH₃COO)⁻ | 2.87 | 8 |
| 120 | n.d. | 417 | 475 (M + CH₃COO)⁻ | 2.78 | 8 |
| 121 | n.d. | 417 | 475 (M + CH₃COO)⁻ | 2.78 | 8 |
| 122 | n.d. | 413 | 471 (M + CH₃COO)⁻ | 2.55 | 5 |
| 123 | 189.5° C. (B) | 417 | 475 (M + CH₃COO)⁻ | 3.92 | 10 |
| 124 | 62.4° C. (B) | 415 | 473 (M + CH₃COO)⁻ | 2.57 | 5 |
| 125 | 165.4 (A, temp. grad.: 3° C./min) | 403 | 461 (M + CH₃COO)⁻ | 1.81 | 5 |
| 126 | 70.5° C. (B) | 415 | 473 (M + CH₃COO)⁻ | 2.49 | 5 |
| 127 | 155.1° C. (B) | 398 | 456 (M + CH₃COO)⁻ | 2.29 | 5 |
| 128 | 139.8° C. (B) | 417 | 475 (M + CH₃COO)⁻ | 1.87 | 5 |
| 129 | 135.1° C. (B) | 401.3 | 459 (M + CH₃COO)⁻ | 2.92 | 8 |
| 130 | 134.4° C. (B) | 401.3 | 459 (M + CH₃COO)⁻ | 2.92 | 8 |
| 131 | 134.7° C. (B) | 423 | 481 (M + CH₃COO)⁻ | 2.36 | 5 |
| 132 | 148° C. (B) | 423 | 481 (M + CH₃COO)⁻ | 2.33 | 5 |
| 133 | 191.5° C. (B) | 417 | 475 (M + CH₃COO)⁻ | 2.70 | 5 |
| 134 | n.d. | 401 | 459 (M + CH₃COO)⁻ | 2.40 | 5 |
| 135 | 76.8° C. (B) | 403 | 461 (M + CH₃COO)⁻ | 1.76 | 5 |
| 136 | 126.2° C. (B) | 427 | 485 (M + CH₃COO)⁻ | 2.38 | 5 |
| 137 | 193.8° C. (B) | 431 | 489 (M + CH₃COO)⁻ | 2.90 | 5 |
| 138 | 173.9° C. (B) | 431 | 489 (M + CH₃COO)⁻ | 2.78 | 5 |
| 140 | 231.5° C. (B) | 403 | 461 (M + CH₃COO)⁻ | 1.62 | 5 |
| 143 | >300° C. (B) | 417 | 475 (M + CH₃COO)⁻ | 2.17 | 5 |
| 144 | 133.2° C. (B) | 417 | 475 (M + CH₃COO)⁻ | 2.06 | 5 |
| 145 | 57.5° C. (B) | 417 | 475 (M + CH₃COO)⁻ | 2.59 | 5 |
| 146 | 166.8° C. (B) | 417 | 475 (M + CH₃COO)⁻ | 2.67 | 5 |
| 147 | 85.9° C. (B) | 402 | 460 (M + CH₃COO)⁻ | 2.01 | 5 |
| 150 | >300° C. (B) | 403 | 461 (M + CH₃COO)⁻ | 2.39 | 5 |
| 151 | 157.6° C. (B) | 398 | 456 (M + CH₃COO)⁻ | 2.28 | 5 |
| 152 | 105.4° C. (B) | 403 | 461 (M + CH₃COO)⁻ | 2.13 | 5 |
| 153 | 162° C. (B) | 387 | 445 (M + CH₃COO)⁻ | 2.15 | 5 |
| 154 | 169.5° C. (B) | 445 | 503 (M + CH₃COO)⁻ | 2.52 | 5 |
| 155 | 101.8° C. (B) | 398 | 456 (M + CH₃COO)⁻ | 1.86 | 5 |
| 157 | 158.9° C. (B) | 415 | 473 (M + CH₃COO)⁻ | 2.37 | 5 |
| 158 | 48.2° C. (B) | 431 | 489 (M + CH₃COO)⁻ | 2.15 | 5 |
| 159 | 71.5° C. (B) | 387 | 445 (M + CH₃COO)⁻ | 2.27 | 5 |
| 160 | 129.5° C. (B) | 417 | 475 (M + CH₃COO)⁻ | 2.04 | 5 |
| 162 | 185.9° C. (B) | 369 | 427 (M + CH₃COO)⁻ | 1.78 | 5 |
| 163 | n.d. | 419 | 477 (M + CH₃COO)⁻ | 2.08 | 5 |
| 164 | 170.3° C. (A, temp. grad.: 3° C./min) | 391 | 389 | 3.75 | 9 |
| 165 | n.d. | 431 | 489 (M + CH₃COO)⁻ | 2.22 | 5 |
| 166 | 99.8° C. (B) | 416 | 474 (M + CH₃COO)⁻ | 2.33 | 5 |
| 168 | 108.5° C. (B) | 419 | 417 | 2.09 | 5 |
| 169 | 64.7° C. (B) | 437 | 495 (M + CH₃COO)⁻ | 2.39 | 5 |
| 171 | 158.8° C. (B) | 401 | 459 (M + CH₃COO)⁻ | 2.32 | 5 |
| 173 | n.d. | 413 | 471 (M + CH₃COO)⁻ | 2.44 | 5 |

TABLE 3a-continued

Analytical data - melting point (M.p.) and LCMS: [M + H]+ means the protonated mass of the free base of the compound, [M − H]− means the deprotonated mass of the free base of the compound or the type of adduct specified [M + CH₃COO]−). R_t means retention time (in min). For some compounds, exact mass was determined.

| Co. No. | M.p. (° C.) | [M + H]+ | [M − H]− or adduct | R_t | LCMS Method |
|---|---|---|---|---|---|
| 174 | 127.5° C. (B) | 403 | 461 (M + CH₃COO)− | 2.12 | 5 |
| 175 | 220.8° C. (B) | 457 | 515 (M + CH₃COO)− | 1.70 | 5 |
| 176 | >300° C. (B) | 457 | 515 (M + CH₃COO)− | 1.78 | 5 |
| 179 | n.d. | 427 | 485 (M + CH₃COO)− | 1.93 | 5 |
| 180 | 76.8° C. (A) | 433 | 491 (M + CH₃COO)− | 2.41 | 5 |
| 181 |  | 423 | 481 (M + CH₃COO)− | 2.08 | 5 |
| 182 | 67.8° C. (B) | 420 | 478 (M + CH₃COO)− | 2.11 | 5 |
| 183 | 125.6° C. (B) | 432 | 490 (M + CH₃COO)− | 2.07 | 5 |
| 184 | n.d. | 420 | 478 (M + CH₃COO)− | 2.73 | 8 |
| 185 | n.d. | 420 | 478 (M + CH₃COO)− | 2.73 | 8 |
| 188 | 161.4° C. (B) | 422 | 480 (M + CH₃COO)− | 2.50 | 5 |
| 189 | 142.4° C. (B) | 432 | 490 (M + CH₃COO)− | 2.46 | 5 |
| 200 | 122.3° C. (A) | 432 | 490 (M + CH₃COO)− | 2.81 | 1 |
| 201 | 119.7° C. (B) | 398 | 456 (M + CH₃COO)− | 2.44 | 5 |
| 204 | 292.8° C. (B) | 422 | 480 (M + CH₃COO)− | 2.51 | 5 |
| 205 | 179.2° C. (B) | 446 | 504 (M + CH₃COO)− | 2.77 | 5 |
| 207 | 147.6° C. (B) | 418 | 476 (M + CH₃COO)− | 2.44 | 5 |
| 208 | 141.3° C. (B) | 418 | 476 (M + CH₃COO)− | 2.60 | 5 |
| 210 | 125.66° C. (D) | 403 | 461 (M + CH₃COO)− | 2.09 | 5 |
| 214 | n.d. | 418 | 476 (M + CH₃COO)− | 1.67 | 5 |
| 216 | n.d. | 417 | 415 | 2.59 | 2 |
| 217 | 255.5° C. (B) | 417 | 415 | 2.61 | 2 |
| 219 | n.d. | 403 | 401 | 1.72 | 5 |
| 220 | n.d. | 513 | 572 (M + CH₃COO)− | 2.48 | 5 |
| 222 | >300° C. (B) | 405 | 463 (M + CH₃COO)− | 2.10 | 5 |
| 225 | n.d. | 499 | 557 (M + CH₃COO)− | 1.38 | 7 |
| 226 | n.d. | 407 | 405 | 1.10 | 7 |
| 227 | n.d. | 407 | 405 | 1.10 | 7 |
| 229 | n.d. | 465 | 523 (M + CH₃COO)− | 2.40 | 5 |
| 235 | 93 (B) | 470 | 528 (M + CH₃COO)− | 1.84 | 5 |
| 236 | >300 (B) | 419 | 477 (M + CH₃COO)− | 2.37 | 5 |
| 237 | 125.82 (D) | 433 | 431 | 2.34 | 5 |
| 238 | n.d. |  | 439.0995 | 2.32 | 13 |
| 240 | 107.87 (D) | 434 | 492 (M + CH₃COO)− | 2.73 | 5 |
| 241 | n.d. | 416 | 474 (M + CH₃COO)− | 2.04 | 5 |
| 248 | n.d. | 416 | 474 (M + CH₃COO)− | 1.35 | 7 |
| 249 | n.d. |  | 478.1874 | 2.47 | 13 | n.d. = not determined

TABLE 3b

Analytical data - melting point (M.p.) and LCMS: [M + H]+ means the protonated mass of the free base of the compound, R_t means retention time (in min), method refers to the method used for LCMS.

| Co. No. | M.p. (° C.) | [M + H]+ | R_t | LCMS Method |
|---|---|---|---|---|
| 16 | 174.0 (A) | 353 | 2.00 | 1 |
| 25 | >300 (A) | 355 | 1.87 | 1 |
| 28 | >300 (A) | 337 | 1.74 | 1 |
| 35 | >300 (A) | 367 | 1.79 | 1 |
| 42 | 250.1 (A) | 377 | 1.71 | 1 |
| 48 | 75.2 (A) | 449 | 2.27 | 1 |
| 58 | 281.9 (C) | 403 | 2.51 | 3 |
| 63 | >300 (C) | 371 | 2.369 | 3 |
| 65 | n.d. | 361 | 2.626 | 3 |
| 66 | 281.8 (C) | 361 | 2.68 | 3 |
| 67 | 138.0 (C) | 405 | 1.16 | 4 |
| 69 | n.d. | 403 | 2.438 | 3 |
| 75 | 186.5 (C) | 362 | 2.087 | 3 |
| 76 | 124.5 (C) | 351 | 2.327 | 3 |
| 78 | 91.1 (B) | 333 | 2.149 | 3 |
| 79 | 266.7 (C) | 377 | 2.314 | 3 |
| 80 | n.d. | 344 | 1.902 | 3 |
| 81 | 288.4 (C) | 363 | 2.241 | 3 |
| 82 | 144.2 (B) | 355 | 2.178 | 3 |
| 83 | 94.5 (A) (10° C./min) | 363 | 2.178 | 3 |
| 84 | 101.2 (A) (10° C./min) | 385 | 2.263 | 3 |
| 85 | 133.0 (A) (10° C./min) | 367 | 2.278 | 3 |
| 86 | 137.9° C. (A) | 319.2 | 2 | 3 |
| 87 | n.d. | 403 | 0.99 | 1 |
| 89 | 136.75 (D) | 369 | 2.17 | 5 |
| 90 | 93.7 (A, temp, grad.: 3° C./min) | 434 | 2.33 | 5 |
| 91 | 86 (A, temp, grad.: 3° C./min) | 434 | 2.34 | 5 |
| 96 | 262.88 (D) | 462 | 2.85 | 6 |
| 98 | n.d. | 419 | 2.15 | 5 |
| 112 | 154.9 (A, temp, grad.: 3° C./min) | 405 | 2.16 | 5 |
| 117 | n.d. | 405 | 2.26 | 5 |
| 139 | 182.3 (B) | 397 | 1.97 | 5 |
| 141 | 93.5 (B) | 375 | 2.51 | 5 |
| 142 | >300 (B) | 403 | 2.45 | 5 |
| 148 | 149.7 (A1, 10° C./min) | 363.2 | 1.79 | 3 |
| 149 | 197.7 (C) | 363 | 0.36 | 3 |
| 156 | 123.7 (B) | 359 | 2.06 | 5 |
| 161 | 82.7 (B) | 383 | 1.92 | 5 |
| 167 | 96.7 (B) | 387 | 2.10 | 5 |
| 170 | 276.2 (B) | 403 | 1.70 | 5 |
| 172 | 124.7 (B) | 367 | 2.02 | 5 |
| 177 | 174.13 (D) | 469 | 2.72 | 5 |
| 178 | n.d. | 368 | 1.81 | 5 |
| 186 | >300 (A) | 388 | 2.28 | 1 |
| 187 | 131.4 (B) | 354 | 2.02 | 1 |
| 190 | 117.6 (B) | 374 | 2.02 | 5 |
| 191 | 60.7 (A, temp, grad.: 3° C./min) | 382 | 1.97 | 5 |
| 192 | 155.9 (B) | 402 | 2.43 | 5 |
| 193 | 58 (B) | 402 | 2.31 | 5 |
| 194 | >300 (B) | 402 | 2.26 | 5 |
| 195 | 75.9 (B) | 398 | 2.08 | 5 |
| 196 | 136.9 (B) | 368 | 2.18 | 5 |
| 197 | 146.6 (A, temp, grad.: 3° C./min) | 392 | 2.37 | 5 |
| 198 | 112.8 (B) | 368 | 2.09 | 5 |
| 199 | 112.8 (A) | 432 | 2.37 | 1 |
| 202 | 255.8 (B) | 388 | 2.35 | 5 |
| 203 | 131.8 (B) | 388 | 2.31 | 5 |
| 206 | n.d. | 384 | 2.21 | 5 |
| 209 | 138.26 (D) | 459 | 2.91 | 6 |
| 211 | n.d. | 374 | 1.99 | 1 |
| 212 | n.d. | 514 | 1.44 | 11 |
| 213 | n.d. | 480 | 1.32 | 7 |
| 215 | n.d. | 407 | 1.33 | 7 |
| 218 | 167.3 (A, temp, grad.: 3° C./min) | 407 | 2.50 | 5 |
| 221 | n.d. | 513 | 2.40 | 5 |
| 223 | n.d. | 451 | 2.97 | 2 |
| 224 | n.d. | 407 | 2.80 | 2 |
| 228 | n.d. | 425 | 1.40 | 7 |
| 230 | n.d. | 445 | 1.25 | 12 |
| 231 | n.d. | 432 | 1.12 | 7 |
| 232 | n.d. | 432 | 1.11 | 7 |
| 233 | n.d. | 418 | 0.96 | 7 |
| 234 | n.d. | 437 | 2.88 | 13 |
| 239 | n.d. | 417 | 0.99 | 7 |
| 242 | n.d. | 432 | 2.44 | 5 |
| 243 | 72.44 (D) | 420.1455 | 2.38 | 13 |
| 244 | 188.41 (D) | 373.0626 (+0.3 mDa) | 1.11 | 12 |
| 245 | n.d. | 446.1820 | 2.0 | 13 |
| 246 | n.d. | 448.1765 (+0.5 mDa) | 2.43 | 13 |
| 247 | 155.12 (D) | 391.1184 (+0.2 mDa) | 2.33 | 13 |
| 250 | 158.03 (D) | 447.1756 (0.0 mDa) | 2.78 | 13 |

TABLE 3b-continued

Analytical data - melting point (M.p.) and LCMS: [M + H]⁺ means the protonated mass of the free base of the compound, $R_t$ means retention time (in min), method refers to the method used for LCMS.

| Co. No. | M.p. (° C.) | [M + H]⁺ | $R_t$ | LCMS Method |
|---|---|---|---|---|
| 251 | 151.45 (D) | 416.1698 (−0.0 mDa) | 2.29 | 13# |
| 252 | n.d. | 437.0994 (+0.2 mDa) | 1.94 | 13 |
| 253 | n.d. | 430.1857 (+0.3 mDa) | 2.63 | 13 |
| 254 | n.d. | 464.1469 (+0.4 mDa) | 2.88 | 13 |
| 255 | 136.39 (D) | 450.1310 (+0.2 mDa) | 2.52 | 13 |
| 256 | 153.60 (D) | 430.1855 (+0.1 mDa) | 2.48 | 13 |
| 257 | n.d. | 416.1046 (+0.1 mDa) | 2.38 | 13 |
| 258 | 121.41 (D) | 444.2012 (+0.1 mDa) | 2.7 | 13 |
| 259 | 115.50 (D) | 430.1856 (+0.2 mDa) | 2.49 | 13 |
| 260 | 141.74 (D) | 442.1852 (−0.2 mDa) | 2.56 | 13 |
| 261 | n.d. | 430.1202 (+0.1 mDa) | 2.54 | 13 |
| 262 | 116.12. | 464.1463 (−0.2 mDa) | 2.71 | 13 |
| 263 | n.d. | 430.1199 (−0.2 mDa) | 2.55 | 13 |
| 264 | n.d. | 464.1465 (+0.0 mDa) | 2.72 | 13 |
| 265 | n.d. | 439.0951 (+0.2 mDa) | 2.50 | 13 |
| 266 | 173.08 | 430.1853 (−0.1 mDa) | 2.51 | 13 |
| 267 | 131.30 | 444.2012 (+0.1 mDa) | 2.69 | 13 | n.d. = not determined

SFC-MS

General Procedure

The SFC measurement was performed using Analytical system from Berger instrument comprising a FCM-1200 dual pump fluid control module for delivering carbon dioxide ($CO_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 μa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

TABLE 4

Analytical SFC-MS Methods (Flow expressed in mL/min; column temperature (T) in ° C.; Pressure in Mpa).

| Method | Column | Mobile Phase | Flow | T | Pressure |
|---|---|---|---|---|---|
| 1 | Chiralcel OD-H 250 × 4.6 mm, 5 μm Daicel | $CO_2$/EtOH (0.3% IPrNH₂) 70/30 | 3 | 35 | 100 |
| 2 | Chiralpak IC 250 × 4.6 mm 5 μm Daicel | $CO_2$/EtOH (0.3% IPrNH₂) 70/30 | 3 | 35 | 100 |
| 3 | Chiralpak IC 250 × 4.6 mm 5 μm Daicel | $CO_2$/EtOH (0.3% IPrNH₂) 60/40 | 3 | 35 | 100 |
| 4 | Chiralpak IC 250 × 4.6 mm, 5 μm Daicel | $CO_2$/MeOH (0.3% IPrNH₂)/iPrOH (0.3% IPrNH₂) 80/10/10 | 3 | 35 | 100 |
| 5 | Chiralpak AD-H 150 × 4.6 mm, 5 μm Daicel | $CO_2$/MeOH (0.3% IPrNH₂)/iPrOH (0.3% IPrNH₂) 60/20/20 | 3 | 35 | 100 |

TABLE 5

Analytical SFC data - $R_t$ means retention time (in minutes), [M + H]⁺ means the protonated mass of the compound, method refers to the method used for SFC/MS analysis of enantiomerically pure compounds. The measurement was compared against the mixture.

| Co. No. | $R_t$ | [M + H]⁺ | UV Area % | Isomer Elution Order | Method |
|---|---|---|---|---|---|
| 130 | 2.65 | 401 | 100 | A | 1 |
| 129 | 3.84 | 401 | 100 | B | 1 |
| 120 | 3.28 | 417 | 100 | A | 2 |
| 121 | 4.40 | 417 | 100 | B | 2 |
| 119 | 4.86 | 417 | 100 | A | 3 |
| 118 | 6.86 | 417 | 100 | B | 3 |
| 116 | 3.74 | 405 | 100 | A | 4 |
| 115 | 5.24 | 405 | 100 | B | 4 |
| 184 | 3.62 | 420 | 100 | A | 5 |
| 185 | 5.22 | 420 | 100 | B | 5 |

Optical Rotations

Optical rotations were measured on a Perkin-Elmer 341 polarimeter with a sodium lamp and reported as follows: [α]° (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 6

Optical Rotation data.

| Co. No. | $\alpha_D$ (°) | Wavelength (nm) | Concentration w/v % | Solvent | Temp. (° C.) |
|---|---|---|---|---|---|
| 1 | +21.2 | 589 | 0.59 | DMF | 20 |
| 3 | +26.4 | 589 | 1.26 | DMF | 20 |
| 4 | +16.8 | 589 | 0.48 | DMF | 20 |
| 7 | +16.9 | 589 | 0.56 | DMF | 20 |
| 8 | +21.5 | 589 | 0.54 | DMF | 20 |
| 9 | +19.8 | 589 | 0.40 | DMF | 20 |
| 10 | +21.6 | 589 | 0.82 | DMF | 20 |
| 12 | +18.8 | 589 | 0.56 | DMF | 20 |
| 13 | +22.4 | 589 | 0.52 | DMF | 20 |
| 14 | +19.9 | 589 | 0.54 | DMF | 20 |
| 16 | +25.8 | 589 | 0.49 | DMF | 20 |
| 18 | +19.1 | 589 | 0.54 | DMF | 20 |
| 19 | +22.5 | 589 | 0.49 | DMF | 20 |
| 21 | +18.6 | 589 | 0.53 | DMF | 20 |
| 23 | +23.5 | 589 | 0.63 | DMF | 20 |
| 24 | +18.6 | 589 | 0.54 | DMF | 20 |
| 26 | −22.5 | 589 | 0.59 | DMF | 20 |
| 27 | +16.6 | 589 | 0.61 | DMF | 20 |
| 28 | +20.7 | 589 | 0.68 | DMF | 20 |
| 29 | +18.6 | 589 | 0.52 | DMF | 20 |
| 30 | +14.9 | 589 | 0.54 | DMF | 20 |
| 31 | −22.9 | 589 | 0.52 | DMF | 20 |
| 34 | +18.1 | 589 | 0.64 | DMF | 20 |
| 36 | +19.6 | 589 | 0.48 | DMF | 20 |
| 37 | +17.7 | 589 | 0.49 | DMF | 20 |
| 42 | +18.2 | 589 | 0.59 | DMF | 20 |
| 43 | +25.1 | 589 | 0.54 | DMF | 20 |
| 44 | +22.9 | 589 | 0.48 | DMF | 20 |
| 45 | +20.5 | 589 | 0.68 | DMF | 20 |
| 46 | +22.3 | 589 | 0.49 | DMF | 20 |
| 47 | +26.0 | 589 | 0.50 | DMF | 20 |
| 48 | +17.0 | 589 | 0.54 | DMF | 20 |
| 49 | +21.1 | 589 | 0.50 | DMF | 20 |
| 50 | +27.4 | 589 | 0.50 | DMF | 20 |

TABLE 6-continued

Optical Rotation data.

| Co. No. | $\alpha_D$ (°) | Wavelength (nm) | Concentration w/v % | Solvent | Temp. (° C.) |
|---|---|---|---|---|---|
| 51 | +19.9 | 589 | 0.52 | DMF | 20 |
| 53 | +23.7 | 589 | 0.40 | DMF | 20 |
| 54 | +26.7 | 589 | 0.50 | DMF | 20 |
| 55 | +24.8 | 589 | 0.65 | DMF | 20 |
| 56 | +16.1 | 589 | 0.50 | DMF | 20 |
| 57 | +24.1 | 589 | 0.58 | DMF | 20 |
| 59 | +27.9 | 589 | 0.42 | DMF | 20 |
| 60 | +20.7 | 589 | 0.57 | DMF | 20 |
| 61 | +23.1 | 589 | 0.52 | DMF | 20 |
| 62 | +23.0 | 589 | 0.55 | DMF | 20 |
| 64 | +20.4 | 589 | 0.58 | DMF | 20 |
| 68 | +24.1 | 589 | 0.59 | DMF | 20 |
| 71 | +24.9 | 589 | 0.50 | DMF | 20 |
| 72 | +22.7 | 589 | 0.48 | DMF | 20 |
| 73 | +22.9 | 589 | 0.58 | DMF | 20 |
| 77 | +16.4 | 589 | 0.48 | DMF | 20 |
| 88 | +20.3 | 589 | 1.0 | DMF | 20 |
| 90 | −2.1 | 589 | 0.53 | DMF | 20 |
| 91 | +3.0 | 589 | 0.51 | DMF | 20 |
| 92 | +24.7 | 589 | 0.50 | DMF | 20 |
| 94 | +22.3 | 589 | 0.60 | DMF | 20 |
| 95 | +26.1 | 589 | 1.00 | DMF | 20 |
| 96 | +45.1 | 589 | 0.60 | DMF | 25 |
| 97 | +32.6 | 589 | 1.50 | DMF | 20 |
| 98 | +22.5 | 589 | 0.45 | DMF | 20 |
| 99 | +18.7 | 589 | 1.45 | DMF | 20 |
| 100 | +26.4 | 589 | 0.49 | DMF | 20 |
| 101 | +20.3 | 589 | 0.50 | DMF | 20 |
| 102 | +21.2 | 589 | 0.51 | DMF | 20 |
| 103 | +27.1 | 589 | 0.88 | DMF | 20 |
| 104 | +25.2 | 589 | 0.50 | DMF | 20 |
| 105 | +21.2 | 589 | 0.55 | DMF | 20 |
| 107 | +18.8 | 589 | 0.55 | DMF | 20 |
| 108 | +19.4 | 589 | 0.55 | DMF | 20 |
| 109 | +26.1 | 589 | 0.51 | DMF | 20 |
| 110 | +22.6 | 589 | 0.52 | DMF | 20 |
| 112 | +20.7 | 589 | 0.49 | DMF | 20 |
| 113 | +15.6 | 589 | 0.53 | DMF | 20 |
| 114 | +20.0 | 589 | 0.49 | DMF | 20 |
| 115 | +3.9 | 589 | 0.52 | DMF | 20 |
| 116 | −2.5 | 589 | 0.56 | DMF | 20 |
| 117 | +26.4 | 589 | 0.48 | DMF | 20 |
| 118 | −33.8 | 589 | 0.61 | DMF | 20 |
| 119 | +38.8 | 589 | 0.58 | DMF | 20 |
| 120 | +44.2 | 589 | 0.63 | DMF | 20 |
| 121 | −45.9 | 589 | 0.61 | DMF | 20 |
| 123 | +18.8 | 589 | 0.62 | DMF | 20 |
| 124 | +23.2 | 589 | 0.53 | DMF | 20 |
| 125 | +23.6 | 589 | 0.52 | DMF | 20 |
| 126 | +17.5 | 589 | 0.58 | DMF | 20 |
| 127 | +25.7 | 589 | 0.58 | DMF | 20 |
| 129 | +12.2 | 589 | 0.54 | DMF | 20 |
| 130 | −12.6 | 589 | 0.52 | DMF | 20 |
| 131 | +21.5 | 589 | 0.51 | DMF | 20 |
| 132 | +21.1 | 589 | 0.6 | DMF | 20 |
| 133 | +18.7 | 589 | 0.71 | DMF | 20 |
| 135 | +19.5 | 589 | 0.55 | DMF | 25 |
| 136 | +15.9 | 589 | 0.53 | DMF | 20 |
| 137 | +17.6 | 589 | 0.50 | DMF | 20 |
| 138 | +11.9 | 589 | 0.51 | DMF | 20 |
| 139 | +21.6 | 589 | 0.57 | DMF | 20 |
| 140 | +20.3 | 589 | 0.57 | DMF | 20 |
| 141 | +17.2 | 589 | 0.45 | DMF | 20 |
| 142 | +25.0 | 589 | 0.49 | DMF | 20 |
| 145 | +18.6 | 589 | 0.54 | DMF | 20 |
| 146 | +21.5 | 589 | 0.61 | DMF | 20 |
| 147 | +21.1 | 589 | 0.51 | DMF | 20 |
| 150 | +20.3 | 589 | 0.49 | DMF | 20 |
| 151 | +19.8 | 589 | 0.59 | DMF | 20 |
| 152 | +15.6 | 589 | 0.50 | DMF | 20 |
| 153 | −30.9 | 589 | 0.58 | DMF | 20 |
| 154 | +20.7 | 589 | 0.51 | DMF | 20 |
| 155 | +19.9 | 589 | 0.51 | DMF | 20 |
| 156 | +14.5 | 589 | 0.48 | DMF | 20 |
| 157 | +22.6 | 589 | 0.52 | DMF | 20 |
| 158 | +27.9 | 589 | 0.60 | DMF | 20 |
| 159 | +14.0 | 589 | 0.51 | DMF | 20 |
| 160 | +16.1 | 589 | 0.62 | DMF | 20 |
| 161 | −16.8 | 589 | 0.46 | DMF | 20 |
| 162 | −33.9 | 589 | 0.54 | DMF | 20 |
| 163 | +20.4 | 589 | 0.50 | DMF | 20 |
| 164 | +27.2 | 589 | 0.50 | DMF | 20 |
| 166 | +21.8 | 589 | 0.50 | DMF | 20 |
| 167 | +12.4 | 589 | 0.41 | DMF | 20 |
| 168 | +22.2 | 589 | 0.61 | DMF | 20 |
| 169 | +21.7 | 589 | 0.77 | DMF | 20 |
| 171 | −0.7 | 589 | 0.74 | DMF | 20 |
| 172 | +16.7 | 589 | 0.64 | DMF | 20 |
| 174 | +25.8 | 589 | 0.52 | DMF | 20 |
| 175 | +15.4 | 589 | 0.51 | DMF | 20 |
| 176 | +13.3 | 589 | 0.50 | DMF | 20 |
| 177 | +19.2 | 589 | 0.49 | DMF | 20 |
| 178 | +11.5 | 589 | 0.49 | DMF | 20 |
| 179 | +13.0 | 589 | 0.49 | DMF | 20 |
| 180 | +15.5 | 589 | 0.45 | DMF | 20 |
| 182 | +18.3 | 589 | 0.40 | DMF | 20 |
| 183 | +19.7 | 589 | 0.40 | DMF | 20 |
| 184 | +0.5 | 589 | 0.47 | DMF | 20 |
| 185 | −4.9 | 589 | 0.51 | DMF | 20 |
| 186 | +11.1 | 589 | 0.46 | DMF | 20 |
| 187 | +30.5 | 589 | 0.49 | DMF | 20 |
| 188 | −16.8 | 589 | 0.59 | DMF | 20 |
| 189 | +42.8 | 589 | 0.53 | DMF | 20 |
| 190 | +29.4 | 589 | 0.54 | DMF | 20 |
| 191 | +28.3 | 589 | 0.53 | DMF | 20 |
| 195 | −55.0 | 589 | 0.53 | DMF | 20 |
| 196 | +26.8 | 589 | 0.62 | DMF | 20 |
| 197 | +33.7 | 589 | 0.54 | DMF | 20 |
| 198 | +35.2 | 589 | 0.52 | DMF | 20 |
| 199 | −16.0 | 589 | 0.48 | DMF | 20 |
| 200 | +0.8 | 589 | 0.46 | DMF | 20 |
| 201 | −5.3 | 589 | 1.00 | DMF | 20 |
| 202 | +24.2 | 589 | 0.54 | DMF | 20 |
| 203 | +39.4 | 589 | 0.52 | DMF | 20 |
| 204 | +46.3 | 589 | 0.84 | DMF | 20 |
| 205 | +3.2 | 589 | 0.50 | DMF | 20 |
| 206 | −2.2 | 589 | 0.49 | DMF | 20 |
| 207 | +33.1 | 589 | 0.58 | DMF | 20 |
| 208 | +1.3 | 589 | 0.54 | DMF | 25 |
| 209 | +5.9 | 589 | 1.40 | DMF | 20 |
| 210 | +28.5 | 589 | 0.51 | DMF | 20 |
| 218 | +17.6 | 589 | 0.49 | DMF | 25 |
| 235 | +18.6 | 589 | 0.60 | DMF | 25 |
| 237 | +10.5 | 589 | 0.50 | DMF | 20 |
| 240 | +2.2 | 589 | 0.55 | DMF | 20 |
| 241 | +20.3 | 589 | 0.50 | DMF | 20 |
| 242 | +21.5 | 589 | 0.50 | DMF | 20 |
| 243 | +19.0 | 589 | 0.51 | DMF | 20 |
| 250 | +2.3 | 589 | 0.48 | DMF | 20 |
| 253 | +16.2 | 589 | 0.69 | DMF | 20 |
| 255 | +25.0 | 589 | 0.54 | DMF | 20 |
| 257 | +16.4 | 589 | 0.40 | DMF | 20 |
| 258 | +23.7 | 589 | 0.80 | DMF | 20 |
| 259 | +21.3 | 589 | 0.57 | DMF | 20 |
| 260 | +19.4 | 589 | 0.49 | DMF | 20 |
| 261 | +21.4 | 589 | 0.54 | DMF | 20 |
| 262 | 25.9 | 589 | 0.51 | DMF | 20 |
| 263 | 19.2 | 589 | 0.52 | DMF | 20 |
| 264 | 23.3 | 589 | 0.49 | DMF | 20 |
| 266 | 20.3 | 589 | 0.53 | DMF | 20 |
| 267 | 20.3 | 589 | 0.51 | DMF | 20 |

NMR

Co. No. 237: $^1$H NMR (500 MHz, CDCl$_3$) δ ppm 1.72 (d, J=6.6 Hz, 3H) 2.96 (d, J=5.2 Hz, 3H) 4.05 (s, 3H) 4.42 (dd, J=13.7, 7.1 Hz, 1H) 4.53-4.59 (m, 1H) 4.64 (dd, J=13.6, 4.0

Hz, 1H) 4.70-4.78 (m, 1H) 6.76 (s, 1H) 6.84 (d, J=5.2 Hz, 1H) 7.78 (d, J=8.7 Hz, 1H) 7.77 (s, 1H) 7.88 (d, J=8.4 Hz, 1H) 8.13 (d, J=5.2 Hz, 1H)

Pharmacological Examples

The compounds provided in the present invention are negative allosteric modulators of mGluR2. These compounds appear to inhibit glutamate responses by binding to an allosteric site other than the glutamate binding site. The response of mGluR2 to a concentration of glutamate is decreased when compounds of Formula (I) are present. Compounds of Formula (I) are expected to have their effect substantially at mGluR2 by virtue of their ability to reduce the function of the receptor. The effects of negative allosteric modulators tested at mGluR2 using the [$^{35}$S]GTPγS binding assay method described below and which is suitable for the identification of such compounds, and more particularly the compounds according to Formula (I), are shown in Table 7.

1) [$^{35}$S]GTPγS binding assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein a subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6x250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 μM GDP. Human mGlu2 receptor-containing membranes were thawed on ice and diluted in assay buffer supplemented with 18 μg/ml saponin. Membranes were pre-incubated with compound together with a predefined (~EC$_{50}$) concentration of glutamate (60 μM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 μg of membrane protein in 10 mM HEPES acid, 10 mM HEPES salt, pH 7.4, 100 mM NaCl, 3 mM MgCl$_2$, 10 μM GDP and 10 μg/ml saponin. Total reaction volume was 200 μl. Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried, and 30 μl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an EC$_{80}$-equivalent concentration of glutamate. Sigmoid concentration-response curves plotting these percentages versus the log concentration of the test compound were analyzed using non-linear regression analysis. The concentration producing half-maximal inhibition was calculated as the IC$_{50}$. The pIC$_{50}$ values were calculated as the −log IC$_{50}$, when the IC$_{50}$ is expressed in M. E$_{max}$ is defined as the relative maximal effect (i.e. maximal % inhibition relative to the control glutamate response).

TABLE 7

Pharmacological data for compounds according to the invention.

| Co. No. | GTPγS - hmGluR2 anGT pIC$_{50}$ | GTPγS - hmGluR2 anGT Emax |
|---|---|---|
| 1 | 8.05 | 106 |
| 2 | 7.65 | 104 |
| 3 | 8.75 | 106 |
| 4 | 8.48 | 104 |
| 5 | 8.29 | 105 |
| 6 | 8.3 | 106 |
| 6a | 8.32 | 112 |
| 7 | 8.12 | 102 |
| 8 | 8.23 | 105 |
| 9 | 7.98 | 103 |
| 10 | 7.93 | 104 |
| 11 | 7.72 | 103 |
| 12 | 7.71 | 104 |
| 13 | 7.53 | 103 |
| 14 | 7.62 | 104 |
| 15 | 7.58 | 103 |
| 16 | 7.29 | 102 |
| 17 | 7.32 | 104 |
| 18 | 7.28 | 102 |
| 19 | 7.16 | 105 |
| 20 | 7.06 | 104 |
| 21 | 7.21 | 107 |
| 22 | 7.16 | 104 |
| 23 | 6.96 | 104 |
| 24 | 6.92 | 104 |
| 25 | 6.84 | 103 |
| 26 | 6.76 | 105 |
| 27 | 6.86 | 104 |
| 28 | 6.62 | 105 |
| 29 | 6.64 | 102 |
| 30 | 6.59 | 104 |
| 31 | 6.36 | 107 |
| 32 | 6.25 | 101 |

TABLE 7-continued

Pharmacological data for compounds according to the invention.

| Co. No. | GTPγS - hmGluR2 anGT pIC$_{50}$ | GTPγS - hmGluR2 anGT Emax |
|---|---|---|
| 33 | 6.24 | 99 |
| 34 | 6.25 | 100 |
| 35 | 6.22 | 100 |
| 36 | 6.08 | 100 |
| 37 | 6.01 | 99 |
| 38 | 6.02 | 103 |
| 39 | 5.79 | 100 |
| 40 | 5.83 | 105 |
| 41 | 5.45 | 95 |
| 42 | 5.51 | 102 |
| 43 | 8.54 | 107 |
| 44 | 8.21 | 105 |
| 45 | 8 | 104 |
| 46 | 8.2 | 105 |
| 47 | 8.19 | 105 |
| 48 | 8.11 | 100 |
| 49 | 8.06 | 103 |
| 50 | 8.02 | 103 |
| 51 | 7.96 | 104 |
| 52 | 7.98 | 107 |
| 53 | 8.01 | 102 |
| 54 | 7.98 | 105 |
| 55 | 7.79 | 104 |
| 56 | 7.79 | 102 |
| 57 | 7.89 | 104 |
| 58 | 7.66 | 107 |
| 59 | 7.45 | 98 |
| 60 | 7.5 | 101 |
| 61 | 7.55 | 106 |
| 62 | 7.48 | 105 |
| 63 | 7.47 | 105 |
| 64 | 7.58 | 103 |
| 65 | 7.35 | 106 |
| 66 | 7.39 | 107 |
| 67 | 7.2 | 104 |
| 68 | 7.15 | 100 |
| 69 | 7.27 | 103 |
| 70 | 7.1 | 106 |
| 71 | 7.01 | 103 |
| 72 | 6.97 | 103 |
| 73 | 6.89 | 102 |
| 74 | 6.67 | 100 |
| 75 | 6.56 | 100 |
| 76 | 6.55 | 100 |
| 77 | 6.41 | 101 |
| 78 | 6.32 | 103 |
| 79 | 6.29 | 104 |
| 80 | 6.29 | 107 |
| 81 | 6.27 | 103 |
| 82 | 6.2 | 101 |
| 83 | 6.1 | 104 |
| 84 | 6.09 | 104 |
| 85 | 6.02 | 101 |
| 86 | 6 | 102 |
| 87 | n.t. | |
| 88 | 7.39 | 102 |
| 89 | 7.38 | 104 |
| 90 | 8.51 | 103 |
| 91 | 7.25 | 103 |
| 92 | 8.53 | 107 |
| 93 | 7.74 | 105 |
| 94 | 7.26 | 108 |
| 95 | 8.75 | 110 |
| 96 | 8.91 | 108 |
| 97 | 8.78 | 104 |
| 98 | 8.19 | 111 |
| 99 | 7.84 | 108 |
| 100 | 8.16 | 109 |
| 101 | 6.39 | 109 |
| 102 | 8.08 | 107 |
| 103 | 8.55 | 107 |
| 104 | 8.43 | 108 |
| 105 | 7.56 | 108 |
| 106 | 6.22 | 109 |
| 107 | 7.75 | 114 |
| 108 | 6.91 | 108 |
| 109 | 7.73 | 107 |
| 110 | 8.29 | 108 |
| 111 | 6.53 | 108 |
| 112 | 7.45 | 103 |
| 113 | 7.04 | 103 |
| 114 | 8.15 | 104 |
| 115 | 8.15 | 108 |
| 116 | 6.25 | 105 |
| 117 | 8.12 | 109 |
| 118 | 7.71 | 105 |
| 119 | 5.6 | 100 |
| 120 | 7.19 | 106 |
| 121 | 4.79 | 75 |
| 122 | 8.43 | 108 |
| 123 | 8.18 | 107 |
| 124 | 8.52 | 108 |
| 125 | 6.75 | 105 |
| 126 | 8.24 | 108 |
| 127 | 7.56 | 103 |
| 128 | 6.23 | 104 |
| 129 | 6.16 | 100 |
| 130 | 7.77 | 102 |
| 131 | 7.61 | 105 |
| 132 | 7.62 | 103 |
| 133 | 8.08 | 104 |
| 134 | 8.49 | 104 |
| 135 | 6.19 | 103 |
| 136 | 7.36 | 102 |
| 137 | 7.74 | 107 |
| 138 | 7.17 | 105 |
| 139 | 7.44 | 106 |
| 140 | 6.29 | 104 |
| 141 | 7.21 | 102 |
| 142 | 8.18 | 105 |
| 143 | 7.61 | 104 |
| 144 | 7.02 | 103 |
| 145 | 7.73 | 105 |
| 146 | 7.78 | 105 |
| 147 | 8.24 | 106 |
| 148 | 5.25 | 100 |
| 149 | <4.3 | 49 |
| 150 | 6.33 | 103 |
| 151 | 5.92 | 103 |
| 152 | 8 | 105 |
| 153 | 7.84 | 103 |
| 154 | 7.7 | 104 |
| 155 | 7.09 | 103 |
| 156 | 7.25 | 106 |
| 157 | 8.06 | 104 |
| 158 | 7.6 | 106 |
| 159 | 7.87 | 104 |
| 160 | 6.97 | 106 |
| 161 | 4.81 | 76 |
| 162 | 6.89 | 102 |
| 163 | 7.96 | 103 |
| 164 | 8.26 | 107 |
| 165 | 7.71 | 102 |
| 166 | 8.6 | 102 |
| 167 | 6.12 | 105 |
| 168 | 7.6 | 106 |
| 169 | 8.22 | 105 |
| 170 | 7.14 | 107 |
| 171 | 4.77 | 94 |
| 172 | 5.98 | 105 |
| 173 | 8.36 | 106 |
| 174 | 8 | 105 |
| 175 | 5.87 | 102 |
| 176 | 5.2 | 85 |
| 177 | 8.03 | 105 |
| 178 | 7.62 | 107 |
| 179 | 7.44 | 103 |
| 180 | 7.88 | 106 |

TABLE 7-continued

Pharmacological data for compounds according to the invention.

| Co. No. | GTPγS - hmGluR2 anGT pIC$_{50}$ | GTPγS - hmGluR2 anGT Emax |
|---|---|---|
| 181 | 6.38 | 103 |
| 182 | 8.08 | 106 |
| 183 | 7.64 | 103 |
| 184 | 6.56 | 105 |
| 185 | 8.22 | 104 |
| 186 | 7.42 | 102 |
| 187 | 6.49 | 108 |
| 188 | 8.39 | 108 |
| 189 | 7.39 | 102 |
| 190 | 6.68 | 105 |
| 191 | 5.97 | 109 |
| 192 | 8.13 | 106 |
| 193 | 7.72 | 103 |
| 194 | 6.86 | 107 |
| 195 | 5.39 | 92 |
| 196 | 7.3 | 107 |
| 197 | 6.82 | 104 |
| 198 | 7.04 | 104 |
| 199 | 4.59 | 67 |
| 200 | 8.23 | 105 |
| 201 | 8.08 | 105 |
| 202 | 7.99 | 103 |
| 203 | 8.17 | 105 |
| 204 | 8.31 | 107 |
| 205 | 7.99 | 102 |
| 206 | 7.75 | 111 |
| 207 | 8.42 | 109 |
| 208 | 7.65 | 107 |
| 209 | 8.19 | 104 |
| 210 | 7.63 | 105 |
| 211 | 5.43 | 92 |
| 212 | n.t. | |
| 213 | n.t. | |
| 214 | n.t. | |
| 215 | n.t. | |
| 216 | n.t. | |
| 217 | 5.35 | 97 |
| 218 | n.t. | |
| 219 | n.t. | |
| 220 | n.t. | |
| 221 | n.t. | |
| 222 | n.t. | |
| 223 | n.t. | |
| 224 | n.t. | |
| 225 | n.t. | |
| 226 | n.t. | |
| 227 | n.t. | |
| 228 | n.t. | |
| 229 | n.t. | |
| 230 | n.t. | |
| 231 | n.t. | |
| 232 | n.t. | |
| 233 | n.t. | |
| 234 | n.t. | |
| 235 | 5.9 | 102 |
| 236 | 8.14 | 105 |
| 237 | 8.5 | 111 |
| 238 | 5.67 | 103 |
| 239 | n.t. | |
| 240 | 8.17 | 109 |
| 241 | 7.74 | 109 |
| 242 | 7.89 | 110 |
| 243 | 7.65 | 116 |
| 244 | 5.06 | 80 |
| 245 | n.t. | |
| 246 | 8.38 | 116 |
| 247 | 7.52 | 109 |
| 248 | n.t. | |
| 249 | 8.08 | 109 |
| 250 | 8.4 | 120 |
| 251 | 8.2 | 116 |
| 252 | n.t. | |
| 253 | 8.21 | 111 |
| 254 | 8.77 | 109 |
| 255 | 8.82 | 107 |
| 256 | 8.44 | 108 |
| 257 | 8.44 | 108 |
| 258 | 8.22 | 108 |
| 259 | 7.75 | 105 |
| 260 | 8.45 | 105 |
| 261 | 7.96 | 107 |
| 262 | 8.21 | 109 |
| 263 | 8.33 | 109 |
| 264 | 8.57 | 108 |
| 265 | 8.26 | 111 |
| 266 | 7.28 | 106 |
| 267 | 7.65 | 107 | n.t. means not tested

2) Reversal of the Effect of the mGluR2 PAM JNJ-42153605 on Scopolamine-Induced Hyperlocomotion Apparatus Motor activity was measured in microprocessor-based motor activity arenas (closed gray PVC cylinders with a height of 39 cm and a diameter of 31 cm). Each arena was placed on an infrared LED (8×8 LEDs) lit box (white PVC squared box; 40×40 cm$^2$; height 12.5 cm. An infrared-sensitive tube camera and a white light source were mounted to the ceiling above the observation chamber to track the animal. The total distance traveled (cm) was recorded and analyzed using the Noldus Ethovision XT Video Tracking System (Version 7.0.418; Noldus, Wageningen, The Netherlands). The intensity of the light within the activity cages (measured in the centre at the level of the floor) ranged between 4 and 8 LUX.

General Procedure

The rats were pretreated with test compound or vehicle at 60 min before the start of the activity recordings and placed into individual cages. The rats were challenged with JNJ-42153605 (3-(cyclopropylmethyl)-7-(4-phenylpiperidin-1-yl)-8-(trifluoromethyl)[1,2,4]triazolo[4,3-a]pyridine; WO2010/130424; Cid et al. *J. Med. Chem.* 2012, 55, 8770-8789) (20 mg/kg, i.v.) 30 min before the start of the activity recording combined with scopolamine (0.16 mg/kg, i.v.) just before the start of the activity measurements Immediately after the injection of scopolamine, the rats were placed into the activity monitors and total distance travelled over the first 30 min was measured.

Solvent-Pretreated Control Rats.

Figure 1:
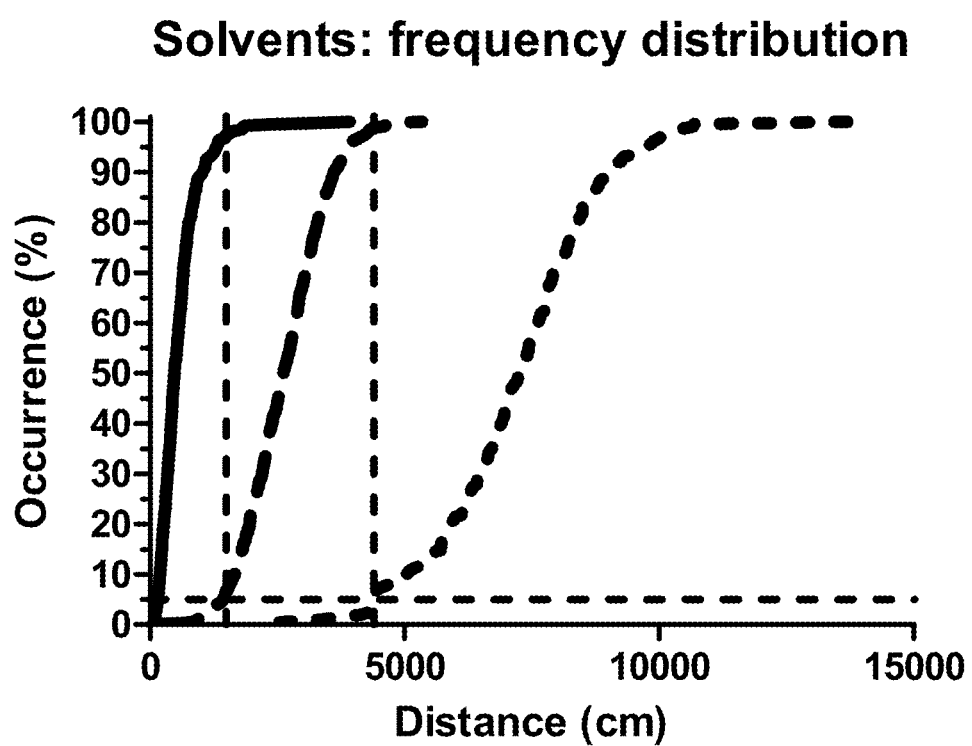
FIG. 1 shows the frequency distributions for distance travelled obtained in historical series of solvent-pretreated control rats.

Frequency distributions obtained in historical series of solvent-pretreated control rats are given in FIG. 1 and Table 8 below. Animals receiving the combination of JNJ-42153605 and scopolamine (n=433) almost always travelled a distance of less than 1500 cm (<1500 cm) (only 2.5% of the control rats travelled a distance of more than 1500 cm (>1500 cm)). On the other hand, animals challenged with scopolamine alone (n=215) always travelled a total distance of more than 1500 cm (>1500 cm) and almost always (in 95.8% of the rats) a distance of more than 4400 cm (>4400 cm). Rats that did not receive any challenge travelled almost always a distance of more than 1500 cm (>1500 cm) (in 93.3% of the rats) and less than 4400 cm (<4400 cm) (in 98.9% of the rats). For reversal of the inhibitory effect of JNJ-42153605 on the scopolamine-induced hyperlocomotion, two all-or-none criteria were adopted: (1) reversal: total distance >1500 cm; (2) normalization: total distance >4400 cm. The results on the reversal of the effect of JNJ-42153605 are shown in table 9 below.

TABLE 8

Frequency distributions obtained in historical series of solvent-pretreated control rats. $N_{tested}$ means number of animals tested.

|  | Median (cm) | >1500 cm (%) | >4400 cm (%) | $N_{tested}$ |
|---|---|---|---|---|
| Combination | 480 | 2.5 | 0.0 | 433 |
| No challenge | 2618 | 93.3 | 1.1 | 638 |
| Scopolamine | 7246 | 100 | 95.8 | 215 |

TABLE 9

Reversal of the effect of JNJ 42153605 on scopolamine-induced hyperlocomotion.

| Co. No. | Route | $ED_{50}$ | Co. No. | Route | $ED_{50}$ |
|---|---|---|---|---|---|
| 26 | SC | >10 |  | SC | ≥10 |
| 1 | PO | 0.45 | 16 | SC | ≥10 |
|  | SC | 3.54 | 15 | PO | 1.26 |
| 8 | PO | 5 | 12 | PO | 1.25 |
| 2 | PO | 1.26 | 201 | PO | >2.5 |
| 186 | PO | 3.15 | 147 | PO | 0.50 |
| 6 | PO | 0.80 | 142 | PO | 1.99 |
| 200 | PO | 3.15 | 236 | PO | >2.5 |
| 4 | PO | 1.26 | 127 | PO | 1.99 |
| 5 | PO | ≥2.5 | 104 | PO | ≥2.5 |
| 14 | PO | 5 | 103 | PO | 0.96 |
| 19 | PO | ≥10 | 102 | PO | ≥2.5 |
| 3 | PO | 1.99 | 100 | PO | >10 |
| 10 | PO | 0.79 | 99 | PO | ≥2.5 |
| 9 | PO | ≥2.5 | 95 | PO | >2.5 |
| 13 | PO | 7.94 | 180 | PO | ≥2.5 |
| 18 | PO | ≥10 | 182 | PO | 1.99 |
| 45 | PO | 1.26 | 237 | PO | 1.99 |
| 46 | PO | ≥2.5 | 242 | PO | >2.5 |
| 43 | PO | 1.26 | 251 | PO | >0.63 |
| 47 | PO | 1.99 | 255 | PO | 0.79 |
| 44 | PO | ≥2.5 | 256 | PO | ≥2.5 |
| 152 | PO | 1.99 | 257 | PO | ≥2.5 |
| 166 | PO | 0.50 |  |  |  |

$ED_{50}$ means effective dose; PO means oral route; SC means subcutaneous route.

3) V-Maze Test

The V-maze-test is a two-trial short term visual-spatial working memory task based on spontaneous exploration of a new and a familiar arm in a 2-arm maze (Embrechts et al. (2013) "Longitudinal characterization of the TauPS2APP mouse model of Alzheimer's disease in a two trial discrimination task of visuo-spatial recognition memory", 45th European Brain and Behaviour Society Meeting 6-9 Sep. 2013, Munich, Abstract P202). Performance in this task can be disrupted by a low dose of PCP, such that the animals do not discriminate anymore between the new and a familiar arm.

Method

Male Long Evans rats (Janvier, France, body weight 280 to 295 g) were group housed in enriched individually ventilated cages and habituated to environmental conditions for 5 days. After acclimatization, animals were single housed for 4 days until testing. During this period animals were handled for 2 min per day and received sham dosing once a day for 3 days prior to the test. The V-maze consisted of two arms (L×W×H: 70×10×30 cm) at a 90° angle to each other to form a V-shaped maze connected by guillotine doors to a center zone. The walls of each arm were of a different context displaying horizontally black and white striped in one arm vs. uniform black walls in the other. Background infra-red illumination was provided via the bottom of the maze and a top view video camera above the platform was used for video recording of the experiments. The animal's exploration of each arm was automatically quantified using Ethovision XT 7.0 (Noldus, The Netherlands). Animals were treated with Co. No. 1 or its vehicle (20% HP-β-CD+1 eq. HCl) administered p.o. 4 h before the start of the test. PCP (0.75 mg/kg s.c.) or its vehicle (0.9% NaCl solution) was administered 30 min prior to the test. The test consisted of 2 sessions of 5 min each: in the first session (exploration) the animal was placed in the center zone and given access to one of both arms (=familiar). After 5 min, the animal was taken out of the maze, the door of the other arm (new) was also opened, and the animal was put back in the center zone for a second session (choice). The time spent in the familiar and new arm respectively during the choice session was recorded for 5 min.

Results

Figure 2:
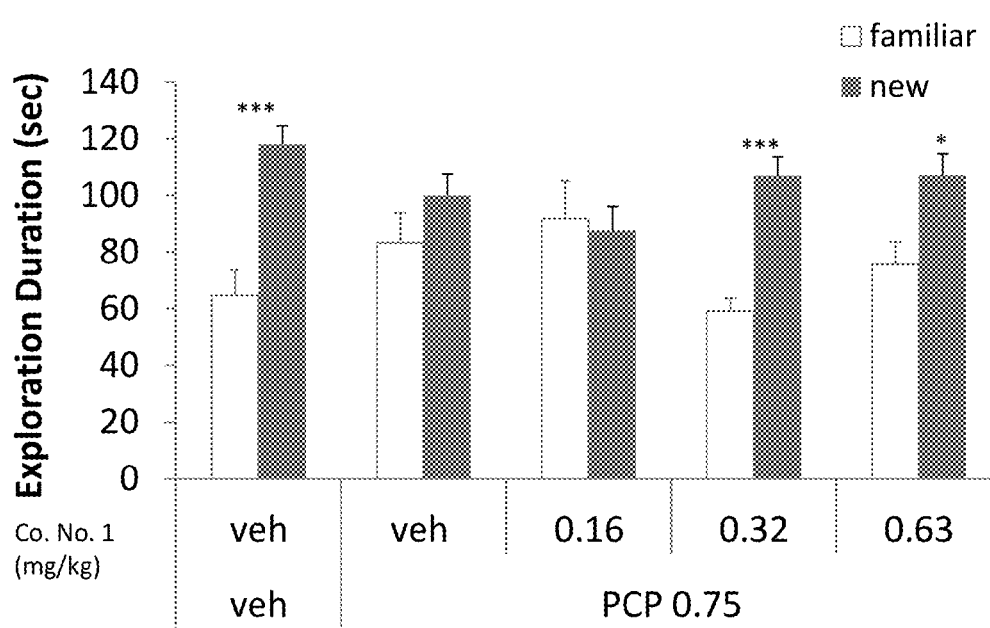
FIG. 2 shows the effect of Co. No. 1 (mg/kg p.o., 4 h prior to test) on exploration times of the new vs. the familiar arm by rats in the absence or presence of PCP (0 (=veh) or 0.75 mg/kg s.c., 0.5 h prior to test) in the V-maze. Data are reported as Mean±SEM, n=12/group; ANOVA with LSD-post hoc, p vs. familiar arm: ***p<0.001, *<0.05.

Co. No. 1 was evaluated in rats in a series of dose-response studies evaluating doses from 0.16 to 10 mg/kg. While control animals (treated with vehicle of the test compound and the vehicle of PCP) displayed a strong preference for exploration of the new vs. the familiar arm in the second session, the PCP-treated rats did not discriminate anymore between both arms in each of these studies. PCP-challenged rats that were pretreated with Co. No. 1 at doses from 0.32 mg/kg onwards showed again a clear preference for the new arm (FIG. 2). This reversal effect against PCP was observed up to the highest dose tested (10 mg/kg).

4) Reserpine Interaction Test in Rats

Some exemplified compounds were observed to induce mydriasis in rats.

It was investigated to what extent the mydriatic action of test compounds was sufficient to counteract the miosis induced by the monoamines-depleting agent reserpine (10 mg/kg; SC) in Wiga rats. Test compounds induced mydriasis before the reserpine challenge (time=−1 h unless otherwise stated; Table 10).

For instance, Co. No. 1 induced mydriasis before the reserpine challenge ($ED_{50}$: 1.78 mg/kg s.c.; 1.55 mg/kg p.o., −1 h; 0.89 mg/kg, p.o., −4 h) and reversed the reserpine-induced ptosis ($ED_{50}$: 1.03 mg/kg s.c.; 0.78 mg/kg p.o., −1 h; 0.78 mg/kg, p.o., −4 h), miosis ($ED_{50}$: 4.1 mg/kg s.c.; 9.4 mg/kg p.o., −1 h; 9.4 mg/kg, p.o., −4 h) and sedation ($ED_{50}$: 9.4 mg/kg s.c.; 7.1 mg/kg p.o., −1 h; 14 mg/kg, p.o., −4 h). The effects are illustrated in FIG. 3. Co. No. 1 did not affect the tail-pinch response before reserpine nor the reserpine-induced blockade of the tail-pinch response and did not induce scratching or hyperemia after reserpine. The reference mGlu2 NAMs RO-4995819 (40 mg/kg, p.o.), RO-4491533 (40 mg/kg, p.o.; 10 mg/kg, s.c.) and [CAS 579473-69-1] (40 mg/kg, s.c.) were devoid of these interactions with reserpine.

Without wishing to be bound by theory, the observed effect may be mediated by a mechanism different from, and additional to, mGluR2 NAM activity.

TABLE 10

Reversal of reserpine-induced ptosis (reserpine; 10 mg/kg; SC; −1 h) in Wiga rats.

| Co. No. | Route | Time | $ED_{50}$ |
|---|---|---|---|
| 40 | PO | 60 | 0.32 |
| 33 | PO | 60 | 0.5 |
| 26 | PO | 60 | 0.50 |
| 31 | PO | 60 | 0.79 |

TABLE 10-continued

Reversal of reserpine-induced ptosis (reserpine; 10 mg/kg; SC; −1 h) in Wiga rats.

| Co. No. | Route | Time | $ED_{50}$ |
|---|---|---|---|
| 1 | PO | 60 | 0.67 |
|  |  | 240 | 0.89 |
|  | SC | 60 | 1.01 |
| 2 | PO | 60 | 0.32 |
| 186 | PO | 60 | 3.15 |
| 200 | PO | 60 | 0.13 |
| 35 | PO | 60 | >10 |
| 41 | PO | 60 | 3.15 |
| 38 | PO | 60 | 5 |
| 36 | PO | 60 | 5 |
| 24 | PO | 60 | ≥10 |
| 34 | PO | 60 | 0.8 |
| 22 | PO | 60 | 0.13 |
| 79 | PO | 60 | 5 |
| 78 | PO | 60 | ≥10 |
| 82 | PO | 60 | 5 |
| 81 | PO | 60 | 5 |
| 80 | PO | 60 | >2.5 |
| 148 | PO | 60 | 1.99 |
| 83 | PO | 60 | 5 |

5) Ro-4-1284 Interaction Test in Rats

The relative ability of Co. No. 1 to increase palpebral opening was also studied in rats challenged with another monoamines depleting agent, viz. Ro-4-1284 (1.25 mg/kg, s.c.). Effects on body temperature immediately before the injection of Ro-4-1284 were also measured. The cumulative palpebral opening score (every 5 min over a 1-h period) was used for evaluation. The median cumulative palpebral opening in solvent-pretreated control animals (n=70) was 18; a scores >25 occurred in only 1.4% of these control animals and was adopted as all-or-none criterion for drug-induced reversal of the Ro-4-1284-induced palpebral ptose. Co. No. 1 increased palpebral opening to scores >25 ($ED_{50}$: 0.51 mg/kg, p.o.) without affecting body temperature (>10 mg/kg, p.o.).

6) Reversal of LY-404039-Induced Decrease of Palpebral Opening in Apomorphine-Challenged Rats.

Male Wiga Wistar rats (Crl:WI; Charles River Germany; 220±40 g) were housed under standard laboratory conditions (21±2° C.; 50-65% relative humidity; light-dark cycle set at 12 h; lights on at 6.00 h) and fasted overnight prior to the start of the experiments (tap water remained available ad libitum). During the test period, they were housed in individual cages. The local Ethical Committee approved all studies in compliance with the Declaration of Helsinki. Palpebral opening was scored every 5 min over the first hour after injection of apomorphine (1.0 mg/kg, i.v.) in animals either pretreated or not pretreated with LY-404039 (2.5 mg/kg, s.c.) at 1 h prior to the apomorphine injection. The animals were also pretreated with test compound or solvent at a predefined interval before apomorphine challenge. The score system was: (5) exophthalmos, (4) wide open, (3) open for three-quarters, (2) half open, (1) open for one-quarter, (0) closed. The scores for palpebral opening were cumulated over the 60-min observation period. A cumulative palpebral opening score >26 was selected for drug-induced reversal of the LY-404039-induced decrease of palpebral opening (occurrence in 3.2% of control animals pretreated with LY-404039 (n=154) versus in 99.5% of control rats not pretreated with LY-404039 (n=6335)).

Table 11a shows the palpebral opening score in control animals receiving apomorphine alone and in animals receiving apomorphine and LY-404039. In animals receiving apomorphine alone the median palpebral opening is 43 whereas in animals receiving apomorphine and LY-404039, the median palpebral opening is 17. In animals treated with apomorphine alone, the palpebral opening score is almost always (in 95.5% of the rats) greater than 34, whereas in animals treated with the combination (apomorphine+LY-404039) only 3.2% of the animals show palpebral opening greater than 26.

TABLE 11a

Palpebral opening score in control animals.

| Measurement | Apomorphine alone (n = 6335) | Apomorphine + LY-404039 (n = 154) |
|---|---|---|
| Palpebral opening score |  |  |
| Median score: | 43 | 17 |
| Occurrence score >26 (%): | 99.5 | 3.2 |
| Occurrence score >34 (%): | 95.9 | 0.0 |

TABLE 11b

Reversal of LY-404039-induced decrease of palpebral opening in apomorphine challenged rats.

| Co. No. | Route | $ED_{50}$ |
|---|---|---|
| 33 | PO | >2.5 |
| 31 | PO | ≥10 |
| 1 | PO | 0.45 |
|  | SC | 0.3 |
| 8 | PO | 5 |
| 15 | PO | 11.22 |
| 2 | PO | 0.50 |
| 5 | PO | >10 |
| 45 | PO | 0.79 |
| 46 | PO | 0.32 |
| 44 | PO | 0.50 |
| 167 | PO | >40 |
| 147 | PO | 1.26 |
| 172 | SC | >40 |
| 140 | PO | 1.99 |

7) Reversal of mGluR2-Agonism in Hippocampal Brain Slices

Introduction

Electrophysiology recordings of field excitatory postsynaptic potentials (fEPSPs) in acute hippocampal brain slices represent a model for testing synaptic transmission and plasticity. The effect of Co. No. 1 on synaptic transmission and plasticity in dentate gyms synapses was investigated using this model. This region was chosen because of the high expression of mGluR 2 (Shigemoto et al., The Journal of Neuroscience, Oct. 1, 1997, 17(19), 7503-7522).

Methods

Recordings of fEPSPs were made from hippocampal brain slices using a multi-electrode array (MEA) biochip, and 3-dimensional-(3D) tip electrodes, according to a standard protocol. These recordings were used to monitor glutamate-mediated synaptic transmission (FIG. 4).

Results

Superfusion of rat hippocampal brain slices with the mGlu2/3-specific agonist LY-354740 (1 µM) depressed fEPSP by 50% within 15 min of application (FIG. 5) and was associated with an increase of the paired-pulse ratio (PPR), indicating a presynaptic mechanism. Fifteen min after the application of 10 µM Co. No. 1 the depression of fEPSP had recovered by 80%. This was associated with a decrease of the PPR, indicating an increase in neurotransmitter release (FIG. 5, n=17 slices from 4 rats).

Subsequently, the effects of Co. No. 1 on synaptic function using long-term potentiation (LTP) protocols in the dentate gyms (Goeldner et. al., Neuropharmacology 2013, 64, 337-346) were evaluated.

Small magnitude LTP (110%) was induced using isolated glutamatergic-mediated fEPSP: trains of theta-burst stimulation that are known to induce LTP at these particular synapses were applied (Dinklo et al., J. Pharmacol. Exp. Ther. 2011, 336(2), 560-574). In the presence of 10 µM Co. No. 1, the magnitude of LTP was enhanced by 150% compared to baseline (p=0.005). Also noteworthy is the finding that the post-theta potentiation (PTP) in the presence of 10 µM Co. No. 1 was significantly different from vehicle treatment: 160% vs. 120% respectively (p=0.01) (FIG. 6, 22 slices from 4 SD rats). At the end of the experiments, addition of 1 mM kynurenic acid to block glutamatergic neurotransmission, confirmed that the post-synaptic response is mediated by glutamate neurotransmission.

Discussion

LY-354740 stimulates presynaptic mGlu2/3 receptors to limit the release of glutamate. Furthermore, the effects of Group II mGluR agonists and antagonists in rodent models of cognition are totally absent in mGluR2 knock-out mice (Higgins et al. Neuropharmacology, 2004, 46, 907-917). Co. No. 1 reversed synaptic depression evoked by the mGlu2/3-agonist LY-354740. These data illustrate that Co. No. 1 is able to restore depressed synaptic transmission in rat hippocampal slices in vitro. The increase in network excitability, as a result of enhanced excitatory neurotransmission, affected the threshold of LTP induction. Thus, LTP was efficiently induced by weak theta stimulation, but only when Co. No. 1 was pre-applied. Thus, the compound might act as a cognitive enhancer via an ability to elevate the synaptic strength in glutamatergic synapses and by priming the system for enhanced LTP.

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

1. Tablets

| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I):

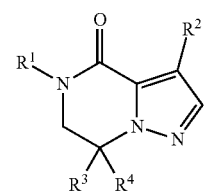

or a stereoisomeric form thereof,
wherein:
$R^1$ is phenyl or 2-pyridinyl, each optionally substituted with one or more substituents independently selected from the group consisting of halo, —$C_{1-4}$alkyl, monohalo$C_{1-4}$alkyl, polyhalo$C_{1-4}$alkyl, —O—$C_{1-4}$alkyl, —$C_{1-4}$alkyl-O—$C_{1-4}$alkyl, monohalo$C_{1-4}$alkyloxy, polyhalo$C_{1-4}$alkyloxy, —$C_{1-4}$alkyl-OH, —$C_{1-4}$alkylthio, monohalo$C_{1-4}$alkylthio, polyhalo$C_{1-4}$alkylthio, cyano, —$C_{3-7}$cycloalkyl optionally substituted with trifluoromethyl and —$SF_5$; or
$R^1$ is

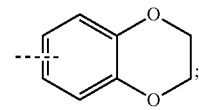

$R^2$ is

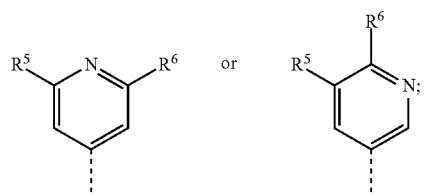

$R^3$ is selected from the group consisting of hydrogen and —$C_{1-4}$alkyl;

R⁴ is selected from the group consisting of hydrogen, —C₁₋₄alkyl, monohaloC₁₋₄alkyl, polyhaloC₁₋₄alkyl, —C₁₋₄alkyl-O—C₁₋₄alkyl and —C₁₋₄alkyl-OH;

R⁵ and R⁶ are each independently selected from the group consisting of hydrogen, halo, cyano, —C₁₋₄alkyl, —C₁₋₄alkyl-OH, —C₃₋₇cycloalkyl, monohaloC₁₋₄alkyl, polyhaloC₁₋₄alkyl, —C₁₋₄alkyl-O—C₁₋₄alkyl, —O—C₁₋₄alkyl, monohaloC₁₋₄alkyloxy, polyhaloC₁₋₄alkyloxy, 1-acetylazetidin-3-yl and —NR'R"; and R' and R" are each independently selected from the group consisting of hydrogen and —C₁₋₄alkyl; or R' and R", together with the nitrogen atom to which they are attached, form a heterocyclic group selected from the group consisting of 1-azetidinyl, 1-pyrrolidinyl, 1-piperidinyl, 1-piperazinyl and 4-morpholinyl, wherein 1-azetidinyl, 1-pyrrolidinyl, 1-piperidinyl, 1-piperazinyl and 4-morpholinyl are optionally substituted with a substituent selected from the group consisting of halo, hydroxy, —C₁₋₄alkyl, monohaloC₁₋₄alkyl, polyhaloC₁₋₄alkyl and —C(O)—C₁₋₄alkyl;

or a N-oxide or a pharmaceutically acceptable salt thereof.

2. The compound of claim 1, wherein:

R¹ is phenyl or 2-pyridinyl, each optionally substituted with one or more substituents independently selected from the group consisting of halo, —C₁₋₄alkyl, monohaloC₁₋₄alkyl, polyhaloC₁₋₄alkyl, —O—C₁₋₄alkyl, —C₁₋₄alkyl-O—C₁₋₄alkyl, monohaloC₁₋₄alkyloxy, polyhaloC₁₋₄alkyloxy, —C₁₋₄alkyl-OH, monohaloC₁₋₄alkylthio, polyhaloC₁₋₄alkylthio, cyano and —SF₅; or R¹ is

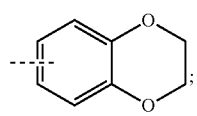

R² is

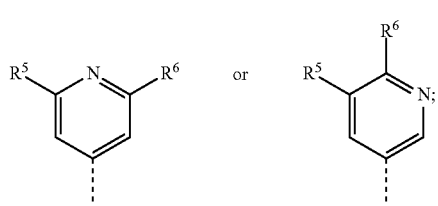

R⁵ and R⁶ are each independently selected from the group consisting of hydrogen, halo, cyano, —C₁₋₄alkyl, —C₁₋₄alkyl-OH, —C₃₋₇cycloalkyl, monohaloC₁₋₄alkyl, polyhaloC₁₋₄alkyl, —C₁₋₄alkyl-O—C₁₋₄alkyl, —O—C₁₋₄alkyl, monohaloC₁₋₄alkyloxy, polyhaloC₁₋₄alkyloxy and —NR'R"; and R' and R" are each independently selected from the group consisting of hydrogen and C₁₋₄alkyl; or R' and R", together with the nitrogen atom to which they are attached, form a heterocyclic group selected from the group consisting of 1-azetidinyl, 1-pyrrolidinyl and 1-piperidinyl, wherein 1-azetidinyl, 1-pyrrolidinyl and 1-piperidinyl are optionally substituted with a halo substituent;

or a N-oxide or a pharmaceutically acceptable salt thereof.

3. The compound of claim 1, wherein:

R¹ is phenyl, optionally substituted with one or more substituents independently selected from the group consisting of halo, —C₁₋₄alkyl, monohaloC₁₋₄alkyl, polyhaloC₁₋₄alkyl, —O—C₁₋₄alkyl, monohaloC₁₋₄alkylthio, polyhaloC₁₋₄alkylthio, cyano and —SF₅; or

R¹

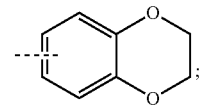

R² is

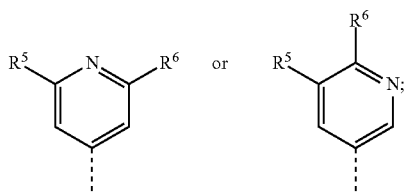

R⁵ and R⁶ are each independently selected from the group consisting of hydrogen, —C₁₋₄alkyl, monohaloC₁₋₄alkyl, polyhaloC₁₋₄alkyl, —C₁₋₄alkyl-O—C₁₋₄alkyl, —O—C₁₋₄alkyl and —NR'R"; and R' and R" are each independently selected from the group consisting of hydrogen and C₁₋₄alkyl;

or a pharmaceutically acceptable salt thereof.

4. The compound of claim 1, wherein:

R¹ is phenyl, optionally substituted with one or more substituents independently selected from the group consisting of halo, —C₁₋₄alkyl, monohaloC₁₋₄alkyl, polyhaloC₁₋₄alkyl, —O—C₁₋₄alkyl, monohaloC₁₋₄alkyloxy, polyhaloC₁₋₄alkyloxy, cyano and —SF₅; or R¹ is

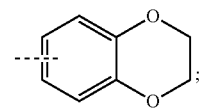

R² is

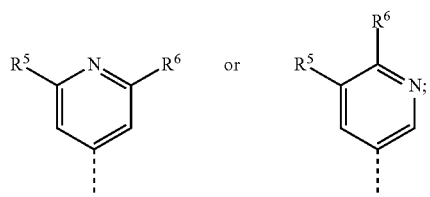

R⁴ is selected from the group consisting of hydrogen and —C₁₋₄alkyl;

R⁵ and R⁶ are each independently selected from the group consisting of hydrogen, —C₁₋₄alkyl, —C₁₋₄alkyl-O—C₁₋₄alkyl and —NR'R"; and R' and R" are each hydrogen;

or a pharmaceutically acceptable salt thereof.

5. The compound of claim 1, wherein:

R¹ is phenyl, optionally substituted with one or more substituents independently selected from the group consisting of halo, —$C_{1-4}$alkyl, polyhalo$C_{1-4}$alkyl and —$SF_5$;

R² is

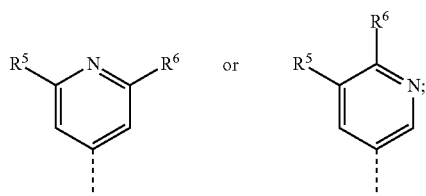

R⁴ is hydrogen; and

R⁵ and R⁶ are each independently selected from the group consisting of hydrogen, —$C_{1-4}$alkyl and —O—$C_{1-4}$alkyl;

or a pharmaceutically acceptable salt thereof.

6. The compound of claim 1, wherein R¹ is selected from the group consisting of

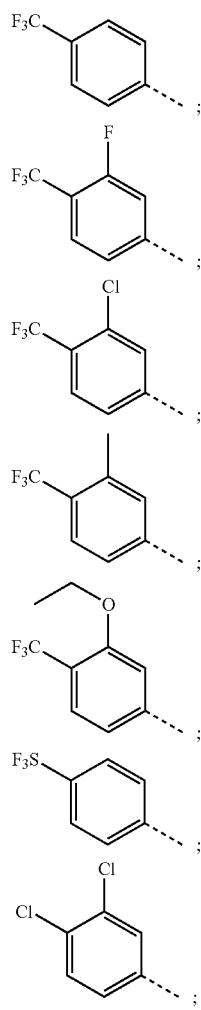

-continued

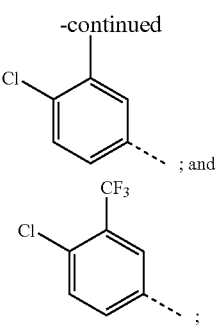

7. The compound of claim 1, wherein the compound is:

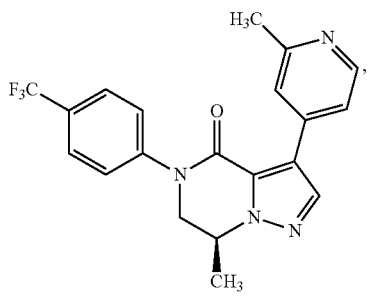

or a N-oxide or a pharmaceutically acceptable salt thereof.

8. The compound of claim 7, wherein the compound is:

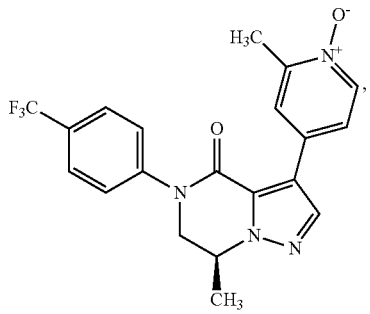 [SMILES: Cc1cc(-c2cnn3c2C(=O)N(c2ccc(C(F)(F)F)cc2)C[C@@H]3C)cc[n+]1[O-]]

or a pharmaceutically acceptable salt thereof.

9. The compound of claim 7, wherein the compound is the free base or a pharmaceutically acceptable salt selected from the group consisting of the hydrochloride salt, the sulfate salt, the methanesulfonate salt and the maleate salt.

10. The compound of claim 1, wherein the compound is:

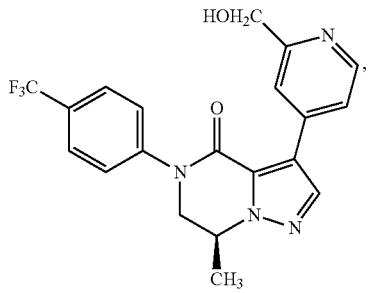 [SMILES: C[C@H]1CN(c2ccc(C(F)(F)F)cc2)C(=O)c2c(-c3ccnc(CO)c3)cnn21]

or a pharmaceutically acceptable salt thereof.

11. A pharmaceutical composition comprising a therapeutically effective amount of a compound of claim 1 and a pharmaceutically acceptable carrier or excipient.

12. A method for modulating metabotropic glutamate receptor 2 activity in a subject, comprising administering to a subject in need thereof a therapeutically effective amount of a compound of claim 1.

13. The method of claim 12, wherein the subject suffers from a central nervous system disorder or condition selected from the group consisting of a depressive disorder, a neurocognitive disorder, a neurodevelopmental disorder, a substance-related disorder, an addictive disorder, a psychotic disorder, a somatic symptom disorder and a hypersomnolence disorder.

14. The method of claim 13, wherein the central nervous system disorder or condition is selected from the group consisting of depression, attention-deficit/hyperactivity disorder, schizophrenia and a neurocognitive disorder.

15. The method of claim 14, wherein the depression is selected from the group consisting of major depressive disorder and treatment resistant depression.

16. The method of claim 12, wherein the subject suffers from a central nervous system disorder or condition selected from the group consisting of a mood disorder, a cognitive disorder, a substance-related disorder, a psychotic disorder, a somatoform disorder and a hypersomnic sleep disorder.

17. The method of claim 12 wherein the central nervous system disorder or condition is selected from the group consisting of major depressive disorder, depression and treatment resistant depression.

18. A method for modulating metabotropic glutamate receptor 2 activity in a subject, comprising administering to a subject in need thereof a therapeutically effective amount of a compound of claim 7.

19. The method of claim 18, wherein the subject suffers from a central nervous system disorder or condition selected from the group consisting of major depressive disorder and treatment resistant depression.

20. A process for the preparation of a compound of Formula (I):

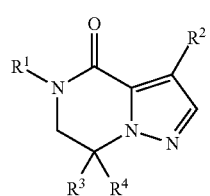

(I)

wherein:
R$^1$ is phenyl or 2-pyridinyl, each optionally substituted with one or more substituents independently selected from the group consisting of halo, —C$_{1-4}$alkyl, monohaloC$_{1-4}$alkyl, polyhaloC$_{1-4}$alkyl, —O—C$_{1-4}$alkyl, —C$_{1-4}$alkyl-O—C$_{1-4}$alkyl, monohaloC$_{1-4}$alkyloxy, polyhaloC$_{1-4}$alkyloxy, —C$_{1-4}$alkyl-OH, —C$_{1-4}$alkylthio, monohaloC$_{1-4}$alkylthio, polyhaloC$_{1-4}$alkylthio, cyano, —C$_{3-7}$cycloalkyl optionally substituted with trifluoromethyl and —SF$_5$; or R$^1$ is

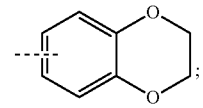

R$^2$ is

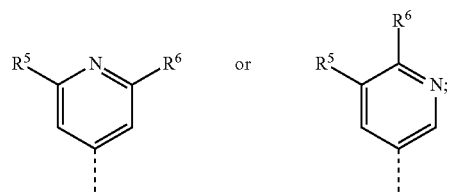

R$^3$ is selected from the group consisting of hydrogen and —C$_{1-4}$alkyl;

R$^4$ is selected from the group consisting of hydrogen, —C$_{1-4}$alkyl, monohaloC$_{1-4}$alkyl, polyhaloC$_{1-4}$alkyl, —C$_{1-4}$alkyl-O—C$_{1-4}$alkyl and —C$_{1-4}$alkyl-OH;

R$^5$ and R$^6$ are each independently selected from the group consisting of hydrogen, halo, cyano, —C$_{1-4}$alkyl, —C$_{1-4}$alkyl-OH, —C$_{3-7}$cycloalkyl, monohaloC$_{1-4}$alkyl, polyhaloC$_{1-4}$alkyl, —C$_{1-4}$alkyl-O—C$_{1-4}$alkyl, —O—C$_{1-4}$alkyl, monohaloC$_{1-4}$alkyloxy, polyhaloC$_{1-4}$alkyloxy, 1-acetylazetidin-3-yl and —NR'R"; and R' and R" are each independently selected from the group consisting of hydrogen and —C$_{1-4}$alkyl; or R' and R", together with the nitrogen atom to which they are attached, form a heterocyclic group selected from the group consisting of 1-azetidinyl, 1-pyrrolidinyl, 1-piperidinyl, 1-piperazinyl and 4-morpholinyl, wherein 1-azetidinyl, 1-pyrrolidinyl, 1-piperidinyl, 1-piperazinyl and 4-morpholinyl are optionally substituted with a substituent selected from the group consisting of halo, hydroxy, —C$_{1-4}$alkyl, monohaloC$_{1-4}$alkyl, polyhaloC$_{1-4}$alkyl and —C(O)—C$_{1-4}$alkyl;

comprising:
a) reacting a compound of Formula (V):

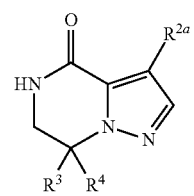

(V)

wherein:
R$^{2a}$ is halo;
R$^3$ is selected from the group consisting of hydrogen and —C$_{1-4}$alkyl; and
R$^4$ is selected from the group consisting of hydrogen, —C$_{1-4}$alkyl, monohaloC$_{1-4}$alkyl, polyhaloC$_{1-4}$alkyl, —C$_{1-4}$alkyl-O—C$_{1-4}$alkyl and —C$_{1-4}$alkyl-OH;

with a compound of Formula (IIIa):

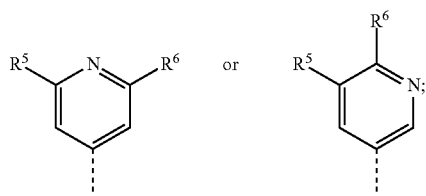
(IIIa)

wherein:
R² is

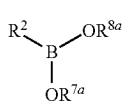

R⁵ and R⁶ are each independently selected from the group consisting of hydrogen, halo, cyano, —C₁₋₄alkyl, —C₁₋₄alkyl-OH, —C₃₋₇cycloalkyl, monohaloC₁₋₄alkyl, polyhaloC₁₋₄alkyl, —C₁₋₄alkyl-O—C₁₋₄alkyl, —O—C₁₋₄alkyl, monohaloC₁₋₄alkyloxy, polyhaloC₁₋₄alkyloxy, 1-acetylazetidin-3-yl and —NR'R";

R' and R" are each independently selected from the group consisting of hydrogen and —C₁₋₄alkyl; or R' and R", together with the nitrogen atom to which they are attached, form a heterocyclic group selected from the group consisting of 1-azetidinyl, 1-pyrrolidinyl, 1-piperidinyl, 1-piperazinyl and 4-morpholinyl, wherein 1-azetidinyl, 1-pyrrolidinyl, 1-piperidinyl, 1-piperazinyl and 4-morpholinyl are optionally substituted with a substituent selected from the group consisting of halo, hydroxy, —C₁₋₄alkyl, monohaloC₁₋₄alkyl, polyhaloC₁₋₄alkyl and —C(O)—C₁₋₄alkyl; R³ is selected from the group consisting of hydrogen and —C₁₋₄alkyl;

R⁷ᵃ and R⁸ᵃ are each independently selected from the group consisting of hydrogen and —C₁₋₄alkyl; or R⁷ᵃ and R⁸ᵃ are taken together to form a bivalent radical of the formula —(CH₂)₂—, —(CH₂)₃— or —C(CH₃)₂—C(CH₃)₂—;

in the presence of a palladium catalyst, a base and solvent, to form a compound of Formula (II):

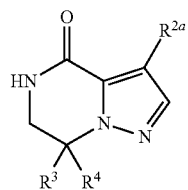
(V)

wherein:
R² is

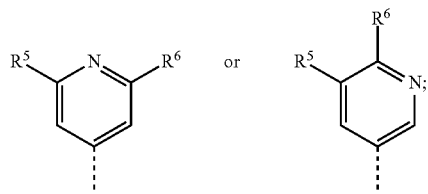

R³ is selected from the group consisting of hydrogen and —C₁₋₄alkyl;

R⁴ is selected from the group consisting of hydrogen, —C₁₋₄alkyl, monohaloC₁₋₄alkyl, polyhaloC₁₋₄alkyl, —C₁₋₄alkyl-O—C₁₋₄alkyl and —C₁₋₄alkyl-OH;

R⁵ and R⁶ are each independently selected from the group consisting of hydrogen, halo, cyano, —C₁₋₄alkyl, —C₁₋₄alkyl-OH, —C₃₋₇cycloalkyl, monohaloC₁₋₄alkyl, polyhaloC₁₋₄alkyl, —C₁₋₄alkyl-O—C₁₋₄alkyl, —O—C₁₋₄alkyl, monohaloC₁₋₄alkyloxy, polyhaloC₁₋₄alkyloxy, 1-acetylazetidin-3-yl and —NR'R"; and R' and R" are each independently selected from the group consisting of hydrogen and C₁₋₄alkyl; or R' and R", together with the nitrogen atom to which they are attached, form a heterocyclic group selected from the group consisting of 1-azetidinyl, 1-pyrrolidinyl, 1-piperidinyl, 1-piperazinyl and 4-morpholinyl, wherein 1-azetidinyl, 1-pyrrolidinyl, 1-piperidinyl, 1-piperazinyl and 4-morpholinyl are optionally substituted with a substituent selected from the group consisting of halo, hydroxy, C₁₋₄alkyl, monohaloC₁₋₄alkyl, polyhaloC₁₋₄alkyl and —C(O)—C₁₋₄alkyl; and b) reacting the compound of Formula (II) above with a compound of Formula (III):

R¹—X   (III)

wherein:
R¹ is phenyl or 2-pyridinyl, each optionally substituted with one or more substituents independently selected from the group consisting of halo, —C₁₋₄alkyl, monohaloC₁₋₄alkyl, polyhaloC₁₋₄alkyl, —O—C₁₋₄alkyl, —C₁₋₄alkyl-O—C₁₋₄alkyl, monohaloC₁₋₄alkyloxy, polyhaloC₁₋₄alkyloxy, —C₁₋₄alkyl-OH, —C₁₋₄alkylthio, monohaloC₁₋₄alkylthio, polyhaloC₁₋₄alkylthio, cyano, —C₃₋₇cycloalkyl optionally substituted with trifluoromethyl and —SF₅; or R¹ is

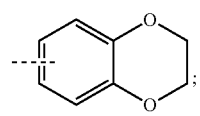

and

X is halo;

in the presence of (i) 2-(7-aza-1H-benzotriazol-1-yl)-1,1,3,3-tetramethyluronium hexafluorophosphate, or (ii) a catalyst, a ligand, a base and solvent, to provide the compound of Formula (I) above.

21. A process for preparing a pharmaceutical composition comprising admixing a pharmaceutically acceptable carrier or excipient with a therapeutically effective amount of a compound of claim 1.

22. A compound of Formula (II):

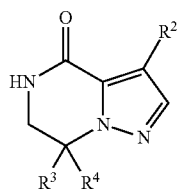

(II)

wherein:

R² is

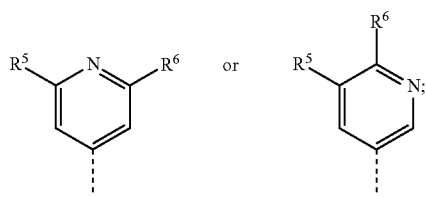

R³ is selected from the group consisting of hydrogen and —C$_{1-4}$alkyl;

R⁴ is selected from the group consisting of hydrogen, —C$_{1-4}$alkyl, monohaloC$_{1-4}$alkyl, polyhaloC$_{1-4}$alkyl, —C$_{1-4}$alkyl-O—C$_{1-4}$alkyl and —C$_{1-4}$alkyl-OH;

R⁵ and R⁶ are each independently selected from the group consisting of hydrogen, halo, cyano, —C$_{1-4}$alkyl, —C$_{1-4}$alkyl-OH, —C$_{3-7}$cycloalkyl, monohaloC$_{1-4}$alkyl, polyhaloC$_{1-4}$alkyl, —C$_{1-4}$alkyl-O—C$_{1-4}$alkyl, —O—C$_{1-4}$alkyl, monohaloC$_{1-4}$alkyloxy, polyhaloC$_{1-4}$alkyloxy, 1-acetylazetidin-3-yl and —NR'R"; and R' and R" are each independently selected from the group consisting of hydrogen and C$_{1-4}$alkyl; or R' and R", together with the nitrogen atom to which they are attached, form a heterocyclic group selected from the group consisting of 1-azetidinyl, 1-pyrrolidinyl, 1-piperidinyl, 1-piperazinyl and 4-morpholinyl, wherein 1-azetidinyl, 1-pyrrolidinyl, 1-piperidinyl, 1-piperazinyl and 4-morpholinyl are optionally substituted with a substituent selected from the group consisting of halo, hydroxy, C$_{1-4}$alkyl, monohaloC$_{1-4}$alkyl, polyhaloC$_{1-4}$alkyl and —C(O)—C$_{1-4}$alkyl.

23. A compound of Formula (V):

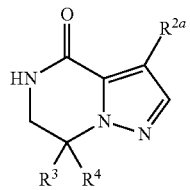

(V)

wherein:

R$^{2a}$ is halo;

R³ is selected from the group consisting of hydrogen and —C$_{1-4}$alkyl; and

R⁴ is selected from the group consisting of hydrogen, —C$_{1-4}$alkyl, monohaloC$_{1-4}$alkyl, polyhaloC$_{1-4}$alkyl, —C$_{1-4}$alkyl-O—C$_{1-4}$alkyl and —C$_{1-4}$alkyl-OH.

24. The compound of claim 23, wherein the compound has the Formula (V'):

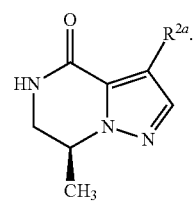

(V')

25. The compound of claim 24, wherein the compound has the Formula (I-13) or Formula (I-13a):

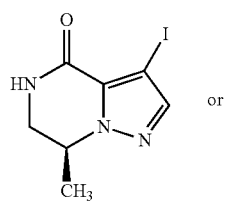

(I-13)

or

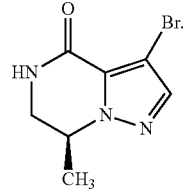

(I-13a)

* * * * *